United States Patent
Cranor et al.

(10) Patent No.: US 8,361,352 B2
(45) Date of Patent: Jan. 29, 2013

(54) CHEMICAL LIGHT PRODUCING FORMULATIONS AND DEVICES CONTAINING BRANCHED OXALATE ESTERS

(75) Inventors: Earl Cranor, Longmeadow, MA (US); Linda Jacob, Woodbridge, CT (US)

(73) Assignee: Cyalume Technologies, Inc., West Springfield, MA (US)

( * ) Notice: Subject to any disclaimer, the term of this patent is extended or adjusted under 35 U.S.C. 154(b) by 48 days.

(21) Appl. No.: 12/903,726

(22) Filed: Oct. 13, 2010

(65) Prior Publication Data

US 2011/0084243 A1    Apr. 14, 2011

Related U.S. Application Data

(60) Provisional application No. 61/250,915, filed on Oct. 13, 2009.

(51) Int. Cl.
   *C09K 11/07*      (2006.01)
   *C07C 69/92*      (2006.01)
(52) U.S. Cl. ............ 252/700; 560/60; 560/65; 560/146
(58) Field of Classification Search .................... 560/60, 560/65, 146
   See application file for complete search history.

(56) References Cited

U.S. PATENT DOCUMENTS

| | | |
|---|---|---|
| 3,584,211 A | 6/1968 | Rauhut |
| 3,511,612 A | 5/1970 | Kennerly et al. |
| 3,539,794 A | 11/1970 | Rauhut et al. |
| 3,576,987 A | 5/1971 | Voight et al. |
| 3,654,525 A | 4/1972 | Maricle et al. |
| 3,749,620 A | 7/1973 | Montgomery |
| 3,749,679 A | 7/1973 | McKay Rauhut |
| 3,752,406 A | 8/1973 | McDermott et al. |
| 3,800,132 A | 3/1974 | Postal |
| 3,808,414 A | 4/1974 | Roberts |
| 3,940,604 A | 2/1976 | Rauhut |

(Continued)

OTHER PUBLICATIONS

STN structure search (Apr. 10, 2012).*

(Continued)

*Primary Examiner* — Vu A Nguyen
(74) *Attorney, Agent, or Firm* — McHale & Slavin, P.A.

(57) ABSTRACT

Chemical light producing systems and the chemiluminescent formulations contained therein are taught which exhibit reduced hydrolysis and thereby are characterized by an inherently long shelf-life and commercial viability. By replacing the typical oxalate ester, e.g. (bis{3,4,6-trichloro-2-[(pentoxy)carbonyl]phenyl}oxalate) with a branched chain oxalic acid ester represented by the general formula:

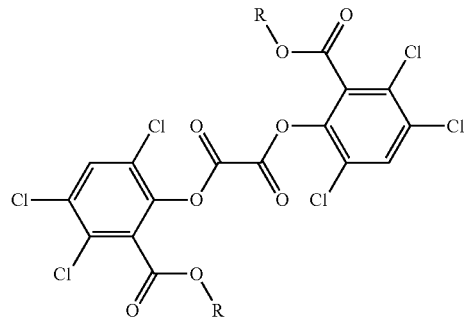

$R = CH_2A$ wherein the group designated as R contains from 4-15 carbons, wherein the carbon of attachment of R to the oxygen is via a primary carbon, and wherein substructure A is composed of substituents selected from the group including alkyl chains, alkyl rings, aromatic rings and combinations thereof such that R is nonlinear, water hydrolysis of the oxalate ester is retarded. This retardation of the hydrolysis changes the storage constraints of the oxalate ester.

40 Claims, 331 Drawing Sheets bis{3,4,6-trichloro-2-[(2-methylpropoxy)carbonyl]phenyl} oxalate

U.S. PATENT DOCUMENTS 3,974,368 A    8/1976   Rauhut
4,064,428 A    12/1977   Van Zandt
4,308,395 A    12/1981   Manfre et al.
4,751,616 A    6/1988   Smithey
5,194,666 A    3/1993   Sedlak et al.

OTHER PUBLICATIONS

C. Dowd et al, "Synthesis and evaluation of diaryl oxalate esters for low-inensity chemiluminescent illumination", Aust. J. Chem., 37:73-86 (Jan. 1984).

* cited by examiner bis{3,4,6-trichloro-2-[(2-methylpropoxy)carbonyl]phenyl} oxalate bis{3,4,6-trichloro-2-[(cyclopropylmethoxy)carbonyl]phenyl} oxalate bis{3,4,6-trichloro-2-[(2-methylbutoxy)carbonyl]phenyl} oxalate bis{3,4,6-trichloro-2-[(3-methylbutoxy)carbonyl]phenyl} oxalate bis{3,4,6-trichloro-2-[(2,2-dimethylpropoxy)carbonyl]phenyl} oxalate bis{3,4,6-trichloro-2-[(cyclobutylmethoxy)carbonyl]phenyl} oxalate bis(3,4,6-trichloro-2-{[(1-methylcyclopropyl)methoxy]carbonyl}phenyl) oxalate bis(3,4,6-trichloro-2-{[(2-methylcyclopropyl)methoxy]carbonyl}phenyl) oxalate bis{3,4,6-trichloro-2-[(2-cyclopropylethoxy)carbonyl]phenyl} oxalate bis{3,4,6-trichloro-2-[(2-methylpentyloxy)carbonyl]phenyl} oxalate bis{3,4,6-trichloro-2-[(3-methylpentyloxy)carbonyl]phenyl} oxalate bis{3,4,6-trichloro-2-[(4-methylpentyloxy)carbonyl]phenyl} oxalate bis{3,4,6-trichloro-2-[(2,2-dimethylbutoxy)carbonyl]phenyl} oxalate bis{3,4,6-trichloro-2-[(2,3-dimethylbutoxy)carbonyl]phenyl} oxalate bis{3,4,6-trichloro-2-[(3,3-dimethylbutoxy)carbonyl]phenyl} oxalate bis{3,4,6-trichloro-2-[(2-ethylbutoxy)carbonyl]phenyl} oxalate bis{3,4,6-trichloro-2-[(cyclopentylmethoxy)carbonyl]phenyl} oxalate bis(3,4,6-trichloro-2-{[(1-methylcyclobutyl)methoxy]carbonyl}phenyl) oxalate bis(3,4,6-trichloro-2-{[(2-methylcyclobutyl)methoxy]carbonyl}phenyl) oxalate bis(3,4,6-trichloro-2-{[(3-methylcyclobutyl)methoxy]carbonyl}phenyl) oxalate bis(3,4,6-trichloro-2-{[(1-ethylcyclopropyl)methoxy]carbonyl}phenyl) oxalate bis(3,4,6-trichloro-2-{[(1,2-dimethylcyclopropyl)methoxy]carbonyl}phenyl) oxalate bis(3,4,6-trichloro-2-{[(2,3-dimethylcyclopropyl)methoxy]carbonyl}phenyl) oxalate bis(3,4,6-trichloro-2-{[(2-ethylcyclopropyl)methoxy]carbonyl}phenyl) oxalate bis(3,4,6-trichloro-2-{[(2,2-dimethylcyclopropyl)methoxy]carbonyl}phenyl) oxalate bis(3,4,6-trichloro-2-{[2-(1-methylcyclopropyl)ethoxy]carbonyl}phenyl) oxalate bis(3,4,6-trichloro-2-{[2-(2-methylcyclopropyl)ethoxy]carbonyl}phenyl) oxalate bis{3,4,6-trichloro-2-[(2-cyclopropylpropoxy)carbonyl]phenyl} oxalate bis{3,4,6-trichloro-2-[(3-cyclopropylpropoxy)carbonyl]phenyl} oxalate bis{2-[(bicyclo[1.1.1]pentan-5-ylmethoxy)carbonyl]-3,4,6-trichlorophenyl} oxalate bis{3,4,6-trichloro-2-[(2-methylhexyloxy)carbonyl]phenyl} oxalate bis{3,4,6-trichloro-2-[(3-methylhexyloxy)carbonyl]phenyl} oxalate bis{3,4,6-trichloro-2-[(4-methylhexyloxy)carbonyl]phenyl} oxalate bis{3,4,6-trichloro-2-[(5-methylhexyloxy)carbonyl]phenyl} oxalate bis{3,4,6-trichloro-2-[(2,2-dimethylpentyloxy)carbonyl]phenyl} oxalate bis{3,4,6-trichloro-2-[(2,3-dimethylpentyloxy)carbonyl]phenyl} oxalate bis{3,4,6-trichloro-2-[(2,4-dimethylpentyloxy)carbonyl]phenyl} oxalate bis{3,4,6-trichloro-2-[(3,3-dimethylpentyloxy)carbonyl]phenyl} oxalate bis{3,4,6-trichloro-2-[(3,4-dimethylpentyloxy)carbonyl]phenyl} oxalate bis{3,4,6-trichloro-2-[(4,4-dimethylpentyloxy)carbonyl]phenyl} oxalate bis{3,4,6-trichloro-2-[(2-ethyl-3-methylbutoxy)carbonyl]phenyl} oxalate bis{3,4,6-trichloro-2-[(2,2,3-trimethylbutoxy)carbonyl]phenyl} oxalate bis{3,4,6-trichloro-2-[(2,3,3-trimethylbutoxy)carbonyl]phenyl} oxalate bis{3,4,6-trichloro-2-[(2-ethylpentyloxy)carbonyl]phenyl} oxalate bis{3,4,6-trichloro-2-[(3-ethylpentyloxy)carbonyl]phenyl} oxalate bis{3,4,6-trichloro-2-[(2-ethyl-2-methylbutoxy)carbonyl]phenyl} oxalate bis{3,4,6-trichloro-2-[(cyclohexylmethoxy)carbonyl]phenyl} oxalate bis(3,4,6-trichloro-2-{[(1-methylcyclopentyl)methoxy]carbonyl}phenyl) oxalate bis(3,4,6-trichloro-2-{[(2-methylcyclopentyl)methoxy]carbonyl}phenyl) oxalate bis(3,4,6-trichloro-2-{[(3-methylcyclopentyl)methoxy]carbonyl}phenyl) oxalate bis{3,4,6-trichloro-2-[(2-cyclopentylethoxy)carbonyl]phenyl} oxalate bis(3,4,6-trichloro-2-{[(1-ethylcyclobutyl)methoxy]carbonyl}phenyl) oxalate bis(3,4,6-trichloro-2-{[(2-ethylcyclobutyl)methoxy]carbonyl}phenyl) oxalate bis(3,4,6-trichloro-2-{[(3-ethylcyclobutyl)methoxy]carbonyl}phenyl) oxalate bis(3,4,6-trichloro-2-{[(1,2-dimethylcyclobutyl)methoxy]carbonyl}phenyl) oxalate bis(3,4,6-trichloro-2-{[(1,3-dimethylcyclobutyl)methoxy]carbonyl}phenyl) oxalate bis(3,4,6-trichloro-2-{[(2,2-dimethylcyclobutyl)methoxy]carbonyl}phenyl) oxalate bis(3,4,6-trichloro-2-{[(2,3-dimethylcyclobutyl)methoxy]carbonyl}phenyl) oxalate bis(3,4,6-trichloro-2-{[(3,3-dimethylcyclobutyl)methoxy]carbonyl}phenyl) oxalate bis(3,4,6-trichloro-2-{[2-(1-methylcyclobutyl)ethoxy]carbonyl}phenyl) oxalate bis(3,4,6-trichloro-2-{[2-(2-methylcyclobutyl)ethoxy]carbonyl}phenyl) oxalate bis(3,4,6-trichloro-2-{[2-(3-methylcyclobutyl)ethoxy]carbonyl}phenyl) oxalate bis{3,4,6-trichloro-2-[(2-cyclobutylpropoxy)carbonyl]phenyl} oxalate bis{3,4,6-trichloro-2-[(3-cyclobutylpropoxy)carbonyl]phenyl} oxalate bis(3,4,6-trichloro-2-{[(1,2,2-trimethylcyclopropyl)methoxy]carbonyl}phenyl) oxalate bis(3,4,6-trichloro-2-{[(1,2,3-trimethylcyclopropyl)methoxy]carbonyl}phenyl) oxalate bis(3,4,6-trichloro-2-{[(1-ethyl-2-methylcyclopropyl)methoxy]carbonyl}phenyl) oxalate bis(3,4,6-trichloro-2-{[(2-ethyl-1-methylcyclopropyl)methoxy]carbonyl}phenyl) oxalate bis[3,4,6-trichloro-2-({[1-(1-methyl-ethyl)cyclopropyl]methoxy}carbonyl)phenyl] oxalate bis[3,4,6-trichloro-2-({[2-(1-methyl-ethyl)cyclopropyl]methoxy}carbonyl)phenyl] oxalate bis(3,4,6-trichloro-2-{[2-(1,2-dimethylcyclopropyl)ethoxy]carbonyl}phenyl) oxalate bis(3,4,6-trichloro-2-{[2-(2,2-dimethylcyclopropyl)ethoxy]carbonyl}phenyl) oxalate bis(3,4,6-trichloro-2-{[2-(2,3-dimethylcyclopropyl)ethoxy]carbonyl}phenyl) oxalate bis(3,4,6-trichloro-2-{[2-(1-ethylcyclopropyl)ethoxy]carbonyl}phenyl) oxalate bis(3,4,6-trichloro-2-{[2-(2-ethylcyclopropyl)ethoxy]carbonyl}phenyl) oxalate bis(3,4,6-trichloro-2-{[2-(1-methylcyclopropyl)propoxy]carbonyl}phenyl) oxalate bis(3,4,6-trichloro-2-{[2-(2-methylcyclopropyl)propoxy]carbonyl}phenyl) oxalate bis{3,4,6-trichloro-2-[(2-cyclopropyl-2-methylpropoxy)carbonyl]phenyl} oxalate bis(3,4,6-trichloro-2-{[3-(1-methylcyclopropyl)propoxy]carbonyl}phenyl) oxalate bis(3,4,6-trichloro-2-{[3-(2-methylcyclopropyl)propoxy]carbonyl}phenyl) oxalate bis{3,4,6-trichloro-2-[(3-cyclopropyl-2-methylpropoxy)carbonyl]phenyl} oxalate bis{3,4,6-trichloro-2-[(2-cyclopropylbutoxy)carbonyl]phenyl} oxalate bis{3,4,6-trichloro-2-[(3-cyclopropylbutoxy)carbonyl]phenyl} oxalate bis{3,4,6-trichloro-2-[(4-cyclopropylbutoxy)carbonyl]phenyl} oxalate bis{2-[(bicyclo[2.1.1]hexan-2-ylmethoxy)carbonyl]-3,4,6-trichlorophenyl} oxalate bis{3,4,6-trichloro-2-[(phenylmethoxy)carbonyl]phenyl} oxalate bis{3,4,6-trichloro-2-[(2-methylheptyloxy)carbonyl]phenyl} oxalate bis{3,4,6-trichloro-2-[(3-methylheptyloxy)carbonyl]phenyl} oxalate bis{3,4,6-trichloro-2-[(4-methylheptyloxy)carbonyl]phenyl} oxalate bis{3,4,6-trichloro-2-[(5-methylheptyloxy)carbonyl]phenyl} oxalate bis{3,4,6-trichloro-2-[(6-methylheptyloxy)carbonyl]phenyl} oxalate bis{3,4,6-trichloro-2-[(2,2-dimethylhexyloxy)carbonyl]phenyl} oxalate bis{3,4,6-trichloro-2-[(2,3-dimethylhexyloxy)carbonyl]phenyl} oxalate bis{3,4,6-trichloro-2-[(2,4-dimethylhexyloxy)carbonyl]phenyl} oxalate bis{3,4,6-trichloro-2-[(2,5-dimethylhexyloxy)carbonyl]phenyl} oxalate bis{3,4,6-trichloro-2-[(3,3-dimethylhexyloxy)carbonyl]phenyl} oxalate bis{3,4,6-trichloro-2-[(3,4-dimethylhexyloxy)carbonyl]phenyl} oxalate bis{3,4,6-trichloro-2-[(3,5-dimethylhexyloxy)carbonyl]phenyl} oxalate bis{3,4,6-trichloro-2-[(4,4-dimethylhexyloxy)carbonyl]phenyl} oxalate bis{3,4,6-trichloro-2-[(4,5-dimethylhexyloxy)carbonyl]phenyl} oxalate bis{3,4,6-trichloro-2-[(5,5-dimethylhexyloxy)carbonyl]phenyl} oxalate bis{3,4,6-trichloro-2-[(2-ethylhexyloxy)carbonyl]phenyl} oxalate bis{3,4,6-trichloro-2-[(3-ethylhexyloxy)carbonyl]phenyl} oxalate bis{3,4,6-trichloro-2-[(4-ethylhexyloxy)carbonyl]phenyl} oxalate bis{3,4,6-trichloro-2-[(2,2,3-trimethylpentyloxy)carbonyl]phenyl} oxalate bis{3,4,6-trichloro-2-[(2,3,3-trimethylpentyloxy)carbonyl]phenyl} oxalate bis{3,4,6-trichloro-2-[(2,2,4-trimethylpentyloxy)carbonyl]phenyl} oxalate bis{3,4,6-trichloro-2-[(2,3,4-trimethylpentyloxy)carbonyl]phenyl} oxalate bis{3,4,6-trichloro-2-[(2,4,4-trimethylpentyloxy)carbonyl]phenyl} oxalate bis{3,4,6-trichloro-2-[(3,3,4-trimethylpentyloxy)carbonyl]phenyl} oxalate bis{3,4,6-trichloro-2-[(3,4,4-trimethylpentyloxy)carbonyl]phenyl} oxalate bis{3,4,6-trichloro-2-[(2-ethyl-3-methylpentyloxy)carbonyl]phenyl} oxalate bis{3,4,6-trichloro-2-[(2-ethyl-4-methylpentyloxy)carbonyl]phenyl} oxalate bis{3,4,6-trichloro-2-[(3-ethyl-2-methylpentyloxy)carbonyl]phenyl} oxalate bis{3,4,6-trichloro-2-[(3-ethyl-4-methylpentyloxy)carbonyl]phenyl} oxalate bis{3,4,6-trichloro-2-[(2-ethyl-2-methylpentyloxy)carbonyl]phenyl} oxalate bis{3,4,6-trichloro-2-[(3-ethyl-3-methylpentyloxy)carbonyl]phenyl} oxalate bis{3,4,6-trichloro-2-[(2,2,3,3-tetramethylbutoxy)carbonyl]phenyl} oxalate bis{3,4,6-trichloro-2-[(2-ethyl-2,3-dimethylbutoxy)carbonyl]phenyl} oxalate bis{3,4,6-trichloro-2-[(2-ethyl-3,3-dimethylbutoxy)carbonyl]phenyl} oxalate bis{3,4,6-trichloro-2-[(cycloheptylmethoxy)carbonyl]phenyl} oxalate bis(3,4,6-trichloro-2-{[(1-methylcyclohexyl)methoxy]carbonyl}phenyl) oxalate bis(3,4,6-trichloro-2-{[(2-methylcyclohexyl)methoxy]carbonyl}phenyl) oxalate bis(3,4,6-trichloro-2-{[(3-methylcyclohexyl)methoxy]carbonyl}phenyl) oxalate bis(3,4,6-trichloro-2-{[(4-methylcyclohexyl)methoxy]carbonyl}phenyl) oxalate bis{3,4,6-trichloro-2-[(2-cyclohexylethoxy)carbonyl]phenyl} oxalate bis(3,4,6-trichloro-2-{[(1,2-dimethylcyclopentyl)methoxy]carbonyl}phenyl) oxalate bis(3,4,6-trichloro-2-{[(1,3-dimethylcyclopentyl)methoxy]carbonyl}phenyl) oxalate bis(3,4,6-trichloro-2-{[(2,2-dimethylcyclopentyl)methoxy]carbonyl}phenyl) oxalate bis(3,4,6-trichloro-2-{[(2,3-dimethylcyclopentyl)methoxy]carbonyl}phenyl) oxalate bis(3,4,6-trichloro-2-{[(2,4-dimethylcyclopentyl)methoxy]carbonyl}phenyl) oxalate bis(3,4,6-trichloro-2-{[(2,5-dimethylcyclopentyl)methoxy]carbonyl}phenyl) oxalate bis(3,4,6-trichloro-2-{[(3,3-dimethylcyclopentyl)methoxy]carbonyl}phenyl) oxalate bis(3,4,6-trichloro-2-{[(3,4-dimethylcyclopentyl)methoxy]carbonyl}phenyl) oxalate bis(3,4,6-trichloro-2-{[(1-ethylcyclopentyl)methoxy]carbonyl}phenyl) oxalate bis(3,4,6-trichloro-2-{[(2-ethylcyclopentyl)methoxy]carbonyl}phenyl) oxalate bis(3,4,6-trichloro-2-{[(3-ethylcyclopentyl)methoxy]carbonyl}phenyl) oxalate bis(3,4,6-trichloro-2-{[2-(1-methylcyclopentyl)ethoxy]carbonyl}phenyl) oxalate bis(3,4,6-trichloro-2-{[2-(2-methylcyclopentyl)ethoxy]carbonyl}phenyl) oxalate bis(3,4,6-trichloro-2-{[2-(3-methylcyclopentyl)ethoxy]carbonyl}phenyl) oxalate bis{3,4,6-trichloro-2-[(2-cyclopentylpropoxy)carbonyl]phenyl} oxalate bis{3,4,6-trichloro-2-[(3-cyclopentylpropoxy)carbonyl]phenyl} oxalate bis(3,4,6-trichloro-2-{[(1,2,2-trimethylcyclobutyl)methoxy]carbonyl}phenyl) oxalate bis(3,4,6-trichloro-2-{[(1,2,3-trimethylcyclobutyl)methoxy]carbonyl}phenyl) oxalate bis(3,4,6-trichloro-2-{[(1,2,4-trimethylcyclobutyl)methoxy]carbonyl}phenyl) oxalate bis(3,4,6-trichloro-2-{[(2,2,3-trimethylcyclobutyl)methoxy]carbonyl}phenyl) oxalate bis(3,4,6-trichloro-2-{[(2,3,3-trimethylcyclobutyl)methoxy]carbonyl}phenyl) oxalate bis(3,4,6-trichloro-2-{[(2,3,4-trimethylcyclobutyl)methoxy]carbonyl}phenyl) oxalate bis(3,4,6-trichloro-2-{[(2-ethyl-1-methylcyclobutyl)methoxy]carbonyl}phenyl) oxalate bis(3,4,6-trichloro-2-{[(3-ethyl-1-methylcyclobutyl)methoxy]carbonyl}phenyl) oxalate bis(3,4,6-trichloro-2-{[(1-ethyl-2-methylcyclobutyl)methoxy]carbonyl}phenyl) oxalate bis(3,4,6-trichloro-2-{[(1-ethyl-3-methylcyclobutyl)methoxy]carbonyl}phenyl) oxalate bis[3,4,6-trichloro-2-({[1-(1-methylethyl)-cyclobutyl]methoxy}carbonyl)phenyl] oxalate bis[3,4,6-trichloro-2-({[2-(1-methylethyl)-cyclobutyl]methoxy}carbonyl)phenyl] oxalate bis[3,4,6-trichloro-2-({[3-(1-methylethyl)-cyclobutyl]methoxy}carbonyl)phenyl] oxalate bis(3,4,6-trichloro-2-{[2-(1,2-dimethylcyclobutyl)ethoxy]carbonyl}phenyl) oxalate bis(3,4,6-trichloro-2-{[2-(1,3-dimethylcyclobutyl)ethoxy]carbonyl}phenyl) oxalate bis(3,4,6-trichloro-2-{[2-(2,2-dimethylcyclobutyl)ethoxy]carbonyl}phenyl) oxalate bis(3,4,6-trichloro-2-{[2-(2,3-dimethylcyclobutyl)ethoxy]carbonyl}phenyl) oxalate bis(3,4,6-trichloro-2-{[2-(2,4-dimethylcyclobutyl)ethoxy]carbonyl}phenyl) oxalate bis(3,4,6-trichloro-2-{[2-(3,3-dimethylcyclobutyl)ethoxy]carbonyl}phenyl) oxalate bis(3,4,6-trichloro-2-{[2-(1-methylcyclobutyl)propoxy]carbonyl}phenyl) oxalate bis(3,4,6-trichloro-2-{[2-(2-methylcyclobutyl)propoxy]carbonyl}phenyl) oxalate bis(3,4,6-trichloro-2-{[2-(3-methylcyclobutyl)propoxy]carbonyl}phenyl) oxalate bis{3,4,6-trichloro-2-[(2-cyclobutyl-2-methylpropoxy)carbonyl]phenyl} oxalate bis(3,4,6-trichloro-2-{[2-(1-ethylcyclobutyl)ethoxy]carbonyl}phenyl) oxalate bis(3,4,6-trichloro-2-{[2-(2-ethylcyclobutyl)ethoxy]carbonyl}phenyl) oxalate bis(3,4,6-trichloro-2-{[2-(3-ethylcyclobutyl)ethoxy]carbonyl}phenyl) oxalate bis(3,4,6-trichloro-2-{[3-(1-methylcyclobutyl)propoxy]carbonyl}phenyl) oxalate bis(3,4,6-trichloro-2-{[3-(2-methylcyclobutyl)propoxy]carbonyl}phenyl) oxalate bis(3,4,6-trichloro-2-{[3-(3-methylcyclobutyl)propoxy]carbonyl}phenyl) oxalate bis{3,4,6-trichloro-2-[(3-cyclobutyl-2-methylpropoxy)carbonyl]phenyl} oxalate bis{3,4,6-trichloro-2-[(2-cyclobutylbutoxy)carbonyl]phenyl} oxalate bis{3,4,6-trichloro-2-[(3-cyclobutylbutoxy)carbonyl]phenyl} oxalate bis{3,4,6-trichloro-2-[(4-cyclobutylbutoxy)carbonyl]phenyl} oxalate bis(3,4,6-trichloro-2-{[(1,2,2,3,3-pentamethylcyclopropyl)methoxy]carbonyl}phenyl) oxalate bis(3,4,6-trichloro-2-{[(3-ethyl-1,2,2-trimethylcyclopropyl)methoxy]carbonyl}phenyl) oxalate bis(3,4,6-trichloro-2-{[(2,3-diethyl-1-methylcyclopropyl)methoxy]carbonyl}phenyl) oxalate bis(3,4,6-trichloro-2-{[(2,2-diethyl-1-methylcyclopropyl)methoxy]carbonyl}phenyl) oxalate bis(3,4,6-trichloro-2-{[(1-ethyl-2-propylcyclopropyl)methoxy]carbonyl}phenyl) oxalate bis(3,4,6-trichloro-2-{[(2-ethyl-1-propylcyclopropyl)methoxy]carbonyl}phenyl) oxalate bis(3,4,6-trichloro-2-{[(2-ethyl-2-propylcyclopropyl)methoxy]carbonyl}phenyl) oxalate bis(3,4,6-trichloro-2-{[(2-ethyl-3-propylcyclopropyl)methoxy]carbonyl}phenyl) oxalate bis(3,4,6-trichloro-2-{[(1-ethyl-2,2,3-trimethylcyclopropyl)methoxy]carbonyl}phenyl) oxalate bis(3,4,6-trichloro-2-{[(1,2-diethyl-3-methylcyclopropyl)methoxy]carbonyl}phenyl) oxalate bis[3,4,6-trichloro-2-({[2,2-dimethyl-1-(1-methylethyl)-cyclopropyl]methoxy}carbonyl)phenyl] oxalate bis[3,4,6-trichloro-2-({[2,3-dimethyl-1-(1-methylethyl)-cyclopropyl]methoxy}carbonyl)phenyl] oxalate bis[3,4,6-trichloro-2-({[2-ethyl-1-(1-methylethyl)-cyclopropyl]methoxy}carbonyl)phenyl] oxalate bis[3,4,6-trichloro-2-({[1-ethyl-2-(1-methylethyl)-cyclopropyl]methoxy}carbonyl)phenyl] oxalate bis[3,4,6-trichloro-2-({[2,2-dimethyl-3-(1-methylethyl)-cyclopropyl]methoxy}carbonyl)phenyl] oxalate bis[3,4,6-trichloro-2-({[2-ethyl-3-(1-methylethyl)-cyclopropyl]methoxy}carbonyl)phenyl] oxalate bis(3,4,6-trichloro-2-{[2-(1,2,2-trimethylcyclopropyl)propoxy]carbonyl}phenyl) oxalate bis(3,4,6-trichloro-2-{[2-(1,2,3-trimethylcyclopropyl)propoxy]carbonyl}phenyl) oxalate bis(3,4,6-trichloro-2-{[2-(2,2,3-trimethylcyclopropyl)propoxy]carbonyl}phenyl) oxalate bis(3,4,6-trichloro-2-{[2-(2,2-dimethylcyclopropyl)propoxy]carbonyl}phenyl) oxalate bis(3,4,6-trichloro-2-{[2-(2,3-dimethylcyclopropyl)propoxy]carbonyl}phenyl) oxalate bis(3,4,6-trichloro-2-{[2-(2-ethyl-3-methylcyclopropyl)ethoxy]carbonyl}phenyl) oxalate bis(3,4,6-trichloro-2-{[2-(2-methylcyclopropyl)butoxy]carbonyl}phenyl) oxalate bis{3,4,6-trichloro-2-[(2-cyclopropyl-2-methylbutoxy)carbonyl]phenyl} oxalate bis(3,4,6-trichloro-2-{[2-(1-methylcyclopropyl)butoxy]carbonyl}phenyl) oxalate bis(3,4,6-trichloro-2-{[2-(2-ethyl-2-methylcyclopropyl)ethoxy]carbonyl}phenyl) oxalate bis(3,4,6-trichloro-2-{[2-methyl-2-(1-methylcyclopropyl)propoxy]carbonyl}phenyl) oxalate bis(3,4,6-trichloro-2-{[2-methyl-2-(2-methylcyclopropyl)propoxy]carbonyl}phenyl) oxalate bis{3,4,6-trichloro-2-[(2-cyclopropyl-3-methylbutoxy)carbonyl]phenyl} oxalate bis(3,4,6-trichloro-2-{[3-(1,2-dimethylcyclopropyl)propoxy]carbonyl}phenyl) oxalate bis(3,4,6-trichloro-2-{[3-(2,2-dimethylcyclopropyl)propoxy]carbonyl}phenyl) oxalate bis{3,4,6-trichloro-2-[(3-cyclopropyl-2-methylbutoxy)carbonyl]phenyl} oxalate bis(3,4,6-trichloro-2-{[2-methyl-3-(1-methylcyclopropyl)propoxy]carbonyl}phenyl) oxalate bis(3,4,6-trichloro-2-{[2-methyl-3-(2-methylcyclopropyl)propoxy]carbonyl}phenyl) oxalate bis{3,4,6-trichloro-2-[(3-cyclopropyl-2,2-dimethylpropoxy)carbonyl]phenyl} oxalate bis{3,4,6-trichloro-2-[(3-cyclopropyl-3-methylbutoxy)carbonyl]phenyl} oxalate bis{3,4,6-trichloro-2-[(2,2dicyclopropylethoxy)carbonyl)phenyl} oxalate bis(3,4,6-trichloro-2-{[4-(1-methylcyclopropyl)butoxy]carbonyl}phenyl) oxalate bis(3,4,6-trichloro-2-{[4-(2-methylcyclopropyl)butoxy]carbonyl}phenyl) oxalate bis{3,4,6-trichloro-2-[(4-cyclopropyl-2-methylbutoxy)carbonyl]phenyl} oxalate bis{3,4,6-trichloro-2-[(4-cyclopropyl-3-methylbutoxy)carbonyl]phenyl} oxalate bis(3,4,6-trichloro-2-{[2-(2-propylcyclopropyl)ethoxy]carbonyl}phenyl) oxalate bis[3,4,6-trichloro-2-({2-[2-(1-methylethyl)cyclopropyl]ethoxy}carbonyl)phenyl] oxalate bis{3,4,6-trichloro-2-[(2-cyclopropylpentyloxy)carbonyl]phenyl} oxalate bis{3,4,6-trichloro-2-[(3-cyclopropylpentyloxy)carbonyl]phenyl} oxalate bis{3,4,6-trichloro-2-[(4-cyclopropylpentyloxy)carbonyl]phenyl} oxalate bis{3,4,6-trichloro-2-[(5-cyclopropylpentyloxy)carbonyl]phenyl} oxalate bis(2-{[2-(bicyclo[1.1.1]pentan-2-yl)propoxy]carbonyl}-3,4,6-trichlorophenyl) oxalate bis(2-{[2-(bicyclo[2.1.1]hexan-2-yl)ethoxy]carbonyl}-3,4,6-trichlorophenyl) oxalate bis{2-[(bicyclo[2.2.1]heptan-2-ylmethoxy)carbonyl]3,4,6-trichlorophenyl} oxalate bis{3,4,6-trichloro-2-[(2-phenylethoxy)carbonyl]phenyl} oxalate bis(3,4,6-trichloro-2-{[(2-methylphenyl)methoxy]carbonyl}phenyl) oxalate bis(3,4,6-trichloro-2-{[(3-methylphenyl)methoxy]carbonyl}phenyl) oxalate bis(3,4,6-trichloro-2-{[(4-methylphenyl)methoxy]carbonyl}phenyl) oxalate bis{3,4,6-trichloro-2-[(2-methyloctyloxy)carbonyl]phenyl} oxalate bis{3,4,6-trichloro-2-[(3-methyloctyloxy)carbonyl]phenyl} oxalate bis{3,4,6-trichloro-2-[(4-methyloctyloxy)carbonyl]phenyl} oxalate bis{3,4,6-trichloro-2-[(5-methyloctyloxy)carbonyl]phenyl} oxalate bis{3,4,6-trichloro-2-[(6-methyloctyloxy)carbonyl]phenyl} oxalate bis{3,4,6-trichloro-2-[(7-methyloctyloxy)carbonyl]phenyl} oxalate bis{3,4,6-trichloro-2-[(2,2-dimethylheptyloxy)carbonyl]phenyl} oxalate bis{3,4,6-trichloro-2-[(2-ethylheptyloxy)carbonyl]phenyl} oxalate bis{3,4,6-trichloro-2-[(2,3-dimethylheptyloxy)carbonyl]phenyl} oxalate bis{3,4,6-trichloro-2-[(2,4-dimethylheptyloxy)carbonyl]phenyl} oxalate bis{3,4,6-trichloro-2-[(2,5-dimethylheptyloxy)carbonyl]phenyl} oxalate bis{3,4,6-trichloro-2-[(2,6-dimethylheptyloxy)carbonyl]phenyl} oxalate bis{3,4,6-trichloro-2-[(3,3-dimethylheptyloxy)carbonyl]phenyl} oxalate bis{3,4,6-trichloro-2-[(3-ethylheptyloxy)carbonyl]phenyl} oxalate bis{3,4,6-trichloro-2-[(3,4-dimethylheptyloxy)carbonyl]phenyl} oxalate bis{3,4,6-trichloro-2-[(3,5-dimethylheptyloxy)carbonyl]phenyl} oxalate bis{3,4,6-trichloro-2-[(3,6-dimethylheptyloxy)carbonyl]phenyl} oxalate bis{3,4,6-trichloro-2-[(4,4-dimethylheptyloxy)carbonyl]phenyl} oxalate bis{3,4,6-trichloro-2-[(4-ethylheptyloxy)carbonyl]phenyl} oxalate bis{3,4,6-trichloro-2-[(4,5-dimethylheptyloxy)carbonyl]phenyl} oxalate bis{3,4,6-trichloro-2-[(4,6-dimethylheptyloxy)carbonyl]phenyl} oxalate bis{3,4,6-trichloro-2-[(5,5-dimethylheptyloxy)carbonyl]phenyl} oxalate bis{3,4,6-trichloro-2-[(5-ethylheptyloxy)carbonyl]phenyl} oxalate bis{3,4,6-trichloro-2-[(5,6-dimethylheptyloxy)carbonyl]phenyl} oxalate bis{3,4,6-trichloro-2-[(6,6-dimethylheptyloxy)carbonyl]phenyl} oxalate bis{3,4,6-trichloro-2-[(2,2,3-trimethylhexyloxy)carbonyl]phenyl} oxalate bis{3,4,6-trichloro-2-[(2,2,4-trimethylhexyloxy)carbonyl]phenyl} oxalate bis{3,4,6-trichloro-2-[(2,2,5-trimethylhexyloxy)carbonyl]phenyl} oxalate bis{3,4,6-trichloro-2-[(2-ethyl-2-methylhexyloxy)carbonyl]phenyl} oxalate bis{3,4,6-trichloro-2-[(2-ethyl-2-methylhexyloxy)carbonyl]phenyl} oxalate bis{3,4,6-trichloro-2-[(2-ethyl-4-methylhexyloxy)carbonyl]phenyl} oxalate bis{3,4,6-trichloro-2-[(2-ethyl-5-methylhexyloxy)carbonyl]phenyl} oxalate bis{3,4,6-trichloro-2-[(2,3,3-trimethylhexyloxy)carbonyl]phenyl} oxalate bis{3,4,6-trichloro-2-[(3,3,4-trimethylhexyloxy)carbonyl]phenyl} oxalate bis{3,4,6-trichloro-2-[(3,3,5-trimethylhexyloxy)carbonyl]phenyl} oxalate bis{3,4,6-trichloro-2-[(3-ethyl-2-methylhexyloxy)carbonyl]phenyl} oxalate bis{3,4,6-trichloro-2-[(3-ethyl-3-methylhexyloxy)carbonyl]phenyl} oxalate bis{3,4,6-trichloro-2-[(3-ethyl-4-methylhexyloxy)carbonyl]phenyl} oxalate bis{3,4,6-trichloro-2-[(3-ethyl-5-methylhexyloxy)carbonyl]phenyl} oxalate bis{3,4,6-trichloro-2-[2,4,4-trimethylhexyloxy)carbonyl]phenyl} oxalate bis{3,4,6-trichloro-2-[(3,4,4-trimethylhexyloxy)carbonyl]phenyl} oxalate bis{3,4,6-trichloro-2-[(4,4,5-trimethylhexyloxy)carbonyl]phenyl} oxalate bis{3,4,6-trichloro-2-[(4-ethyl-2-methylhexyloxy)carbonyl]phenyl} oxalate bis{3,4,6-trichloro-2-[(4-ethyl-3-methylhexyloxy)carbonyl]phenyl} oxalate bis{3,4,6-trichloro-2-[(4-ethyl-4-methylhexyloxy)carbonyl]phenyl} oxalate bis{3,4,6-trichloro-2-[(4-ethyl-5-methylhexyloxy)carbonyl]phenyl} oxalate bis{3,4,6-trichloro-2-[(2,5,5-trimethylhexyloxy)carbonyl]phenyl} oxalate bis{3,4,6-trichloro-2-[(3,5,5-trimethylhexyloxy)carbonyl]phenyl} oxalate bis{3,4,6-trichloro-2-[(4,5,5-trimethylhexyloxy)carbonyl]phenyl} oxalate bis{3,4,6-trichloro-2-[(2-propylhexyloxy)carbonyl]phenyl} oxalate bis{3,4,6-trichloro-2-[(3-propylhexyloxy)carbonyl]phenyl} oxalate bis(3,4,6-trichloro-2-{[2-(1-methylethyl)hexyloxy]carbonyl}phenyl) oxalate bis(3,4,6-trichloro-2-{[3-(1-methylethyl)hexyloxy]carbonyl}phenyl) oxalate bis{3,4,6-trichloro-2-[(2,2,3,3-tetramethylpentyloxy)carbonyl]phenyl} oxalate bis{3,4,6-trichloro-2-[(2,2,3,4-tetramethylpentyloxy)carbonyl]phenyl} oxalate bis{3,4,6-trichloro-2-[(2,2,4,4-tetramethylpentyloxy)carbonyl]phenyl} oxalate bis{3,4,6-trichloro-2-[(2,3,3,4-tetramethylpentyloxy)carbonyl]phenyl} oxalate bis{3,4,6-trichloro-2-[(2-ethyl-2,3-dimethylpentyloxy)carbonyl]phenyl} oxalate bis{3,4,6-trichloro-2-[(2-ethyl-2,4-dimethylpentyloxy)carbonyl]phenyl} oxalate bis{3,4,6-trichloro-2-[(2-ethyl-3,3-dimethylpentyloxy)carbonyl]phenyl} oxalate bis{3,4,6-trichloro-2-[(2-ethyl-3,4-dimethylpentyloxy)carbonyl]phenyl} oxalate bis{3,4,6-trichloro-2-[(2-ethyl-4,4-dimethylpentyloxy)carbonyl]phenyl} oxalate bis{3,4,6-trichloro-2-[(2-propyl-2-methylpentyloxy)carbonyl]phenyl} oxalate bis{3,4,6-trichloro-2-[(2-propyl-3-methylpentyloxy)carbonyl]phenyl} oxalate bis{3,4,6-trichloro-2-[(2-propyl-4-methylpentyloxy)carbonyl]phenyl} oxalate bis(3,4,6-trichloro-2-{[2-methyl-2-(1-methylethyl)pentyloxy]carbonyl}phenyl) oxalate bis(3,4,6-trichloro-2-{[3-methyl-2-(1-methylethyl)pentyloxy]carbonyl}phenyl) oxalate bis(3,4,6-trichloro-2-{[4-methyl-2-(1-methylethyl)pentyloxy]carbonyl}phenyl) oxalate bis{3,4,6-trichloro-2-[(3-ethyl-2,4-dimethylpentyloxy)carbonyl]phenyl} oxalate bis{3,4,6-trichloro-2-[(3-ethyl-3,4-dimethylpentyloxy)carbonyl]phenyl} oxalate bis(3,4,6-trichloro-2-{[4-methyl-3-(1-methylethyl)pentyloxy]carbonyl}phenyl) oxalate bis(3,4,6-trichloro-2-{[2-(1,1-dimethylethyl)pentyloxy]carbonyl}phenyl) oxalate bis(3,4,6-trichloro-2-{[2-(1,1-dimethylethyl)pentyloxy]carbonyl}phenyl) oxalate bis{3,4,6-trichloro-2-[(2-ethyl-2,3,3-trimethylbutoxy)carbonyl]phenyl} oxalate bis(3,4,6-trichloro-2-{[3,3-dimethyl-2-(1-methylethyl)butoxy]carbonyl}phenyl) oxalate bis(3,4,6-trichloro-2-{[2,3-dimethyl-2-(1-methylethyl)butoxy]carbonyl}phenyl) oxalate bis{3,4,6-trichloro-2-[(cyclooctylmethoxy)carbonyl]phenyl} oxalate bis(3,4,6-trichloro-2-{[(1-methylcyclooctyl)methoxy]carbonyl}phenyl) oxalate bis(3,4,6-trichloro-2-{[(2-methylcyclooctyl)methoxy]carbonyl}phenyl) oxalate bis(3,4,6-trichloro-2-{[(3-methylcyclooctyl)methoxy]carbonyl}phenyl) oxalate bis(3,4,6-trichloro-2-{[(4-methylcyclooctyl)methoxy]carbonyl}phenyl) oxalate bis{3,4,6-trichloro-2-[(2-cycloheptylethoxy)carbonyl]phenyl} oxalate bis(3,4,6-trichloro-2-{[(1,2-dimethylcyclohexyl)methoxy]carbonyl}phenyl) oxalate bis(3,4,6-trichloro-2-{[(1,3-dimethylcyclohexyl)methoxy]carbonyl}phenyl) oxalate bis(3,4,6-trichloro-2-{[(1,4-dimethylcyclohexyl)methoxy]carbonyl}phenyl) oxalate bis(3,4,6-trichloro-2-{[(2,2-dimethylcyclohexyl)methoxy]carbonyl}phenyl) oxalate bis(3,4,6-trichloro-2-{[(2,3-dimethylcyclohexyl)methoxy]carbonyl}phenyl) oxalate bis(3,4,6-trichloro-2-{[(2,4-dimethylcyclohexyl)methoxy]carbonyl}phenyl) oxalate bis(3,4,6-trichloro-2-{[(2,5-dimethylcyclohexyl)methoxy]carbonyl}phenyl) oxalate bis(3,4,6-trichloro-2-{[(2,6-dimethylcyclohexyl)methoxy]carbonyl}phenyl) oxalate bis(3,4,6-trichloro-2-{[(3,3-dimethylcyclohexyl)methoxy]carbonyl}phenyl) oxalate bis(3,4,6-trichloro-2-{[(3,4-dimethylcyclohexyl)methoxy]carbonyl}phenyl) oxalate bis(3,4,6-trichloro-2-{[(3,5-dimethylcyclohexyl)methoxy]carbonyl}phenyl) oxalate bis(3,4,6-trichloro-2-{[(4,4-dimethylcyclohexyl)methoxy]carbonyl}phenyl) oxalate bis(3,4,6-trichloro-2-{[1-ethylcyclohexyl)methoxy]carbonyl}phenyl) oxalate bis(3,4,6-trichloro-2-{[2-ethylcyclohexyl)methoxy]carbonyl}phenyl) oxalate bis(3,4,6-trichloro-2-{[3-ethylcyclohexyl)methoxy]carbonyl}phenyl) oxalate bis(3,4,6-trichloro-2-{[4-ethylcyclohexyl)methoxy]carbonyl}phenyl) oxalate bis(3,4,6-trichloro-2-{[2-(1-methylcyclohexyl)ethoxy]carbonyl}phenyl) oxalate bis(3,4,6-trichloro-2-{[2-(2-methylcyclohexyl)ethoxy]carbonyl}phenyl) oxalate bis(3,4,6-trichloro-2-{[2-(3-methylcyclohexyl)ethoxy]carbonyl}phenyl) oxalate bis(3,4,6-trichloro-2-{[2-(4-methylcyclohexyl)ethoxy]carbonyl}phenyl) oxalate bis{3,4,6-trichloro-2-[(2-cyclohexylpropoxy)carbonyl]phenyl} oxalate bis{3,4,6-trichloro-2-[(3-cyclohexylpropoxy)carbonyl]phenyl} oxalate bis(3,4,6-trichloro-2-{[(1,2,2-trimethylcyclopentyl)methoxy]carbonyl}phenyl) oxalate bis(3,4,6-trichloro-2-{[(2,2,3-trimethylcyclopentyl)methoxy]carbonyl}phenyl) oxalate bis(3,4,6-trichloro-2-{[(2,2,4-trimethylcyclopentyl)methoxy]carbonyl}phenyl) oxalate bis(3,4,6-trichloro-2-{[(2,2,5-trimethylcyclopentyl)methoxy]carbonyl}phenyl) oxalate bis(3,4,6-trichloro-2-{[(1,3,3-trimethylcyclopentyl)methoxy]carbonyl}phenyl) oxalate bis(3,4,6-trichloro-2-{[(2,3,3-trimethylcyclopentyl)methoxy]carbonyl}phenyl) oxalate bis(3,4,6-trichloro-2-{[(3,3,4-trimethylcyclopentyl)methoxy]carbonyl}phenyl) oxalate bis(3,4,6-trichloro-2-{[(2,4,4-trimethylcyclopentyl)methoxy]carbonyl}phenyl) oxalate bis(3,4,6-trichloro-2-{[(1,2,3-trimethylcyclopentyl)methoxy]carbonyl}phenyl) oxalate bis(3,4,6-trichloro-2-{[(1,2,4-trimethylcyclopentyl)methoxy]carbonyl}phenyl) oxalate bis(3,4,6-trichloro-2-{[(1,2,5-trimethylcyclopentyl)methoxy]carbonyl}phenyl) oxalate bis(3,4,6-trichloro-2-{[(1,3,4-trimethylcyclopentyl)methoxy]carbonyl}phenyl) oxalate bis(3,4,6-trichloro-2-{[(2,3,4-trimethylcyclopentyl)methoxy]carbonyl}phenyl) oxalate bis(3,4,6-trichloro-2-{[(2,3,5-trimethylcyclopentyl)methoxy]carbonyl}phenyl) oxalate bis(3,4,6-trichloro-2-{[(2-ethyl-1-methylcyclopentyl)methoxy]carbonyl}phenyl) oxalate bis(3,4,6-trichloro-2-{[(3-ethyl-1-methylcyclopentyl)methoxy]carbonyl}phenyl) oxalate bis(3,4,6-trichloro-2-{[(1-ethyl-2-methylcyclopentyl)methoxy]carbonyl}phenyl) oxalate bis(3,4,6-trichloro-2-{[(1-ethyl-3-methylcyclopentyl)methoxy]carbonyl}phenyl) oxalate bis(3,4,6-trichloro-2-{[(3-ethyl-2-methylcyclopentyl)methoxy]carbonyl}phenyl) oxalate bis(3,4,6-trichloro-2-{[(4-ethyl-2-methylcyclopentyl)methoxy]carbonyl}phenyl) oxalate bis(3,4,6-trichloro-2-{[(2-ethyl-5-methylcyclopentyl)methoxy]carbonyl}phenyl) oxalate bis(3,4,6-trichloro-2-{[(2-ethyl-3-methylcyclopentyl)methoxy]carbonyl}phenyl) oxalate bis(3,4,6-trichloro-2-{[(2-ethyl-4-methylcyclopentyl)methoxy]carbonyl}phenyl) oxalate bis(3,4,6-trichloro-2-{[(3-ethyl-4-methylcyclopentyl)methoxy]carbonyl}phenyl) oxalate bis(3,4,6-trichloro-2-{[(2-ethyl-2-methylcyclopentyl)methoxy]carbonyl}phenyl) oxalate bis(3,4,6-trichloro-2-{[(3-ethyl-3-methylcyclopentyl)methoxy]carbonyl}phenyl) oxalate bis(3,4,6-trichloro-2-{[(1-propylcyclopentyl)methoxy]carbonyl}phenyl) oxalate bis(3,4,6-trichloro-2-{[(2-propylcyclopentyl)methoxy]carbonyl}phenyl) oxalate bis(3,4,6-trichloro-2-{[(3-propylcyclopentyl)methoxy]carbonyl}phenyl) oxalate bis[3,4,6-trichloro-2-({[1-(1-methylethyl)-cyclopentyl]methoxy}carbonyl)phenyl] oxalate bis[3,4,6-trichloro-2-({[2-(1-methylethyl)-cyclopentyl]methoxy}carbonyl)phenyl] oxalate bis[3,4,6-trichloro-2-({[3-(1-methylethyl)-cyclopentyl]methoxy}carbonyl)phenyl] oxalate bis(3,4,6-trichloro-2-{[2-(1,2-dimethylcyclopentyl)ethoxy]carbonyl}phenyl) oxalate bis(3,4,6-trichloro-2-{[2-(1,3-dimethylcyclopentyl)ethoxy]carbonyl}phenyl) oxalate bis(3,4,6-trichloro-2-{[2-(2,3-dimethylcyclopentyl)ethoxy]carbonyl}phenyl) oxalate bis(3,4,6-trichloro-2-{[2-(2,4-dimethylcyclopentyl)ethoxy]carbonyl}phenyl) oxalate bis(3,4,6-trichloro-2-{[2-(2,5-dimethylcyclopentyl)ethoxy]carbonyl}phenyl) oxalate bis(3,4,6-trichloro-2-{[2-(3,4-dimethylcyclopentyl)ethoxy]carbonyl}phenyl) oxalate bis(3,4,6-trichloro-2-{[2-(2,2-dimethylcyclopentyl)ethoxy]carbonyl}phenyl) oxalate bis(3,4,6-trichloro-2-{[2-(3,3-dimethylcyclopentyl)ethoxy]carbonyl}phenyl) oxalate bis(3,4,6-trichloro-2-{[2-(1-ethylcyclopentyl)ethoxy]carbonyl}phenyl) oxalate bis(3,4,6-trichloro-2-{[2-(2-ethylcyclopentyl)ethoxy]carbonyl}phenyl) oxalate bis(3,4,6-trichloro-2-{[2-(3-ethylcyclopentyl)ethoxy]carbonyl}phenyl) oxalate bis{3,4,6-trichloro-2-[(2-cyclopentyl-2-methylpropoxy)carbonyl]phenyl} oxalate bis(3,4,6-trichloro-2-{[2-(1-methylcyclopentyl)propoxy]carbonyl}phenyl) oxalate bis(3,4,6-trichloro-2-{[2-(2-methylcyclopentyl)propoxy]carbonyl}phenyl) oxalate bis(3,4,6-trichloro-2-{[2-(3-methylcyclopentyl)propoxy]carbonyl}phenyl) oxalate bis{3,4,6-trichloro-2-[(3-cyclopentyl-2-methylpropoxy)carbonyl]phenyl} oxalate bis(3,4,6-trichloro-2-{[3-(1-methylcyclopentyl)propoxy]carbonyl}phenyl) oxalate bis(3,4,6-trichloro-2-{[3-(2-methylcyclopentyl)propoxy]carbonyl}phenyl) oxalate bis(3,4,6-trichloro-2-{[3-(3-methylcyclopentyl)propoxy]carbonyl}phenyl) oxalate bis{3,4,6-trichloro-2-[(2-cyclopentylbutoxy)carbonyl]phenyl} oxalate bis{3,4,6-trichloro-2-[(3-cyclopentylbutoxy)carbonyl]phenyl} oxalate bis{3,4,6-trichloro-2-[(4-cyclopentylbutoxy)carbonyl]phenyl} oxalate bis(3,4,6-trichloro-2-{[(1,2,2,3-tetramethylcyclobutyl)methoxy]carbonyl}phenyl) oxalate bis(3,4,6-trichloro-2-{[(1,2,2,4-tetramethylcyclobutyl)methoxy]carbonyl}phenyl) oxalate bis(3,4,6-trichloro-2-{[(1,2,3,3-tetramethylcyclobutyl)methoxy]carbonyl}phenyl) oxalate bis(3,4,6-trichloro-2-{[(1,2,3,4-tetramethylcyclobutyl)methoxy]carbonyl}phenyl) oxalate bis(3,4,6-trichloro-2-{[(2,2,3,4-tetramethylcyclobutyl)methoxy]carbonyl}phenyl) oxalate bis(3,4,6-trichloro-2-{[(2,3,3,4-tetramethylcyclobutyl)methoxy]carbonyl}phenyl) oxalate bis(3,4,6-trichloro-2-{[(2,2,3,3-tetramethylcyclobutyl)methoxy]carbonyl}phenyl) oxalate bis(3,4,6-trichloro-2-{[(2,2,4,4-tetramethylcyclobutyl)methoxy]carbonyl}phenyl) oxalate bis(3,4,6-trichloro-2-{[(1-ethyl-2,2-dimethylcyclobutyl)methoxy]carbonyl}phenyl) oxalate bis(3,4,6-trichloro-2-{[(1-ethyl-2,3-dimethylcyclobutyl)methoxy]carbonyl}phenyl) oxalate bis(3,4,6-trichloro-2-{[(1-ethyl-2,4-dimethylcyclobutyl)methoxy]carbonyl}phenyl) oxalate bis(3,4,6-trichloro-2-{[(1-ethyl-3,3-dimethylcyclobutyl)methoxy]carbonyl}phenyl) oxalate bis(3,4,6-trichloro-2-{[(2-ethyl-1,2-dimethylcyclobutyl)methoxy]carbonyl}phenyl) oxalate bis(3,4,6-trichloro-2-{[(2-ethyl-1,3-dimethylcyclobutyl)methoxy]carbonyl}phenyl) oxalate bis(3,4,6-trichloro-2-{[(2-ethyl-1,4-dimethylcyclobutyl)methoxy]carbonyl}phenyl) oxalate bis(3,4,6-trichloro-2-{[(2-ethyl-3,3-dimethylcyclobutyl)methoxy]carbonyl}phenyl) oxalate bis(3,4,6-trichloro-2-{[(2-ethyl-3,4-dimethylcyclobutyl)methoxy]carbonyl}phenyl) oxalate bis(3,4,6-trichloro-2-{[(2-ethyl-4,4-dimethylcyclobutyl)methoxy]carbonyl}phenyl) oxalate bis(3,4,6-trichloro-2-{[(1,2-diethylcyclobutyl)methoxy]carbonyl}phenyl) oxalate bis(3,4,6-trichloro-2-{[(1,3-diethylcyclobutyl)methoxy]carbonyl}phenyl) oxalate bis(3,4,6-trichloro-2-{[(2,2-diethylcyclobutyl)methoxy]carbonyl}phenyl) oxalate bis(3,4,6-trichloro-2-{[(3,3-diethylcyclobutyl)methoxy]carbonyl}phenyl) oxalate bis(3,4,6-trichloro-2-{[(1-methyl-2-propylcyclobutyl)methoxy]carbonyl}phenyl) oxalate bis(3,4,6-trichloro-2-{[(2-methyl-2-propylcyclobutyl)methoxy]carbonyl}phenyl) oxalate bis(3,4,6-trichloro-2-{[(2-methyl-1-propylcyclobutyl)methoxy]carbonyl}phenyl) oxalate bis(3,4,6-trichloro-2-{[(3-methyl-1-propylcyclobutyl)methoxy]carbonyl}phenyl) oxalate bis(3,4,6-trichloro-2-{[(3-methyl-2-propylcyclobutyl)methoxy]carbonyl}phenyl) oxalate bis(3,4,6-trichloro-2-{[(2-methyl-4-propylcyclobutyl)methoxy]carbonyl}phenyl) oxalate bis(3,4,6-trichloro-2-{[(1-methyl-3-propylcyclobutyl)methoxy]carbonyl}phenyl) oxalate bis(3,4,6-trichloro-2-{[(2-methyl-3-propylcyclobutyl)methoxy]carbonyl}phenyl) oxalate bis(3,4,6-trichloro-2-{[(3-methyl-3-propylcyclobutyl)methoxy]carbonyl}phenyl) oxalate bis[3,4,6-trichloro-2-({[2-methyl-1-(1-methylethyl)cyclobutyl]methoxy}carbonyl)phenyl] oxalate bis[3,4,6-trichloro-2-({[3-methyl-1-(1-methylethyl)cyclobutyl]methoxy}carbonyl)phenyl] oxalate bis[3,4,6-trichloro-2-({[1-methyl-2-(1-methylethyl)cyclobutyl]methoxy}carbonyl)phenyl] oxalate bis[3,4,6-trichloro-2-({[2-methyl-2-(1-methylethyl)cyclobutyl]methoxy}carbonyl)phenyl] oxalate bis[3,4,6-trichloro-2-({[3-methyl-2-(1-methylethyl)cyclobutyl]methoxy}carbonyl)phenyl] oxalate bis[3,4,6-trichloro-2-({[2-methyl-4-(1-methylethyl)cyclobutyl]methoxy}carbonyl)phenyl] oxalate bis[3,4,6-trichloro-2-({[3-methyl-3-(1-methylethyl)cyclobutyl]methoxy}carbonyl)phenyl] oxalate bis(3,4,6-trichloro-2-{[(1-butylcyclobutyl)methoxy]carbonyl}phenyl) oxalate bis(3,4,6-trichloro-2-{[(2-butylcyclobutyl)methoxy]carbonyl}phenyl) oxalate bis(3,4,6-trichloro-2-{[(3-butylcyclobutyl)methoxy]carbonyl}phenyl) oxalate bis[3,4,6-trichloro-2-({[1-(1-methylpropyl)cyclobutyl]methoxy}carbonyl)phenyl] oxalate bis[3,4,6-trichloro-2-({[1-(2-methylpropyl)cyclobutyl]methoxy}carbonyl)phenyl] oxalate bis[3,4,6-trichloro-2-({[2-(1-methylpropyl)cyclobutyl]methoxy}carbonyl)phenyl] oxalate bis[3,4,6-trichloro-2-({[2-(2-methylpropyl)cyclobutyl]methoxy}carbonyl)phenyl] oxalate bis[3,4,6-trichloro-2-({[3-(1-methylpropyl)cyclobutyl]methoxy}carbonyl)phenyl] oxalate bis[3,4,6-trichloro-2-({[3-(2-methylpropyl)cyclobutyl]methoxy}carbonyl)phenyl] oxalate bis(3,4,6-trichloro-2-{[2-(1,2,2-trimethylcyclobutyl)ethoxy]carbonyl}phenyl) oxalate bis(3,4,6-trichloro-2-{[2-(1,2,3-trimethylcyclobutyl)ethoxy]carbonyl}phenyl) oxalate bis(3,4,6-trichloro-2-{[2-(1,2,4-trimethylcyclobutyl)ethoxy]carbonyl}phenyl) oxalate bis(3,4,6-trichloro-2-{[2-(1,3,3-trimethylcyclobutyl)ethoxy]carbonyl}phenyl) oxalate bis(3,4,6-trichloro-2-{[2-(2,2,3-trimethylcyclobutyl)ethoxy]carbonyl}phenyl) oxalate bis(3,4,6-trichloro-2-{[2-(2,2,4-trimethylcyclobutyl)ethoxy]carbonyl}phenyl) oxalate bis(3,4,6-trichloro-2-{[2-(2,3,4-trimethylcyclobutyl)ethoxy]carbonyl}phenyl) oxalate bis(3,4,6-trichloro-2-{[2-(2-ethyl-1-methylcyclobutyl)ethoxy]carbonyl}phenyl) oxalate bis(3,4,6-trichloro-2-{[2-(3-ethyl-1-methylcyclobutyl)ethoxy]carbonyl}phenyl) oxalate bis(3,4,6-trichloro-2-{[2-(1-ethyl-2-methylcyclobutyl)ethoxy]carbonyl}phenyl) oxalate bis(3,4,6-trichloro-2-{[2-(1-ethyl-3-methylcyclobutyl)ethoxy]carbonyl}phenyl) oxalate bis(3,4,6-trichloro-2-{[2-(2-ethyl-2-methylcyclobutyl)ethoxy]carbonyl}phenyl) oxalate bis(3,4,6-trichloro-2-{[2-(2-ethyl-3-methylcyclobutyl)ethoxy]carbonyl}phenyl) oxalate bis(3,4,6-trichloro-2-{[2-(2-ethyl-4-methylcyclobutyl)ethoxy]carbonyl}phenyl) oxalate bis(3,4,6-trichloro-2-{[2-(3-ethyl-2-methylcyclobutyl)ethoxy]carbonyl}phenyl) oxalate bis(3,4,6-trichloro-2-{[2-(3-ethyl-3-methylcyclobutyl)ethoxy]carbonyl}phenyl) oxalate bis(3,4,6-trichloro-2-{[2-(1-propylcyclobutyl)ethoxy]carbonyl}phenyl) oxalate bis(3,4,6-trichloro-2-{[2-(2-propylcyclobutyl)ethoxy]carbonyl}phenyl) oxalate bis(3,4,6-trichloro-2-{[2-(3-propylcyclobutyl)ethoxy]carbonyl}phenyl) oxalate bis[3,4,6-trichloro-2-({2-[1-(1-methylethyl)cyclobutyl]ethoxy}carbonyl)phenyl] oxalate bis[3,4,6-trichloro-2-({2-[2-(1-methylethyl)cyclobutyl]ethoxy}carbonyl)phenyl] oxalate bis[3,4,6-trichloro-2-({2-[3-(1-methylethyl)cyclobutyl]ethoxy}carbonyl)phenyl] oxalate bis(3,4,6-trichloro-2-{[2-methyl-2-(1-methylcyclobutylpropoxy]carbonyl}phenyl) oxalate bis(3,4,6-trichloro-2-{[2-methyl-2-(2-methylcyclobutylpropoxy]carbonyl}phenyl) oxalate bis(3,4,6-trichloro-2-{[2-methyl-2-(3-methylcyclobutylpropoxy]carbonyl}phenyl) oxalate bis(3,4,6-trichloro-2-{[2-(1,2-dimethylcyclobutylpropoxy]carbonyl}phenyl) oxalate bis(3,4,6-trichloro-2-{[2-(1,3-dimethylcyclobutylpropoxy]carbonyl}phenyl) oxalate bis(3,4,6-trichloro-2-{[2-(1,2,2-triimethylcyclobutylethoxy]carbonyl}phenyl) oxalate bis(3,4,6-trichloro-2-{[2-(1,2,3-triimethylcyclobutylethoxy]carbonyl}phenyl) oxalate bis(3,4,6-trichloro-2-{[2-(1,2,4-triimethylcyclobutylethoxy]carbonyl}phenyl) oxalate bis(3,4,6-trichloro-2-{[2-(1,3,3-triimethylcyclobutylethoxy]carbonyl}phenyl) oxalate bis(3,4,6-trichloro-2-{[2-(2,2,3-triimethylcyclobutylethoxy]carbonyl}phenyl) oxalate bis(3,4,6-trichloro-2-{[2-(2,3,3-triimethylcyclobutylethoxy]carbonyl}phenyl) oxalate bis(3,4,6-trichloro-2-{[2-(2,2,4-triimethylcyclobutylethoxy]carbonyl}phenyl) oxalate bis(3,4,6-trichloro-2-{[2-(2,3,4-triimethylcyclobutylethoxy]carbonyl}phenyl) oxalate bis(3,4,6-trichloro-2-{[3-(1,2-dimethylcyclobutylpropoxy]carbonyl}phenyl) oxalate bis(3,4,6-trichloro-2-{[3-(1,3-dimethylcyclobutylpropoxy]carbonyl}phenyl) oxalate bis(3,4,6-trichloro-2-{[3-(2,2-dimethylcyclobutylpropoxy]carbonyl}phenyl) oxalate bis(3,4,6-trichloro-2-{[3-(2,3-dimethylcyclobutylpropoxy]carbonyl}phenyl) oxalate bis(3,4,6-trichloro-2-{[3-(2,4-dimethylcyclobutylpropoxy]carbonyl}phenyl) oxalate bis(3,4,6-trichloro-2-{[3-(3,3-dimethylcyclobutylpropoxy]carbonyl}phenyl) oxalate bis(3,4,6-trichloro-2-{[3-(1-ethylcyclobutylpropoxy]carbonyl}phenyl) oxalate bis(3,4,6-trichloro-2-{[3-(2-ethylcyclobutylpropoxy]carbonyl}phenyl) oxalate bis(3,4,6-trichloro-2-{[3-(3-ethylcyclobutylpropoxy]carbonyl}phenyl) oxalate bis(3,4,6-trichloro-2-{[2-(1-methylcyclobutylbutoxy]carbonyl}phenyl) oxalate bis(3,4,6-trichloro-2-{[2-(2-methylcyclobutylbutoxy]carbonyl}phenyl) oxalate bis(3,4,6-trichloro-2-{[2-(3-methylcyclobutylbutoxy]carbonyl}phenyl) oxalate bis{3,4,6-trichloro-2-[(3-cyclobutyl-2-methylbutoxy)carbonyl]phenyl} oxalate bis{3,4,6-trichloro-2-[(3-cyclobutyl-3-methylbutoxy)carbonyl]phenyl} oxalate bis(3,4,6-trichloro-2-{[3-(1-methylcyclobutylbutoxy]carbonyl}phenyl) oxalate bis(3,4,6-trichloro-2-{[3-(2-methylcyclobutylbutoxy]carbonyl}phenyl) oxalate bis(3,4,6-trichloro-2-{[3-(2-methylcyclobutylbutoxy]carbonyl}phenyl) oxalate bis{3,4,6-trichloro-2-[(4-cyclobutyl-2-methylbutoxy)carbonyl]phenyl} oxalate bis{3,4,6-trichloro-2-[(4-cyclobutyl-3-methylbutoxy)carbonyl]phenyl} oxalate bis(3,4,6-trichloro-2-{[4-(1-methylcyclobutylbutoxy]carbonyl}phenyl) oxalate bis(3,4,6-trichloro-2-{[4-(2-methylcyclobutylbutoxy]carbonyl}phenyl) oxalate bis(3,4,6-trichloro-2-{[4-(3-methylcyclobutylbutoxy]carbonyl}phenyl) oxalate bis{3,4,6-trichloro-2-[(2-cyclobutylpentyloxy)carbonyl]phenyl} oxalate bis{3,4,6-trichloro-2-[(3-cyclobutylpentyloxy)carbonyl]phenyl} oxalate bis{3,4,6-trichloro-2-[(4-cyclobutylpentyloxy)carbonyl]phenyl} oxalate bis{3,4,6-trichloro-2-[(5-cyclobutylpentyloxy)carbonyl]phenyl} oxalate bis(3,4,6-trichloro-2-{[(1,2,2,3,3-pentamethylcyclopropyl)methoxy]carbonyl}phenyl) oxalate bis(3,4,6-trichloro-2-{[(3-ethyl-1,2,2-trimethylcyclopropyl)methoxy]carbonyl}phenyl) oxalate bis(3,4,6-trichloro-2-{[(2-ethyl-1,2,3-trimethylcyclopropyl)methoxy]carbonyl}phenyl) oxalate bis(3,4,6-trichloro-2-{[(1-ethyl-2,2,3-trimethylcyclopropyl)methoxy]carbonyl}phenyl) oxalate bis(3,4,6-trichloro-2-{[(2,2-dimethyl-3-propylcyclopropyl)methoxy]carbonyl}phenyl) oxalate bis[3,4,6-trichloro-2-({[2,2-dimethyl-3-(1-methylethyl)cyclopropyl]methoxy}carbonyl)phenyl] oxalate bis(3,4,6-trichloro-2-{[(2,3-dimethyl-1-propylcyclopropyl)methoxy]carbonyl}phenyl) oxalate bis[3,4,6-trichloro-2-({[2,3-dimethyl-1-(1-methylethyl)cyclopropyl]methoxy}carbonyl)phenyl] oxalate bis(3,4,6-trichloro-2-{[(2-ethyl-1-propylcyclopropyl)methoxy]carbonyl}phenyl) oxalate bis(3,4,6-trichloro-2-{[(1-ethyl-2-propylcyclopropyl)methoxy]carbonyl}phenyl) oxalate bis[3,4,6-trichloro-2-({[1-ethyl-2-(1-methylethyl)cyclopropyl]methoxy}carbonyl)phenyl] oxalate bis(3,4,6-trichloro-2-{[(1,2-diethyl-3-methylcyclopropyl)methoxy]carbonyl}phenyl) oxalate bis(3,4,6-trichloro-2-{[(1-butyl-2-methylcyclopropyl)methoxy]carbonyl}phenyl) oxalate bis[3,4,6-trichloro-2-({[2-methyl-1-(2-methylpropyl)cyclopropyl]methoxy}carbonyl)phenyl] oxalate bis[3,4,6-trichloro-2-({[2-methyl-1-(1-methylpropyl)cyclopropyl]methoxy}carbonyl)phenyl] oxalate bis(3,4,6-trichloro-2-{[(2-butyl-1-methylcyclopropyl)methoxy]carbonyl}phenyl) oxalate bis[3,4,6-trichloro-2-({[1-methyl-2-(1-methylpropyl)cyclopropyl]methoxy}carbonyl)phenyl] oxalate bis[3,4,6-trichloro-2-({[1-methyl-2-(2-methylpropyl)cyclopropyl]methoxy}carbonyl)phenyl] oxalate bis(3,4,6-trichloro-2-{[(2-butyl-3-methylcyclopropyl)methoxy]carbonyl}phenyl) oxalate bis[3,4,6-trichloro-2-({[2-methyl-3-(1-methylpropyl)cyclopropyl]methoxy}carbonyl)phenyl] oxalate bis[3,4,6-trichloro-2-({[2-methyl-3-(2-methylpropyl)cyclopropyl]methoxy}carbonyl)phenyl] oxalate bis[3,4,6-trichloro-2-({[1-(1,1-dimethylpropyl)cyclopropyl]methoxy}carbonyl)phenyl] oxalate bis[3,4,6-trichloro-2-({[1-(2,2-dimethylpropyl)cyclopropyl]methoxy}carbonyl)phenyl] oxalate bis[3,4,6-trichloro-2-({[1-(1,2-dimethylpropyl)cyclopropyl]methoxy}carbonyl)phenyl] oxalate bis[3,4,6-trichloro-2-({[1-(1-methylbutyl)cyclopropyl]methoxy}carbonyl)phenyl] oxalate bis[3,4,6-trichloro-2-({[1-(2-methylbutyl)cyclopropyl]methoxy}carbonyl)phenyl] oxalate bis[3,4,6-trichloro-2-({[1-(3-methylbutyl)cyclopropyl]methoxy}carbonyl)phenyl] oxalate bis(3,4,6-trichloro-2-{[(1-pentylcyclopropyl)methoxy]carbonyl}phenyl) oxalate bis[3,4,6-trichloro-2-({[2-(1,1-dimethylpropyl)cyclopropyl]methoxy}carbonyl)phenyl] oxalate bis[3,4,6-trichloro-2-({[2-(2,2-dimethylpropyl)cyclopropyl]methoxy}carbonyl)phenyl] oxalate bis[3,4,6-trichloro-2-({[2-(1,2-dimethylpropyl)cyclopropyl]methoxy}carbonyl)phenyl] oxalate bis[3,4,6-trichloro-2-({[2-(1-methylbutyl)cyclopropyl]methoxy}carbonyl)phenyl] oxalate bis[3,4,6-trichloro-2-({[2-(2-methylbutyl)cyclopropyl]methoxy}carbonyl)phenyl] oxalate bis[3,4,6-trichloro-2-({[2-(3-methylbutyl)cyclopropyl]methoxy}carbonyl)phenyl] oxalate bis(3,4,6-trichloro-2-{[(2-pentylcyclopropyl)methoxy]carbonyl}phenyl) oxalate bis(3,4,6-trichloro-2-{[2-(1,2,2,3-tetramethylcyclopropyl)ethoxy]carbonyl}phenyl) oxalate bis(3,4,6-trichloro-2-{[2-(2,2,3,3-tetramethylcyclopropyl)ethoxy]carbonyl}phenyl) oxalate bis(3,4,6-trichloro-2-{[2-(1-ethyl-2,3-dimethylcyclopropyl)ethoxy]carbonyl}phenyl) oxalate bis(3,4,6-trichloro-2-{[2-(1-ethyl-2,2-dimethylcyclopropyl)ethoxy]carbonyl}phenyl) oxalate bis(3,4,6-trichloro-2-{[2-(2-ethyl-1,3-dimethylcyclopropyl)ethoxy]carbonyl}phenyl) oxalate bis(3,4,6-trichloro-2-{[2-(3-ethyl-2,2-dimethylcyclopropyl)ethoxy]carbonyl}phenyl) oxalate bis(3,4,6-trichloro-2-{[2-(1,2-diethylcyclopropyl)ethoxy]carbonyl}phenyl) oxalate bis(3,4,6-trichloro-2-{[2-(2,2-diethylcyclopropyl)ethoxy]carbonyl}phenyl) oxalate bis(3,4,6-trichloro-2-{[2-(2,3-diethylcyclopropyl)ethoxy]carbonyl}phenyl) oxalate bis(3,4,6-trichloro-2-{[2-(1-methyl-3-propylcyclopropyl)ethoxy]carbonyl}phenyl) oxalate bis(3,4,6-trichloro-2-{[2-(3-methyl-1-propylcyclopropyl)ethoxy]carbonyl}phenyl) oxalate bis(3,4,6-trichloro-2-{[2-(2-methyl-3-propylcyclopropyl)ethoxy]carbonyl}phenyl) oxalate bis(3,4,6-trichloro-2-{[2-(2-methyl-2-propylcyclopropyl)ethoxy]carbonyl}phenyl) oxalate bis[3,4,6-trichloro-2-({2-[1-methyl-2-(1-methylethyl)cyclopropyl]ethoxy}carbonyl)phenyl] oxalate bis[3,4,6-trichloro-2-({2-[2-methyl-1-(1-methylethyl)cyclopropyl]ethoxy}carbonyl)phenyl] oxalate bis[3,4,6-trichloro-2-({2-[2-methyl-3-(1-methylethyl)cyclopropyl]ethoxy}carbonyl)phenyl] oxalate bis[3,4,6-trichloro-2-({2-[2-methyl-1-(1-methylethyl)cyclopropyl]ethoxy}carbonyl)phenyl] oxalate bis(3,4,6-trichloro-2-{[2-(1-butylcyclopropyl)ethoxy]carbonyl}phenyl) oxalate bis[3,4,6-trichloro-2-({2-[1-(1-methylpropyl)cyclopropyl]ethoxy}carbonyl)phenyl] oxalate bis[3,4,6-trichloro-2-({2-[1-(2-methylpropyl)cyclopropyl]ethoxy}carbonyl)phenyl] oxalate bis(3,4,6-trichloro-2-{[2-(2-butylcyclopropyl)ethoxy]carbonyl}phenyl) oxalate bis[3,4,6-trichloro-2-({2-[2-(1-methylpropyl)cyclopropyl]ethoxy}carbonyl)phenyl] oxalate bis[3,4,6-trichloro-2-({2-[2-(2-methylpropyl)cyclopropyl]ethoxy}carbonyl)phenyl] oxalate bis(3,4,6-trichloro-2-{[2-(1,2,2-trimethylcyclopropyl)propoxy]carbonyl}phenyl) oxalate bis(3,4,6-trichloro-2-{[2-(1,2,3-trimethylcyclopropyl)propoxy]carbonyl}phenyl) oxalate bis(3,4,6-trichloro-2-{[2-(2,2,3-trimethylcyclopropyl)propoxy]carbonyl}phenyl) oxalate bis(3,4,6-trichloro-2-{[2-methyl-2-(2,3-dimethylcyclopropyl)propoxy]carbonyl}phenyl) oxalate bis(3,4,6-trichloro-2-{[2-(1-ethyl-2-methylcyclopropyl)propoxy]carbonyl}phenyl) oxalate bis(3,4,6-trichloro-2-{[2-(2-ethyl-1-methylcyclopropyl)propoxy]carbonyl}phenyl) oxalate bis(3,4,6-trichloro-2-{[2-(2-ethyl-3-methylcyclopropyl)propoxy]carbonyl}phenyl) oxalate bis(3,4,6-trichloro-2-{[2-(2-ethyl-2-methylcyclopropyl)propoxy]carbonyl}phenyl) oxalate bis(3,4,6-trichloro-2-{[2-(1-propylcyclopropyl)propoxy]carbonyl}phenyl) oxalate bis(3,4,6-trichloro-2-{[2-(2-propylcyclopropyl)propoxy]carbonyl}phenyl) oxalate bis[3,4,6-trichloro-2-({2-[1-(1-methylethyl)cyclopropyl]propoxy}carbonyl)phenyl] oxalate bis[3,4,6-trichloro-2-({2-[1-(1-methylethyl)cyclopropyl]propoxy}carbonyl)phenyl] oxalate bis(3,4,6-trichloro-2-{[2-methyl-2-(1,2-dimethylcyclopropyl)propoxy]carbonyl}phenyl) oxalate bis(3,4,6-trichloro-2-{[2-methyl-2-(2,2-dimethylcyclopropyl)propoxy]carbonyl}phenyl) oxalate bis(3,4,6-trichloro-2-{[-2-(1-ethylcyclopropyl)-2-methylpropoxy]carbonyl}phenyl) oxalate bis(3,4,6-trichloro-2-{[-2-(2-ethylcyclopropyl)-2-methylpropoxy]carbonyl}phenyl) oxalate bis(3,4,6-trichloro-2-{[2,2-dimethyl-3-(1-methylcyclopropyl)propoxy]carbonyl}phenyl) oxalate bis(3,4,6-trichloro-2-{[2,2-dimethyl-3-(2-methylcyclopropyl)propoxy]carbonyl}phenyl) oxalate bis(3,4,6-trichloro-2-{[2,3-dimethyl-3-(1-methylcyclopropyl)propoxy]carbonyl}phenyl) oxalate bis(3,4,6-trichloro-2-{[2,3-dimethyl-3-(2-methylcyclopropyl)propoxy]carbonyl}phenyl) oxalate bis(3,4,6-trichloro-2-{[2-methyl-3-(1,2-dimethylcyclopropyl)propoxy]carbonyl}phenyl) oxalate bis(3,4,6-trichloro-2-{[2-methyl-3-(2,3-dimethylcyclopropyl)propoxy]carbonyl}phenyl) oxalate bis(3,4,6-trichloro-2-{[2-methyl-3-(1-ethylcyclopropyl)propoxy]carbonyl}phenyl) oxalate bis(3,4,6-trichloro-2-{[2-methyl-3-(2-ethylcyclopropyl)propoxy]carbonyl}phenyl) oxalate bis(3,4,6-trichloro-2-{[3-(1,2,2-trimethylcyclopropyl)propoxy]carbonyl}phenyl) oxalate bis(3,4,6-trichloro-2-{[3-(1,2,3-trimethylcyclopropyl)propoxy]carbonyl}phenyl) oxalate bis(3,4,6-trichloro-2-{[3-(2-ethyl-1-methylcyclopropyl)propoxy]carbonyl}phenyl) oxalate bis(3,4,6-trichloro-2-{[3-(1-ethyl-2-methylcyclopropyl)propoxy]carbonyl}phenyl) oxalate bis(3,4,6-trichloro-2-{[3-(2-ethyl-3-methylcyclopropyl)propoxy]carbonyl}phenyl) oxalate bis(3,4,6-trichloro-2-{[3-(2-ethyl-2-methylcyclopropyl)propoxy]carbonyl}phenyl) oxalate bis(3,4,6-trichloro-2-{[3-(1-propylcyclopropyl)propoxy]carbonyl}phenyl) oxalate bis[3,4,6-trichloro-2-({3-[1-(1-methylethyl)cyclopropyl]propoxy}carbonyl)phenyl] oxalate bis(3,4,6-trichloro-2-{[3-(2-propylcyclopropyl)propoxy]carbonyl}phenyl) oxalate bis[3,4,6-trichloro-2-({3-[2-(1-methylethyl)cyclopropyl]propoxy}carbonyl)phenyl] oxalate bis{3,4,6-trichloro-2-[(2-cyclopropyl-3,3-dimethylbutoxy)carbonyl]phenyl} oxalate bis(3,4,6-trichloro-2-{[3-(1-ethylcyclopropyl)butoxy]carbonyl}phenyl) oxalate bis(3,4,6-trichloro-2-{[2-methyl-4-(1-methylcyclopropyl)butoxy]carbonyl}phenyl) oxalate bis(3,4,6-trichloro-2-{[3-methyl-4-(1-methylcyclopropyl)butoxy]carbonyl}phenyl) oxalate bis{3,4,6-trichloro-2-[(4-cyclopropyl-2-ethylbutoxy)carbonyl]phenyl} oxalate bis{3,4,6-trichloro-2-[(4-cyclopropyl-3,3-dimethylbutoxy)carbonyl]phenyl} oxalate bis{3,4,6-trichloro-2-[(4-cyclopropyl-3-methylpentyloxy)carbonyl]phenyl} oxalate bis(3,4,6-trichloro-2-{[4-(1,2-dimethylcyclopropyl)-3-methylbutoxy]carbonyl}phenyl) oxalate bis(3,4,6-trichloro-2-{[4-(1-ethylcyclopropyl)butoxy]carbonyl}phenyl) oxalate bis{3,4,6-trichloro-2-[(4-cyclopropyl-4-methylpentyloxy)carbonyl]phenyl} oxalate bis(3,4,6-trichloro-2-{[4-(1-methylcyclopropyl)pentyloxy]carbonyl}phenyl) oxalate bis(3,4,6-trichloro-2-{[4-(2-methylcyclopropyl)pentyloxy]carbonyl}phenyl) oxalate bis{3,4,6-trichloro-2-[(3-cyclopropyl-4-methylpentyloxy)carbonyl]phenyl} oxalate bis{3,4,6-trichloro-2-[(2-cyclopropyl-2-methylpentyloxy)carbonyl]phenyl} oxalate bis{3,4,6-trichloro-2-[(2-cyclopropyl-3-methylpentyloxy)carbonyl]phenyl} oxalate bis{3,4,6-trichloro-2-[(2-cyclopropyl-4-methylpentyloxy)carbonyl]phenyl} oxalate bis{3,4,6-trichloro-2-[(3-cyclopropyl-2-methylpentyloxy)carbonyl]phenyl} oxalate bis{3,4,6-trichloro-2-[(5-cyclopropyl-2-methylpentyloxy)carbonyl]phenyl} oxalate bis{3,4,6-trichloro-2-[(5-cyclopropyl-3-methylpentyloxy)carbonyl]phenyl} oxalate bis{3,4,6-trichloro-2-[(5-cyclopropyl-4-methylpentyloxy)carbonyl]phenyl} oxalate bis(3,4,6-trichloro-2-{[3-(cyclopropylmethyl)pentyloxy]carbonyl}phenyl) oxalate bis(3,4,6-trichloro-2-{[5-(1-methylcyclopropyl)pentyloxy]carbonyl}phenyl) oxalate bis{3,4,6-trichloro-2-[(2-cyclopropylhexyloxy)carbonyl]phenyl} oxalate bis{3,4,6-trichloro-2-[(3-cyclopropylhexyloxy)carbonyl]phenyl} oxalate bis{3,4,6-trichloro-2-[(4-cyclopropylhexyloxy)carbonyl]phenyl} oxalate bis{3,4,6-trichloro-2-[(5-cyclopropylhexyloxy)carbonyl]phenyl} oxalate bis{3,4,6-trichloro-2-[(6-cyclopropylhexyloxy)carbonyl]phenyl} oxalate bis{3,4,6-trichloro-2-[(2,2-dicyclopropylpropoxy)carbonyl]phenyl} oxalate bis{3,4,6-trichloro-2-[(3,3-dicyclopropylpropoxy)carbonyl]phenyl} oxalate bis{3,4,6-trichloro-2-[(2-cyclobutyl-2-cyclopropylethoxy)carbonyl]phenyl} oxalate bis{2-[(bicyclo[2.2.2]octan-2-ylmethoxy)carbonyl]3,4,6-trichlorophenyl} oxalate bis{2-[(bicyclo[3.3.0]octan-3-ylmethoxy)carbonyl]3,4,6-trichlorophenyl} oxalate bis(3,4,6-trichloro-2-{[(2,3-dimethylphenyl)methoxy]carbonyl}phenyl) oxalate bis(3,4,6-trichloro-2-{[(2,4-dimethylphenyl)methoxy]carbonyl}phenyl) oxalate bis(3,4,6-trichloro-2-{[3,4-dimethylphenyl)methoxy]carbonyl}phenyl) oxalate bis(3,4,6-trichloro-2-{[(3,5-dimethylphenyl)methoxy]carbonyl}phenyl) oxalate bis(3,4,6-trichloro-2-{[(2,6-dimethylphenyl)methoxy]carbonyl}phenyl) oxalate bis(3,4,6-trichloro-2-{[(2-ethylphenyl)methoxy]carbonyl}phenyl) oxalate bis(3,4,6-trichloro-2-{[(3-ethylphenyl)methoxy]carbonyl}phenyl) oxalate bis(3,4,6-trichloro-2-{[(4-ethylphenyl)methoxy]carbonyl}phenyl) oxalate bis(3,4,6-trichloro-2-{[2-(2-methylphenyl)ethoxy]carbonyl}phenyl) oxalate bis(3,4,6-trichloro-2-{[2-(3-methylphenyl)ethoxy]carbonyl}phenyl) oxalate bis(3,4,6-trichloro-2-{[2-(4-methylphenyl)ethoxy]carbonyl}phenyl) oxalate bis{3,4,6-trichloro-2-[(2-phenylpropoxy)carbonyl]phenyl} oxalate bis{3,4,6-trichloro-2-[(3-phenylpropoxy)carbonyl]phenyl} oxalate bis{3,4,6-trichloro-2-[(2-methylnonyloxy)carbonyl]phenyl} oxalate bis{3,4,6-trichloro-2-[(3-methylnonyloxy)carbonyl]phenyl} oxalate bis{3,4,6-trichloro-2-[(4-methylnonyloxy)carbonyl]phenyl} oxalate bis{3,4,6-trichloro-2-[(5-methylnonyloxy)carbonyl]phenyl} oxalate bis{3,4,6-trichloro-2-[(6-methylnonyloxy)carbonyl]phenyl} oxalate bis{3,4,6-trichloro-2-[(7-methylnonyloxy)carbonyl]phenyl} oxalate bis{3,4,6-trichloro-2-[(8-methylnonyloxy)carbonyl]phenyl} oxalate bis{3,4,6-trichloro-2-[(3,7-dimethyloctyloxy)carbonyl]phenyl} oxalate bis{3,4,6-trichloro-2-[(4-ethyloctyloxy)carbonyl]phenyl} oxalate bis{3,4,6-trichloro-2-[(2-propylheptyloxy)carbonyl]phenyl} oxalate bis{3,4,6-trichloro-2-[(2-butylhexyloxy)carbonyl]phenyl} oxalate bis{3,4,6-trichloro-2-[(4-cyclohexylbutoxy)carbonyl]phenyl} oxalate bis(2-{[(6,6-dimethylbicyclo[3.1.1]heptan-2-yl)methoxy]carbonyl}3,4,6-trichlorophenyl) oxalate bis(3,4,6-trichloro-2-{[(2,4,6-trimethylphenyl)methoxy]carbonyl}phenyl) oxalate bis(3,4,6-trichloro-2-{[(4-propylphenyl)methoxy]carbonyl}phenyl) oxalate bis[3,4,6-trichloro-2-({[4-(1-methylethyl)phenyl]methoxy}carbonyl)phenyl] oxalate bis{3,4,6-trichloro-2-[(2-phenylbutoxy)carbonyl]phenyl} oxalate bis{3,4,6-trichloro-2-[(3-phenylbutoxy)carbonyl]phenyl} oxalate bis{3,4,6-trichloro-2-[(4-phenylbutoxy)carbonyl]phenyl} oxalate bis(3,4,6-trichloro-2-{[(2-phenylcyclopropyl)methoxy]carbonyl}phenyl) oxalate bis{3,4,6-trichloro-2-[(1-adamantylmethoxy)carbonyl]phenyl} oxalate bis{3,4,6-trichloro-2-[(2,2-dicyclohexylethoxy)carbonyl]phenyl} oxalate bis(3,4,6-trichloro-2-{[(4-butylphenyl)methoxy]carbonyl}phenyl) oxalate bis[3,4,6-trichloro-2-({[4-(1,1-dimethylethyl)phenyl]methoxy}carbonyl)phenyl] oxalate bis{3,4,6-trichloro-2-[(5-phenylpentyloxy)carbonyl]phenyl} oxalate bis{3,4,6-trichloro-2-[1-naphthalenylmethoxy)carbonyl]phenyl} oxalate bis{3,4,6-trichloro-2-[2-naphthalenylmethoxy)carbonyl]phenyl} oxalate bis{3,4,6-trichloro-2-[(2,2-diphenylethoxy)carbonyl]phenyl} oxalate bis{3,4,6-trichloro-2-[(9-fluorenylmethoxy)carbonyl]phenyl} oxalate bis{3,4,6-trichloro-2-[(9-anthracenylmethoxy)carbonyl]phenyl} oxalate

CHEMICAL LIGHT PRODUCING FORMULATIONS AND DEVICES CONTAINING BRANCHED OXALATE ESTERS

CROSS REFERENCE TO RELATED APPLICATIONS

This application claims benefit of the filing date of U.S. Provisional Patent Application No. 61/250,915, filed on Oct. 13, 2009, the contents of which are herein incorporated by reference.

FIELD OF THE INVENTION

This invention relates to chemical light producing devices and the chemiluminescent oxalate esters contained therein, which exhibit reduced hydrolysis owing to the utilization of non-straight chain oxalate ester (i.e. a branched chain or ring structure oxalate ester), and thereby are characterized by an inherently long shelf-life and commercial viability.

BACKGROUND OF THE INVENTION

Chemical light devices are useful for providing a source of non-electric light and have become exceedingly popular especially for emergency and outdoor use. Typical chemical light devices contain two liquids that produce light upon mixing. Typically, one of these liquids was referred to as an oxalate solution. It typically contained a carrier solvent, an oxalate ester, and a fluorescer. The second liquid was referred to as an activator solution. It typically contained a carrier solvent, hydrogen peroxide, and a catalyst.

The oxalate ester is the component of the system which is most deleteriously affected by moisture, although other components such as yellow and blue fluorescers and salicylate catalysts may also be affected. The instant invention provides oxalate esters, methods of synthesis of said esters, and methods for the prevention of the deterioration of the oxalate esters.

A typical commercially available chemiluminescent device of the dual container variety contains a diluent solution of oxalate ester and fluorescer in the outer container and a diluent solution of hydrogen peroxide and catalyst in the inner container. Typical devices are disclosed in one or more of the following U.S. Pat. Nos. 3,511,612; 3,539,794; 3,576,987; 3,584,211; 3,654,525; 3,749,620; 3,752,406; 3,800,132; 3,808,414; 3,940,604; 3,974,368; 4,064,428; each of which is hereby incorporated herein by reference.

The chemiluminescent light is obtained by the reaction of the hydrogen peroxide of the activator solution with the chemiluminescent composition which comprises the oxalate ester, fluorescer, and catalyst. Typical oxalate esters have heretofore included compounds such as bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl-4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyloxalate, bis(1,2-dihydro-2-oxo-1-pyridyl) glyoxal, bis-N-phthalmidyl oxalate. The preferred oxalate, is bis{3,4,6-trichloro-2-[(pentoxy)carbonyl]phenyl}oxalate.

The extreme sensitivity of these oxalates to water hydrolysis has created the need to package them carefully and store under refrigerated conditions. Water can and will migrate, at varying rates, through most non-metal and non-glass materials of construction. If the prior art oxalate esters were not packaged within a polymer lined metal (foil) pouch that is then stored in an inert (dry) gas containing metal drum that is stored under refrigerated conditions, the oxalate ester would hydrolyze and would fail to retain commercially viable shelf life.

The present invention discloses a novel family of branched chain oxalate esters which are useful in chemical lighting systems while being substantially non-hydrolyzing, thus eliminating the need for such careful and expensive handling and packaging requirements. This satisfies a long felt need in the art.

SUMMARY OF THE INVENTION

In order to overcome the hydrolysis issues experienced by prior art oxalate esters in chemical light systems, the present inventors have created a novel family of branched chain oxalate esters having a specific requisite construction, a process for their synthesis, and novel chemical light systems which include the novel branched chain oxalate esters.

The approach adopted involved using derivatives of primary alcohols, to facilitate the synthesis of the initial salicylate ester. Additionally, it was hypothesized that the introduction of steric hindrance by including branching and/or ring structure(s) on the remainder of the alcohol would retard hydrolysis issues typically experienced by prior art oxalate esters, while providing compounds which would be eminently useful in a chemical light system.

This construction is characterized by the following structure:

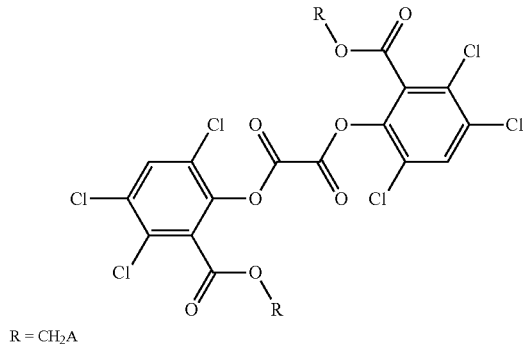

R = CH$_2$A

The group designated as R contains from 4-15 carbons. Furthermore, the carbon of R attached to the oxygen is a primary carbon and includes a substructure labeled A. The substructure A is composed of substituents selected from the group including alkyl chains, alkyl rings, and aromatic rings or combinations thereof such that R is nonlinear.

FIGS. 1-662 are illustrative, albeit non-limiting embodiments, of branched chain oxalate esters useful in chemical lighting systems. It is understood that any additional compounds which fall within the definition as outlined above are contemplated as useful in the instant invention.

It has been unexpectedly discovered that replacing the typical oxalate ester (bis{3,4,6-trichloro-2-[(pentoxy)carbonyl]phenyl}oxalate) with a non-straight chain, substituted methyl oxalate ester (i.e. a branched chain or ring structure oxalate ester made from a primary alcohol) retards water hydrolysis of the oxalate ester. This retardation of the hydrolysis changes significantly the storage and transportation constraints for the oxalate ester. The need for metal pouches or moisture barrier packaging is obviated without sacrificing commercially viable shelf-life.

Accordingly, it is a primary objective of the instant invention to teach non-straight chain oxalate esters, inclusive of branched chain or ring structure oxalate esters, for use in conjunction with chemiluminescent formulations and chemical light producing devices.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

As follows.

FIG. 1 illustrates a bis{3,4,6-trichloro-2-[(2-methylpropoxy)carbonyl]phenyl}oxalate;

FIG. 119 illustrates a bis{3,4,6-trichloro-2-[(2-ethyl-2,3-dimethylbutoxy)carbonyl]phenyl}oxalate;

FIG. 120 illustrates a bis{3,4,6-trichloro-2-[(2-ethyl-3,3-dimethylbutoxy)carbonyl]phenyl}oxalate;

FIG. 121 illustrates a bis{3,4,6-trichloro-2-[(cycloheptylmethoxy)carbonyl]phenyl}oxalate;

FIG. 122 illustrates a bis(3,4,6-trichloro-2-{[(1-methylcyclohexyl)methoxy]carbonyl}phenyl) oxalate;

FIG. 123 illustrates a bis(3,4,6-trichloro-2-{[(2-methylcyclohexyl)methoxy]carbonyl}phenyl) oxalate;

FIG. 124 illustrates a bis(3,4,6-trichloro-2-{[(3-methylcyclohexyl)methoxy]carbonyl}phenyl) oxalate;

FIG. 125 illustrates a bis(3,4,6-trichloro-2-{[(4-methylcyclohexyl)methoxy]carbonyl}phenyl) oxalate;

FIG. 126 illustrates a bis{3,4,6-trichloro-2-[(2-cyclohexylethoxy)carbonyl]phenyl}oxalate;

FIG. 127 illustrates a bis(3,4,6-trichloro-2-{[(1,2-dimethylcyclopentyl)methoxy]carbonyl}phenyl) oxalate;

FIG. 128 illustrates a bis(3,4,6-trichloro-2-{[(1,3-dimethylcyclopentyl)methoxy]carbonyl}phenyl) oxalate;

FIG. 129 illustrates a bis(3,4,6-trichloro-2-{[(2,2-dimethylcyclopentyl)methoxy]carbonyl}phenyl) oxalate;

FIG. 130 illustrates a bis(3,4,6-trichloro-2-{[(2,3-dimethylcyclopentyl)methoxy]carbonyl}phenyl) oxalate;

Figure 131:
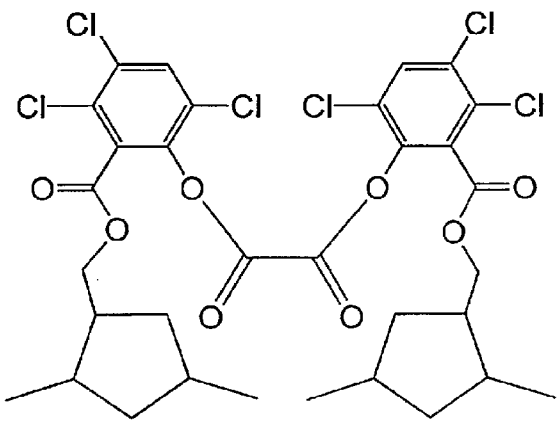
Figure 132:
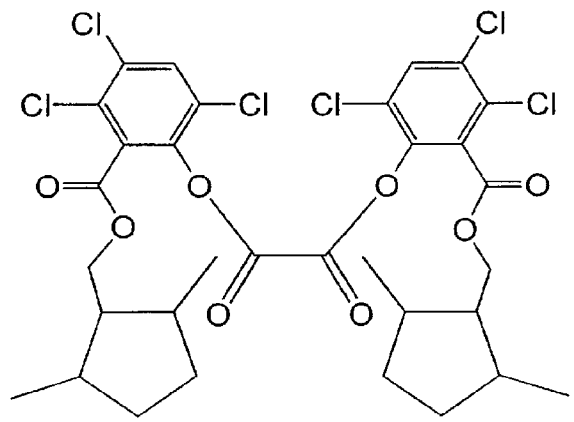
Figure 133:
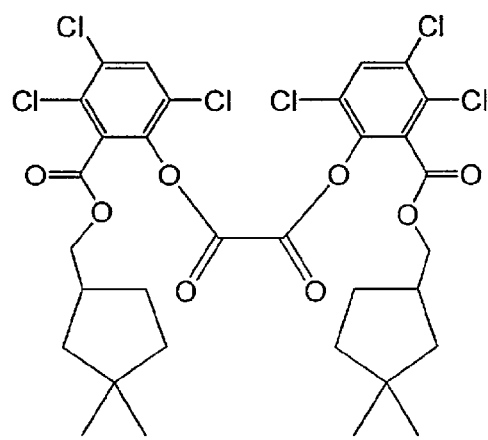
Figure 134:
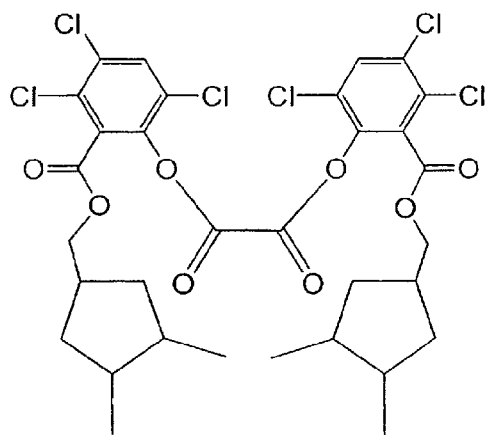
Figure 135:
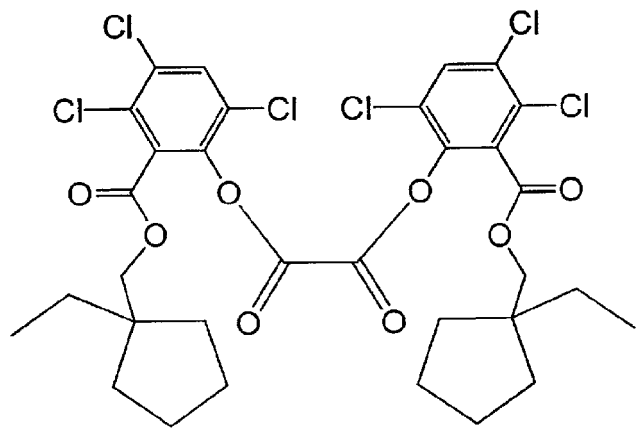
Figure 136:
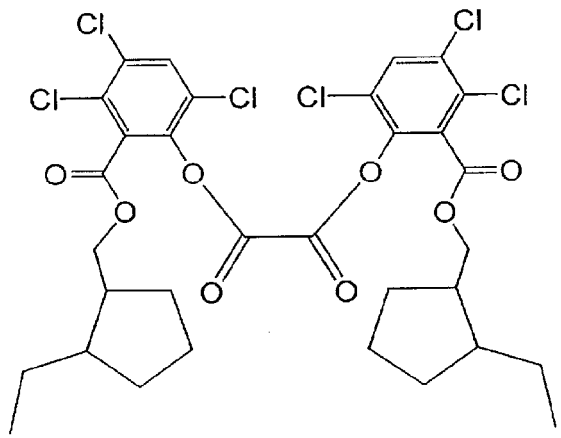
Figure 137:
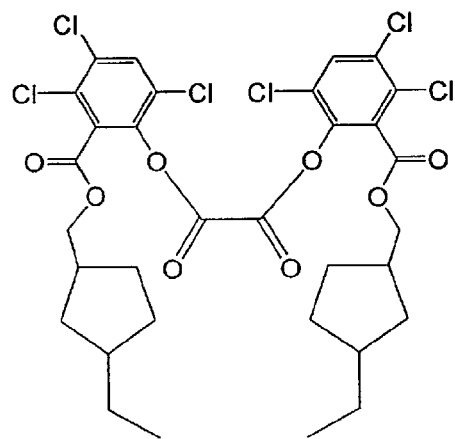
Figure 138:
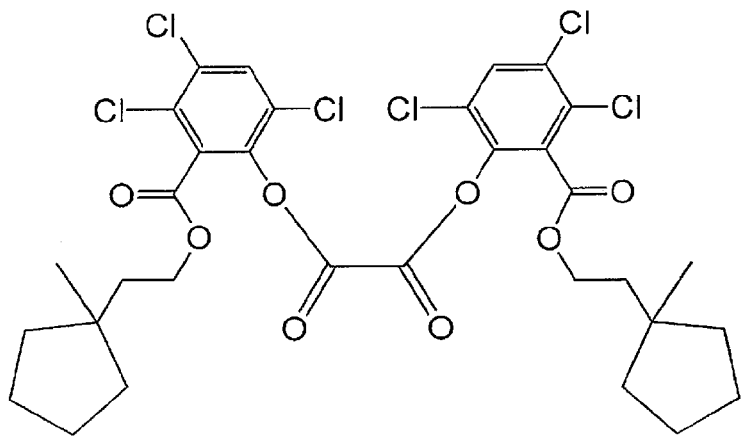
Figure 139:
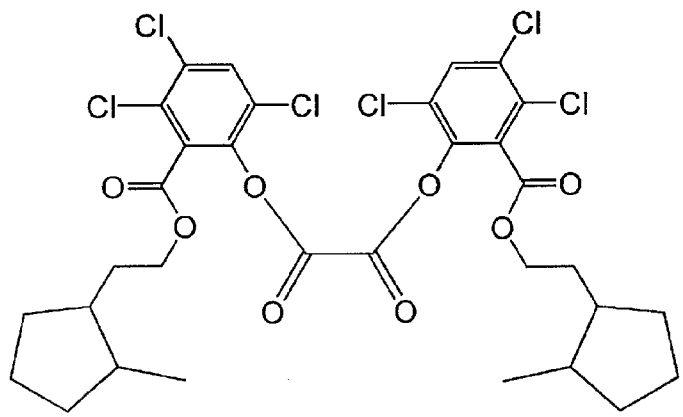
Figure 140:
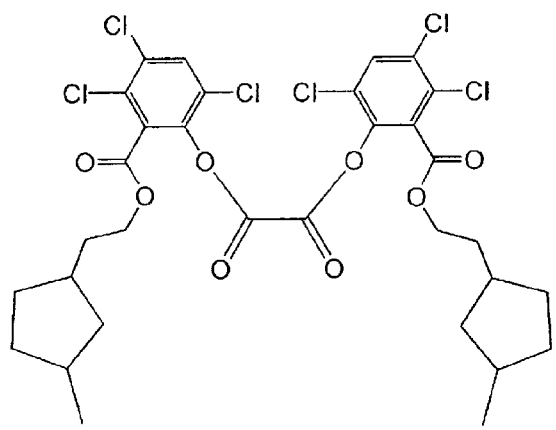
Figure 141:
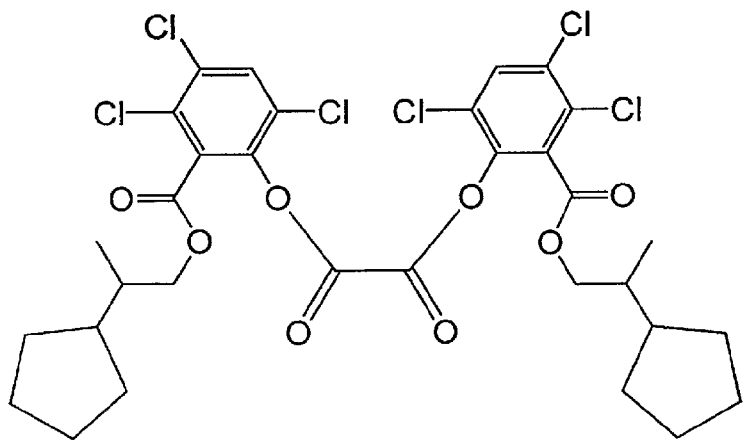
Figure 142:
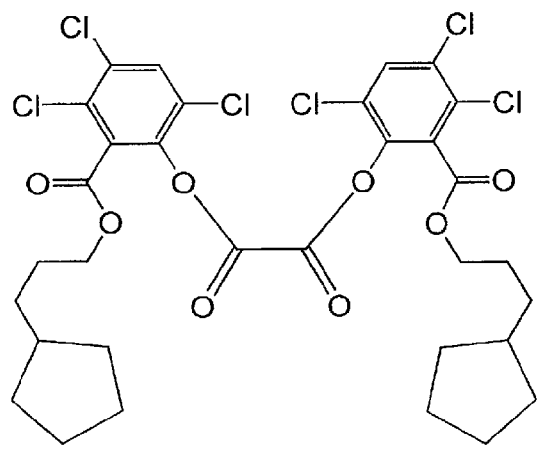
Figure 143:
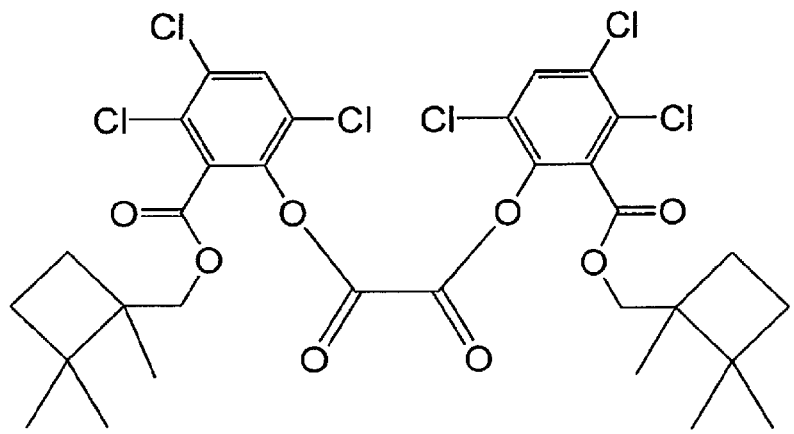
Figure 144:
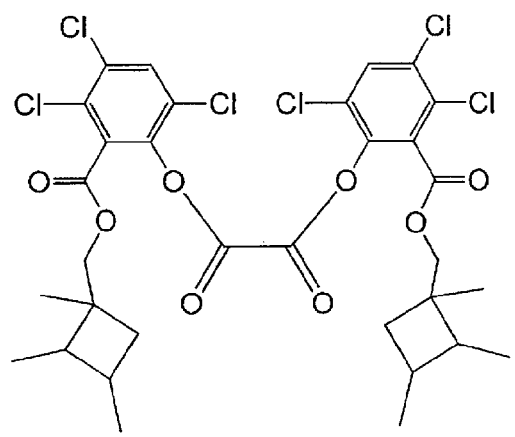
Figure 145:
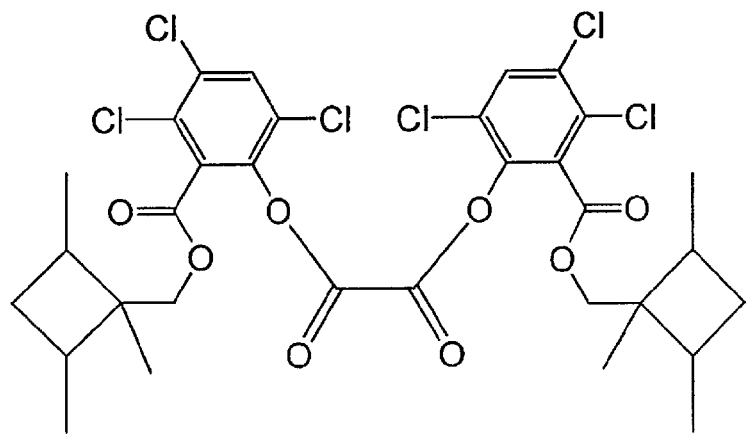
Figure 146:
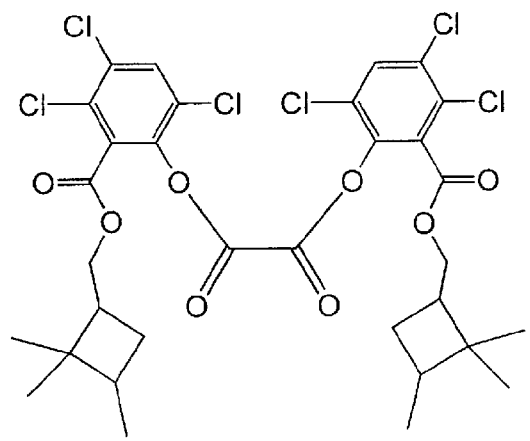
Figure 147:
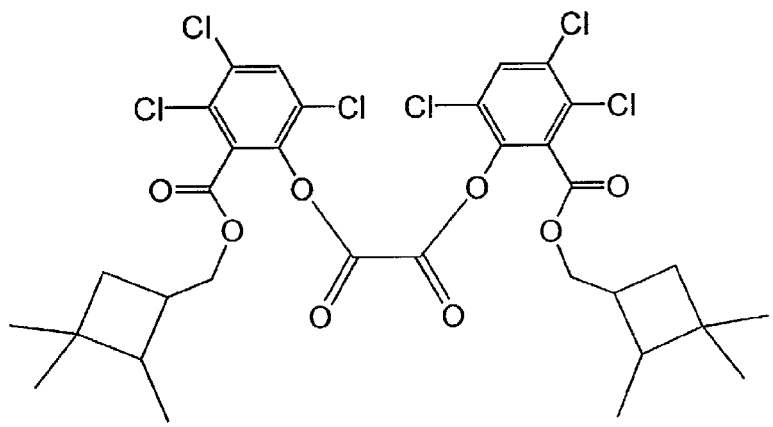
Figure 148:
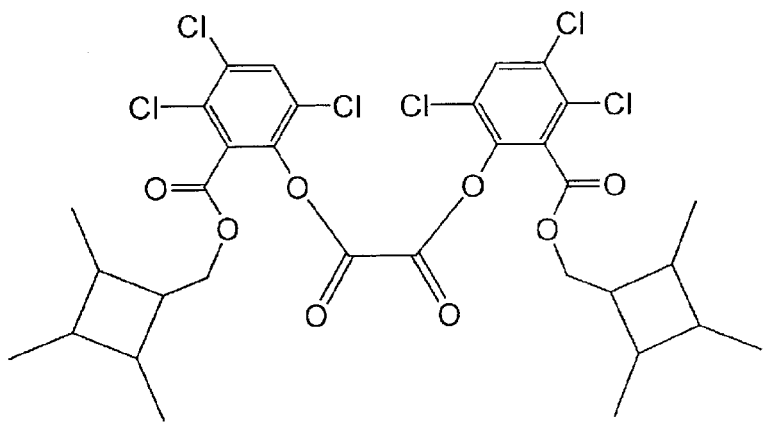
Figure 149:
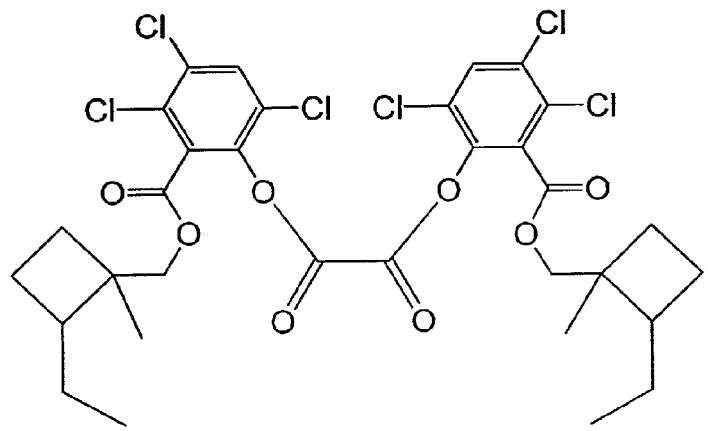
Figure 150:
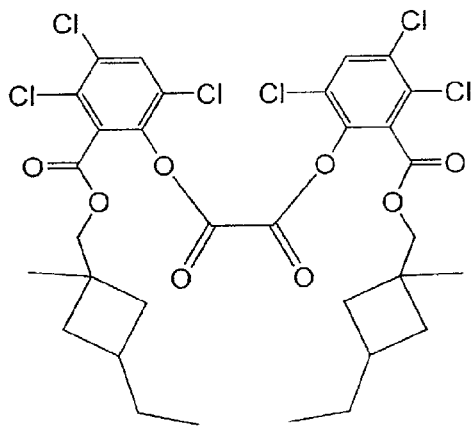
Figure 151:
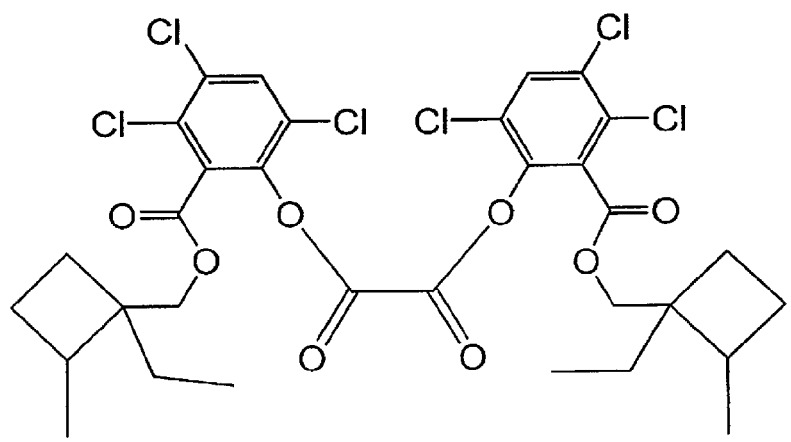
Figure 152:
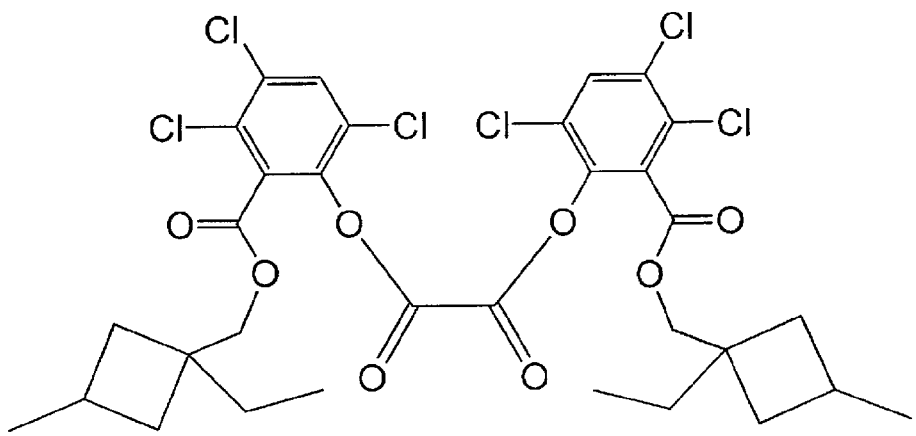
Figure 153:
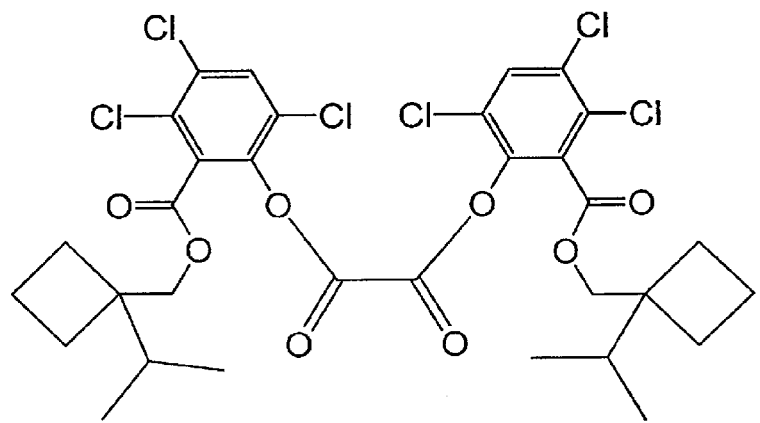
Figure 154:
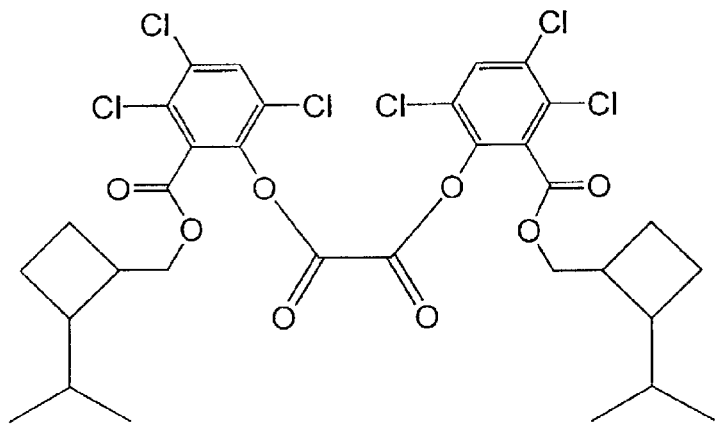
Figure 155:
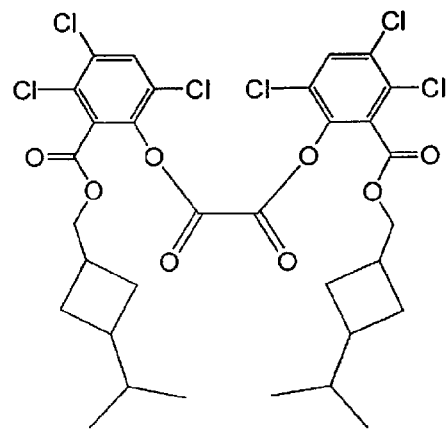
Figure 156:
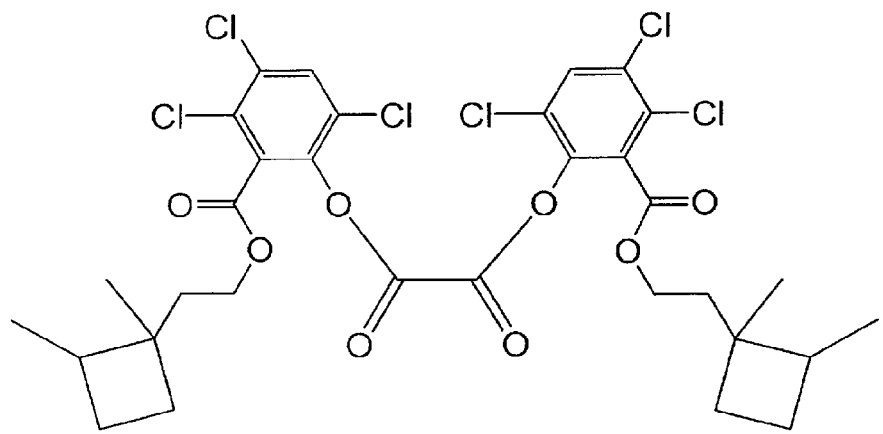
Figure 157:
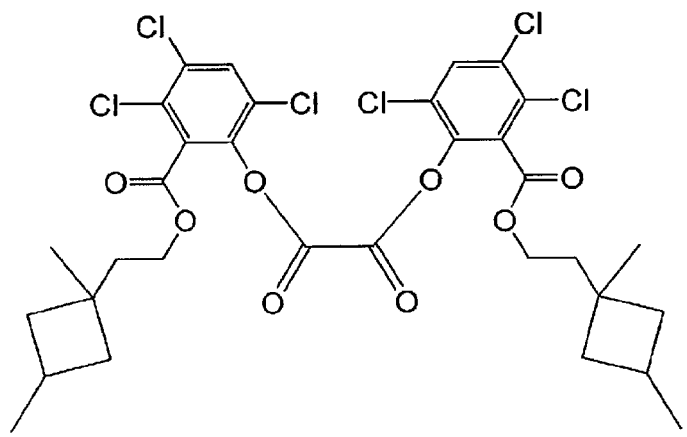
Figure 158:
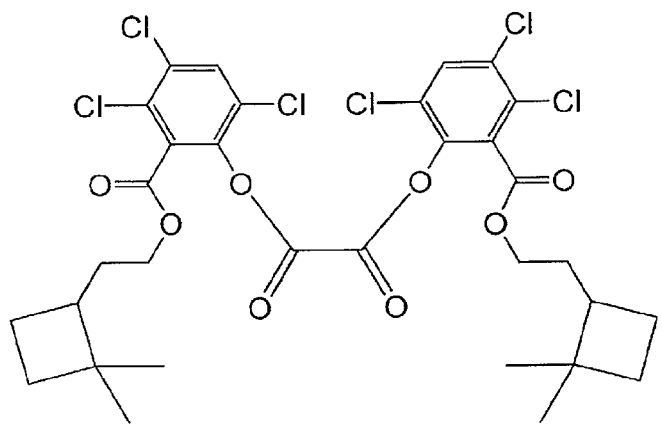
Figure 159:
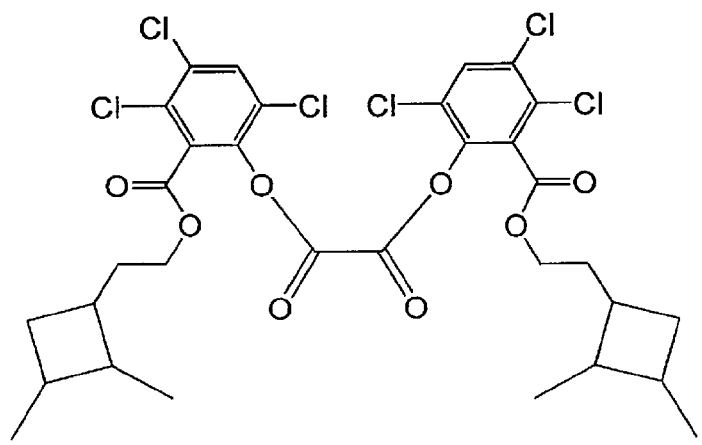
Figure 160:
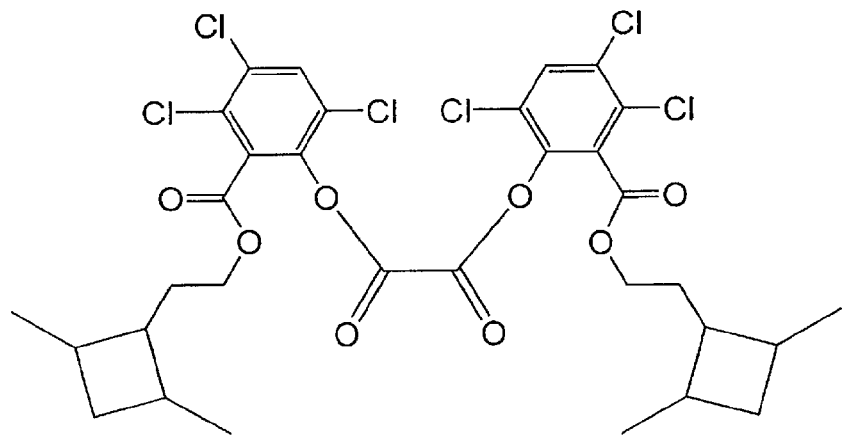
Figure 161:
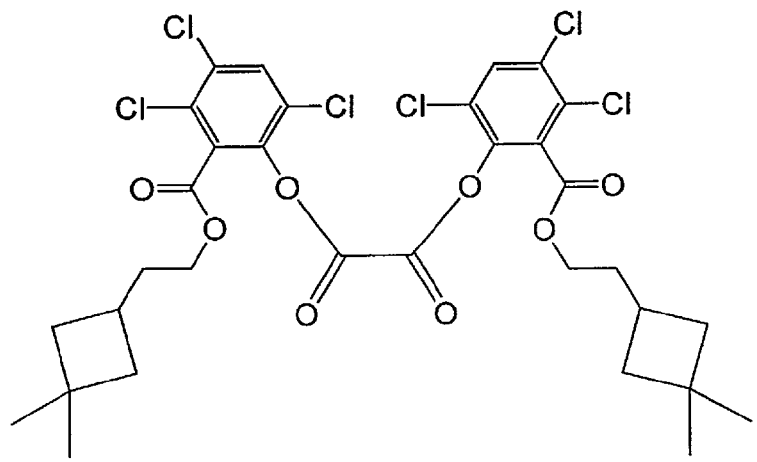
Figure 162:
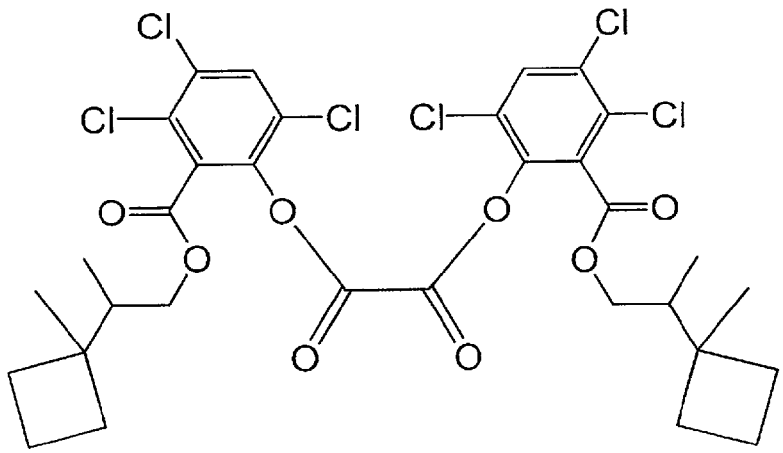
Figure 163:
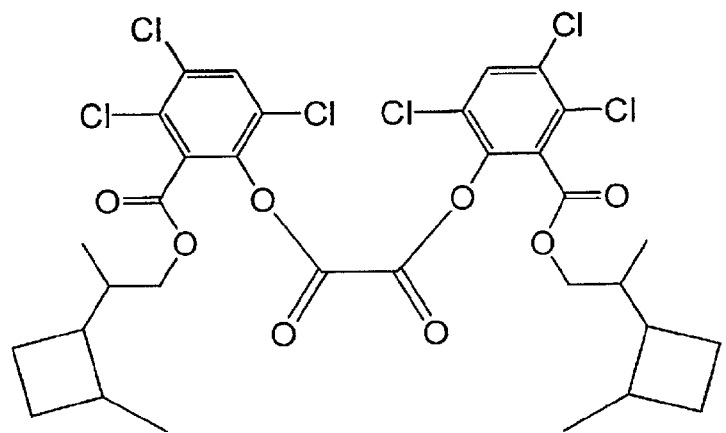
Figure 164:
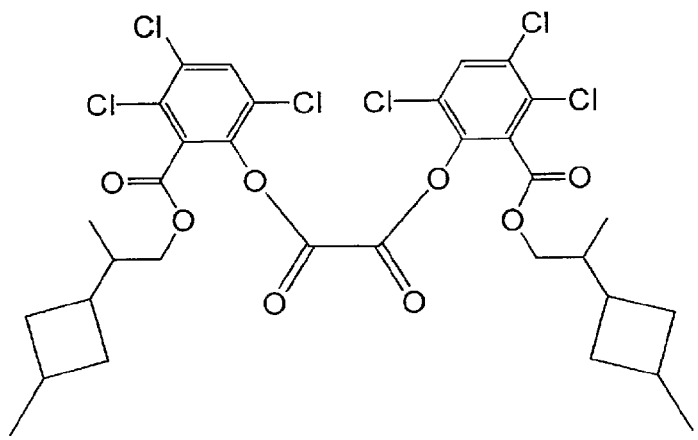
Figure 165:
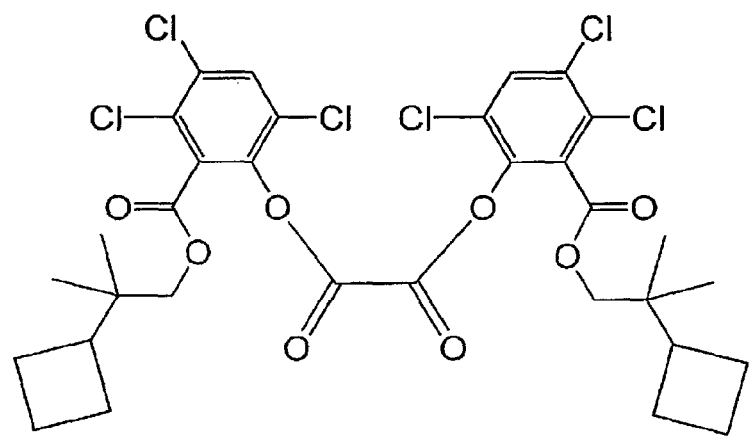
Figure 166:
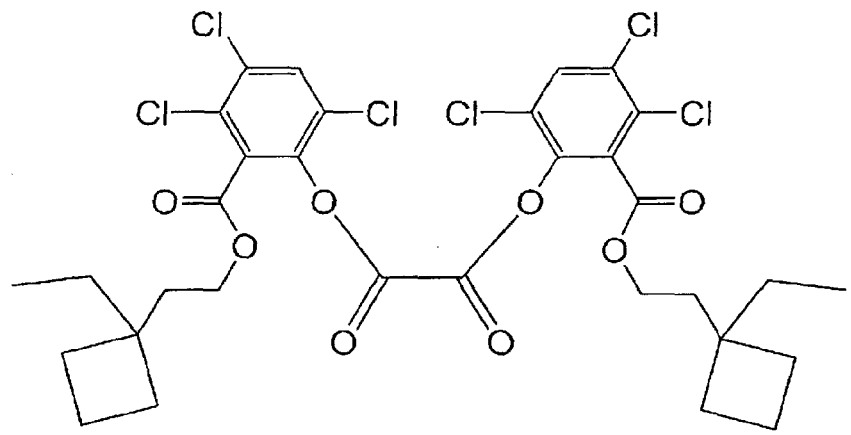
Figure 167:
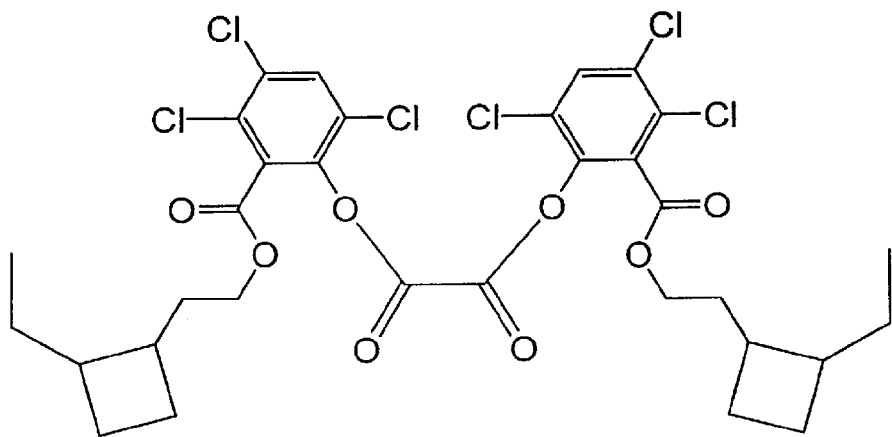
Figure 168:
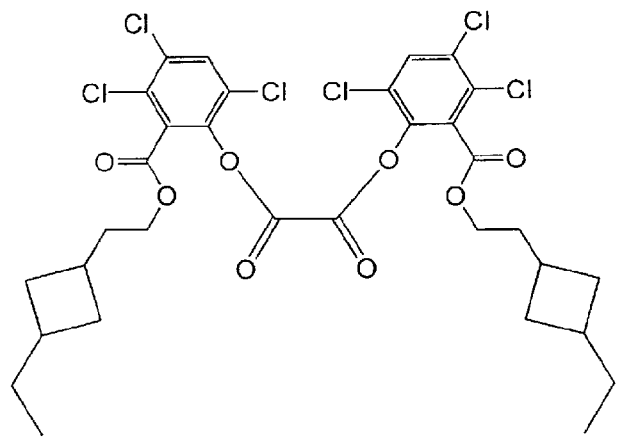
Figure 169:
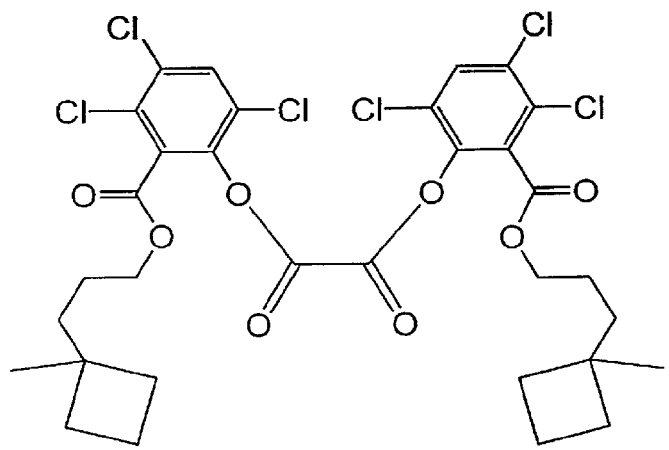
Figure 170:
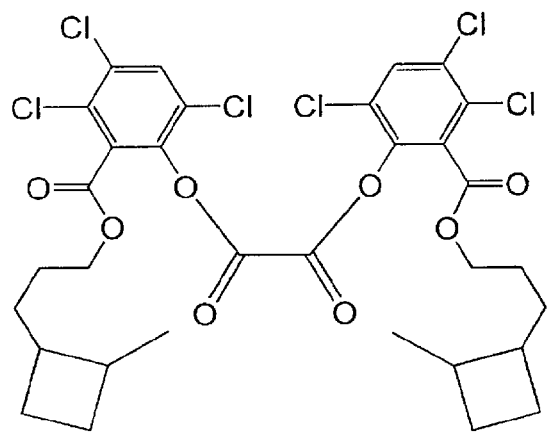
Figure 171:
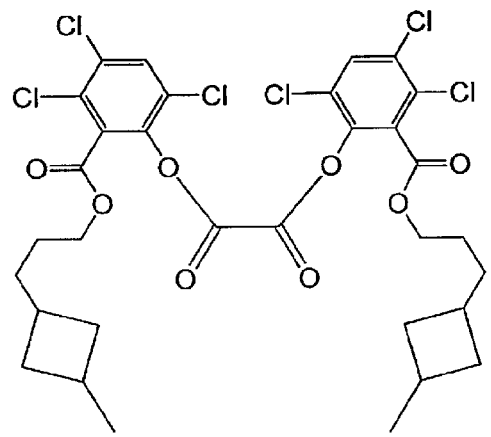
Figure 172:
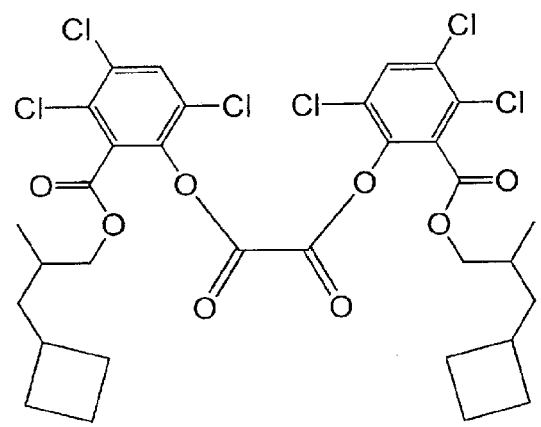
Figure 173:
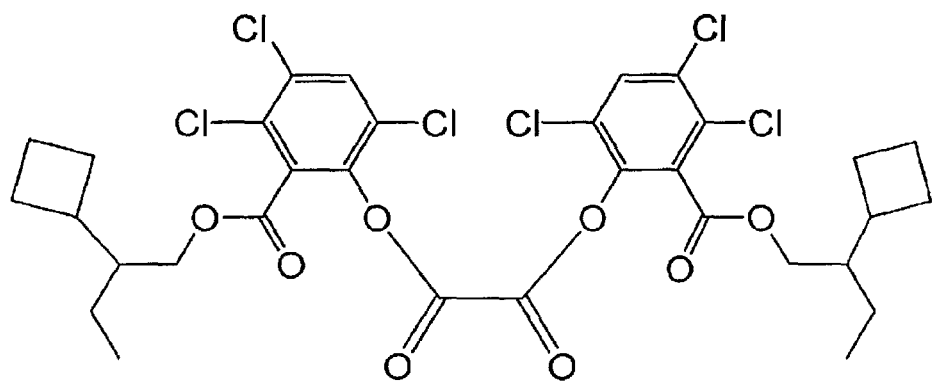
Figure 174:
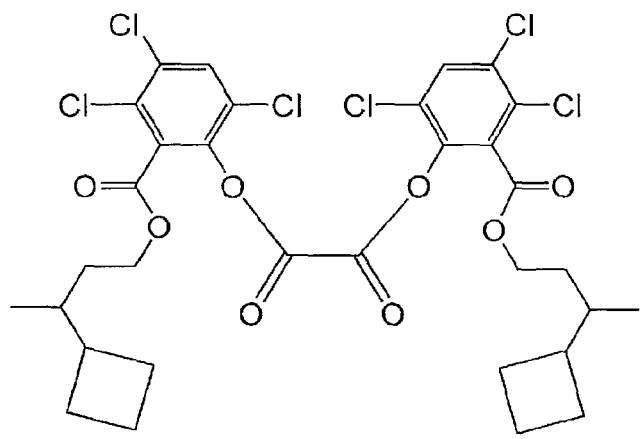
Figure 175:
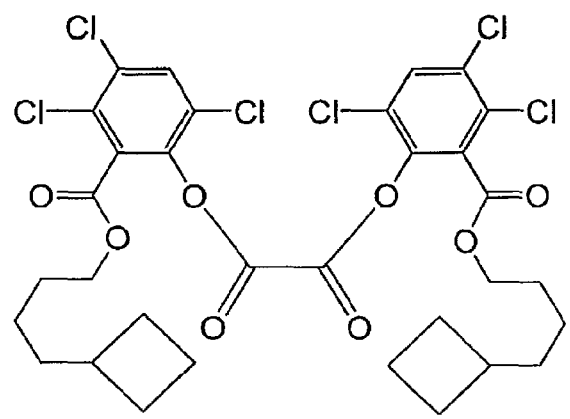
Figure 176:
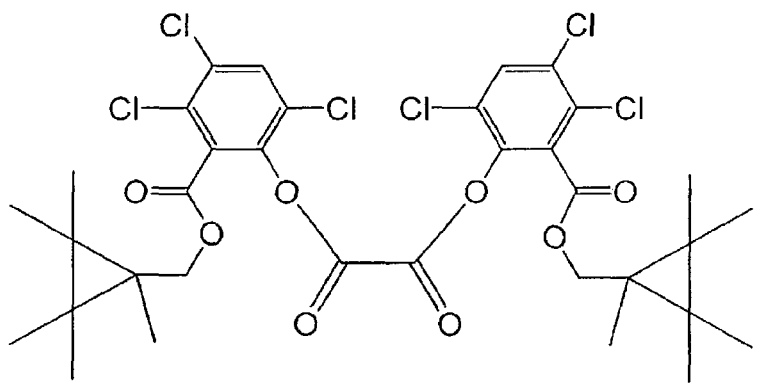
Figure 177:
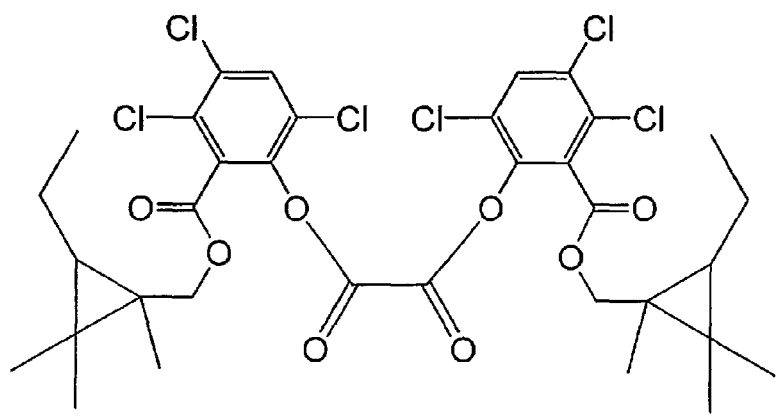
Figure 178:
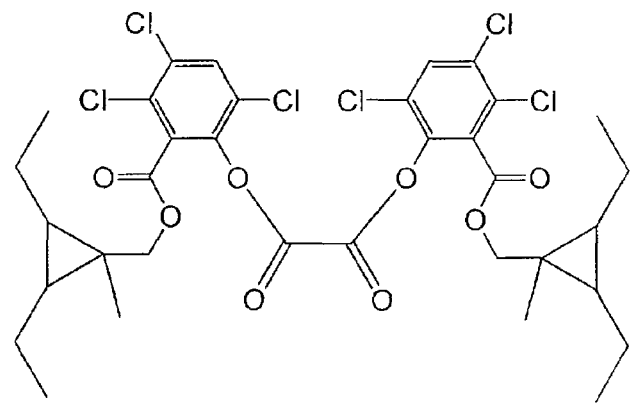
Figure 179:
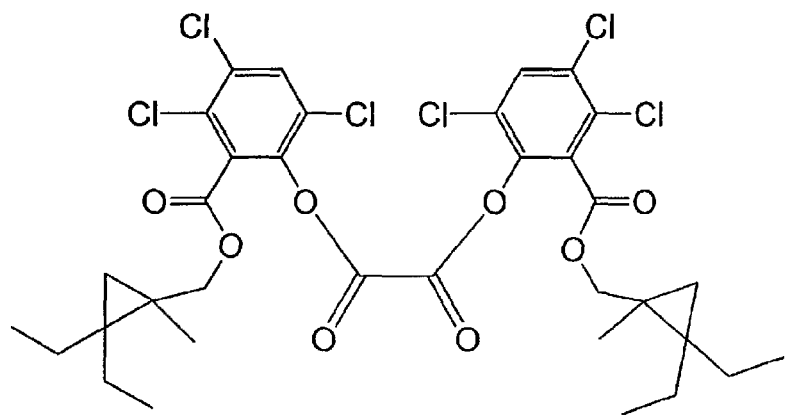
Figure 180:
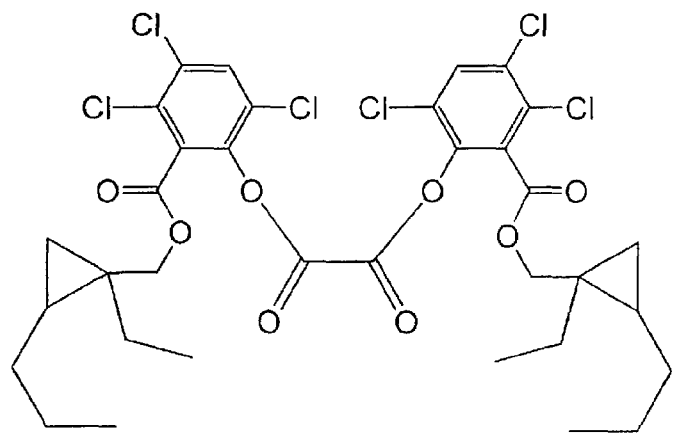
Figure 181:
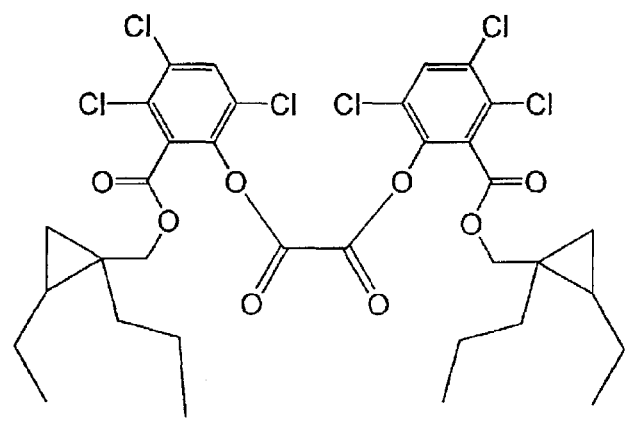
Figure 182:
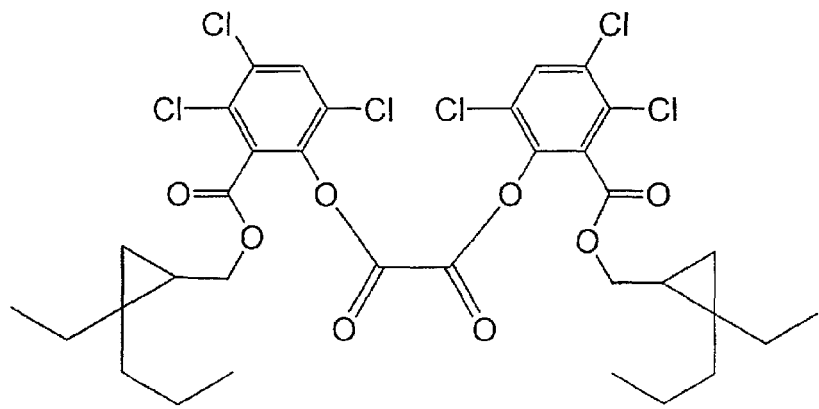
Figure 183:
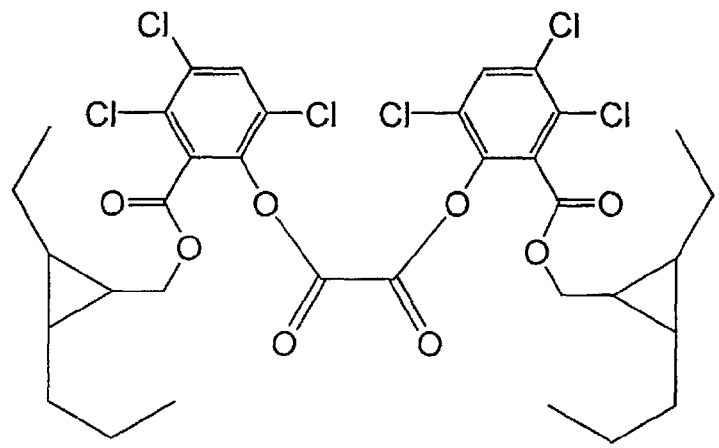
Figure 184:
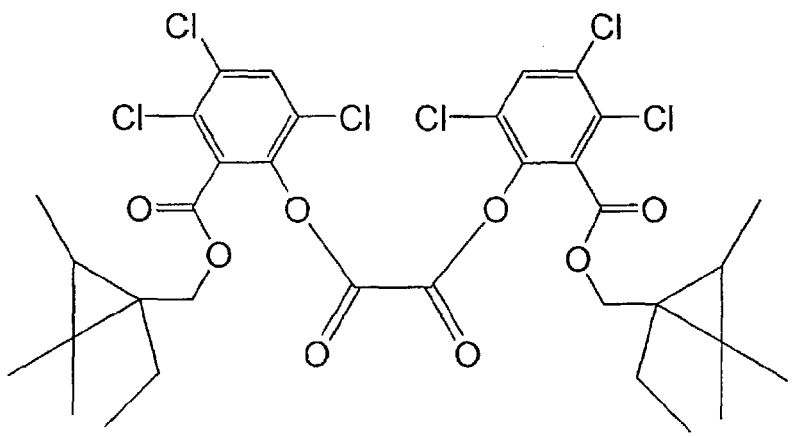
Figure 185:
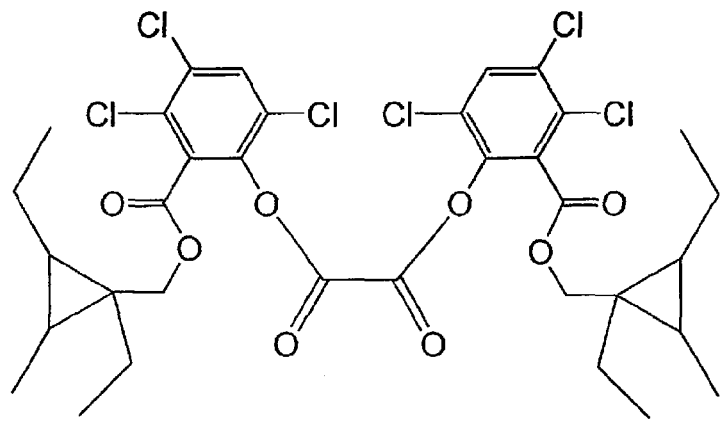
Figure 186:
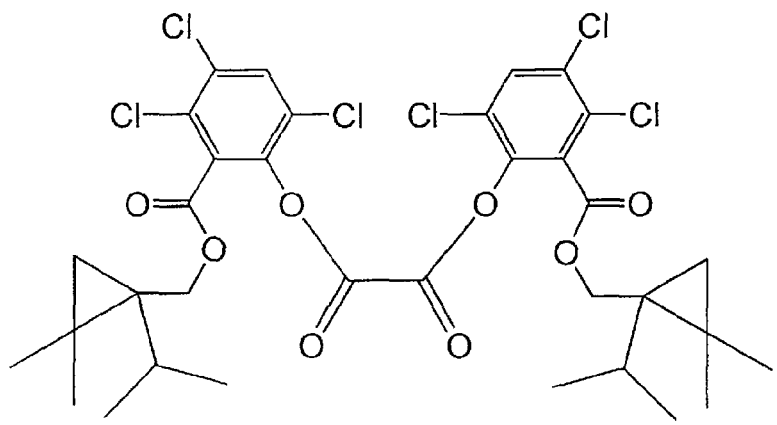
Figure 187:
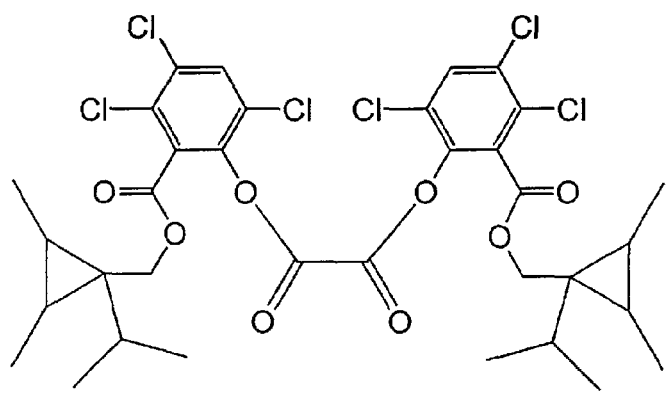
Figure 188:
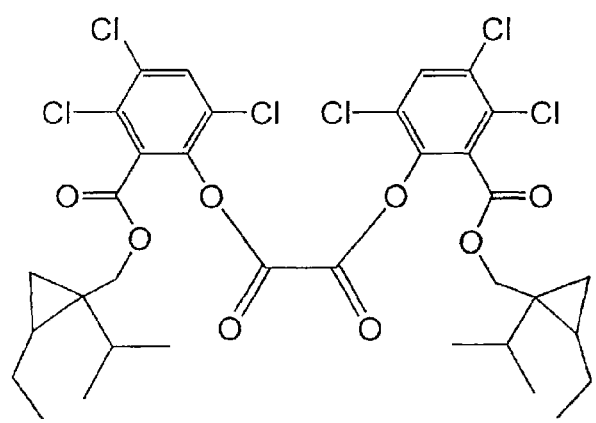
Figure 189:
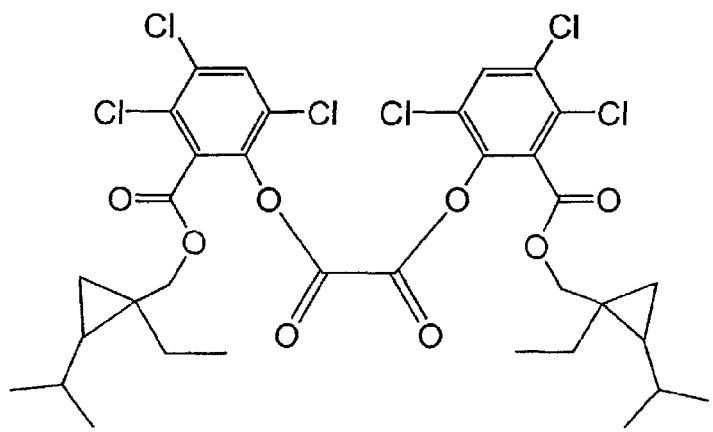
Figure 190:
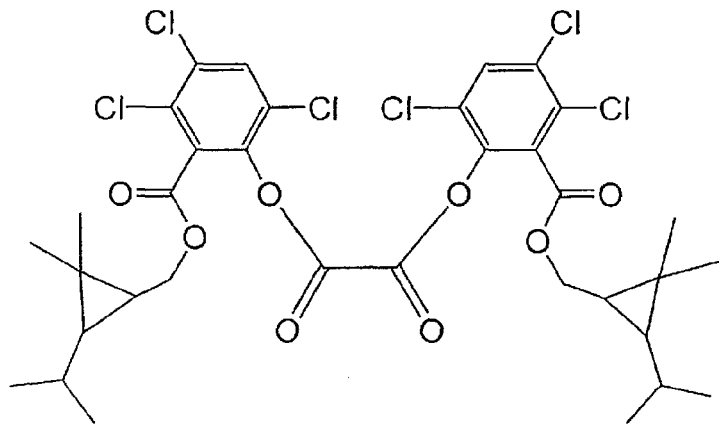
Figure 191:
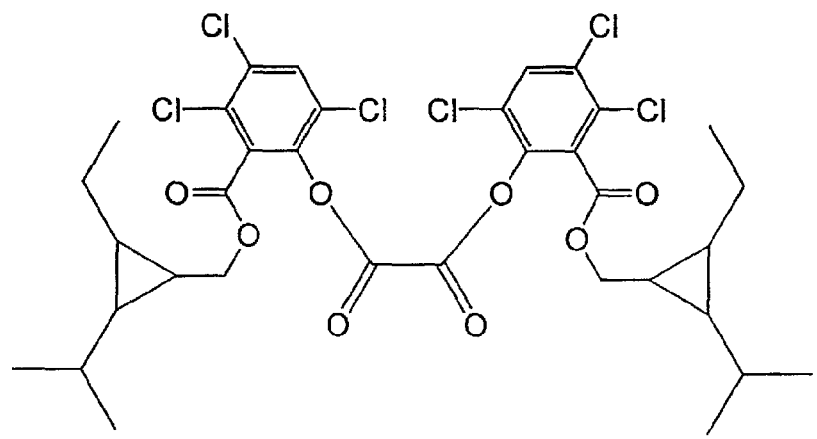
Figure 192:
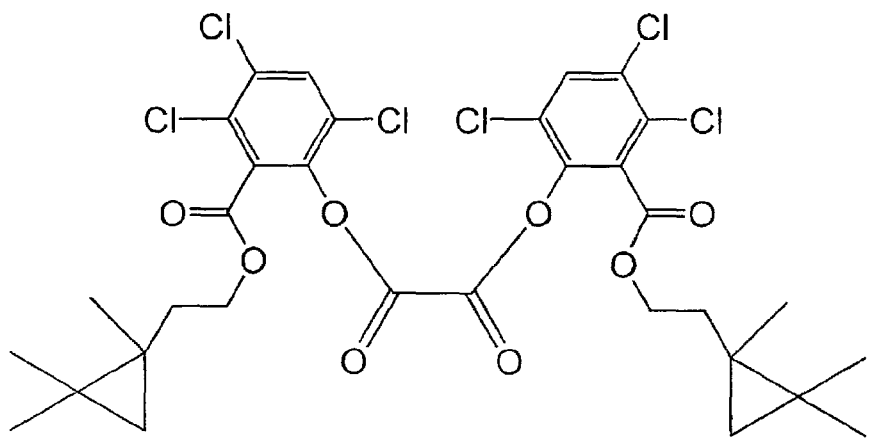
Figure 193:
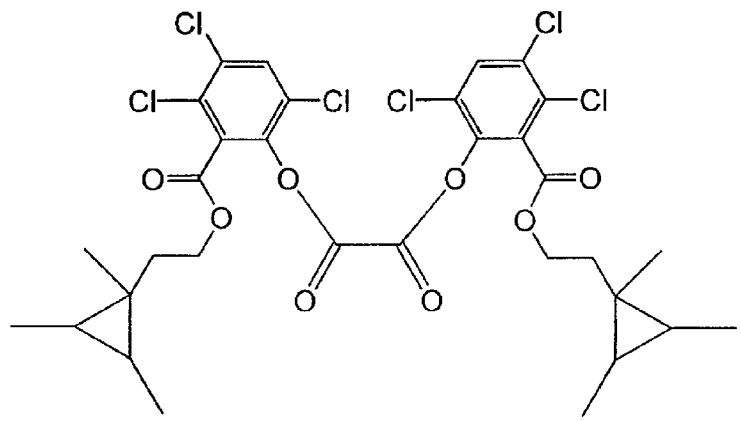
Figure 194:
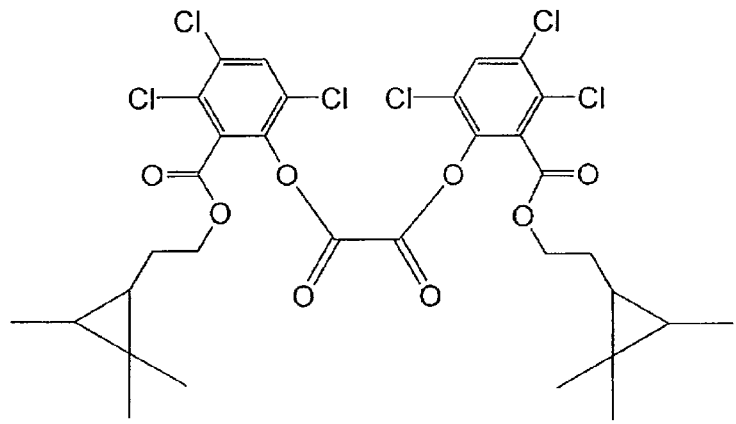
Figure 195:
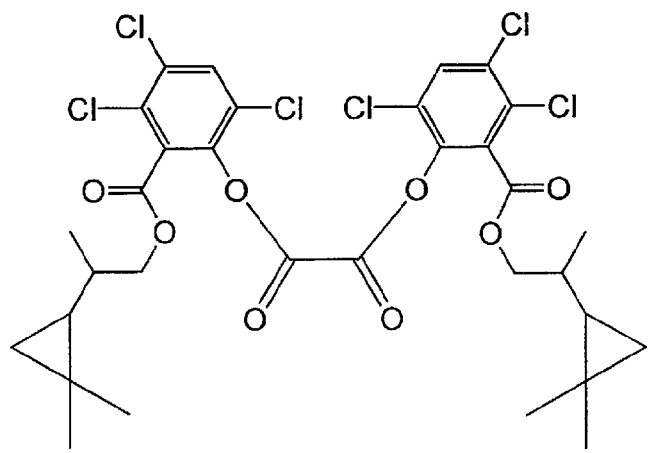
Figure 196:
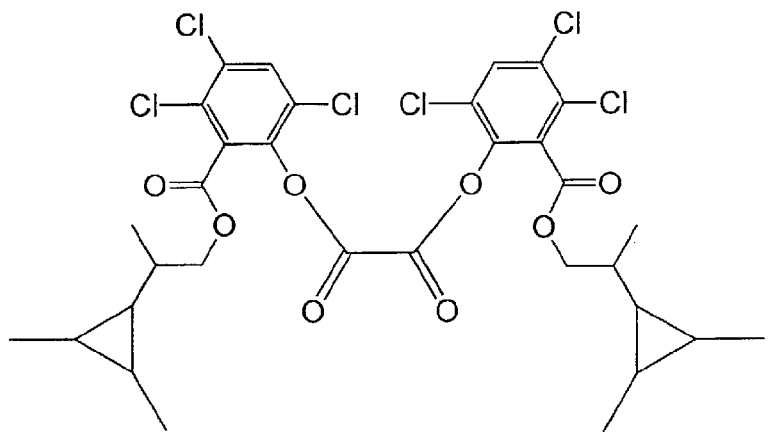
Figure 197:
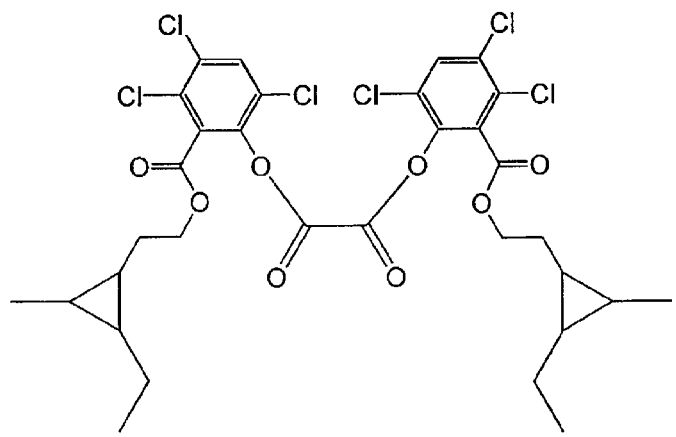
Figure 198:
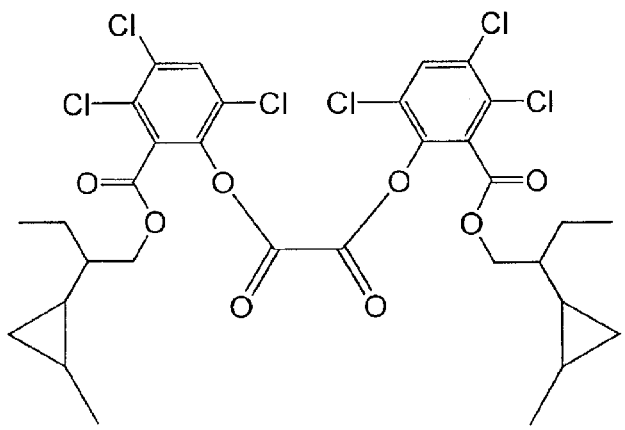
Figure 199:
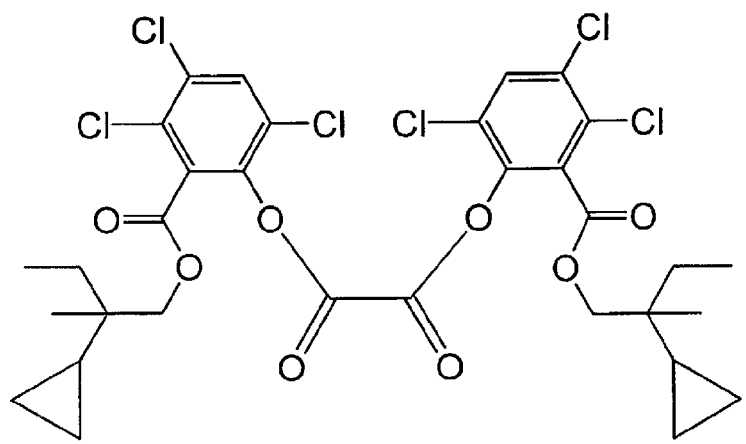
Figure 200:
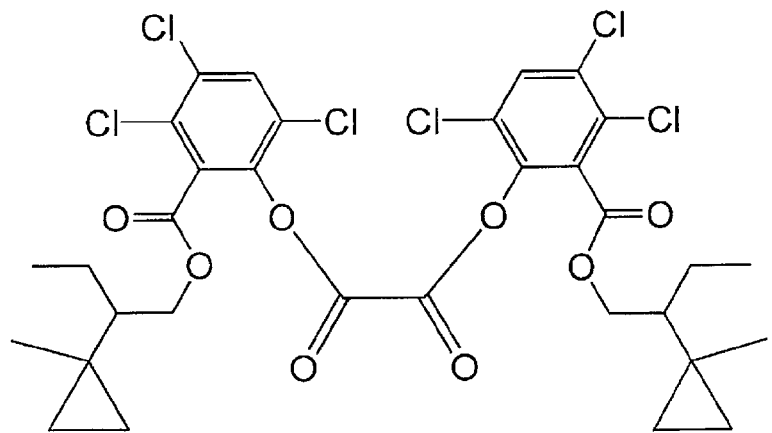
Figure 201:
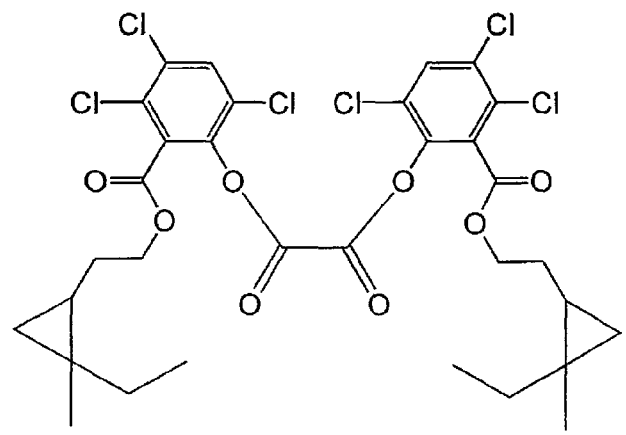
Figure 202:
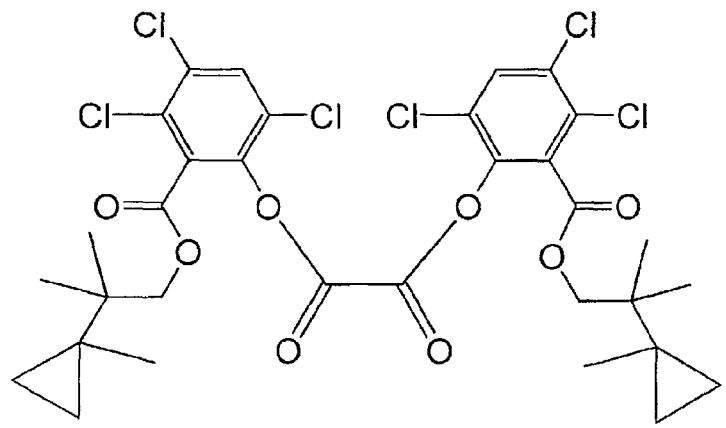
Figure 203:
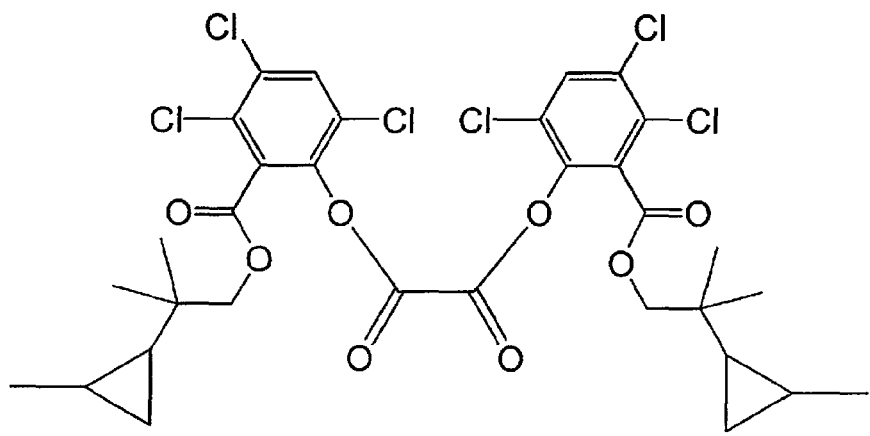
Figure 204:
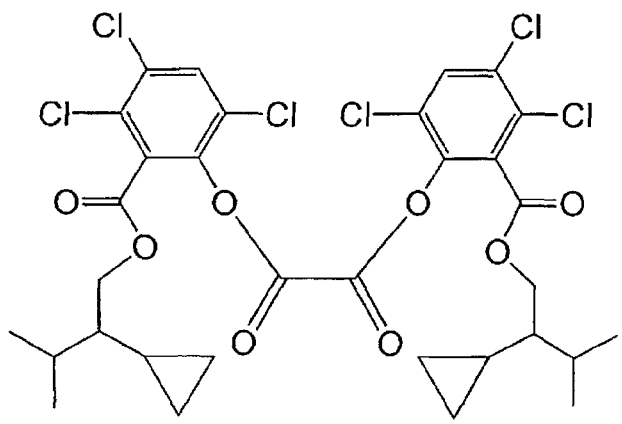
Figure 205:
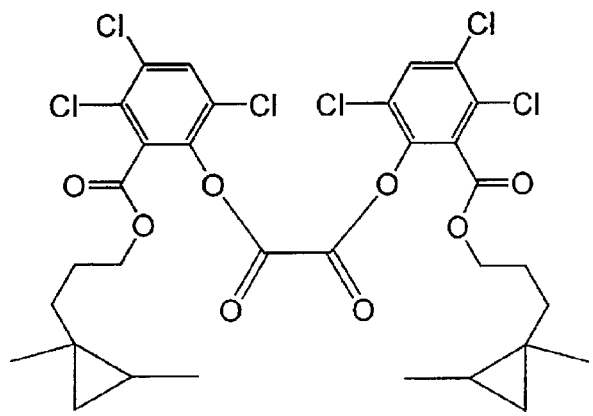
Figure 206:
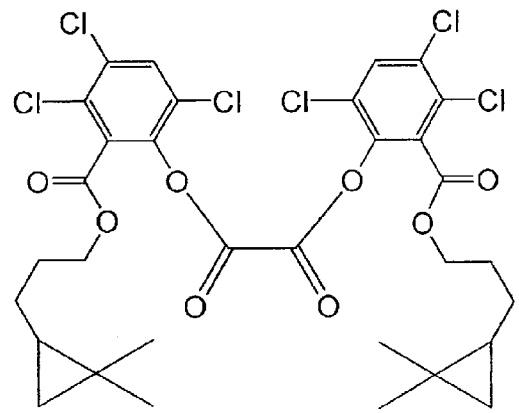
Figure 207:
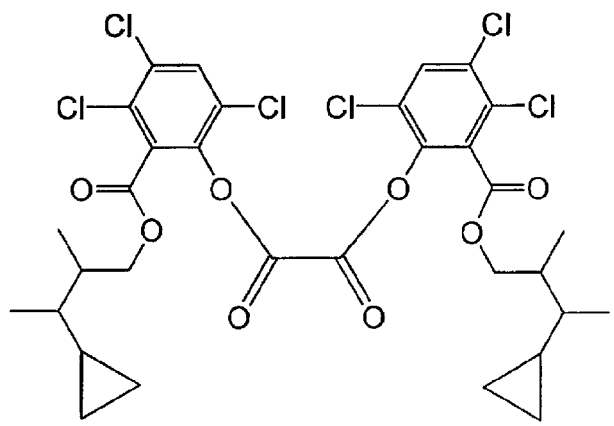
Figure 208:
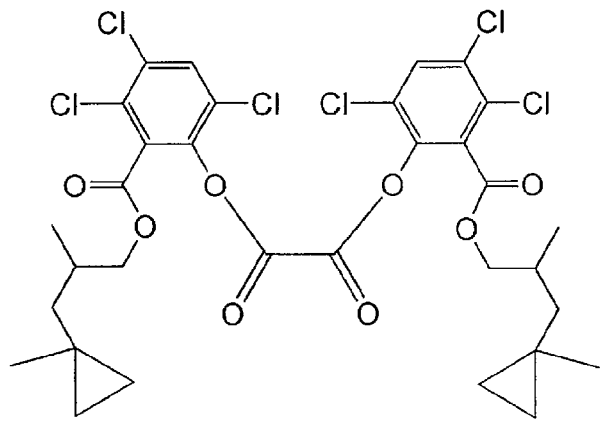
Figure 209:
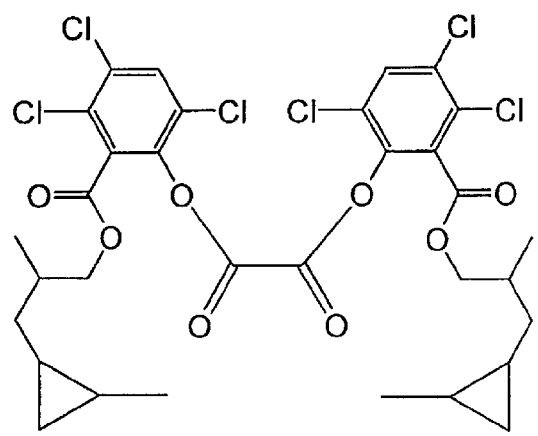
Figure 210:
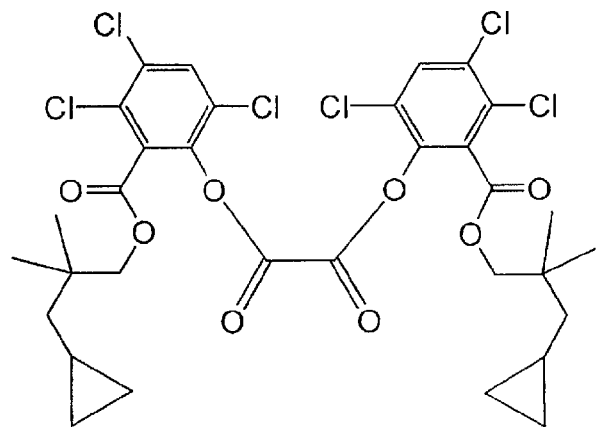
Figure 211:
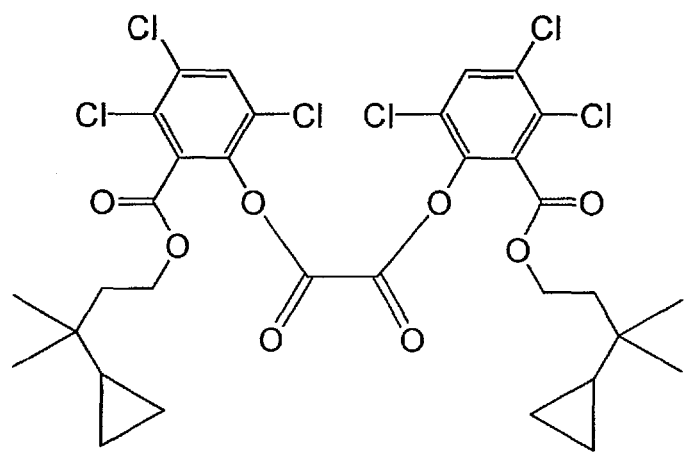
Figure 212:
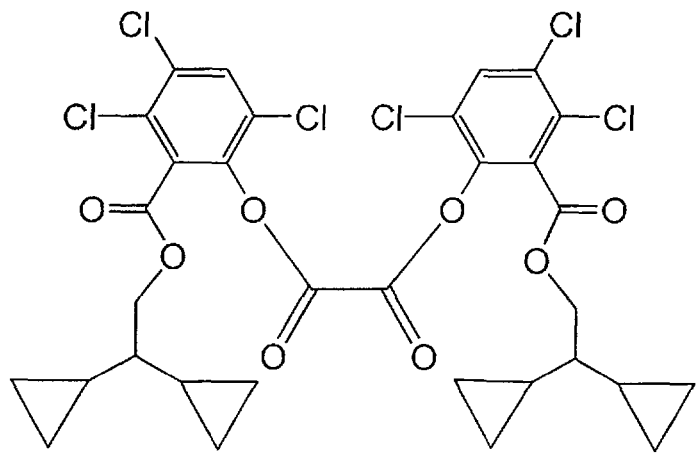
Figure 213:
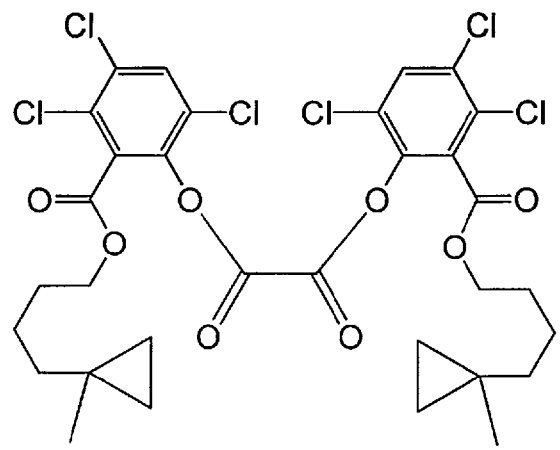
Figure 214:
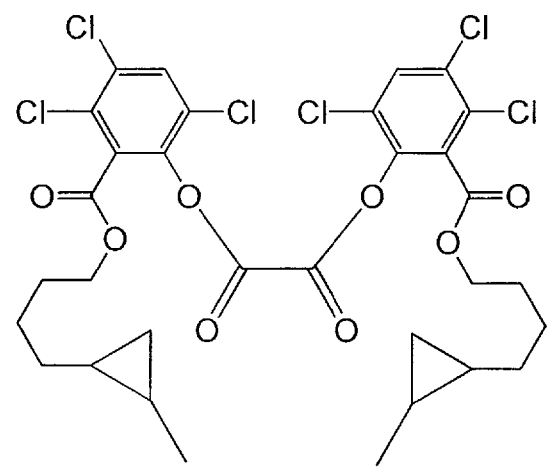
Figure 215:
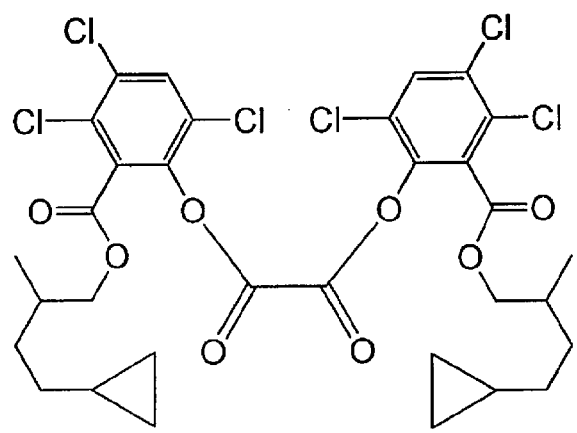
Figure 216:
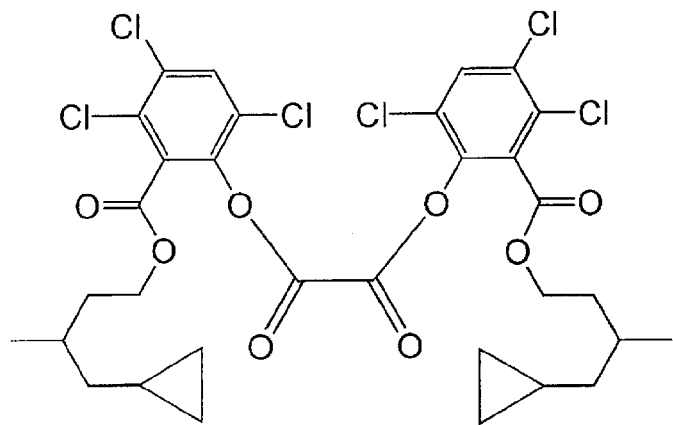
Figure 217:
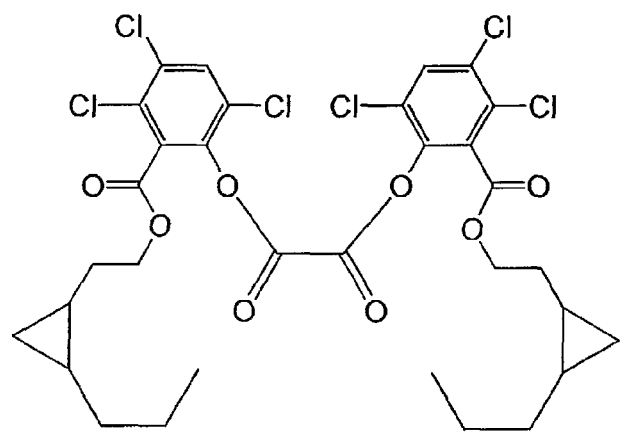
Figure 218:
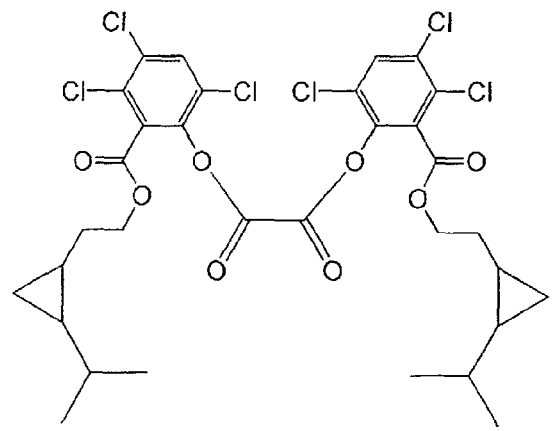
Figure 219:
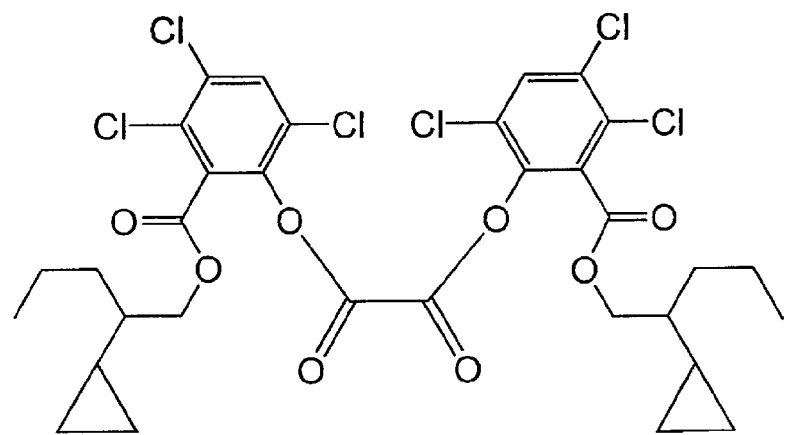
Figure 220:
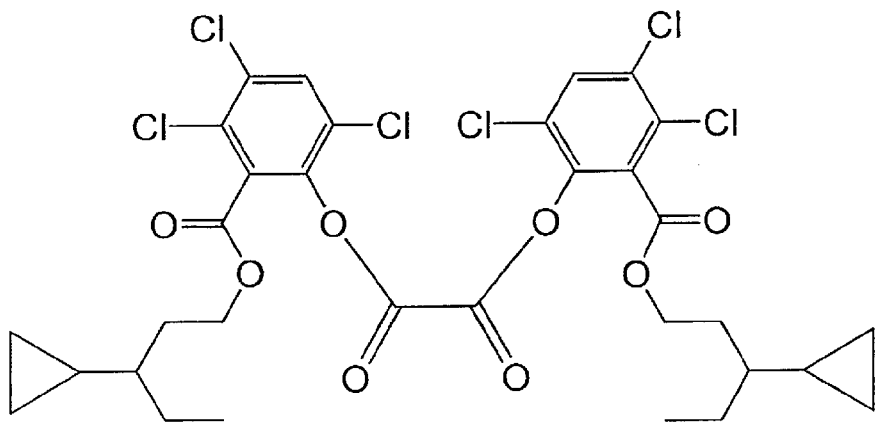
Figure 221:
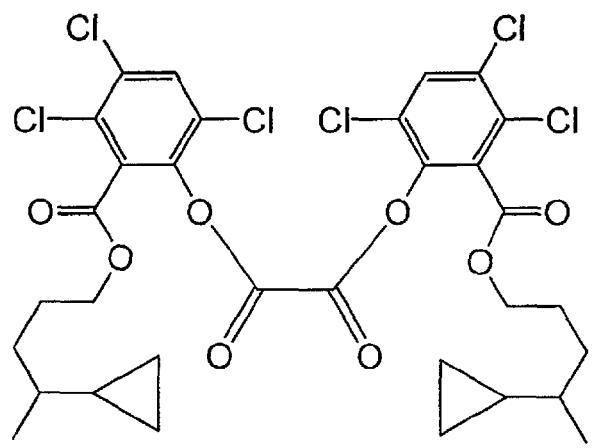
Figure 222:
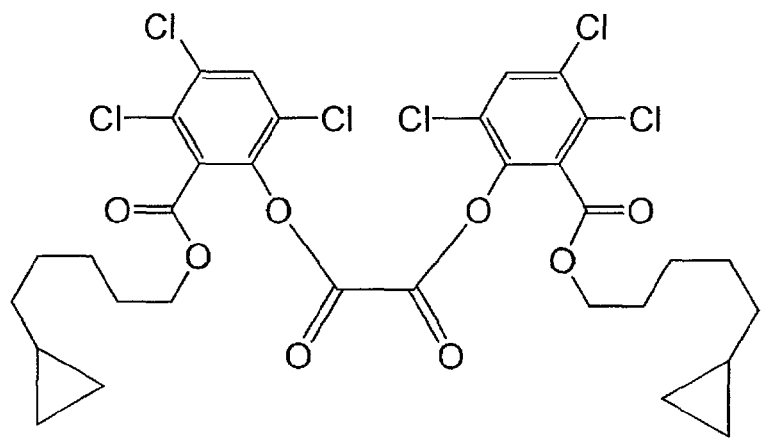
Figure 223:
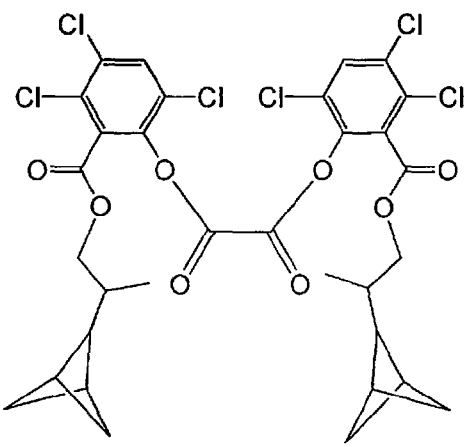
Figure 224:
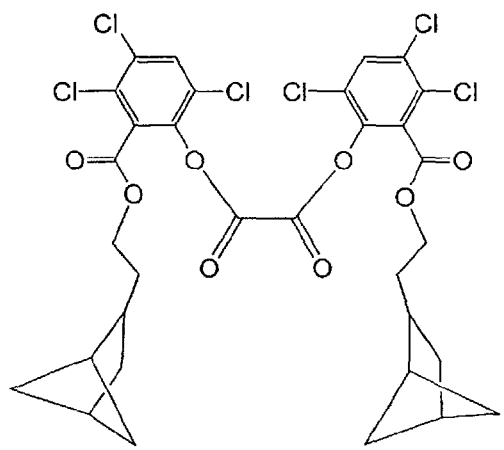
Figure 225:
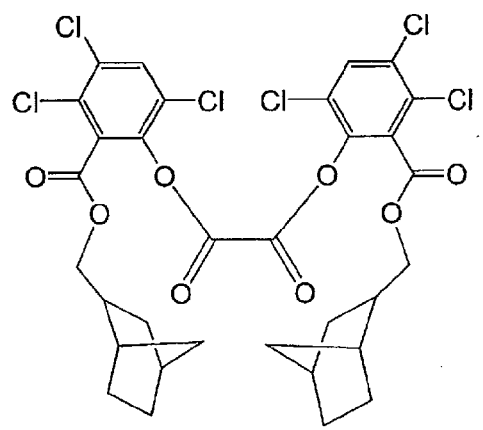
Figure 226:
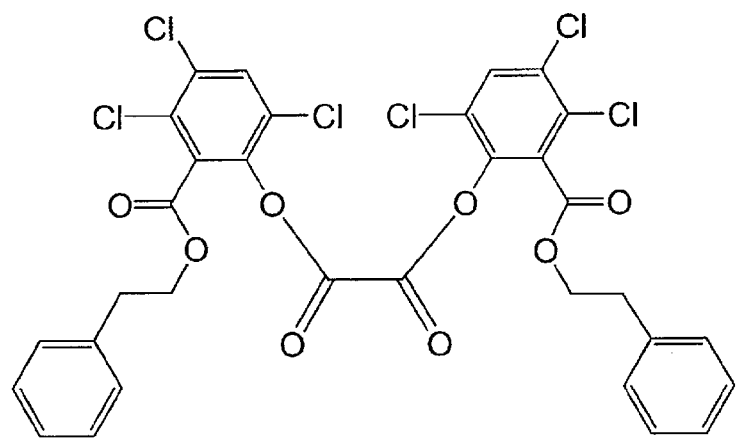
Figure 227:
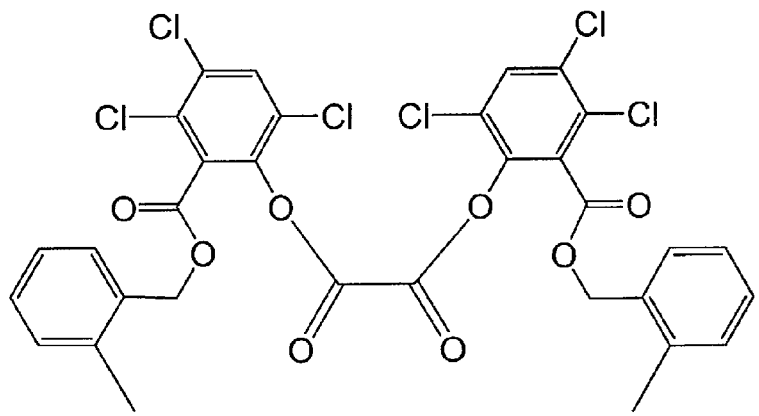
Figure 228:
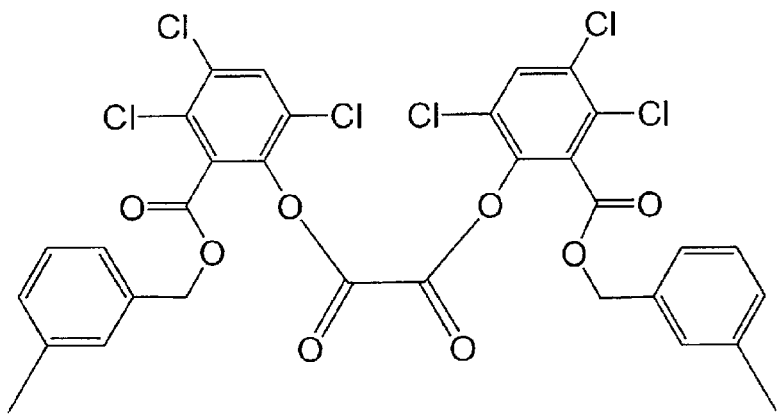
Figure 229:
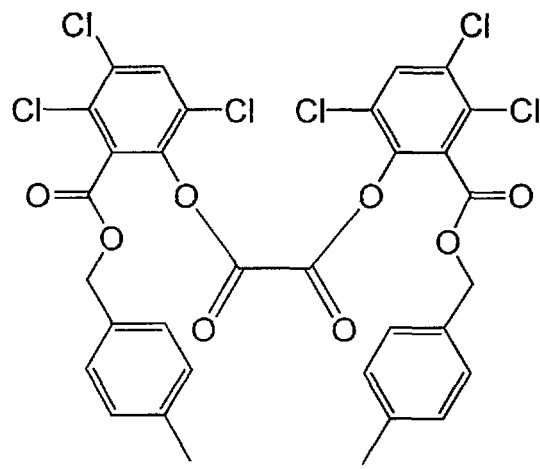
Figure 230:
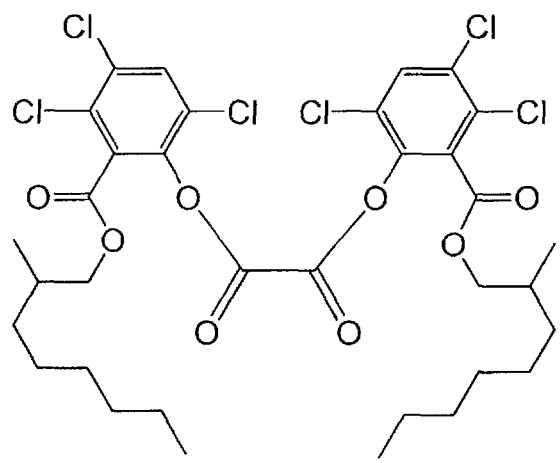
Figure 231:
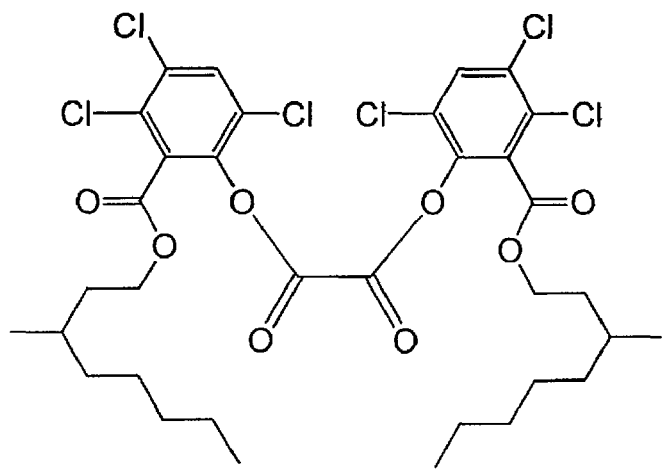
Figure 232:
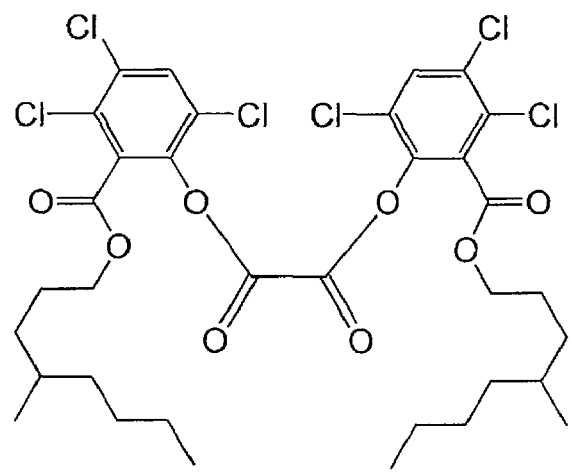
Figure 233:
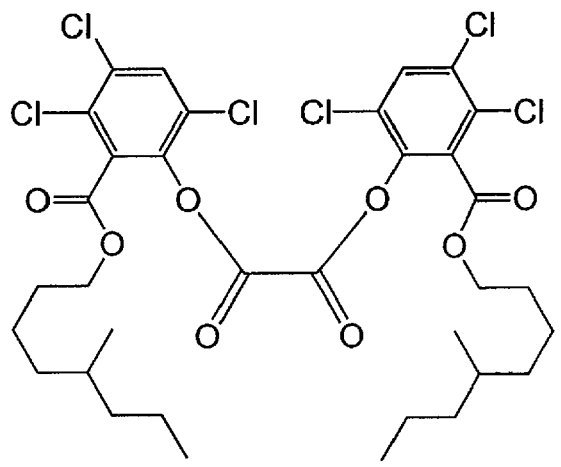
Figure 234:
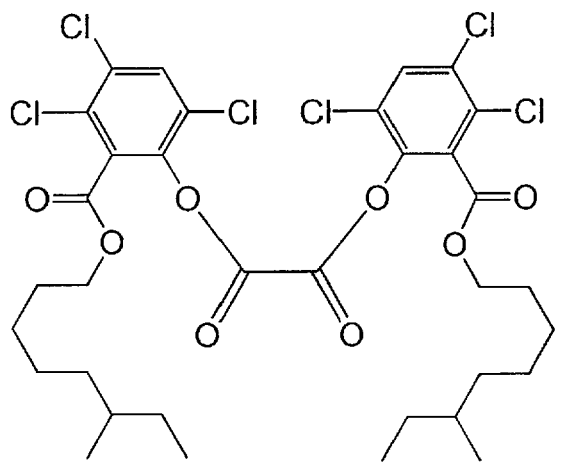
Figure 235:
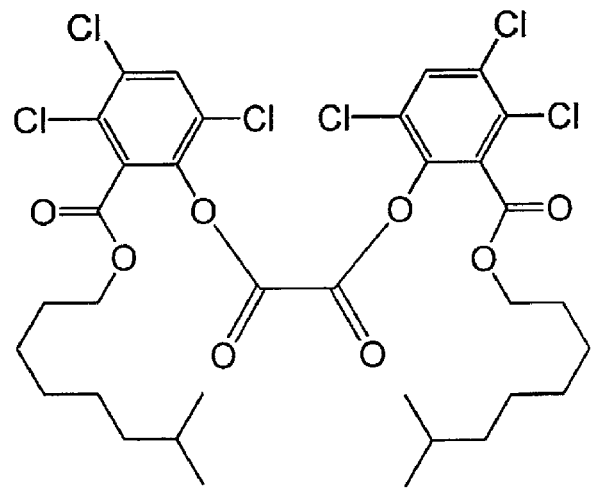
Figure 236:
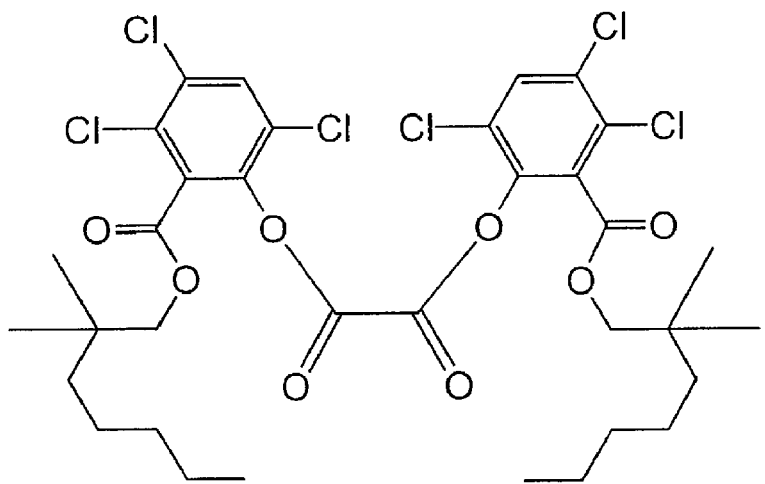
Figure 237:
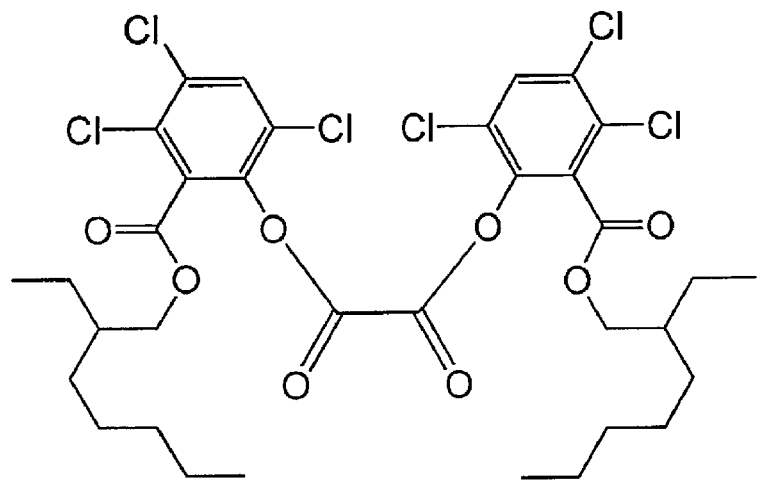
Figure 238:
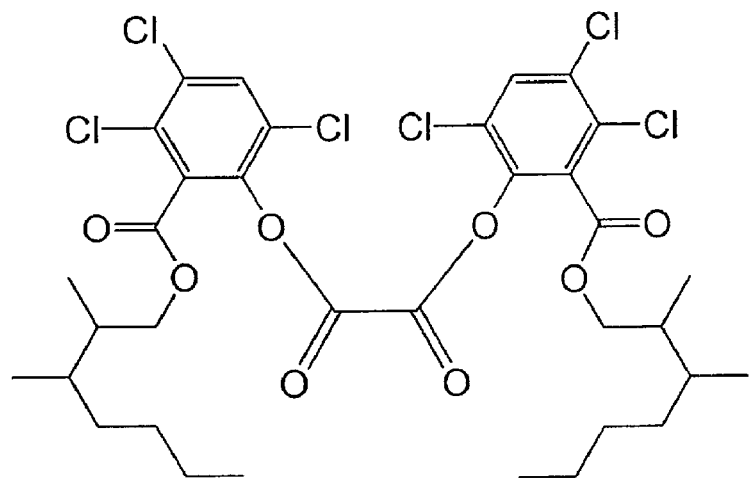
Figure 239:
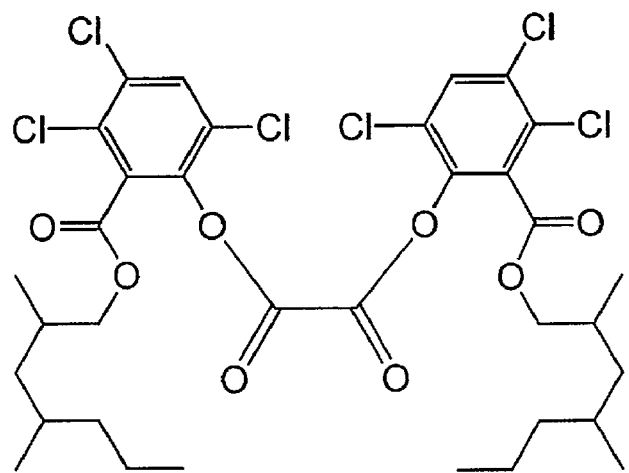
Figure 240:
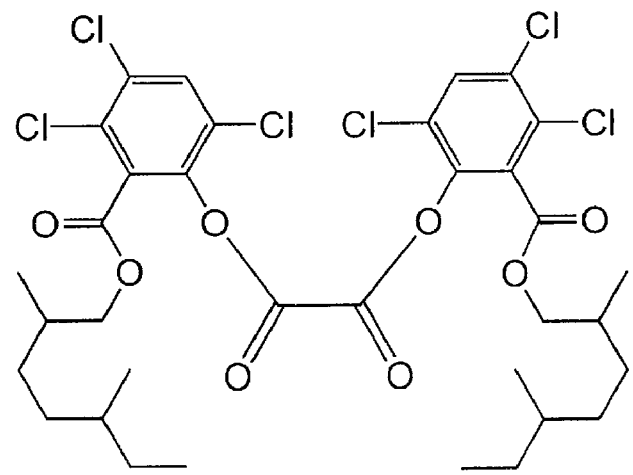
Figure 241:
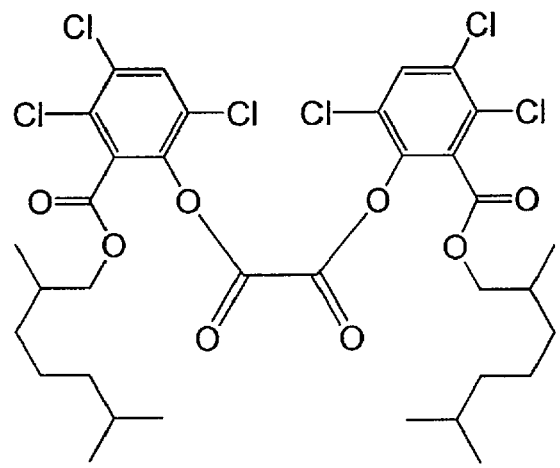
Figure 242:
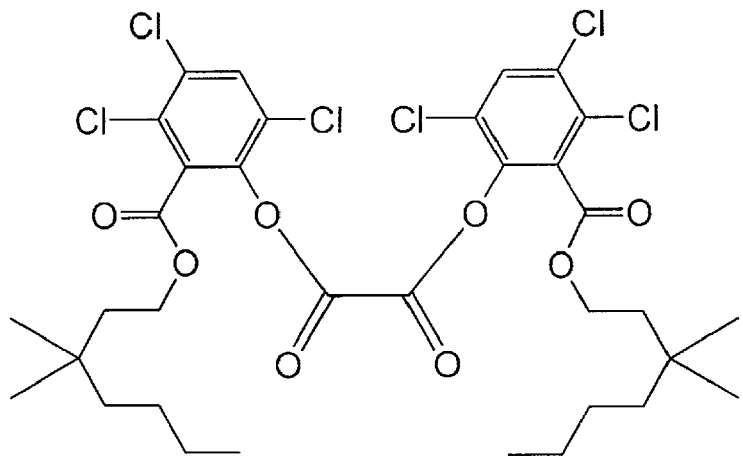
Figure 243:
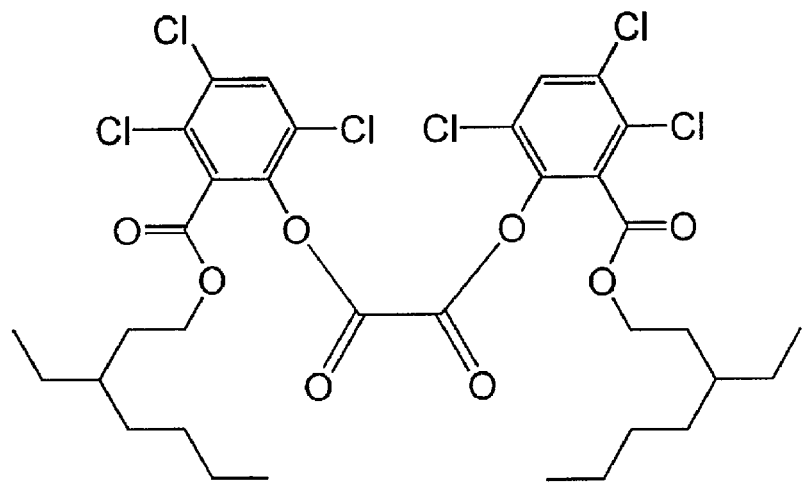
Figure 244:
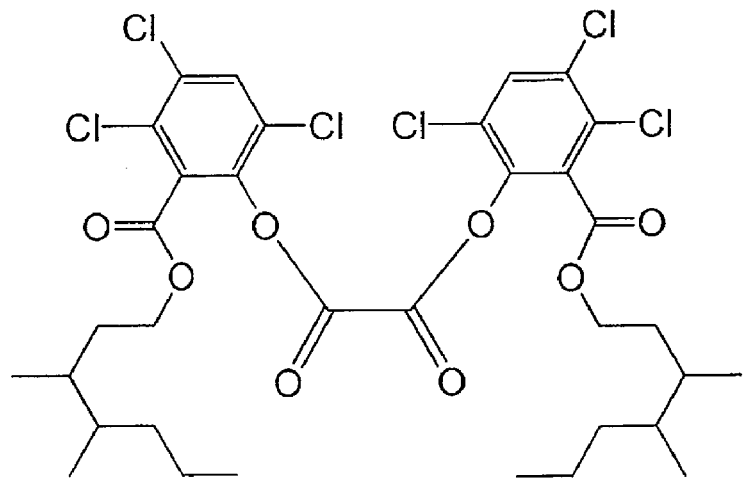
Figure 245:
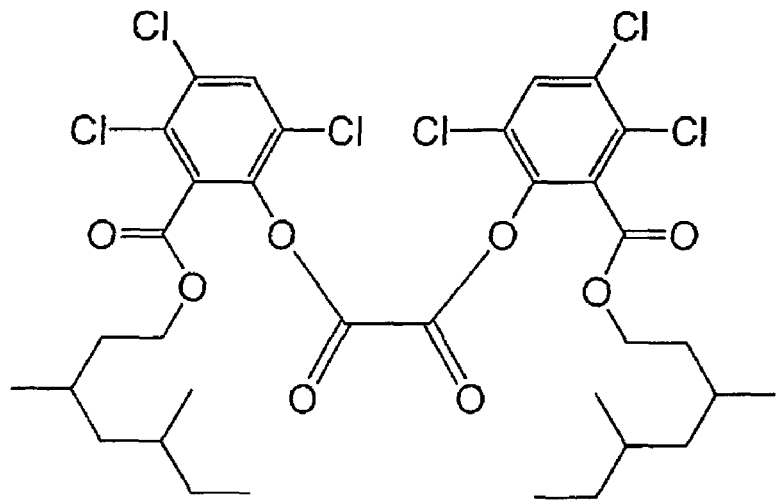
Figure 246:
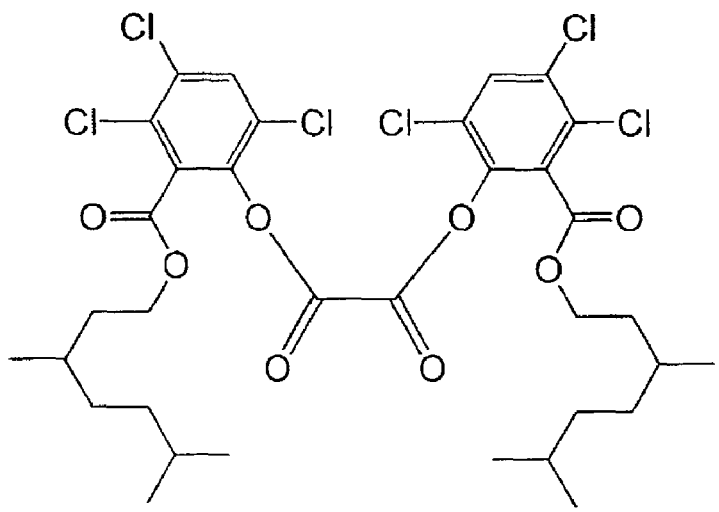
Figure 247:
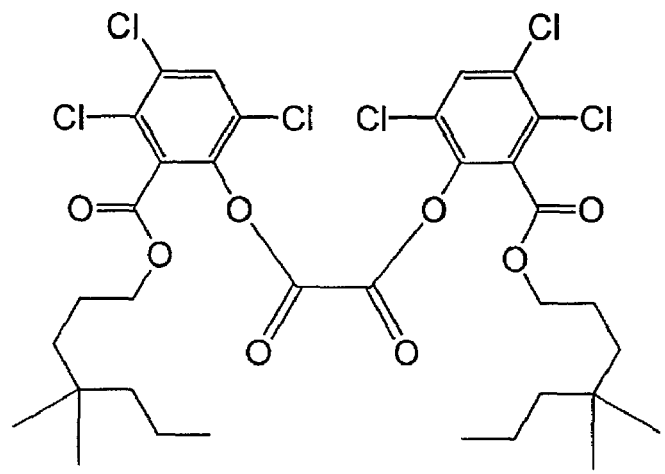
Figure 248:
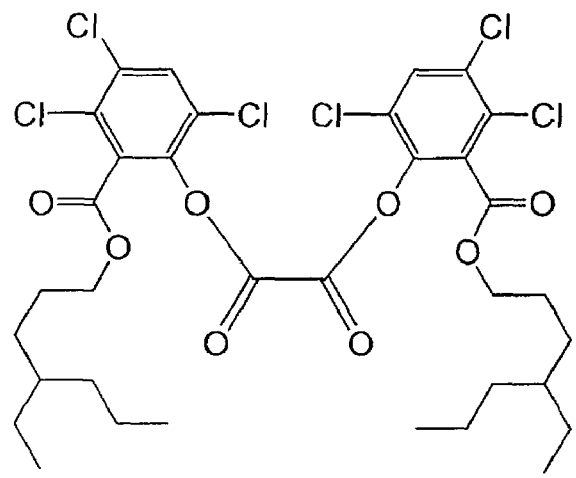
Figure 249:
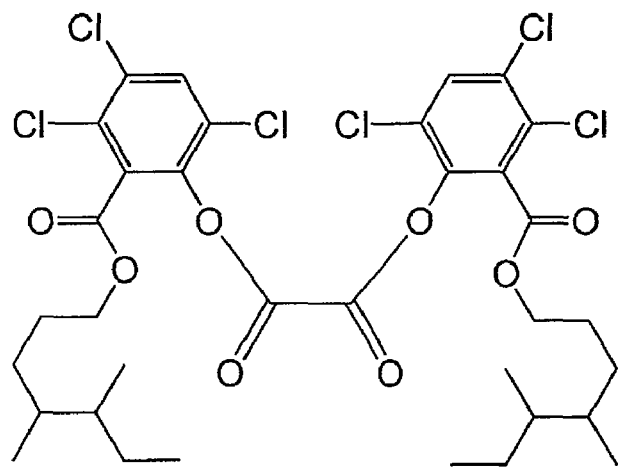
Figure 250:
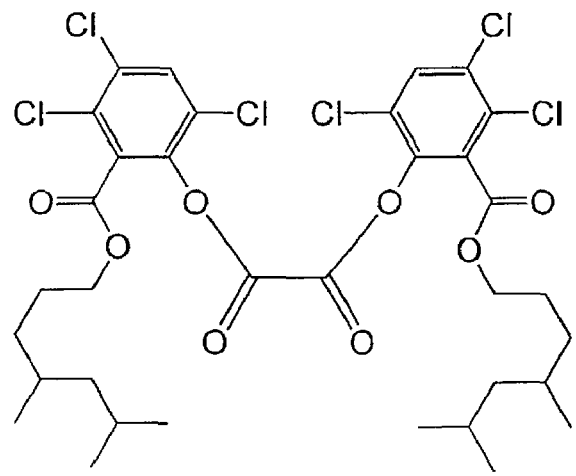
Figure 251:
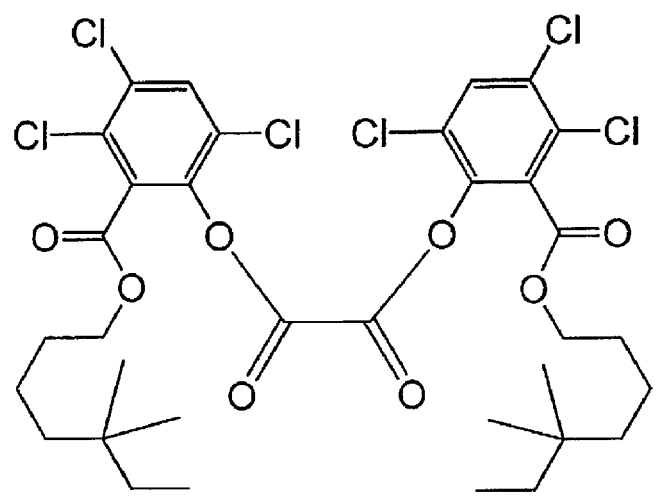
Figure 252:
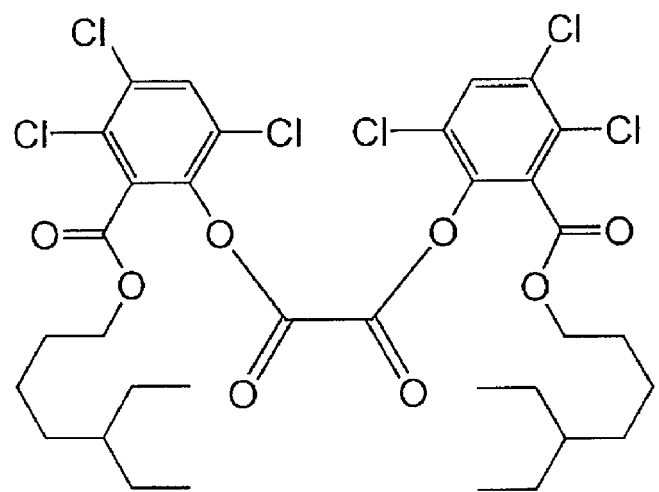
Figure 253:
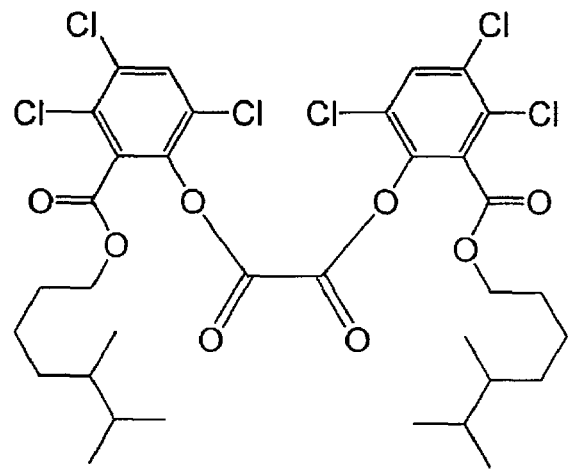
Figure 254:
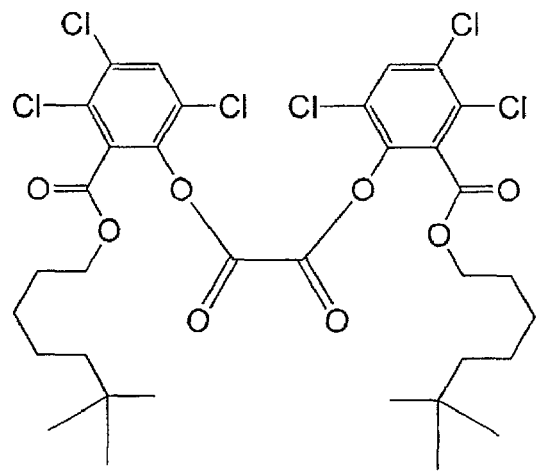
Figure 255:
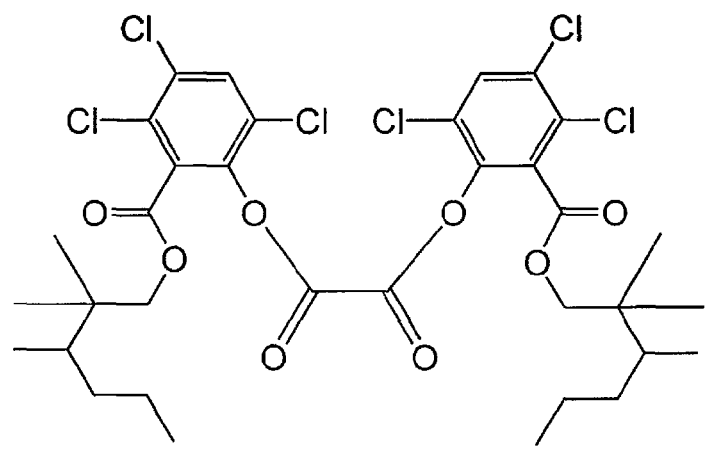
Figure 256:
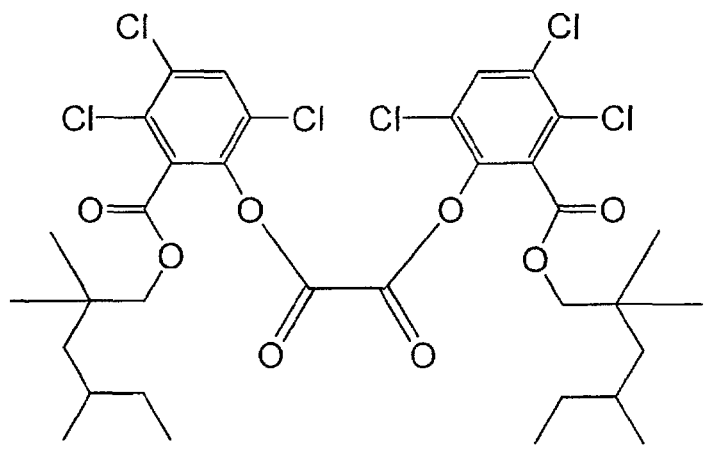
Figure 257:
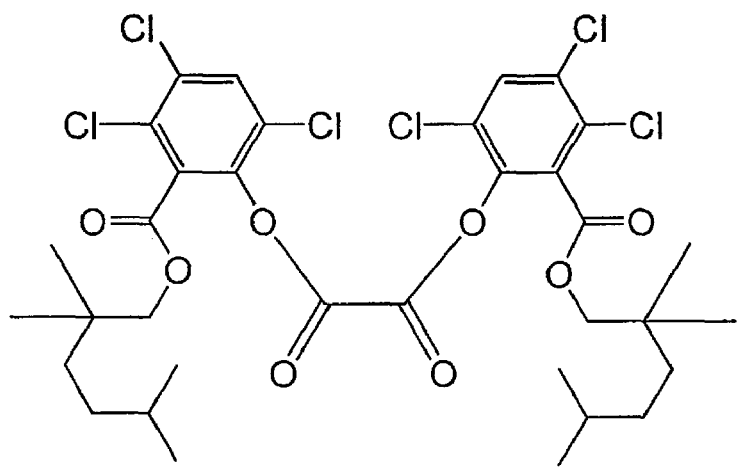
Figure 258:
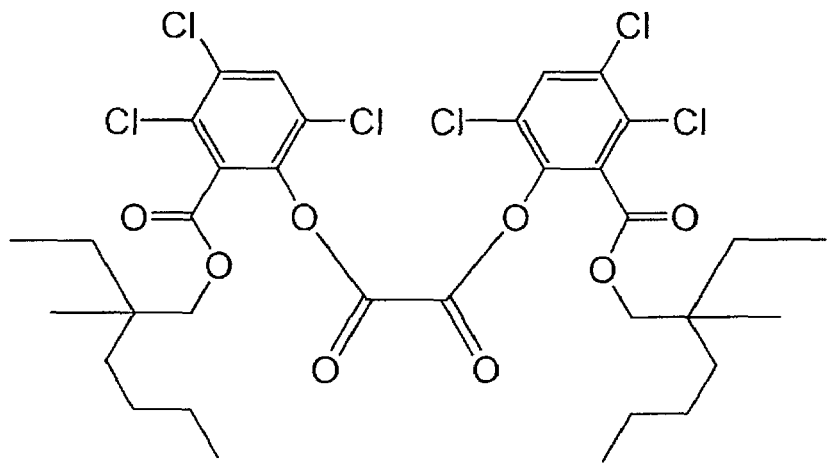
Figure 259:
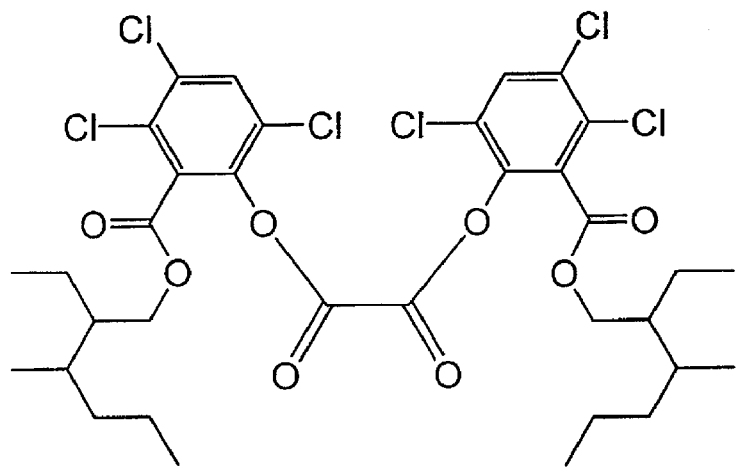
Figure 260:
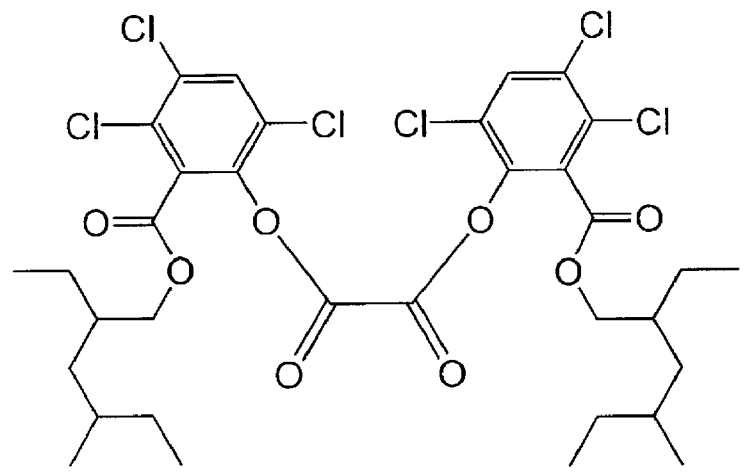
Figure 261:
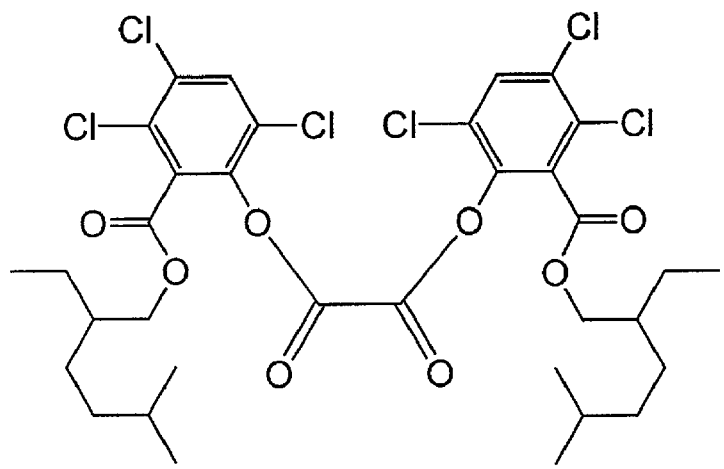
Figure 262:
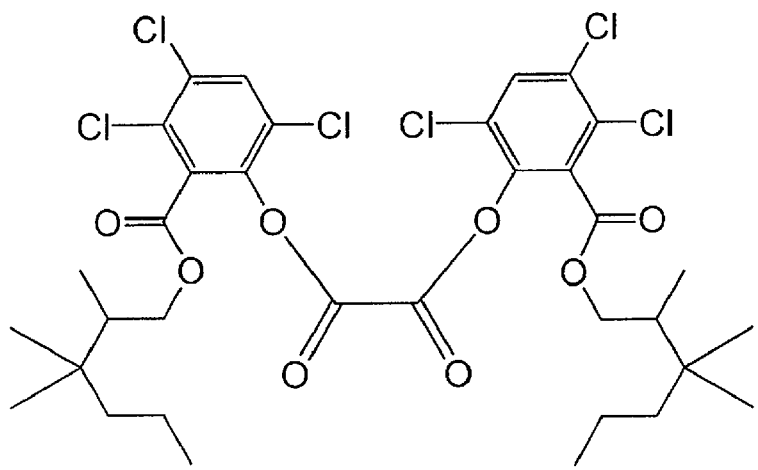
Figure 263:
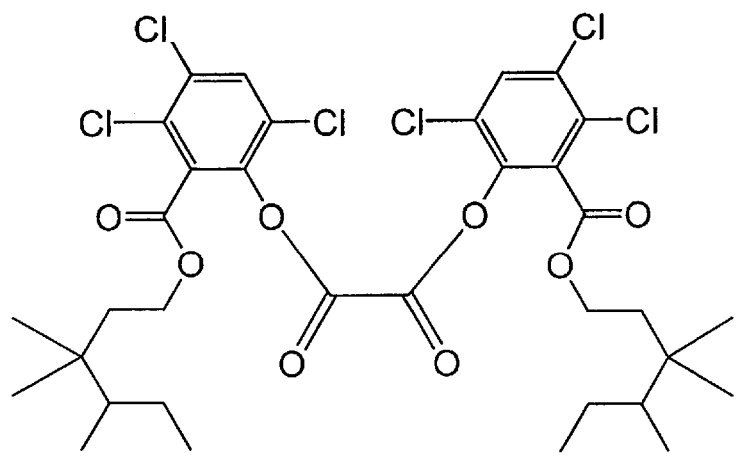
Figure 264:
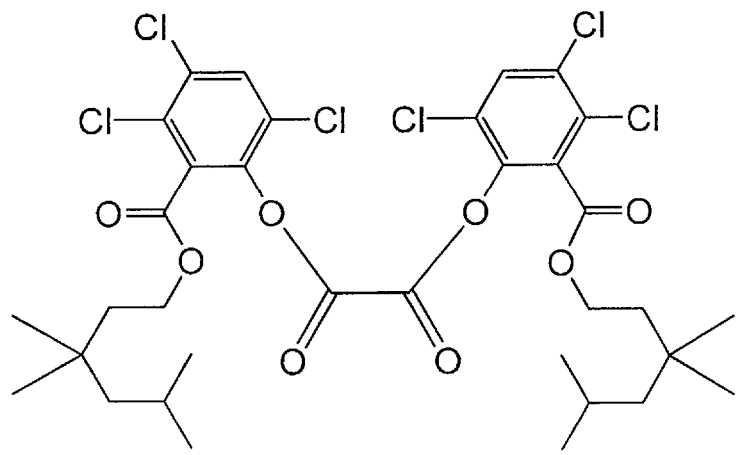
Figure 265:
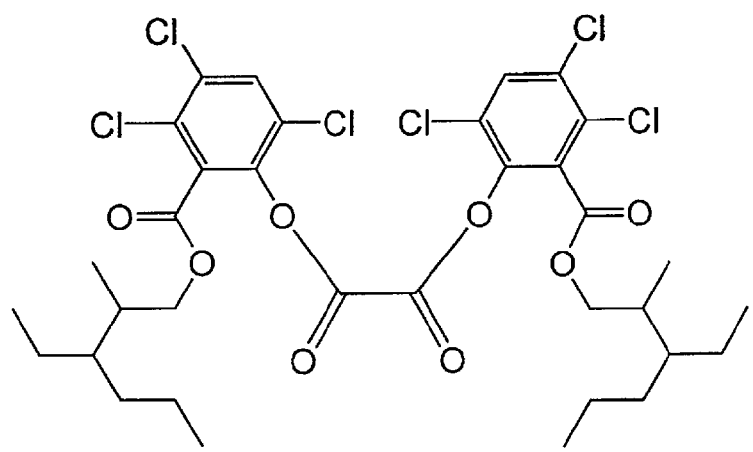
Figure 266:
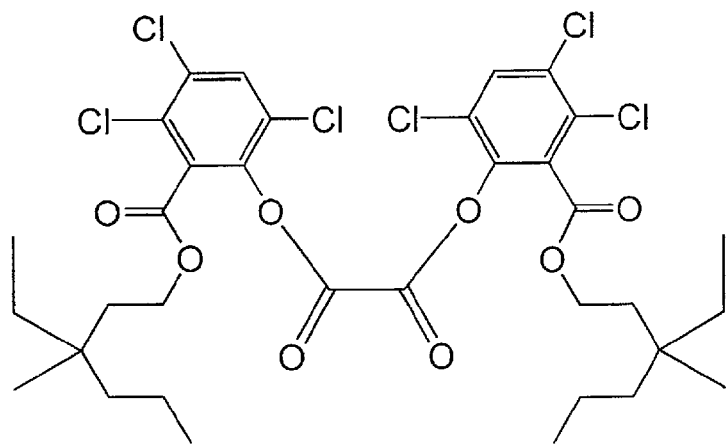
Figure 267:
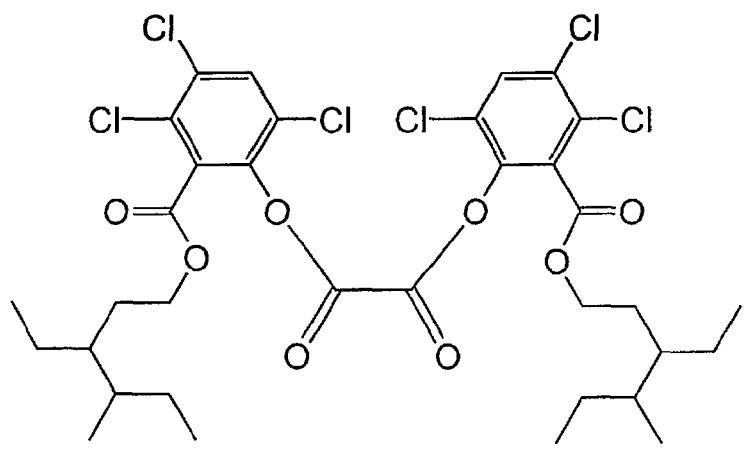
Figure 268:
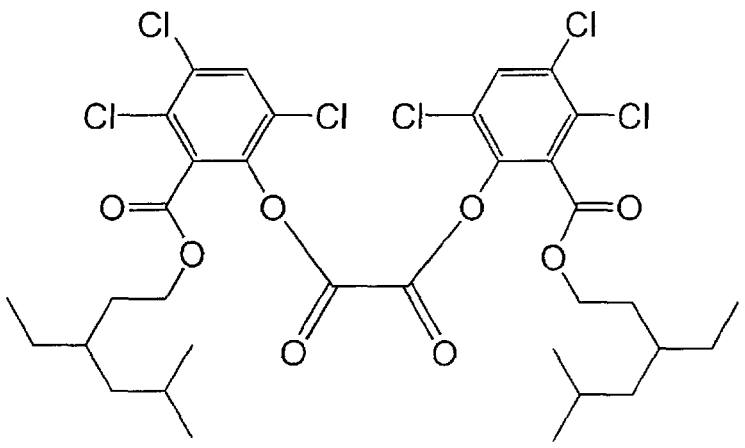
Figure 269:
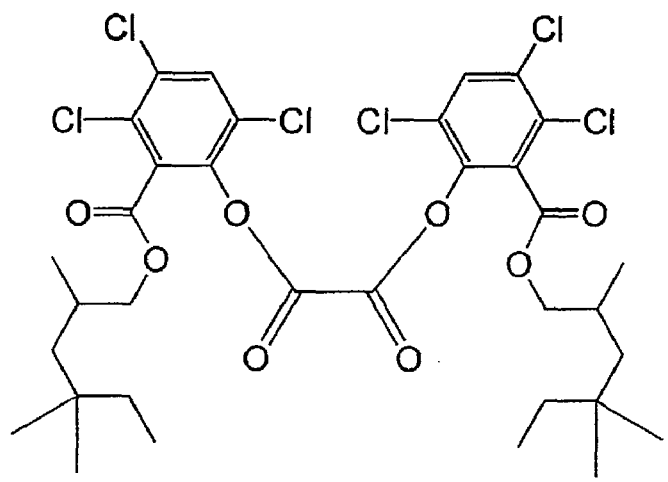
Figure 270:
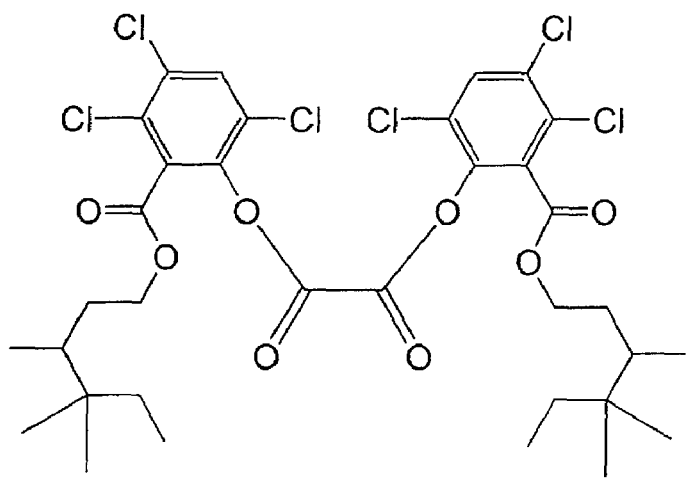
Figure 271:
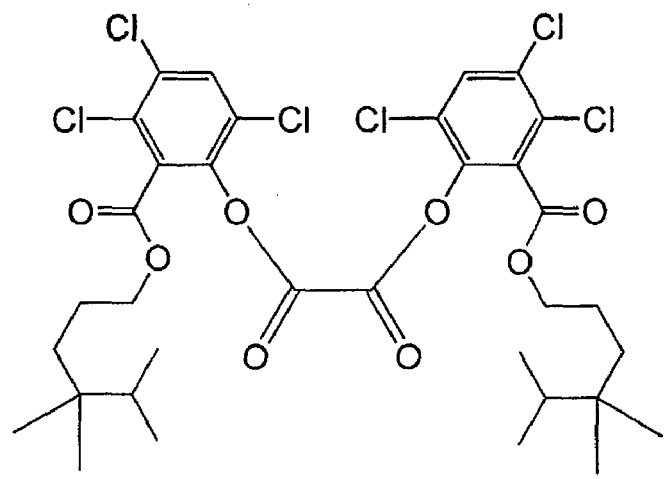
Figure 272:
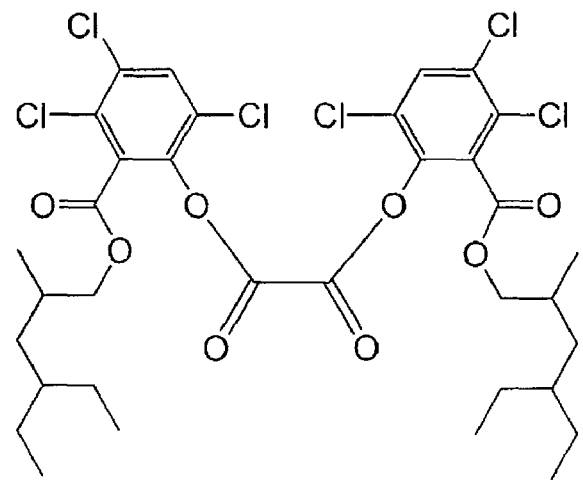
Figure 273:
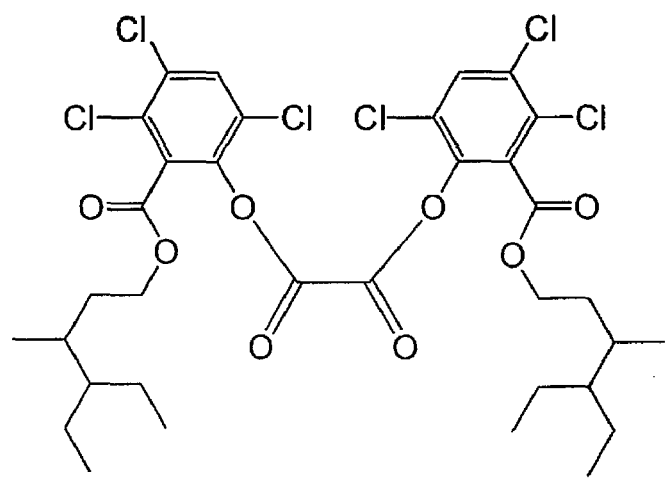
Figure 274:
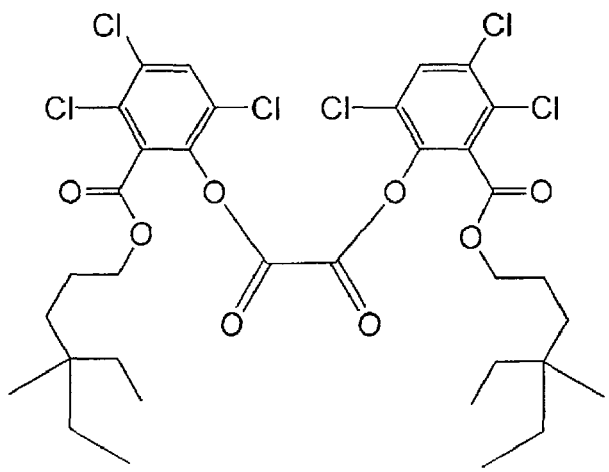
Figure 275:
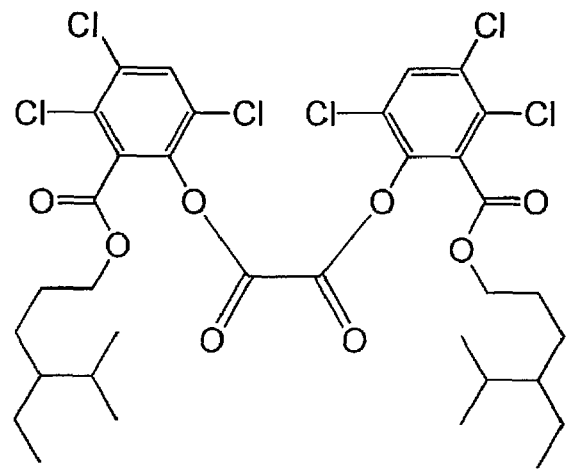
Figure 276:
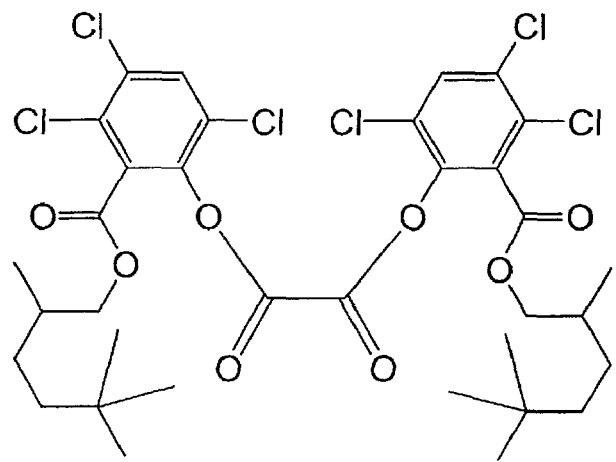
Figure 277:
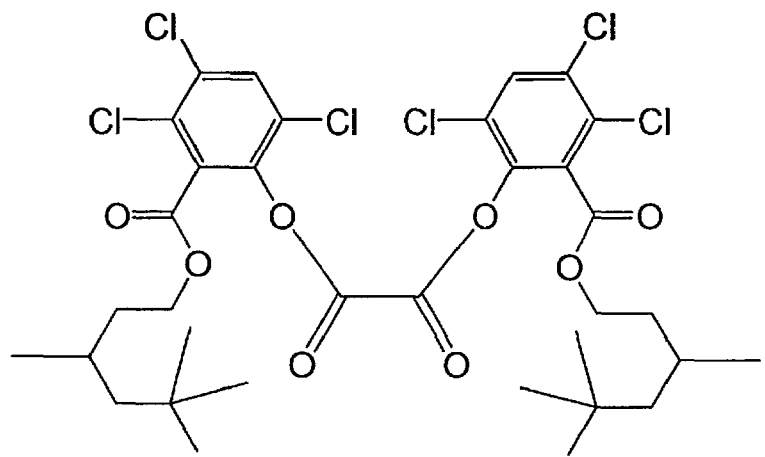
Figure 278:
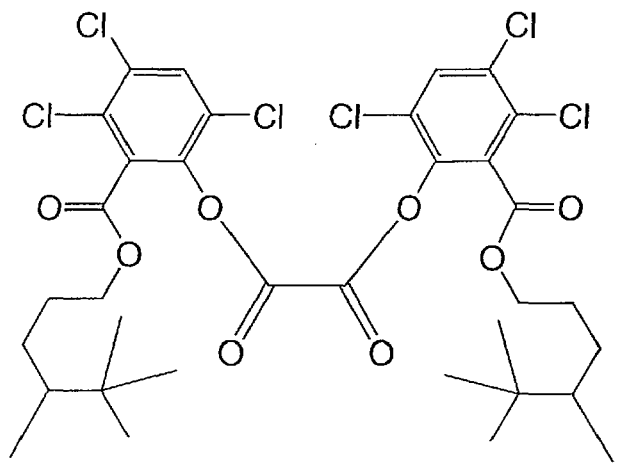
Figure 279:
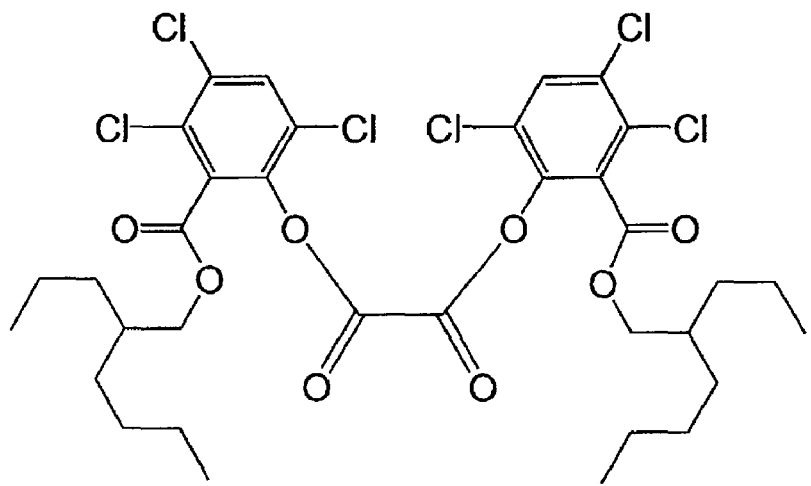
Figure 280:
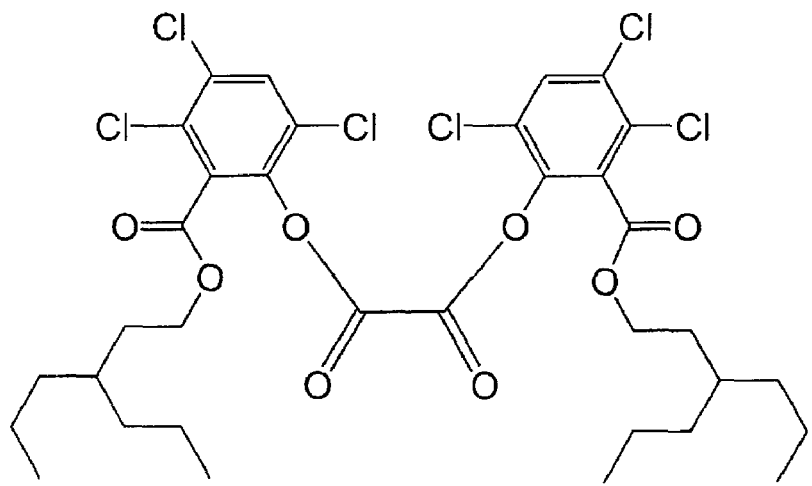
Figure 281:
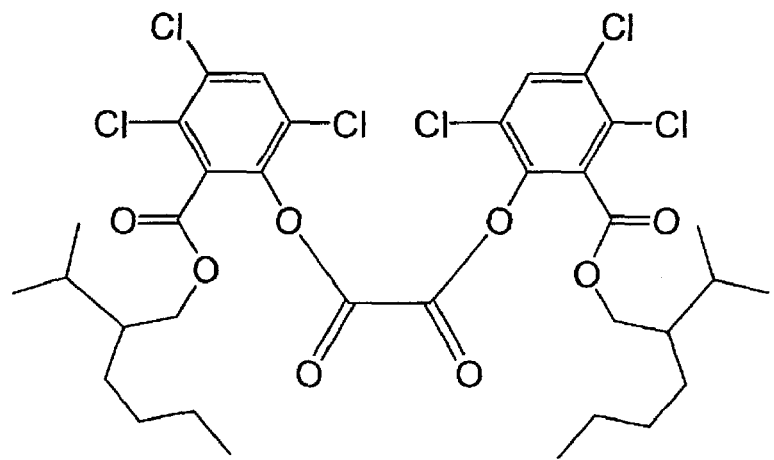
Figure 282:
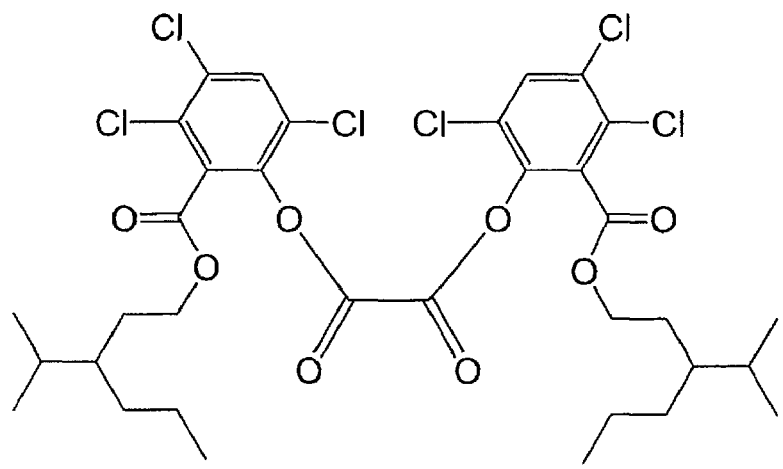
Figure 283:
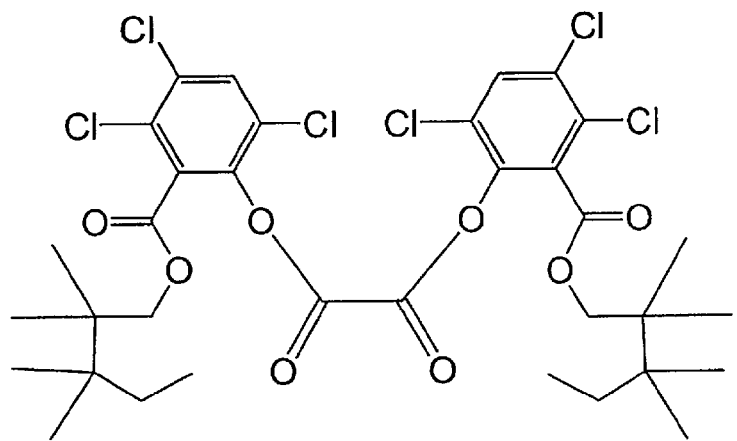
Figure 284:
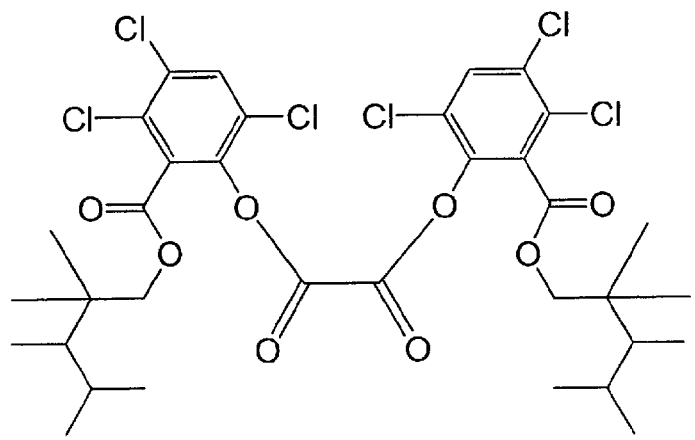
Figure 285:
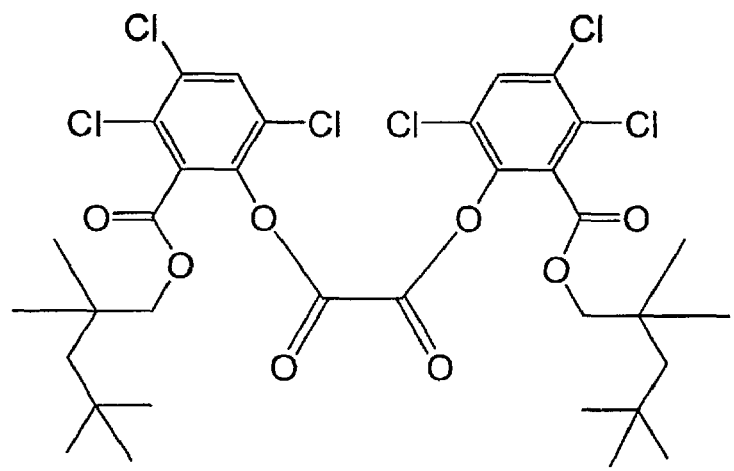
Figure 286:
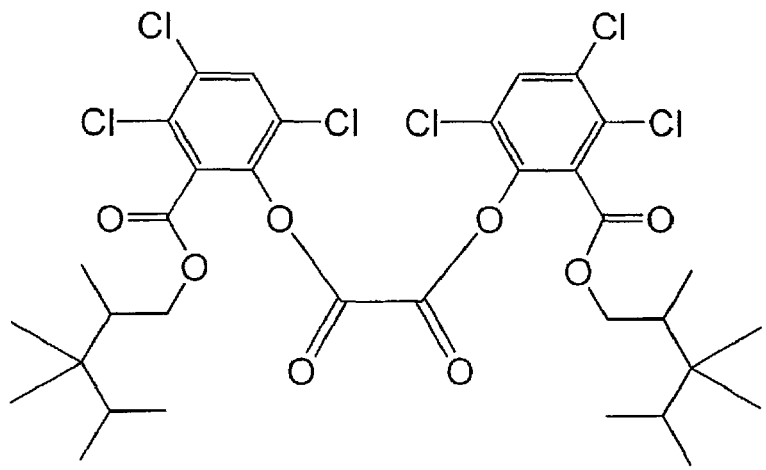
Figure 287:
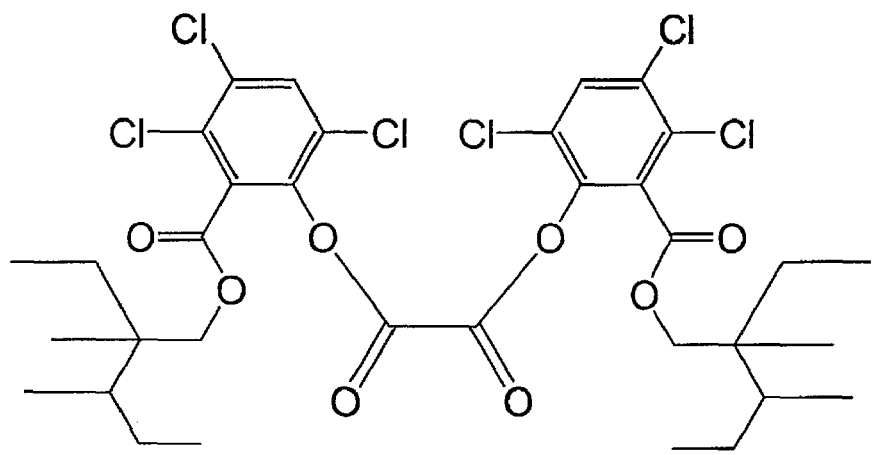
Figure 288:
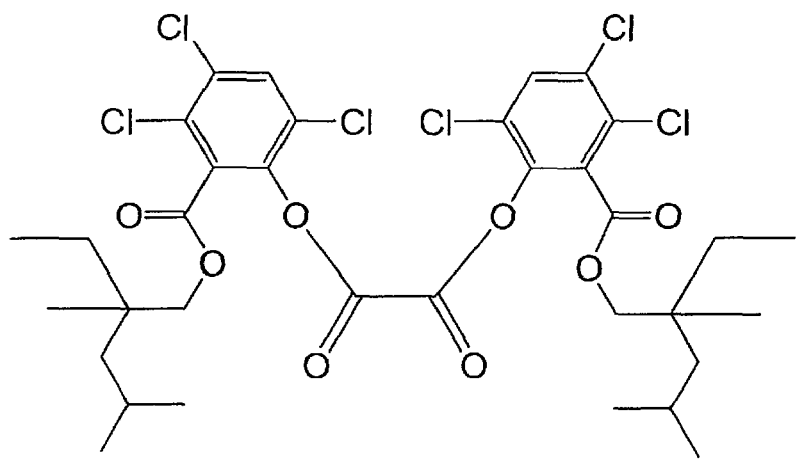
Figure 289:
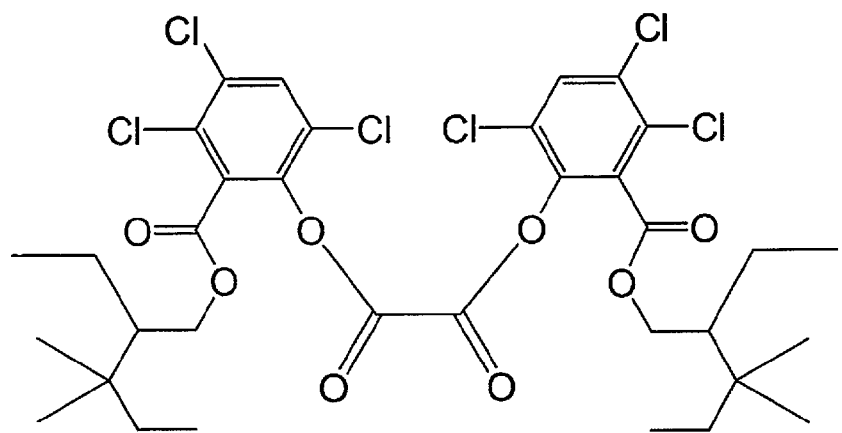
Figure 290:
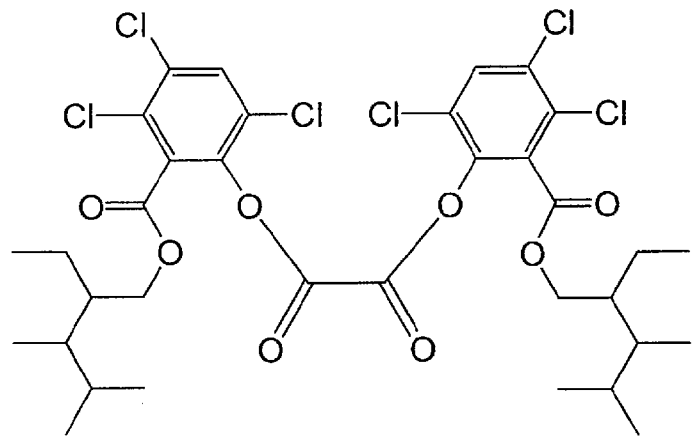
Figure 291:
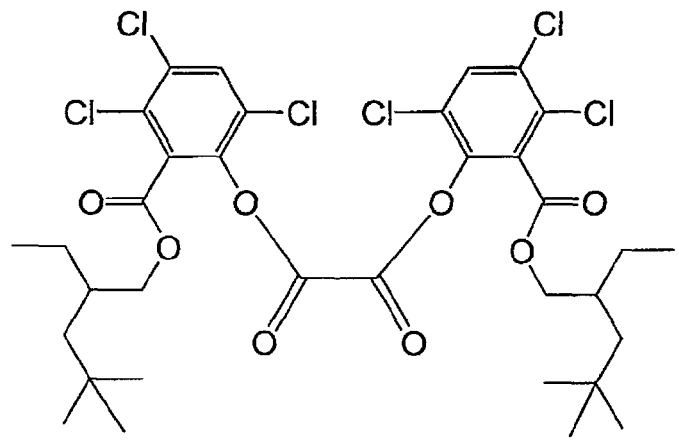
Figure 292:
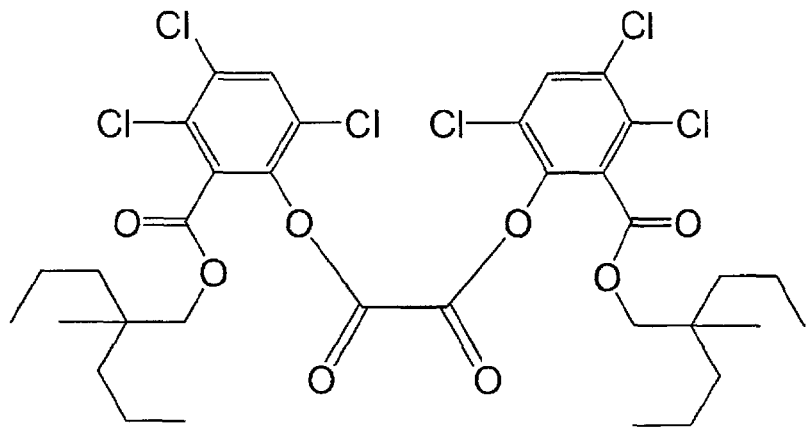
Figure 293:
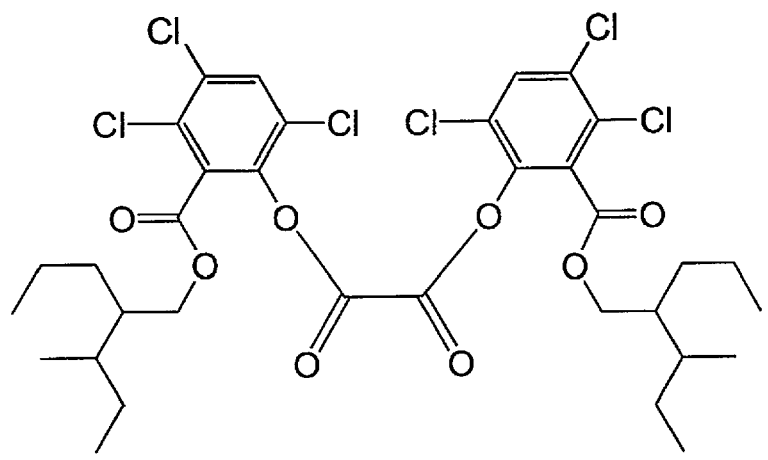
Figure 294:
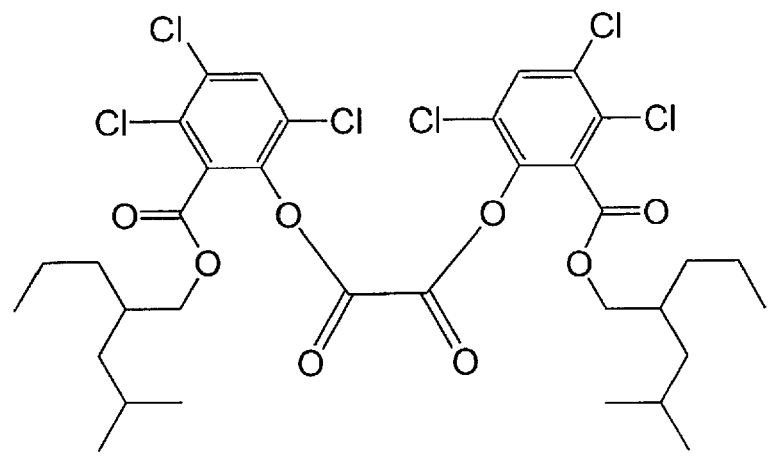
Figure 295:
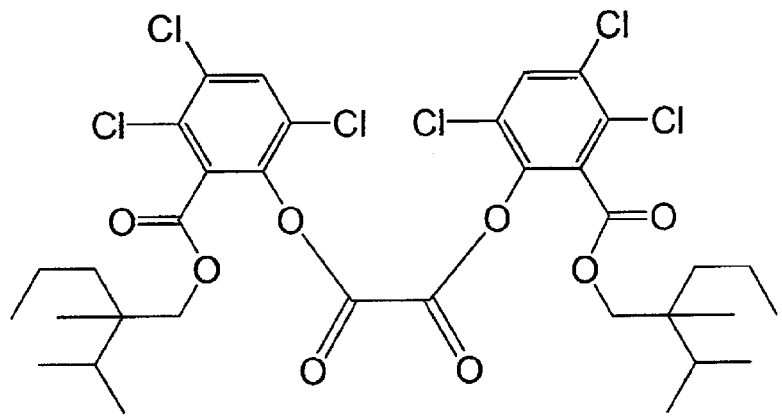
Figure 296:
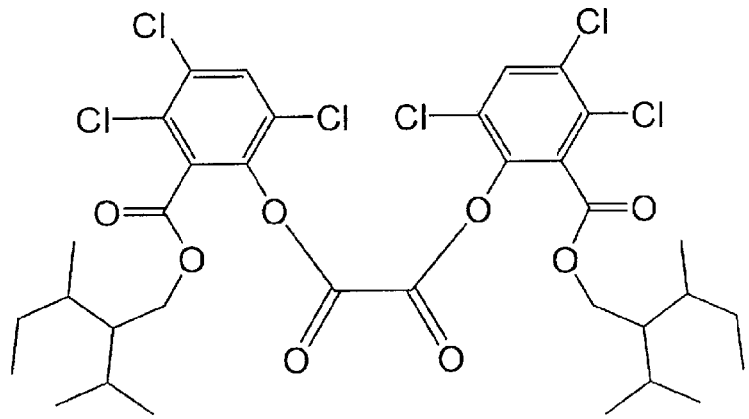
Figure 297:
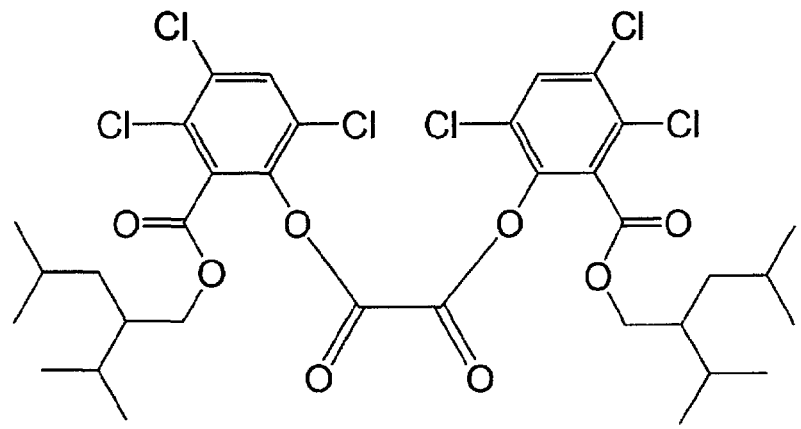
Figure 298:
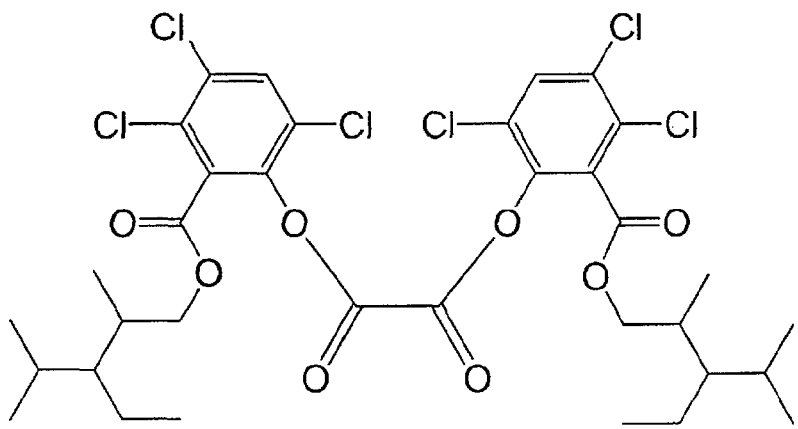
Figure 299:
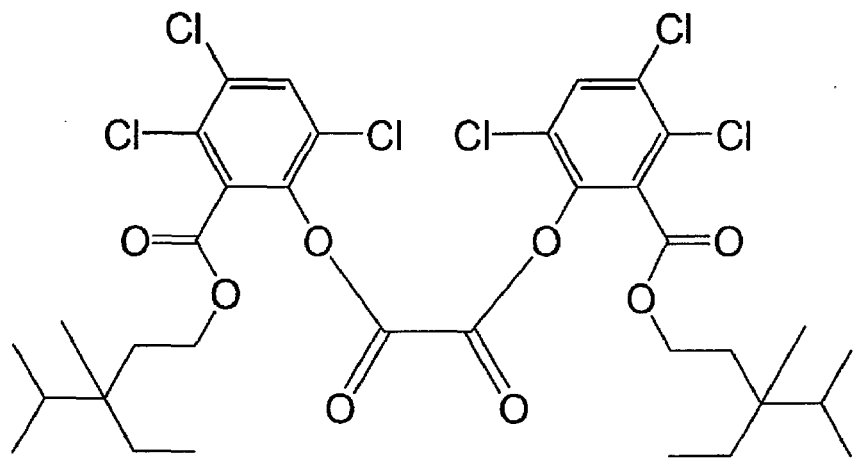
Figure 300:
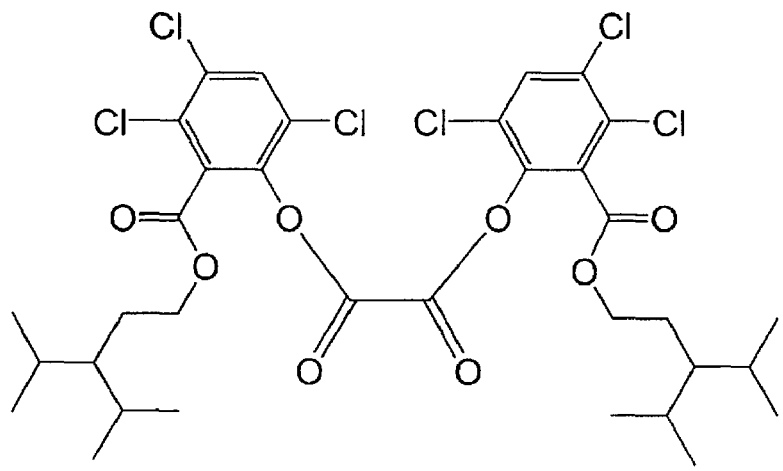
Figure 301:
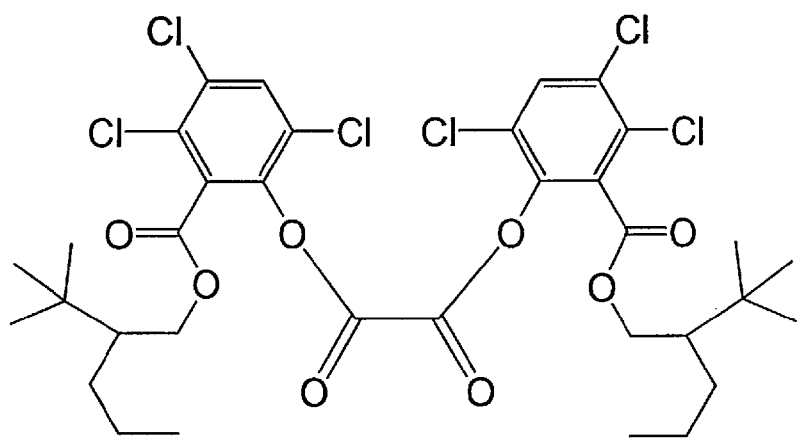
Figure 302:
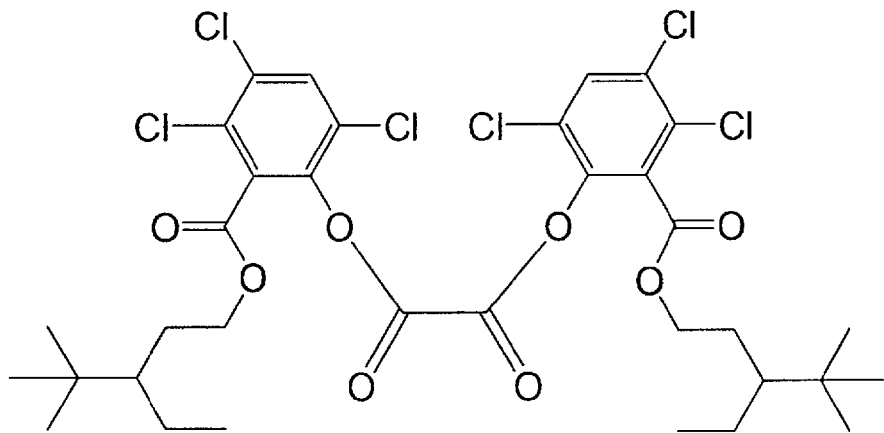
Figure 303:
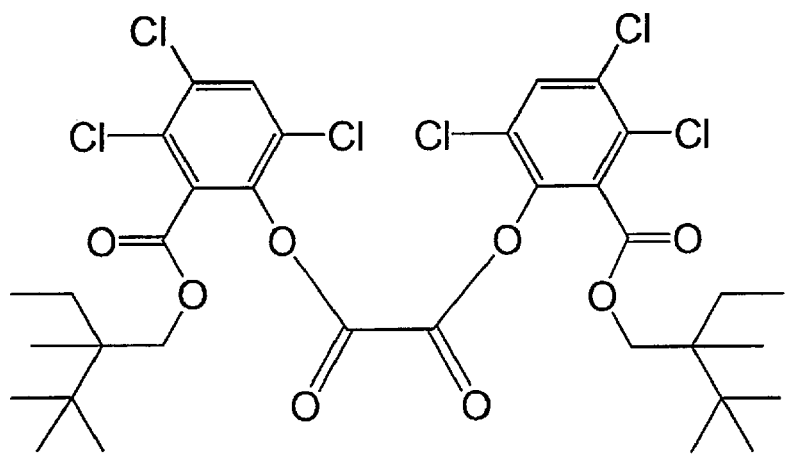
Figure 304:
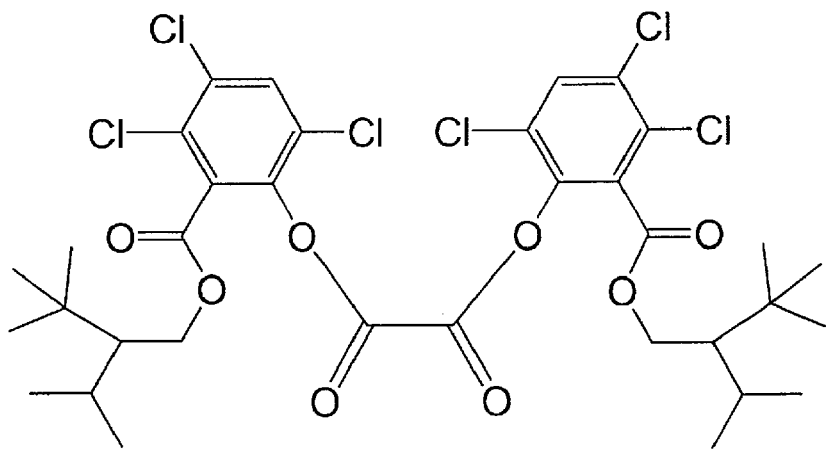
Figure 305:
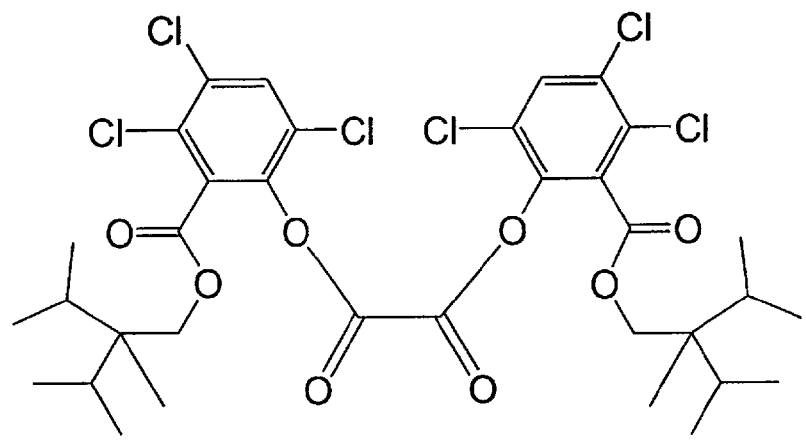
Figure 306:
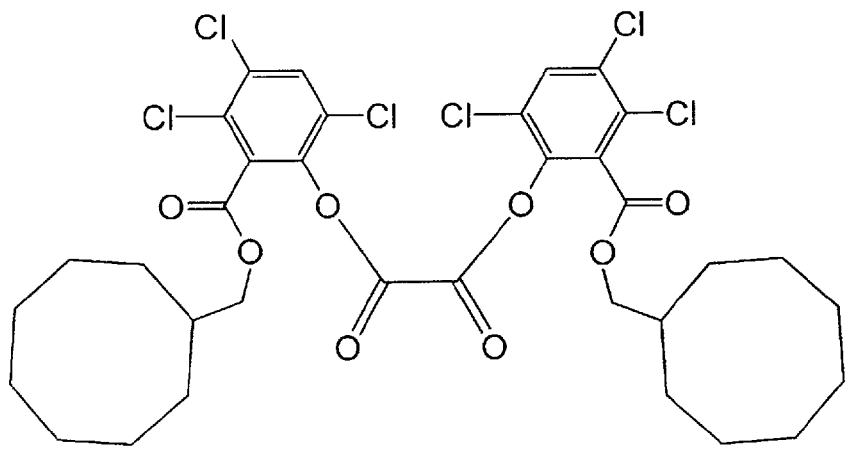
Figure 307:
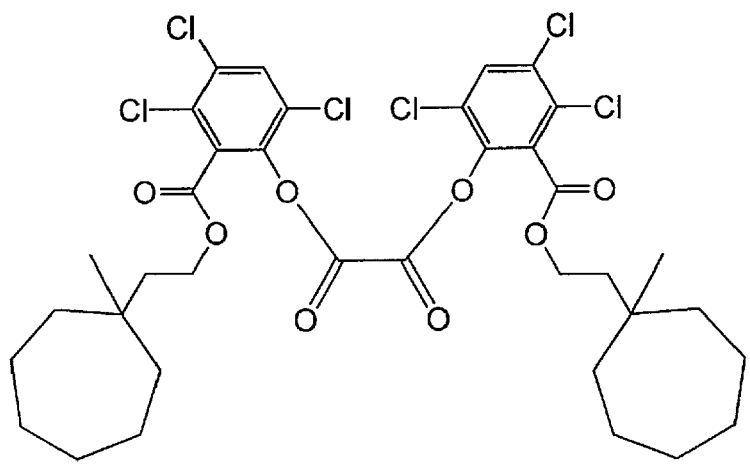
Figure 308:
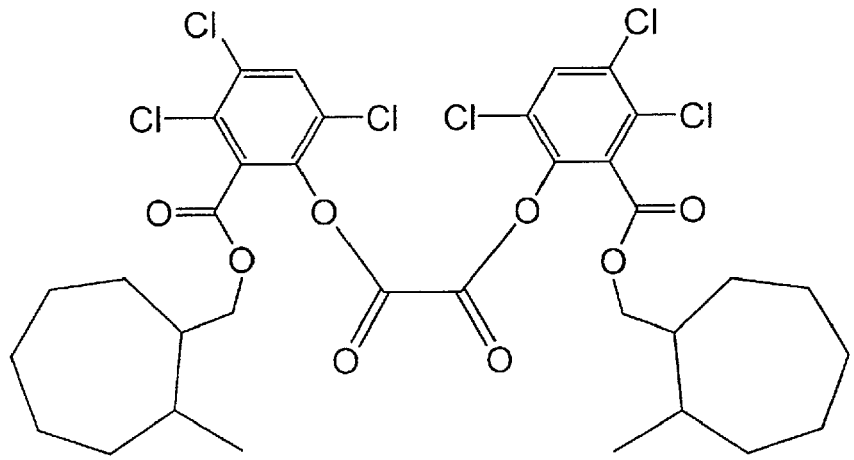
Figure 309:
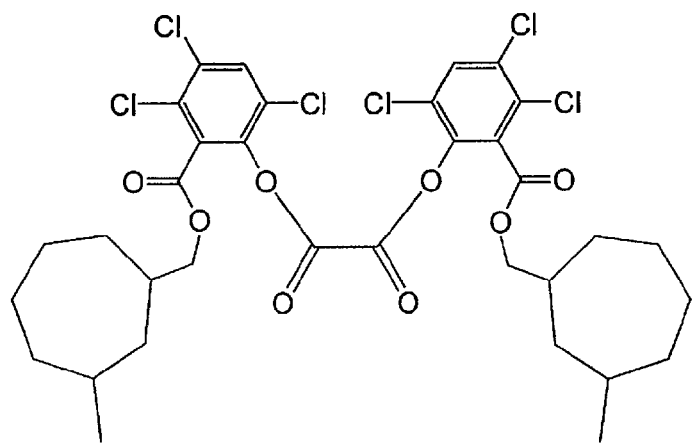
Figure 310:
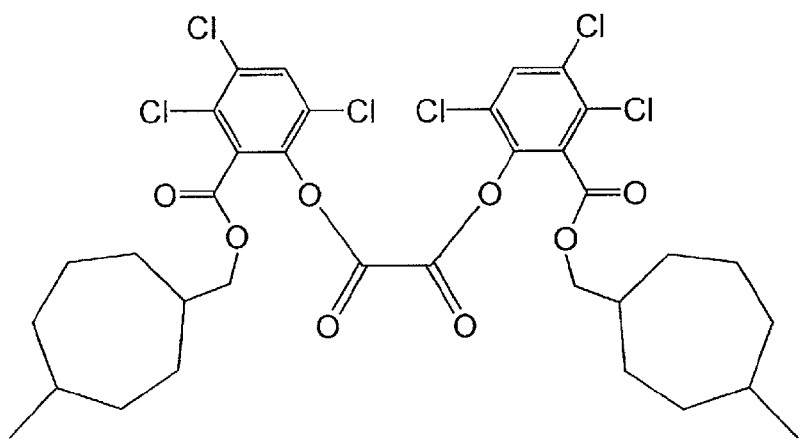
Figure 311:
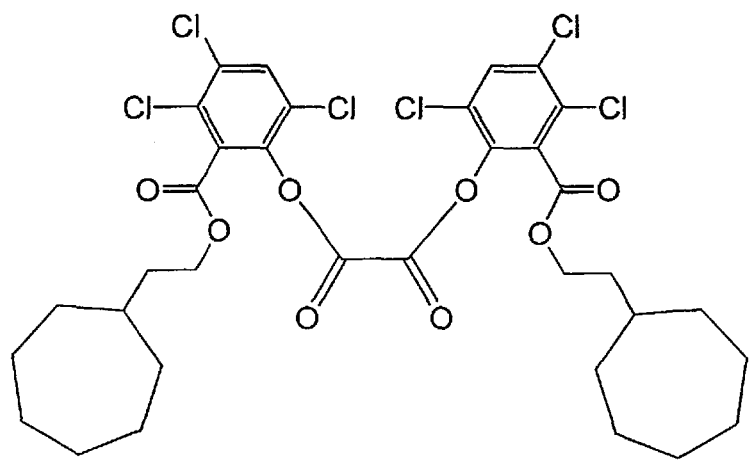
Figure 312:
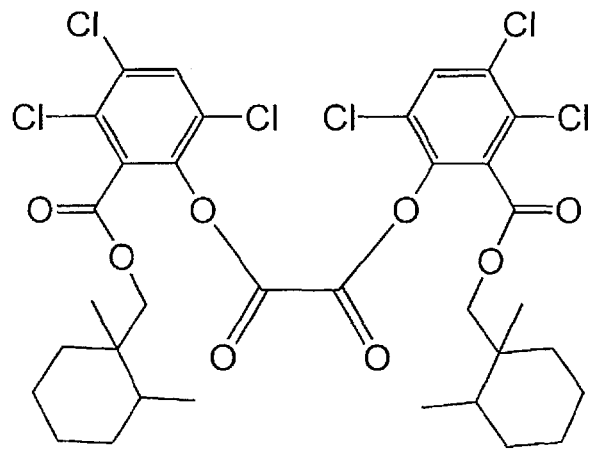
Figure 313:
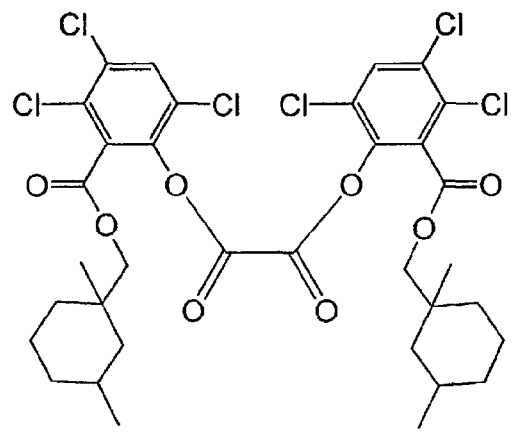
Figure 314:
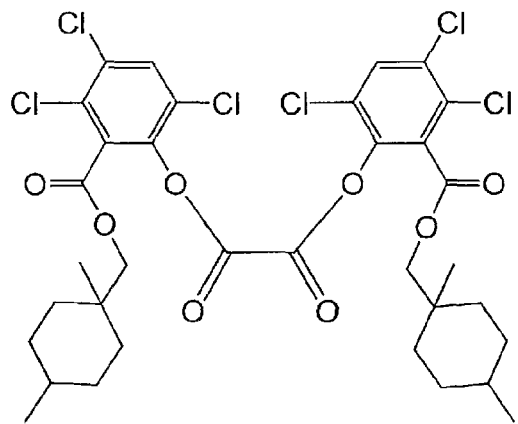
Figure 315:
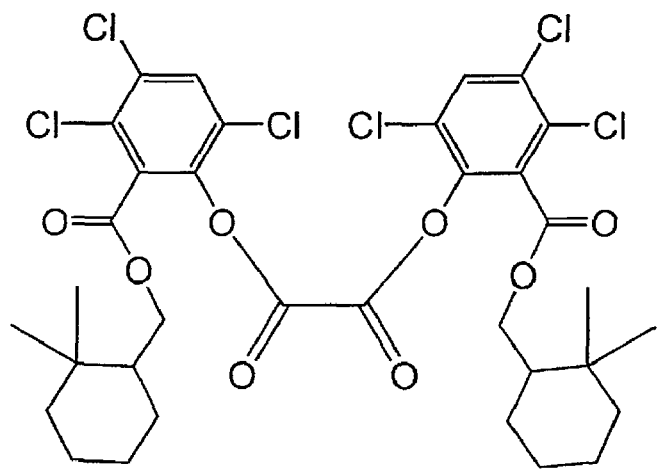
Figure 316:
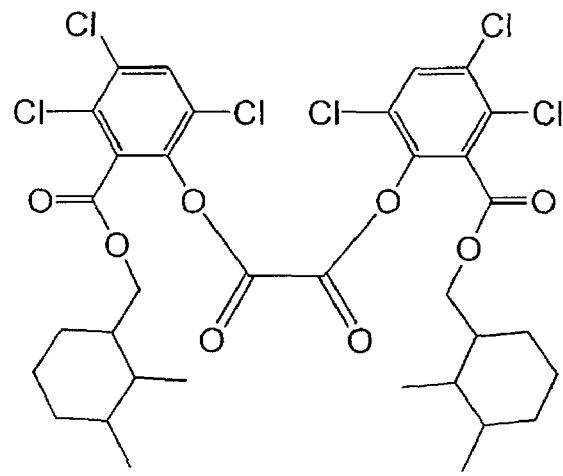
Figure 317:
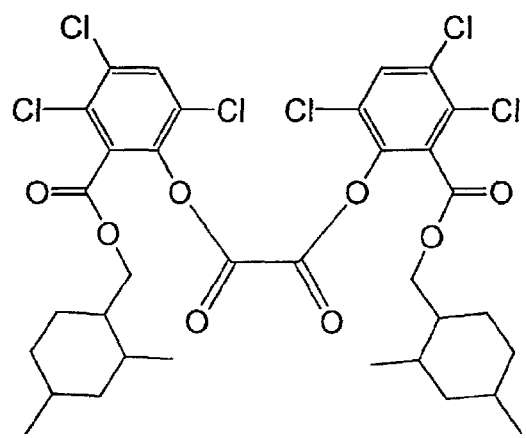
Figure 318:
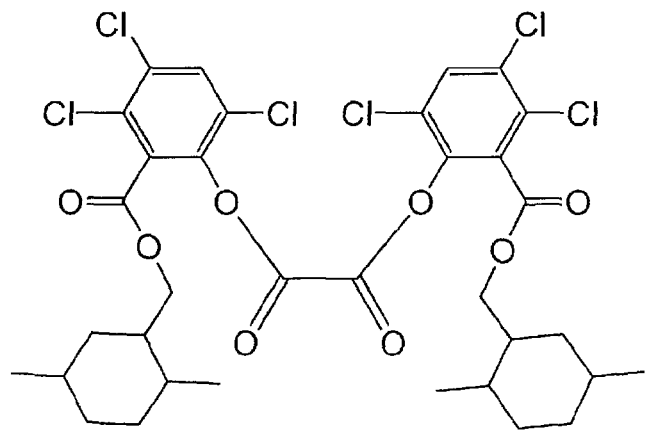
Figure 319:
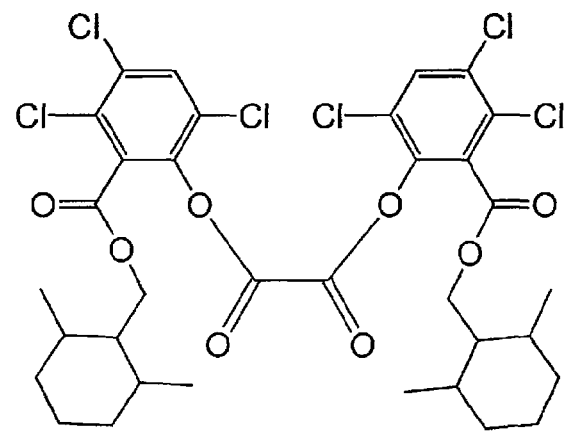
Figure 320:
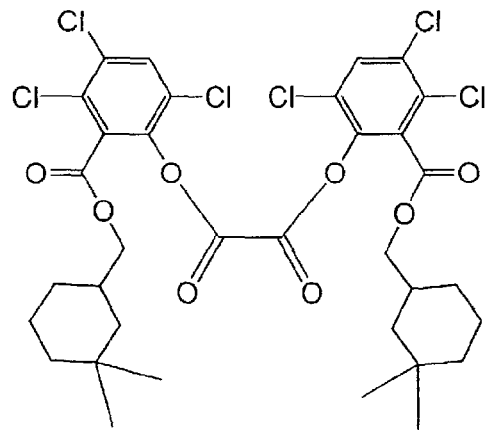
Figure 321:
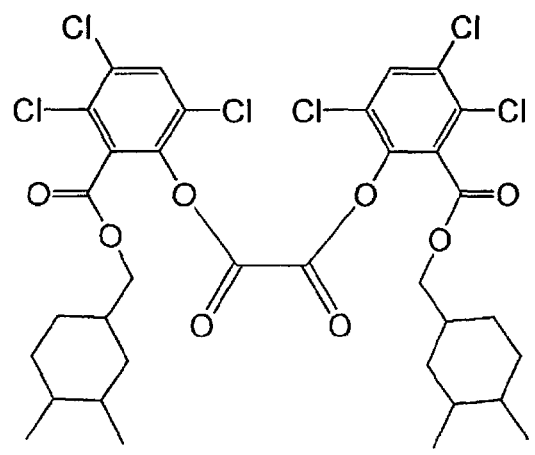
Figure 322:
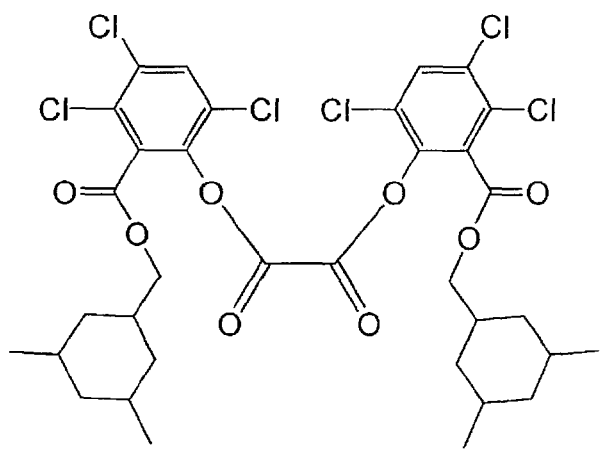
Figure 323:
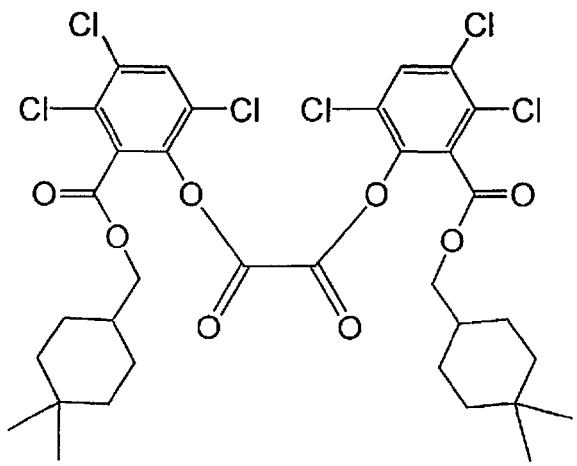
Figure 324:
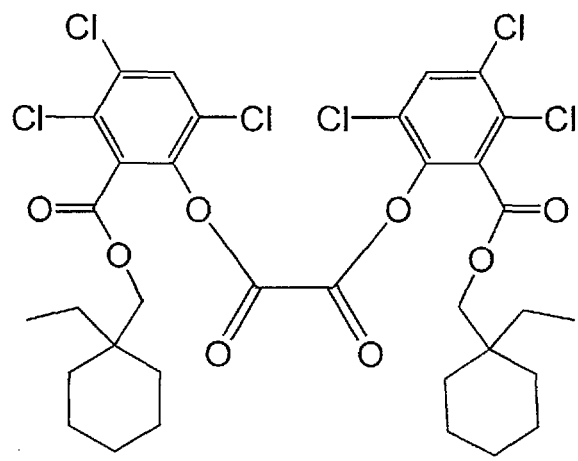
Figure 325:
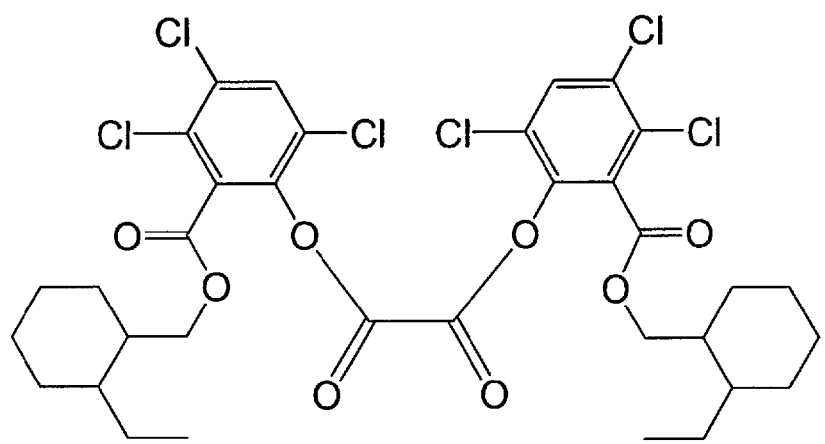
Figure 326:
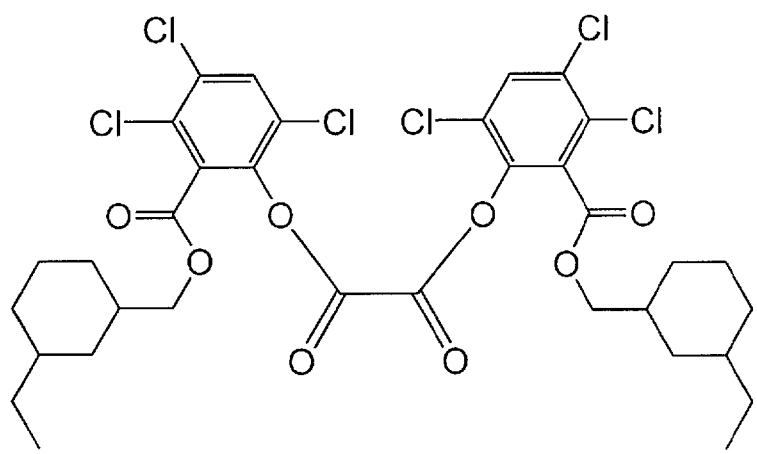
Figure 327:
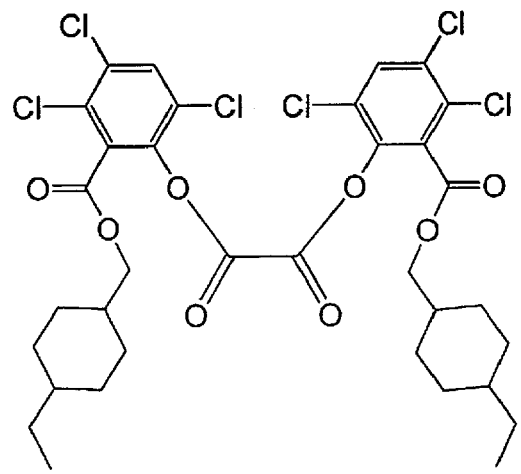
Figure 328:
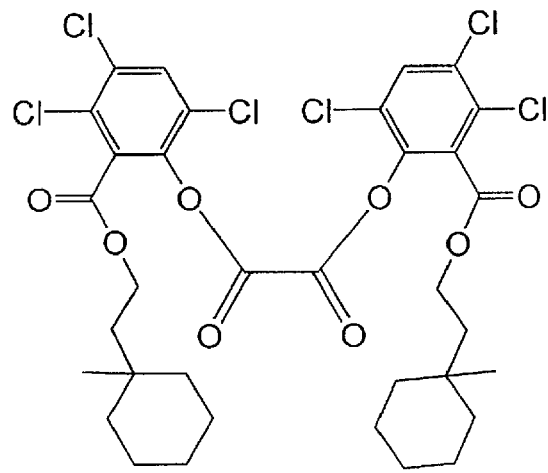
Figure 329:
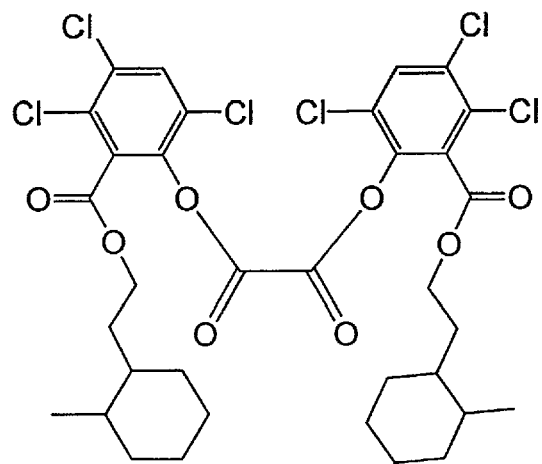
Figure 330:
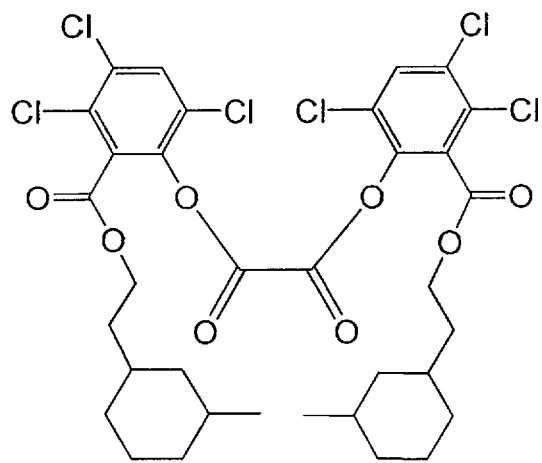
Figure 331:
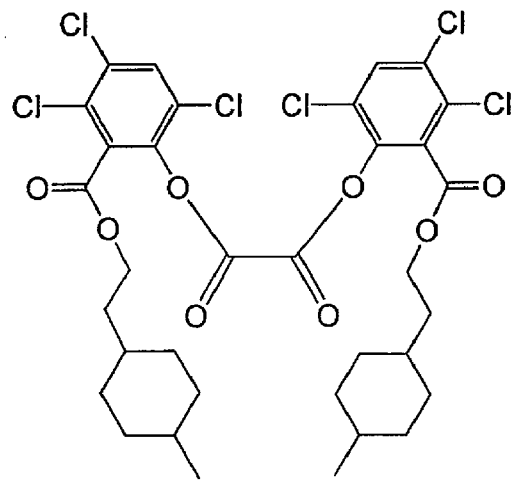
Figure 332:
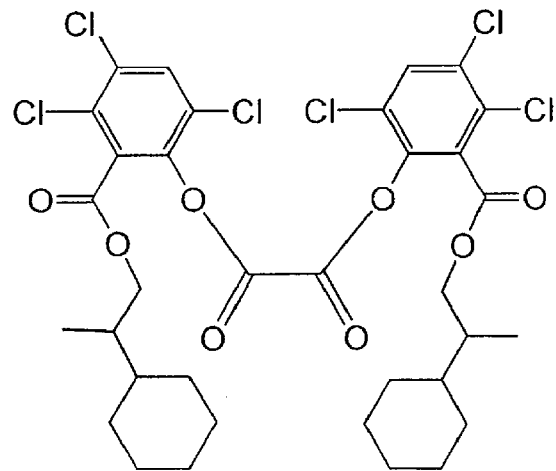
Figure 333:
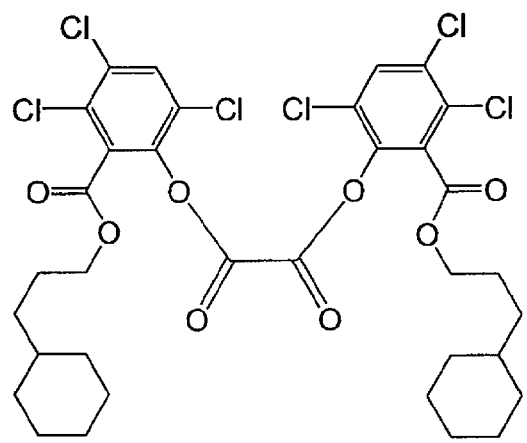
Figure 334:
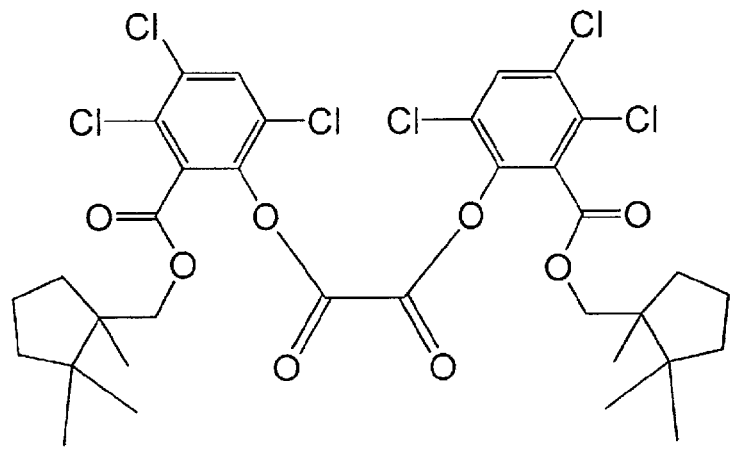
Figure 335:
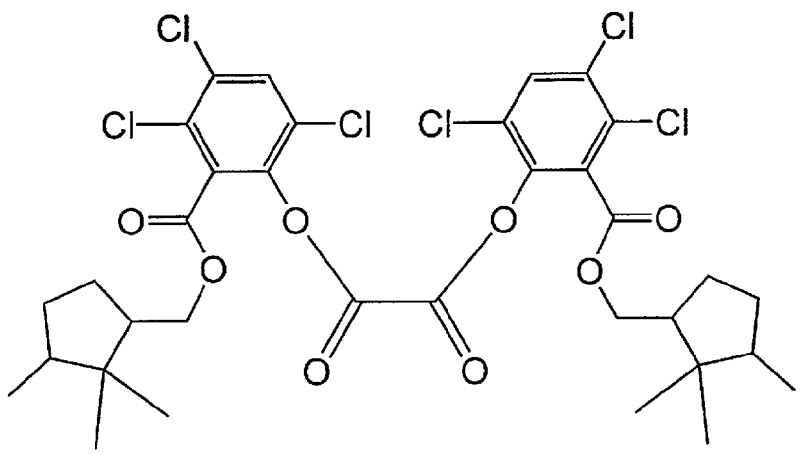
Figure 336:
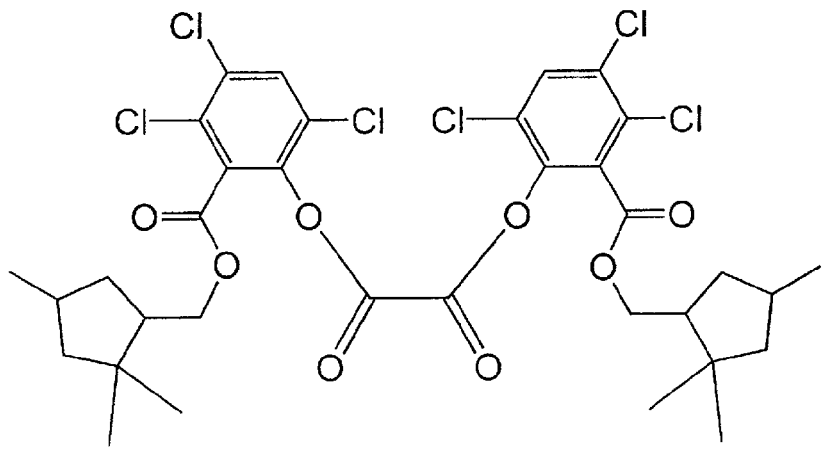
Figure 337:
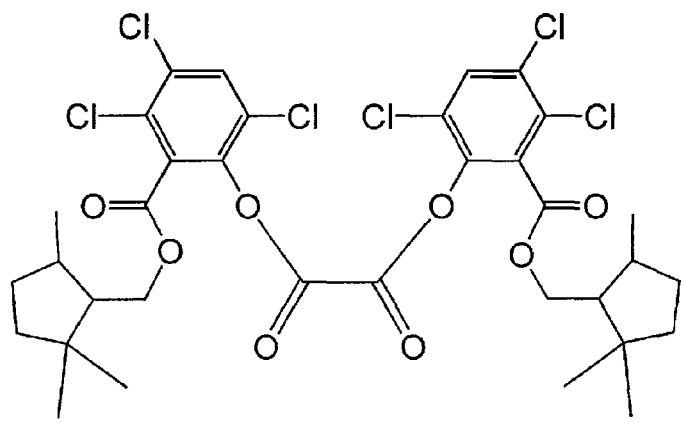
Figure 338:
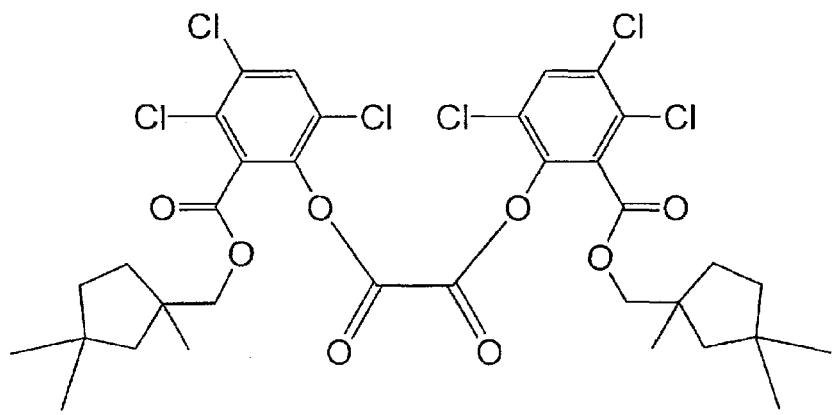
Figure 339:
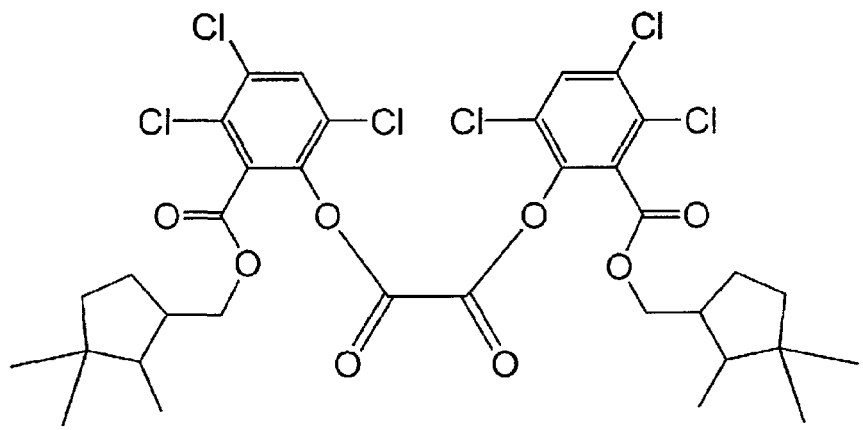
Figure 340:
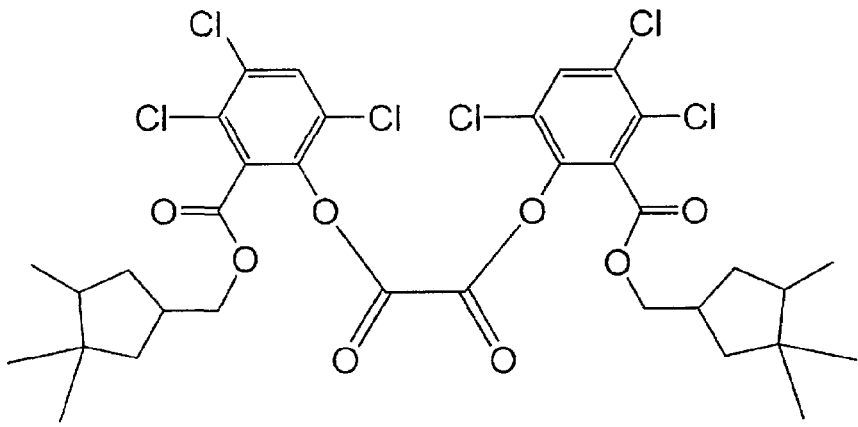
Figure 341:
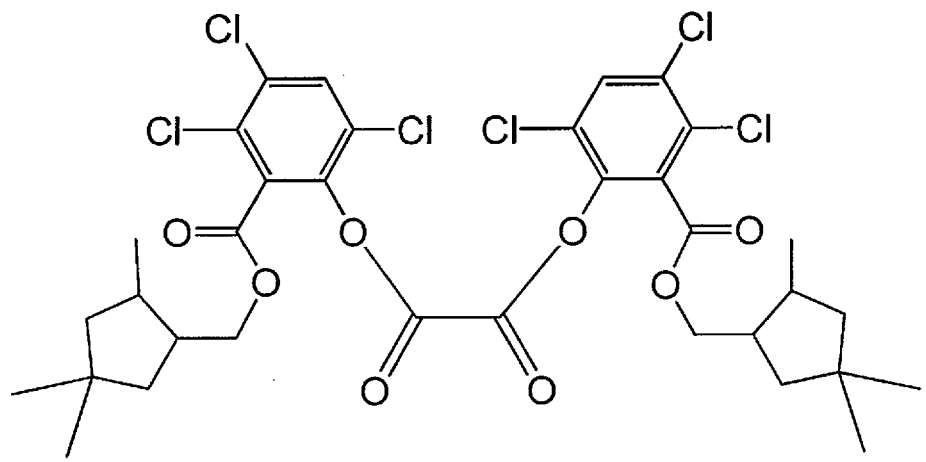
Figure 342:
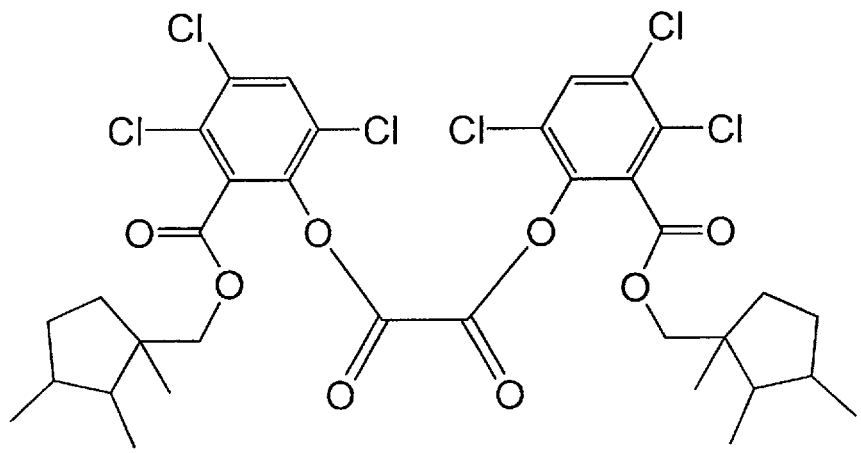
Figure 343:
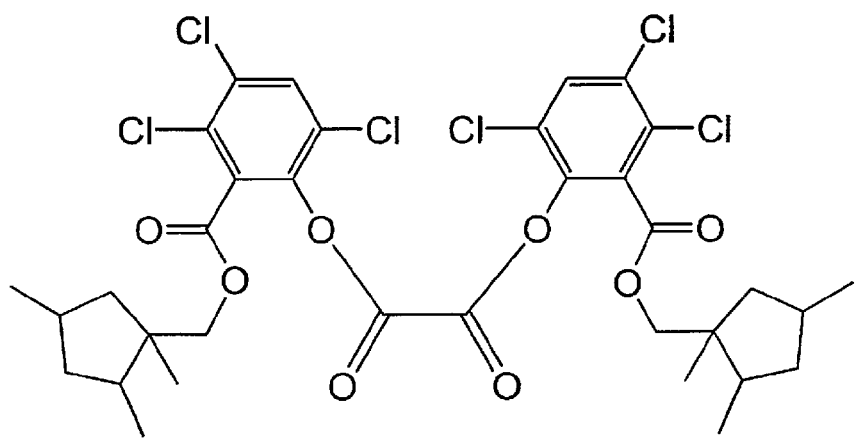
Figure 344:
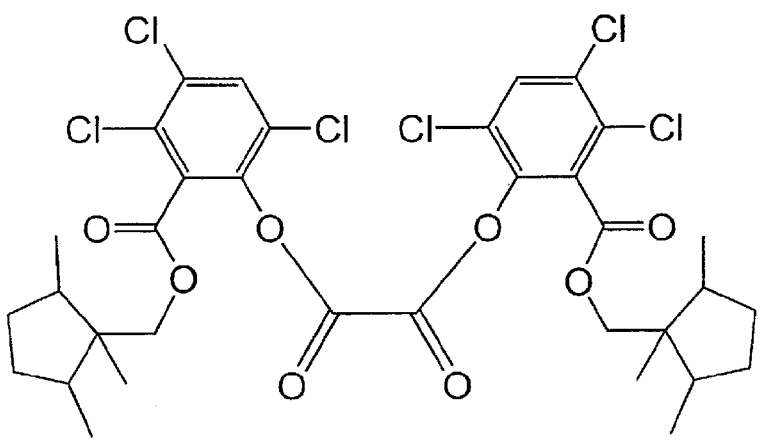
Figure 345:
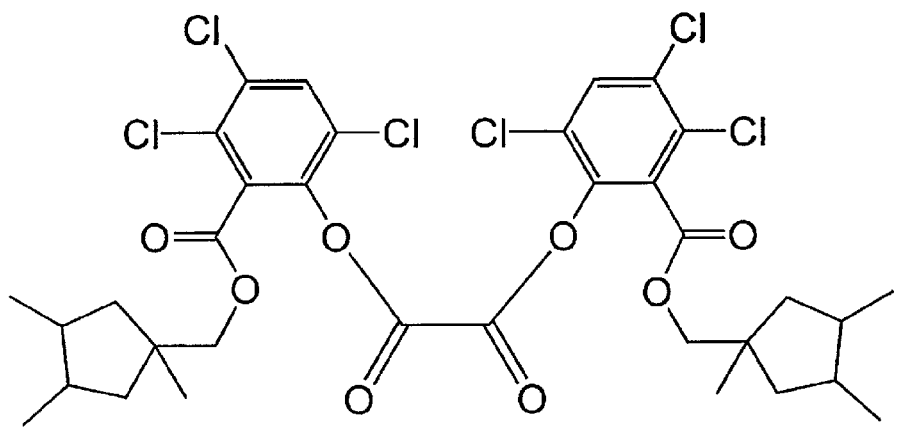
Figure 346:
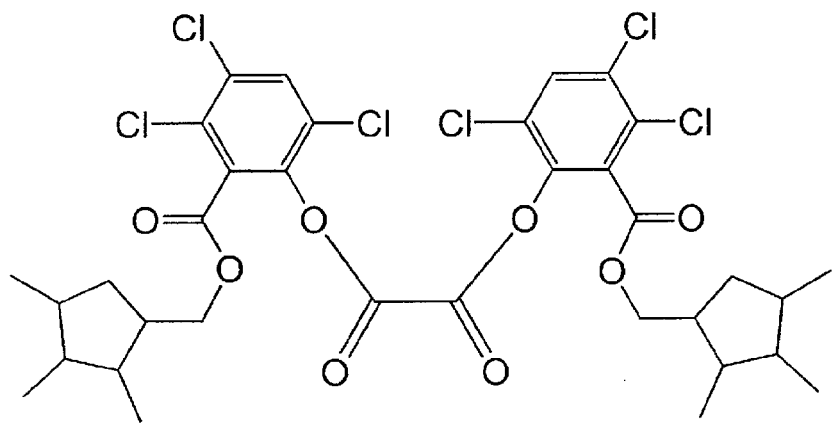
Figure 347:
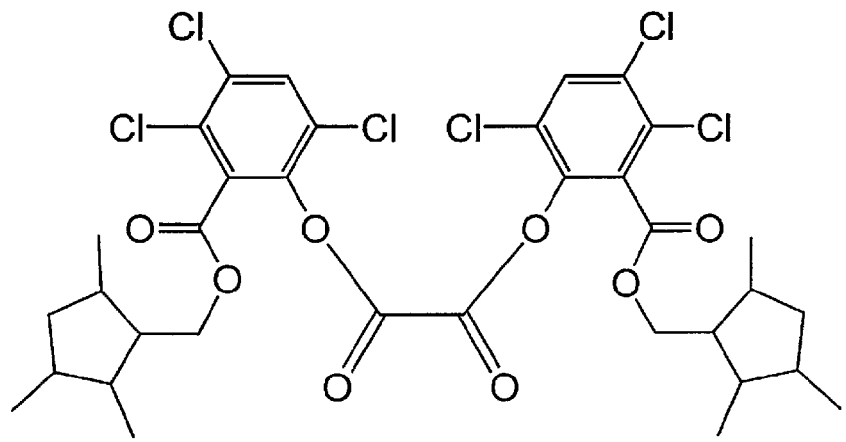
Figure 348:
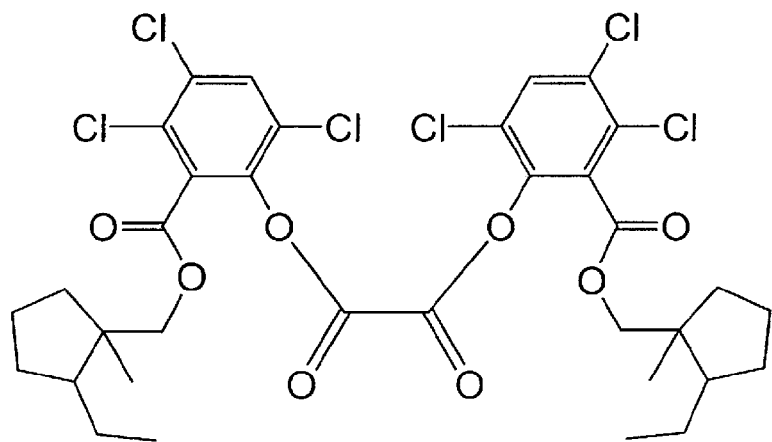
Figure 349:
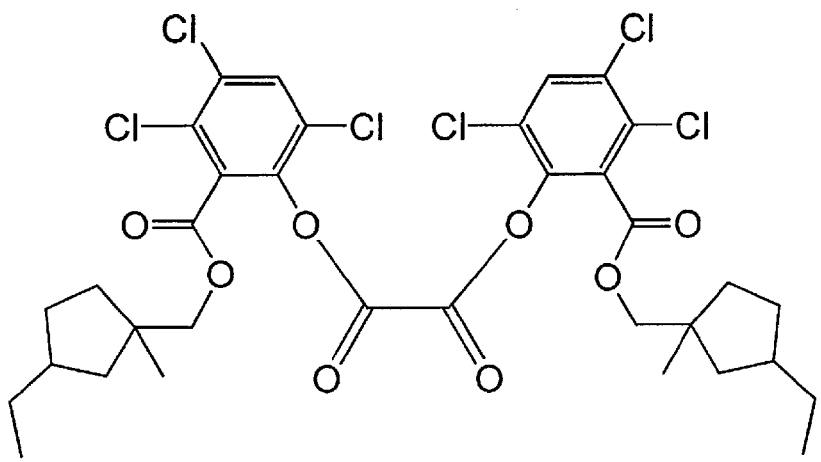
Figure 350:
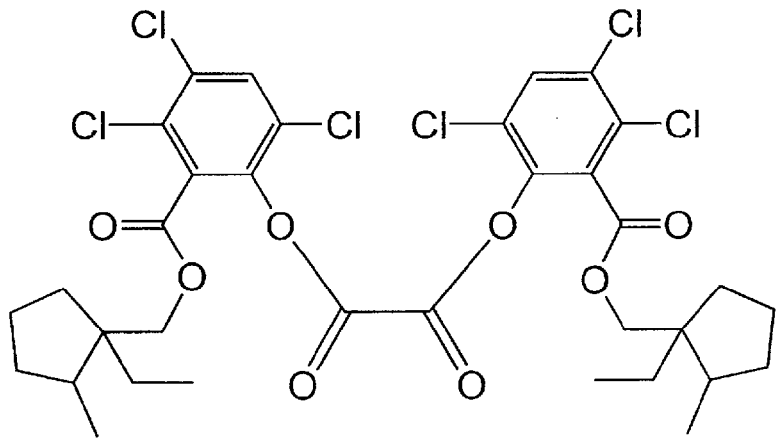
Figure 351:
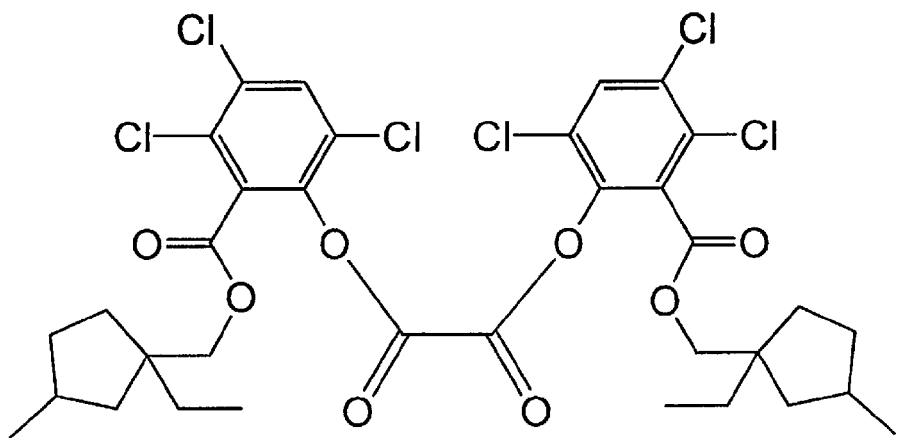
Figure 352:
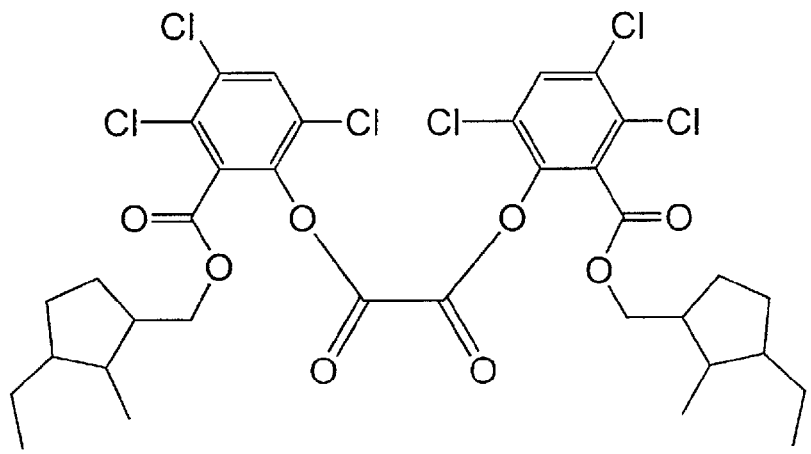
Figure 353:
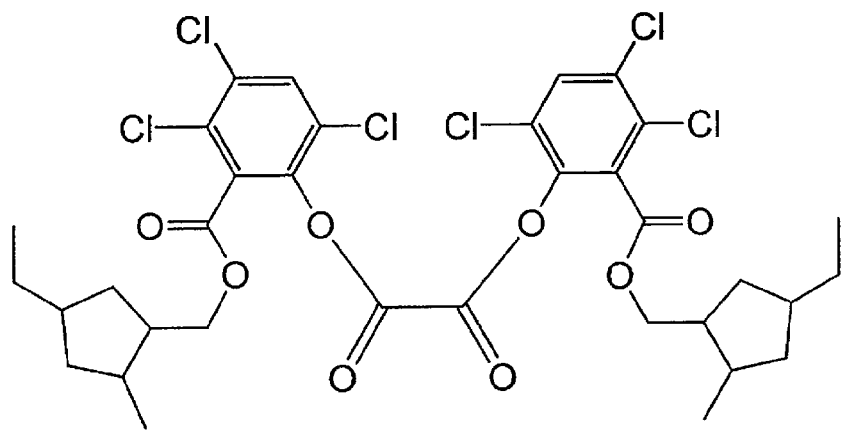
Figure 354:
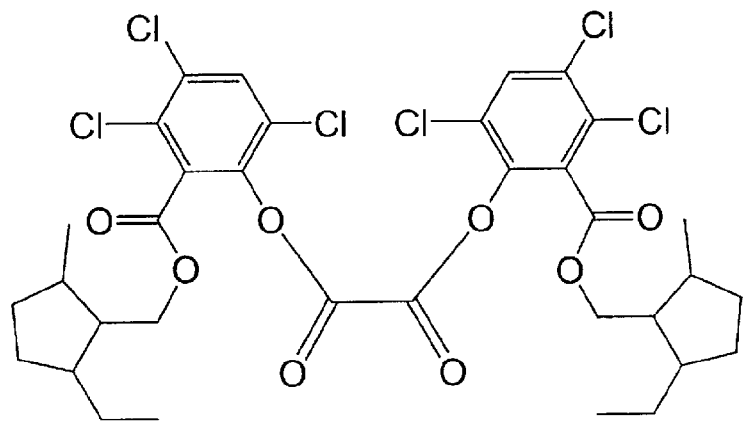
Figure 355:
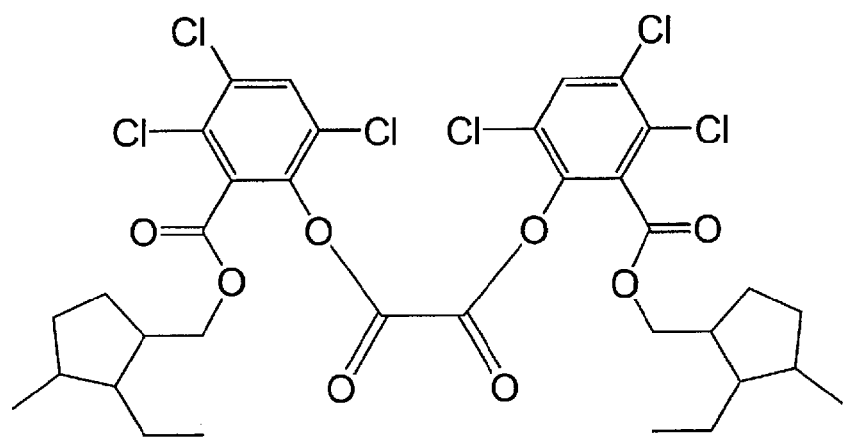
Figure 356:
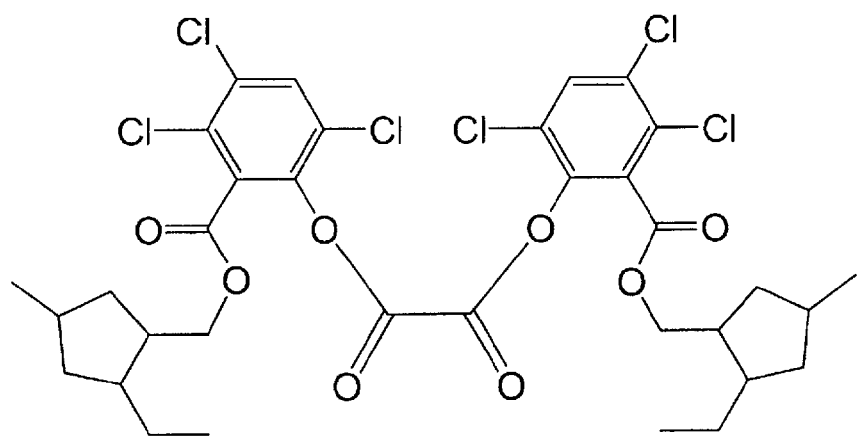
Figure 357:
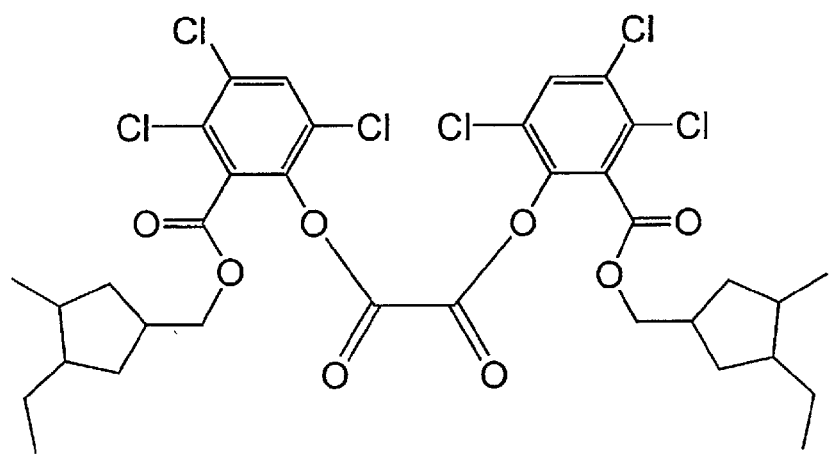
Figure 358:
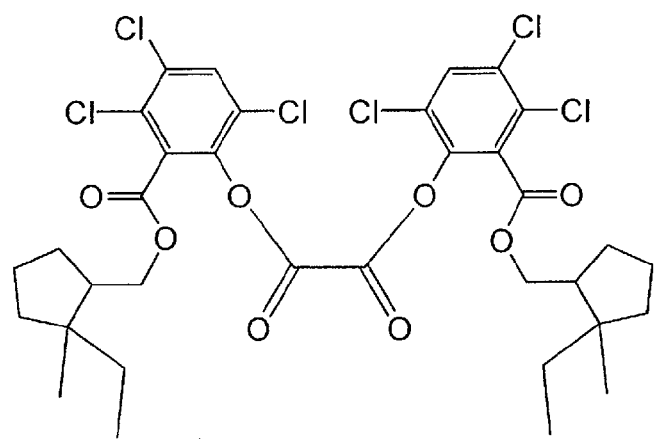
Figure 359:
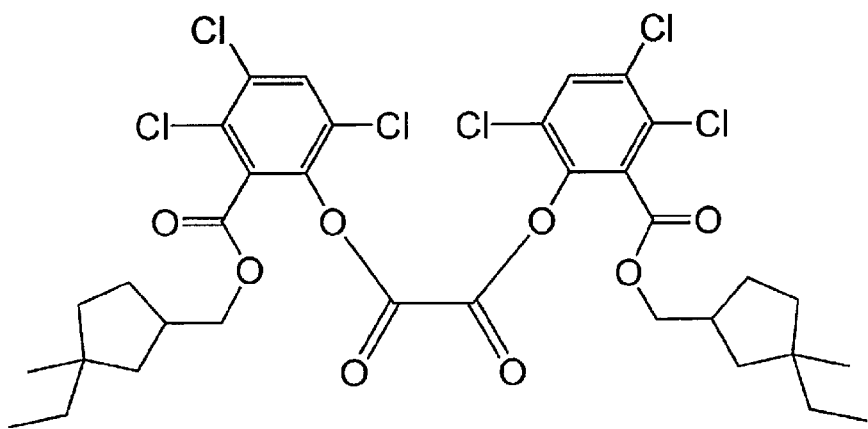
Figure 360:
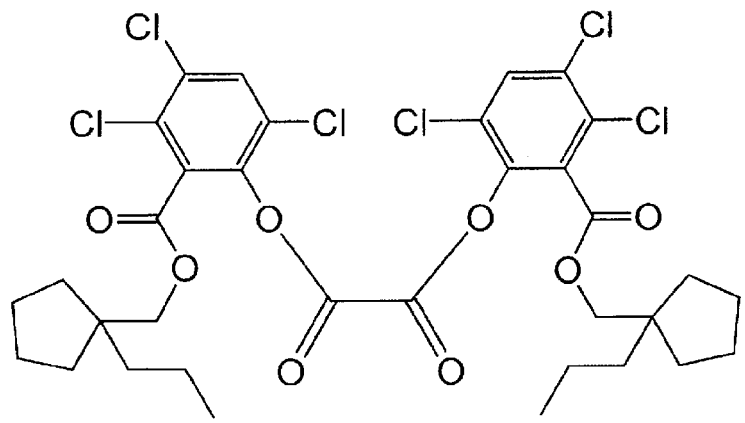
Figure 361:
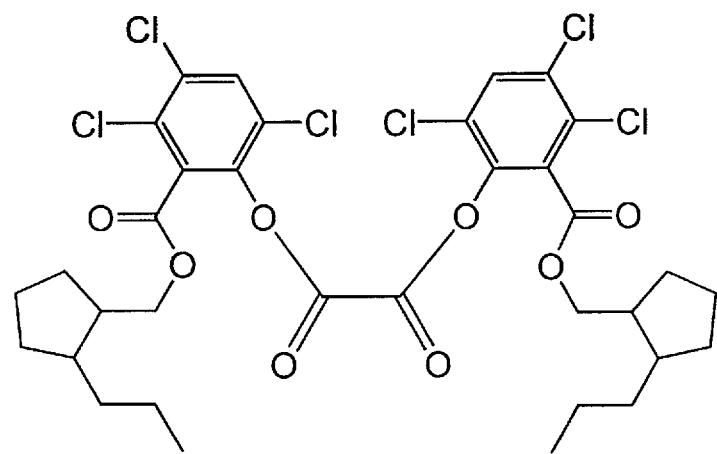
Figure 362:
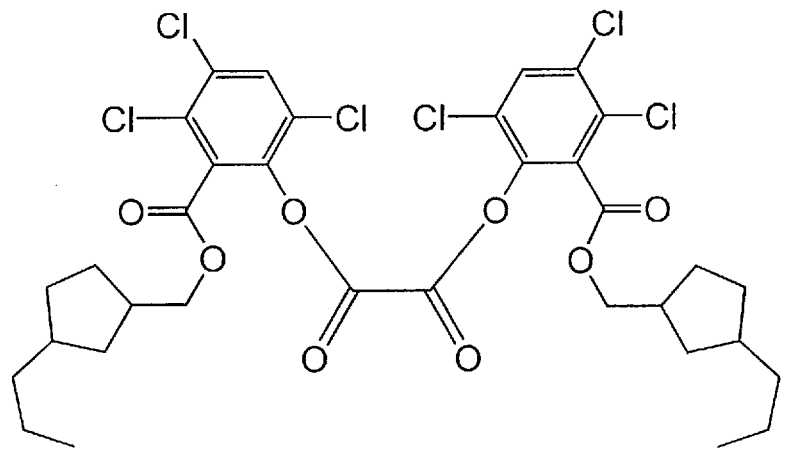
Figure 363:
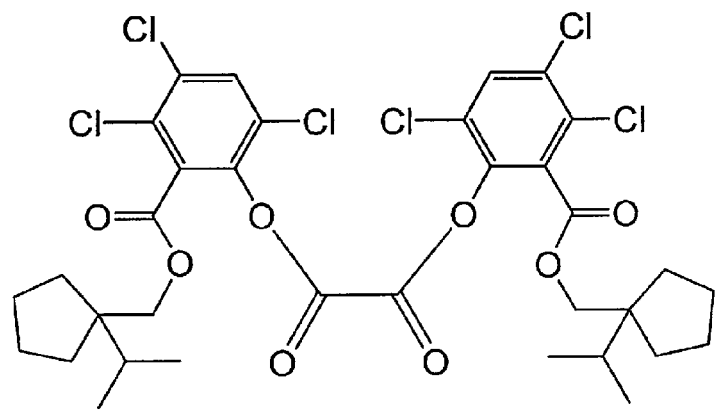
Figure 364:
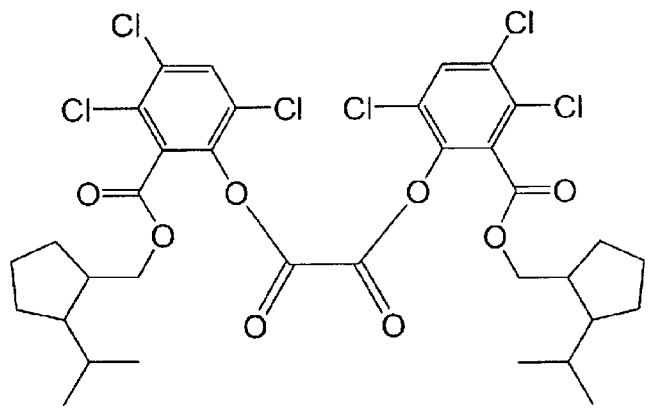
Figure 365:
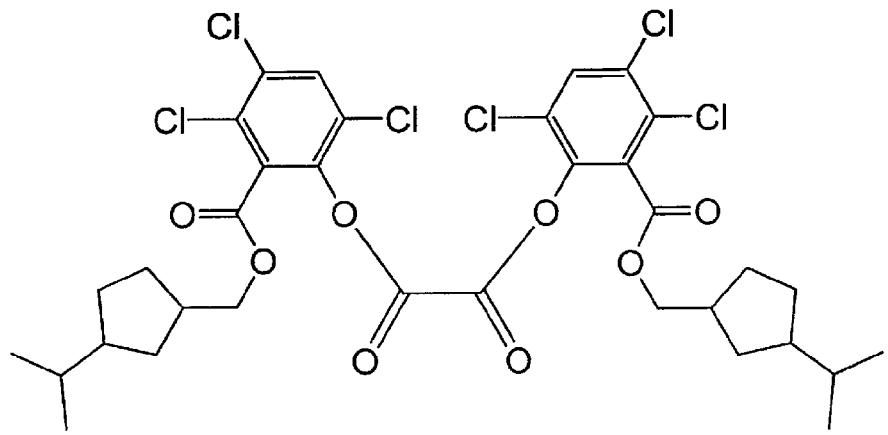
Figure 366:
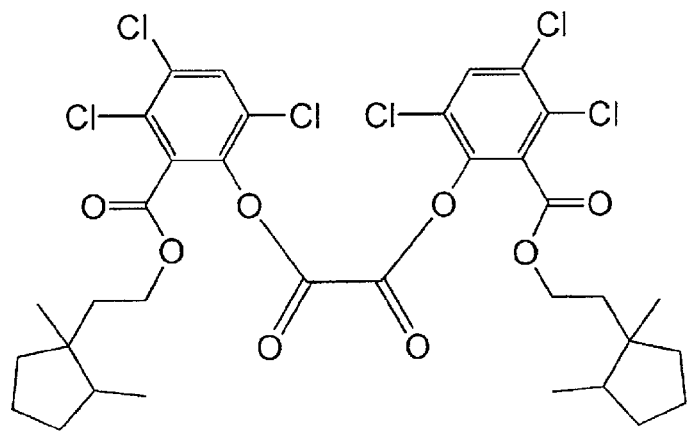
Figure 367:
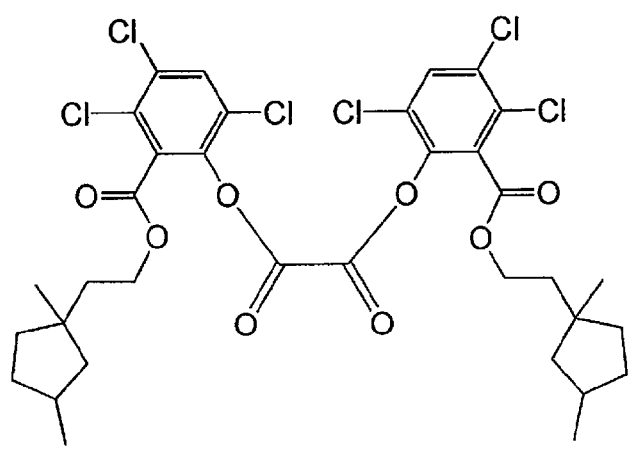
Figure 368:
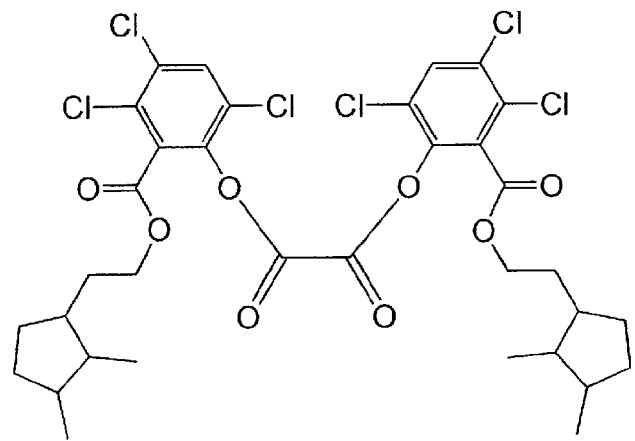
Figure 369:
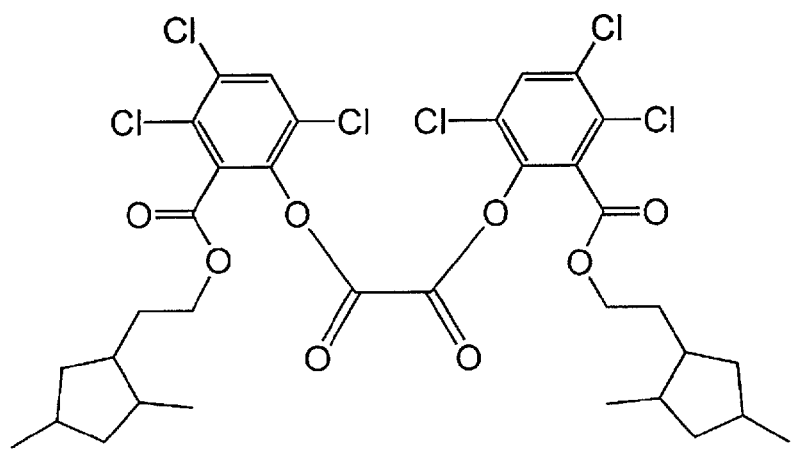
Figure 370:
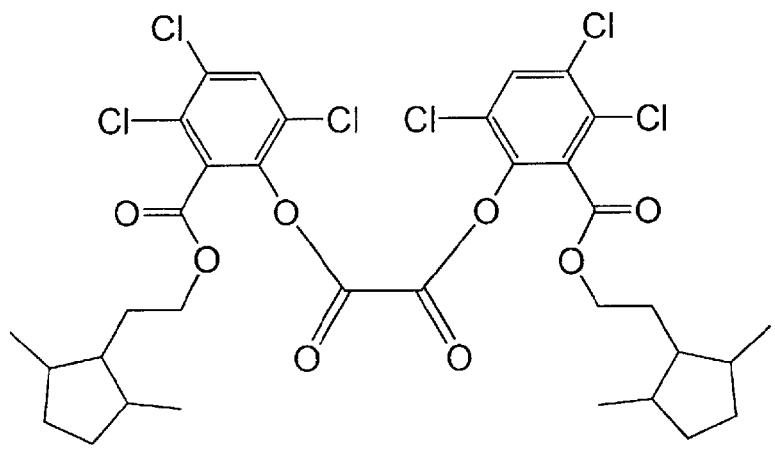
Figure 371:
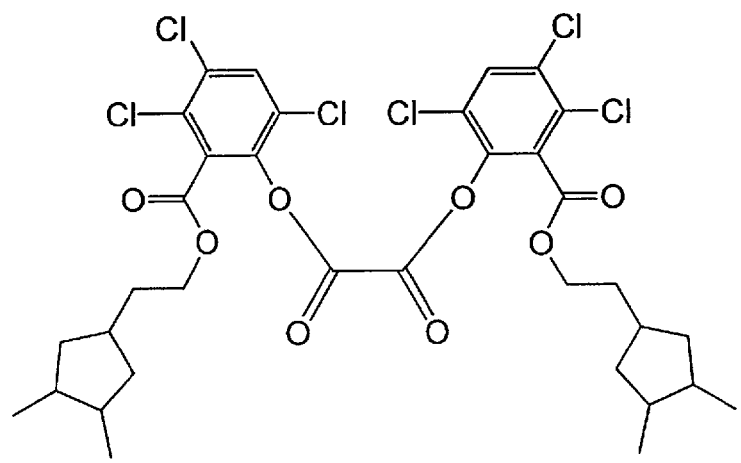
Figure 372:
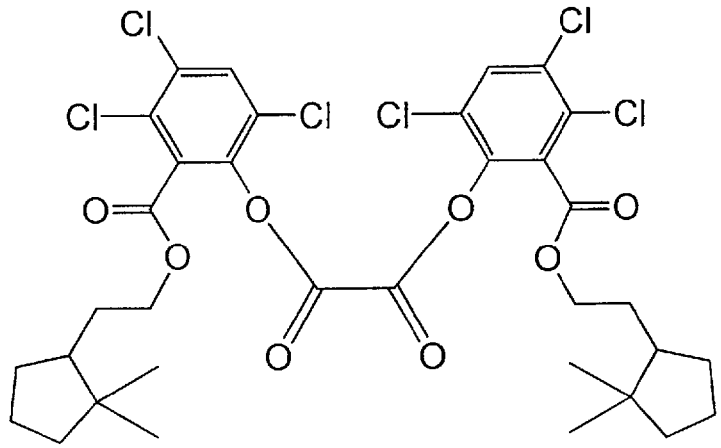
Figure 373:
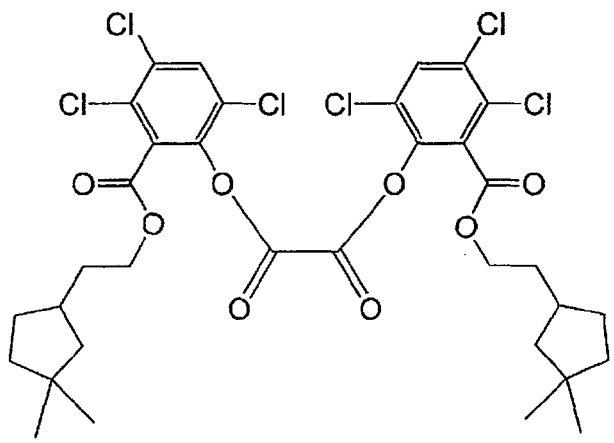
Figure 374:
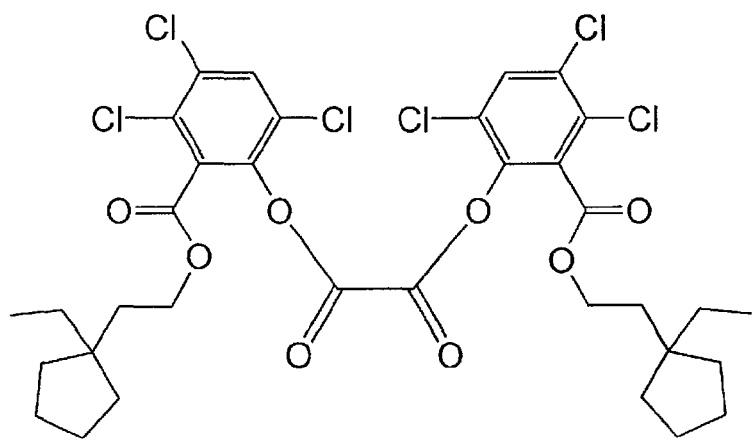
Figure 375:
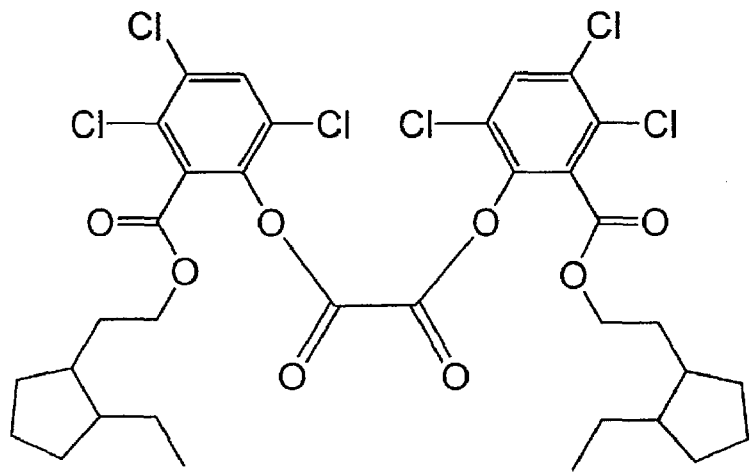
Figure 376:
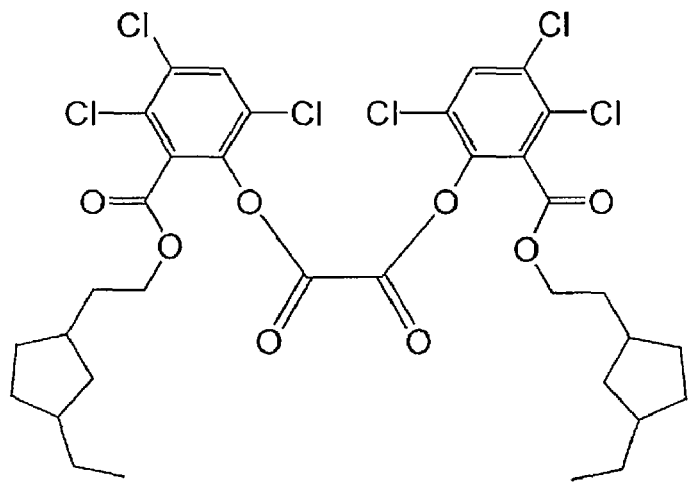
Figure 377:
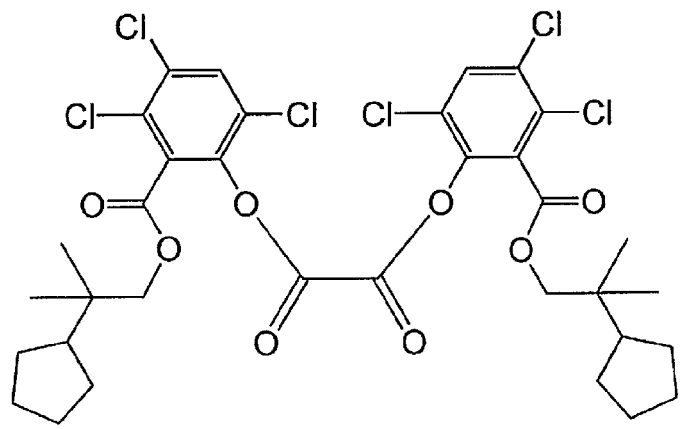
Figure 378:
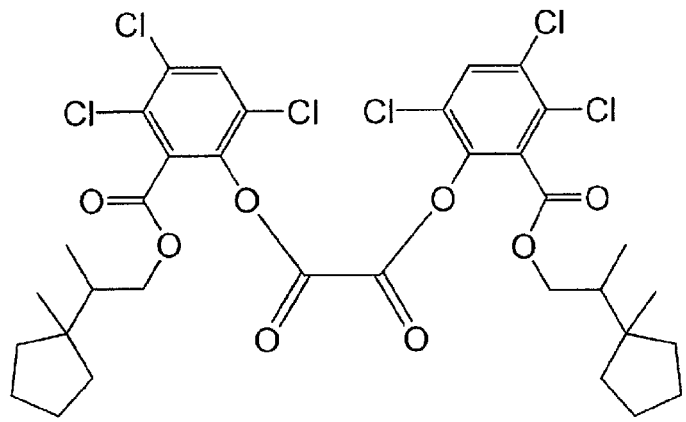
Figure 379:
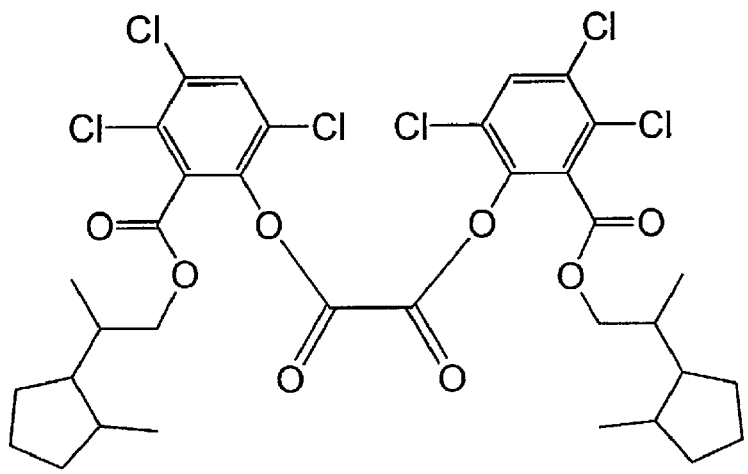
Figure 380:
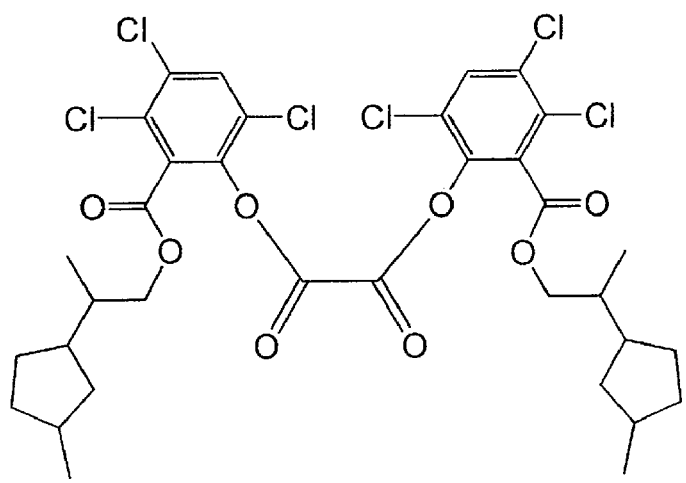
Figure 381:
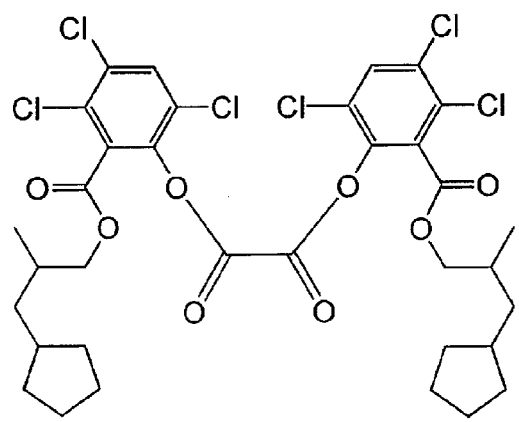
Figure 382:
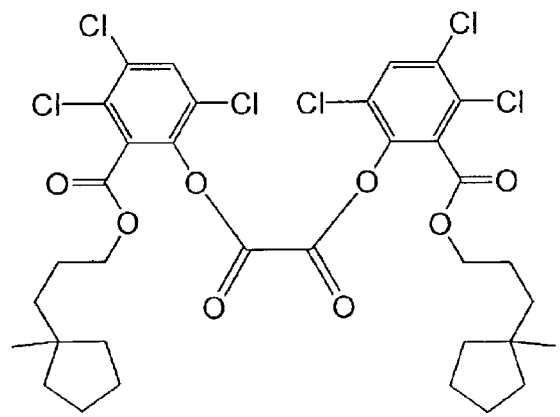
Figure 383:
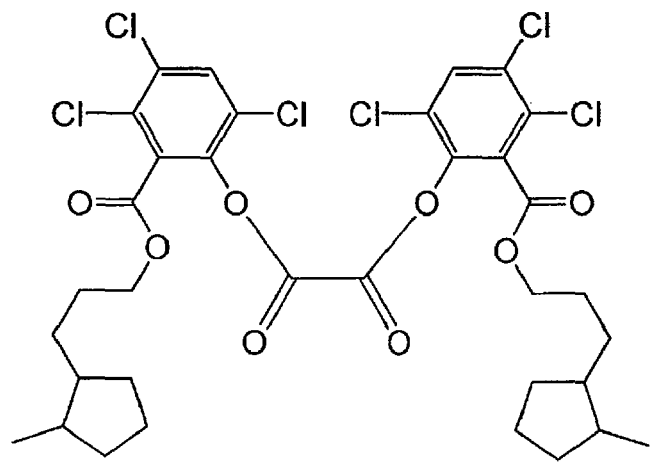
Figure 384:
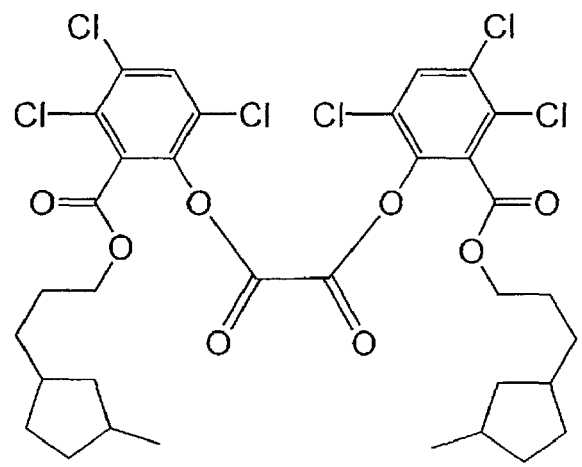
Figure 385:
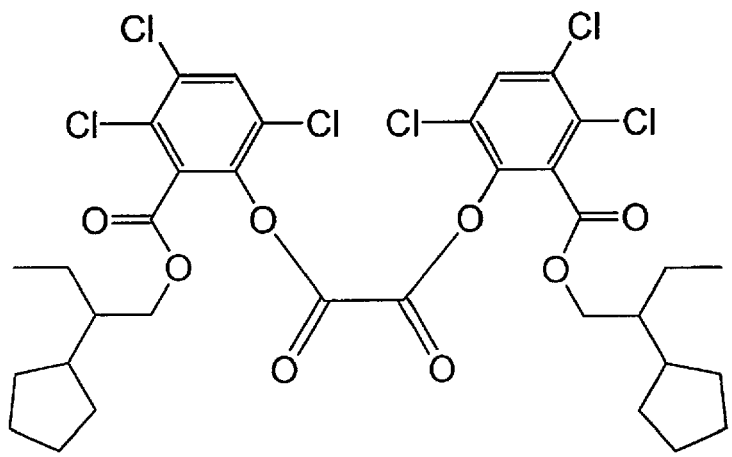
Figure 386:
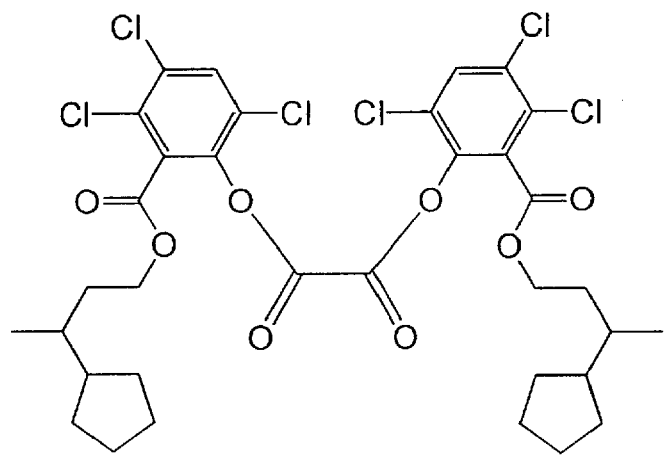
Figure 387:
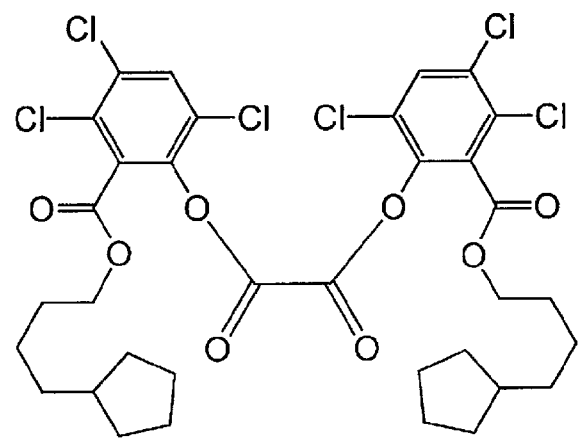
Figure 388:
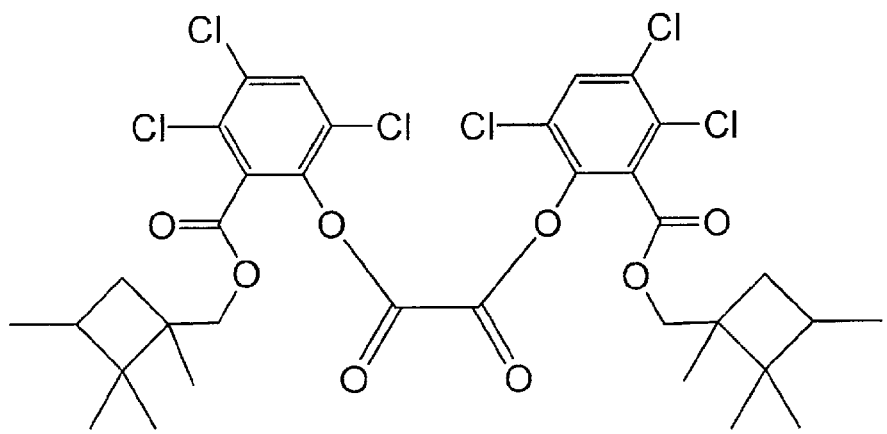
Figure 389:
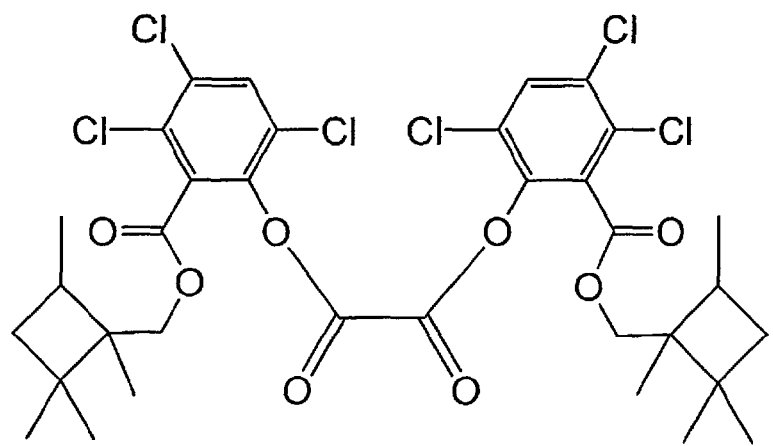
Figure 390:
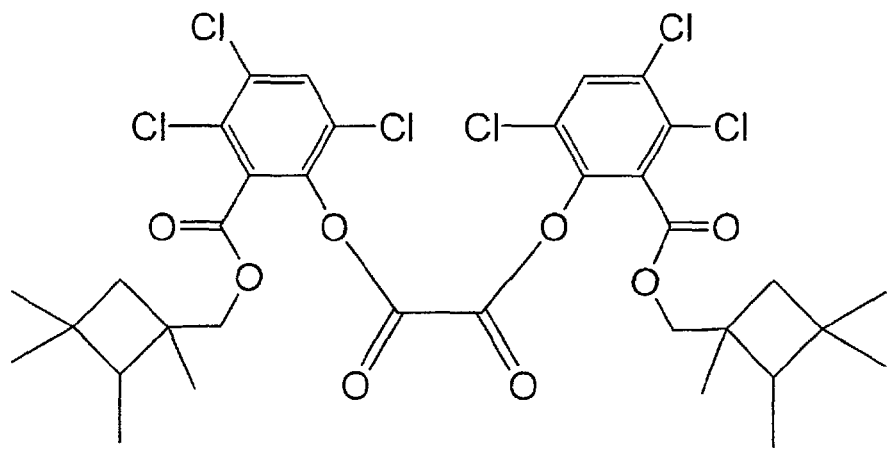
Figure 391:
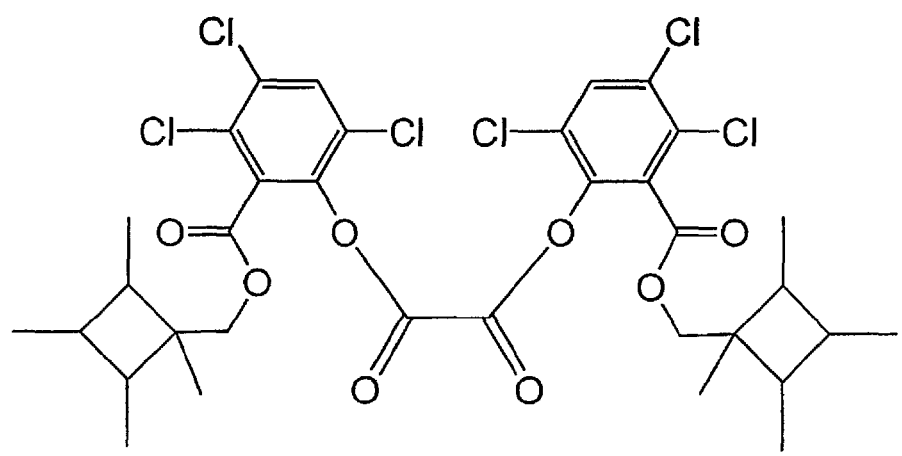
Figure 392:
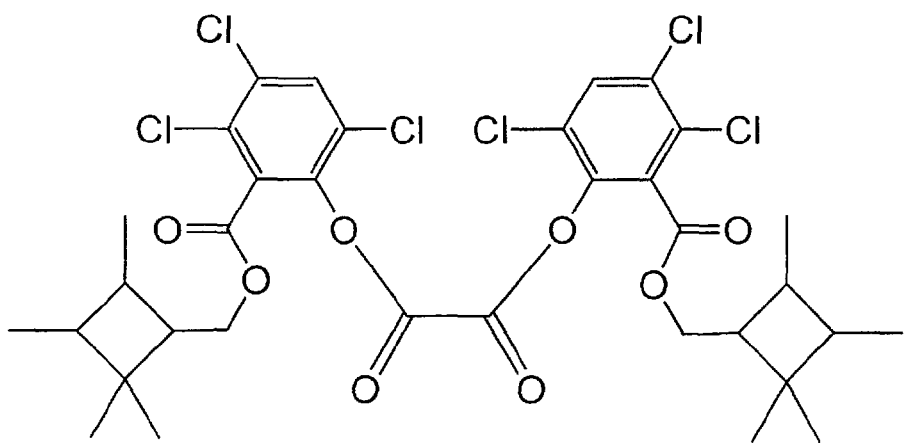
Figure 393:
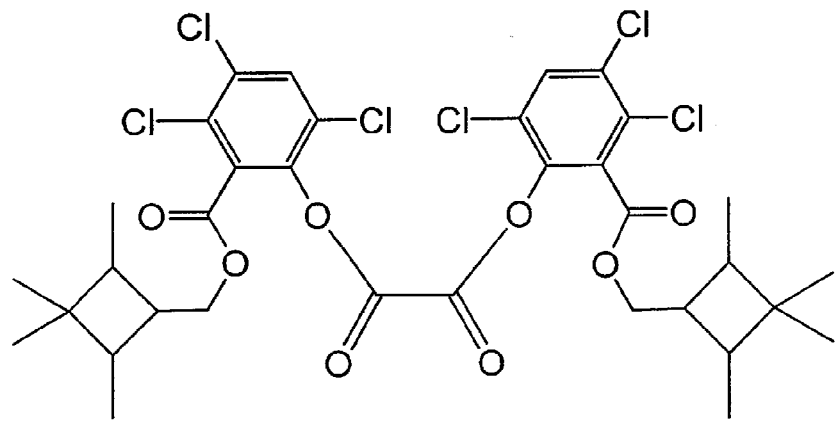
Figure 394:
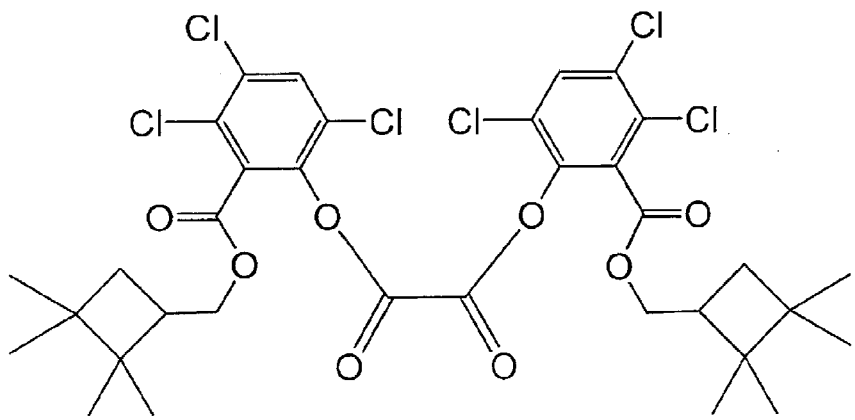
Figure 395:
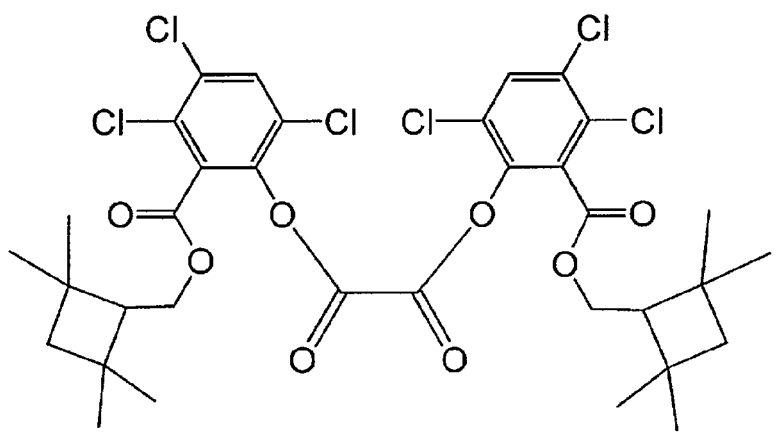
Figure 396:
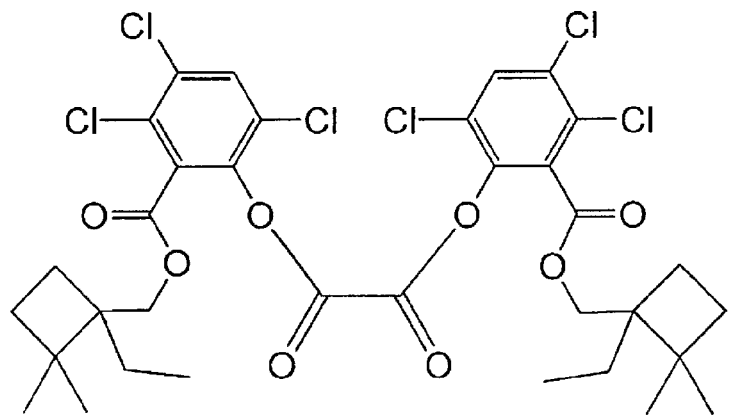
Figure 397:
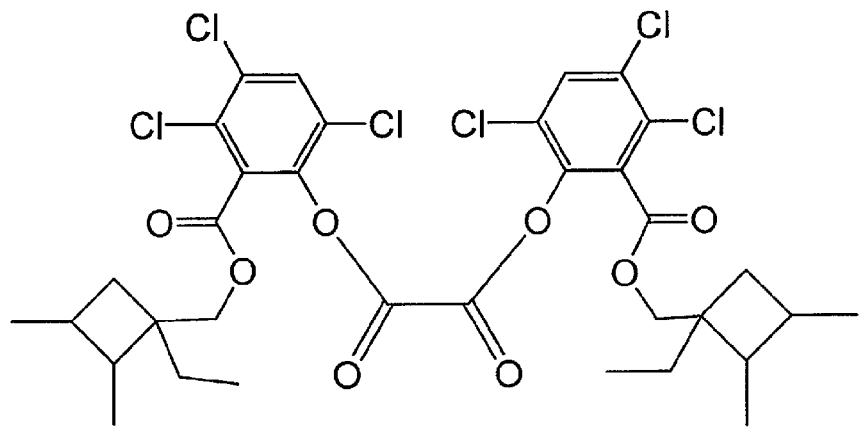
Figure 398:
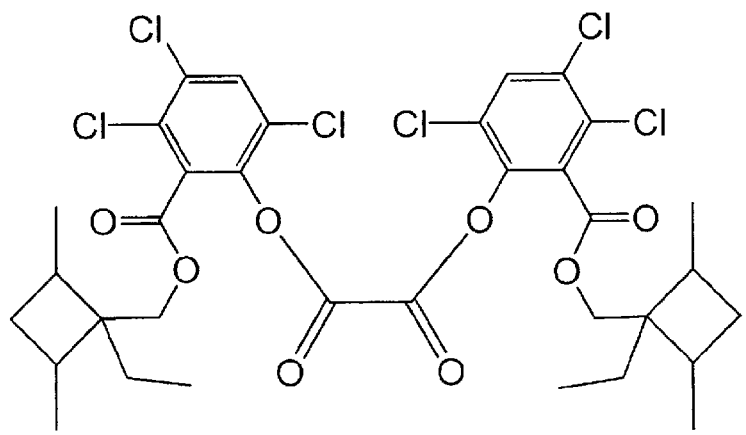
Figure 399:
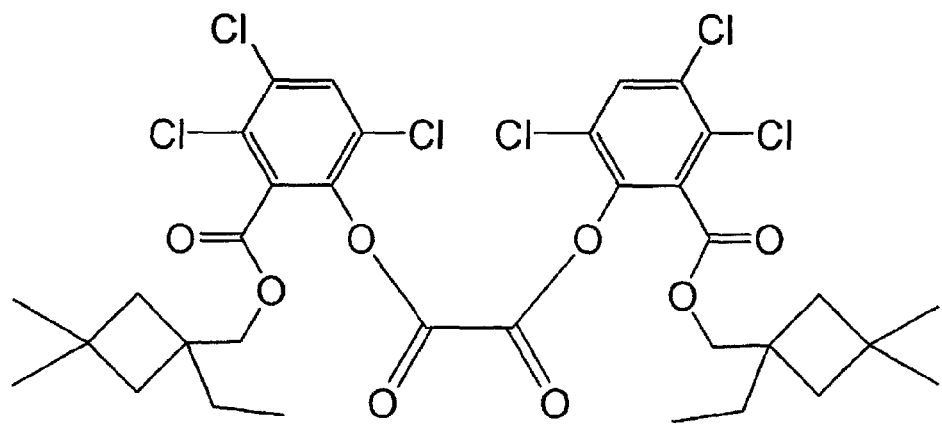
Figure 400:
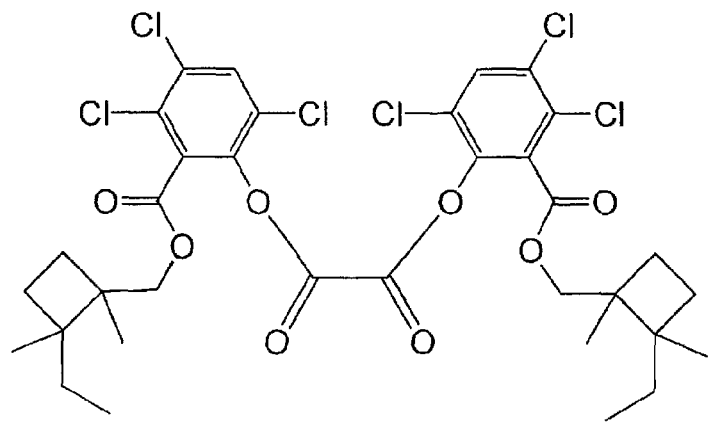
Figure 401:
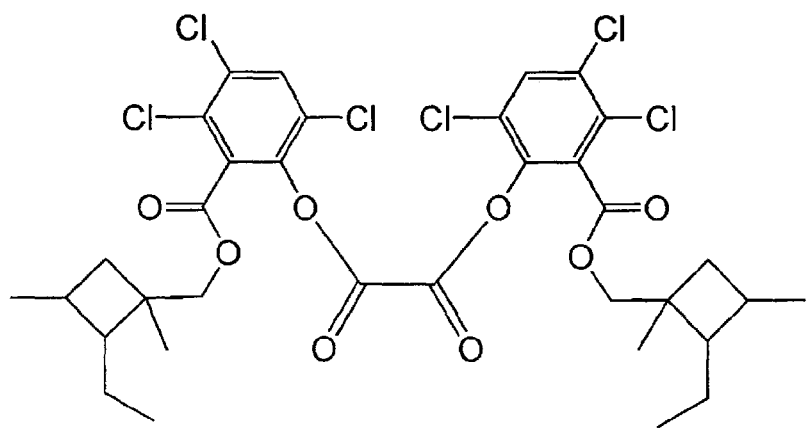
Figure 402:
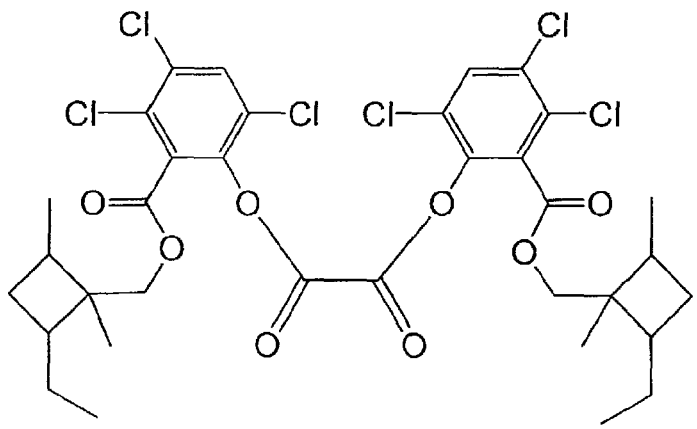
Figure 403:
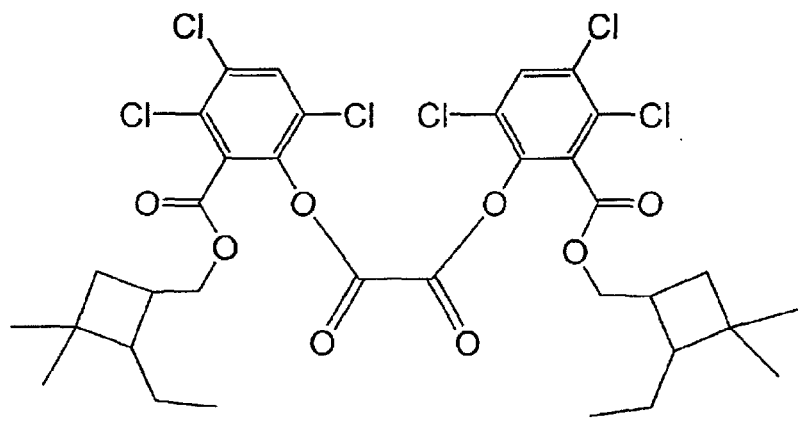
Figure 404:
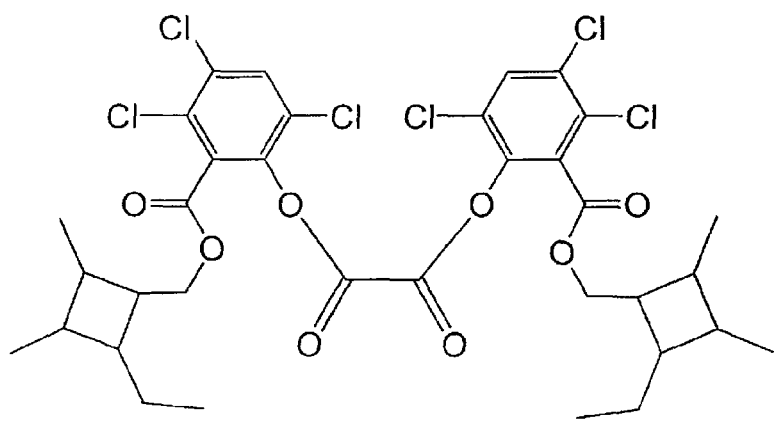
Figure 405:
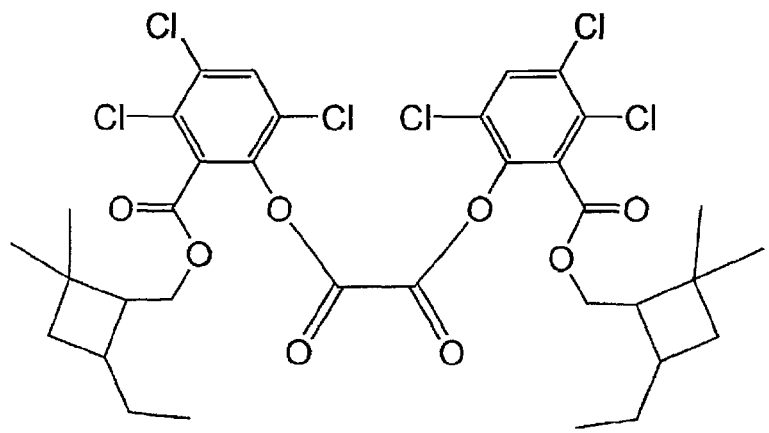
Figure 406:
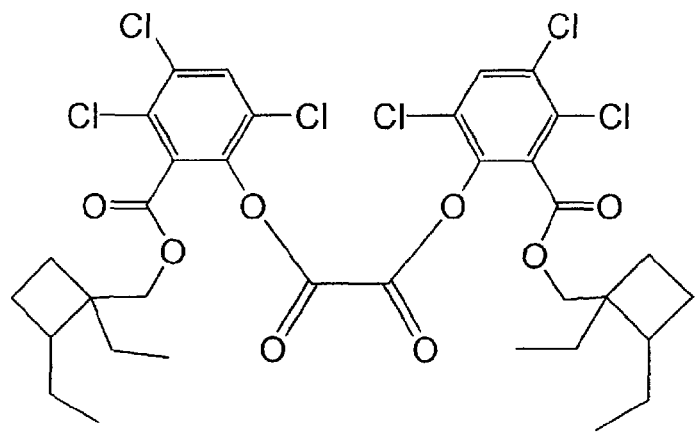
Figure 407:
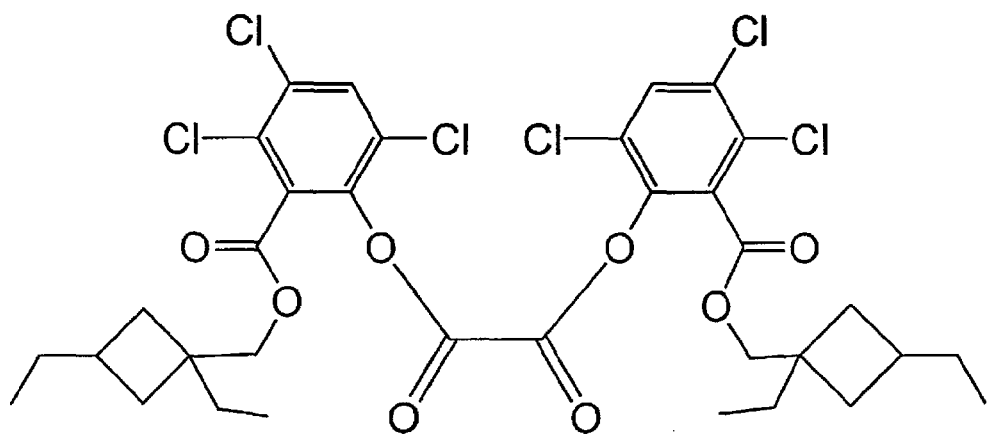
Figure 408:
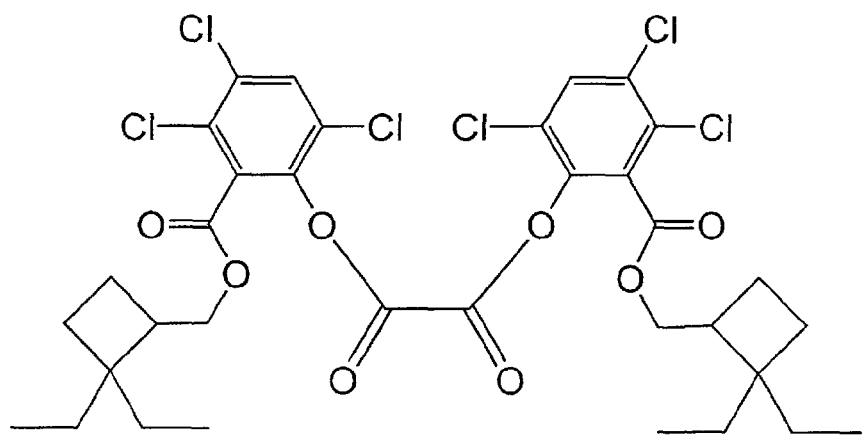
Figure 409:
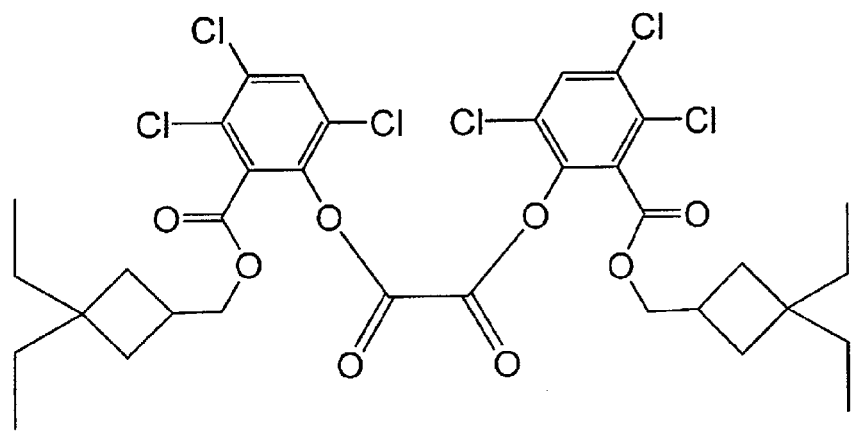
Figure 410:
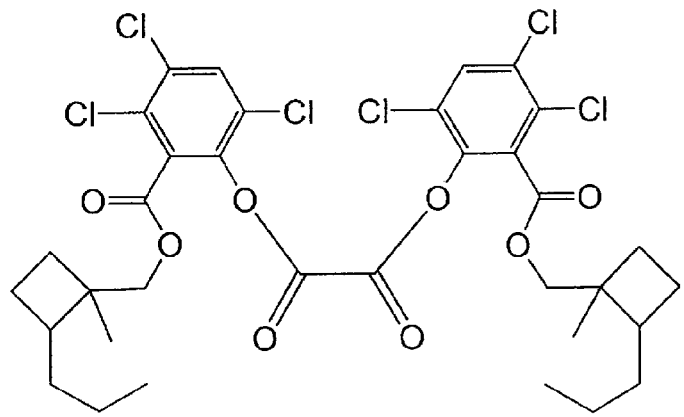
Figure 411:
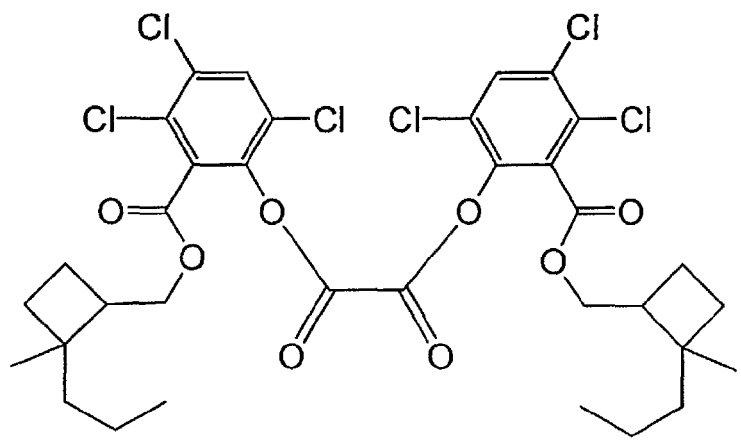
Figure 412:
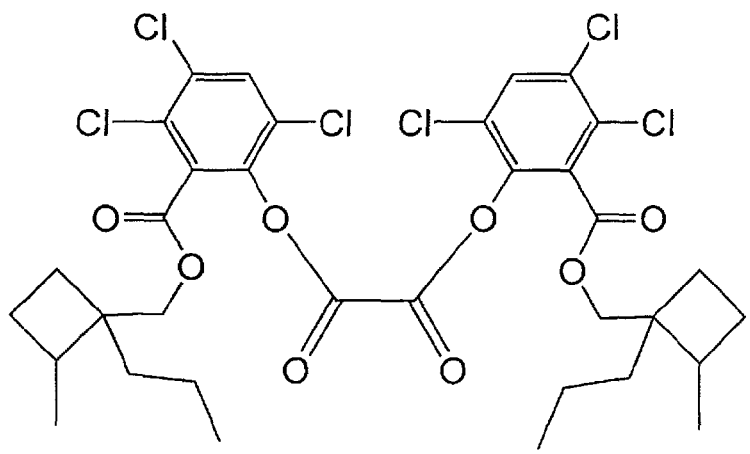
Figure 413:
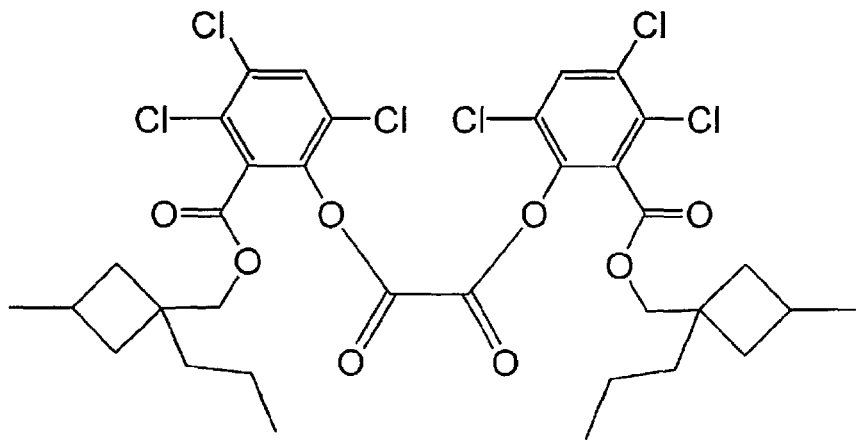
Figure 414:
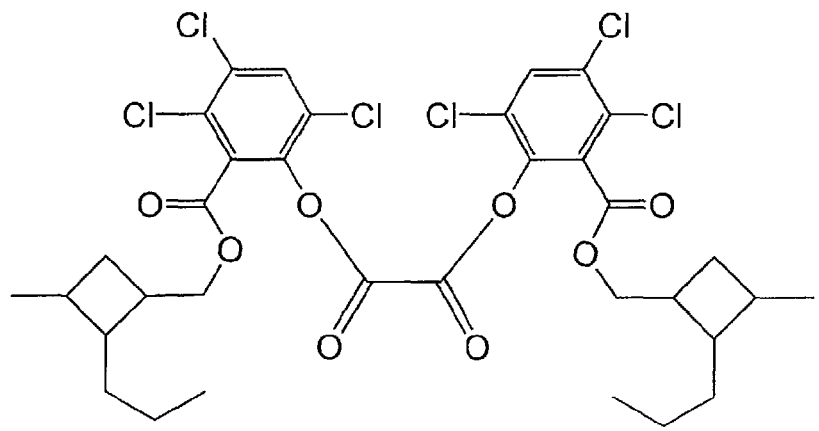
Figure 415:
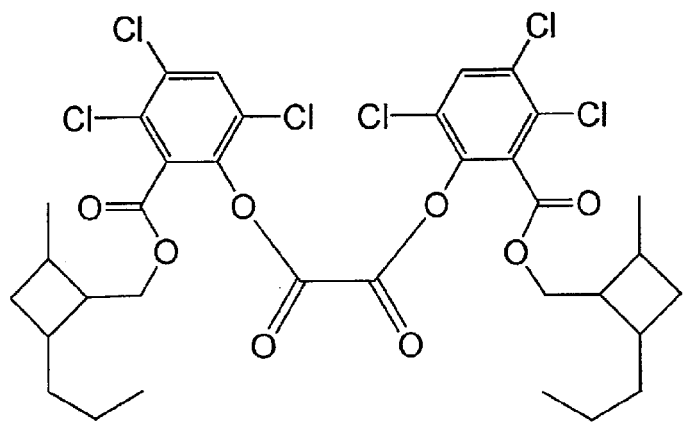
Figure 416:
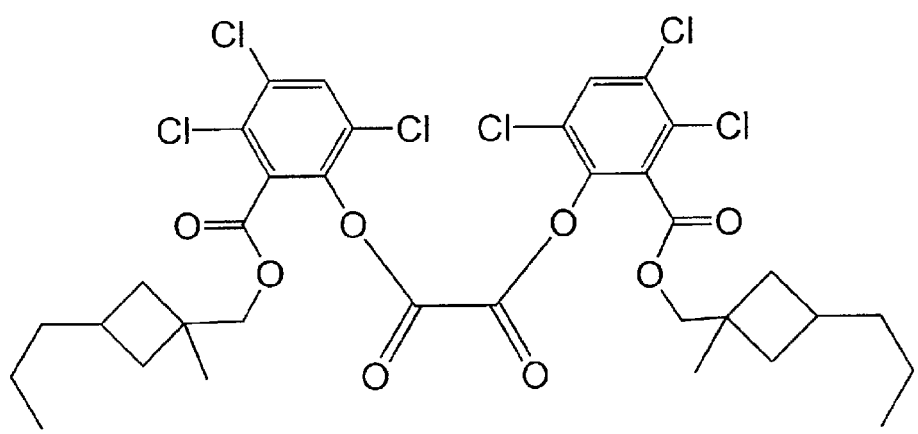
Figure 417:
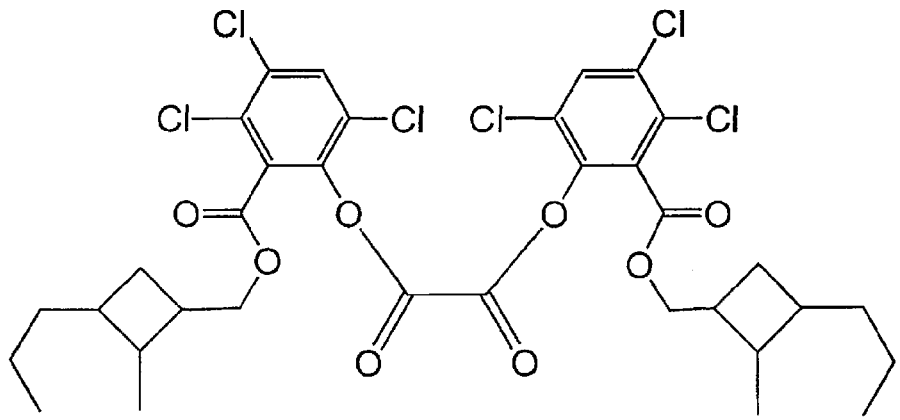
Figure 418:
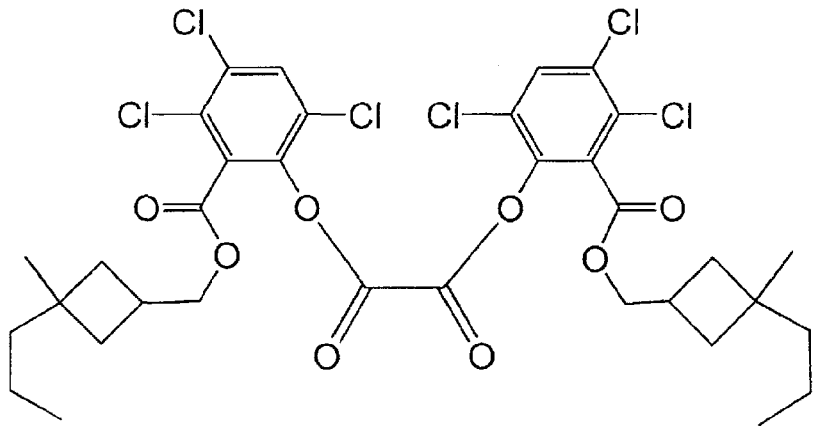
Figure 419:
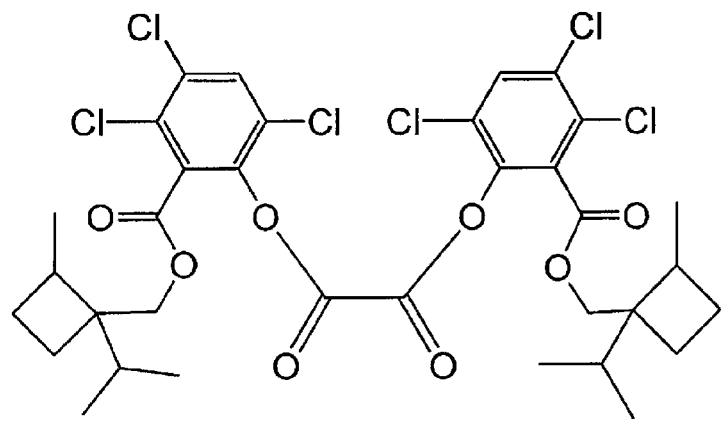
Figure 420:
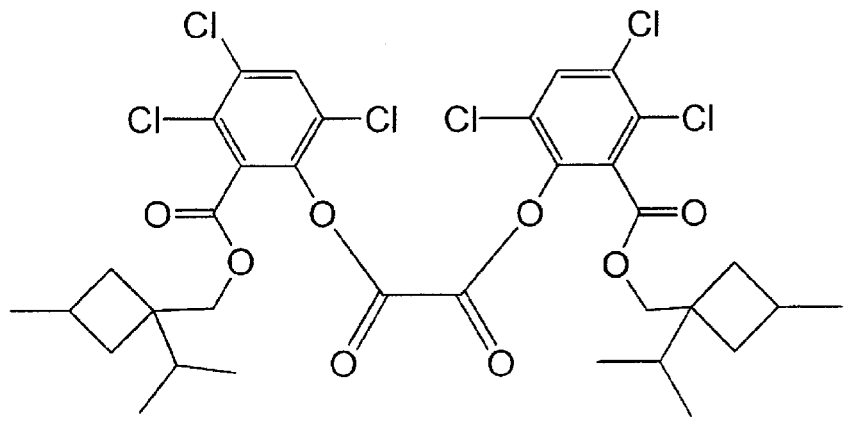
Figure 421:
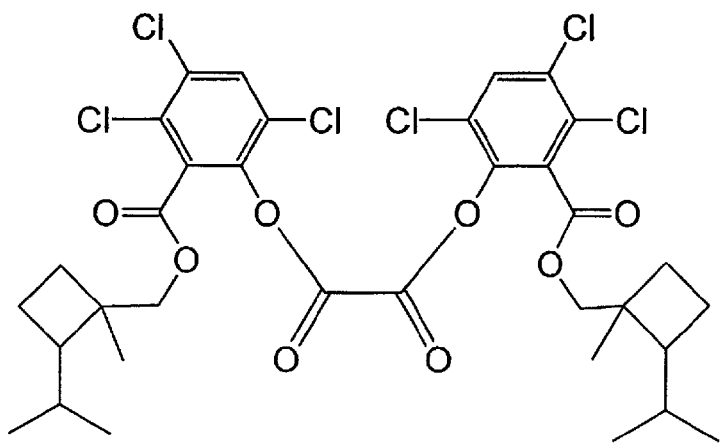
Figure 422:
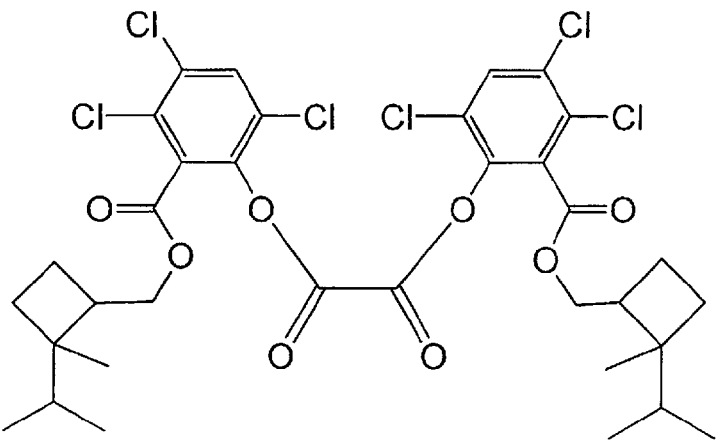
Figure 423:
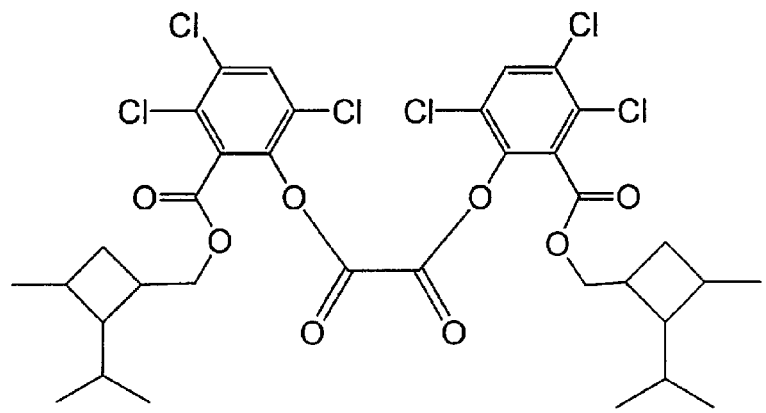
Figure 424:
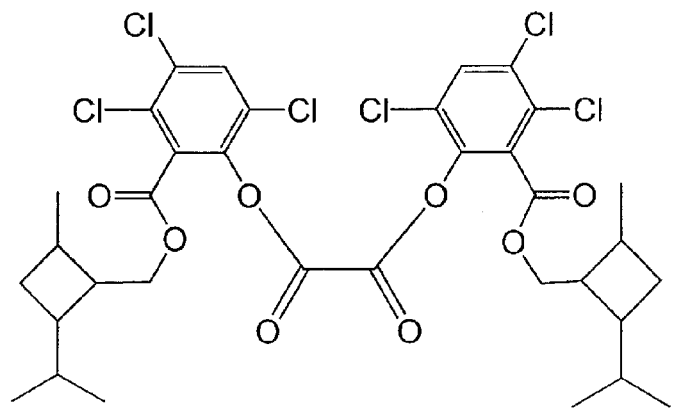
Figure 425:
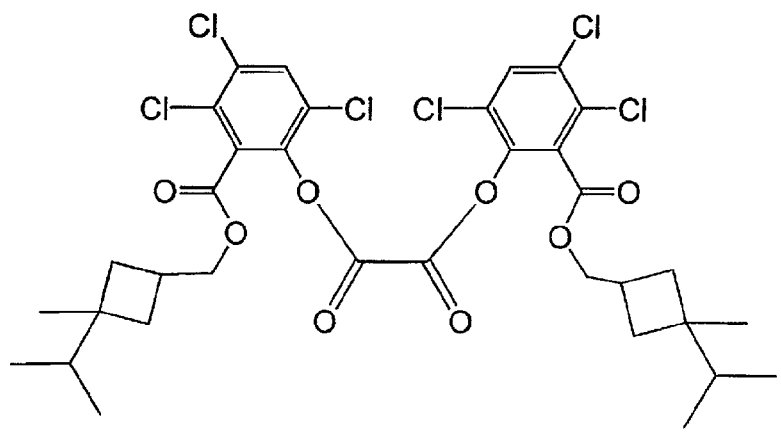
Figure 426:
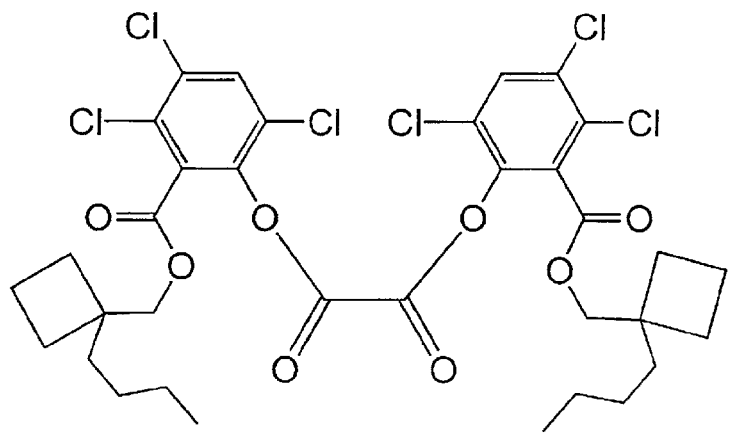
Figure 427:
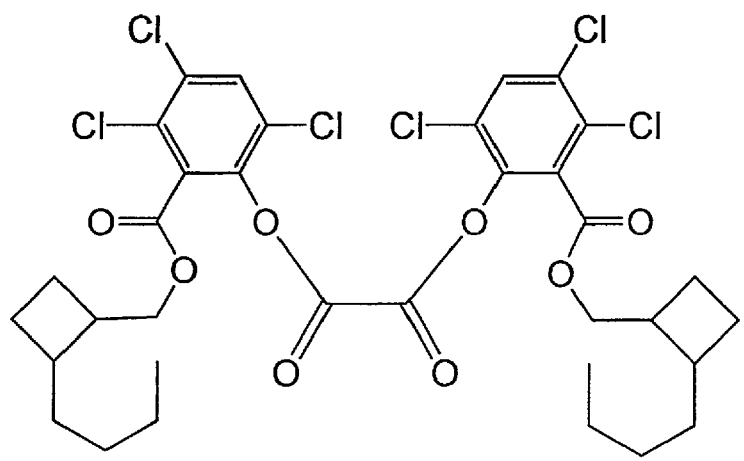
Figure 428:
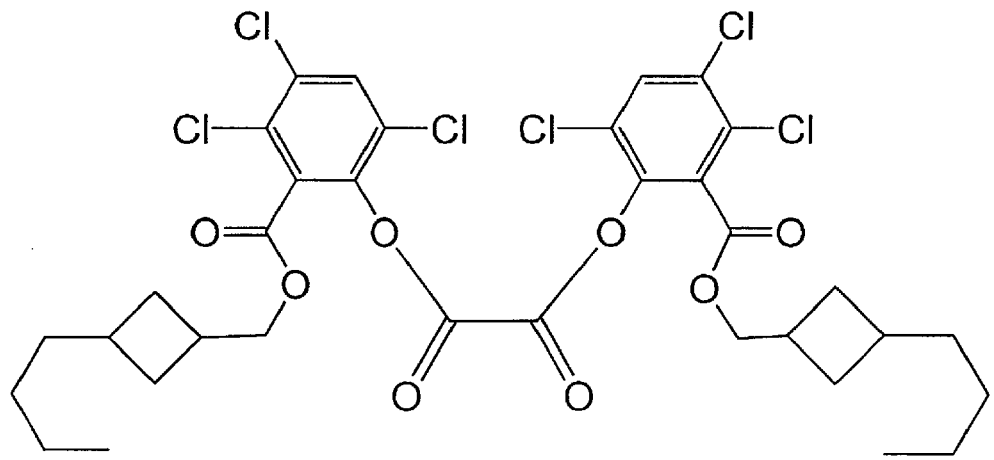
Figure 429:
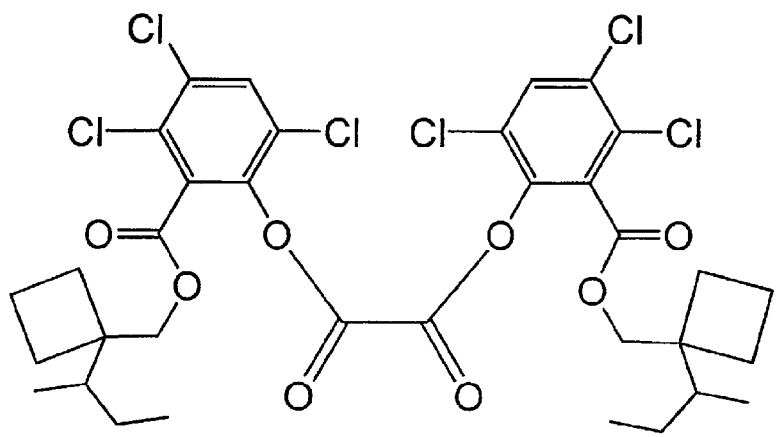
Figure 430:
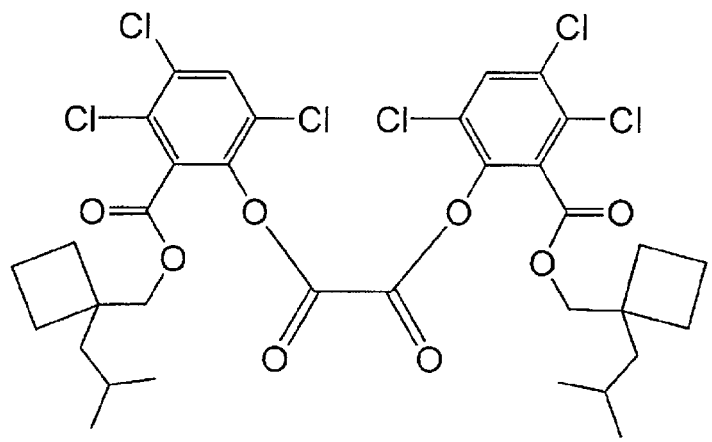
Figure 431:
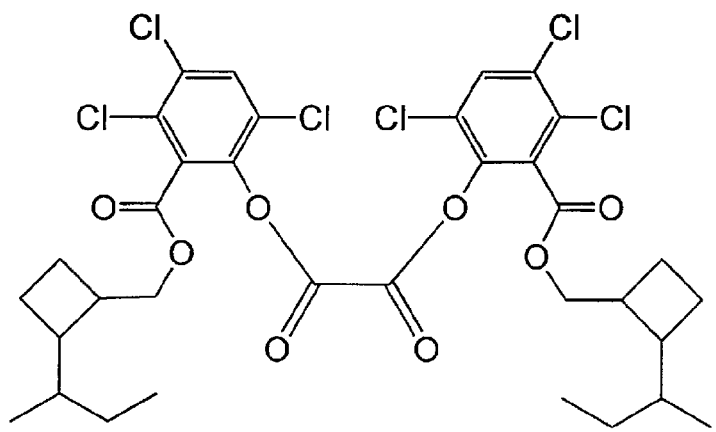
Figure 432:
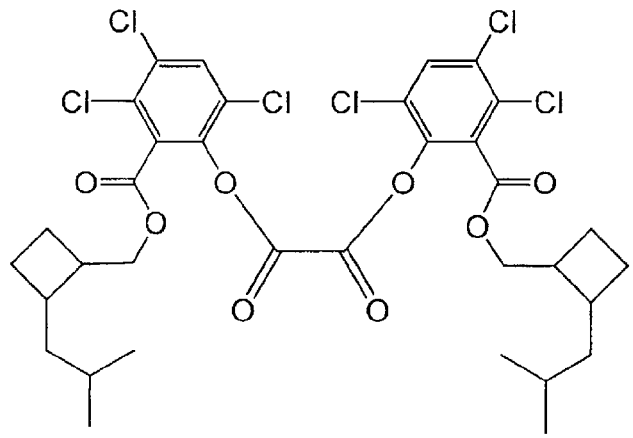
Figure 433:
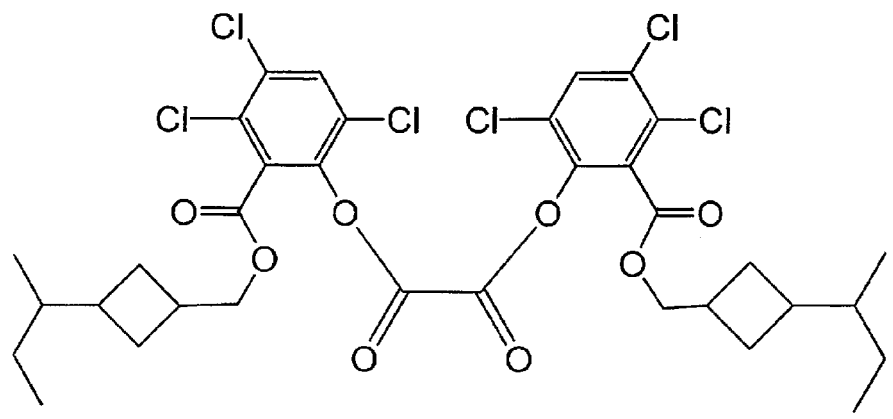
Figure 434:
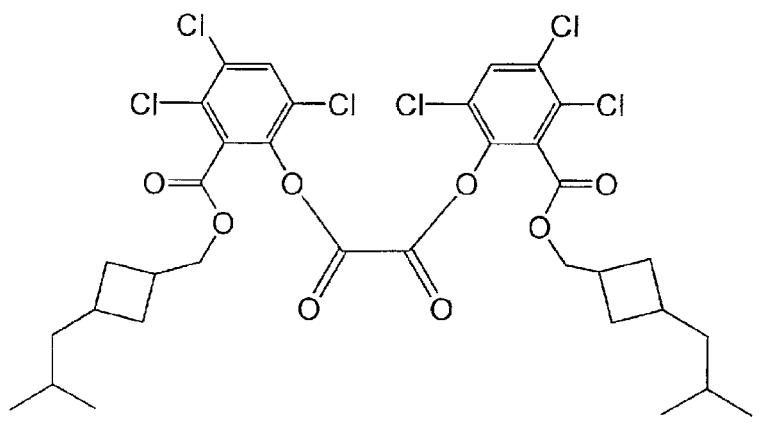
Figure 435:
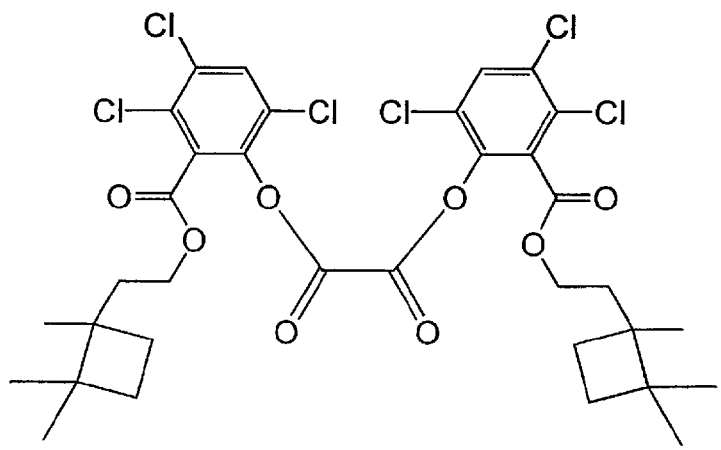
Figure 436:
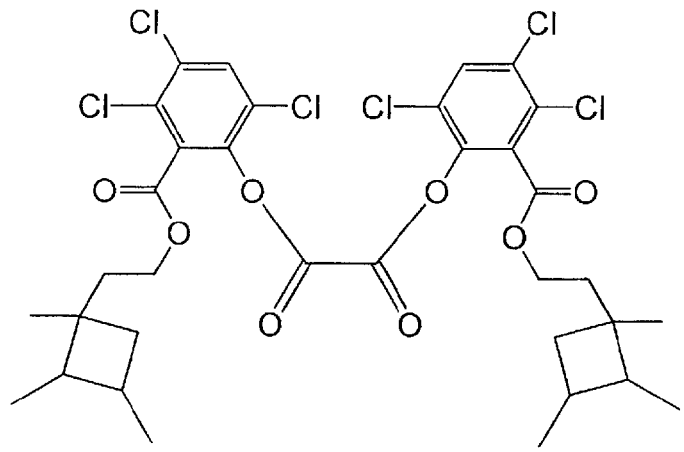
Figure 437:
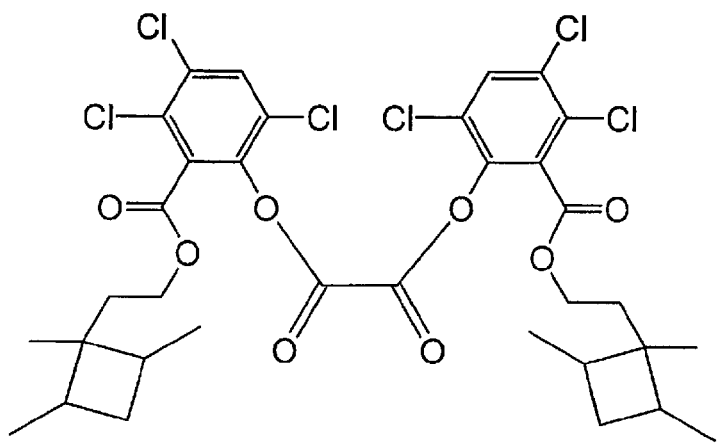
Figure 438:
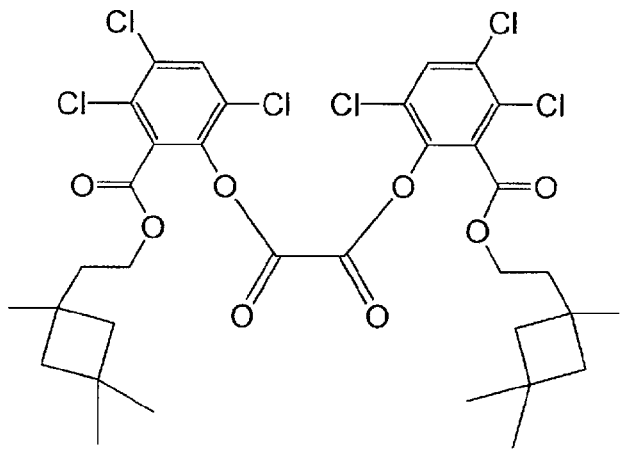
Figure 439:
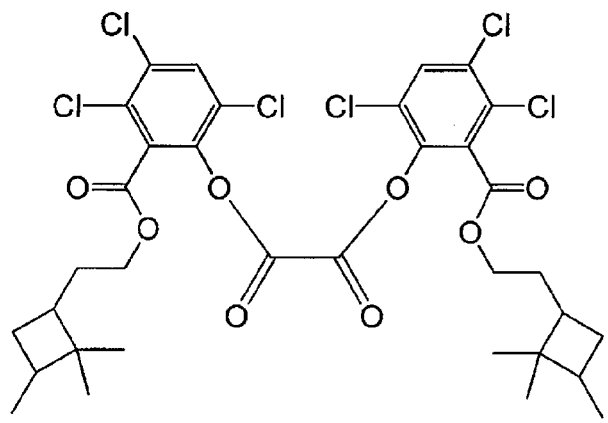
Figure 440:
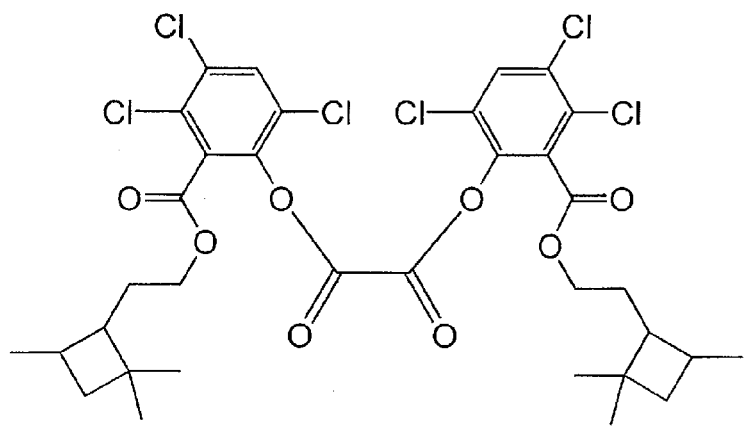
Figure 441:
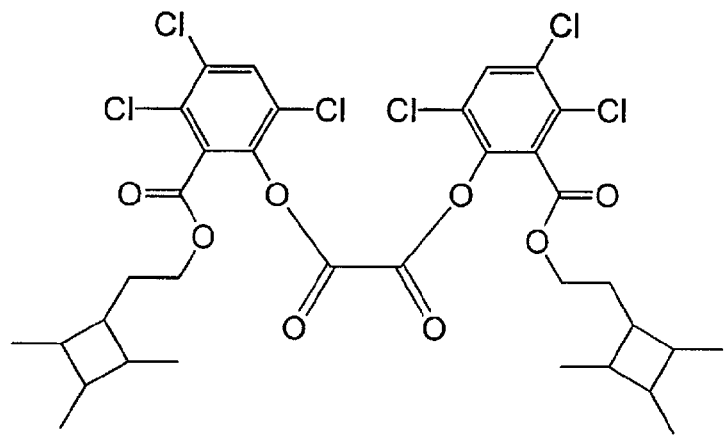
Figure 442:
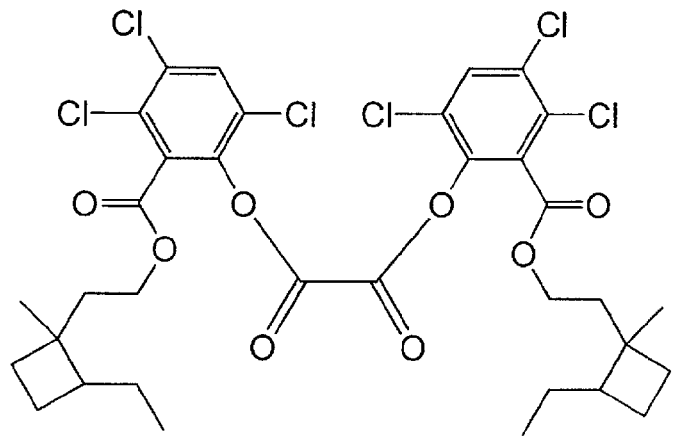
Figure 443:
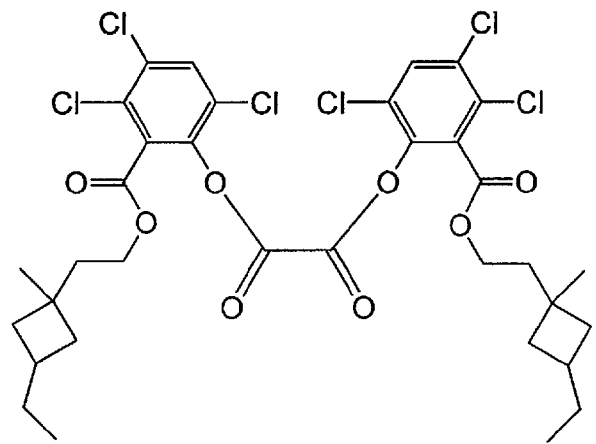
Figure 444:
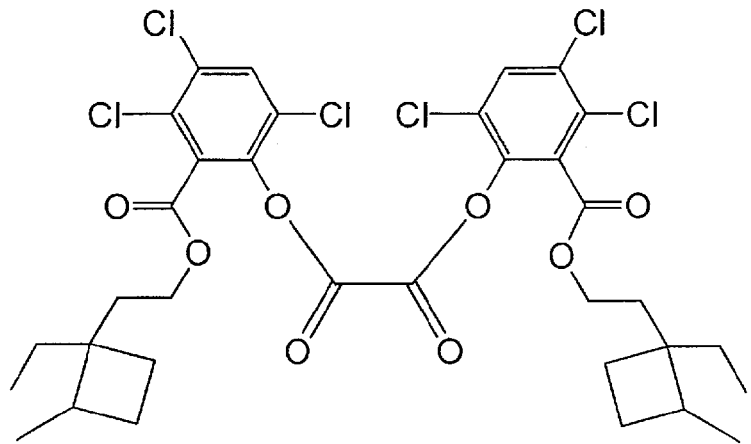
Figure 445:
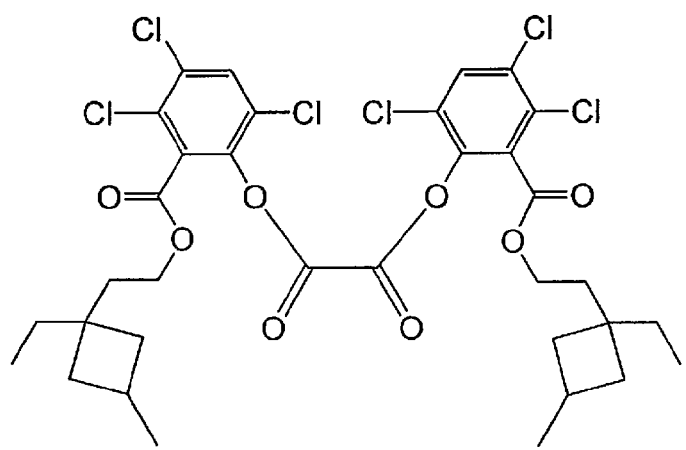
Figure 446:
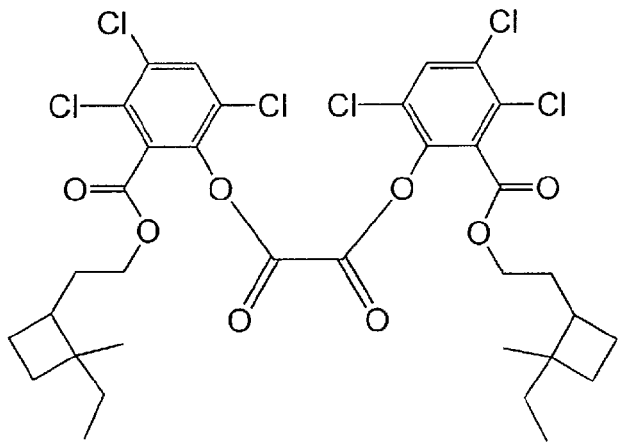
Figure 447:
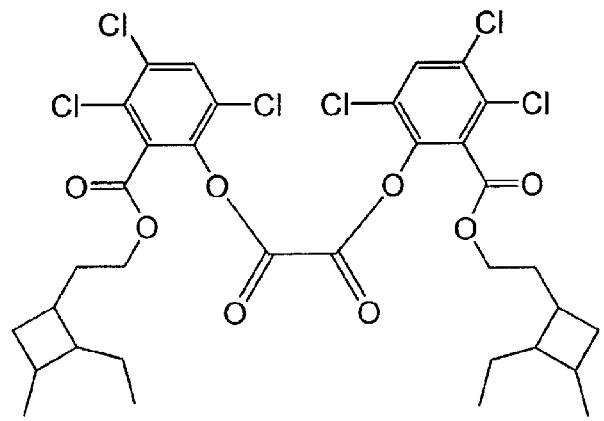
Figure 448:
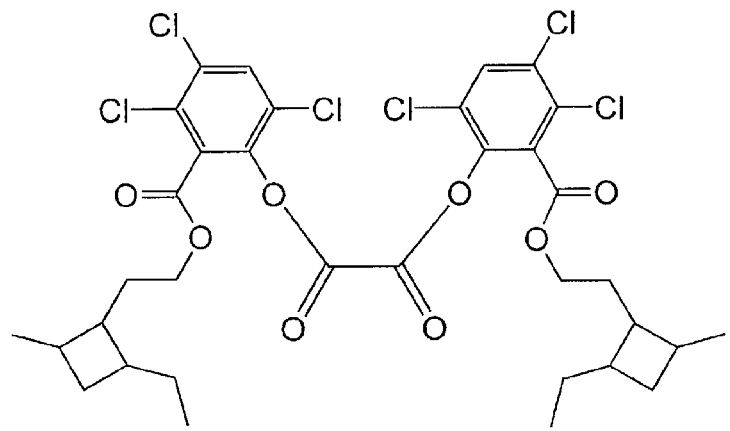
Figure 449:
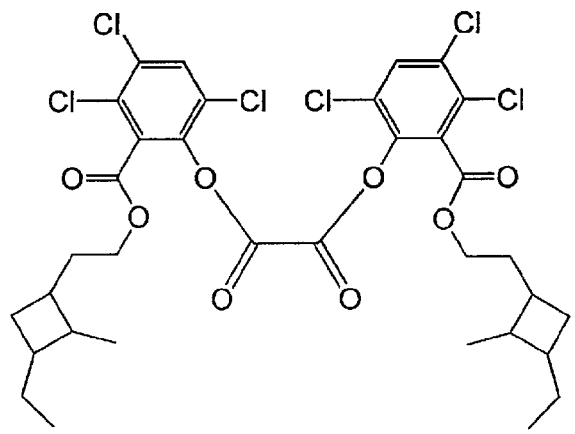
Figure 450:
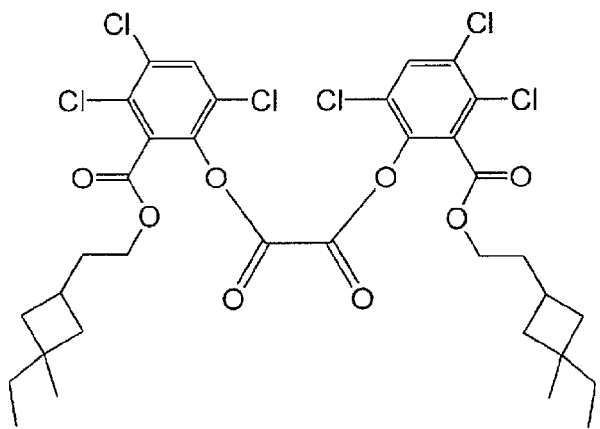
Figure 451:
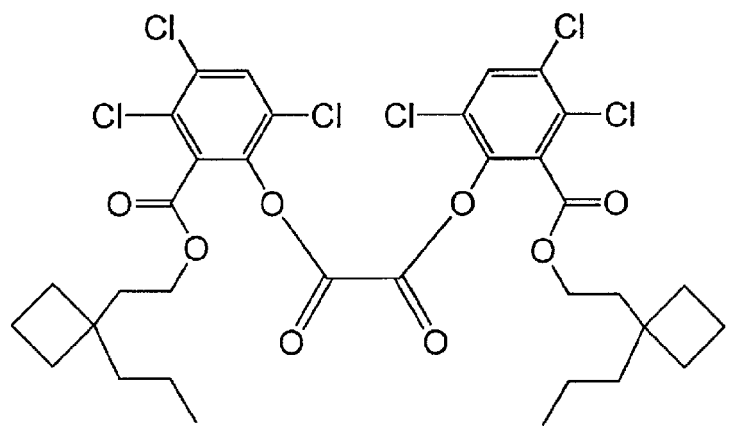
Figure 452:
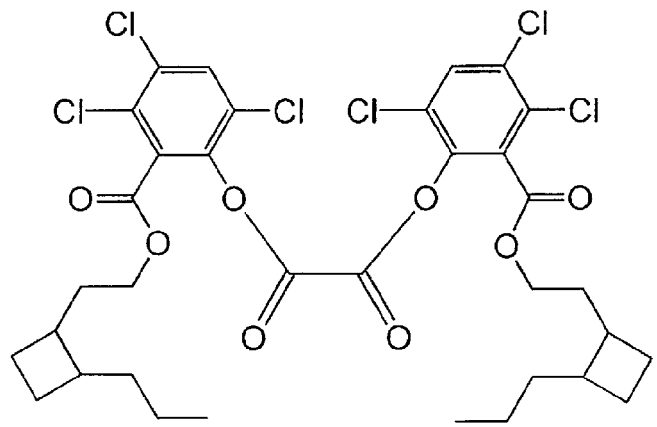
Figure 453:
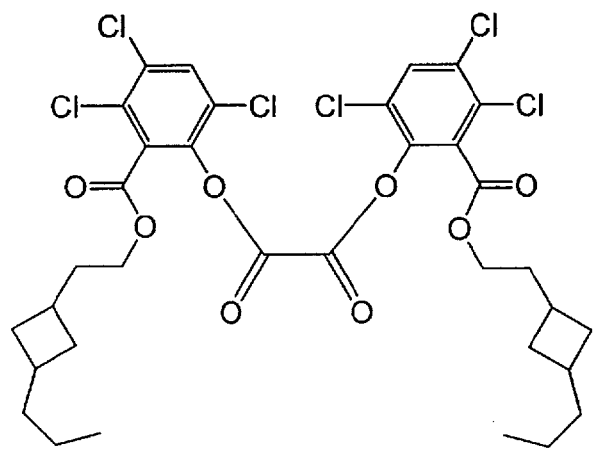
Figure 454:
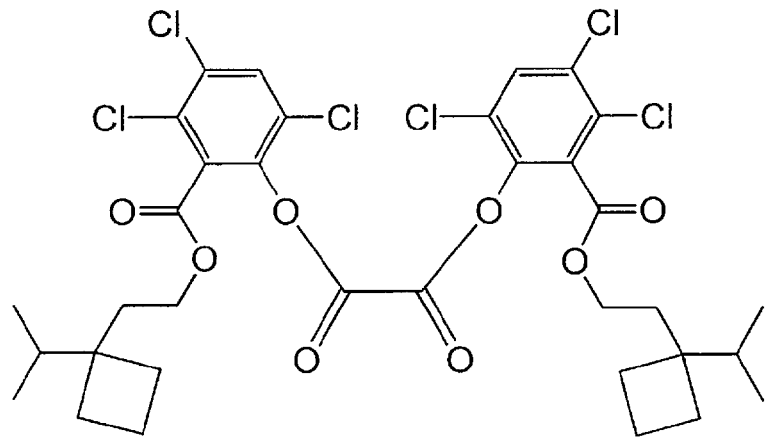
Figure 455:
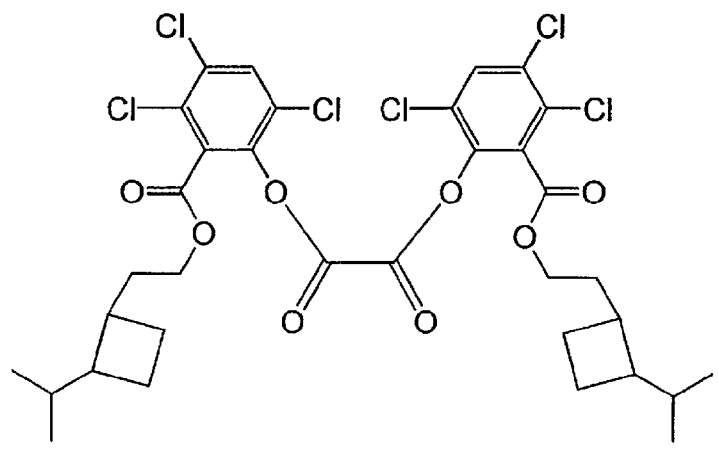
Figure 456:
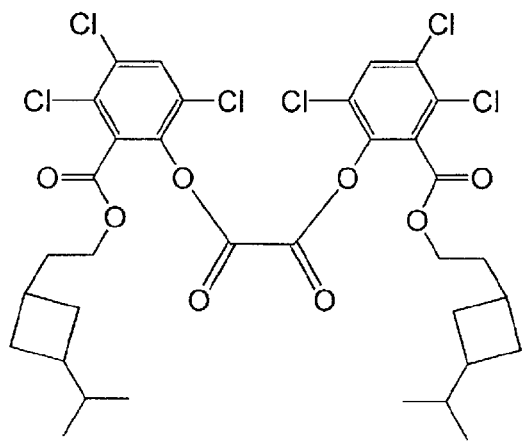
Figure 457:
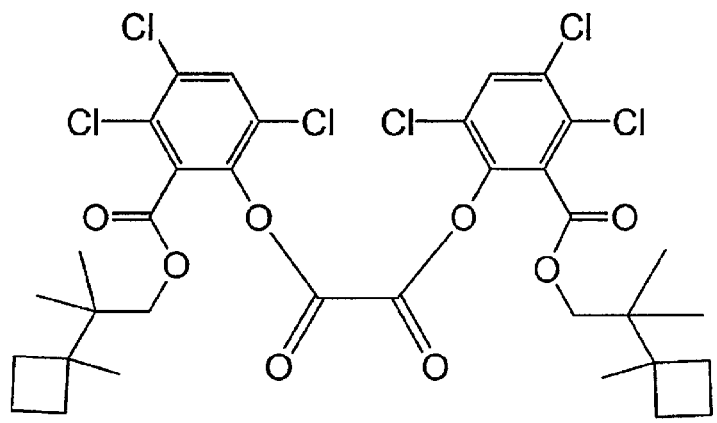
Figure 458:
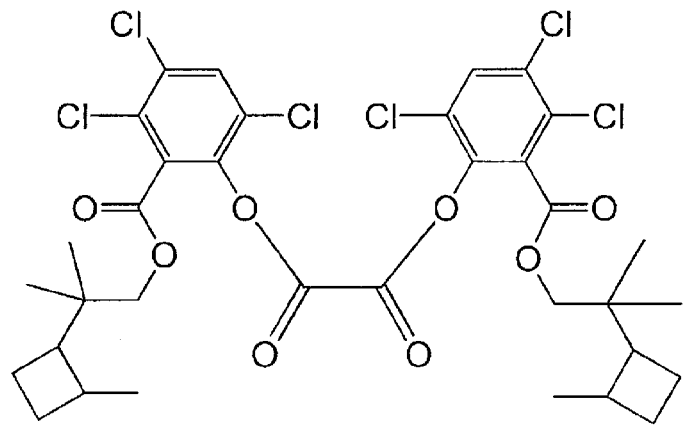
Figure 459:
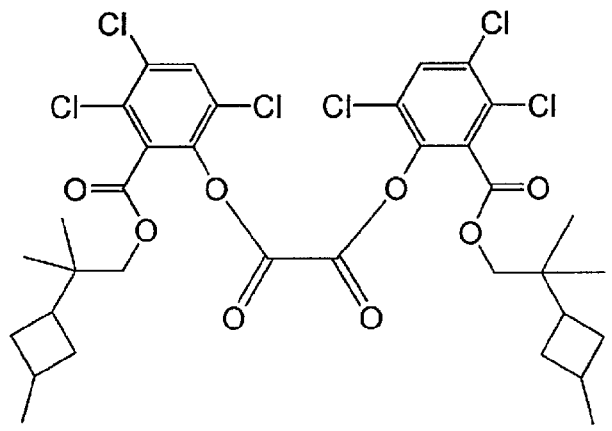
Figure 460:
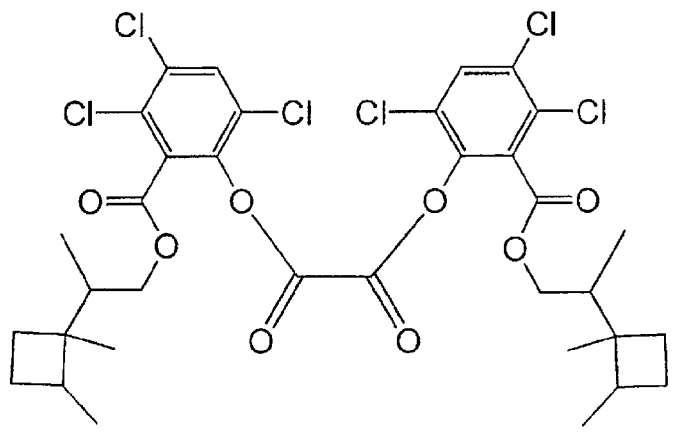
Figure 461:
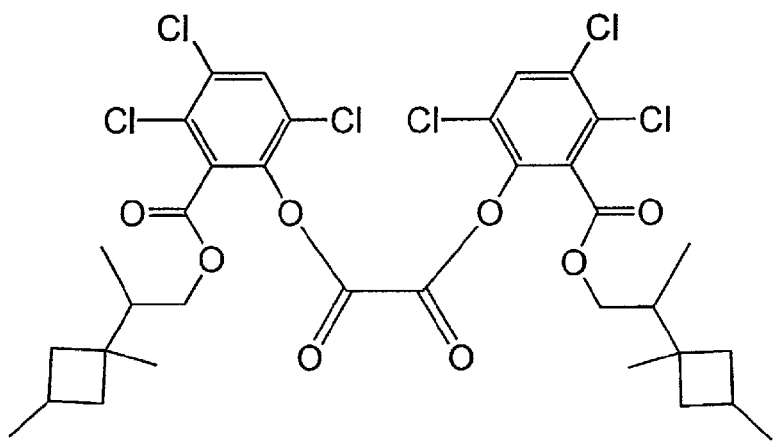
Figure 462:
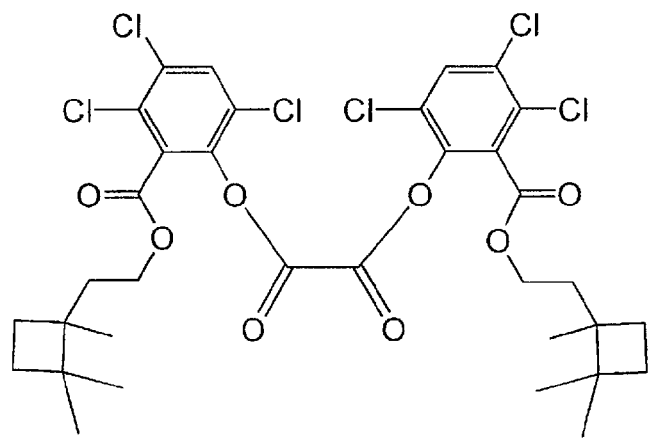
Figure 463:
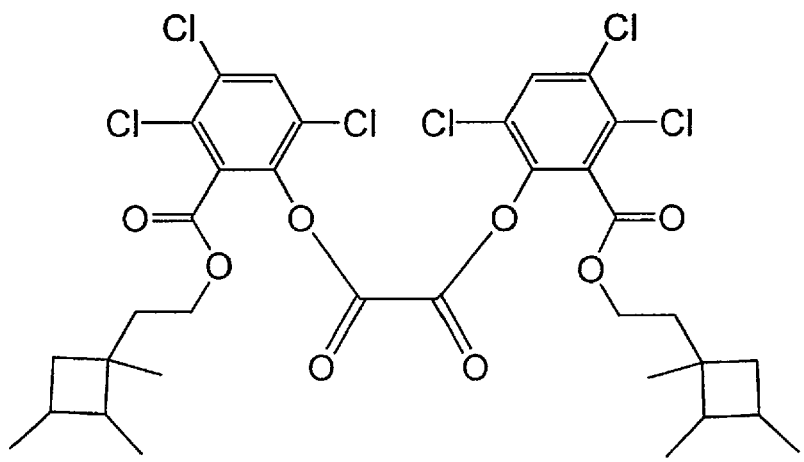
Figure 464:
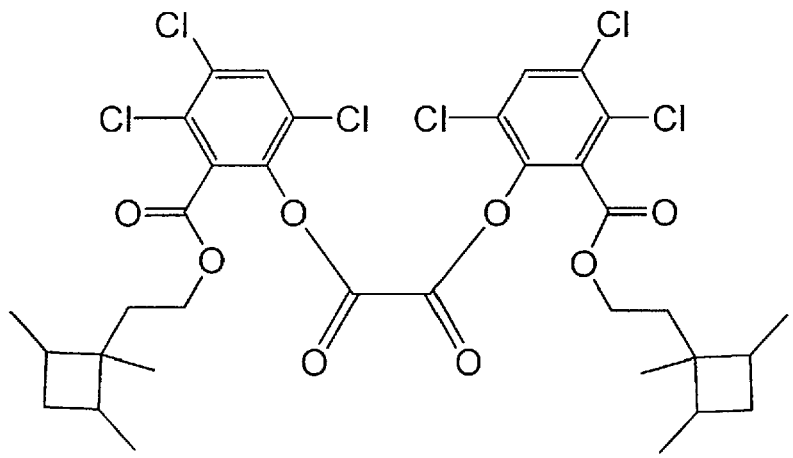
Figure 465:
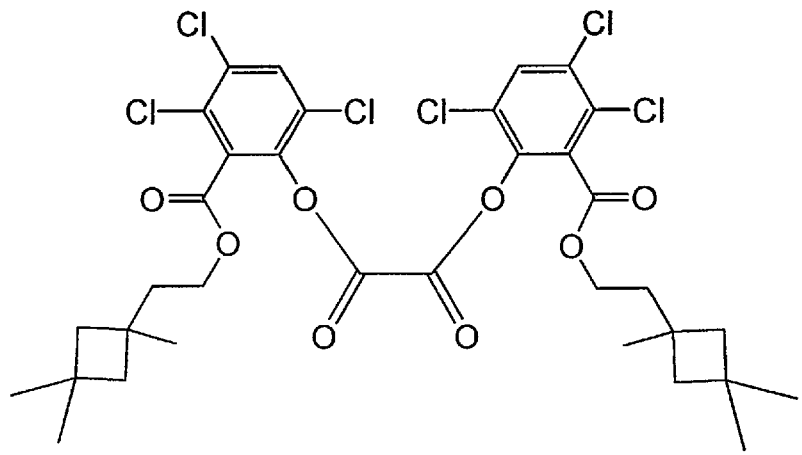
Figure 466:
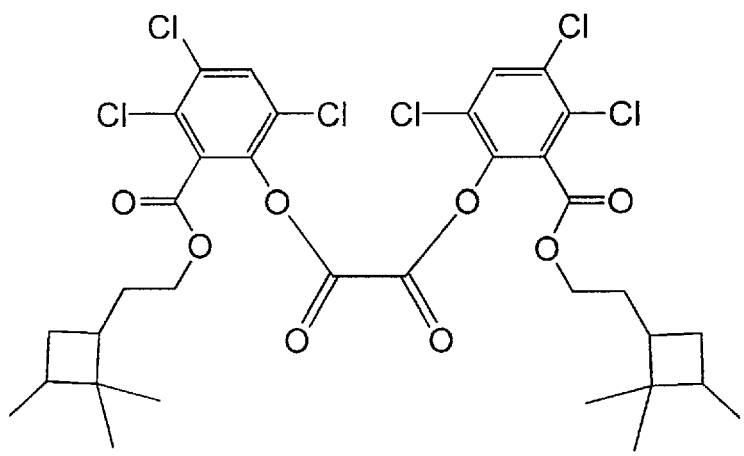
Figure 467:
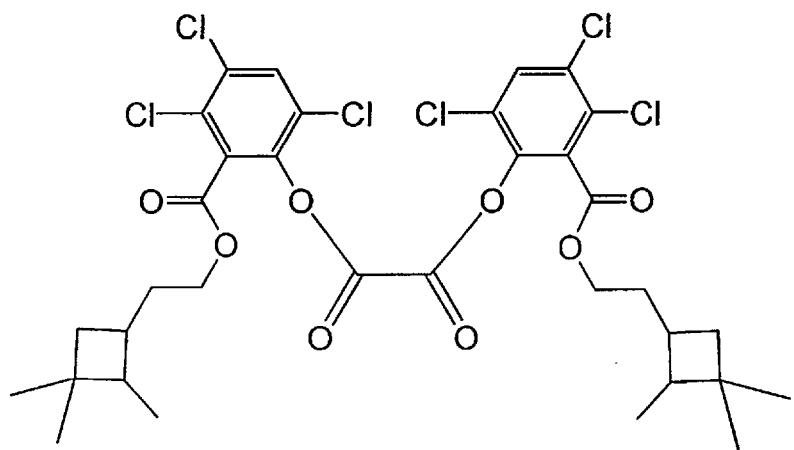
Figure 468:
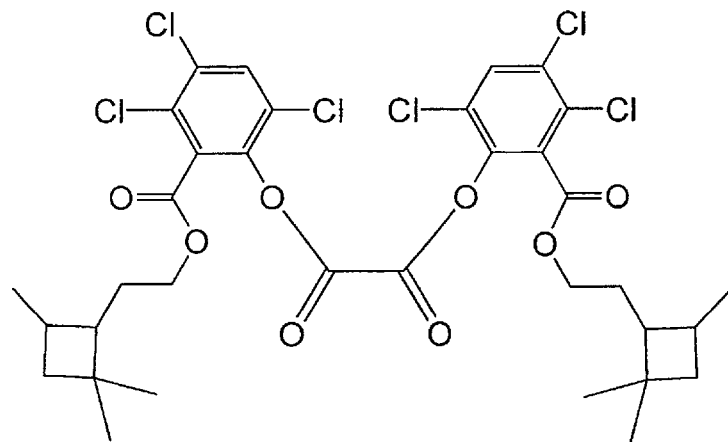
Figure 469:
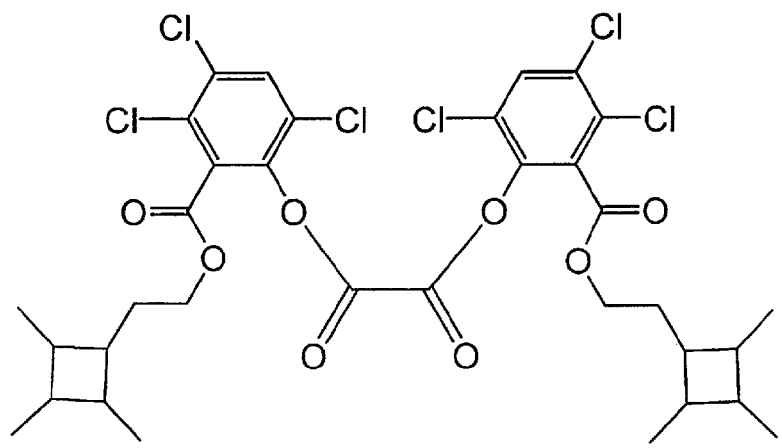
Figure 470:
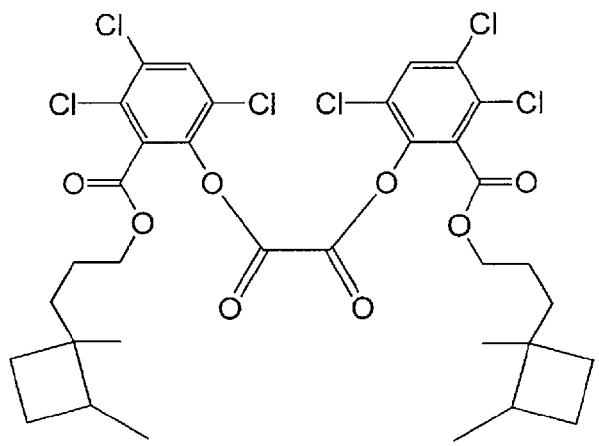
Figure 471:
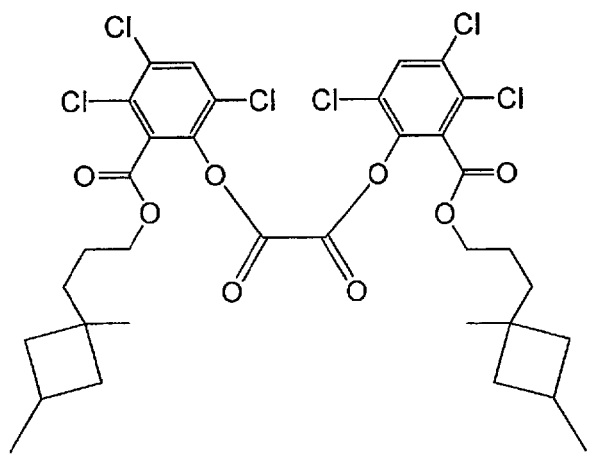
Figure 472:
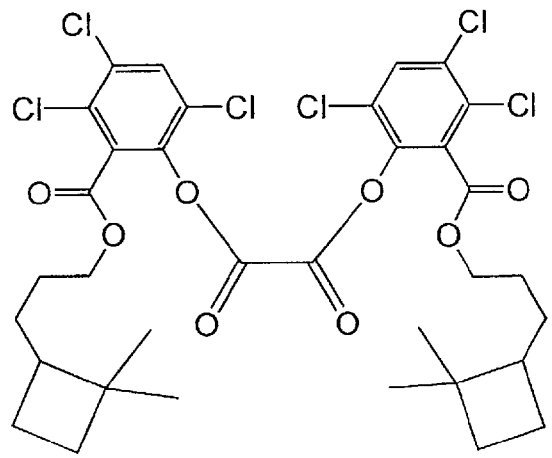
Figure 473:
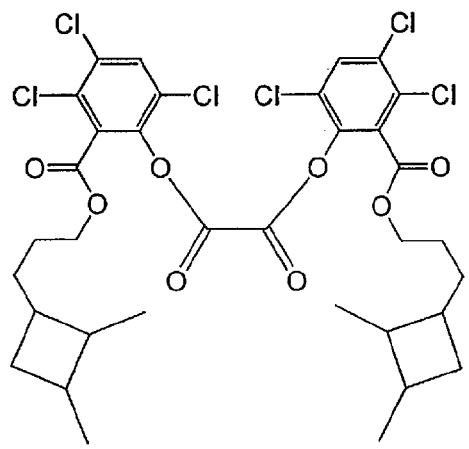
Figure 474:
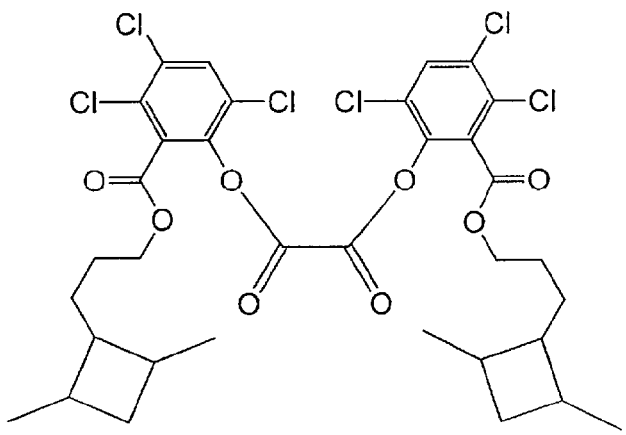
Figure 475:
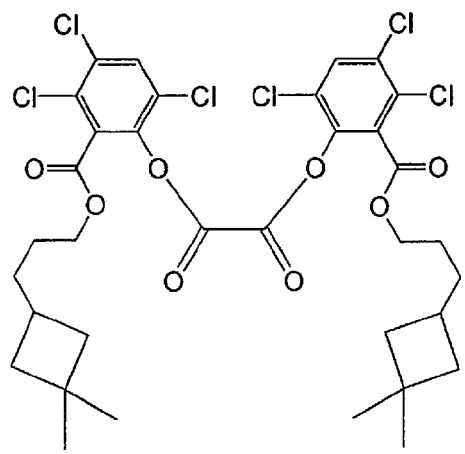
Figure 476:
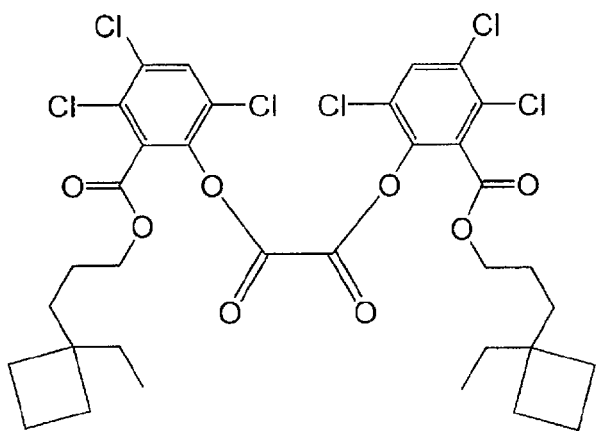
Figure 477:
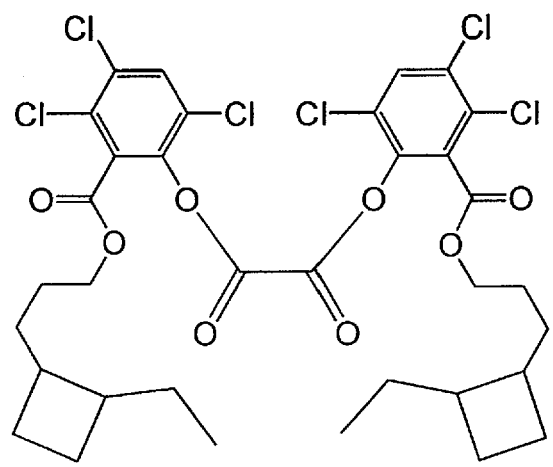
Figure 478:
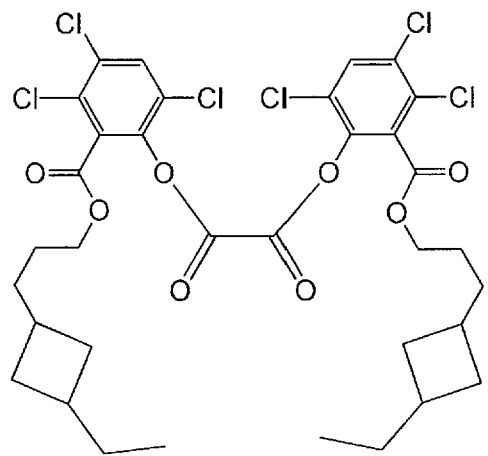
Figure 479:
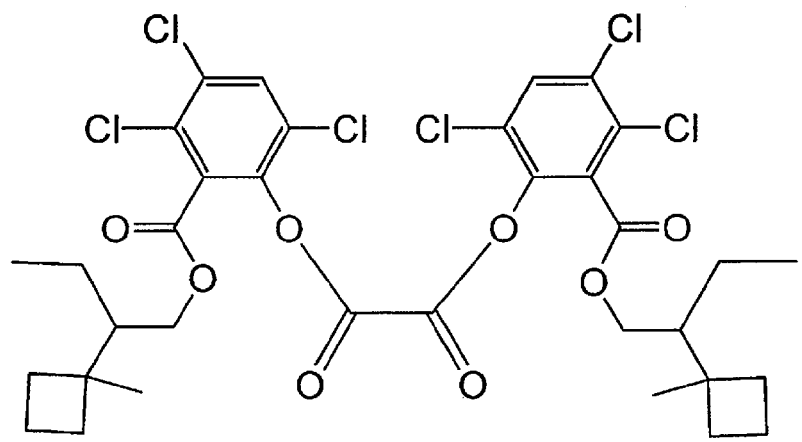
Figure 480:
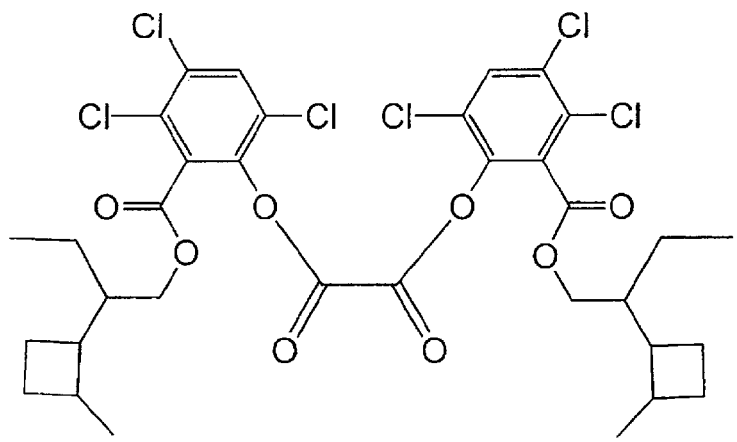
Figure 481:
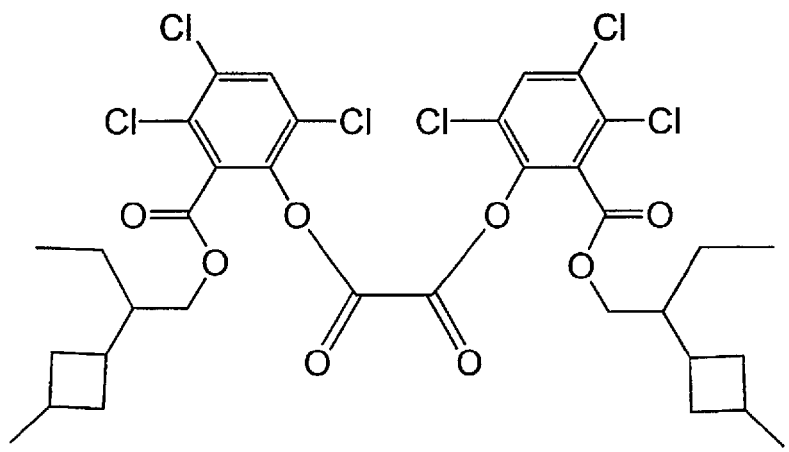
Figure 482:
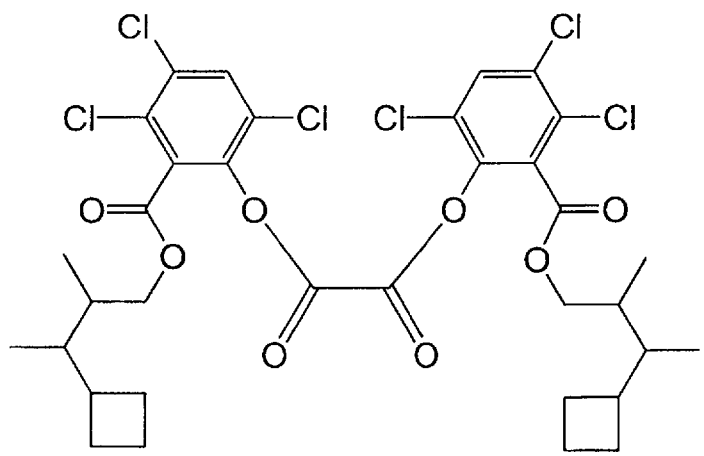
Figure 483:
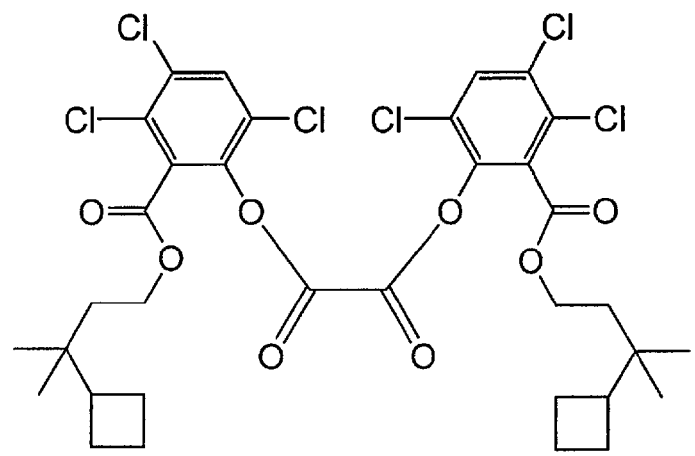
Figure 484:
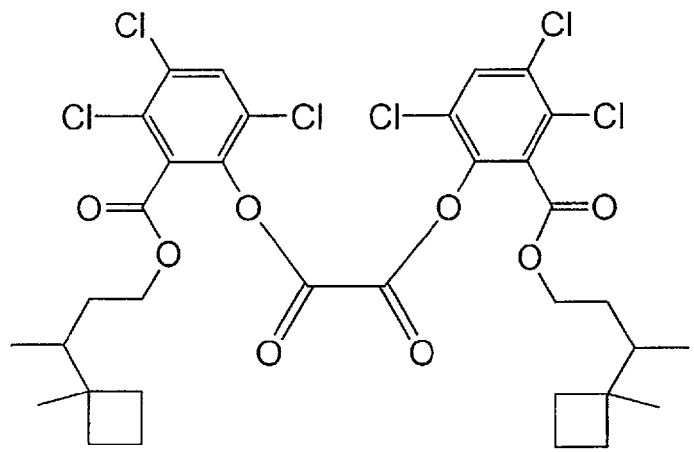
Figure 485:
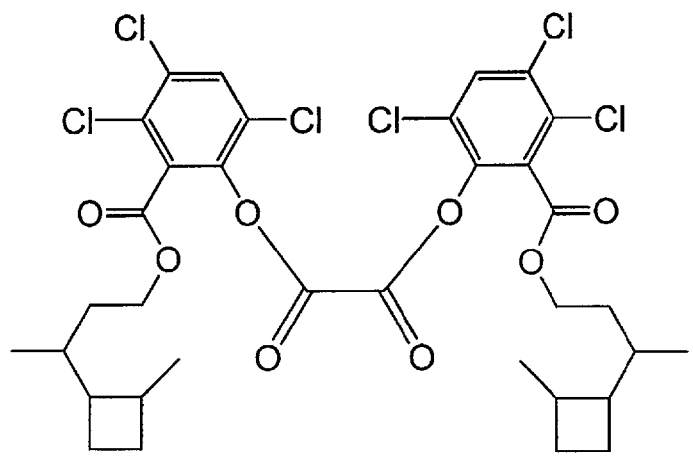
Figure 486:
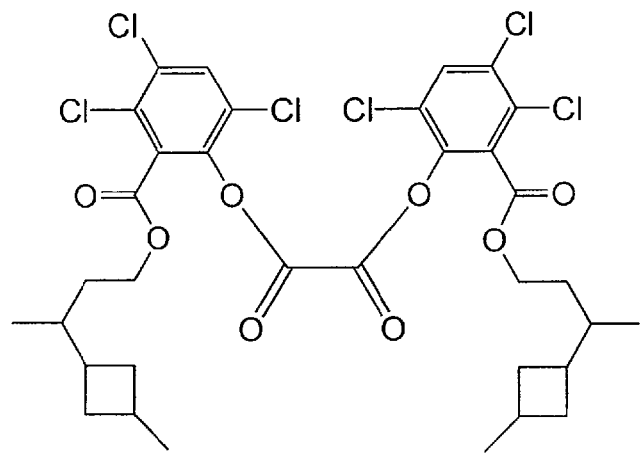
Figure 487:
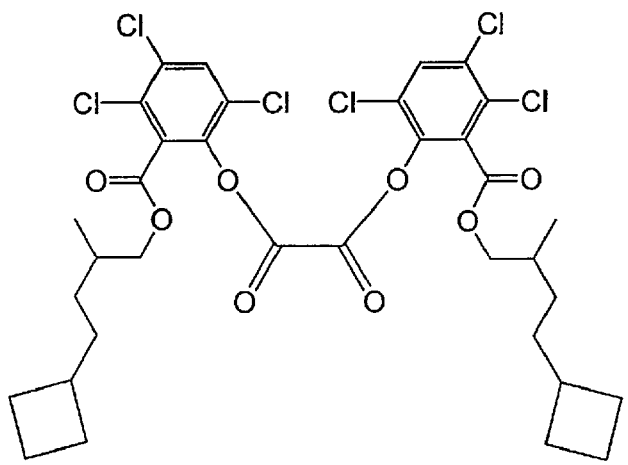
Figure 488:
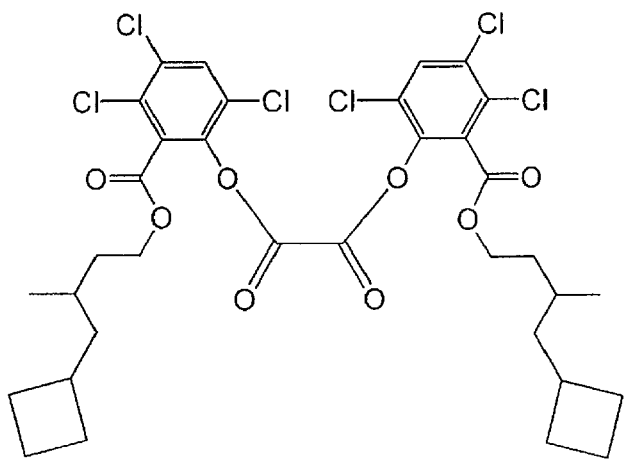
Figure 489:
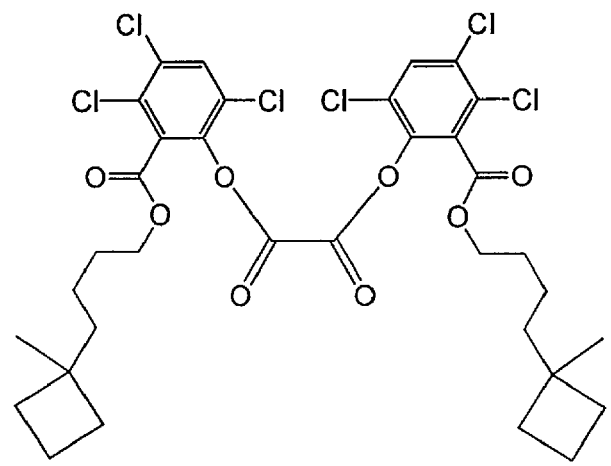
Figure 490:
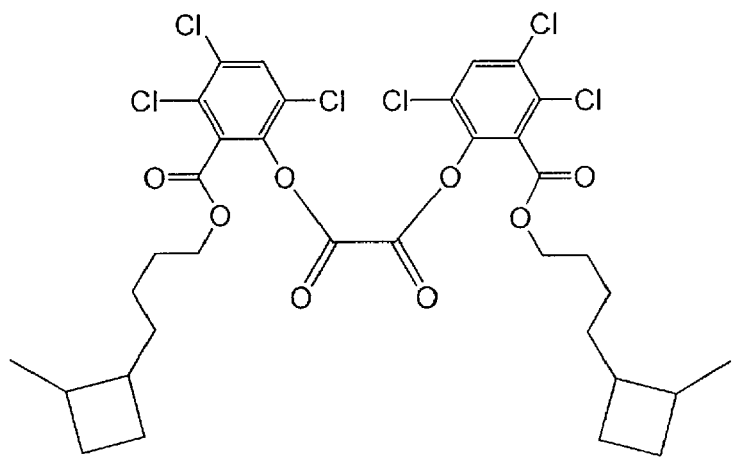
Figure 491:
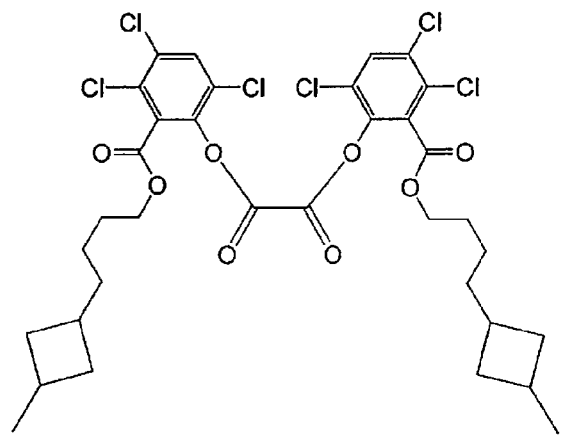
Figure 492:
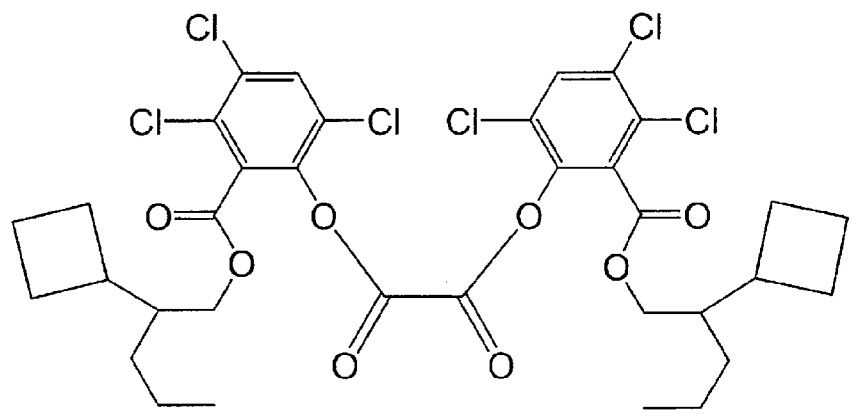
Figure 493:
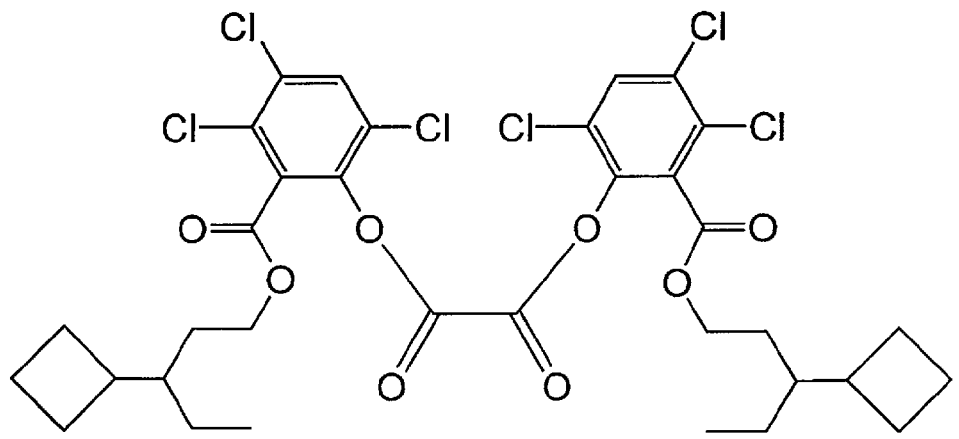
Figure 494:
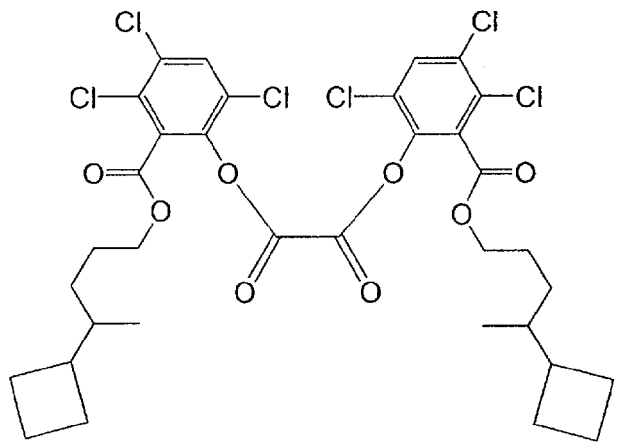
Figure 495:
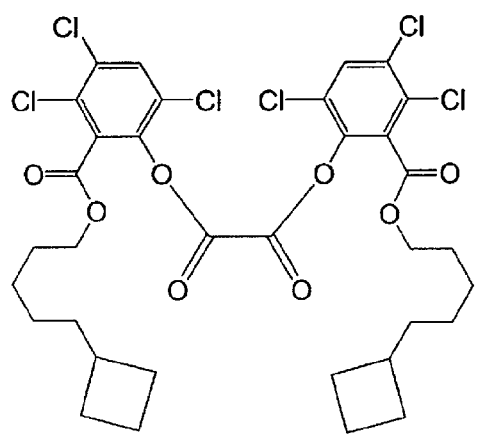
Figure 496:
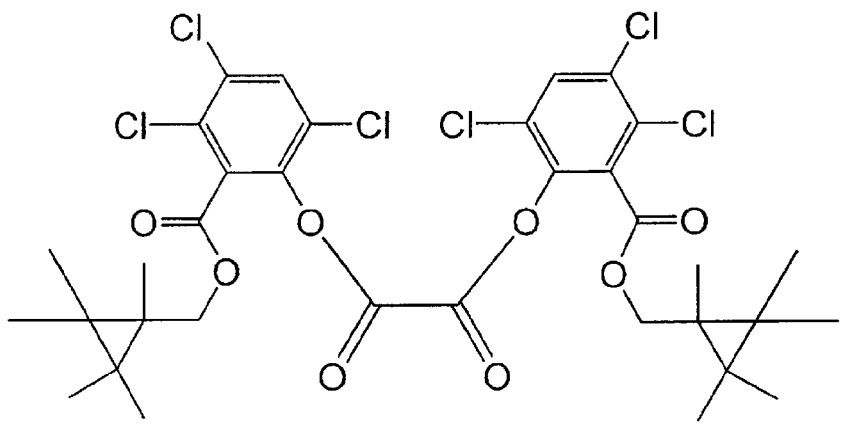
Figure 497:
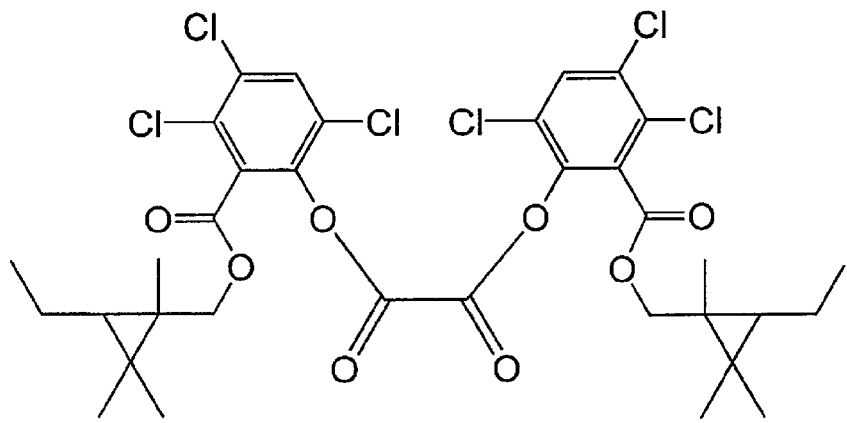
Figure 498:
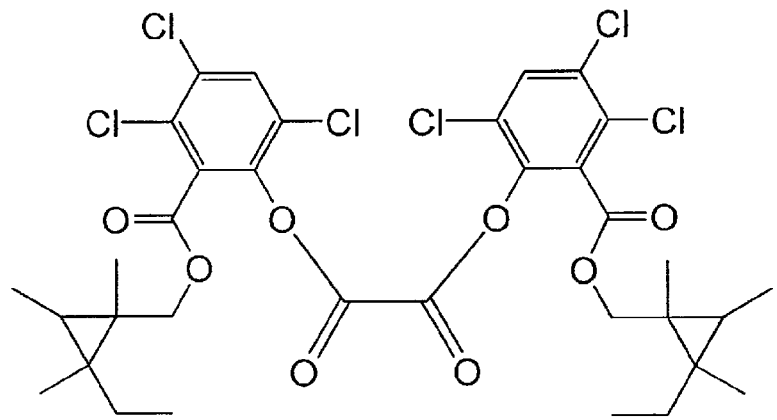
Figure 499:
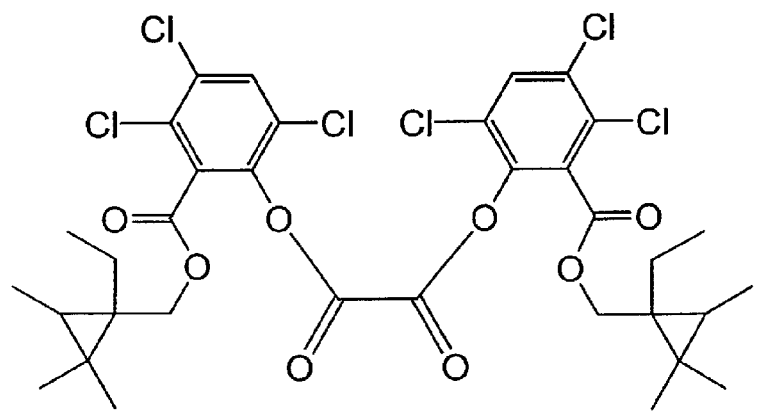
Figure 500:
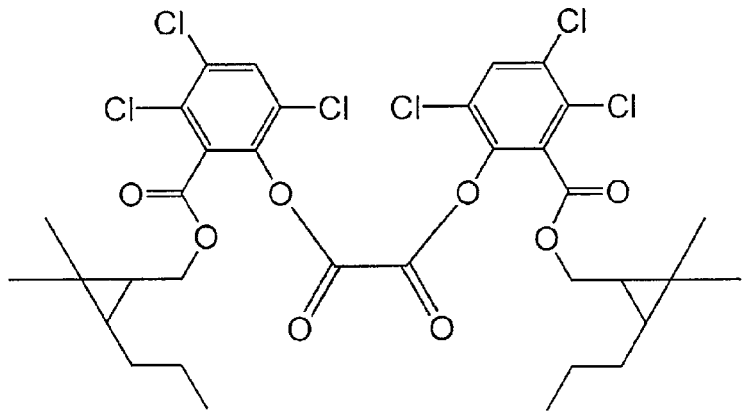
Figure 501:
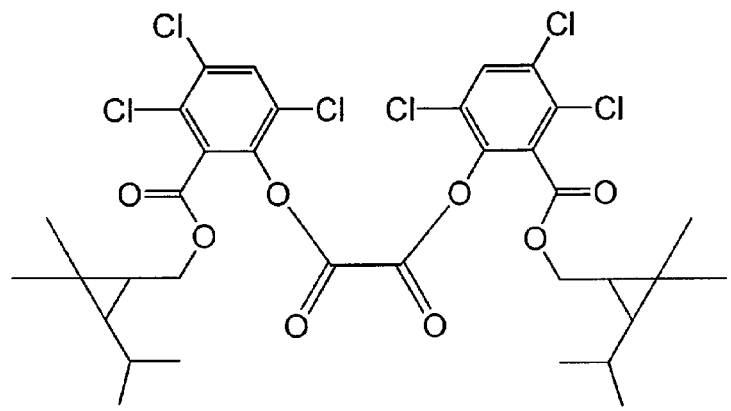
Figure 502:
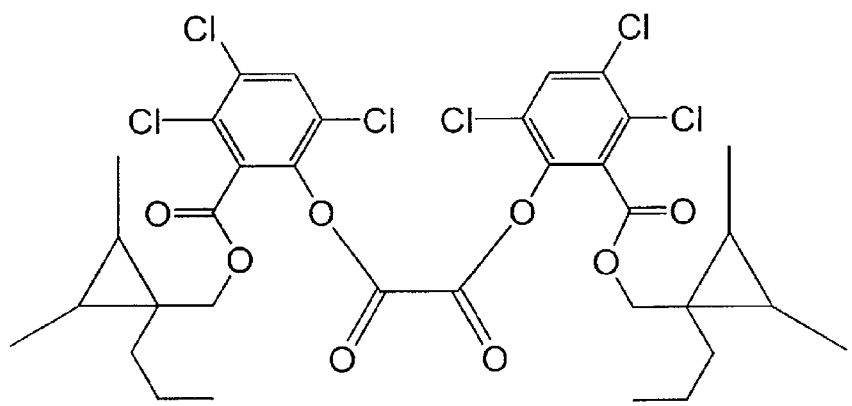
Figure 503:
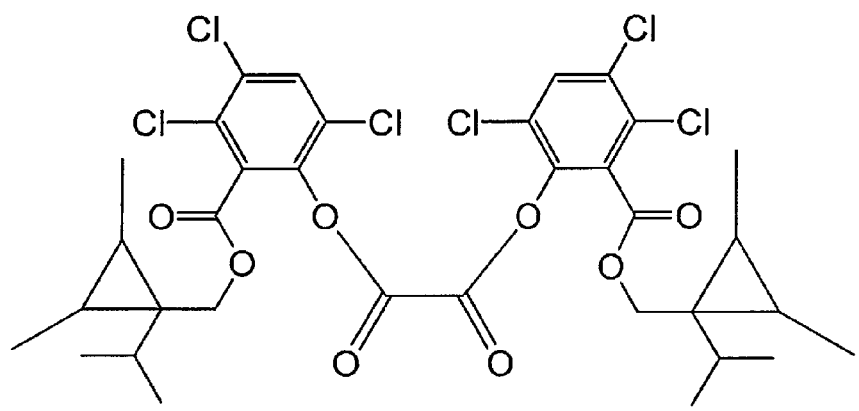
Figure 504:
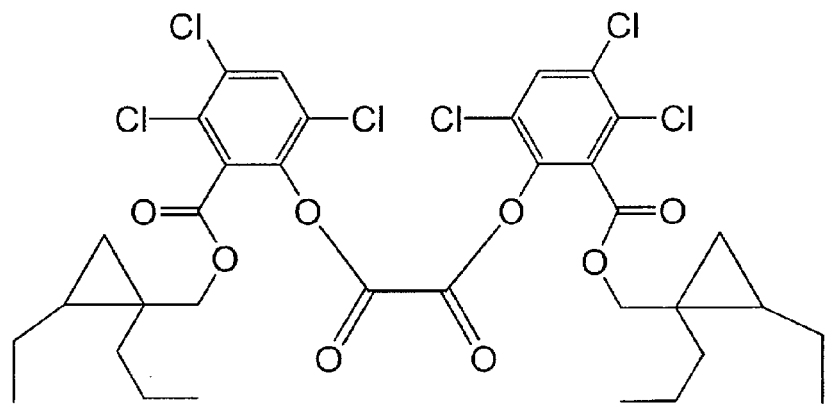
Figure 505:
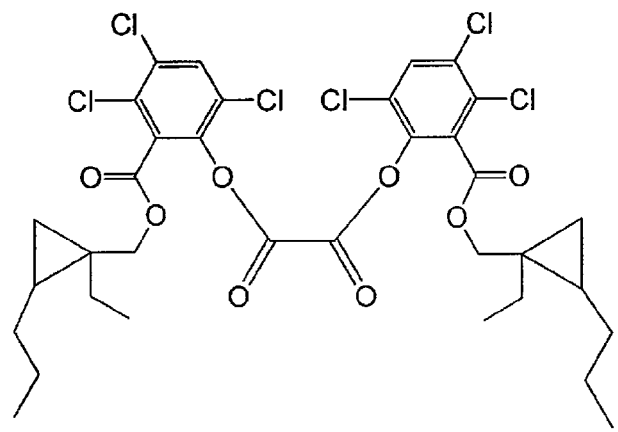
Figure 506:
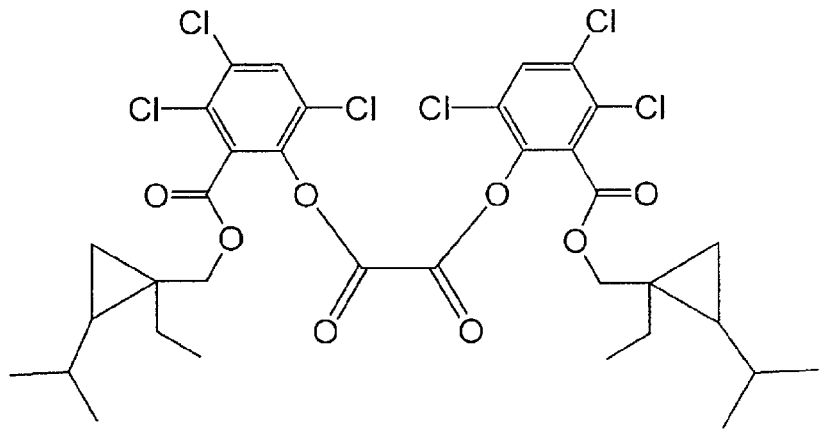
Figure 507:
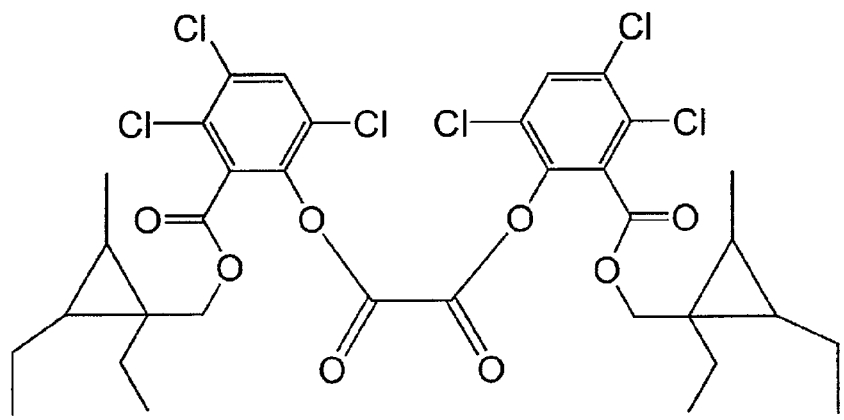
Figure 508:
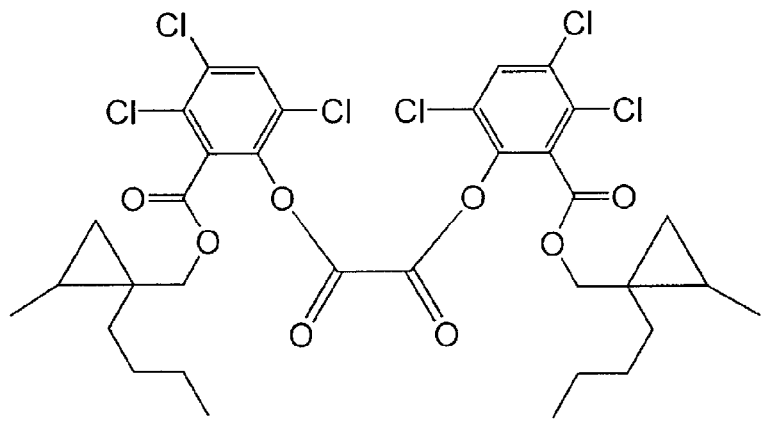
Figure 509:
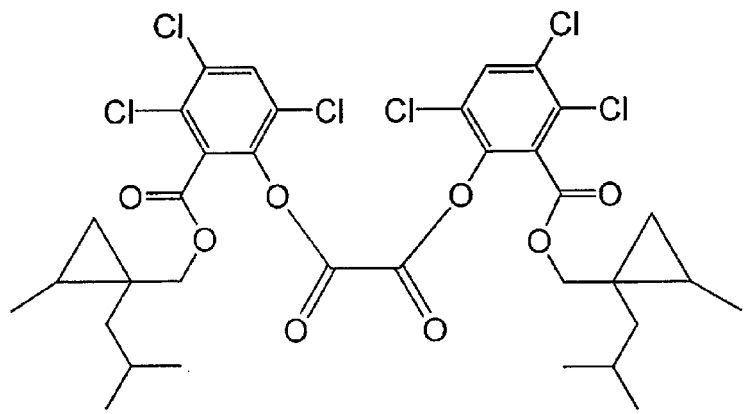
Figure 510:
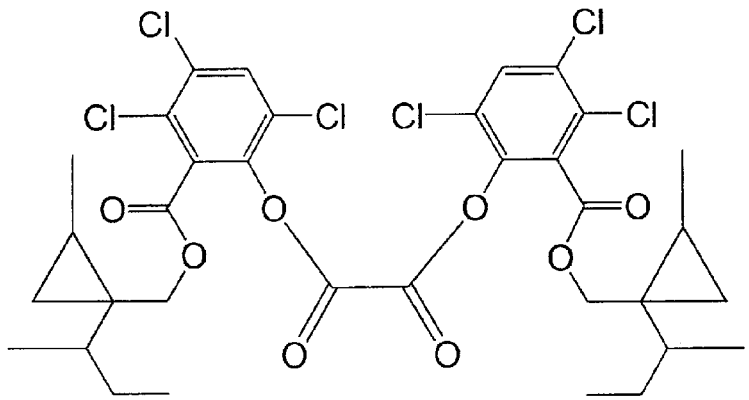
Figure 511:
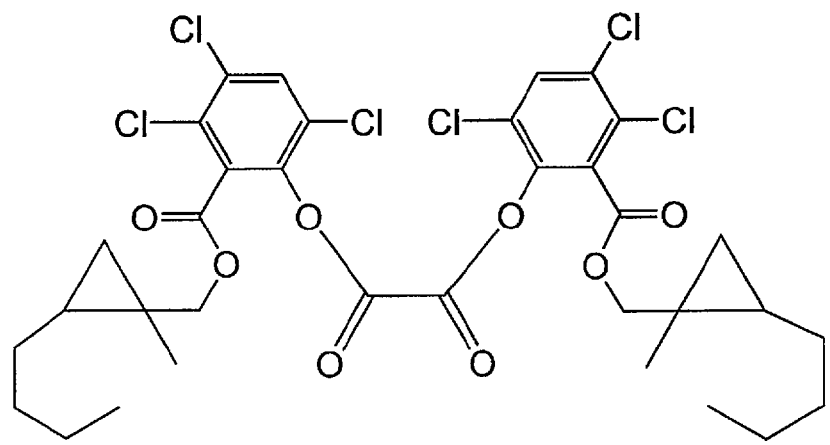
Figure 512:
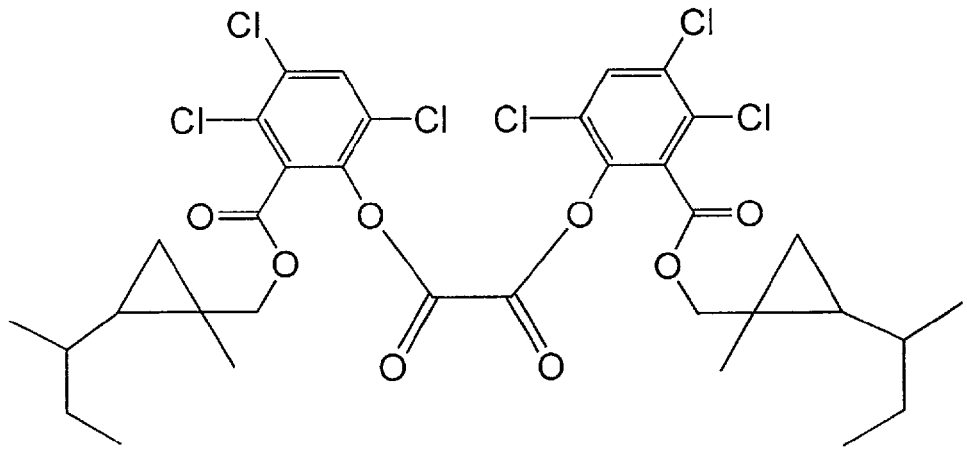
Figure 513:
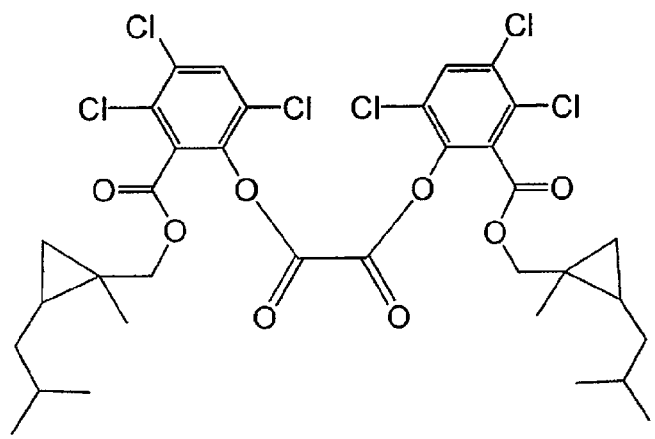
Figure 514:
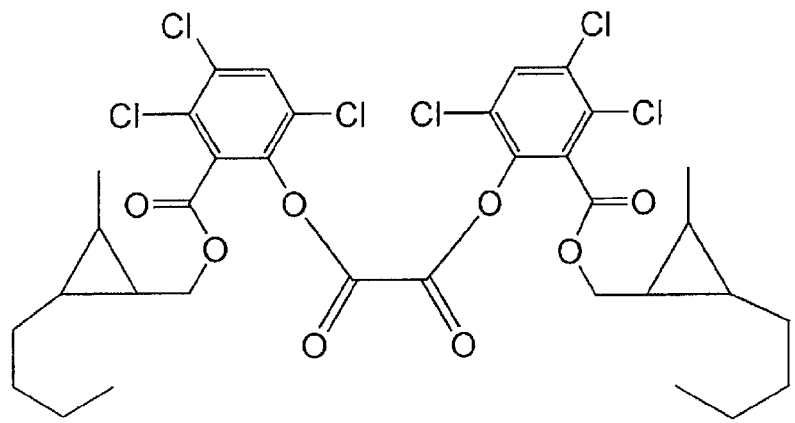
Figure 515:
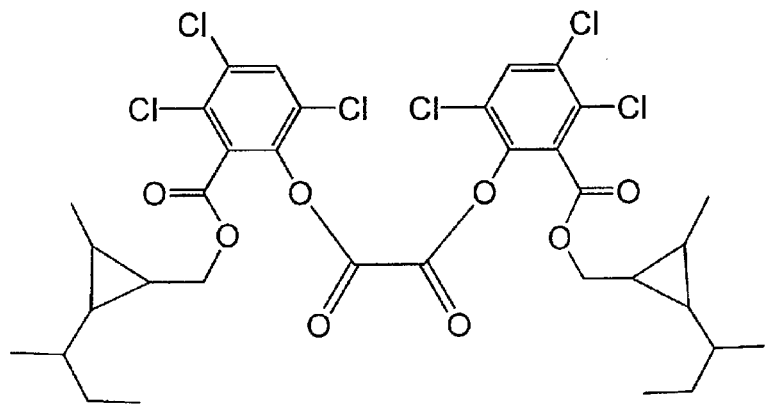
Figure 516:
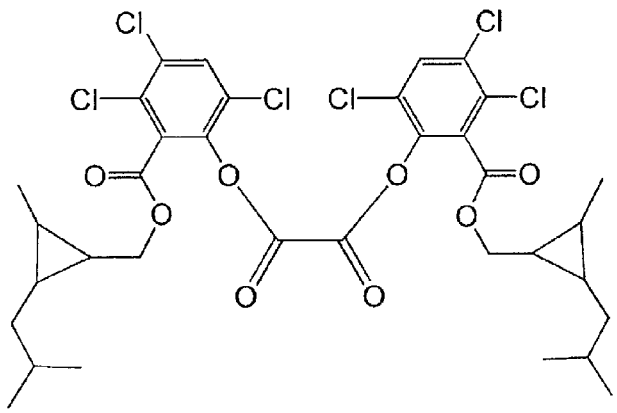
Figure 517:
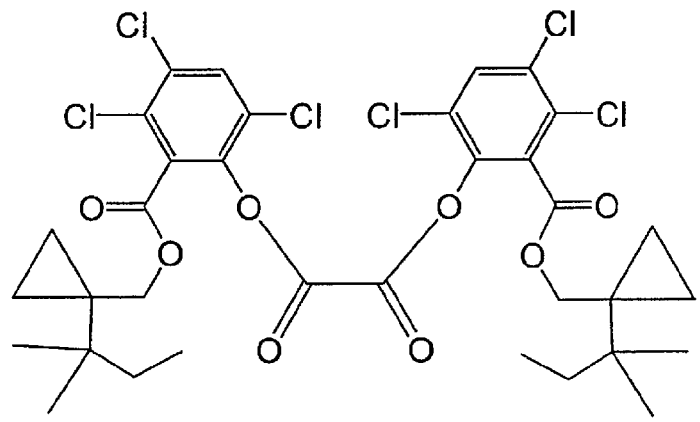
Figure 518:
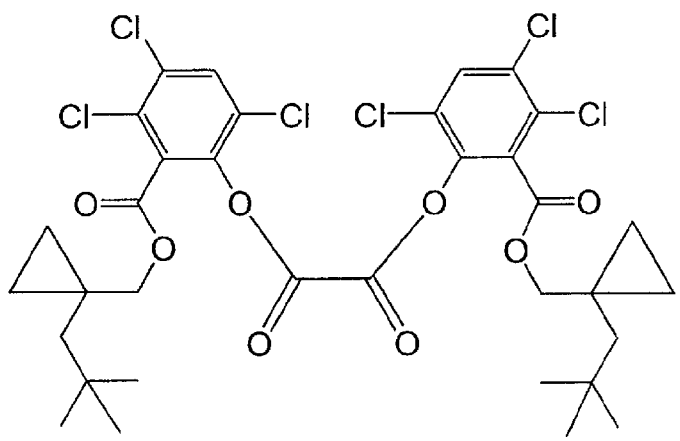
Figure 519:
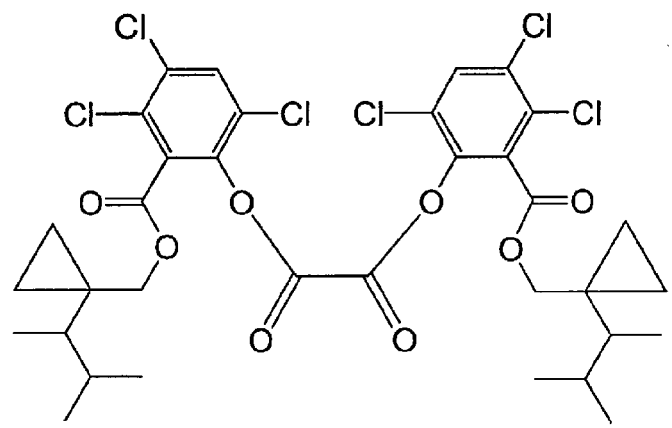
Figure 520:
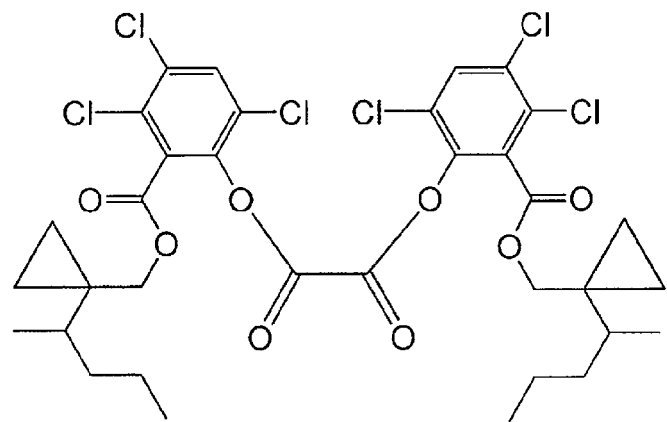
Figure 521:
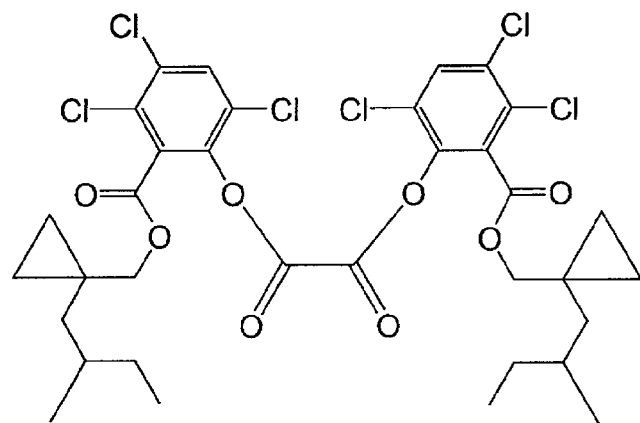
Figure 522:
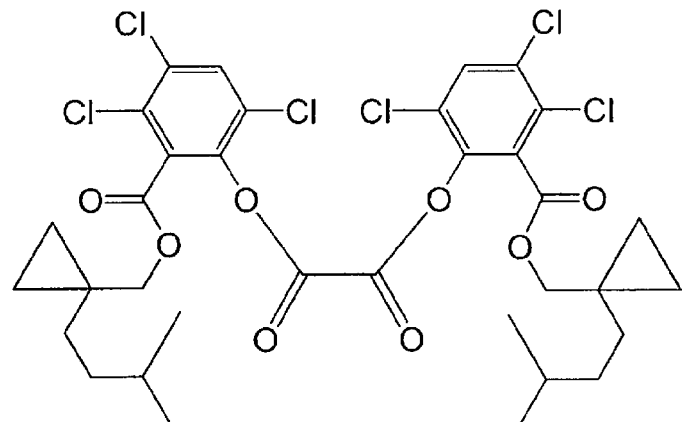
Figure 523:
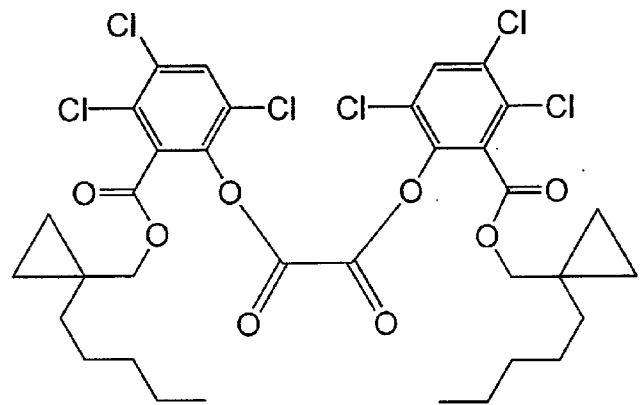
Figure 524:
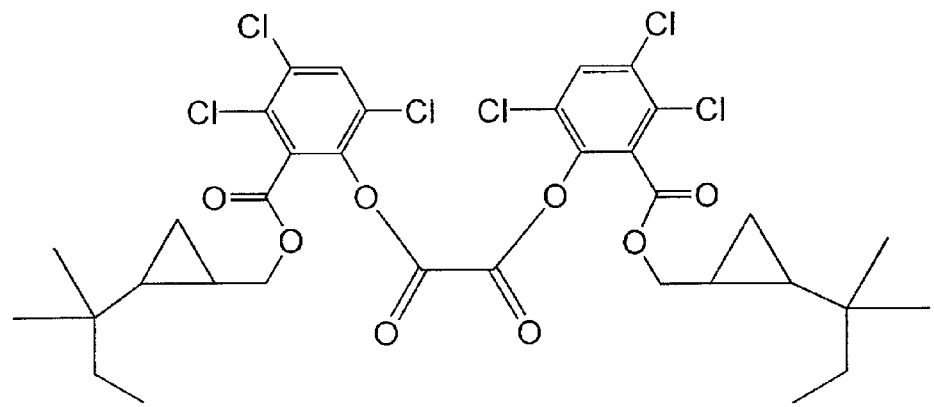
Figure 525:
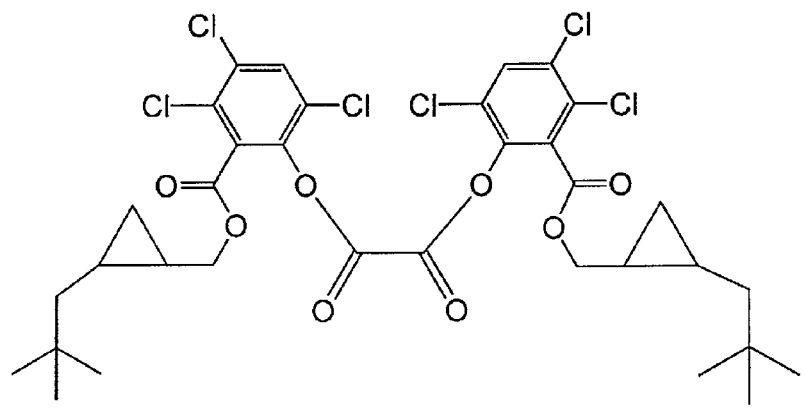
Figure 526:
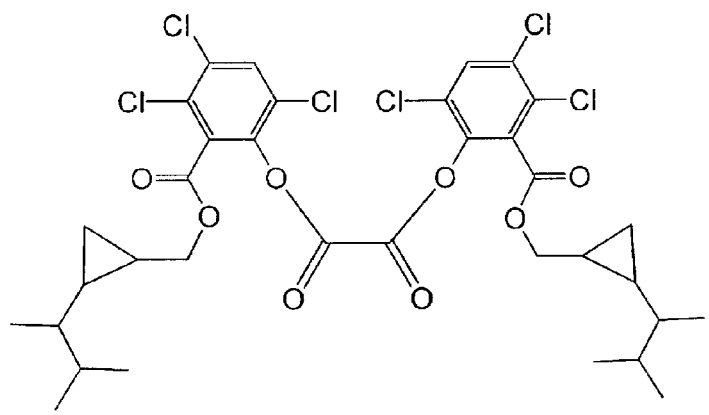
Figure 527:
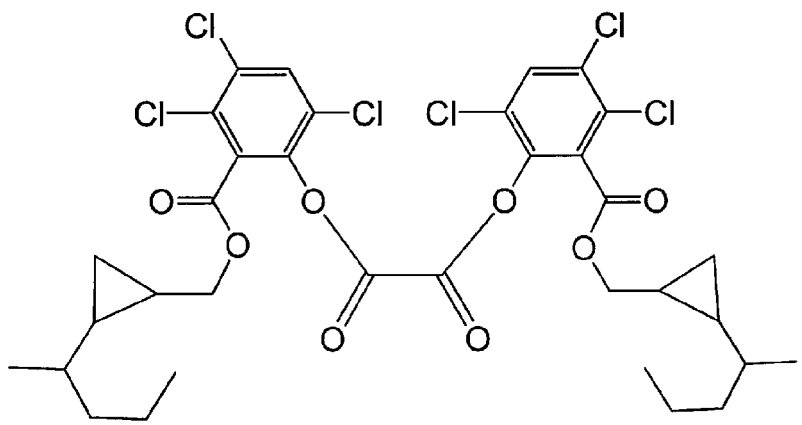
Figure 528:
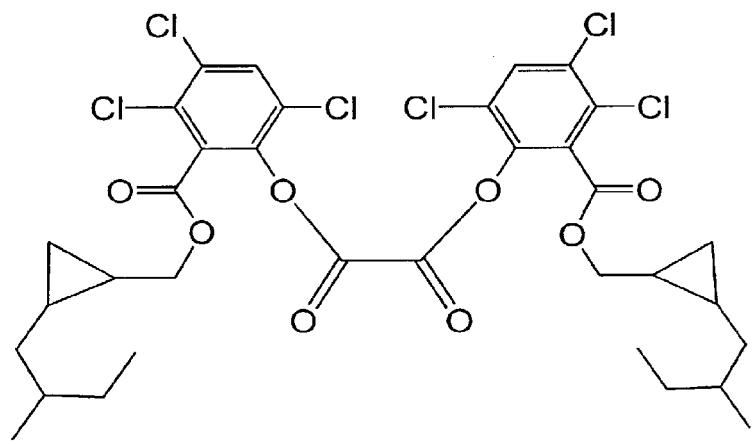
Figure 529:
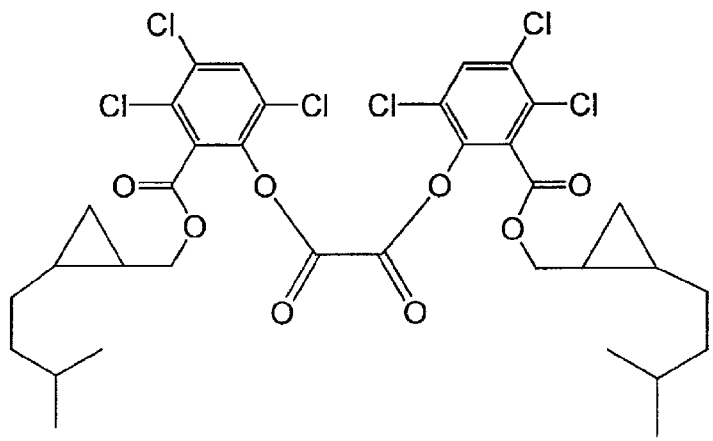
Figure 530:
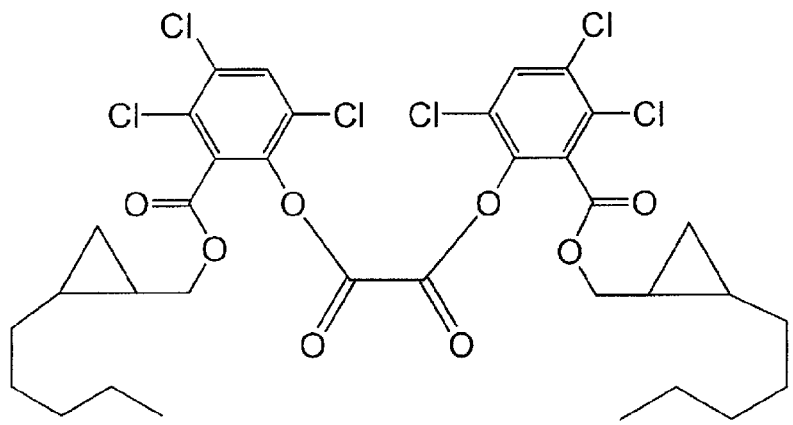
Figure 531:
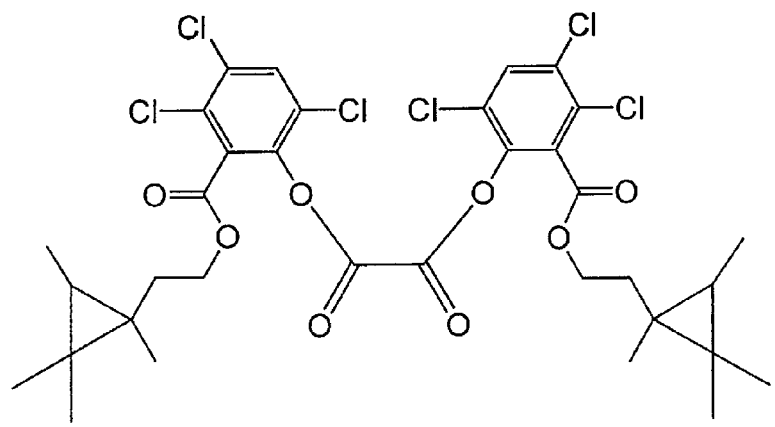
Figure 532:
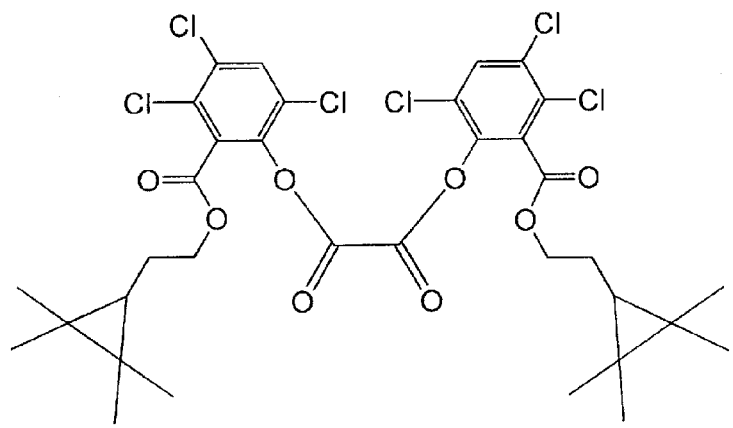
Figure 533:
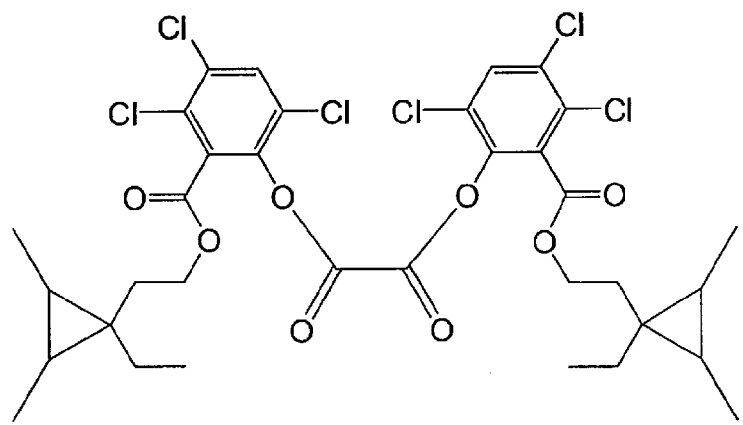
Figure 534:
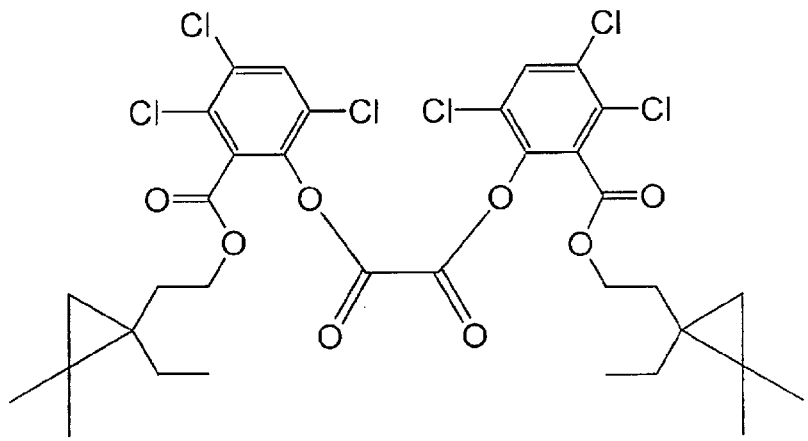
Figure 535:
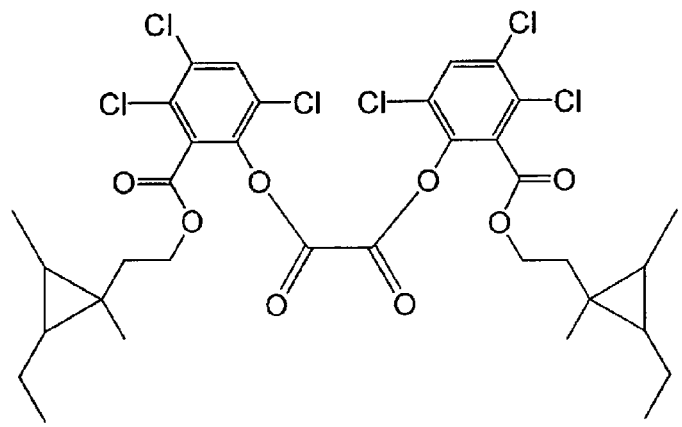
Figure 536:
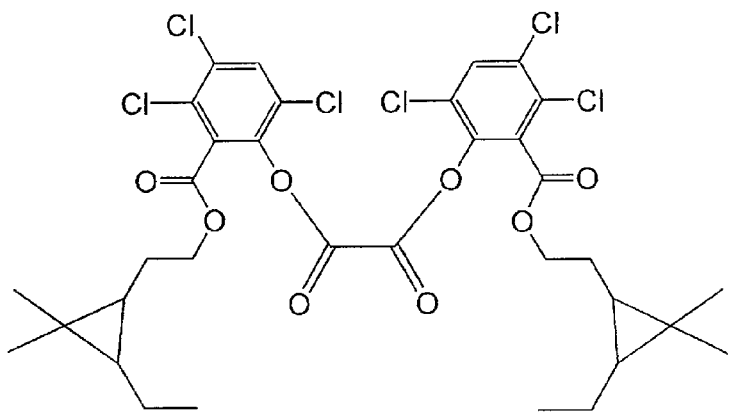
Figure 537:
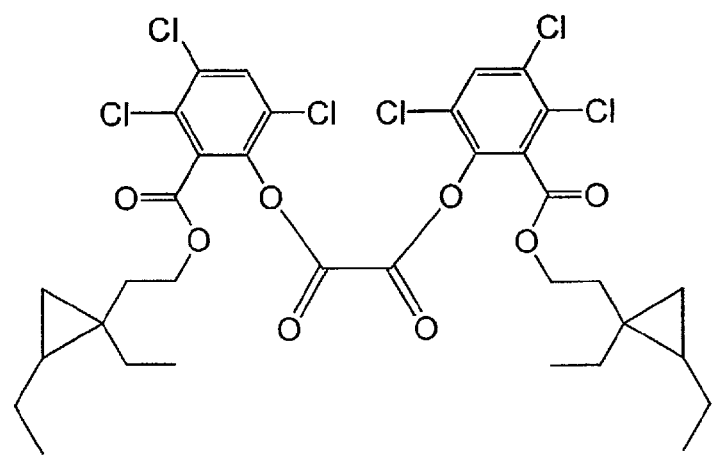
Figure 538:
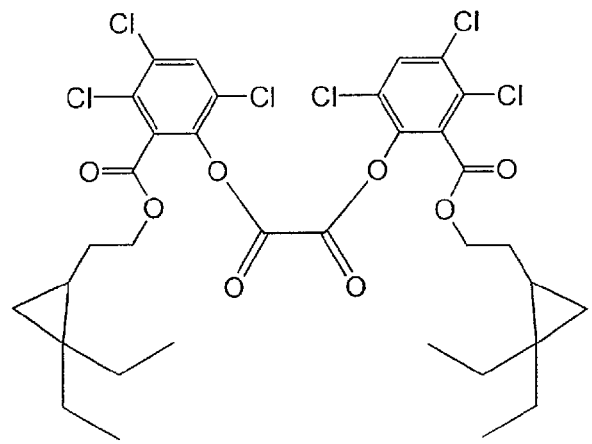
Figure 539:
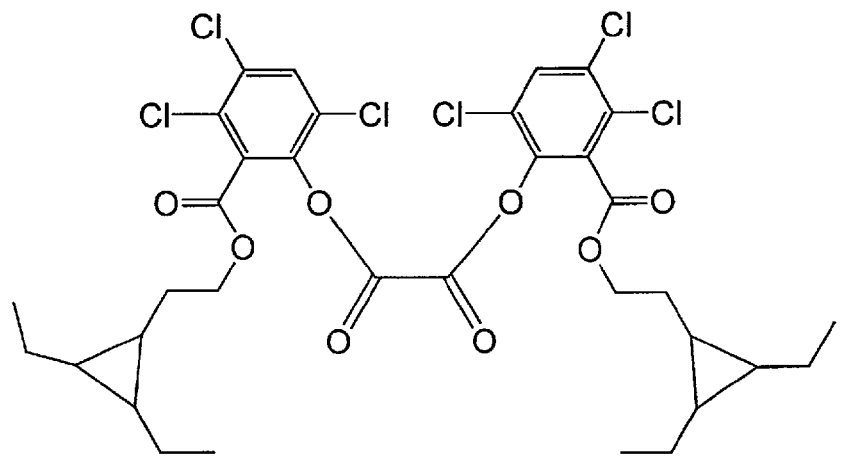
Figure 540:
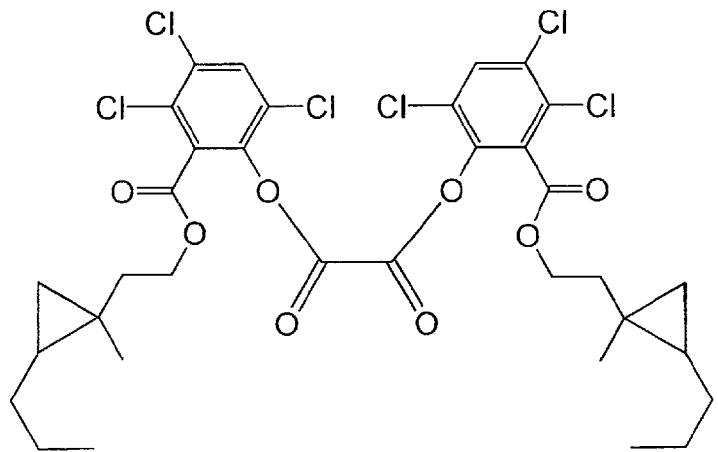
Figure 541:
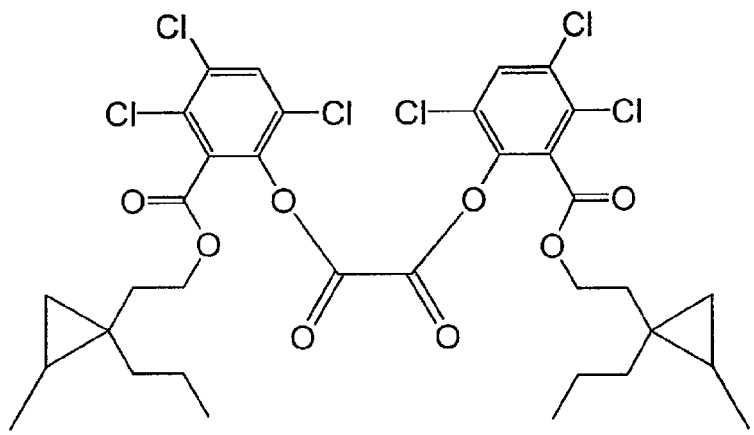
Figure 542:
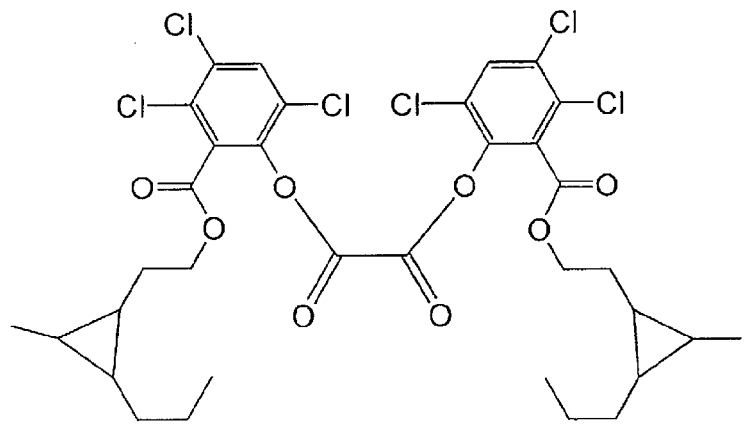
Figure 543:
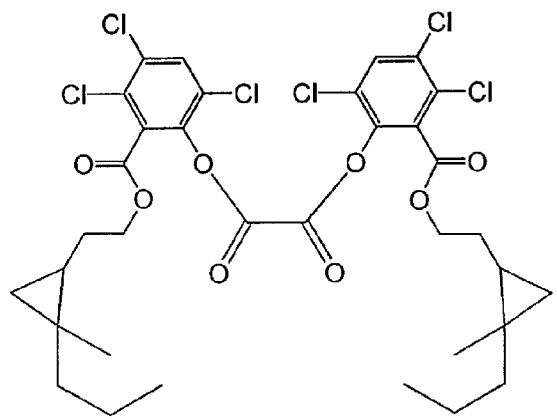
Figure 544:
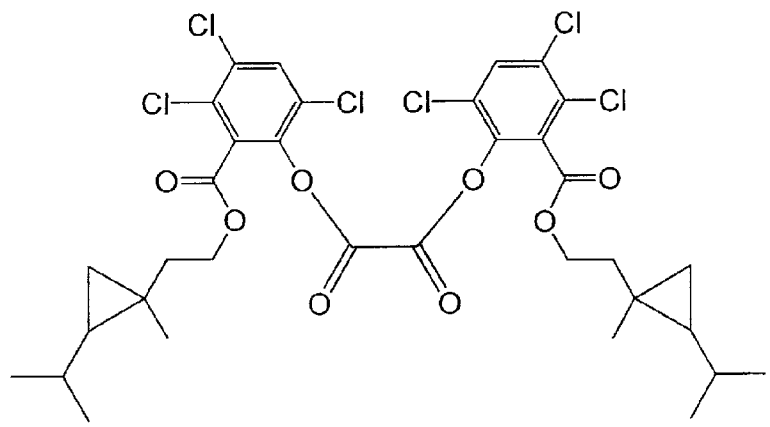
Figure 545:
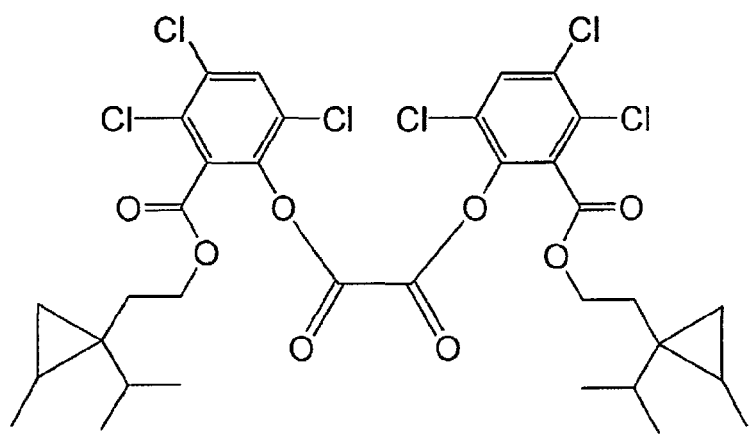
Figure 546:
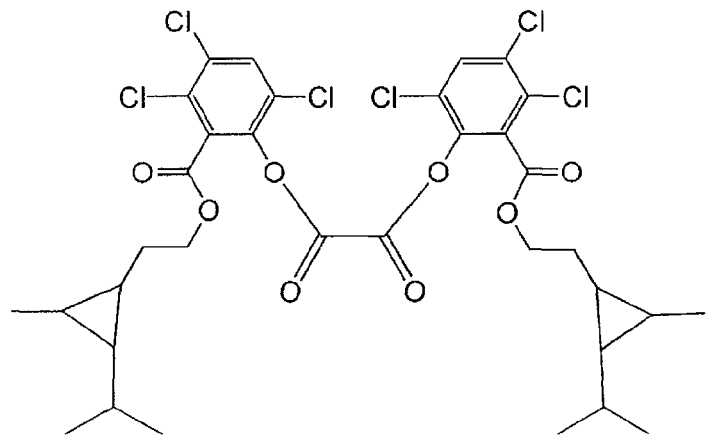
Figure 547:
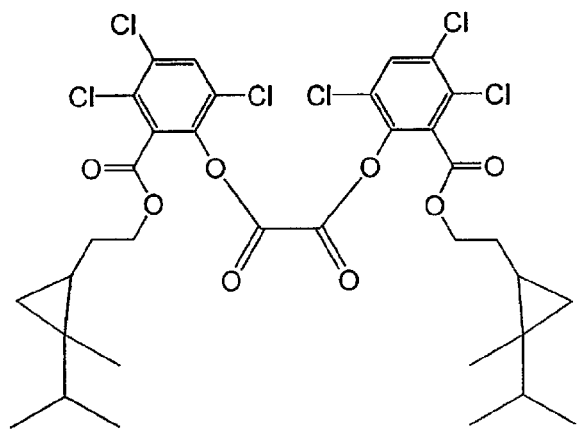
Figure 548:
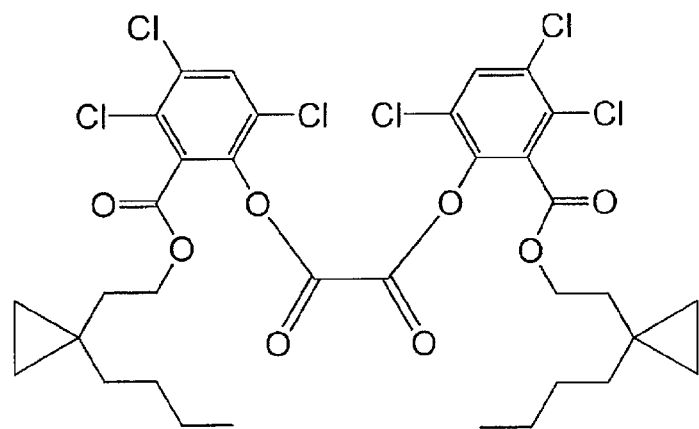
Figure 549:
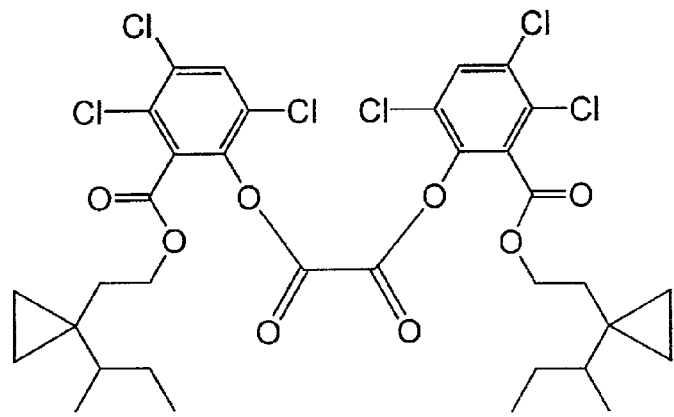
Figure 550:
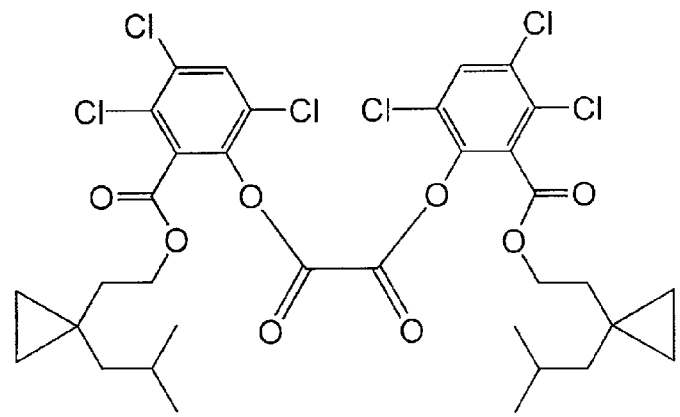
Figure 551:
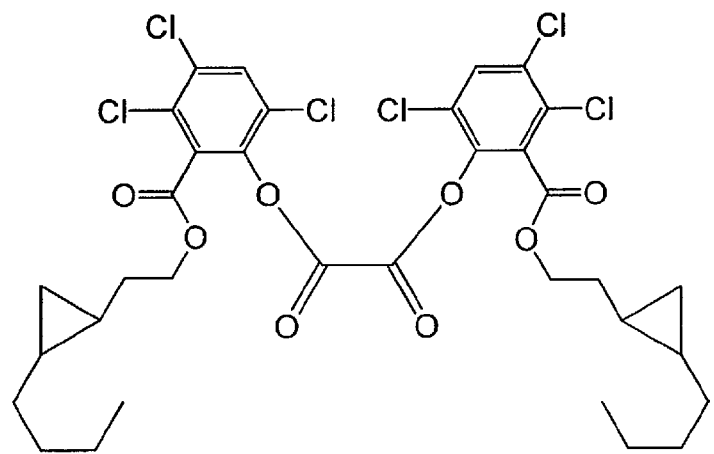
Figure 552:
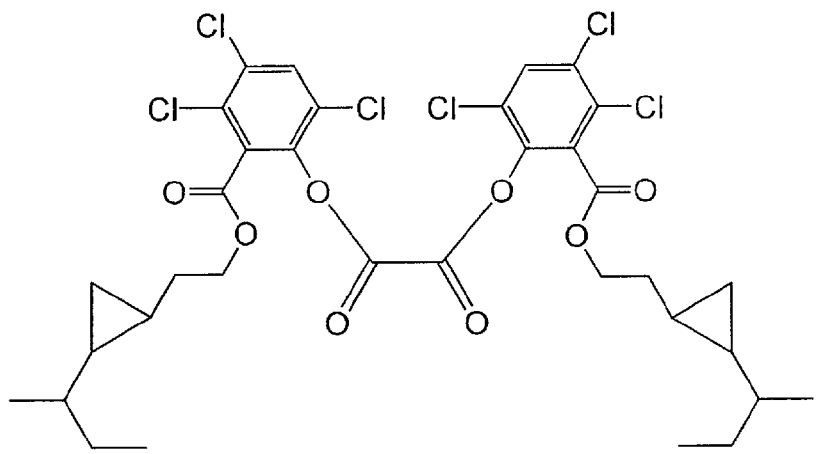
Figure 553:
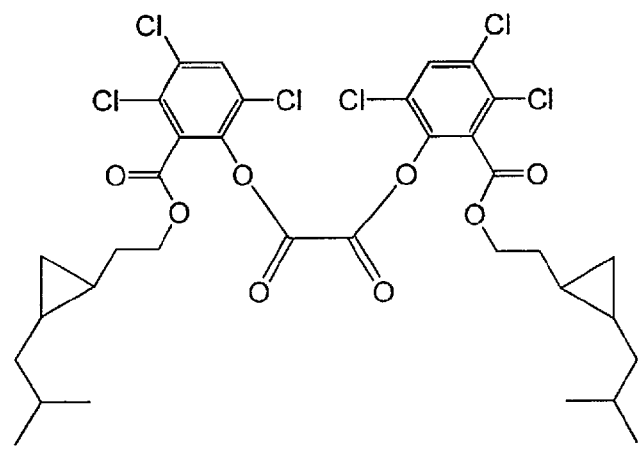
Figure 554:
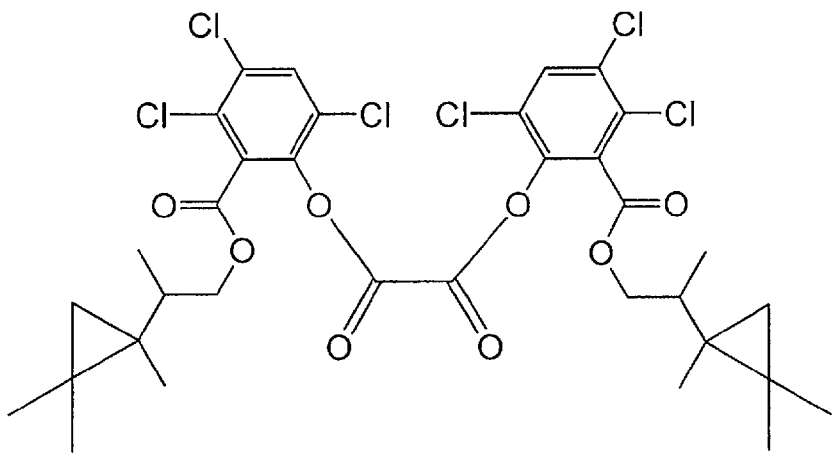
Figure 555:
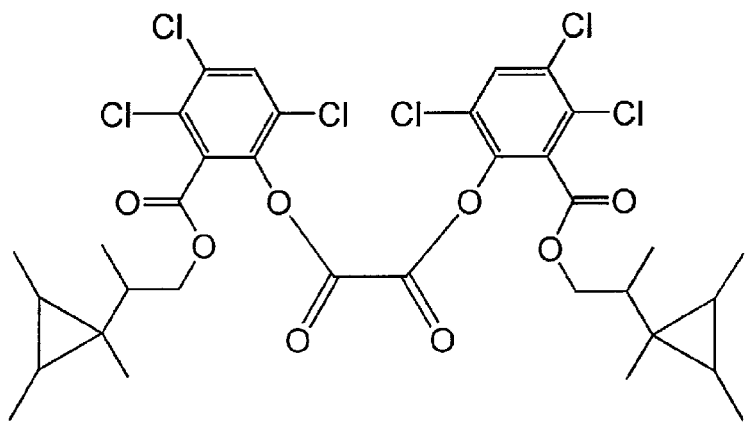
Figure 556:
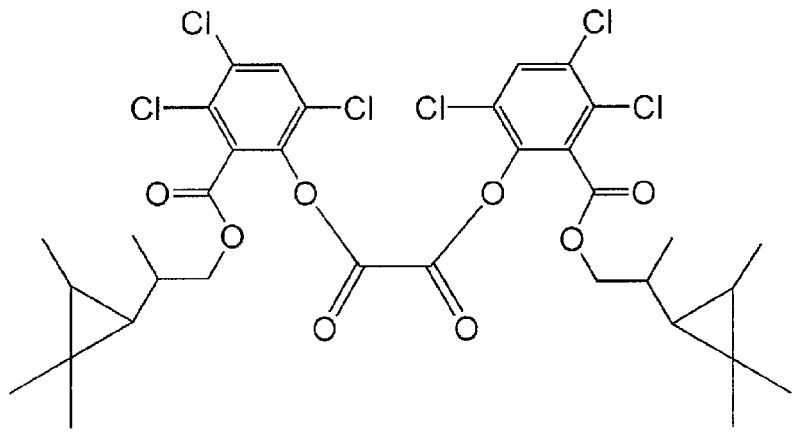
Figure 557:
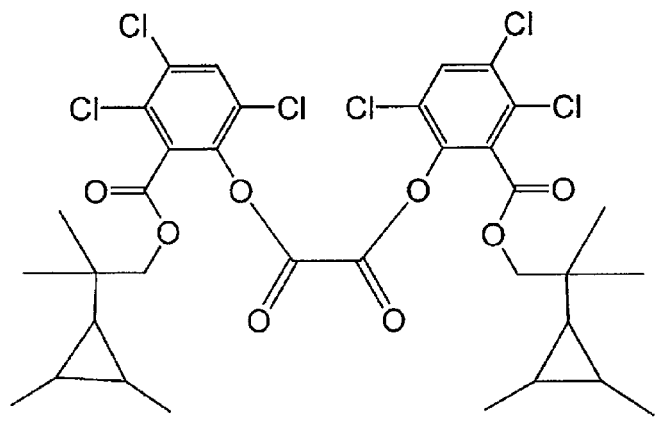
Figure 558:
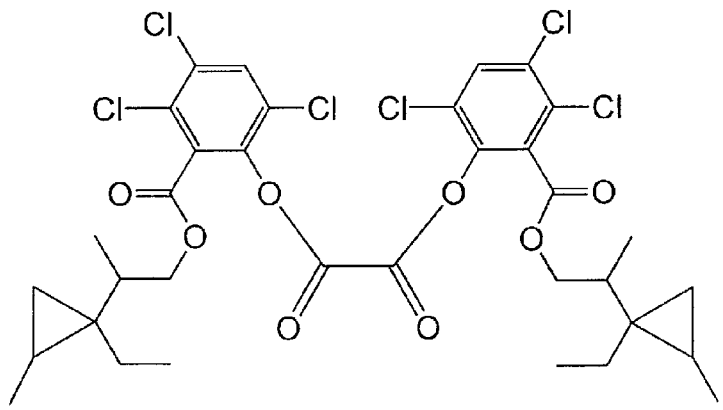
Figure 559:
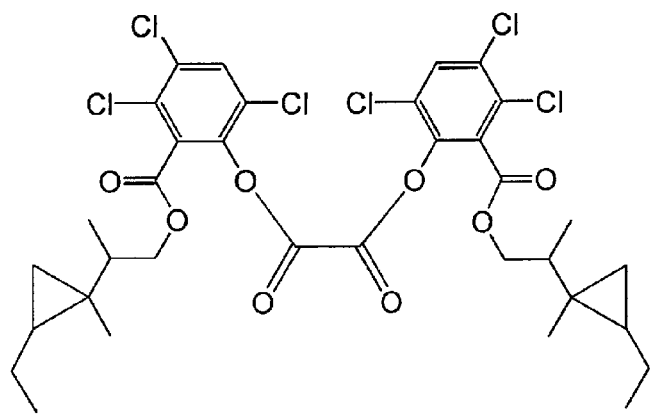
Figure 560:
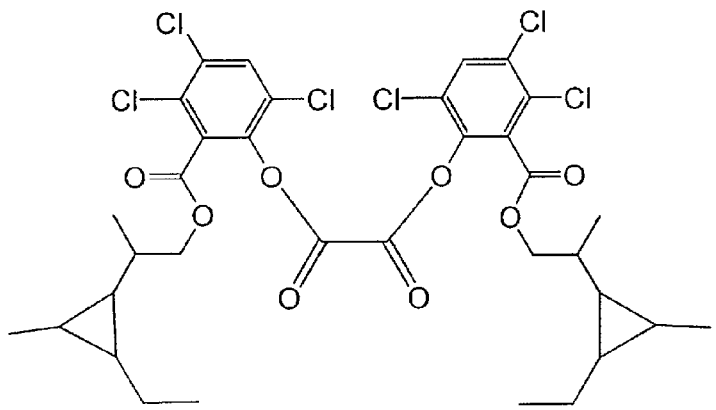
Figure 561:
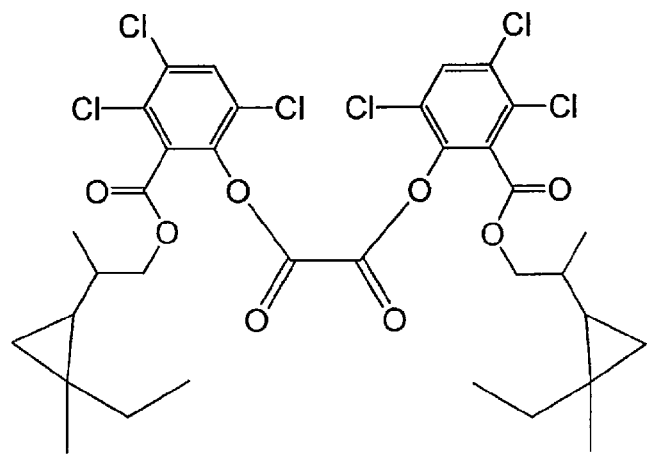
Figure 562:
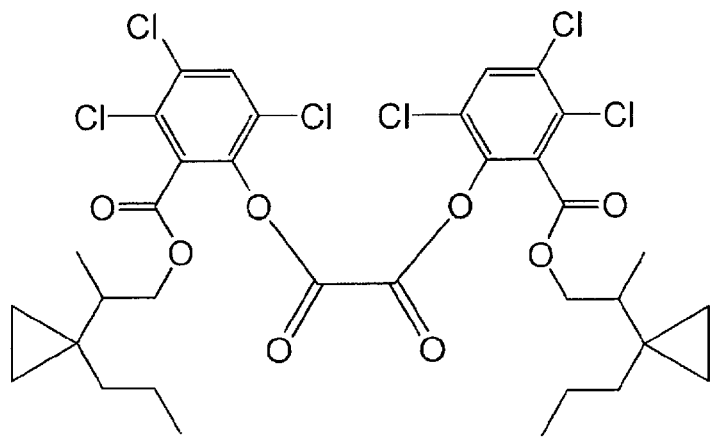
Figure 563:
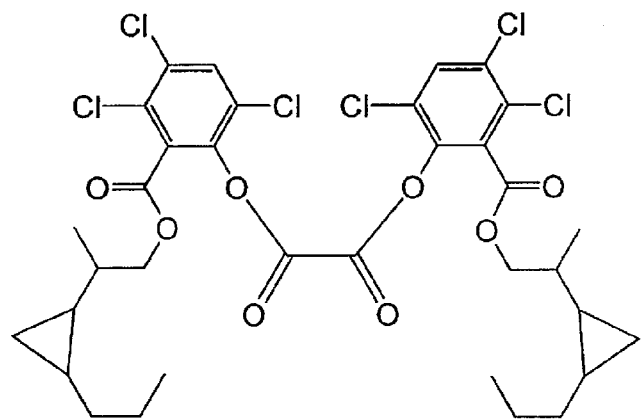
Figure 564:
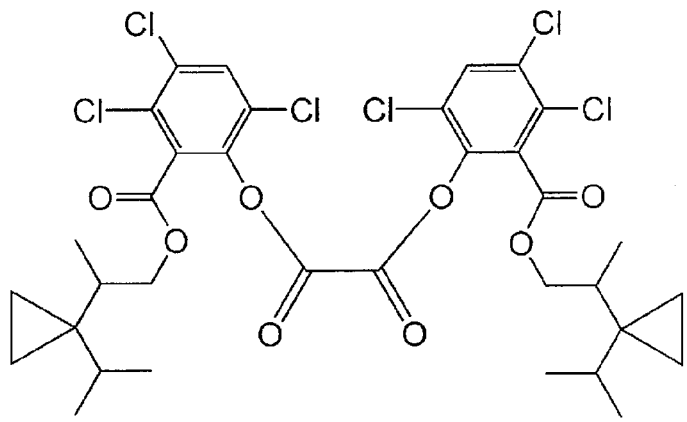
Figure 565:
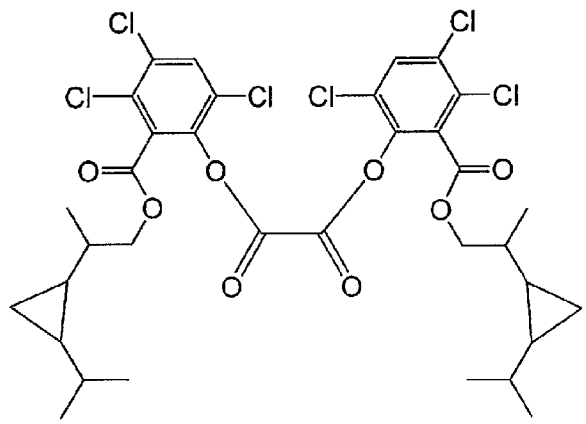
Figure 566:
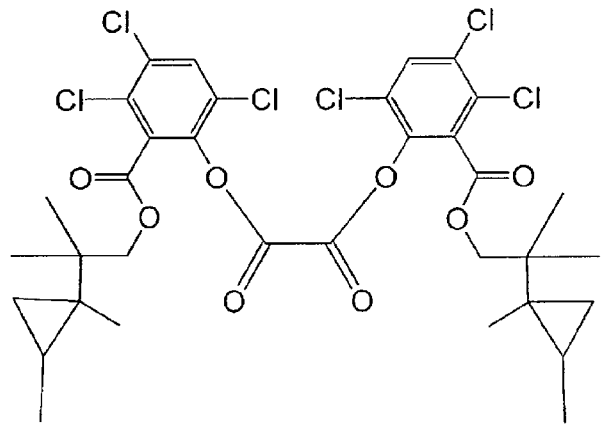
Figure 567:
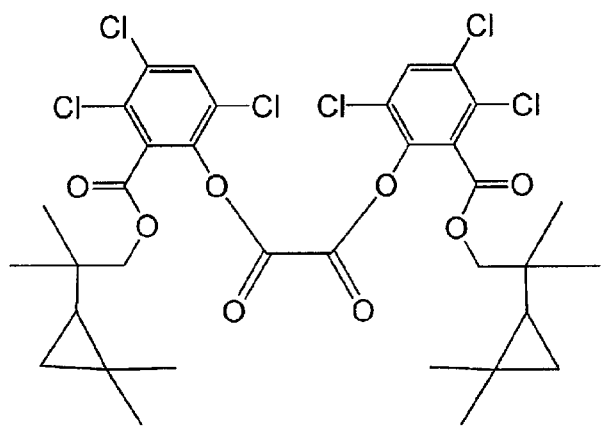
Figure 568:
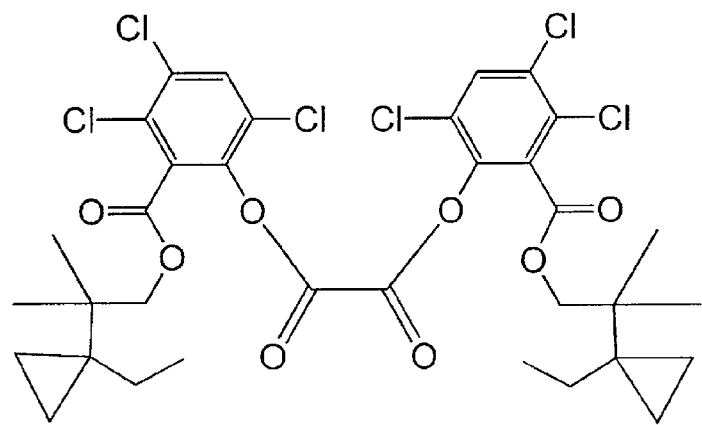
Figure 569:
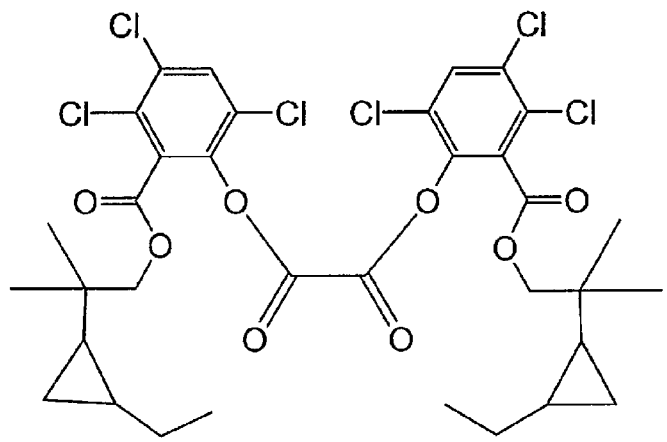
Figure 570:
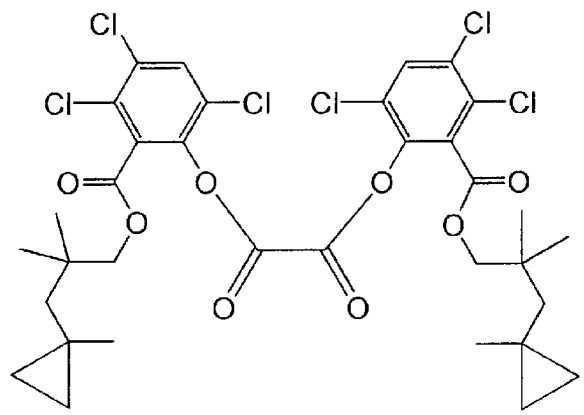
Figure 571:
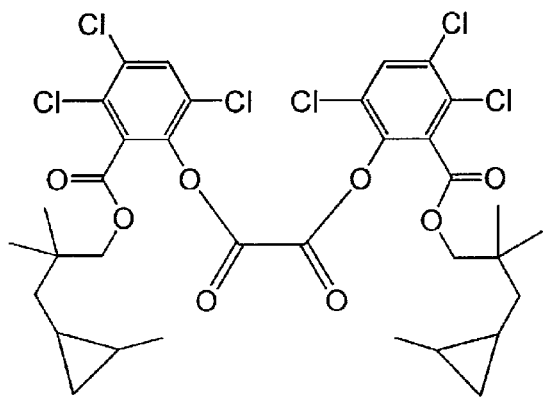
Figure 572:
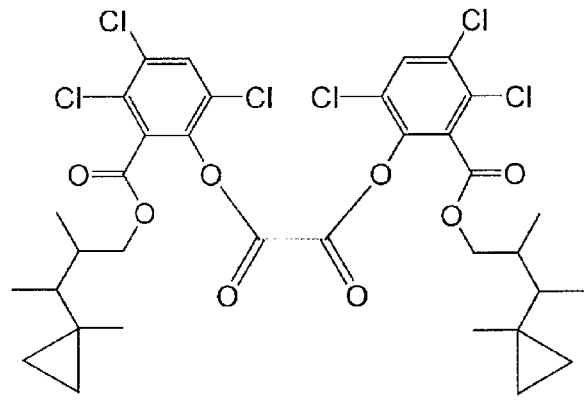
Figure 573:
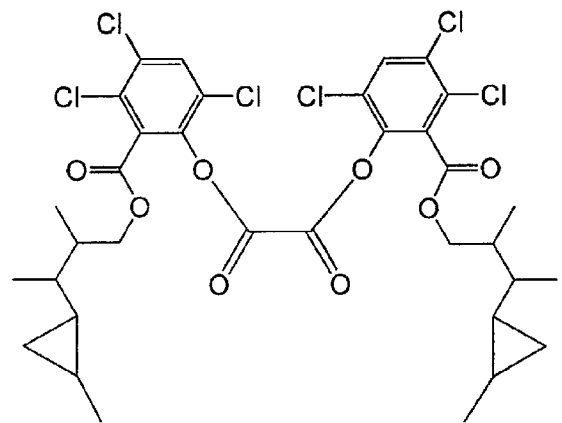
Figure 574:
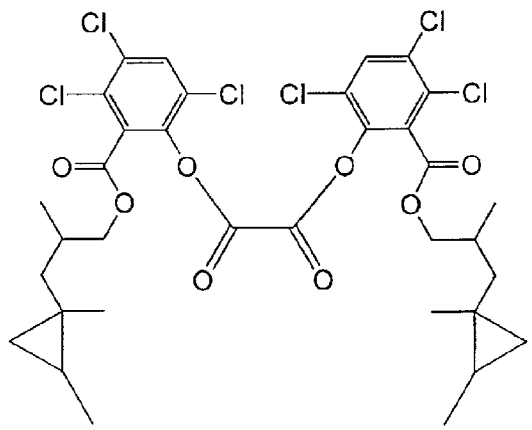
Figure 575:
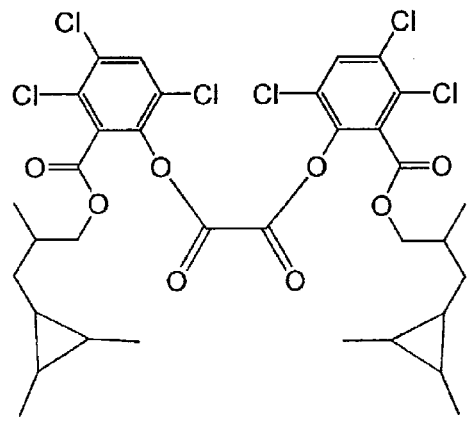
Figure 576:
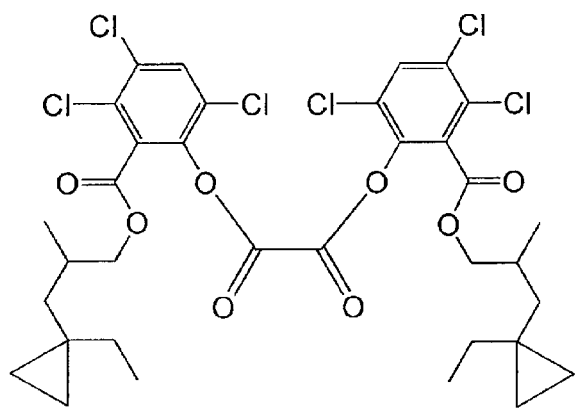
Figure 577:
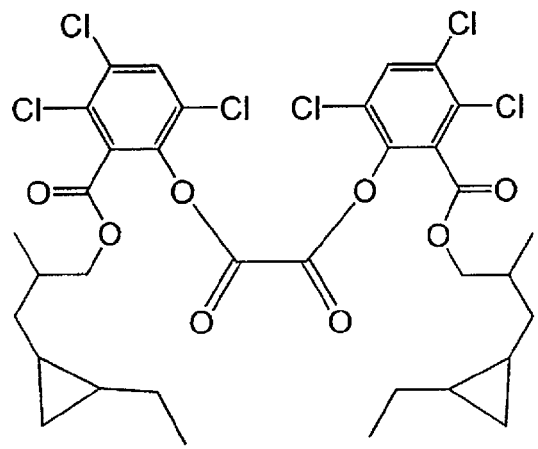
Figure 578:
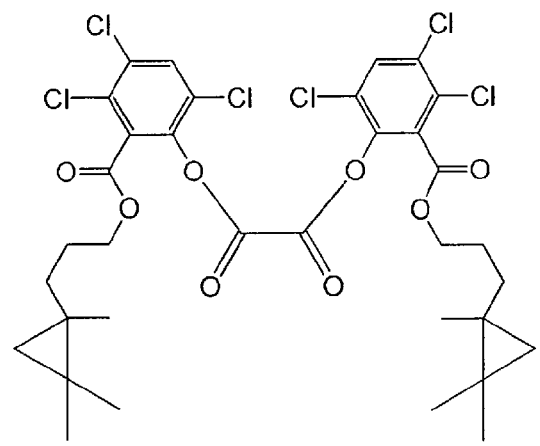
Figure 579:
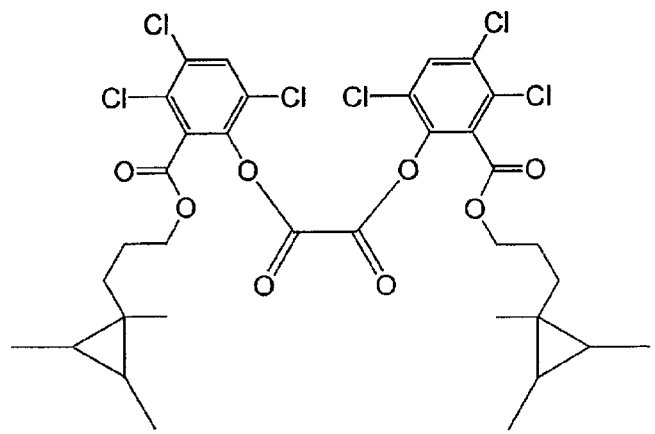
Figure 580:
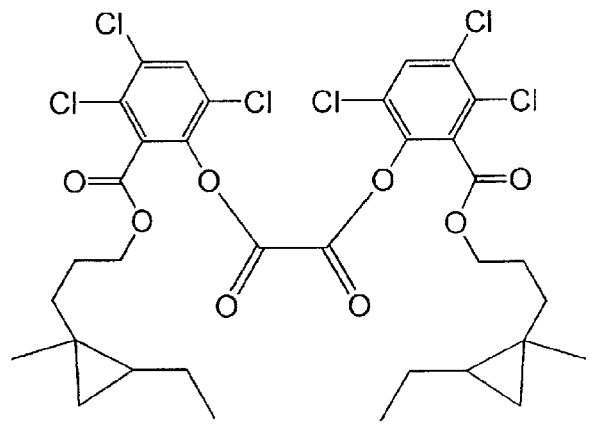
Figure 581:
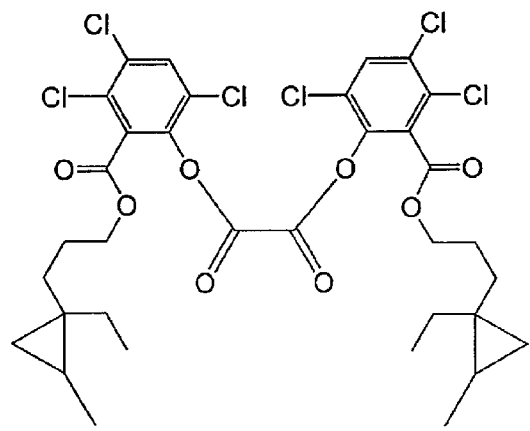
Figure 582:
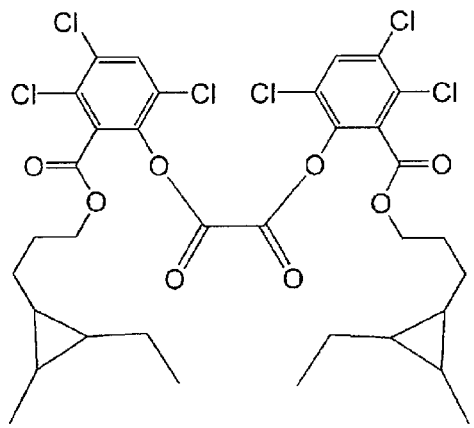
Figure 583:
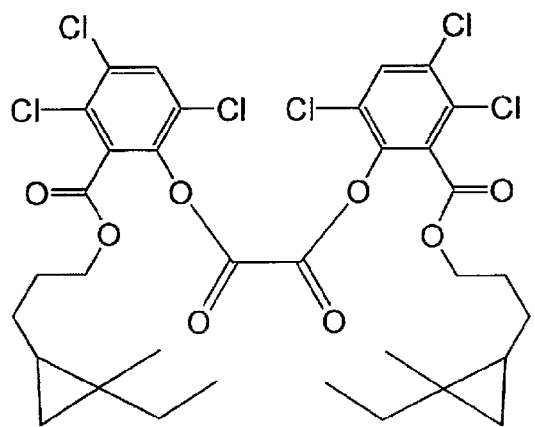
Figure 584:
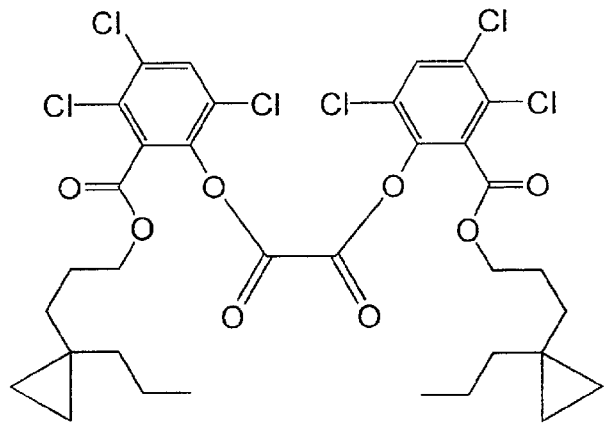
Figure 585:
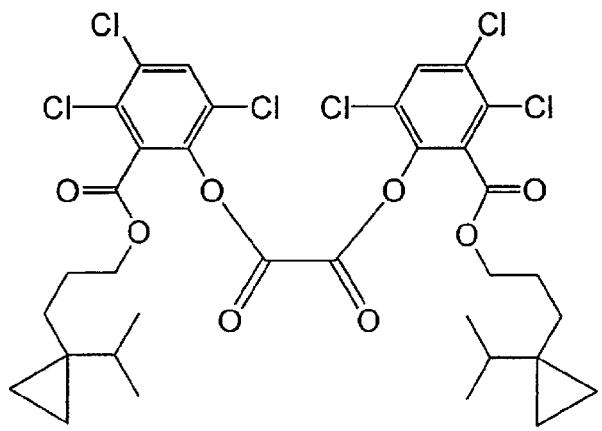
Figure 586:
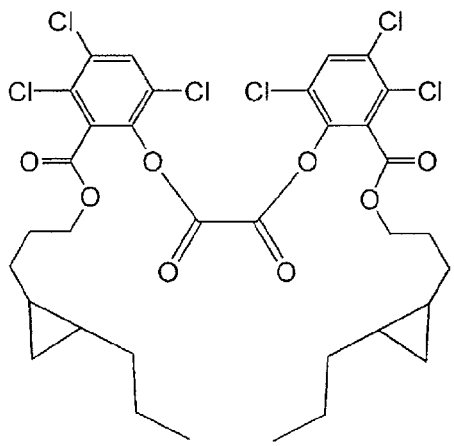
Figure 587:
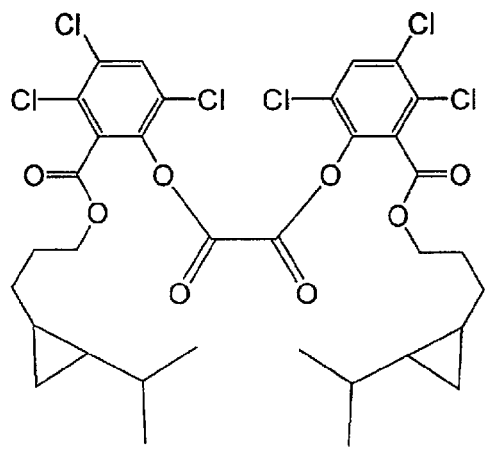
Figure 588:
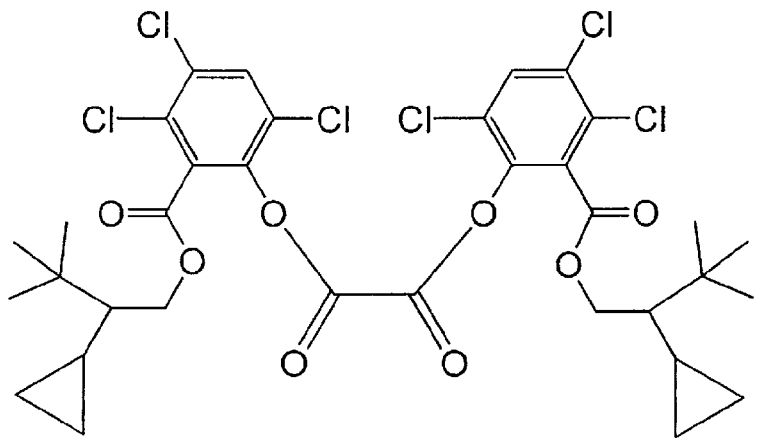
Figure 589:
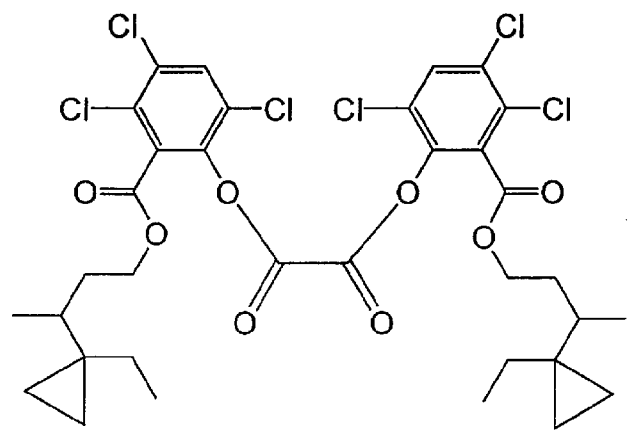
Figure 590:
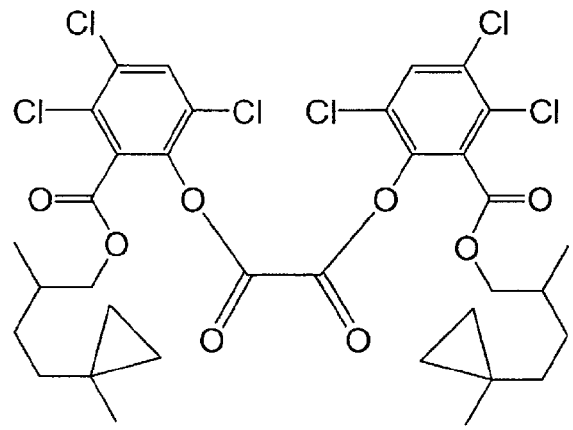
Figure 591:
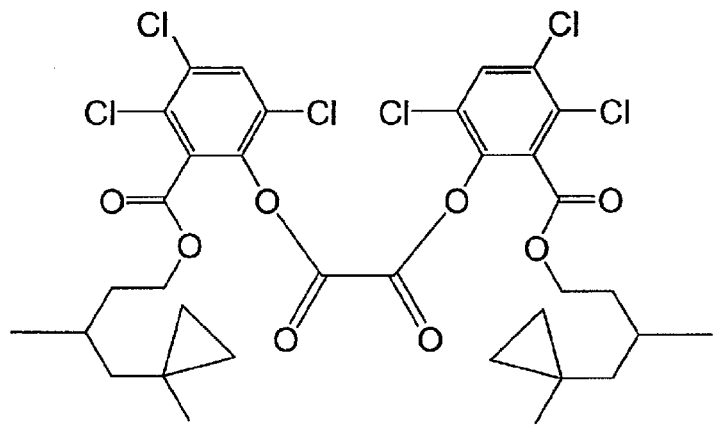
Figure 592:
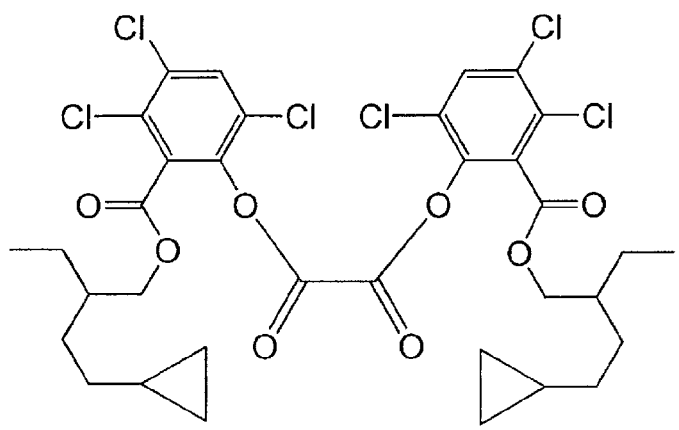
Figure 593:
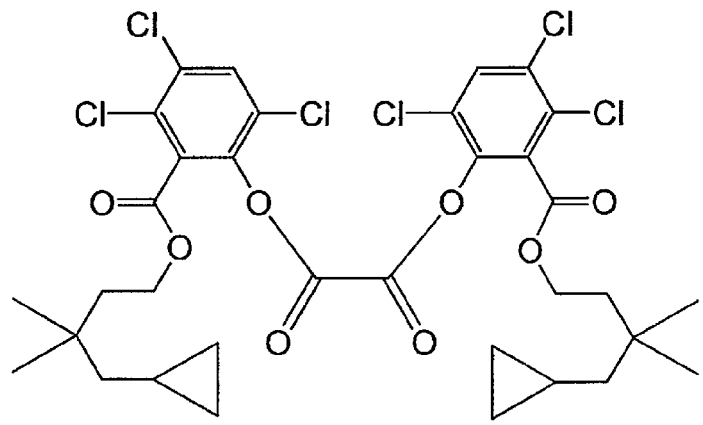
Figure 594:
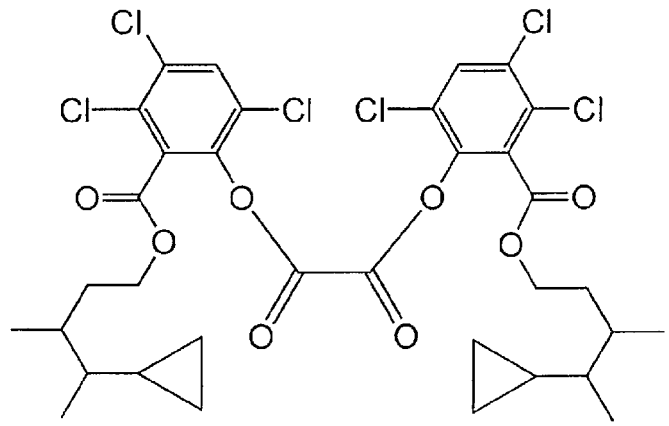
Figure 595:
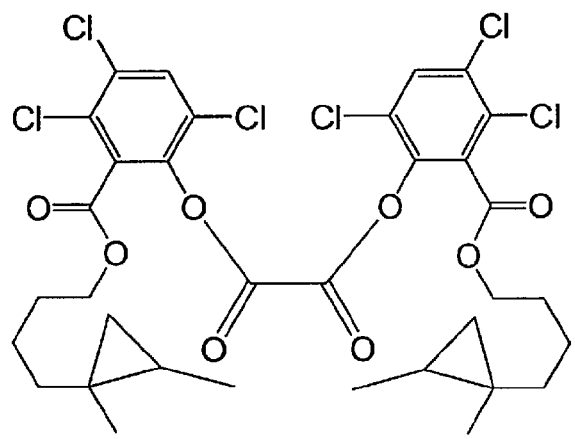
Figure 596:
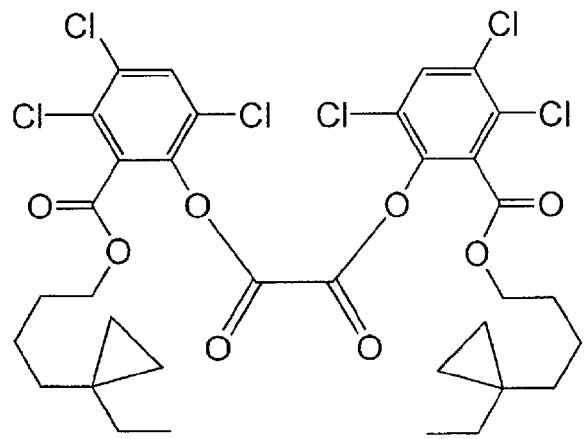
Figure 597:
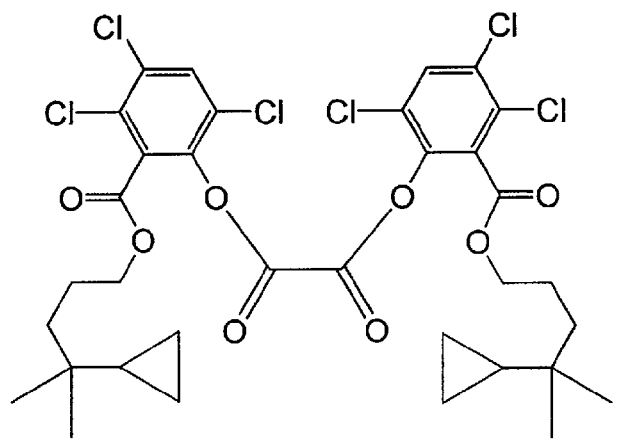
Figure 598:
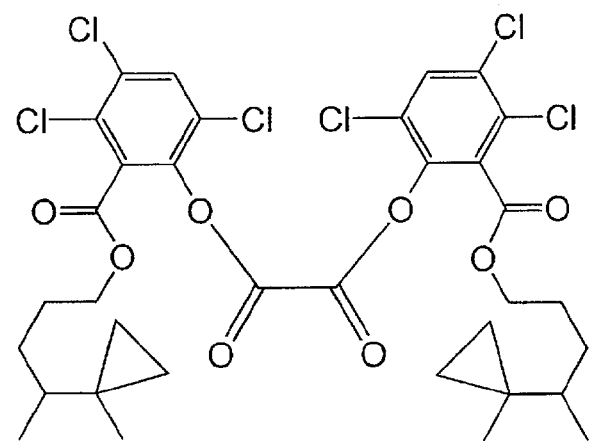
Figure 599:
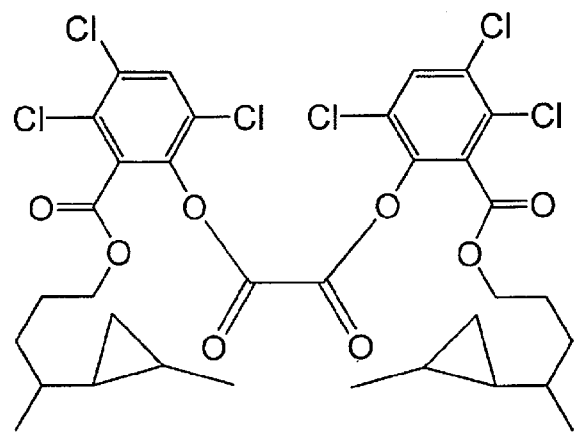
Figure 600:
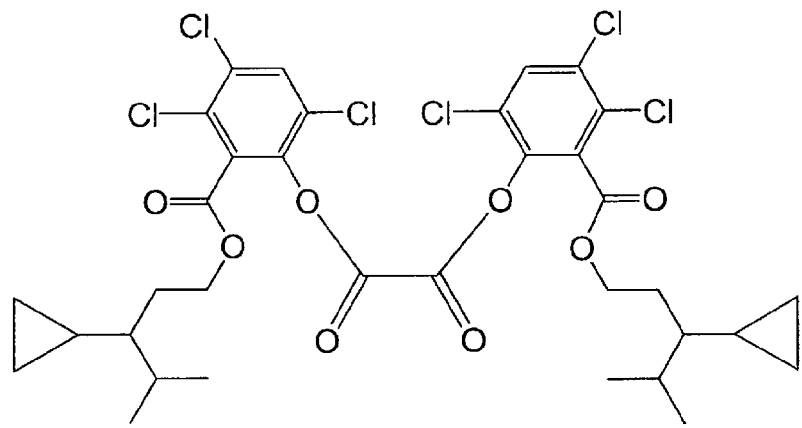
Figure 601:
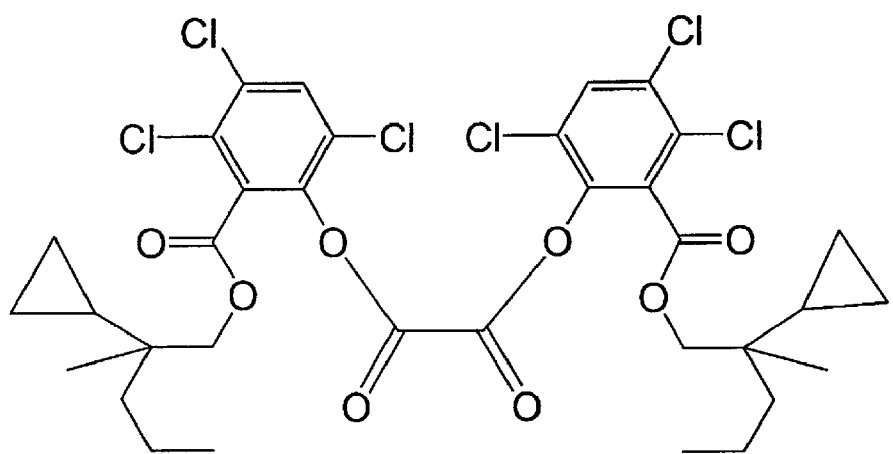
Figure 602:
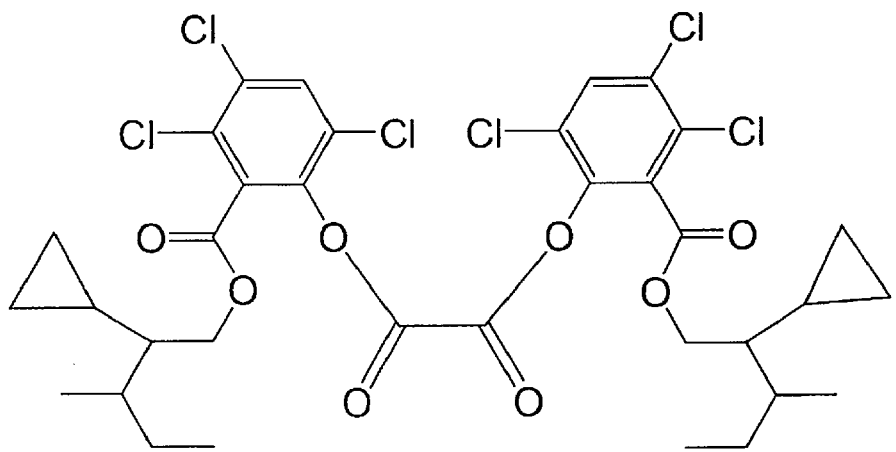
Figure 603:
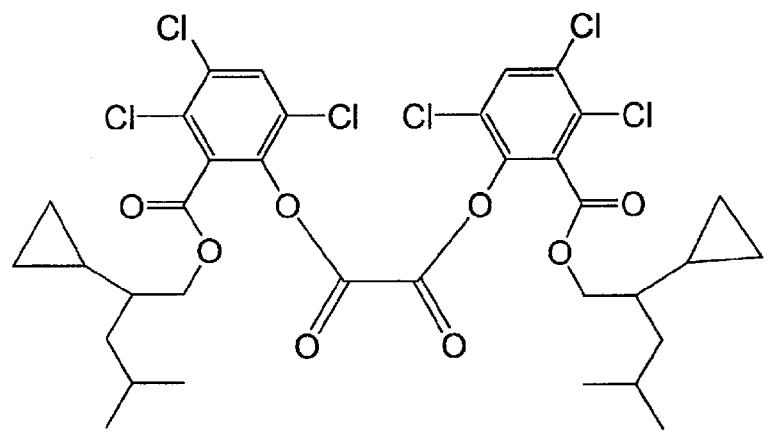
Figure 604:
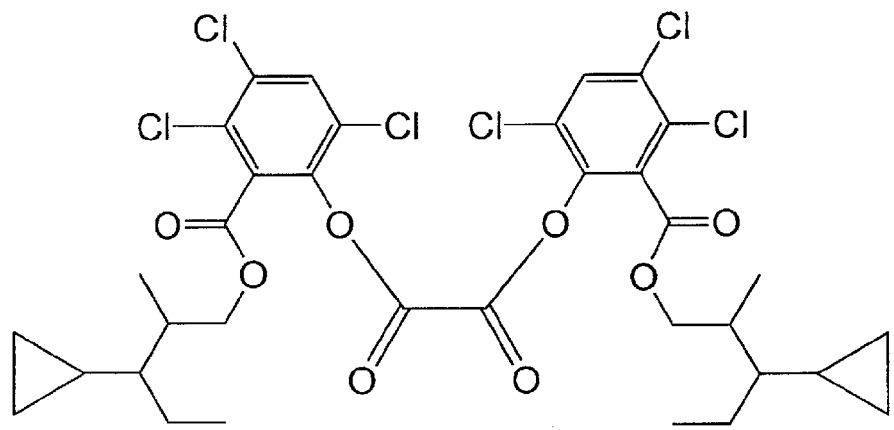
Figure 605:
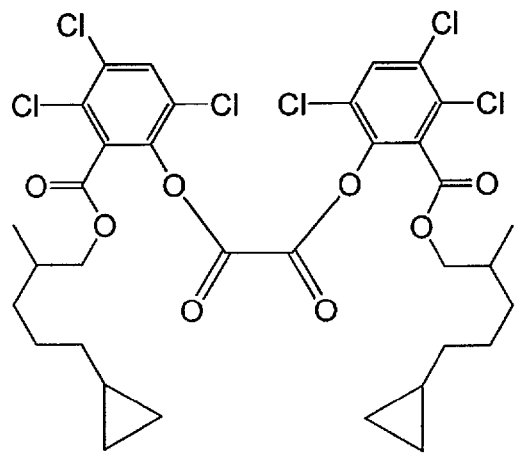
Figure 606:
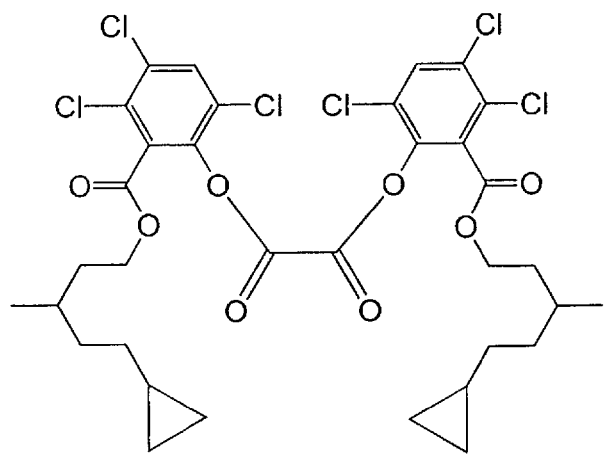
Figure 607:
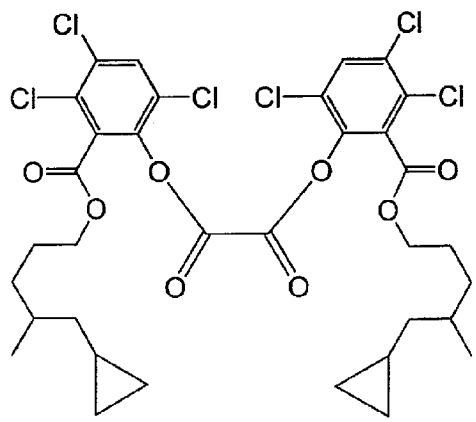
Figure 608:
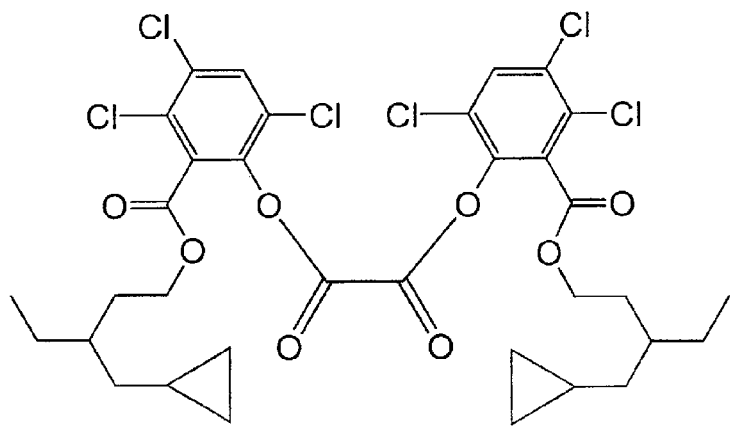
Figure 609:
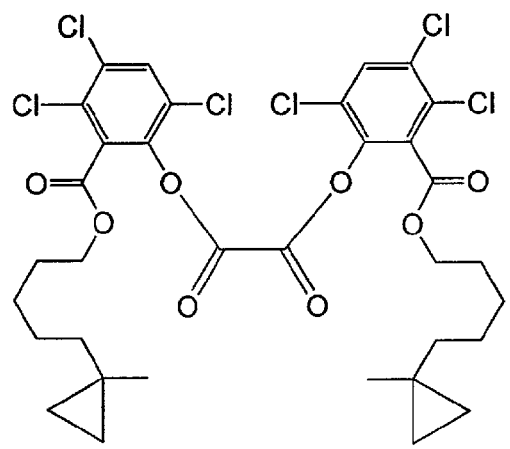
Figure 610:
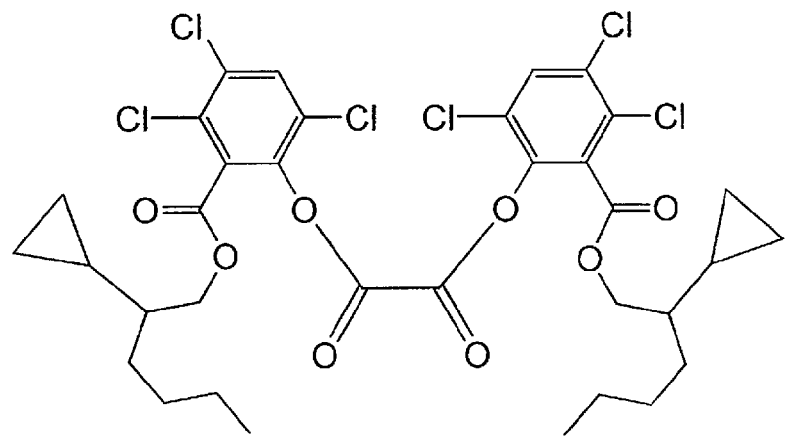
Figure 611:
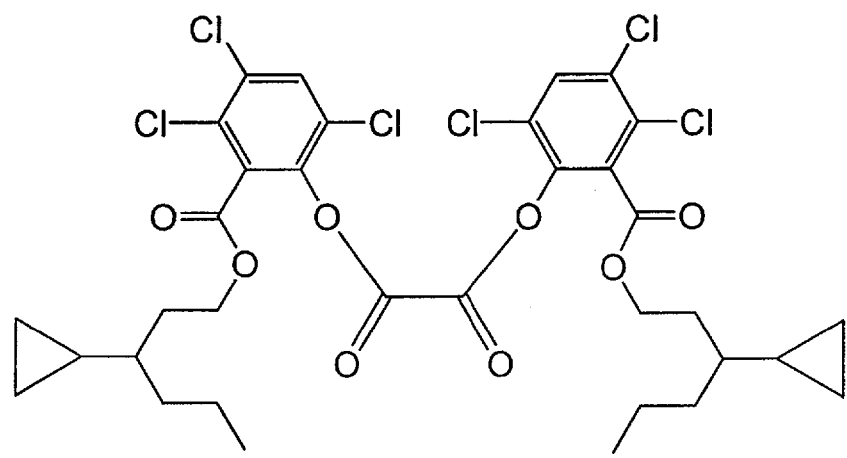
Figure 612:
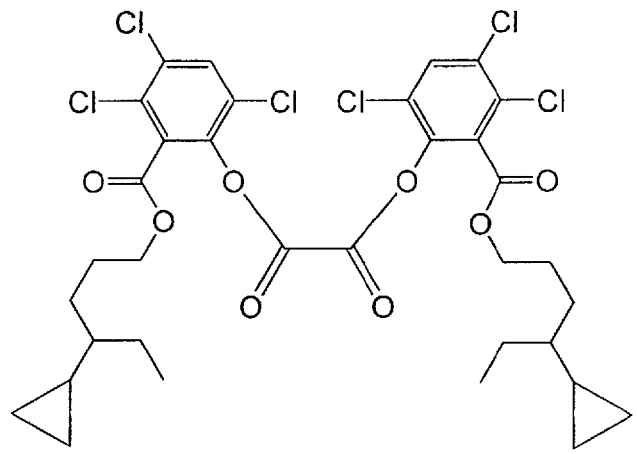
Figure 613:
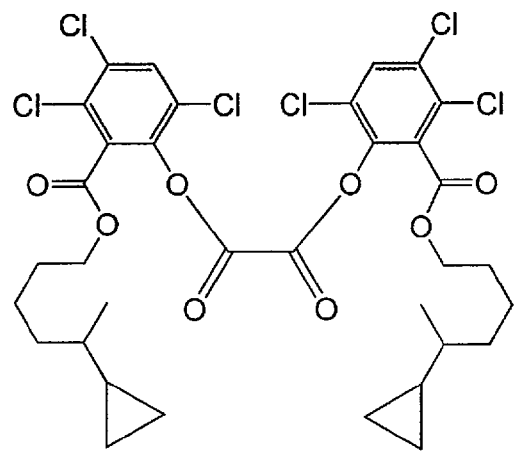
Figure 614:
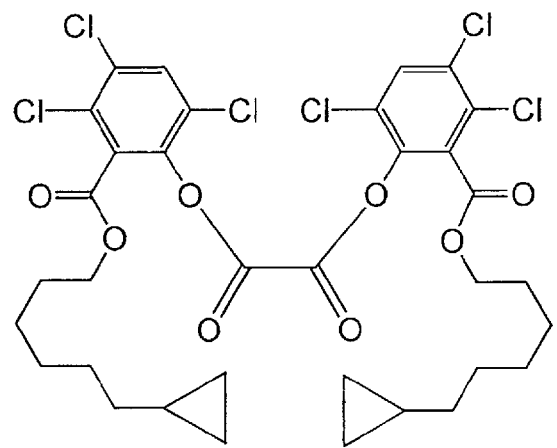
Figure 615:
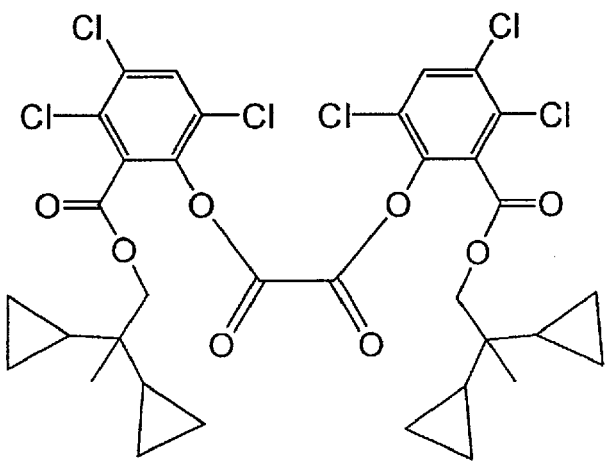
Figure 616:
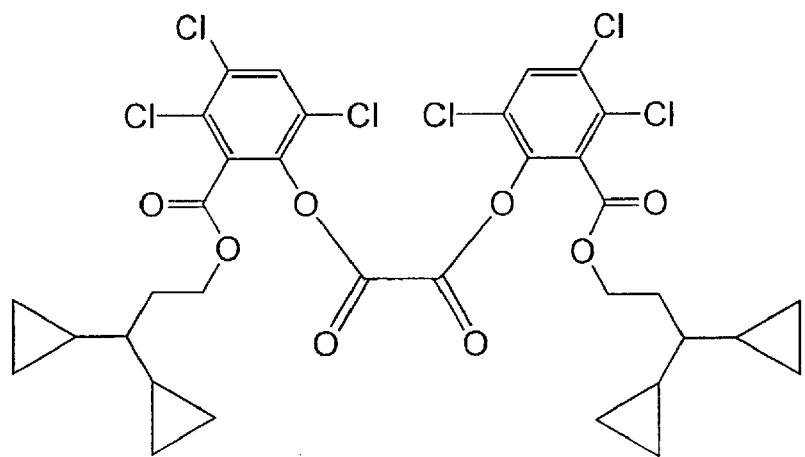
Figure 617:
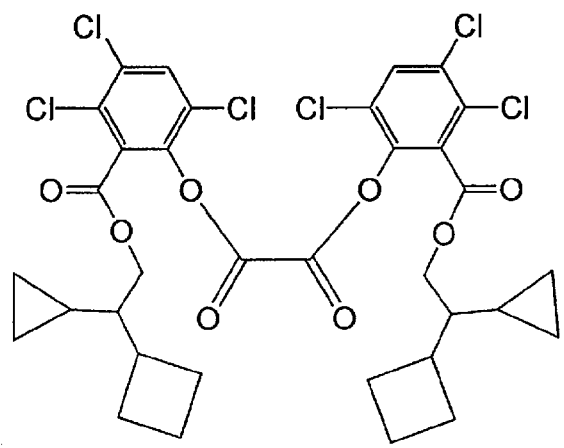
Figure 618:
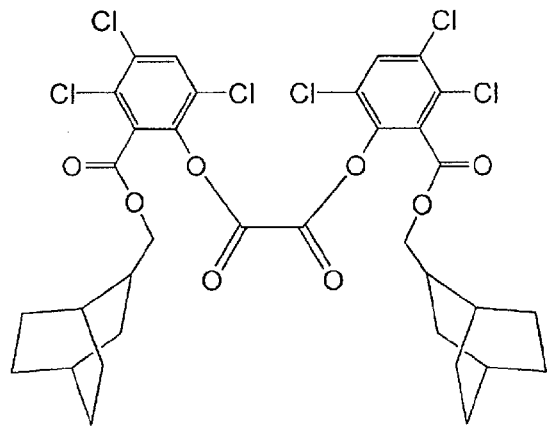
Figure 619:
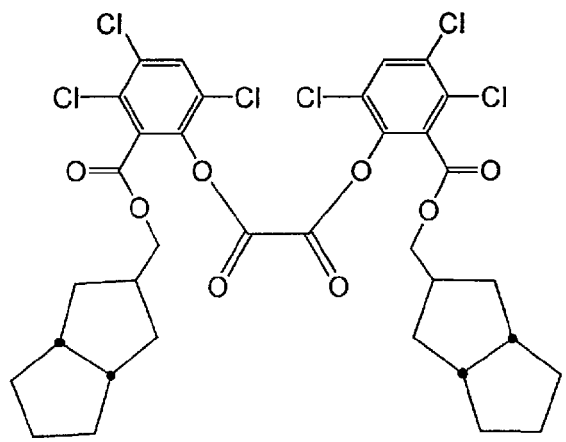
Figure 620:
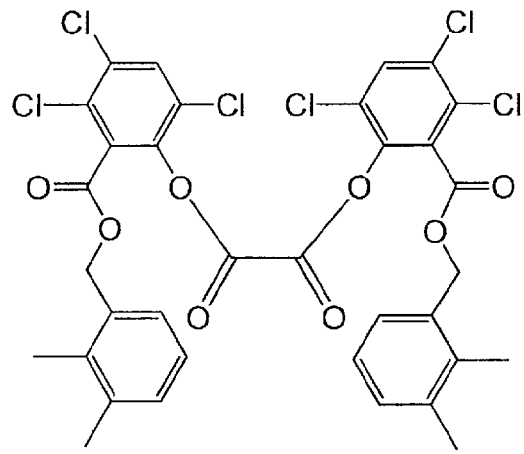
Figure 621:
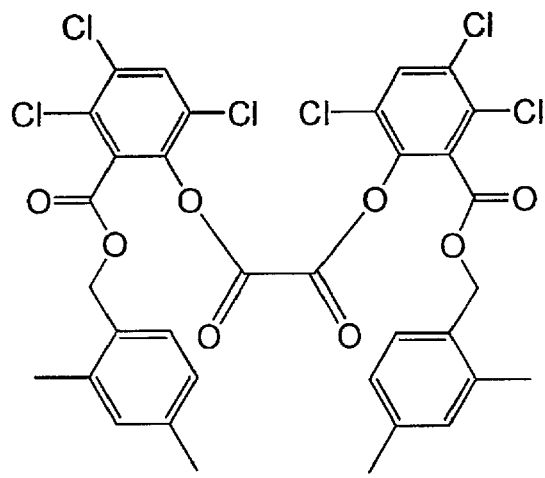
Figure 622:
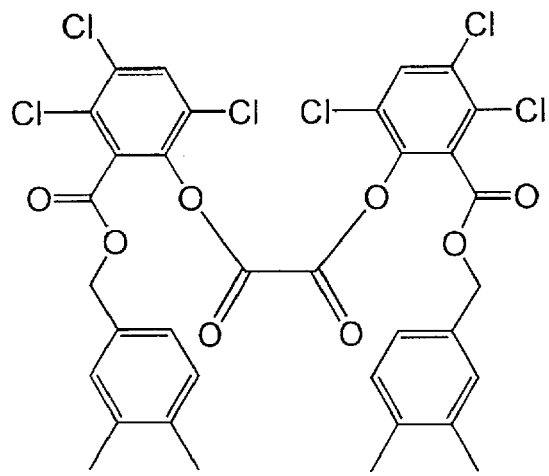
Figure 623:
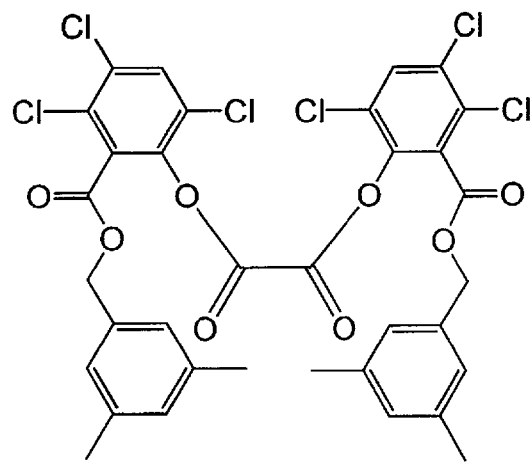
Figure 624:
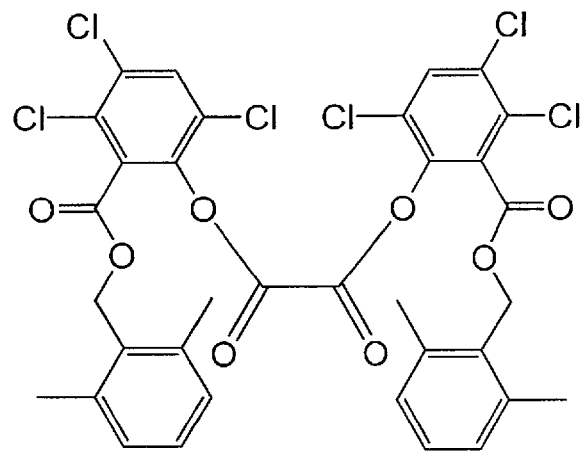
Figure 625:
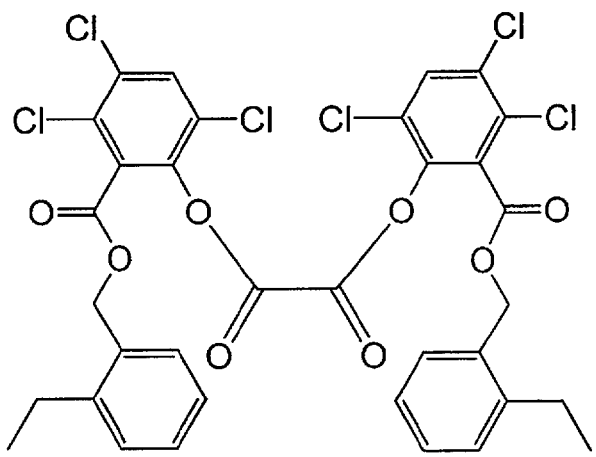
Figure 626:
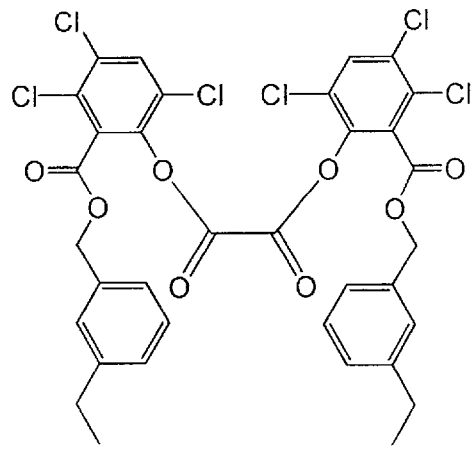
Figure 627:
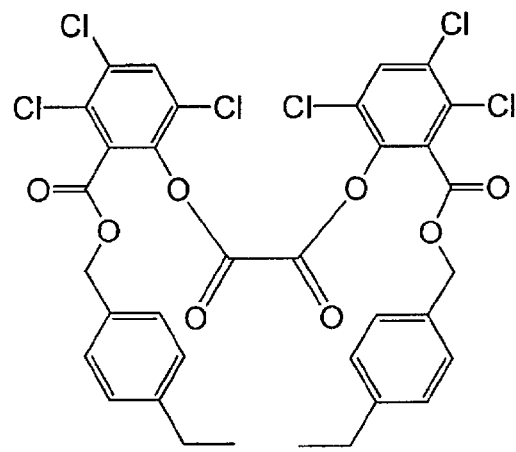
Figure 628:
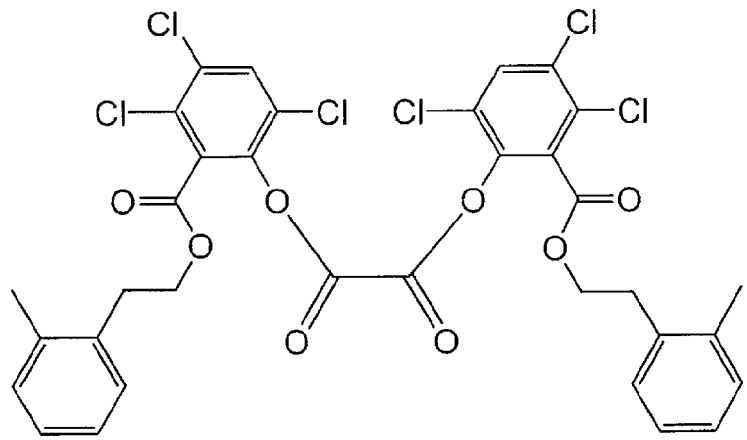
Figure 629:
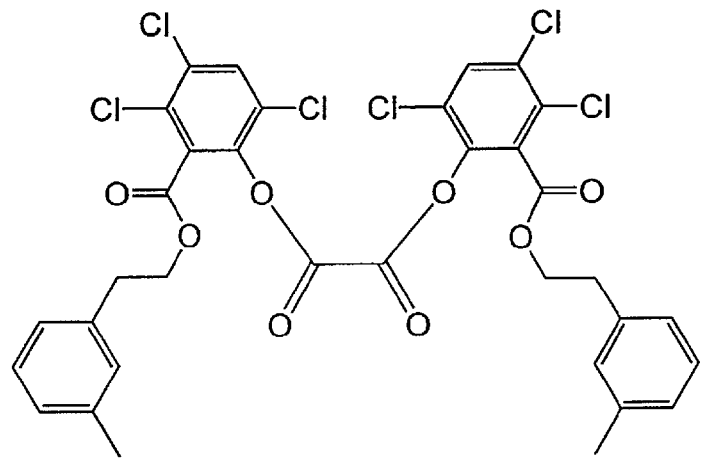
Figure 630:
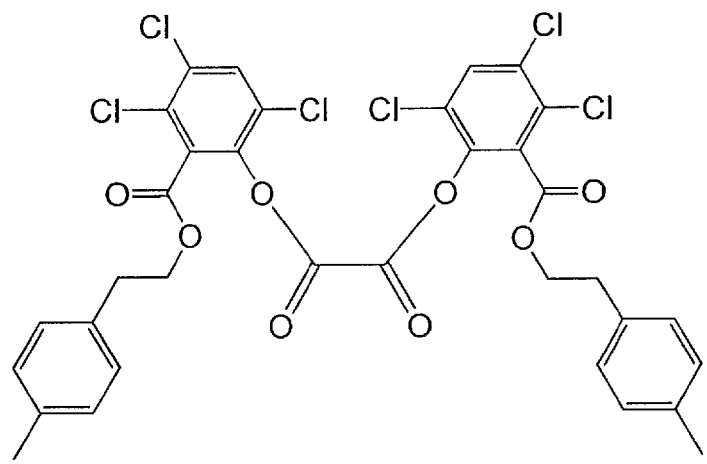
Figure 631:
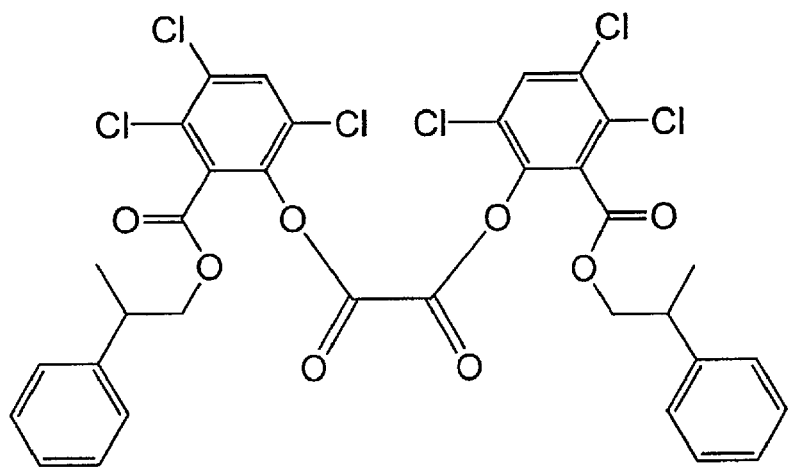
Figure 632:
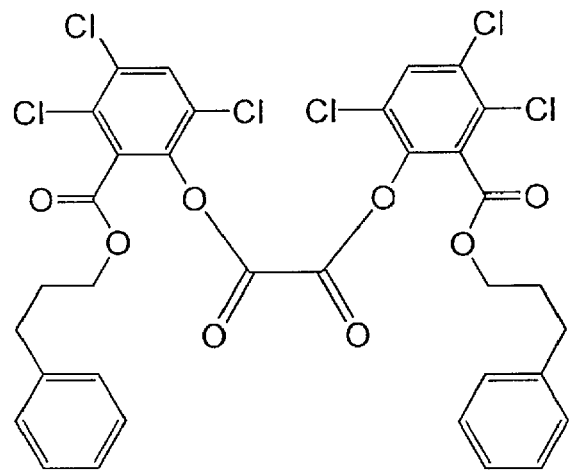
Figure 633:
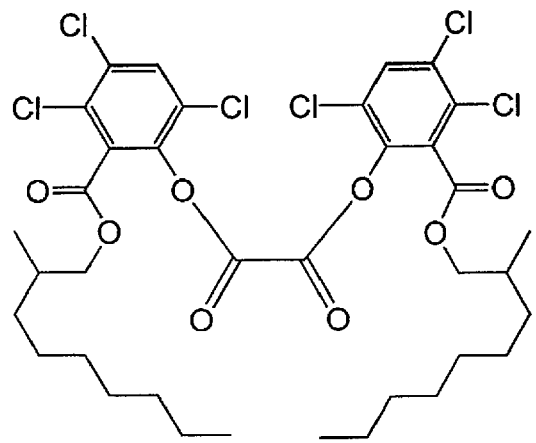
Figure 634:
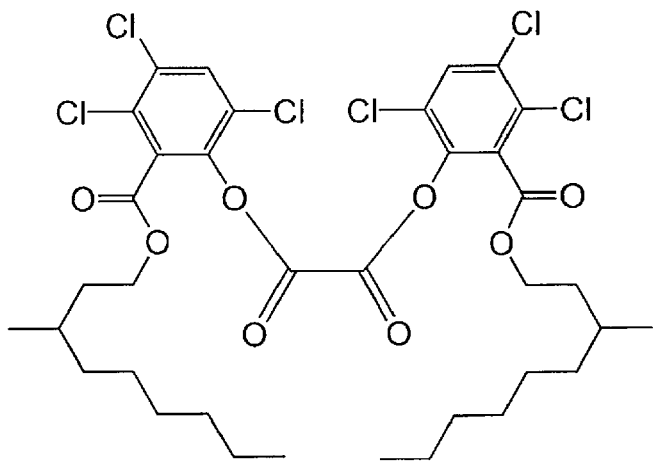
Figure 635:
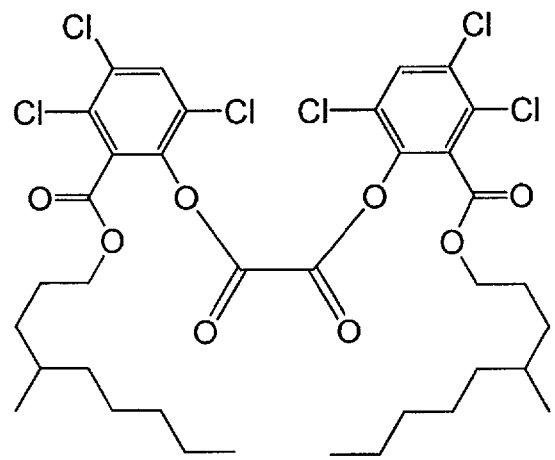
Figure 636:
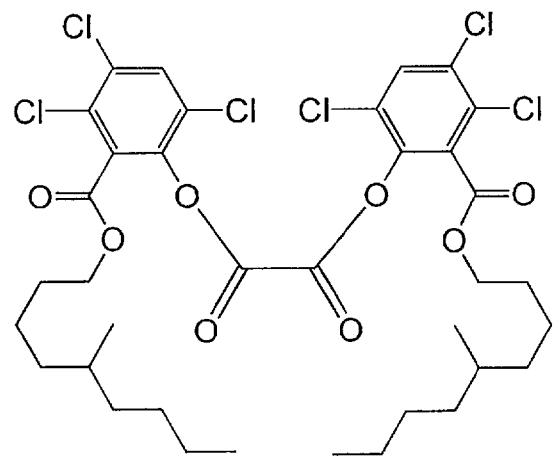
Figure 637:
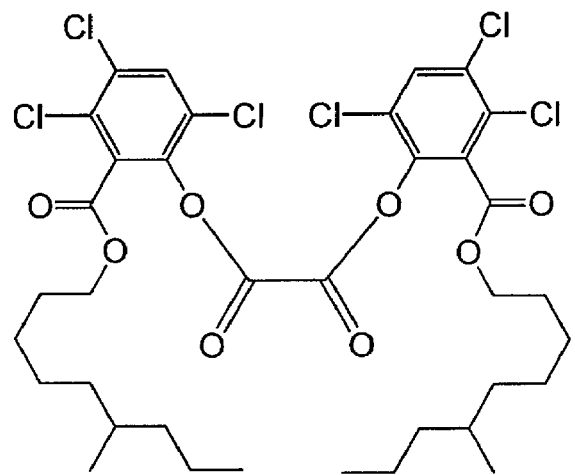
Figure 638:
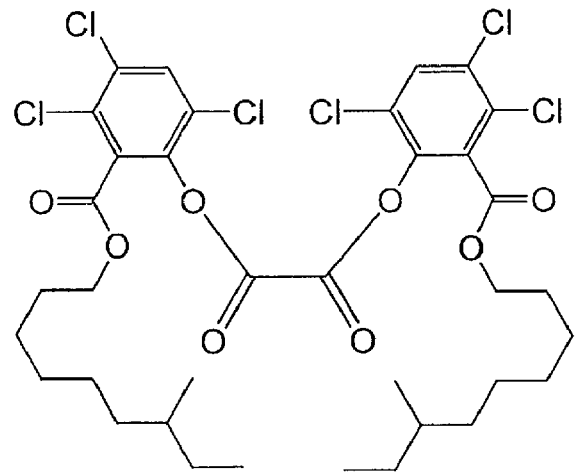
Figure 639:
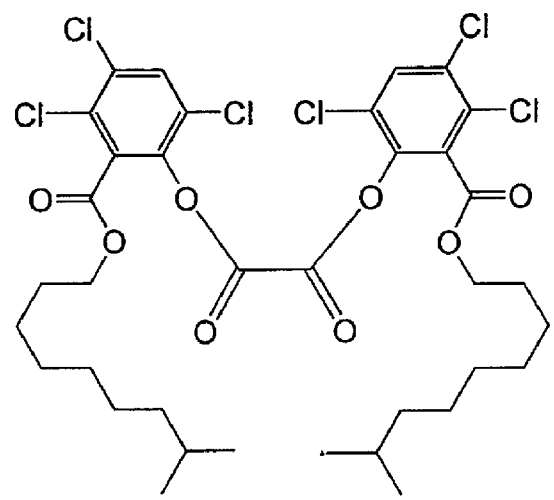
Figure 640:
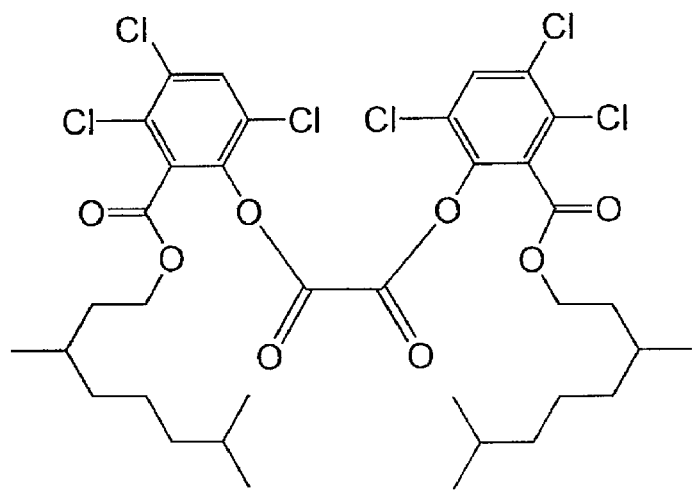
Figure 641:
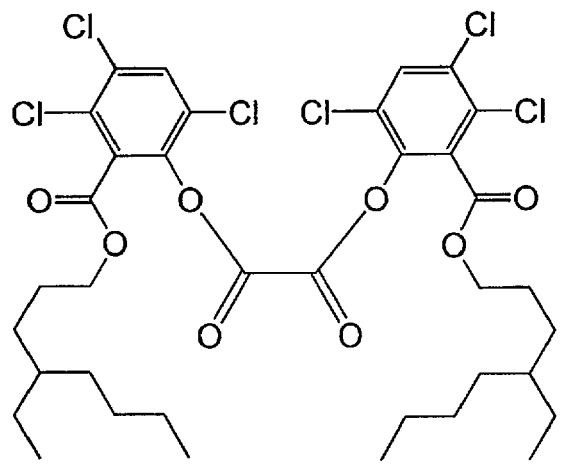
Figure 642:
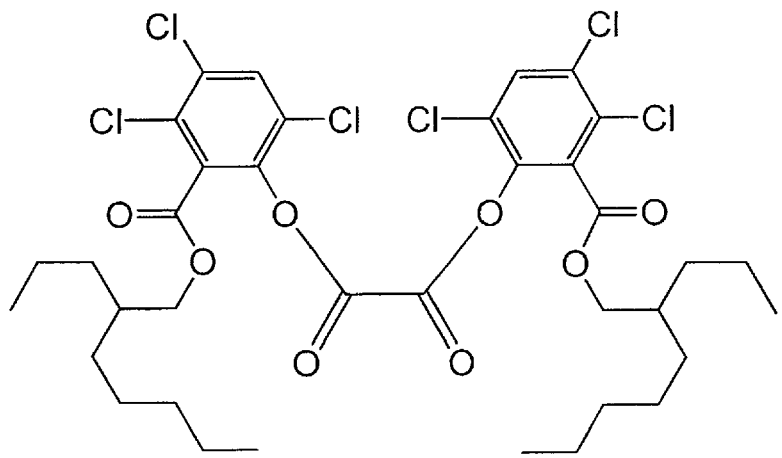
Figure 643:
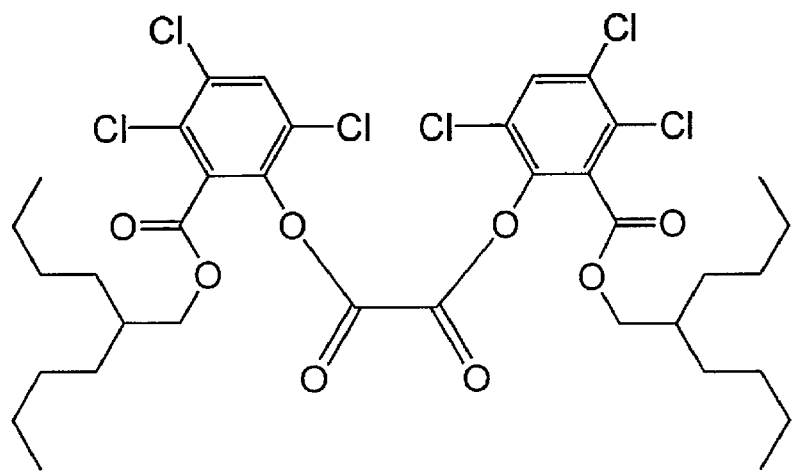
Figure 644:
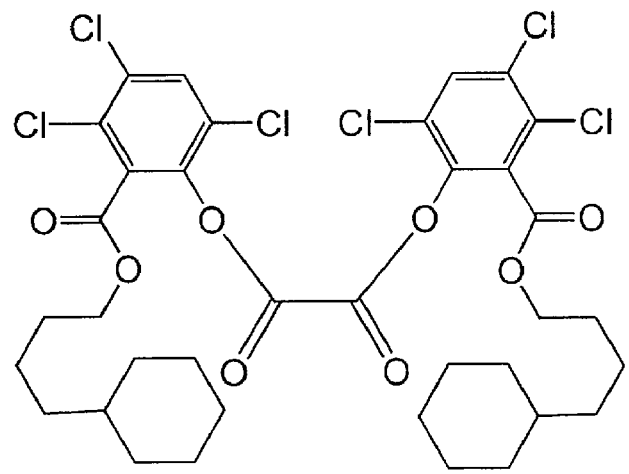
Figure 645:
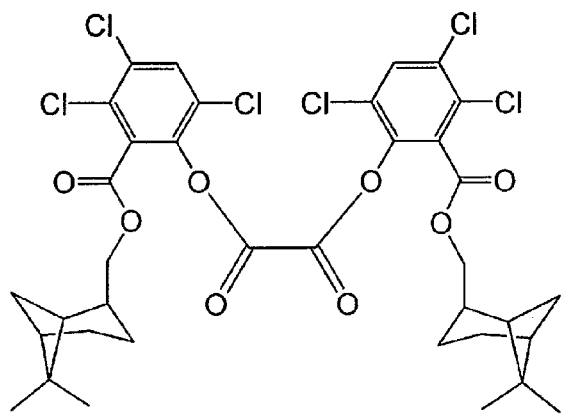
Figure 646:
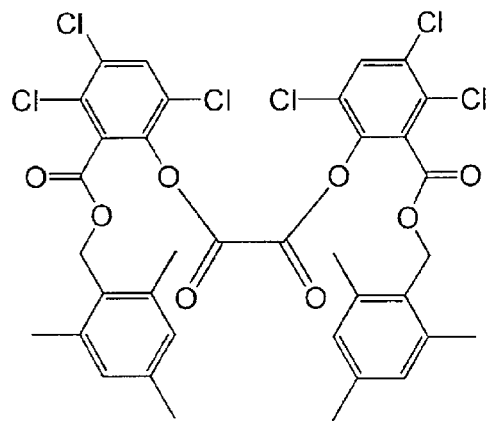
Figure 647:
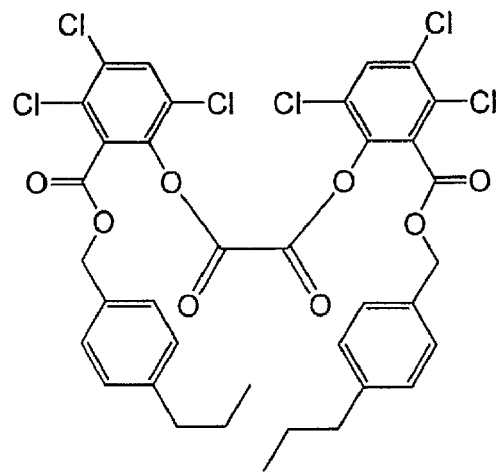
Figure 648:
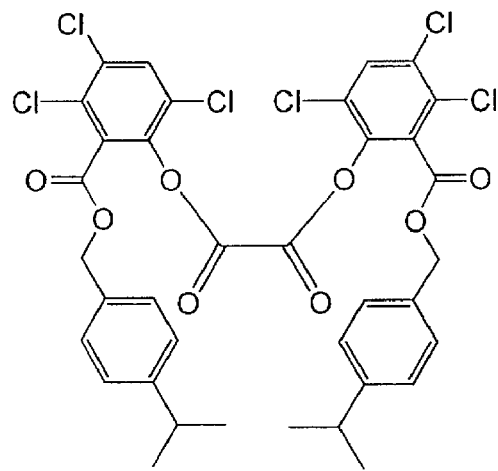
Figure 649:
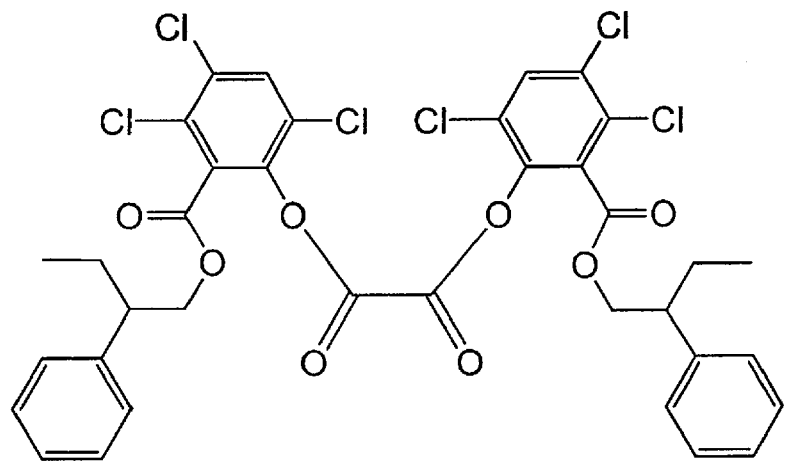
Figure 650:
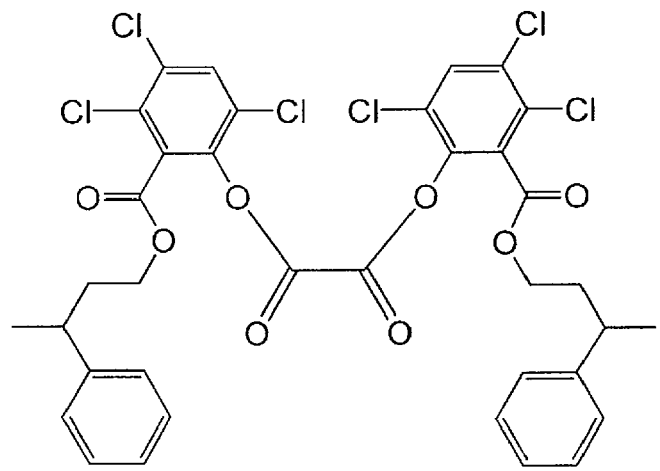
Figure 651:
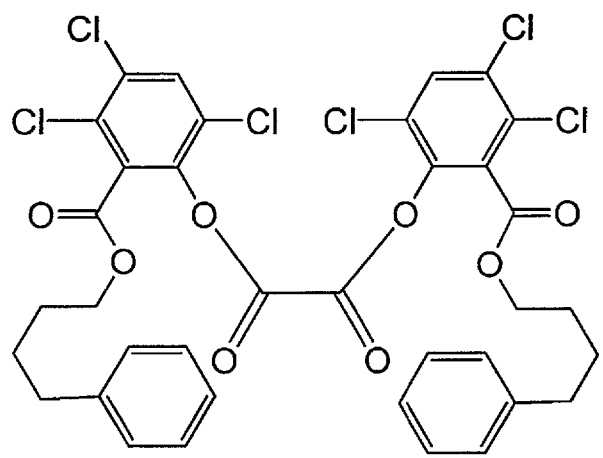
Figure 652:
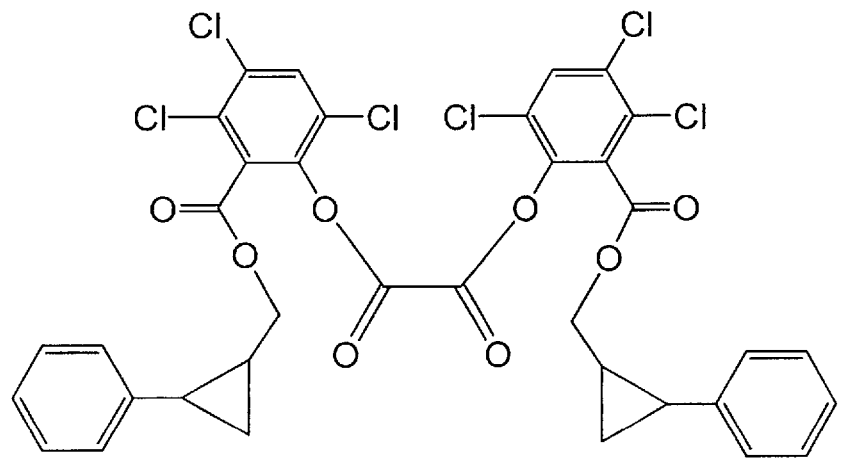
Figure 653:
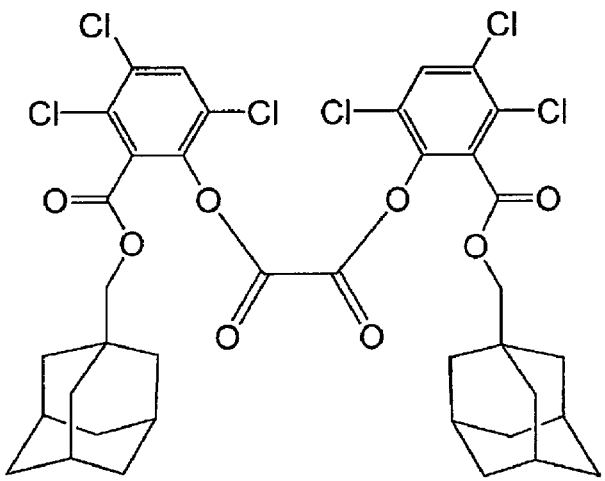
Figure 654:
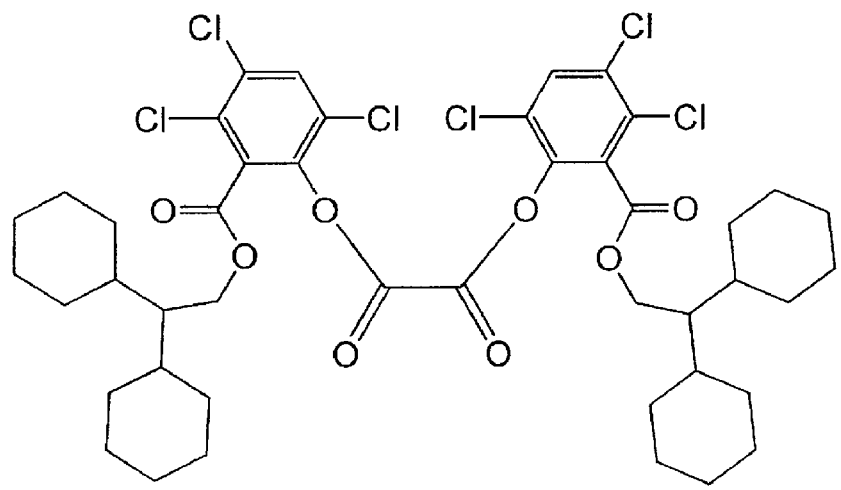
Figure 655:
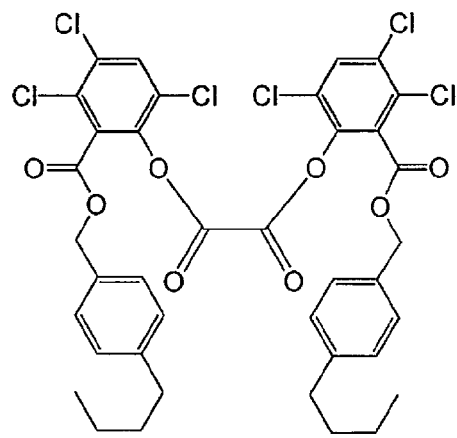
Figure 656:
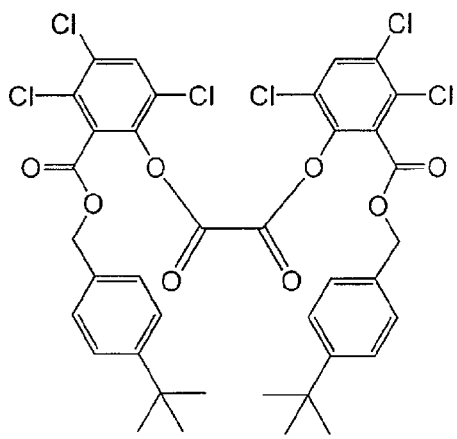
Figure 657:
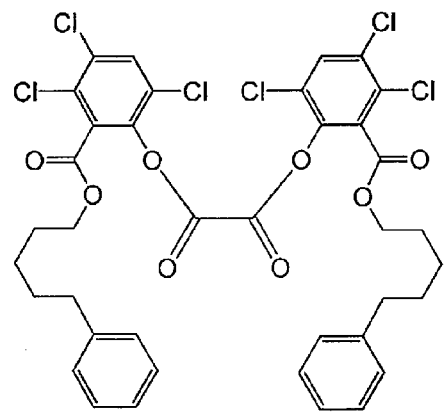
Figure 658:
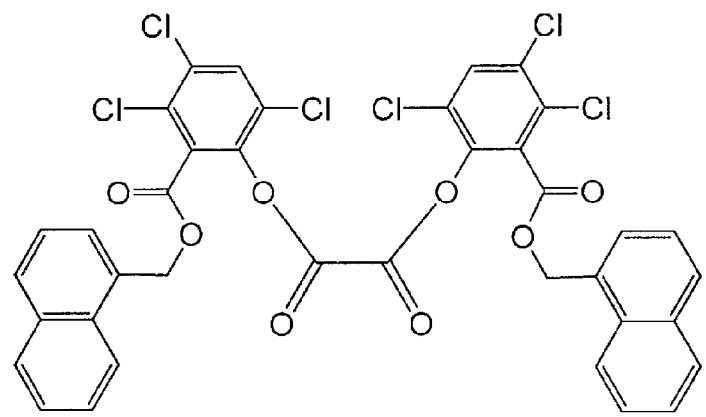
Figure 659:
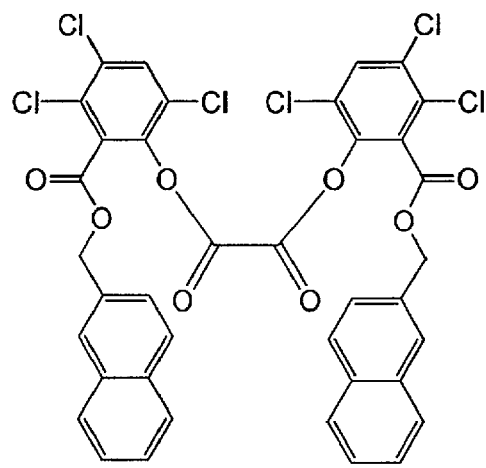
Figure 660:
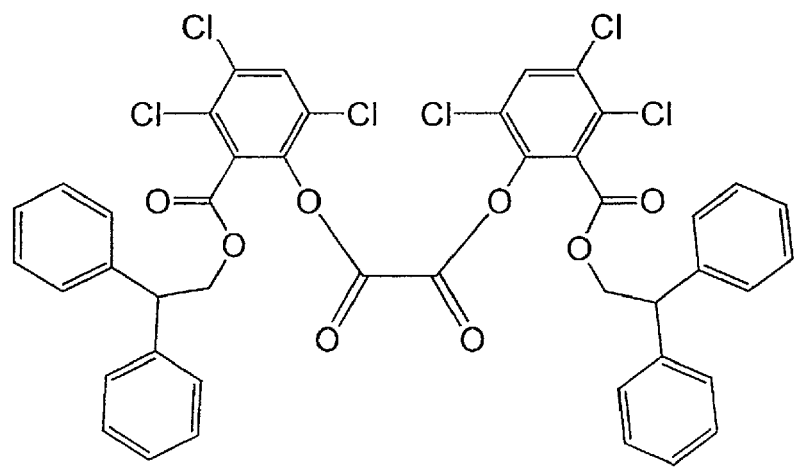
Figure 661:
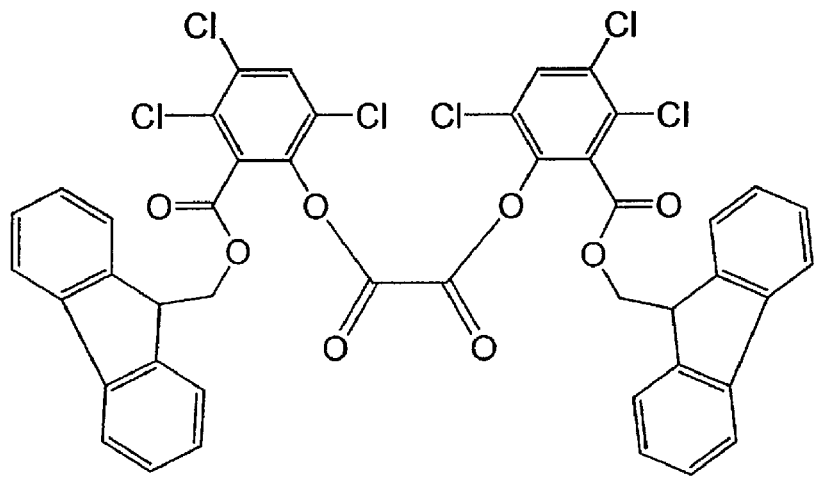
Figure 662:
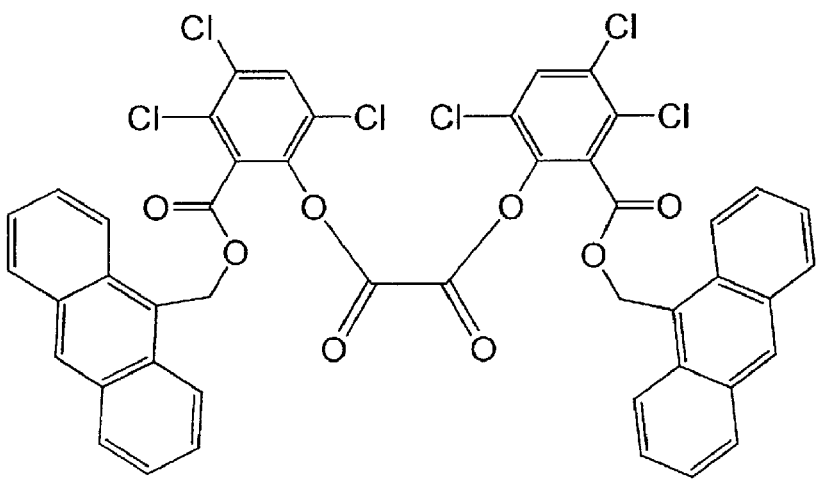

FIG. 131 illustrates a bis(3,4,6-trichloro-2-{[(2,4-dimethylcyclopentyl)methoxy]carbonyl}phenyl) oxalate;

FIG. 132 illustrates a bis(3,4,6-trichloro-2-{[(2,5-dimethylcyclopentyl)methoxy]carbonyl}phenyl) oxalate;

FIG. 133 illustrates a bis(3,4,6-trichloro-2-{[(3,3-dimethylcyclopentyl)methoxy]carbonyl}phenyl) oxalate;

FIG. 134 illustrates a bis(3,4,6-trichloro-2-{[(3,4-dimethylcyclopentyl)methoxy]carbonyl}phenyl) oxalate;

FIG. 135 illustrates a bis(3,4,6-trichloro-2-{[(1-ethylcyclopentyl)methoxy]carbonyl}phenyl) oxalate;

FIG. 136 illustrates a bis(3,4,6-trichloro-2-{[(2-ethylcyclopentyl)methoxy]carbonyl}phenyl) oxalate;

FIG. 137 illustrates a bis(3,4,6-trichloro-2-{[(3-ethylcyclopentyl)methoxy]carbonyl}phenyl) oxalate;

FIG. 138 illustrates a bis(3,4,6-trichloro-2-{[2-(1-methylcyclopentyl)ethoxy]carbonyl}phenyl) oxalate;

FIG. 139 illustrates a bis(3,4,6-trichloro-2-{[2-(2-methylcyclopentyl)ethoxy]carbonyl}phenyl) oxalate;

FIG. 140 illustrates a bis(3,4,6-trichloro-2-{[2-(3-methylcyclopentyl)ethoxy]carbonyl}phenyl) oxalate;

FIG. 141 illustrates a bis{3,4,6-trichloro-2-[(2-cyclopentylpropoxy)carbonyl]phenyl}oxalate;

FIG. 142 illustrates a bis{3,4,6-trichloro-2-[(3-cyclopentylpropoxy)carbonyl]phenyl}oxalate;

FIG. 143 illustrates a bis(3,4,6-trichloro-2-{[(1,2,2-trimethylcyclobutyl)methoxy]carbonyl}phenyl) oxalate;

FIG. 144 illustrates a bis(3,4,6-trichloro-2-{[(1,2,3-trimethylcyclobutyl)methoxy]carbonyl}phenyl) oxalate;

FIG. 145 illustrates a bis(3,4,6-trichloro-2-{[(1,2,4-trimethylcyclobutyl)methoxy]carbonyl}phenyl) oxalate;

FIG. 146 illustrates a bis(3,4,6-trichloro-2-{[(2,2,3-trimethylcyclobutyl)methoxy]carbonyl}phenyl) oxalate;

FIG. 147 illustrates a bis(3,4,6-trichloro-2-{[(2,3,3-trimethylcyclobutyl)methoxy]carbonyl}phenyl) oxalate FIG. 148 illustrates a bis(3,4,6-trichloro-2-{[(2,3,4-trimethylcyclobutyl)methoxy]carbonyl}phenyl) oxalate;

FIG. 149 illustrates a bis(3,4,6-trichloro-2-{[(2-ethyl-1-methylcyclobutyl)methoxy]carbonyl}phenyl) oxalate;

FIG. 150 illustrates a bis(3,4,6-trichloro-2-{[(3 methylcyclobutyl)methoxy]carbonyl}phenyl) oxalate;

FIG. 151 illustrates a bis(3,4,6-trichloro-2-{[(1-ethyl-2-methylcyclobutyl)methoxy]carbonyl}phenyl) oxalate;

FIG. 152 illustrates a bis(3,4,6-trichloro-2-{[(1-ethyl-3-methylcyclobutyl)methoxy]carbonyl}phenyl) oxalate;

FIG. 153 illustrates a bis(3,4,6-trichloro-2-({[1-(1-methylethyl)-cyclobutyl]methoxy}carbonyl)phenyl) oxalate;

FIG. 154 illustrates a bis(3,4,6-trichloro-2-({[2-(1-methylethyl)-cyclobutyl]methoxy}carbonyl)phenyl) oxalate;

FIG. 155 illustrates a bis(3,4,6-trichloro-2-({[3-(1-methylethyl)-cyclobutyl]methoxy}carbonyl)phenyl) oxalate;

FIG. 156 illustrates a bis(3,4,6-trichloro-2-{[2-(1,2-dimethylcyclobutyl)ethoxy]carbonyl}phenyl) oxalate;

FIG. 157 illustrates a bis(3,4,6-trichloro-2-{[2-(1,3-dimethylcyclobutyl)ethoxy]carbonyl}phenyl) oxalate;

FIG. 158 illustrates a bis(3,4,6-trichloro-2-{[2-(2,2-dimethylcyclobutyl)ethoxy]carbonyl}phenyl) oxalate;

FIG. 159 illustrates a bis(3,4,6-trichloro-2-{[2-(2,3-dimethylcyclobutyl)ethoxy]carbonyl}phenyl) oxalate;

FIG. 160 illustrates a bis(3,4,6-trichloro-2-{[2-(2,4-dimethylcyclobutyl)ethoxy]carbonyl}phenyl) oxalate;

FIG. 161 illustrates a bis(3,4,6-trichloro-2-{[2-(3,3-dimethylcyclobutyl)ethoxy]carbonyl}phenyl) oxalate;

FIG. 162 illustrates a bis(3,4,6-trichloro-2-{[2-(1-methylcyclobutyl)propoxy]carbonyl}phenyl) oxalate;

FIG. 163 illustrates a bis(3,4,6-trichloro-2-{[2-(2-methylcyclobutyl)propoxy]carbonyl}phenyl) oxalate;

FIG. 164 illustrates a bis(3,4,6-trichloro-2-{[2-(3-methylcyclobutyl)propoxy]carbonyl}phenyl) oxalate;

FIG. 165 illustrates a bis{3,4,6-trichloro-2-[(2-cyclobutyl-2-methylpropoxy)carbonyl]phenyl}oxalate;

FIG. 166 illustrates a bis(3,4,6-trichloro-2-{[2-(1-ethylcyclobutyl)ethoxy]carbonyl}phenyl) oxalate;

FIG. 167 illustrates a bis(3,4,6-trichloro-2-{[2-(2-ethylcyclobutyl)ethoxy]carbonyl}phenyl) oxalate;

FIG. 168 illustrates a bis(3,4,6-trichloro-2-{[2-(3-ethylcyclobutyl)ethoxy]carbonyl}phenyl) oxalate;

FIG. 169 illustrates a bis(3,4,6-trichloro-2-{[3-(1-methylcyclobutyl)propoxy]carbonyl}phenyl) oxalate;

FIG. 170 illustrates a bis(3,4,6-trichloro-2-{[3-(2-methylcyclobutyl)propoxy]carbonyl}phenyl) oxalate;

FIG. 171 illustrates a bis(3,4,6-trichloro-2-{[3-(3-methylcyclobutyl)propoxy]carbonyl}phenyl) oxalate;

FIG. 172 illustrates a bis{3,4,6-trichloro-2-[(3-cyclobutyl-2-methylpropoxy)carbonyl]phenyl}oxalate;

FIG. 173 illustrates a bis{3,4,6-trichloro-2-[(2-cyclobutylbutoxy)carbonyl]phenyl}oxalate;

FIG. 174 illustrates a bis{3,4,6-trichloro-2-[(3-cyclobutylbutoxy)carbonyl]phenyl}oxalate;

FIG. 175 illustrates a bis{3,4,6-trichloro-2-[(4-cyclobutylbutoxy)carbonyl]phenyl}oxalate;

FIG. 176 illustrates a bis(3,4,6-trichloro-2-{[(1,2,2,3,3-pentamethylcyclopropyl)methoxy]carbonyl}phenyl) oxalate;

FIG. 177 illustrates a bis(3,4,6-trichloro-2-{[(3-ethyl-1,2,2-trimethylcyclopropyl)methoxy]carbonyl}phenyl) oxalate;

FIG. 178 illustrates a bis(3,4,6-trichloro-2-{[(2,3-diethyl-1-methylcyclopropyl)methoxy]carbonyl}phenyl) oxalate;

FIG. 179 illustrates a bis(3,4,6-trichloro-2-{[(2,2-diethyl-1-methylcyclopropyl)methoxy]carbonyl}phenyl) oxalate;

FIG. 180 illustrates a bis(3,4,6-trichloro-2-{[(1-ethyl-2-propylcyclopropyl)methoxy]carbonyl}phenyl) oxalate;

FIG. 181 illustrates a bis(3,4,6-trichloro-2-{[(2-ethyl-1-propylcyclopropyl)methoxy]carbonyl}phenyl) oxalate;

FIG. 182 illustrates a bis(3,4,6-trichloro-2-{[(2-ethyl-2-propylcyclopropyl)methoxy]carbonyl}phenyl) oxalate;

FIG. 183 illustrates a bis(3,4,6-trichloro-2-{[(2-ethyl-3-propylcyclopropyl)methoxy]carbonyl}phenyl) oxalate;

FIG. 184 illustrates a bis(3,4,6-trichloro-2-{[(1-ethyl-2,2,3-trimethylcyclopropyl)methoxy]carbonyl}phenyl) oxalate;

FIG. 185 illustrates a bis(3,4,6-trichloro-2-{[(1,2-diethyl-3-methylcyclopropyl)methoxy]carbonyl}phenyl) oxalate;

FIG. 186 illustrates a bis[3,4,6-trichloro-2-({[2,2-dimethyl-1-(1-methylethyl)-cyclopropyl]methoxy}carbonyl)phenyl]oxalate;

FIG. 187 illustrates a bis[3,4,6-trichloro-2-({[2,3-dimethyl-1-(1-methylethyl)-cyclopropyl]methoxy}carbonyl)phenyl]oxalate;

FIG. 188 illustrates a bis[3,4,6-trichloro-2-({[2-ethyl-1-(1-methylethyl)-cyclopropyl]methoxy}carbonyl)phenyl]oxalate;

FIG. 189 illustrates a bis[3,4,6-trichloro-2-({[1-ethyl-2-(1-methylethyl)-cyclopropyl]methoxy}carbonyl)phenyl]oxalate;

FIG. 190 illustrates a bis[3,4,6-trichloro-2-({[2,2-dimethyl-3-(1-methylethyl)-cyclopropyl]methoxy}carbonyl)phenyl]oxalate;

FIG. 191 illustrates a bis[3,4,6-trichloro-2-({[2-ethyl-3-(1-methylethyl)-cyclopropyl]methoxy}carbonyl)phenyl]oxalate;

FIG. 192 illustrates a bis(3,4,6-trichloro-2-{[2-(1,2,2-trimethylcyclopropyl)propoxy]carbonyl}phenyl) oxalate;

FIG. 193 illustrates a bis(3,4,6-trichloro-2-{[2-(1,2,3-trimethylcyclopropyl)propoxy]carbonyl}phenyl) oxalate;

FIG. 194 illustrates a bis(3,4,6-trichloro-2-{[2-(2,2,3-trimethylcyclopropyl)propoxy]carbonyl}phenyl) oxalate;

FIG. 195 illustrates a bis(3,4,6-trichloro-2-{[2-(2,2-dimethylcyclopropyl)propoxy]carbonyl}phenyl) oxalate;

FIG. 196 illustrates a bis(3,4,6-trichloro-2-{[2-(2,3-dimethylcyclopropyl)propoxy]carbonyl}phenyl) oxalate;

FIG. 197 illustrates a bis(3,4,6-trichloro-2-{[2-(2-ethyl-3-methylcyclopropyl)ethoxy]carbonyl}phenyl) oxalate;

FIG. 198 illustrates a bis(3,4,6-trichloro-2-{[2-(2-methylcyclopropyl)butoxy]carbonyl}phenyl) oxalate;

FIG. 199 illustrates a bis{3,4,6-trichloro-2-[(2-cyclopropyl-2-methylbutoxy)carbonyl]phenyl} oxalate;

FIG. 200 illustrates a bis(3,4,6-trichloro-2-{[2-(1-methylcyclopropyl)butoxy]carbonyl}phenyl) oxalate;

FIG. 201 illustrates a bis(3,4,6-trichloro-2-{[2-(2-ethyl-2-methylcyclopropyl)ethoxy]carbonyl}phenyl) oxalate;

FIG. 202 illustrates a bis(3,4,6-trichloro-2-{[2-methyl-2-(1-methylcyclopropyl)propoxy]carbonyl}phenyl) oxalate;

FIG. 203 illustrates a bis(3,4,6-trichloro-2-{[2-methyl-2-(2-methylcyclopropyl)propoxy]carbonyl}phenyl) oxalate;

FIG. 204 illustrates a bis{3,4,6-trichloro-2-[(2-cyclopropyl-3-methylbutoxy)carbonyl]phenyl} oxalate;

FIG. 205 illustrates a bis(3,4,6-trichloro-2-{[3-(1,2-dimethylcyclopropyl)propoxy]carbonyl}phenyl) oxalate;

FIG. 206 illustrates a bis(3,4,6-trichloro-2-{[3-(2,2-dimethylcyclopropyl)propoxy]carbonyl}phenyl) oxalate;

FIG. 207 illustrates a bis{3,4,6-trichloro-2-[(3-cyclopropyl-2-methylbutoxy)carbonyl]phenyl} oxalate;

FIG. 208 illustrates a bis(3,4,6-trichloro-2-{[2-methyl-3-(1-methylcyclopropyl)propoxy]carbonyl}phenyl) oxalate;

FIG. 209 illustrates a bis(3,4,6-trichloro-2-{[2-methyl-3-(2-methylcyclopropyl)propoxy]carbonyl}phenyl) oxalate;

FIG. 210 illustrates a bis{3,4,6-trichloro-2-[(3-cyclopropyl-2,2-dimethylpropoxy)carbonyl]phenyl} oxalate;

FIG. 211 illustrates a bis{3,4,6-trichloro-2-[(3-cyclopropyl-3-methylbutoxy)carbonyl]phenyl} oxalate;

FIG. 212 illustrates a bis{3,4,6-trichloro-2-[(2,2dicyclopropylethoxy)carbonyl)phenyl} oxalate;

FIG. 213 illustrates a bis(3,4,6-trichloro-2-{[4-(1-methylcyclopropyl)butoxy]carbonyl}phenyl) oxalate;

FIG. 214 illustrates a bis(3,4,6-trichloro-2-{[4-(2-methylcyclopropyl)butoxy]carbonyl}phenyl) oxalate;

FIG. 215 illustrates a bis{3,4,6-trichloro-2-[(4-cyclopropyl-2-methylbutoxy)carbonyl]phenyl} oxalate;

FIG. 216 illustrates a bis{3,4,6-trichloro-2-[(4-cyclopropyl-3-methylbutoxy)carbonyl]phenyl} oxalate;

FIG. 217 illustrates a bis(3,4,6-trichloro-2-{[2-(2-propylcyclopropyl)ethoxy]carbonyl}phenyl) oxalate;

FIG. 218 illustrates a bis[3,4,6-trichloro-2-({2-[2-(1-methylethyl)cyclopropyl]ethoxy}carbonyl)phenyl]oxalate;

FIG. 219 illustrates a bis{3,4,6-trichloro-2-[(2-cyclopropylpentyloxy)carbonyl]phenyl}oxalate;

FIG. 220 illustrates a bis{3,4,6-trichloro-2-[(3-cyclopropylpentyloxy)carbonyl]phenyl}oxalate;

FIG. 221 illustrates a bis{3,4,6-trichloro-2-[(4-cyclopropylpentyloxy)carbonyl]phenyl}oxalate;

FIG. 222 illustrates a bis{3,4,6-trichloro-2-[(5-cyclopropylpentyloxy)carbonyl]phenyl}oxalate;

FIG. 223 illustrates a bis(2-{[2-(bicyclo[1.1.1]pentan-2-yl)propoxy]carbonyl}-3,4,6-trichlorophenyl) oxalate;

FIG. 224 illustrates a bis(2-{[2-(bicyclo[2.1.1]hexan-2-yl)ethoxy]carbonyl}-3,4,6-trichlorophenyl) oxalate;

FIG. 225 illustrates a bis{2-[(bicyclo[2.2.1]heptan-2-ylmethoxy)carbonyl]3,4,6-trichlorophenyl}oxalate;

FIG. 226 illustrates a bis{3,4,6-trichloro-2-[(2-phenylethoxy)carbonyl]phenyl}oxalate;

FIG. 227 illustrates a bis(3,4,6-trichloro-2-{[(2-methylphenyl)methoxy]carbonyl}phenyl) oxalate;

FIG. 228 illustrates a bis(3,4,6-trichloro-2-{[(3-methylphenyl)methoxy]carbonyl}phenyl) oxalate;

FIG. 229 illustrates a bis(3,4,6-trichloro-2-{[(4-methylphenyl)methoxy]carbonyl}phenyl) oxalate;

FIG. 230 illustrates a bis{3,4,6-trichloro-2-[(2-methyloctyloxy)carbonyl]phenyl}oxalate;

FIG. 231 illustrates a bis{3,4,6-trichloro-2-[(3-methyloctyloxy)carbonyl]phenyl}oxalate;

FIG. 232 illustrates a bis{3,4,6-trichloro-2-[(4-methyloctyloxy)carbonyl]phenyl}oxalate;

FIG. 233 illustrates a bis{3,4,6-trichloro-2-[(5-methyloctyloxy)carbonyl]phenyl}oxalate;

FIG. 234 illustrates a bis{3,4,6-trichloro-2-[(6-methyloctyloxy)carbonyl]phenyl}oxalate;

FIG. 235 illustrates a bis{3,4,6-trichloro-2-[(7-methyloctyloxy)carbonyl]phenyl}oxalate;

FIG. 236 illustrates a bis{3,4,6-trichloro-2-[(2,2-dimethylheptyloxy)carbonyl]phenyl}oxalate;

FIG. 237 illustrates a bis{3,4,6-trichloro-2-[(2-ethylheptyloxy)carbonyl]phenyl}oxalate;

FIG. 238 illustrates a bis{3,4,6-trichloro-2-[(2,3-dimethylheptyloxy)carbonyl]phenyl}oxalate;

FIG. 239 illustrates a bis{3,4,6-trichloro-2-[(2,4-dimethylheptyloxy)carbonyl]phenyl}oxalate;

FIG. 240 illustrates a bis{3,4,6-trichloro-2-[(2,5-dimethylheptyloxy)carbonyl]phenyl}oxalate;

FIG. 241 illustrates a bis{3,4,6-trichloro-2-[(2,6-dimethylheptyloxy)carbonyl]phenyl}oxalate;

FIG. 242 illustrates a bis{3,4,6-trichloro-2-[(3,3-dimethylheptyloxy)carbonyl]phenyl}oxalate;

FIG. 243 illustrates a bis{3,4,6-trichloro-2-[(3-ethylheptyloxy)carbonyl]phenyl}oxalate;

FIG. 244 illustrates a bis{3,4,6-trichloro-2-[(3,4-dimethylheptyloxy)carbonyl]phenyl}oxalate;

FIG. 245 illustrates a bis{3,4,6-trichloro-2-[(3,5-dimethylheptyloxy)carbonyl]phenyl}oxalate;

FIG. 246 illustrates a bis{3,4,6-trichloro-2-[(3,6-dimethylheptyloxy)carbonyl]phenyl}oxalate;

FIG. 247 illustrates a bis{3,4,6-trichloro-2-[(4,4-dimethylheptyloxy)carbonyl]phenyl}oxalate;

FIG. 248 illustrates a bis{3,4,6-trichloro-2-[(4-ethylheptyloxy)carbonyl]phenyl}oxalate;

FIG. 249 illustrates a bis{3,4,6-trichloro-2-[(4,5-dimethylheptyloxy)carbonyl]phenyl}oxalate;

FIG. 250 illustrates a bis{3,4,6-trichloro-2-[(4,6-dimethylheptyloxy)carbonyl]phenyl}oxalate;

FIG. 251 illustrates a bis{3,4,6-trichloro-2-[(5,5-dimethylheptyloxy)carbonyl]phenyl}oxalate;

FIG. 252 illustrates a bis{3,4,6-trichloro-2-[(5-ethylheptyloxy)carbonyl]phenyl}oxalate;

FIG. 253 illustrates a bis{3,4,6-trichloro-2-[(5,6-dimethylheptyloxy)carbonyl]phenyl}oxalate;

FIG. 254 illustrates a bis{3,4,6-trichloro-2-[(6,6-dimethylheptyloxy)carbonyl]phenyl}oxalate;

FIG. 255 illustrates a bis{3,4,6-trichloro-2-[(2,2,3-trimethylhexyloxy)carbonyl]phenyl}oxalate;

FIG. 256 illustrates a bis{3,4,6-trichloro-2-[(2,2,4-trimethylhexyloxy)carbonyl]phenyl}oxalate;

FIG. 257 illustrates a bis{3,4,6-trichloro-2-[(2,2,5-trimethylhexyloxy)carbonyl]phenyl}oxalate;

FIG. 258 illustrates a bis{3,4,6-trichloro-2-[(2-ethyl-2-methylhexyloxy)carbonyl]phenyl}oxalate;

FIG. 259 illustrates a bis{3,4,6-trichloro-2-[(2-ethyl-2-methylhexyloxy)carbonyl]phenyl}oxalate;

FIG. 260 illustrates a bis{3,4,6-trichloro-2-[(2-ethyl-4-methylhexyloxy)carbonyl]phenyl}oxalate;

FIG. 261 illustrates a bis{3,4,6-trichloro-2-[(2-ethyl-5-methylhexyloxy)carbonyl]phenyl}oxalate;

FIG. 262 illustrates a bis{3,4,6-trichloro-2-[(2,3,3-trimethylhexyloxy)carbonyl]phenyl}oxalate;

FIG. 263 illustrates a bis{3,4,6-trichloro-2-[(3,3,4-trimethylhexyloxy)carbonyl]phenyl}oxalate;

FIG. 264 illustrates a s{3,4,6-trichloro-2-[(3,3,5-trimethylhexyloxy)carbonyl]phenyl}oxalate;

FIG. 265 illustrates a bis{3,4,6-trichloro-2-[(3-ethyl-2-methylhexyloxy)carbonyl]phenyl}oxalate;

FIG. 266 illustrates a bis{3,4,6-trichloro-2-[(3-ethyl-3-methylhexyloxy)carbonyl]phenyl}oxalate;

FIG. 267 illustrates a bis{3,4,6-trichloro-2-[(3-ethyl-4-methylhexyloxy)carbonyl]phenyl}oxalate;

FIG. 268 illustrates a bis{3,4,6-trichloro-2-[(3-ethyl-5-methylhexyloxy)carbonyl]phenyl}oxalate;

FIG. 269 illustrates a bis{3,4,6-trichloro-2-[2,4,4-trimethylhexyloxy)carbonyl]phenyl}oxalate;

FIG. 270 illustrates a bis{3,4,6-trichloro-2-[(3,4,4-trimethylhexyloxy)carbonyl]phenyl}oxalate;

FIG. 271 illustrates a bis{3,4,6-trichloro-2-[(4,4,5-trimethylhexyloxy)carbonyl]phenyl}oxalate;

FIG. 272 illustrates a bis{3,4,6-trichloro-2-[(4-ethyl-2-methylhexyloxy)carbonyl]phenyl}oxalate;

FIG. 273 illustrates a bis{3,4,6-trichloro-2-[(4-ethyl-3-methylhexyloxy)carbonyl]phenyl}oxalate;

FIG. 274 illustrates a bis{3,4,6-trichloro-2-[(4-ethyl-4-methylhexyloxy)carbonyl]phenyl}oxalate;

FIG. 275 illustrates a bis{3,4,6-trichloro-2-[(4-ethyl-5-methylhexyloxy)carbonyl]phenyl}oxalate;

FIG. 276 illustrates a bis{3,4,6-trichloro-2-[(2,5,5-trimethylhexyloxy)carbonyl]phenyl}oxalate;

FIG. 277 illustrates a bis{3,4,6-trichloro-2-[(3,5,5-trimethylhexyloxy)carbonyl]phenyl}oxalate;

FIG. 278 illustrates a bis{3,4,6-trichloro-2-[(4,5,5-trimethylhexyloxy)carbonyl]phenyl}oxalate;

FIG. 279 illustrates a bis{3,4,6-trichloro-2-[(2-propylhexyloxy)carbonyl]phenyl}oxalate;

FIG. 280 illustrates a bis{3,4,6-trichloro-2-[(3-propylhexyloxy)carbonyl]phenyl}oxalate;

FIG. 281 illustrates a bis(3,4,6-trichloro-2-{[2-(1-methylethyl)hexyloxy]carbonyl}phenyl) oxalate;

FIG. 282 illustrates a bis(3,4,6-trichloro-2-{[3-(1-methylethyl)hexyloxy]carbonyl}phenyl) oxalate;

FIG. 283 illustrates a bis{3,4,6-trichloro-2-[(2,2,3,3-tetramethylpentyloxy)carbonyl]phenyl}oxalate;

FIG. 284 illustrates a bis{3,4,6-trichloro-2-[(2,2,3,4-tetramethylpentyloxy)carbonyl]phenyl}oxalate;

FIG. 285 illustrates a bis{3,4,6-trichloro-2-[(2,2,4,4-tetramethylpentyloxy)carbonyl]phenyl}oxalate;

FIG. 286 illustrates a bis{3,4,6-trichloro-2-[(2,3,3,4-tetramethylpentyloxy)carbonyl]phenyl}oxalate;

FIG. 287 illustrates a bis{3,4,6-trichloro-2-[(2-ethyl-2,3-dimethylpentyloxy)carbonyl]phenyl}oxalate;

FIG. 288 illustrates a bis{3,4,6-trichloro-2-[(2-ethyl-2,4-dimethylpentyloxy)carbonyl]phenyl}oxalate;

FIG. 289 illustrates a bis{3,4,6-trichloro-2-[(2-ethyl-3,3-dimethylpentyloxy)carbonyl]phenyl}oxalate;

FIG. 290 illustrates a bis{3,4,6-trichloro-2-[(2-ethyl-3,4-dimethylpentyloxy)carbonyl]phenyl}oxalate;

FIG. 291 illustrates a bis{3,4,6-trichloro-2-[(2-ethyl-4,4-dimethylpentyloxy)carbonyl]phenyl}oxalate;

FIG. 292 illustrates a bis{3,4,6-trichloro-2-[(2-propyl-2-methylpentyloxy)carbonyl]phenyl}oxalate;

FIG. 293 illustrates a bis{3,4,6-trichloro-2-[(2-propyl-3-methylpentyloxy)carbonyl]phenyl}oxalate;

FIG. 294 illustrates a bis{3,4,6-trichloro-2-[(2-propyl-4-methylpentyloxy)carbonyl]phenyl}oxalate;

FIG. 295 illustrates a bis(3,4,6-trichloro-2-{[2-methyl-2-(1-methylethyl)pentyloxy]carbonyl}phenyl) oxalate;

FIG. 296 illustrates a bis(3,4,6-trichloro-2-{[3-methyl-2-(1-methylethyl)pentyloxy]carbonyl}phenyl) oxalate;

FIG. 297 illustrates a bis(3,4,6-trichloro-2-{[4-methyl-2-(1-methylethyl)pentyloxy]carbonyl}phenyl) oxalate;

FIG. 298 illustrates a bis{3,4,6-trichloro-2-[(3-ethyl-2,4-dimethylpentyloxy)carbonyl]phenyl}oxalate;

FIG. 299 illustrates a bis{3,4,6-trichloro-2-[(3-ethyl-3,4-dimethylpentyloxy)carbonyl]phenyl}oxalate;

FIG. 300 illustrates a bis(3,4,6-trichloro-2-{[4-methyl-3-(1-methylethyl)pentyloxy]carbonyl}phenyl) oxalate;

FIG. 301 illustrates a bis(3,4,6-trichloro-2-{[2-(1,1-dimethylethyl)pentyloxy]carbonyl}phenyl) oxalate;

FIG. 302 illustrates a bis(3,4,6-trichloro-2-{[2-(1,1-dimethylethyl)pentyloxy]carbonyl}phenyl) oxalate;

FIG. 303 illustrates a bis{3,4,6-trichloro-2-[(2-ethyl-2,3,3-trimethylbutoxy)carbonyl]phenyl}oxalate;

FIG. 304 illustrates a bis(3,4,6-trichloro-2-{[3,3-dimethyl-2-(1-methylethyl)butoxy]carbonyl}phenyl) oxalate;

FIG. 305 illustrates a bis(3,4,6-trichloro-2-{[2,3-dimethyl-2-(1-methylethyl)butoxy]carbonyl}phenyl) oxalate;

FIG. 306 illustrates a bis{3,4,6-trichloro-2-[(cyclooctylmethoxy)carbonyl]phenyl}oxalate;

FIG. 307 illustrates a bis(3,4,6-trichloro-2-{[(1-methylcyclooctyl)methoxy]carbonyl}phenyl) oxalate;

FIG. 308 illustrates a bis(3,4,6-trichloro-2-{[(2-methylcyclooctyl)methoxy]carbonyl}phenyl) oxalate;

FIG. 309 illustrates a bis(3,4,6-trichloro-2-{[(3-methylcyclooctyl)methoxy]carbonyl}phenyl) oxalate;

FIG. 310 illustrates a bis(3,4,6-trichloro-2-{[(4-methylcyclooctyl)methoxy]carbonyl}phenyl) oxalate;

FIG. 311 illustrates a bis{3,4,6-trichloro-2-[(2-cycloheptylethoxy)carbonyl]phenyl}oxalate;

FIG. 312 illustrates a bis(3,4,6-trichloro-2-{[(1,2-dimethylcyclohexyl)methoxy]carbonyl}phenyl) oxalate;

FIG. 313 illustrates a bis(3,4,6-trichloro-2-{[(1,3-dimethylcyclohexyl)methoxy]carbonyl}phenyl) oxalate;

FIG. 314 illustrates a bis(3,4,6-trichloro-2-{[(1,4-dimethylcyclohexyl)methoxy]carbonyl}phenyl) oxalate;

FIG. 315 illustrates a bis(3,4,6-trichloro-2-{[(2,2-dimethylcyclohexyl)methoxy]carbonyl}phenyl) oxalate;

FIG. 316 illustrates a bis(3,4,6-trichloro-2-{[(2,3-dimethylcyclohexyl)methoxy]carbonyl}phenyl) oxalate;

FIG. 317 illustrates a bis(3,4,6-trichloro-2-{[(2,4-dimethylcyclohexyl)methoxy]carbonyl}phenyl) oxalate;

FIG. 318 illustrates a bis(3,4,6-trichloro-2-{[(2,5-dimethylcyclohexyl)methoxy]carbonyl}phenyl) oxalate;

FIG. 319 illustrates a bis(3,4,6-trichloro-2-{[(2,6-dimethylcyclohexyl)methoxy]carbonyl}phenyl) oxalate;

FIG. 320 illustrates a bis(3,4,6-trichloro-2-{[(3,3-dimethylcyclohexyl)methoxy]carbonyl}phenyl) oxalate;

FIG. 321 illustrates a bis(3,4,6-trichloro-2-{[(3,4-dimethylcyclohexyl)methoxy]carbonyl}phenyl) oxalate;

FIG. 322 illustrates a bis(3,4,6-trichloro-2-{[(3,5-dimethylcyclohexyl)methoxy]carbonyl}phenyl) oxalate;

FIG. 323 illustrates a bis(3,4,6-trichloro-2-{[(4,4-dimethylcyclohexyl)methoxy]carbonyl}phenyl) oxalate;

FIG. 324 illustrates a bis(3,4,6-trichloro-2-{[1-ethylcyclohexyl)methoxy]carbonyl}phenyl) oxalate;

FIG. 325 illustrates a bis(3,4,6-trichloro-2-{[2-ethylcyclohexyl)methoxy]carbonyl}phenyl) oxalate;

FIG. 326 illustrates a bis(3,4,6-trichloro-2-{[3-ethylcyclohexyl)methoxy]carbonyl}phenyl) oxalate;

FIG. 327 illustrates a bis(3,4,6-trichloro-2-{[4-ethylcyclohexyl)methoxy]carbonyl}phenyl) oxalate;

FIG. 328 illustrates a bis(3,4,6-trichloro-2-{[2-(1-methylcyclohexyl)ethoxy]carbonyl}phenyl) oxalate;

FIG. 329 illustrates a bis(3,4,6-trichloro-2-{[2-(2-methylcyclohexyl)ethoxy]carbonyl}phenyl) oxalate;

FIG. 330 illustrates a bis(3,4,6-trichloro-2-{[2-(3-methylcyclohexyl)ethoxy]carbonyl}phenyl) oxalate;

FIG. 331 illustrates a bis(3,4,6-trichloro-2-{[2-(4-methylcyclohexyl)ethoxy]carbonyl}phenyl) oxalate;

FIG. 332 illustrates a bis{3,4,6-trichloro-2-[(2-cyclohexylpropoxy)carbonyl]phenyl}oxalate;

FIG. 333 illustrates a bis{3,4,6-trichloro-2-[(3-cyclohexylpropoxy)carbonyl]phenyl}oxalate;

FIG. 334 illustrates a bis(3,4,6-trichloro-2-{[(1,2,2-trimethylcyclopentyl)methoxy]carbonyl}phenyl) oxalate;

FIG. 335 illustrates a bis(3,4,6-trichloro-2-{[(2,2,3-trimethylcyclopentyl)methoxy]carbonyl}phenyl) oxalate;

FIG. 336 illustrates a bis(3,4,6-trichloro-2-{[(2,2,4-trimethylcyclopentyl)methoxy]carbonyl}phenyl) oxalate;

FIG. 337 illustrates a bis(3,4,6-trichloro-2-{[(2,2,5-trimethylcyclopentyl)methoxy]carbonyl}phenyl) oxalate;

FIG. 338 illustrates a bis(3,4,6-trichloro-2-{[(1,3,3-trimethylcyclopentyl)methoxy]carbonyl}phenyl) oxalate;

FIG. 339 illustrates a bis(3,4,6-trichloro-2-{[(2,3,3-trimethylcyclopentyl)methoxy]carbonyl}phenyl) oxalate;

FIG. 340 illustrates a bis(3,4,6-trichloro-2-{[(3,3,4-trimethylcyclopentyl)methoxy]carbonyl}phenyl) oxalate;

FIG. 341 illustrates a bis(3,4,6-trichloro-2-{[(2,4,4-trimethylcyclopentyl)methoxy]carbonyl}phenyl) oxalate;

FIG. 342 illustrates a bis(3,4,6-trichloro-2-{[(1,2,3-trimethylcyclopentyl)methoxy]carbonyl}phenyl) oxalate;

FIG. 343 illustrates a bis(3,4,6-trichloro-2-{[(1,2,4-trimethylcyclopentyl)methoxy]carbonyl}phenyl) oxalate;

FIG. 344 illustrates a bis(3,4,6-trichloro-2-{[(1,2,5-trimethylcyclopentyl)methoxy]carbonyl}phenyl) oxalate;

FIG. 345 illustrates a bis(3,4,6-trichloro-2-{[(1,3,4-trimethylcyclopentyl)methoxy]carbonyl}phenyl) oxalate;

FIG. 346 illustrates a bis(3,4,6-trichloro-2-{[(2,3,4-trimethylcyclopentyl)methoxy]carbonyl}phenyl) oxalate;

FIG. 347 illustrates a bis(3,4,6-trichloro-2-{[(2,3,5-trimethylcyclopentyl)methoxy]carbonyl}phenyl) oxalate;

FIG. 348 illustrates a bis(3,4,6-trichloro-2-{[(2-ethyl-1-methylcyclopentyl)methoxy]carbonyl}phenyl) oxalate;

FIG. 349 illustrates a bis(3,4,6-trichloro-2-{[(3-ethyl-1-methylcyclopentyl)methoxy]carbonyl}phenyl) oxalate;

FIG. 350 illustrates a bis(3,4,6-trichloro-2-{[(1-ethyl-2-methylcyclopentyl)methoxy]carbonyl}phenyl) oxalate;

FIG. 351 illustrates a bis(3,4,6-trichloro-2-{[(1-ethyl-3-methylcyclopentyl)methoxy]carbonyl}phenyl) oxalate;

FIG. 352 illustrates a bis(3,4,6-trichloro-2-{[(3-ethyl-2-methylcyclopentyl)methoxy]carbonyl}phenyl) oxalate;

FIG. 353 illustrates a bis(3,4,6-trichloro-2-{[(4-ethyl-2-methylcyclopentyl)methoxy]carbonyl}phenyl) oxalate;

FIG. 354 illustrates a bis(3,4,6-trichloro-2-{[(2-ethyl-5-methylcyclopentyl)methoxy]carbonyl}phenyl) oxalate;

FIG. 355 illustrates a bis(3,4,6-trichloro-2-{[(2-ethyl-3-methylcyclopentyl)methoxy]carbonyl}phenyl) oxalate;

FIG. 356 illustrates a bis(3,4,6-trichloro-2-{[(2-ethyl-4-methylcyclopentyl)methoxy]carbonyl}phenyl) oxalate;

FIG. 357 illustrates a bis(3,4,6-trichloro-2-{[(3-ethyl-4-methylcyclopentyl)methoxy]carbonyl}phenyl) oxalate;

FIG. 358 illustrates a bis(3,4,6-trichloro-2-{[(2-ethyl-2-methylcyclopentyl)methoxy]carbonyl}phenyl) oxalate;

FIG. 359 illustrates a bis(3,4,6-trichloro-2-{[(3-ethyl-3-methylcyclopentyl)methoxy]carbonyl}phenyl) oxalate;

FIG. 360 illustrates a bis(3,4,6-trichloro-2-{[(1-propylcyclopentyl)methoxy]carbonyl}phenyl) oxalate;

FIG. 361 illustrates a bis(3,4,6-trichloro-2-{[(2-propylcyclopentyl)methoxy]carbonyl}phenyl) oxalate;

FIG. 362 illustrates a bis(3,4,6-trichloro-2-{[(3-propylcyclopentyl)methoxy]carbonyl}phenyl) oxalate;

FIG. 363 illustrates a bis[3,4,6-trichloro-2-({[1-(1-methylethyl)-cyclopentyl]methoxy}carbonyl)phenyl]oxalate;

FIG. 364 illustrates a bis[3,4,6-trichloro-2-({[2-(1-methylethyl)-cyclopentyl]methoxy}carbonyl)phenyl]oxalate;

FIG. 365 illustrates a bis[3,4,6-trichloro-2-({[3-(1-methylethyl)-cyclopentyl]methoxy}carbonyl)phenyl]oxalate;

FIG. 366 illustrates a bis(3,4,6-trichloro-2-{[2-(1,2-dimethylcyclopentyl)ethoxy]carbonyl}phenyl) oxalate;

FIG. 367 illustrates a bis(3,4,6-trichloro-2-{[2-(1,3-dimethylcyclopentyl)ethoxy]carbonyl}phenyl) oxalate;

FIG. 368 illustrates a bis(3,4,6-trichloro-2-{[2-(2,3-dimethylcyclopentyl)ethoxy]carbonyl}phenyl) oxalate;

FIG. 369 illustrates a bis(3,4,6-trichloro-2-{[2-(2,4-dimethylcyclopentyl)ethoxy]carbonyl}phenyl) oxalate;

FIG. 370 illustrates a bis(3,4,6-trichloro-2-{[2-(2,5-dimethylcyclopentyl)ethoxy]carbonyl}phenyl) oxalate;

FIG. 371 illustrates a bis(3,4,6-trichloro-2-{[2-(3,4-dimethylcyclopentyl)ethoxy]carbonyl}phenyl) oxalate;

FIG. 372 illustrates a bis(3,4,6-trichloro-2-{[2-(2,2-dimethylcyclopentyl)ethoxy]carbonyl}phenyl) oxalate;

FIG. 373 illustrates a bis(3,4,6-trichloro-2-{[2-(3,3-dimethylcyclopentyl)ethoxy]carbonyl}phenyl) oxalate;

FIG. 374 illustrates a bis(3,4,6-trichloro-2-{[2-(1-ethylcyclopentyl)ethoxy]carbonyl}phenyl) oxalate;

FIG. 375 illustrates a bis(3,4,6-trichloro-2-{[2-(2-ethylcyclopentyl)ethoxy]carbonyl}phenyl) oxalate;

FIG. 376 illustrates a bis(3,4,6-trichloro-2-{[2-(3-ethylcyclopentyl)ethoxy]carbonyl}phenyl) oxalate;

FIG. 377 illustrates a bis{3,4,6-trichloro-2-[(2-cyclopentyl-2-methylpropoxy)carbonyl]phenyl}oxalate;

FIG. 378 illustrates a bis(3,4,6-trichloro-2-{[2-(1-methylcyclopentyl)propoxy]carbonyl}phenyl) oxalate;

FIG. 379 illustrates a bis(3,4,6-trichloro-2-{[2-(2-methylcyclopentyl)propoxy]carbonyl}phenyl) oxalate;

FIG. 380 illustrates a bis(3,4,6-trichloro-2-{[2-(3-methylcyclopentyl)propoxy]carbonyl}phenyl) oxalate;

FIG. 381 illustrates a bis{3,4,6-trichloro-2-[(3-cyclopentyl-2-methylpropoxy)carbonyl]phenyl}oxalate;

FIG. 382 illustrates a bis(3,4,6-trichloro-2-{[3-(1-methylcyclopentyl)propoxy]carbonyl}phenyl) oxalate;

FIG. 383 illustrates a bis(3,4,6-trichloro-2-{[3-(2-methylcyclopentyl)propoxy]carbonyl}phenyl) oxalate;

FIG. 384 illustrates a bis(3,4,6-trichloro-2-{[3-(3-methylcyclopentyl)propoxy]carbonyl}phenyl) oxalate;

FIG. 385 illustrates a bis{3,4,6-trichloro-2-[(2-cyclopentylbutoxy)carbonyl]phenyl}oxalate;

FIG. 386 illustrates a bis{3,4,6-trichloro-2-[(3-cyclopentylbutoxy)carbonyl]phenyl}oxalate;

FIG. 387 illustrates a bis{3,4,6-trichloro-2-[(4-cyclopentylbutoxy)carbonyl]phenyl}oxalate;

FIG. 388 illustrates a bis(3,4,6-trichloro-2-{[(1,2,2,3-tetramethylcyclobutyl)methoxy]carbonyl}phenyl) oxalate;

FIG. 389 illustrates a bis(3,4,6-trichloro-2-{[(1,2,2,4-tetramethylcyclobutyl)methoxy]carbonyl}phenyl) oxalate;

FIG. 390 illustrates a bis(3,4,6-trichloro-2-{[(1,2,3,3-tetramethylcyclobutyl)methoxy]carbonyl}phenyl) oxalate;

FIG. 391 illustrates a bis(3,4,6-trichloro-2-{[(1,2,3,4-tetramethylcyclobutyl)methoxy]carbonyl}phenyl) oxalate;

FIG. 392 illustrates a bis(3,4,6-trichloro-2-{[(2,2,3,4-tetramethylcyclobutyl)methoxy]carbonyl}phenyl) oxalate;

FIG. 393 illustrates a bis(3,4,6-trichloro-2-{[(2,3,3,4-tetramethylcyclobutyl)methoxy]carbonyl}phenyl) oxalate;

FIG. 394 illustrates a bis(3,4,6-trichloro-2-{[(2,2,3,3-tetramethylcyclobutyl)methoxy]carbonyl}phenyl) oxalate;

FIG. 395 illustrates a bis(3,4,6-trichloro-2-{[(2,2,4,4-tetramethylcyclobutyl)methoxy]carbonyl}phenyl) oxalate;

FIG. 396 illustrates a bis(3,4,6-trichloro-2-{[(1-ethyl-2,2-dimethylcyclobutyl)methoxy]carbonyl}phenyl) oxalate;

FIG. 397 illustrates a bis(3,4,6-trichloro-2-{[(1-ethyl-2,3-dimethylcyclobutyl)methoxy]carbonyl}phenyl) oxalate;

FIG. 398 illustrates a bis(3,4,6-trichloro-2-{[(1-ethyl-2,4-dimethylcyclobutyl)methoxy]carbonyl}phenyl) oxalate;

FIG. 399 illustrates a bis(3,4,6-trichloro-2-{[(1-ethyl-3,3-dimethylcyclobutyl)methoxy]carbonyl}phenyl) oxalate;

FIG. 400 illustrates a bis(3,4,6-trichloro-2-{[(2-ethyl-1,2-dimethylcyclobutyl)methoxy]carbonyl}phenyl) oxalate;

FIG. 401 illustrates a bis(3,4,6-trichloro-2-{[(2-ethyl-1,3-dimethylcyclobutyl)methoxy]carbonyl}phenyl) oxalate;

FIG. 402 illustrates a bis(3,4,6-trichloro-2-{[(2-ethyl-1,4-dimethylcyclobutyl)methoxy]carbonyl}phenyl) oxalate;

FIG. 403 illustrates a bis(3,4,6-trichloro-2-{[(2-ethyl-3,3-dimethylcyclobutyl)methoxy]carbonyl}phenyl) oxalate;

FIG. 404 illustrates a bis(3,4,6-trichloro-2-{[(2-ethyl-3,4-dimethylcyclobutyl)methoxy]carbonyl}phenyl) oxalate;

FIG. 405 illustrates a bis(3,4,6-trichloro-2-{[(2-ethyl-4,4-dimethylcyclobutyl)methoxy]carbonyl}phenyl) oxalate;

FIG. 406 illustrates a bis(3,4,6-trichloro-2-{[(1,2-diethylcyclobutyl)methoxy]carbonyl}phenyl) oxalate;

FIG. 407 illustrates a bis(3,4,6-trichloro-2-{[(1,3-diethylcyclobutyl)methoxy]carbonyl}phenyl) oxalate;

FIG. 408 illustrates a bis(3,4,6-trichloro-2-{[(2,2-diethylcyclobutyl)methoxy]carbonyl}phenyl) oxalate;

FIG. 409 illustrates a bis(3,4,6-trichloro-2-{[(3,3-diethylcyclobutyl)methoxy]carbonyl}phenyl) oxalate;

FIG. 410 illustrates a bis(3,4,6-trichloro-2-{[(1-methyl-2-propylcyclobutyl)methoxy]carbonyl}phenyl) oxalate;

FIG. 411 illustrates a bis(3,4,6-trichloro-2-{[(2-methyl-2-propylcyclobutyl)methoxy]carbonyl}phenyl) oxalate;

FIG. 412 illustrates a bis(3,4,6-trichloro-2-{[(2-methyl-1-propylcyclobutyl)methoxy]carbonyl}phenyl) oxalate;

FIG. 413 illustrates a bis(3,4,6-trichloro-2-{[(3-methyl-1-propylcyclobutyl)methoxy]carbonyl}phenyl) oxalate;

FIG. 414 illustrates a bis(3,4,6-trichloro-2-{[(3-methyl-2-propylcyclobutyl)methoxy]carbonyl}phenyl) oxalate;

FIG. 415 illustrates a bis(3,4,6-trichloro-2-{[(2-methyl-4-propylcyclobutyl)methoxy]carbonyl}phenyl) oxalate;

FIG. 416 illustrates a bis(3,4,6-trichloro-2-{[(1-methyl-3-propylcyclobutyl)methoxy]carbonyl}phenyl) oxalate;

FIG. 417 illustrates a bis(3,4,6-trichloro-2-{[(2-methyl-3-propylcyclobutyl)methoxy]carbonyl}phenyl) oxalate;

FIG. 418 illustrates a bis(3,4,6-trichloro-2-{[(3-methyl-3-propylcyclobutyl)methoxy]carbonyl}phenyl) oxalate;

FIG. 419 illustrates a bis[3,4,6-trichloro-2-({[2-methyl-1-(1-methylethyl)cyclobutyl]methoxy}carbonyl)phenyl]oxalate;

FIG. 420 illustrates a bis[3,4,6-trichloro-2-({[3-methyl-1-(1-methylethyl)cyclobutyl]methoxy}carbonyl)phenyl]oxalate;

FIG. 421 illustrates a bis[3,4,6-trichloro-2-({[1-methyl-2-(1-methylethyl)cyclobutyl]methoxy}carbonyl)phenyl]oxalate;

FIG. 422 illustrates a bis[3,4,6-trichloro-2-({[2-methyl-2-(1-methylethyl)cyclobutyl]methoxy}carbonyl)phenyl]oxalate;

FIG. 423 illustrates a bis[3,4,6-trichloro-2-({[3-methyl-2-(1-methylethyl)cyclobutyl]methoxy}carbonyl)phenyl]oxalate;

FIG. 424 illustrates a bis[3,4,6-trichloro-2-({[2-methyl-4-(1-methylethyl)cyclobutyl]methoxy}carbonyl)phenyl]oxalate;

FIG. 425 illustrates a bis[3,4,6-trichloro-2-({[3-methyl-3-(1-methylethyl)cyclobutyl]methoxy}carbonyl)phenyl]oxalate;

FIG. 426 illustrates a bis(3,4,6-trichloro-2-{[(1-butylcyclobutyl)methoxy]carbonyl}phenyl) oxalate;

FIG. 427 illustrates a bis(3,4,6-trichloro-2-{[(2-butylcyclobutyl)methoxy]carbonyl}phenyl) oxalate;

FIG. 428 illustrates a bis(3,4,6-trichloro-2-{[(3-butylcyclobutyl)methoxy]carbonyl}phenyl) oxalate;

FIG. 429 illustrates a bis[3,4,6-trichloro-2-({[1-(1-methylpropyl)cyclobutyl]methoxy}carbonyl)phenyl]oxalate;

FIG. 430 illustrates a bis[3,4,6-trichloro-2-({[1-(2-methylpropyl)cyclobutyl]methoxy}carbonyl)phenyl]oxalate;

FIG. 431 illustrates a bis[3,4,6-trichloro-2-({[2-(1-methylpropyl)cyclobutyl]methoxy}carbonyl)phenyl]oxalate;

FIG. 432 illustrates a bis[3,4,6-trichloro-2-({[2-(2-methylpropyl)cyclobutyl]methoxy}carbonyl)phenyl]oxalate;

FIG. 433 illustrates a bis[3,4,6-trichloro-2-({[3-(1-methylpropyl)cyclobutyl]methoxy}carbonyl)phenyl]oxalate;

FIG. 434 illustrates a bis[3,4,6-trichloro-2-({[3-(2-methylpropyl)cyclobutyl]methoxy}carbonyl)phenyl]oxalate;

FIG. 435 illustrates a bis(3,4,6-trichloro-2-{[2-(1,2,2-trimethylcyclobutyl)ethoxy]carbonyl}phenyl) oxalate;

FIG. 436 illustrates a bis(3,4,6-trichloro-2-{[2-(1,2,3-trimethylcyclobutyl)ethoxy]carbonyl}phenyl) oxalate;

FIG. 437 illustrates a bis(3,4,6-trichloro-2-{[2-(1,2,4-trimethylcyclobutyl)ethoxy]carbonyl}phenyl) oxalate;

FIG. 438 illustrates a bis(3,4,6-trichloro-2-{[2-(1,3,3-trimethylcyclobutyl)ethoxy]carbonyl}phenyl) oxalate;

FIG. 439 illustrates a bis(3,4,6-trichloro-2-{[2-(2,2,3-trimethylcyclobutyl)ethoxy]carbonyl}phenyl) oxalate;

FIG. 440 illustrates a bis(3,4,6-trichloro-2-{[2-(2,2,4-trimethylcyclobutyl)ethoxy]carbonyl}phenyl) oxalate;

FIG. 441 illustrates a bis(3,4,6-trichloro-2-{[2-(2,3,4-trimethylcyclobutyl)ethoxy]carbonyl}phenyl) oxalate;

FIG. 442 illustrates a bis(3,4,6-trichloro-2-{[2-(2-ethyl-1-methylcyclobutyl)ethoxy]carbonyl}phenyl) oxalate;

FIG. 443 illustrates a bis(3,4,6-trichloro-2-{[2-(3-ethyl-1-methylcyclobutyl)ethoxy]carbonyl}phenyl) oxalate;

FIG. 444 illustrates a bis(3,4,6-trichloro-2-{[2-(1-ethyl-2-methylcyclobutyl)ethoxy]carbonyl}phenyl) oxalate;

FIG. 445 illustrates a bis(3,4,6-trichloro-2-{[2-(1-ethyl-3-methylcyclobutyl)ethoxy]carbonyl}phenyl) oxalate;

FIG. 446 illustrates a bis(3,4,6-trichloro-2-{[2-(2-ethyl-2-methylcyclobutyl)ethoxy]carbonyl}phenyl) oxalate;

FIG. 447 illustrates a bis(3,4,6-trichloro-2-{[2-(2-ethyl-3-methylcyclobutyl)ethoxy]carbonyl}phenyl) oxalate;

FIG. 448 illustrates a bis(3,4,6-trichloro-2-{[2-(2-ethyl-4-methylcyclobutyl)ethoxy]carbonyl}phenyl) oxalate;

FIG. 449 illustrates a bis(3,4,6-trichloro-2-{[2-(3-ethyl-2-methylcyclobutyl)ethoxy]carbonyl}phenyl) oxalate;

FIG. 450 illustrates a bis(3,4,6-trichloro-2-{[2-(3-ethyl-3-methylcyclobutyl)ethoxy]carbonyl}phenyl) oxalate;

FIG. 451 illustrates a bis(3,4,6-trichloro-2-{[2-(1-propyl-cyclobutyl)ethoxy]carbonyl}phenyl) oxalate;

FIG. 452 illustrates a bis(3,4,6-trichloro-2-{[2-(2-propyl-cyclobutyl)ethoxy]carbonyl}phenyl) oxalate;

FIG. 453 illustrates a bis(3,4,6-trichloro-2-{[2-(3-propyl-cyclobutyl)ethoxy]carbonyl}phenyl) oxalate;

FIG. 454 illustrates a bis[3,4,6-trichloro-2-({2-[1-(1-methylethyl)cyclobutyl]ethoxy}carbonyl)phenyl]oxalate;

FIG. 455 illustrates a bis[3,4,6-trichloro-2-({2-[2-(1-methylethyl)cyclobutyl]ethoxy}carbonyl)phenyl]oxalate;

FIG. 456 illustrates a bis[3,4,6-trichloro-2-({2-[3-(1-methylethyl)cyclobutyl]ethoxy}carbonyl)phenyl]oxalate;

FIG. 457 illustrates a bis(3,4,6-trichloro-2-{[2-methyl-2-(1-methylcyclobutylpropoxy]carbonyl}phenyl) oxalate;

FIG. 458 illustrates a bis(3,4,6-trichloro-2-{[2-methyl-2-(2-methylcyclobutylpropoxy]carbonyl}phenyl) oxalate;

FIG. 459 illustrates a bis(3,4,6-trichloro-2-{[2-methyl-2-(3-methylcyclobutylpropoxy]carbonyl}phenyl) oxalate;

FIG. 460 illustrates a bis(3,4,6-trichloro-2-{[2-(1,2-dimethylcyclobutylpropoxy]carbonyl}phenyl) oxalate;

FIG. 461 illustrates a bis(3,4,6-trichloro-2-{[2-(1,3-dimethylcyclobutylpropoxy]carbonyl}phenyl) oxalate;

FIG. 462 illustrates a bis(3,4,6-trichloro-2-{[2-(1,2,2-trimethylcyclobutylethoxy]carbonyl}phenyl) oxalate;

FIG. 463 illustrates a bis(3,4,6-trichloro-2-{[2-(1,2,3-trimethylcyclobutylethoxy]carbonyl}phenyl) oxalate;

FIG. 464 illustrates a bis(3,4,6-trichloro-2-{[2-(1,2,4-trimethylcyclobutylethoxy]carbonyl}phenyl) oxalate;

FIG. 465 illustrates a bis(3,4,6-trichloro-2-{[2-(1,3,3-trimethylcyclobutylethoxy]carbonyl}phenyl) oxalate;

FIG. 466 illustrates a bis(3,4,6-trichloro-2-{[2-(2,2,3-trimethylcyclobutylethoxy]carbonyl}phenyl) oxalate;

FIG. 467 illustrates a bis(3,4,6-trichloro-2-{[2-(2,3,3-trimethylcyclobutylethoxy]carbonyl}phenyl) oxalate;

FIG. 468 illustrates a bis(3,4,6-trichloro-2-{[2-(2,2,4-trimethylcyclobutylethoxy]carbonyl}phenyl) oxalate;

FIG. 469 illustrates a bis(3,4,6-trichloro-2-{[2-(2,3,4-trimethylcyclobutylethoxy]carbonyl}phenyl) oxalate;

FIG. 470 illustrates a bis(3,4,6-trichloro-2-{[3-(1,2-dimethylcyclobutylpropoxy]carbonyl}phenyl) oxalate;

FIG. 471 illustrates a bis(3,4,6-trichloro-2-{[3-(1,3-dimethylcyclobutylpropoxy]carbonyl}phenyl) oxalate;

FIG. 472 illustrates a bis(3,4,6-trichloro-2-{[3-(2,2-dimethylcyclobutylpropoxy]carbonyl}phenyl) oxalate;

FIG. 473 illustrates a bis(3,4,6-trichloro-2-{[3-(2,3-dimethylcyclobutylpropoxy]carbonyl}phenyl) oxalate;

FIG. 474 illustrates a bis(3,4,6-trichloro-2-{[3-(2,4-dimethylcyclobutylpropoxy]carbonyl}phenyl) oxalate;

FIG. 475 illustrates a bis(3,4,6-trichloro-2-{[3-(3,3-dimethylcyclobutylpropoxy]carbonyl}phenyl) oxalate;

FIG. 476 illustrates a bis(3,4,6-trichloro-2-{[3-(1-ethylcyclobutylpropoxy]carbonyl}phenyl) oxalate;

FIG. 477 illustrates a bis(3,4,6-trichloro-2-{[3-(2-ethylcyclobutylpropoxy]carbonyl}phenyl) oxalate;

FIG. 478 illustrates a bis(3,4,6-trichloro-2-{[3-(3-ethylcyclobutylpropoxy]carbonyl}phenyl) oxalate;

FIG. 479 illustrates a bis(3,4,6-trichloro-2-{[2-(1-methylcyclobutylbutoxy]carbonyl}phenyl) oxalate;

FIG. 480 illustrates a bis(3,4,6-trichloro-2-{[2-(2-methylcyclobutylbutoxy]carbonyl}phenyl) oxalate;

FIG. 481 illustrates a bis(3,4,6-trichloro-2-{[2-(3-methylcyclobutylbutoxy]carbonyl}phenyl) oxalate;

FIG. 482 illustrates a bis{3,4,6-trichloro-2-[(3-cyclobutyl-2-methylbutoxy)carbonyl]phenyl}oxalate;

FIG. 483 illustrates a bis{3,4,6-trichloro-2-[(3-cyclobutyl-3-methylbutoxy)carbonyl]phenyl}oxalate;

FIG. 484 illustrates a bis(3,4,6-trichloro-2-{[3-(1-methylcyclobutylbutoxy]carbonyl}phenyl) oxalate;

FIG. 485 illustrates a bis(3,4,6-trichloro-2-{[3-(2-methylcyclobutylbutoxy]carbonyl}phenyl) oxalate;

FIG. 486 illustrates a bis(3,4,6-trichloro-2-{[3-(2-methylcyclobutylbutoxy]carbonyl}phenyl) oxalate;

FIG. 487 illustrates a bis{3,4,6-trichloro-2-[(4-cyclobutyl-2-methylbutoxy)carbonyl]phenyl}oxalate;

FIG. 488 illustrates a bis{3,4,6-trichloro-2-[(4-cyclobutyl-3-methylbutoxy)carbonyl]phenyl}oxalate;

FIG. 489 illustrates a bis(3,4,6-trichloro-2-{[4-(1-methylcyclobutylbutoxy]carbonyl}phenyl) oxalate;

FIG. 490 illustrates a bis(3,4,6-trichloro-2-{[4-(2-methylcyclobutylbutoxy]carbonyl}phenyl) oxalate;

FIG. 491 illustrates a bis(3,4,6-trichloro-2-{[4-(3-methylcyclobutylbutoxy]carbonyl}phenyl) oxalate;

FIG. 492 illustrates a bis{3,4,6-trichloro-2-[(2-cyclobutylpentyloxy)carbonyl]phenyl}oxalate;

FIG. 493 illustrates a bis{3,4,6-trichloro-2-[(3-cyclobutylpentyloxy)carbonyl]phenyl}oxalate;

FIG. 494 illustrates a bis{3,4,6-trichloro-2-[(4-cyclobutylpentyloxy)carbonyl]phenyl}oxalate;

FIG. 495 illustrates a bis{3,4,6-trichloro-2-[(5-cyclobutylpentyloxy)carbonyl]phenyl}oxalate;

FIG. 496 illustrates a bis(3,4,6-trichloro-2-{[(1,2,2,3,3-pentamethylcyclopropyl)methoxy]carbonyl}phenyl) oxalate;

FIG. 497 illustrates a bis(3,4,6-trichloro-2-{[(3-ethyl-1,2,2-trimethylcyclopropyl)methoxy]carbonyl}phenyl) oxalate;

FIG. 498 illustrates a bis(3,4,6-trichloro-2-{[(2-ethyl-1,2,3-trimethylcyclopropyl)methoxy]carbonyl}phenyl) oxalate;

FIG. 499 illustrates a bis(3,4,6-trichloro-2-{[(1-ethyl-2,2,3-trimethylcyclopropyl)methoxy]carbonyl}phenyl) oxalate;

FIG. 500 illustrates a bis(3,4,6-trichloro-2-{[(2,2-dimethyl-3-propylcyclopropyl)methoxy]carbonyl}phenyl) oxalate;

FIG. 501 illustrates a bis[3,4,6-trichloro-2-({[2,2-dimethyl-3-(1-methylethyl)cyclopropyl]methoxy}carbonyl)phenyl]oxalate;

FIG. 502 illustrates a bis(3,4,6-trichloro-2-{[(2,3-dimethyl-1-propylcyclopropyl)methoxy]carbonyl}phenyl) oxalate;

FIG. 503 illustrates a bis[3,4,6-trichloro-2-({[2,3-dimethyl-1-(1-methylethyl)cyclopropyl]methoxy}carbonyl)phenyl]oxalate;

FIG. 504 illustrates a bis(3,4,6-trichloro-2-{[(2-ethyl-1-propylcyclopropyl)methoxy]carbonyl}phenyl) oxalate;

FIG. 505 illustrates a bis(3,4,6-trichloro-2-{[(1-ethyl-2-propylcyclopropyl)methoxy]carbonyl}phenyl) oxalate;

FIG. 506 illustrates a bis[3,4,6-trichloro-2-({[1-ethyl-2-(1-methylethyl)cyclopropyl]methoxy}carbonyl)phenyl]oxalate;

FIG. 507 illustrates a bis(3,4,6-trichloro-2-{[(1,2-diethyl-3-methylcyclopropyl)methoxy]carbonyl}phenyl) oxalate;

FIG. 508 illustrates a bis(3,4,6-trichloro-2-{[(1-butyl-2-methylcyclopropyl)methoxy]carbonyl}phenyl) oxalate;

FIG. 509 illustrates a bis[3,4,6-trichloro-2-({[2-methyl-1-(2-methylpropyl)cyclopropyl]methoxy}carbonyl)phenyl]oxalate;

FIG. 510 illustrates a bis[3,4,6-trichloro-2-({[2-methyl-1-(1-methylpropyl)cyclopropyl]methoxy}carbonyl)phenyl] oxalate;

FIG. 511 illustrates a bis(3,4,6-trichloro-2-{[(2-butyl-1-methylcyclopropyl)methoxy]carbonyl}phenyl) oxalate;

FIG. 512 illustrates a bis[3,4,6-trichloro-2-({[1-methyl-2-(1-methylpropyl)cyclopropyl]methoxy}carbonyl)phenyl] oxalate;

FIG. 513 illustrates a bis[3,4,6-trichloro-2-({[1-methyl-2-(2-methylpropyl)cyclopropyl]methoxy}carbonyl)phenyl] oxalate;

FIG. 514 illustrates a bis(3,4,6-trichloro-2-{[(2-butyl-3-methylcyclopropyl)methoxy]carbonyl}phenyl) oxalate;

FIG. 515 illustrates a bis[3,4,6-trichloro-2-({[2-methyl-3-(1-methylpropyl)cyclopropyl]methoxy}carbonyl)phenyl] oxalate;

FIG. 516 illustrates a bis[3,4,6-trichloro-2-({[2-methyl-3-(2-methylpropyl)cyclopropyl]methoxy}carbonyl)phenyl] oxalate;

FIG. 517 illustrates a bis[3,4,6-trichloro-2-({[1-(1,1-dimethylpropyl)cyclopropyl]methoxy}carbonyl)phenyl]oxalate;

FIG. 518 illustrates a bis[3,4,6-trichloro-2-({[1-(2,2-dimethylpropyl)cyclopropyl]methoxy}carbonyl)phenyl]oxalate;

FIG. 519 illustrates a bis[3,4,6-trichloro-2-({[1-(1,2-dimethylpropyl)cyclopropyl]methoxy}carbonyl)phenyl]oxalate;

FIG. 520 illustrates a bis[3,4,6-trichloro-2-({[1-(1-methylbutyl)cyclopropyl]methoxy}carbonyl)phenyl]oxalate;

FIG. 521 illustrates a bis[3,4,6-trichloro-2-({[1-(2-methylbutyl)cyclopropyl]methoxy}carbonyl)phenyl]oxalate;

FIG. 522 illustrates a bis[3,4,6-trichloro-2-({[1-(3-methylbutyl)cyclopropyl]methoxy}carbonyl)phenyl]oxalate;

FIG. 523 illustrates a bis(3,4,6-trichloro-2-{[(1-pentylcyclopropyl)methoxy]carbonyl}phenyl) oxalate;

FIG. 524 illustrates a bis[3,4,6-trichloro-2-({[2-(1,1-dimethylpropyl)cyclopropyl]methoxy}carbonyl)phenyl]oxalate;

FIG. 525 illustrates a bis[3,4,6-trichloro-2-({[2-(2,2-dimethylpropyl)cyclopropyl]methoxy}carbonyl)phenyl]oxalate;

FIG. 526 illustrates a bis[3,4,6-trichloro-2-({[2-(1,2-dimethylpropyl)cyclopropyl]methoxy}carbonyl)phenyl]oxalate;

FIG. 527 illustrates a bis[3,4,6-trichloro-2-({[2-(1-methylbutyl)cyclopropyl]methoxy}carbonyl)phenyl]oxalate;

FIG. 528 illustrates a bis[3,4,6-trichloro-2-({[2-(2-methylbutyl)cyclopropyl]methoxy}carbonyl)phenyl]oxalate;

FIG. 529 illustrates a bis[3,4,6-trichloro-2-({[2-(3-methylbutyl)cyclopropyl]methoxy}carbonyl)phenyl]oxalate;

FIG. 530 illustrates a bis(3,4,6-trichloro-2-{[(2-pentylcyclopropyl)methoxy]carbonyl}phenyl) oxalate;

FIG. 531 illustrates a bis(3,4,6-trichloro-2-{[2-(1,2,2,3-tetramethylcyclopropyl)ethoxy]carbonyl}phenyl) oxalate;

FIG. 532 illustrates a bis(3,4,6-trichloro-2-{[2-(2,2,3,3-tetramethylcyclopropyl)ethoxy]carbonyl}phenyl) oxalate;

FIG. 533 illustrates a bis(3,4,6-trichloro-2-{[2-(1-ethyl-2,3-dimethylcyclopropyl)ethoxy]carbonyl}phenyl) oxalate;

FIG. 534 illustrates a bis(3,4,6-trichloro-2-{[2-(1-ethyl-2,2-dimethylcyclopropyl)ethoxy]carbonyl}phenyl) oxalate;

FIG. 535 illustrates a bis(3,4,6-trichloro-2-{[2-(2-ethyl-1,3-dimethylcyclopropyl)ethoxy]carbonyl}phenyl) oxalate;

FIG. 536 illustrates a bis(3,4,6-trichloro-2-{[2-(3-ethyl-2,2-dimethylcyclopropyl)ethoxy]carbonyl}phenyl) oxalate;

FIG. 537 illustrates a bis(3,4,6-trichloro-2-{[2-(1,2-diethylcyclopropyl)ethoxy]carbonyl}phenyl) oxalate;

FIG. 538 illustrates a bis(3,4,6-trichloro-2-{[2-(2,2-diethylcyclopropyl)ethoxy]carbonyl}phenyl) oxalate;

FIG. 539 illustrates a bis(3,4,6-trichloro-2-{[2-(2,3-diethylcyclopropyl)ethoxy]carbonyl}phenyl) oxalate;

FIG. 540 illustrates a bis(3,4,6-trichloro-2-{[2-(1-methyl-3-propylcyclopropyl)ethoxy]carbonyl}phenyl) oxalate;

FIG. 541 illustrates a bis(3,4,6-trichloro-2-{[2-(3-methyl-1-propylcyclopropyl)ethoxy]carbonyl}phenyl) oxalate;

FIG. 542 illustrates a bis(3,4,6-trichloro-2-{[2-(2-methyl-3-propylcyclopropyl)ethoxy]carbonyl}phenyl) oxalate;

FIG. 543 illustrates a bis(3,4,6-trichloro-2-{[2-(2-methyl-2-propylcyclopropyl)ethoxy]carbonyl}phenyl) oxalate;

FIG. 544 illustrates a bis[3,4,6-trichloro-2-({2-[1-methyl-2-(1-methylethyl)cyclopropyl]ethoxy}carbonyl)phenyl]oxalate;

FIG. 545 illustrates a bis[3,4,6-trichloro-2-({2-[2-methyl-1-(1-methylethyl)cyclopropyl]ethoxy}carbonyl)phenyl]oxalate;

FIG. 546 illustrates a bis[3,4,6-trichloro-2-({2-[2-methyl-3-(1-methylethyl)cyclopropyl]ethoxy}carbonyl)phenyl]oxalate;

FIG. 547 illustrates a bis[3,4,6-trichloro-2-({2-[2-methyl-1-(1-methylethyl)cyclopropyl]ethoxy}carbonyl)phenyl]oxalate;

FIG. 548 illustrates a bis(3,4,6-trichloro-2-{[2-(1-butylcyclopropyl)ethoxy]carbonyl}phenyl) oxalate;

FIG. 549 illustrates a bis[3,4,6-trichloro-2-({2-[1-(1-methylpropyl)cyclopropyl]ethoxy}carbonyl)phenyl]oxalate;

FIG. 550 illustrates a bis[3,4,6-trichloro-2-({2-[1-(2-methylpropyl)cyclopropyl]ethoxy}carbonyl)phenyl]oxalate;

FIG. 551 illustrates a bis(3,4,6-trichloro-2-{[2-(2-butylcyclopropyl)ethoxy]carbonyl}phenyl) oxalate;

FIG. 552 illustrates a bis[3,4,6-trichloro-2-({2-[2-(1-methylpropyl)cyclopropyl]ethoxy}carbonyl)phenyl]oxalate;

FIG. 553 illustrates a bis[3,4,6-trichloro-2-({2-[2-(2-methylpropyl)cyclopropyl]ethoxy}carbonyl)phenyl]oxalate;

FIG. 554 illustrates a bis(3,4,6-trichloro-2-{[2-(1,2,2-trimethylcyclopropyl)propoxy]carbonyl}phenyl) oxalate;

FIG. 555 illustrates a bis(3,4,6-trichloro-2-{[2-(1,2,3-trimethylcyclopropyl)propoxy]carbonyl}phenyl) oxalate;

FIG. 556 illustrates a bis(3,4,6-trichloro-2-{[2-(2,2,3-trimethylcyclopropyl)propoxy]carbonyl}phenyl) oxalate;

FIG. 557 illustrates a bis(3,4,6-trichloro-2-{[2-methyl-2-(2,3-dimethylcyclopropyl)propoxy]carbonyl}phenyl) oxalate;

FIG. 558 illustrates a bis(3,4,6-trichloro-2-{[2-(1-ethyl-2-methylcyclopropyl)propoxy]carbonyl}phenyl) oxalate;

FIG. 559 illustrates a bis(3,4,6-trichloro-2-{[2-(2-ethyl-1-methylcyclopropyl)propoxy]carbonyl}phenyl) oxalate;

FIG. 560 illustrates a bis(3,4,6-trichloro-2-{[2-(2-ethyl-3-methylcyclopropyl)propoxy]carbonyl}phenyl) oxalate;

FIG. 561 illustrates a bis(3,4,6-trichloro-2-[2-{(2-ethyl-2-methylcyclopropyl)propoxy]carbonyl}phenyl) oxalate;

FIG. 562 illustrates a bis(3,4,6-trichloro-2-{[2-(1-propylcyclopropyl)propoxy]carbonyl}phenyl) oxalate;

FIG. 563 illustrates a bis(3,4,6-trichloro-2-{[2-(2-propylcyclopropyl)propoxy]carbonyl}phenyl) oxalate;

FIG. 564 illustrates a bis[3,4,6-trichloro-2-({2-[1-(1-methylethyl)cyclopropyl]propoxy}carbonyl)phenyl]oxalate;

FIG. 565 illustrates a bis[3,4,6-trichloro-2-({2-[1-(1-methylethyl)cyclopropyl]propoxy}carbonyl)phenyl]oxalate;

FIG. 566 illustrates a bis(3,4,6-trichloro-2-{[2-methyl-2-(1,2-dimethylcyclopropyl)propoxy]carbonyl}phenyl) oxalate;

FIG. 567 illustrates a bis(3,4,6-trichloro-2-{[2-methyl-2-(2,2-dimethylcyclopropyl)propoxy]carbonyl}phenyl) oxalate;

FIG. 568 illustrates a bis(3,4,6-trichloro-2-{[-2-(1-ethyl-cyclopropyl)-2-methylpropoxy]carbonyl}phenyl) oxalate;

FIG. 569 illustrates a bis(3,4,6-trichloro-2-{[-2-(2-ethyl-cyclopropyl)-2-methylpropoxy]carbonyl}phenyl) oxalate;

FIG. 570 illustrates a bis(3,4,6-trichloro-2-{[2,2-dimethyl-3-(1-methylcyclopropyl)propoxy]carbonyl}phenyl) oxalate;

FIG. 571 illustrates a bis(3,4,6-trichloro-2-{[2,2-dimethyl-3-(2-methylcyclopropyl)propoxy]carbonyl}phenyl) oxalate;

FIG. 572 illustrates a bis(3,4,6-trichloro-2-{[2,3-dimethyl-3-(1-methylcyclopropyl)propoxy]carbonyl}phenyl) oxalate;

FIG. 573 illustrates a bis(3,4,6-trichloro-2-{[2,3-dimethyl-3-(2-methylcyclopropyl)propoxy]carbonyl}phenyl) oxalate;

FIG. 574 illustrates a bis(3,4,6-trichloro-2-{[2-methyl-3-(1,2-dimethylcyclopropyl)propoxy]carbonyl}phenyl) oxalate;

FIG. 575 illustrates a bis(3,4,6-trichloro-2-{[2-methyl-3-(2,3-dimethylcyclopropyl)propoxy]carbonyl}phenyl) oxalate;

FIG. 576 illustrates a bis(3,4,6-trichloro-2-{[2-methyl-3-(1-ethylcyclopropyl)propoxy]carbonyl}phenyl) oxalate;

FIG. 577 illustrates a bis(3,4,6-trichloro-2-{[2-methyl-3-(2-ethylcyclopropyl)propoxy]carbonyl}phenyl) oxalate;

FIG. 578 illustrates a bis(3,4,6-trichloro-2-{[3-(1,2,2-trimethylcyclopropyl)propoxy]carbonyl}phenyl) oxalate;

FIG. 579 illustrates a bis(3,4,6-trichloro-2-{[3-(1,2,3-trimethylcyclopropyl)propoxy]carbonyl}phenyl) oxalate;

FIG. 580 illustrates a bis(3,4,6-trichloro-2-{[3-(2-ethyl-1-methylcyclopropyl)propoxy]carbonyl}phenyl) oxalate;

FIG. 581 illustrates a bis(3,4,6-trichloro-2-{[3-(1-ethyl-2-methylcyclopropyl)propoxy]carbonyl}phenyl) oxalate;

FIG. 582 illustrates a bis(3,4,6-trichloro-2-{[3-(2-ethyl-3-methylcyclopropyl)propoxy]carbonyl}phenyl) oxalate;

FIG. 583 illustrates a bis(3,4,6-trichloro-2-{[3-(2-ethyl-2-methylcyclopropyl)propoxy]carbonyl}phenyl) oxalate;

FIG. 584 illustrates a bis(3,4,6-trichloro-2-{[3-(1-propyl-cyclopropyl)propoxy]carbonyl}phenyl) oxalate;

FIG. 585 illustrates a bis(3,4,6-trichloro-2-{[3-(1-propyl-cyclopropyl)propoxy]carbonyl}phenyl) oxalate;

FIG. 586 illustrates a bis(3,4,6-trichloro-2-{[3-(2-propyl-cyclopropyl)propoxy]carbonyl}phenyl) oxalate;

FIG. 587 illustrates a bis[3,4,6-trichloro-2-({3-[2-(1-methylethyl)cyclopropyl]propoxy}carbonyl)phenyl]oxalate;

FIG. 588 illustrates a bis{3,4,6-trichloro-2-[(2-cyclopropyl-3,3-dimethylbutoxy)carbonyl]phenyl}oxalate;

FIG. 589 illustrates a bis(3,4,6-trichloro-2-{[3-(1-ethylcyclopropyl)butoxy]carbonyl}phenyl) oxalate;

FIG. 590 illustrates a bis(3,4,6-trichloro-2-{[2-methyl-4-(1-methylcyclopropyl)butoxy]carbonyl}phenyl) oxalate;

FIG. 591 illustrates a bis(3,4,6-trichloro-2-{[3-methyl-4-(1-methylcyclopropyl)butoxy]carbonyl}phenyl) oxalate;

FIG. 592 illustrates a bis{3,4,6-trichloro-2-[(4-cyclopropyl-2-ethylbutoxy)carbonyl]phenyl}oxalate;

FIG. 593 illustrates a bis{3,4,6-trichloro-2-[(4-cyclopropyl-3,3-dimethylbutoxy)carbonyl]phenyl}oxalate;

FIG. 594 illustrates a bis{3,4,6-trichloro-2-[(4-cyclopropyl-3-methylpentyloxy)carbonyl]phenyl}oxalate;

FIG. 595 illustrates a bis(3,4,6-trichloro-2-{[4-(1,2-dimethylcyclopropyl)-3-methylbutoxy]carbonyl}phenyl) oxalate;

FIG. 596 illustrates a bis(3,4,6-trichloro-2-{[4-(1-ethylcyclopropyl)butoxy]carbonyl}phenyl) oxalate;

FIG. 597 illustrates a bis{3,4,6-trichloro-2-[(4-cyclopropyl-4-methylpentyloxy)carbonyl]phenyl}oxalate;

FIG. 598 illustrates a bis(3,4,6-trichloro-2-{[4-(1-methylcyclopropyl)pentyloxy]carbonyl}phenyl) oxalate;

FIG. 599 illustrates a bis(3,4,6-trichloro-2-{[4-(2-methylcyclopropyl)pentyloxy]carbonyl}phenyl) oxalate;

FIG. 600 illustrates a bis{3,4,6-trichloro-2-[(3-cyclopropyl-4-methylpentyloxy)carbonyl]phenyl}oxalate;

FIG. 601 illustrates a bis{3,4,6-trichloro-2-[(2-cyclopropyl-2-methylpentyloxy)carbonyl]phenyl}oxalate;

FIG. 602 illustrates a bis{3,4,6-trichloro-2-[(2-cyclopropyl-3-methylpentyloxy)carbonyl]phenyl}oxalate;

FIG. 603 illustrates a bis{3,4,6-trichloro-2-[(2-cyclopropyl-4-methylpentyloxy)carbonyl]phenyl}oxalate;

FIG. 604 illustrates a bis{3,4,6-trichloro-2-[(3-cyclopropyl-2-methylpentyloxy)carbonyl]phenyl}oxalate;

FIG. 605 illustrates a bis{3,4,6-trichloro-2-[(5-cyclopropyl-2-methylpentyloxy)carbonyl]phenyl}oxalate;

FIG. 606 illustrates a bis{3,4,6-trichloro-2-[(5-cyclopropyl-3-methylpentyloxy)carbonyl]phenyl}oxalate;

FIG. 607 illustrates a bis{3,4,6-trichloro-2-[(5-cyclopropyl-4-methylpentyloxy)carbonyl]phenyl}oxalate;

FIG. 608 illustrates a bis(3,4,6-trichloro-2-{[3-(cyclopropylmethyl)pentyloxy]carbonyl}phenyl) oxalate;

FIG. 609 illustrates a bis(3,4,6-trichloro-2-{[5-(1-methylcyclopropyl)pentyloxy]carbonyl}phenyl) oxalate;

FIG. 610 illustrates a bis{3,4,6-trichloro-2-[(2-cyclopropylhexyloxy)carbonyl]phenyl}oxalate;

FIG. 611 illustrates a bis{3,4,6-trichloro-2-[(3-cyclopropylhexyloxy)carbonyl]phenyl}oxalate;

FIG. 612 illustrates a bis{3,4,6-trichloro-2-[(4-cyclopropylhexyloxy)carbonyl]phenyl}oxalate;

FIG. 613 illustrates a bis{3,4,6-trichloro-2-[(5-cyclopropylhexyloxy)carbonyl]phenyl}oxalate;

FIG. 614 illustrates a bis{3,4,6-trichloro-2-[(6-cyclopropylhexyloxy)carbonyl]phenyl}oxalate;

FIG. 615 illustrates a bis{3,4,6-trichloro-2-[(2,2-dicyclopropylpropoxy)carbonyl]phenyl}oxalate;

FIG. 616 illustrates a bis{3,4,6-trichloro-2-[(3,3-dicyclopropylpropoxy)carbonyl]phenyl}oxalate;

FIG. 617 illustrates a bis{3,4,6-trichloro-2-[(2-cyclobutyl-2-cyclopropylethoxy)carbonyl]phenyl}oxalate;

FIG. 618 illustrates a bis{2-[(bicyclo[2.2.2]octan-2-ylmethoxy)carbonyl]-3,4,6-trichlorophenyl}oxalate;

FIG. 619 illustrates a bis{2-[(bicyclo[3.3.0]octan-3-ylmethoxy)carbonyl]-3,4,6-trichlorophenyl}oxalate;

FIG. 620 illustrates a bis(3,4,6-trichloro-2-{[(2,3-dimethylphenyl)methoxy]carbonyl}phenyl) oxalate;

FIG. 621 illustrates a bis(3,4,6-trichloro-2-{[(2,4-dimethylphenyl)methoxy]carbonyl}phenyl) oxalate;

FIG. 622 illustrates a bis(3,4,6-trichloro-2-{[3,4-dimethylphenyl)methoxy]carbonyl}phenyl) oxalate;

FIG. 623 illustrates a bis(3,4,6-trichloro-2-{[(3,5-dimethylphenyl)methoxy]carbonyl}phenyl) oxalate;

FIG. 624 illustrates a bis(3,4,6-trichloro-2-{[(2,6-dimethylphenyl)methoxy]carbonyl}phenyl) oxalate;

FIG. 625 illustrates a bis(3,4,6-trichloro-2-{[(2-ethylphenyl)methoxy]carbonyl}phenyl) oxalate;

FIG. 626 illustrates a bis(3,4,6-trichloro-2-{[(3-ethylphenyl)methoxy]carbonyl}phenyl) oxalate;

FIG. 627 illustrates a bis(3,4,6-trichloro-2-{[(4-ethylphenyl)methoxy]carbonyl}phenyl) oxalate;

FIG. 628 illustrates a bis(3,4,6-trichloro-2-{[2-(2-methylphenyl)ethoxy]carbonyl}phenyl) oxalate;

FIG. 629 illustrates a bis(3,4,6-trichloro-2-{[2-(3-methylphenyl)ethoxy]carbonyl}phenyl) oxalate;

FIG. 630 illustrates a bis(3,4,6-trichloro-2-{[2-(4-methylphenyl)ethoxy]carbonyl}phenyl) oxalate;

FIG. 631 illustrates a bis{3,4,6-trichloro-2-[(2-phenylpropoxy)carbonyl]phenyl}oxalate;

FIG. 632 illustrates a bis{3,4,6-trichloro-2-[(3-phenylpropoxy)carbonyl]phenyl}oxalate;

FIG. 633 illustrates a bis{3,4,6-trichloro-2-[(2-methylnonyloxy)carbonyl]phenyl}oxalate;

FIG. 634 illustrates a bis{3,4,6-trichloro-2-[(3-methylnonyloxy)carbonyl]phenyl}oxalate;

FIG. 635 illustrates a bis{3,4,6-trichloro-2-[(4-methylnonyloxy)carbonyl]phenyl}oxalate;

FIG. 636 illustrates a bis{3,4,6-trichloro-2-[(5-methylnonyloxy)carbonyl]phenyl}oxalate;

FIG. 637 illustrates a bis{3,4,6-trichloro-2-[(6-methylnonyloxy)carbonyl]phenyl}oxalate;

FIG. 638 illustrates a bis{3,4,6-trichloro-2-[(7-methylnonyloxy)carbonyl]phenyl}oxalate;

FIG. 639 illustrates a bis{3,4,6-trichloro-2-[(8-methylnonyloxy)carbonyl]phenyl}oxalate;

FIG. 640 illustrates a bis{3,4,6-trichloro-2-[(3,7-dimethyloctyloxy)carbonyl]phenyl}oxalate;

FIG. 641 illustrates a bis{3,4,6-trichloro-2-[(4-ethyloctyloxy)carbonyl]phenyl}oxalate;

FIG. 642 illustrates a bis{3,4,6-trichloro-2-[(2-propylheptyloxy)carbonyl]phenyl}oxalate;

FIG. 643 illustrates a bis{3,4,6-trichloro-2-[(2-butylhexyloxy)carbonyl]phenyl}oxalate;

FIG. 644 illustrates a bis{3,4,6-trichloro-2-[(4-cyclohexylbutoxy)carbonyl]phenyl}oxalate;

FIG. 645 illustrates a bis(2-{[(6,6-dimethylbicyclo[3.1.1]heptan-2-yl)methoxy]carbonyl}3,4,6-trichlorophenyl) oxalate;

FIG. 646 illustrates a bis(3,4,6-trichloro-2-{[(2,4,6-trimethylphenyl)methoxy]carbonyl}phenyl) oxalate;

FIG. 647 illustrates a bis(3,4,6-trichloro-2-{[(4-propylphenyl)methoxy]carbonyl}phenyl) oxalate;

FIG. 648 illustrates a bis[3,4,6-trichloro-2-({[4-(1-methylethyl)phenyl]methoxy}carbonyl)phenyl]oxalate;

FIG. 649 illustrates a bis{3,4,6-trichloro-2-[(2-phenylbutoxy)carbonyl]phenyl}oxalate;

FIG. 650 illustrates a bis{3,4,6-trichloro-2-[(3-phenylbutoxy)carbonyl]phenyl}oxalate;

FIG. 651 illustrates a bis{3,4,6-trichloro-2-[(4-phenylbutoxy)carbonyl]phenyl}oxalate;

FIG. 652 illustrates a bis(3,4,6-trichloro-2-{[(2-phenylcyclopropyl)methoxy]carbonyl}phenyl) oxalate;

FIG. 653 illustrates a bis{3,4,6-trichloro-2-[(1-adamantylmethoxy)carbonyl]phenyl}oxalate;

FIG. 654 illustrates a bis{3,4,6-trichloro-2-[(2,2-dicyclohexylethoxy)carbonyl]phenyl}oxalate;

FIG. 655 illustrates a bis(3,4,6-trichloro-2-{[(4-butylphenyl)methoxy]carbonyl}phenyl) oxalate;

FIG. 656 illustrates a bis[3,4,6-trichloro-2-({[4-(1,1-dimethylethyl)phenyl]methoxy}carbonyl)phenyl]oxalate;

FIG. 657 illustrates a bis{3,4,6-trichloro-2-[(5-phenylpentyloxy)carbonyl]phenyl}oxalate;

FIG. 658 illustrates a bis{3,4,6-trichloro-2-[1-naphthalenylmethoxy)carbonyl]phenyl}oxalate;

FIG. 659 illustrates a bis{3,4,6-trichloro-2-[2-naphthalenylmethoxy)carbonyl]phenyl}oxalate;

FIG. 660 illustrates a bis{3,4,6-trichloro-2-[(2,2-diphenylethoxy)carbonyl]phenyl}oxalate;

FIG. 661 illustrates a bis{3,4,6-trichloro-2-[(9-fluorenylmethoxy)carbonyl]phenyl}oxalate;

FIG. 662 illustrates a bis{3,4,6-trichloro-2-[(9-anthracenylmethoxy)carbonyl]phenyl}oxalate.

DETAILED DESCRIPTION OF THE INVENTION

Examples

Starting materials and solvents were purchased from Aldrich, VWR, Strem, and Alfa Aesar. All of the desired compounds were analyzed via HPLC, and their spectra (NMR) recorded.

Example 1

Figure 1:
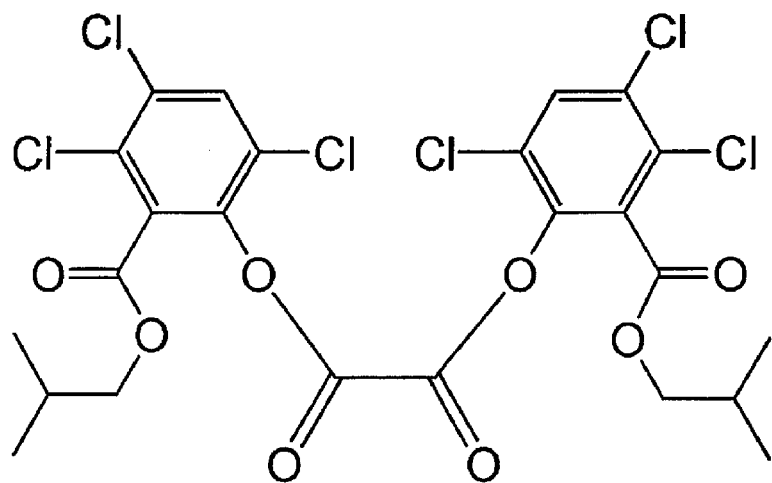
FIGS. 1-662 illustrate oxalates useful in chemical light systems for the production of chemiluminescent light as herein after described.
Figure 2:
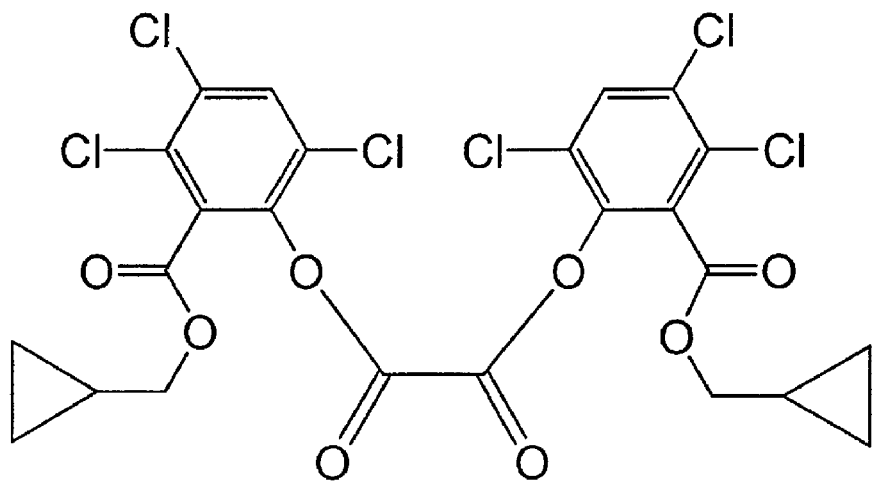
FIG. 2 illustrates a bis{3,4,6-trichloro-2-[(cyclopropylmethoxy)carbonyl]phenyl}oxalate.
Figure 3:
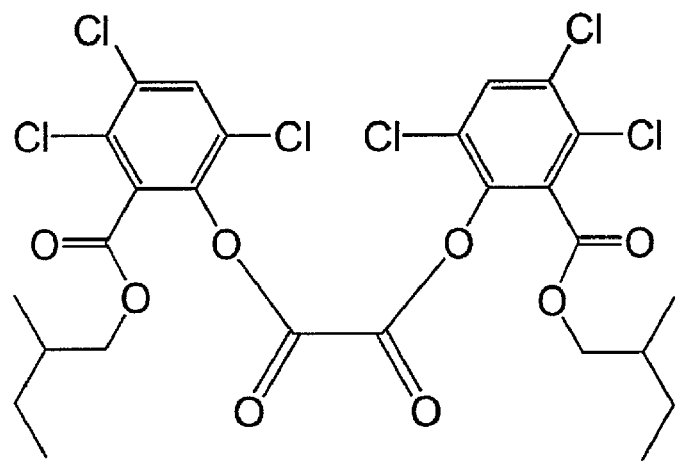
FIG. 3 illustrates a bis{3,4,6-trichloro-2-[(2-methylbutoxy)carbonyl]phenyl}oxalate.
Figure 4:
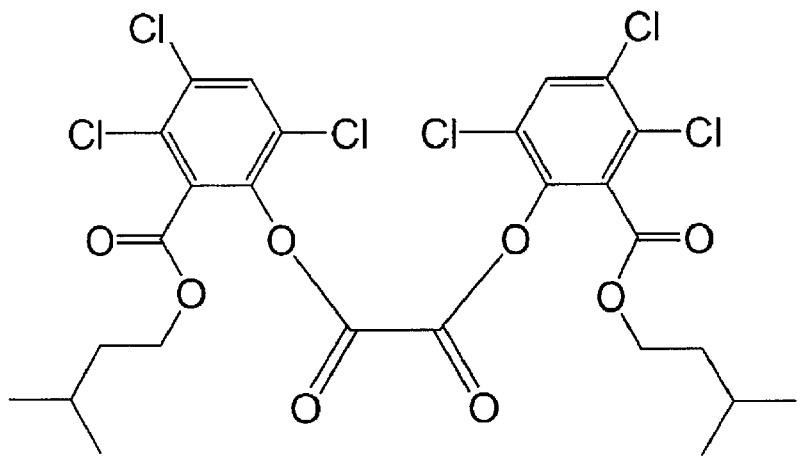
FIG. 4 illustrates a bis{3,4,6-trichloro-2-[(3-methylbutoxy)carbonyl]phenyl}oxalate.

Procedure For Producing Bis{3,4,6-Trichloro-2-[(2-Methylpropoxy)Carbonyl]Phenyl}Oxalate (FIG. 1)

Aliphatic 3,5,6-trichlorosalicylate esters, including 2-methylbutyl 3,5,6-trichlorosalicylate can be made via the procedures taught in U.S. Pat. No. 4,308,395 and U.S. Pat. No. 5,194,666, the contents of which are herein incorporated by reference in their entireties. The material was analyzed by HPLC and used without further purification in the next step.

The oxalate, bis{3,4,6-trichloro-2-[(2-methylpropoxy)carbonyl]phenyl}oxalate (Compound in FIG. 1) can be made using processes described in U.S. Pat. No. 3,749,679, the contents of which is herein incorporated by reference in its entirety. The recrystallization solvent of choice is acetonitrile.

This method of synthesis was used for the compounds shown in FIGS. 1, 3-5, 9-16, 26-29, 31-46, 51, 60-64, 71-84, 87-120, 126, 138-142, 156-175, 192-224, 226, 230-305, 311, 328-333, 336-387, 435-496, 531-617, 628-644, 649-651, 654, and 657.

Additionally, xylene can be used for the first step and a tertiary amine other than triethylamine can be used for the oxalate, including tripropyl amine, tri-n-butyl amine, triisobutylamine, triisopropylamine, triisopentylamine, and N,N-diisopropylethyl amine.

Example 2

Figure 86:
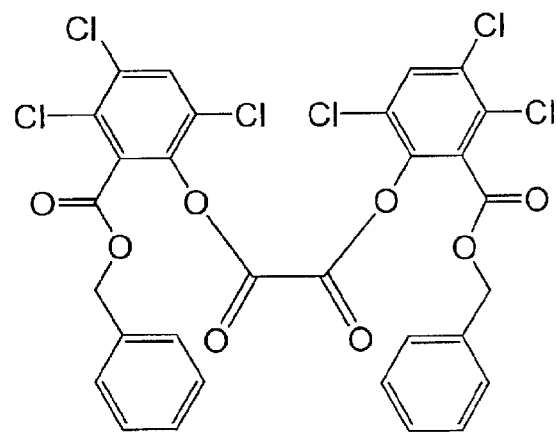
FIG. 86 illustrates a bis{3,4,6-trichloro-2-[(phenylmethoxy)carbonyl]phenyl}oxalate.
Figure 87:
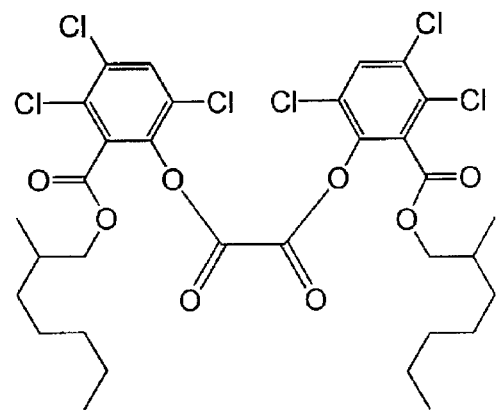
FIG. 87 illustrates a bis{3,4,6-trichloro-2-[(2-methylheptyloxy)carbonyl]phenyl}oxalate.
Figure 88:
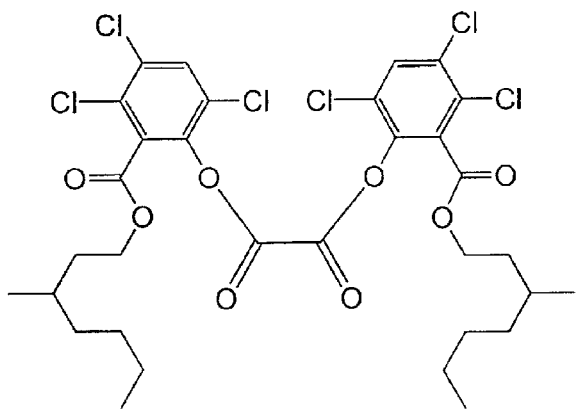
FIG. 88 illustrates a bis{3,4,6-trichloro-2-[(3-methylheptyloxy)carbonyl]phenyl}oxalate.
Figure 89:
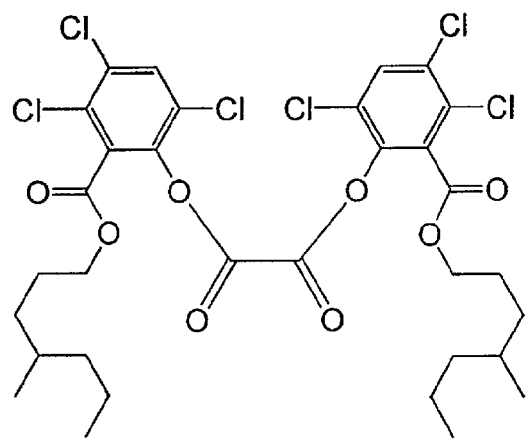
FIG. 89 illustrates a bis{3,4,6-trichloro-2-[(4-methylheptyloxy)carbonyl]phenyl}oxalate.
Figure 90:
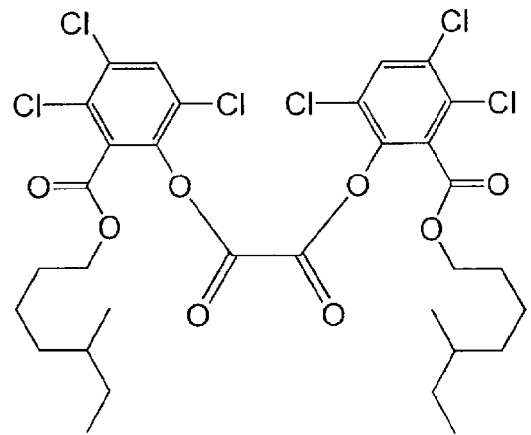
FIG. 90 illustrates a bis{3,4,6-trichloro-2-[(5-methylheptyloxy)carbonyl]phenyl}oxalate.
Figure 91:
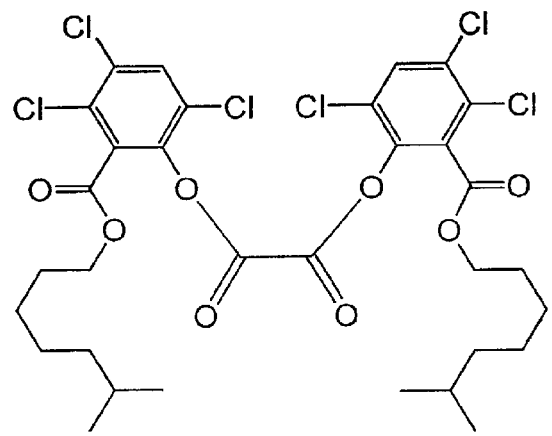
FIG. 91 illustrates a bis{3,4,6-trichloro-2-[(6-methylheptyloxy)carbonyl]phenyl}oxalate.
Figure 92:
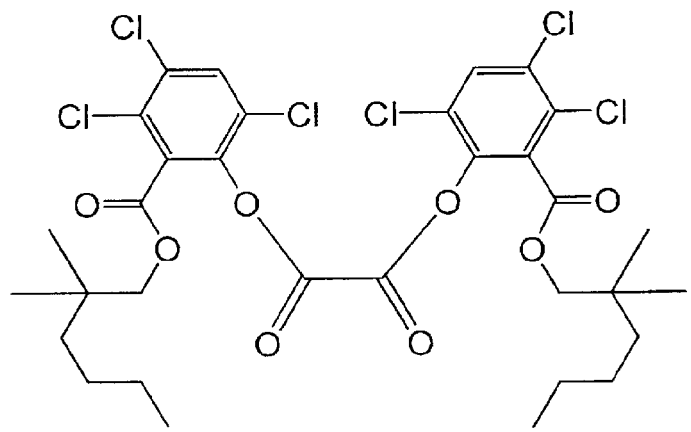
FIG. 92 illustrates a bis{3,4,6-trichloro-2-[(2,2-dimethylhexyloxy)carbonyl]phenyl}oxalate.
Figure 93:
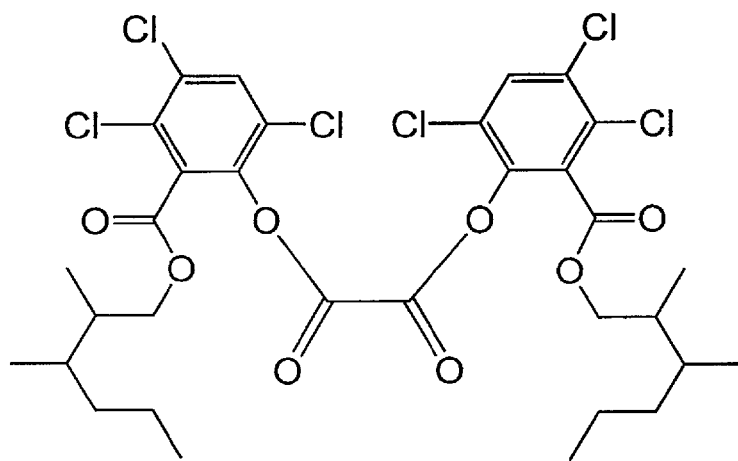
FIG. 93 illustrates a bis{3,4,6-trichloro-2-[(2,3-dimethylhexyloxy)carbonyl]phenyl}oxalate.
Figure 94:
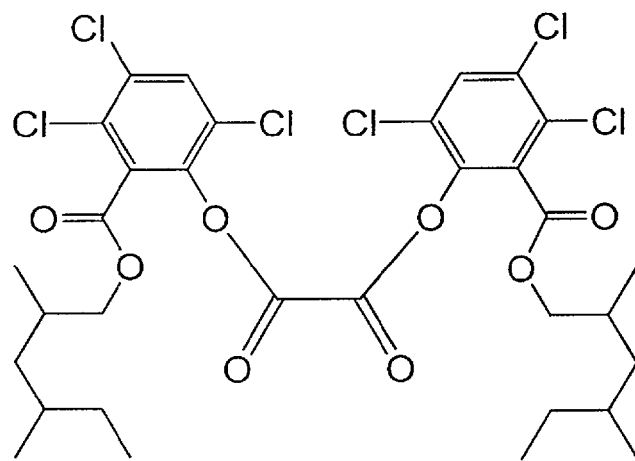
FIG. 94 illustrates a bis{3,4,6-trichloro-2-[(2,4-dimethylhexyloxy)carbonyl]phenyl}oxalate.
Figure 95:
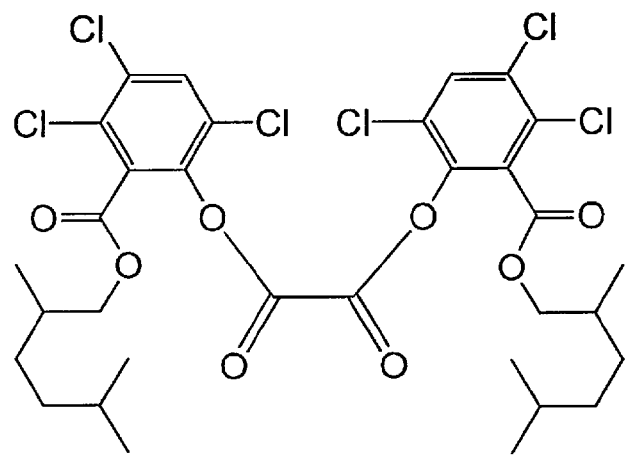
FIG. 95 illustrates a bis{3,4,6-trichloro-2-[(2,5-dimethylhexyloxy)carbonyl]phenyl}oxalate.
Figure 96:
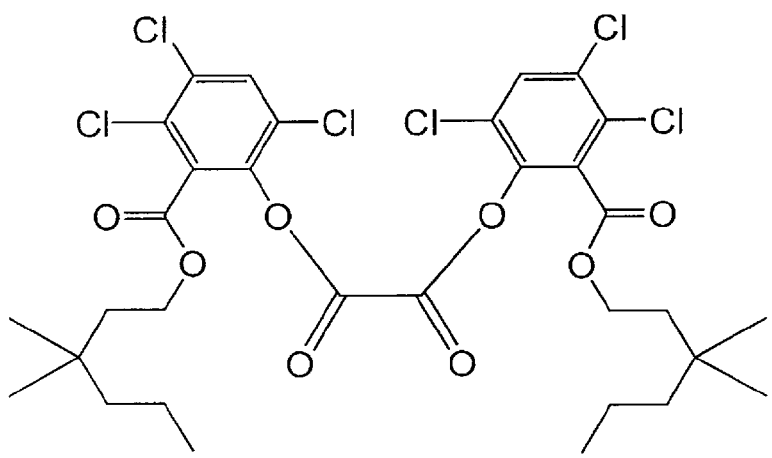
FIG. 96 illustrates a bis{3,4,6-trichloro-2-[(3,3-dimethylhexyloxy)carbonyl]phenyl}oxalate.
Figure 97:
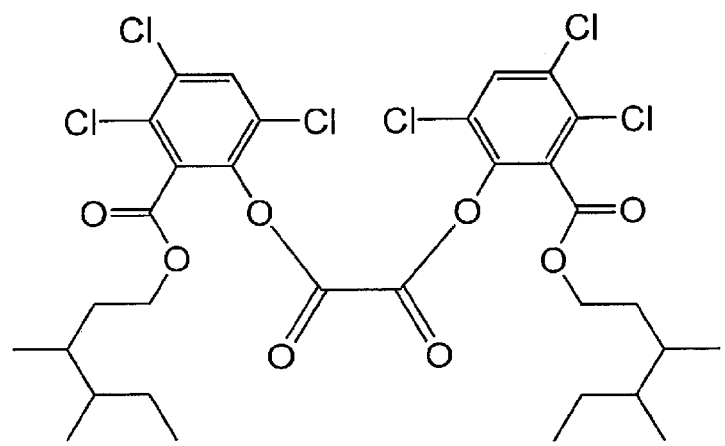
FIG. 97 illustrates a bis{3,4,6-trichloro-2-[(3,4-dimethylhexyloxy)carbonyl]phenyl}oxalate.
Figure 98:
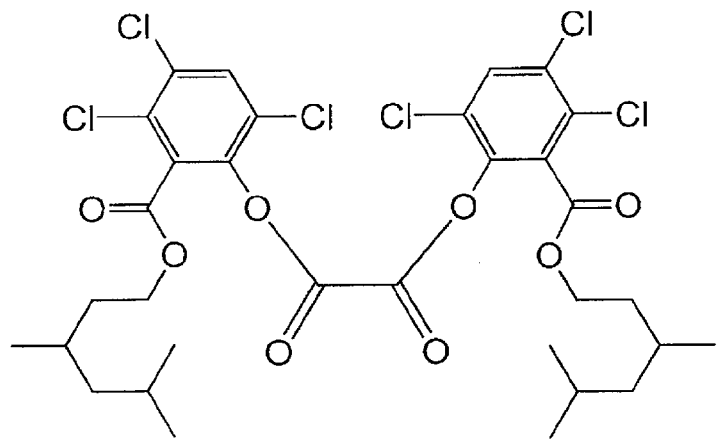
FIG. 98 illustrates a bis{3,4,6-trichloro-2-[(3,5-dimethylhexyloxy)carbonyl]phenyl}oxalate.
Figure 99:
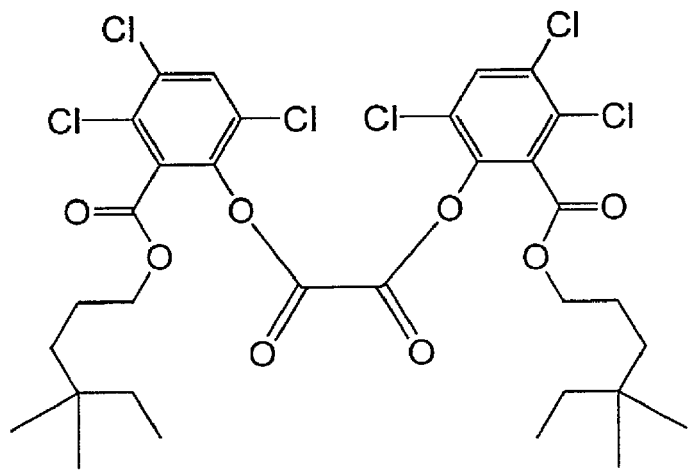
FIG. 99 illustrates a bis{3,4,6-trichloro-2-[(4,4-dimethylhexyloxy)carbonyl]phenyl}oxalate.
Figure 100:
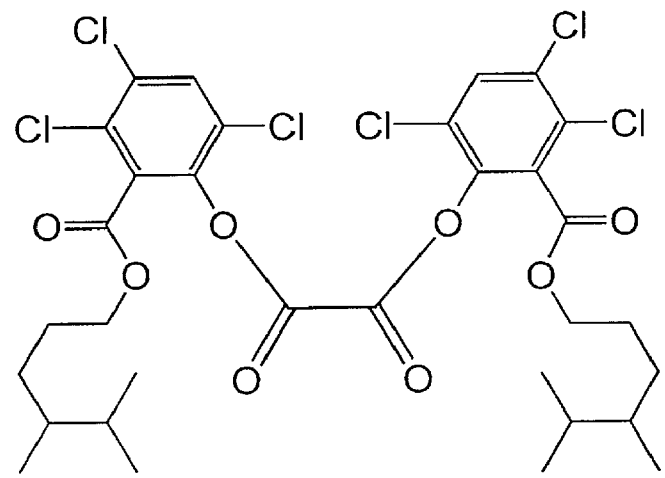
FIG. 100 illustrates a bis{3,4,6-trichloro-2-[(4,5-dimethylhexyloxy)carbonyl]phenyl}oxalate.
Figure 101:
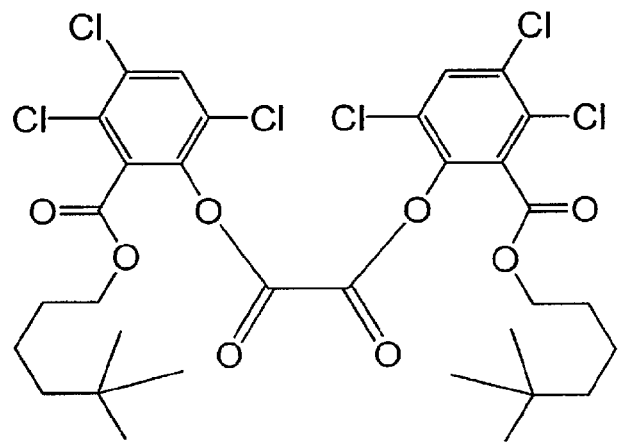
FIG. 101 illustrates a bis{3,4,6-trichloro-2-[(5,5-dimethylhexyloxy)carbonyl]phenyl}oxalate.
Figure 102:
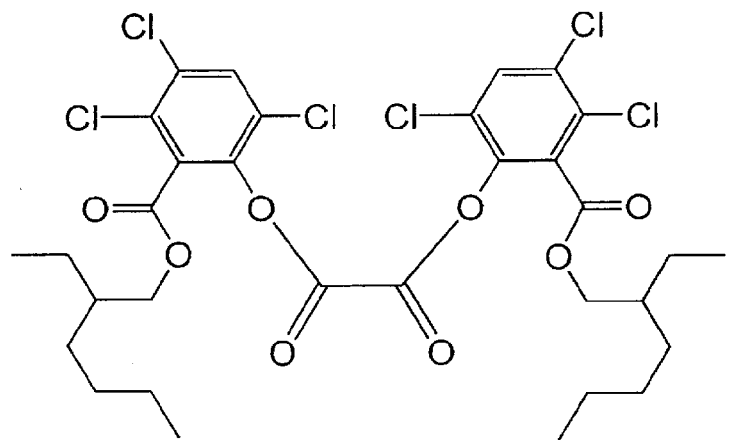
FIG. 102 illustrates a bis{3,4,6-trichloro-2-[(2-ethylhexyloxy)carbonyl]phenyl}oxalate.
Figure 103:
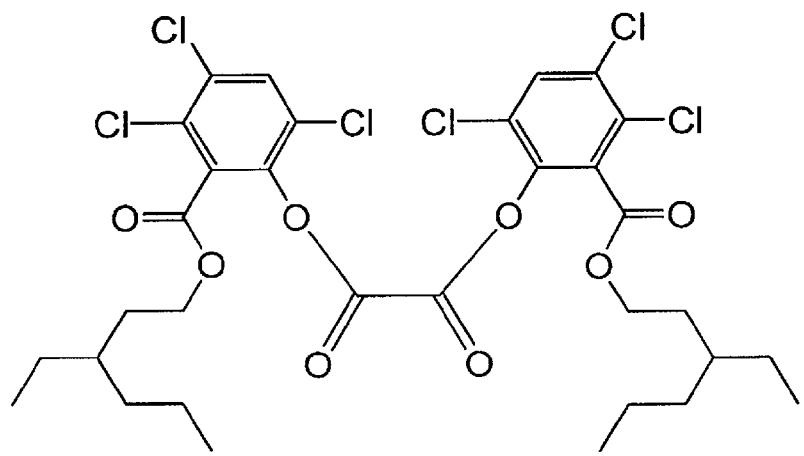
FIG. 103 illustrates a bis{3,4,6-trichloro-2-[(3-ethylhexyloxy)carbonyl]phenyl}oxalate.
Figure 104:
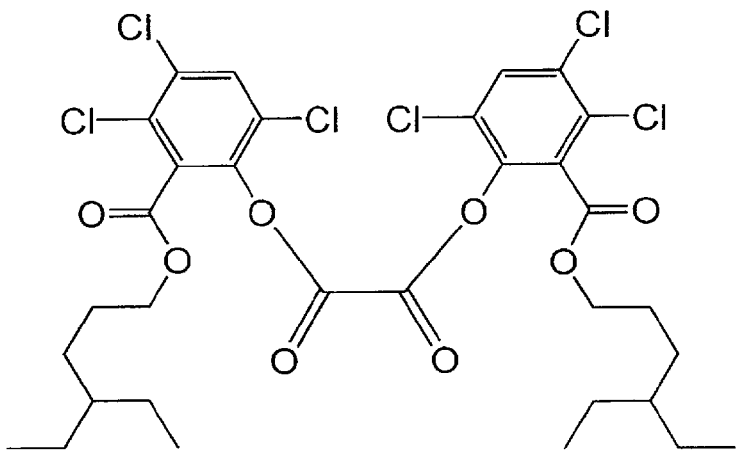
FIG. 104 illustrates a bis{3,4,6-trichloro-2-[(4-ethylhexyloxy)carbonyl]phenyl}oxalate.
Figure 105:
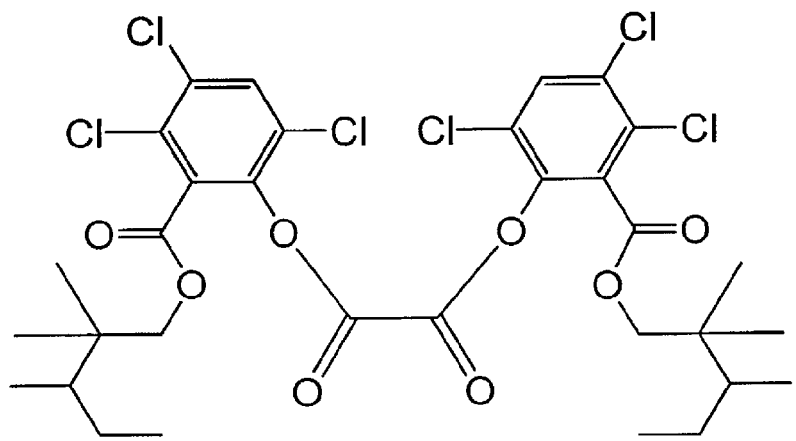
FIG. 105 illustrates a bis{3,4,6-trichloro-2-[(2,2,3-trimethylpentyloxy)carbonyl]phenyl}oxalate.
Figure 106:
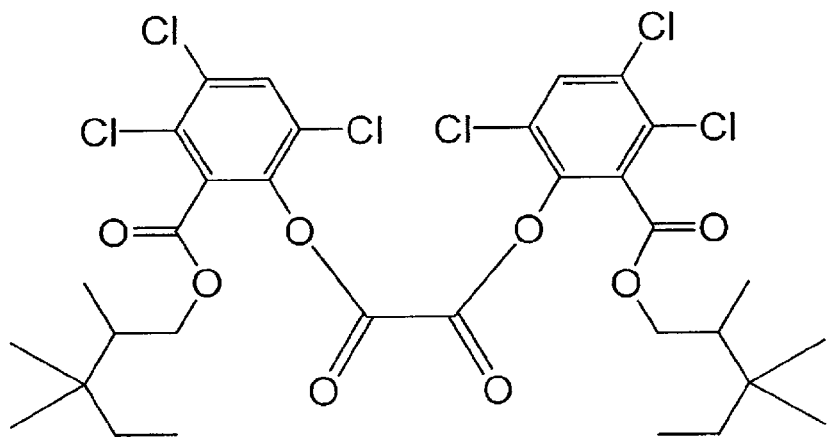
FIG. 106 illustrates a bis{3,4,6-trichloro-2-[(2,3,3-trimethylpentyloxy)carbonyl]phenyl}oxalate.
Figure 107:
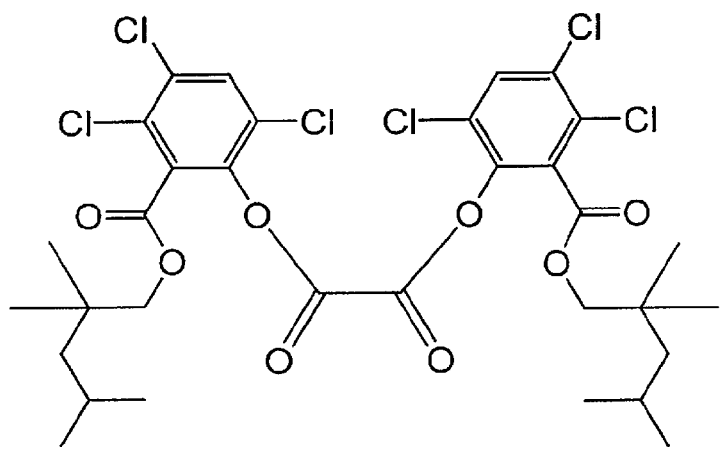
FIG. 107 illustrates a bis{3,4,6-trichloro-2-[(2,2,4-trimethylpentyloxy)carbonyl]phenyl}oxalate.
Figure 108:
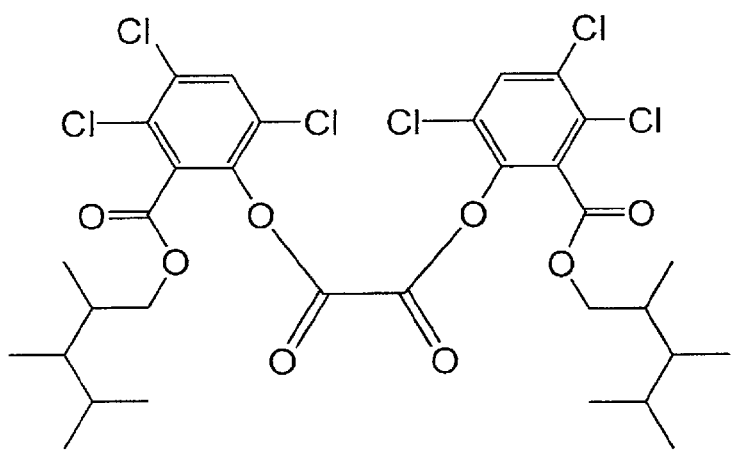
FIG. 108 illustrates a bis{3,4,6-trichloro-2-[(2,3,4-trimethylpentyloxy)carbonyl]phenyl}oxalate.
Figure 109:
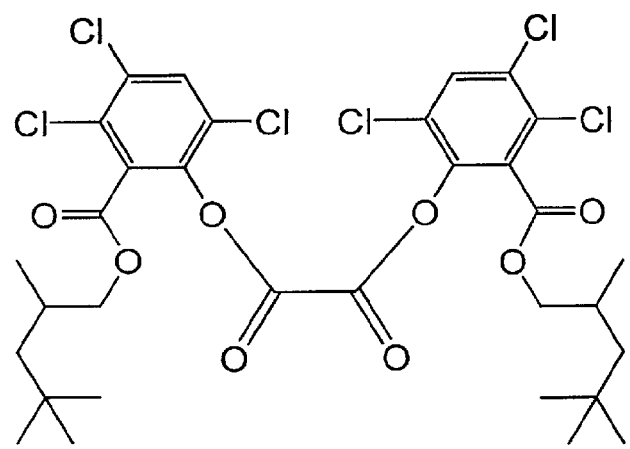
FIG. 109 illustrates a bis{3,4,6-trichloro-2-[(2,4,4-trimethylpentyloxy)carbonyl]phenyl}oxalate.
Figure 110:
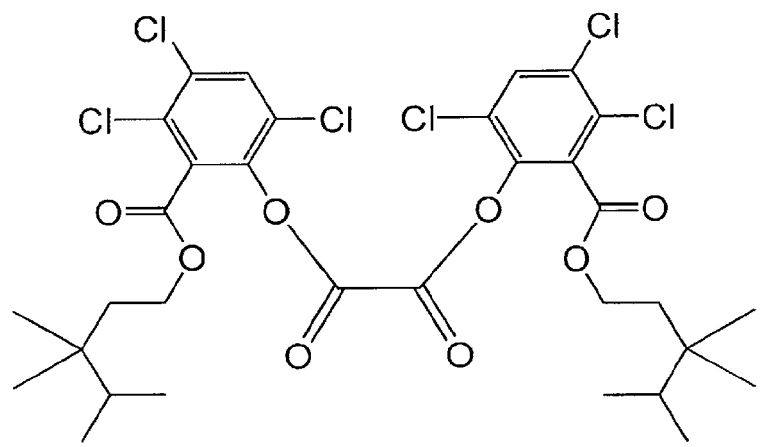
FIG. 110 illustrates a bis{3,4,6-trichloro-2-[(3,3,4-trimethylpentyloxy)carbonyl]phenyl}oxalate.
Figure 111:
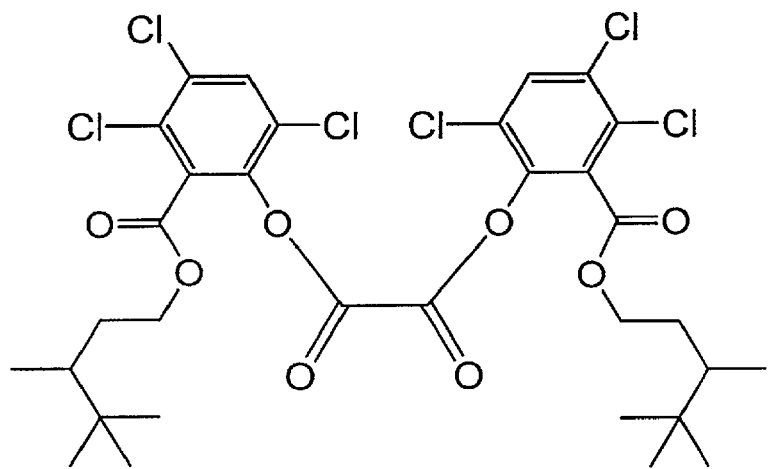
FIG. 111 illustrates a bis{3,4,6-trichloro-2-[(3,4,4-trimethylpentyloxy)carbonyl]phenyl}oxalate.
Figure 112:
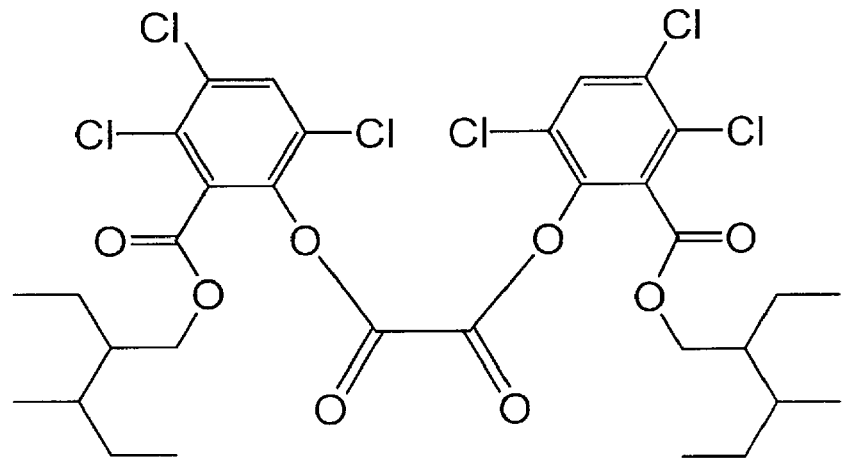
FIG. 112 illustrates a bis{3,4,6-trichloro-2-[(2-ethyl-3-methylpentyloxy)carbonyl]phenyl}oxalate.
Figure 113:
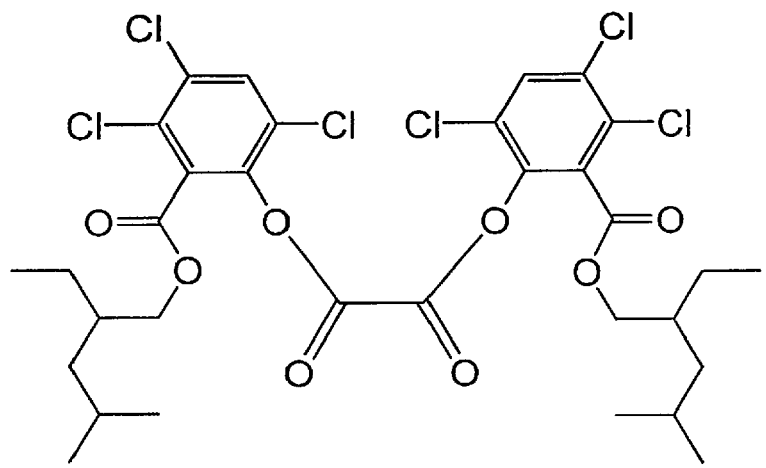
FIG. 113 illustrates a bis{3,4,6-trichloro-2-[(2-ethyl-4-methylpentyloxy)carbonyl]phenyl}oxalate.
Figure 114:
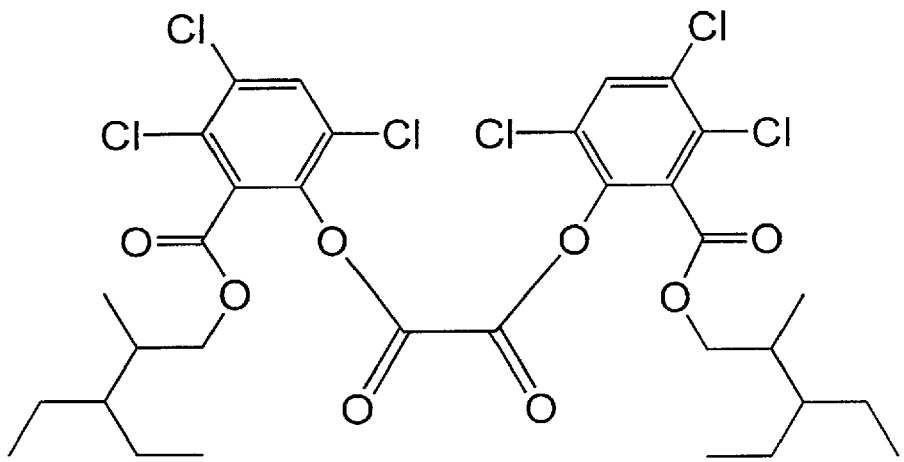
FIG. 114 illustrates a bis{3,4,6-trichloro-2-[(3-ethyl-2-methylpentyloxy)carbonyl]phenyl}oxalate.
Figure 115:
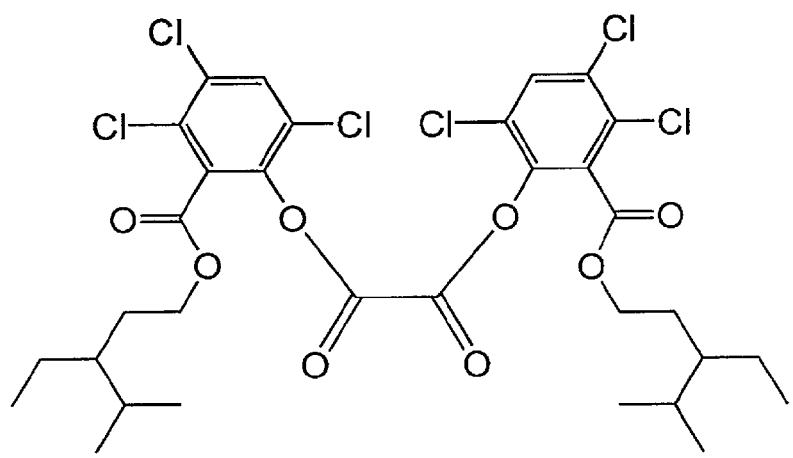
FIG. 115 illustrates a bis{3,4,6-trichloro-2-[(3-ethyl-4-methylpentyloxy)carbonyl]phenyl}oxalate.
Figure 116:
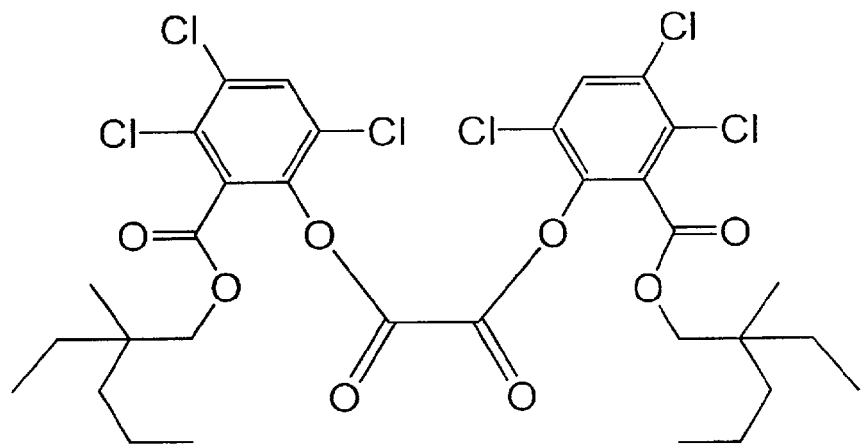
FIG. 116 illustrates a bis{3,4,6-trichloro-2-[(2-ethyl-2-methylpentyloxy)carbonyl]phenyl}oxalate.
Figure 117:
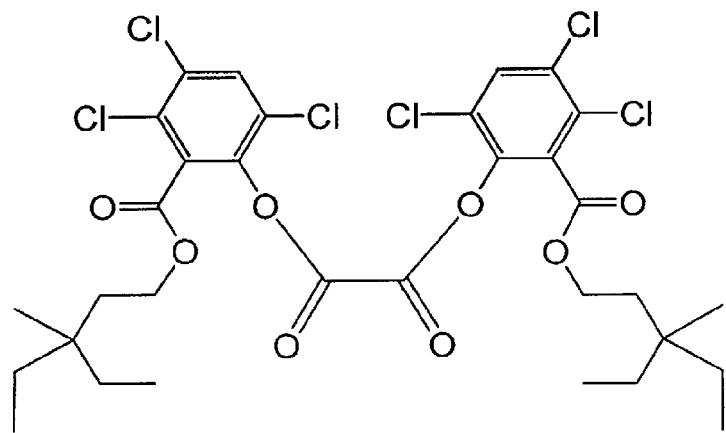
FIG. 117 illustrates a bis{3,4,6-trichloro-2-[(3-ethyl-3-methylpentyloxy)carbonyl]phenyl}oxalate.
Figure 118:
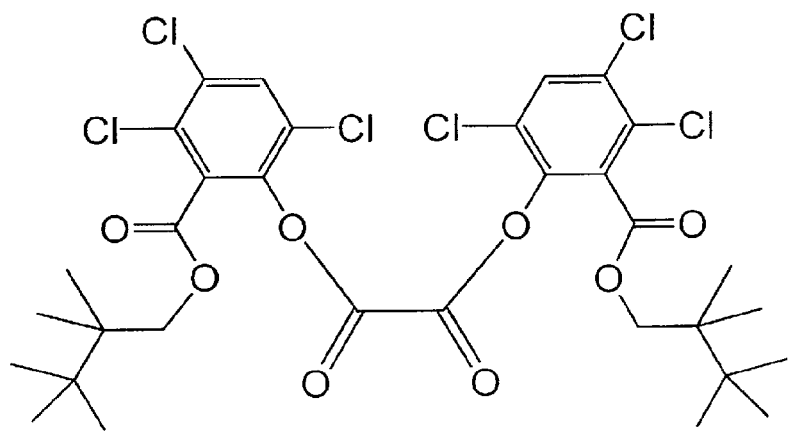
FIG. 118 illustrates a bis{3,4,6-trichloro-2-[(2,2,3,3-tetramethylbutyloxy)carbonyl]phenyl}oxalate.
Figure 119:
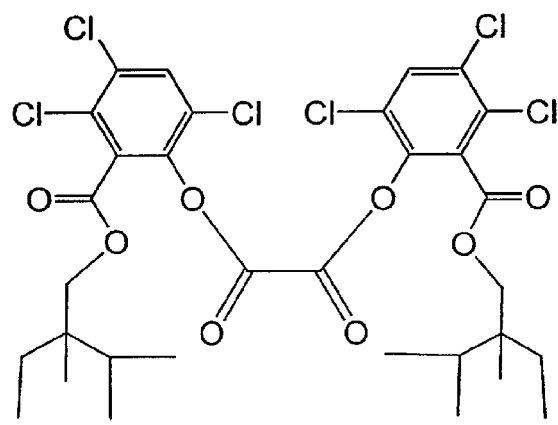
Figure 120:
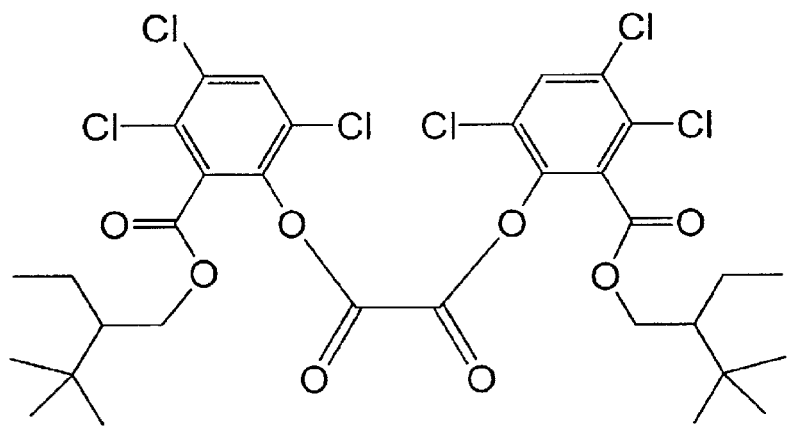
Figure 121:
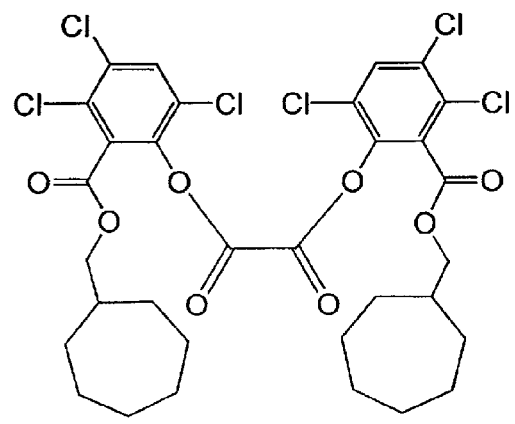
Figure 122:
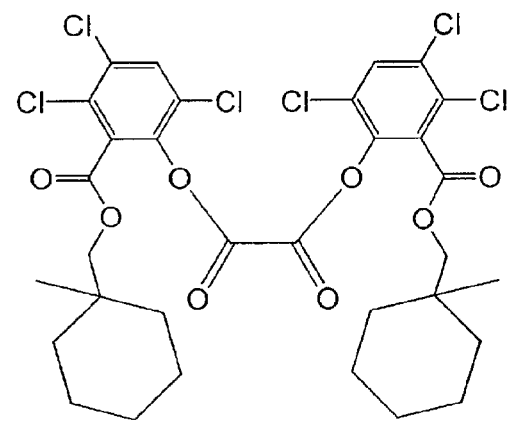
Figure 123:
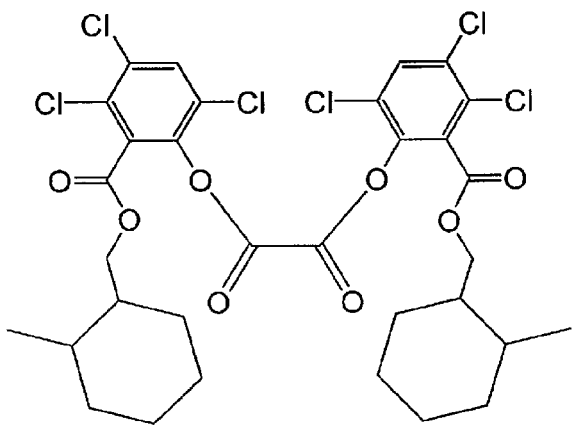
Figure 124:
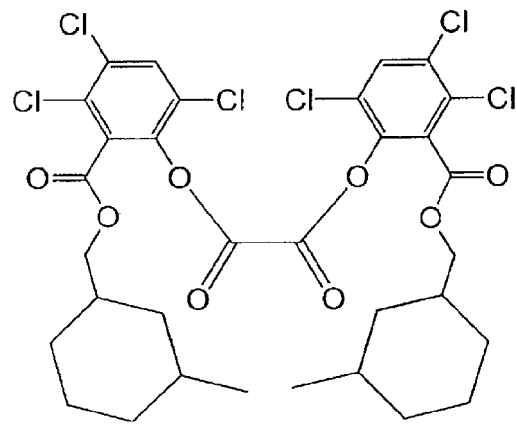
Figure 125:
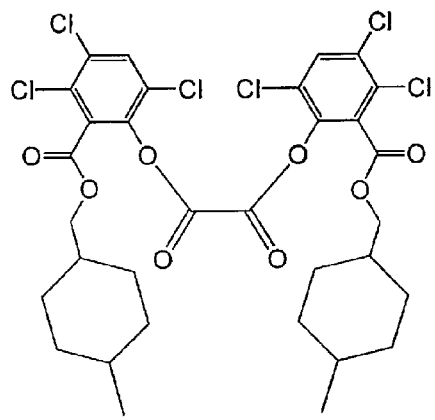
Figure 126:
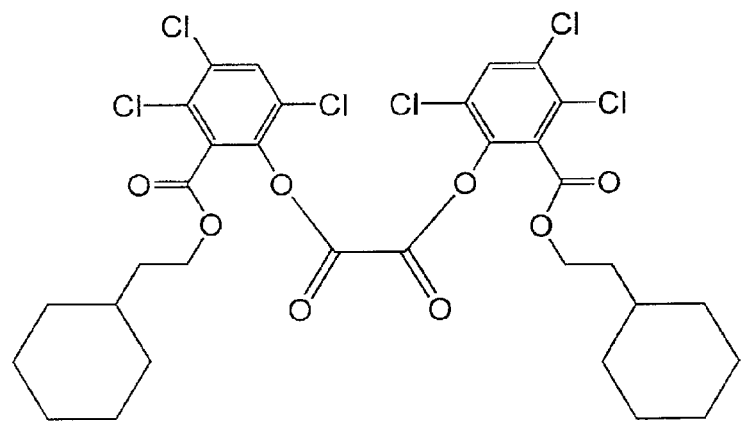
Figure 127:
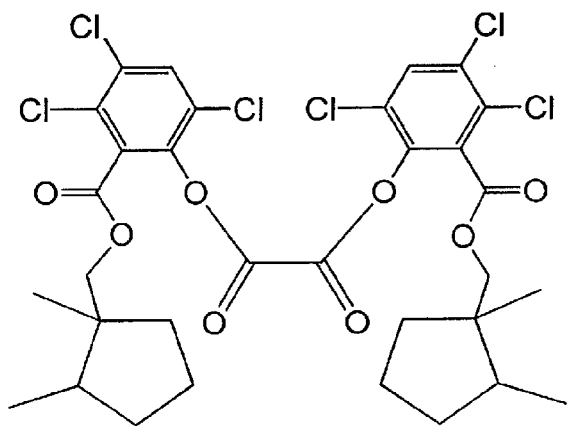
Figure 128:
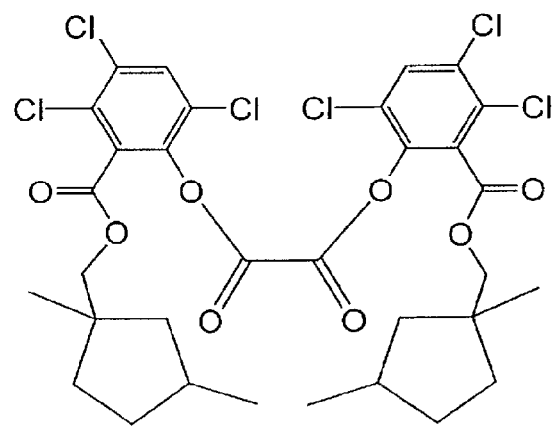
Figure 129:
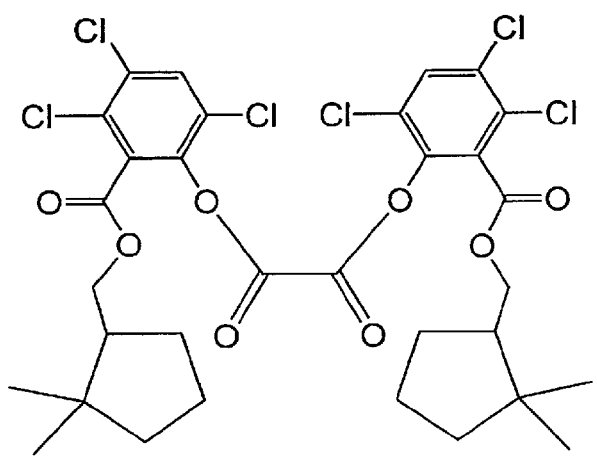
Figure 130:
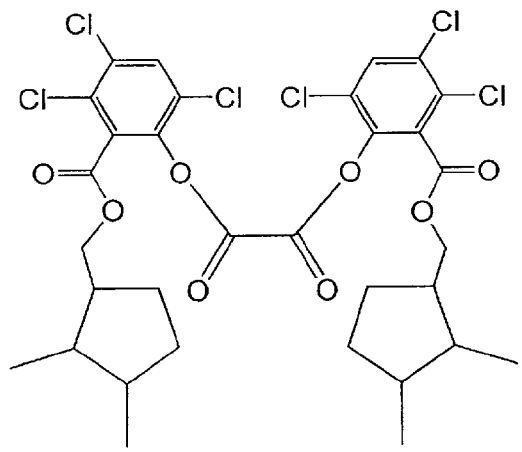

Procedure For Producing Bis{3,4,6-Trichloro-2-[(Phenylmethoxy)Carbonyl]Phenyl}Oxalate (FIG. 86)

A five liter 3-necked flask fitted with a mechanical stirrer and a Barrett or Dean-Stark trap was charged with 483 g (2.0 mol) of 3,5,6-trichlorosalicylic acid, 2000 mL of toluene, 228 mL (2.2 mol) of benzyl alcohol, and 7.86 g (30 mmol) of titanium oxide bis(acetylacetonate). The mixture was heated at reflux overnight or until the theoretical amount of water had been captured in the trap. After cooling to room temperature, the reaction product was treated with 750 mL of saturated aqueous sodium hydrogen carbonate and stirred for 1-2 hours. If the ester precipitates out at this time, add sufficient ethyl acetate or other water immiscible solvent to dissolve the material. After adding 750 mL of water and stirring for an additional 10-15 minutes, the mixture was filtered through a pad of CELITE. The mixture was separated in a filter funnel and the organic layer washed with 750 mL of brine. The organic layer was dried, filtered, and concentrated under reduced pressure. Once all of the material had been concentrated, an aliquot of xylene was added and removed under reduced pressure to ensure complete removal of any excess alcohol and water. If the product precipitated once the alcohol was removed, the residue was triturated with hexane, filtered, and dried. Yield was 254 g (76.5%). The material was analyzed by HPLC and used without further purification in the next step.

The oxalate, bis{3,4,6-trichloro-2-[(phenylmethoxy)carbonyl]phenyl}oxalate (FIG. 86), can be made using processes described in the following: U.S. Pat. No. 3,749,679. The recrystallization solvent of choice is ethyl acetate and one of the following: hexane, heptane, triethyl citrate, or toluene. The yield on this scale was 192.7 g (70%).

This method was used for the compounds shown in FIGS. 86, 227-229, 620-627, 646-648, 655-656, 658-659, and 661-662.

Additionally, xylene can be used for the first step and a tertiary amine other than triethylamine can be used for the oxalate, including tripropyl amine, tri-n-butyl amine, tri-isobutylamine, triisopropylamine, triisopentylamine, and N,N-diisopropylethyl amine.

Example 3

Figure 5:
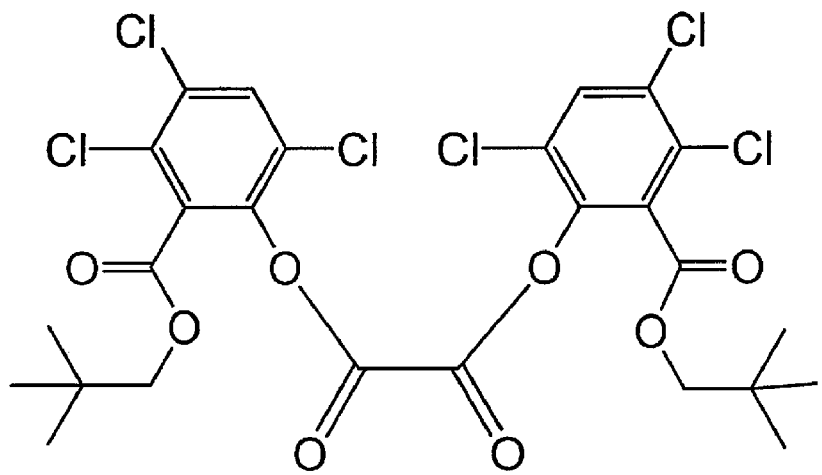
FIG. 5 illustrates a bis{3,4,6-trichloro-2-[(2,2-dimethylpropoxy)carbonyl]phenyl}oxalate.
Figure 6:
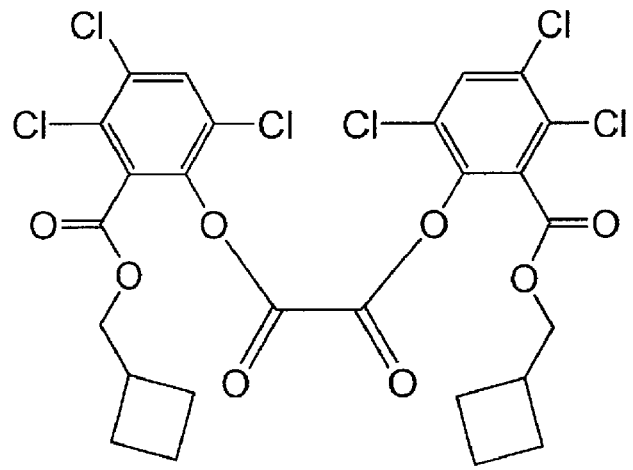
FIG. 6 illustrates a bis{3,4,6-trichloro-2-[(cyclobutylmethoxy)carbonyl]phenyl}oxalate.
Figure 7:
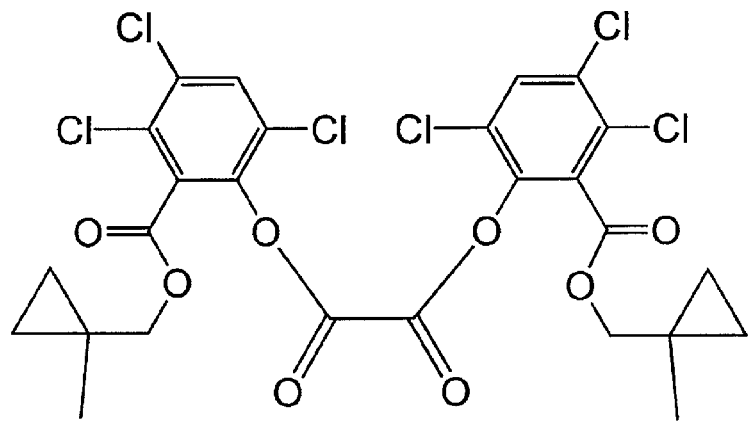
FIG. 7 illustrates a bis(3,4,6-trichloro-2-{[(1-methylcyclopropyl)methoxy]carbonyl}phenyl) oxalate.
Figure 8:
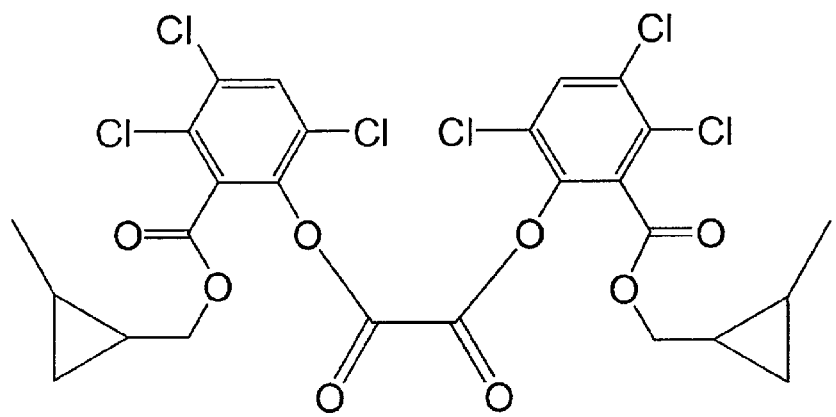
FIG. 8 illustrates a bis(3,4,6-trichloro-2-{[(2-methylcyclopropyl)methoxy]carbonyl}phenyl) oxalate.
Figure 9:
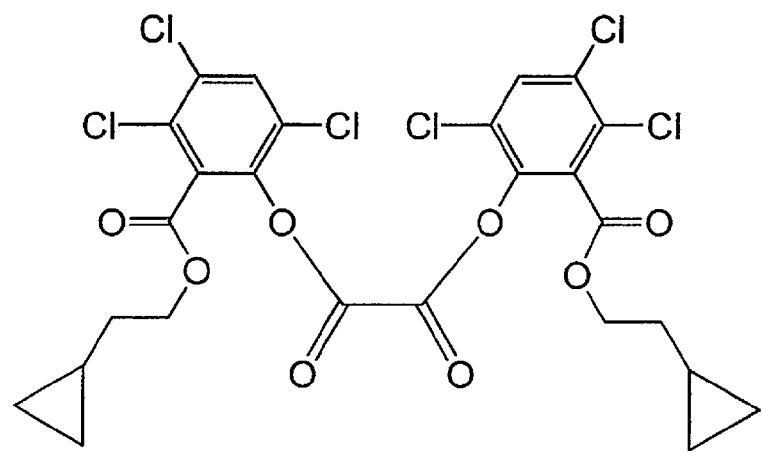
FIG. 9 illustrates a bis{3,4,6-trichloro-2-[(2-cyclopropylethoxy)carbonyl]phenyl}oxalate.
Figure 10:
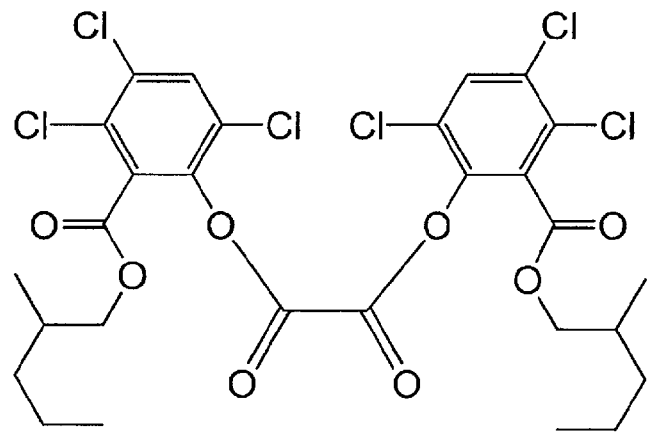
FIG. 10 illustrates a bis{3,4,6-trichloro-2-[(2-methylpentyloxy)carbonyl]phenyl}oxalate.
Figure 11:
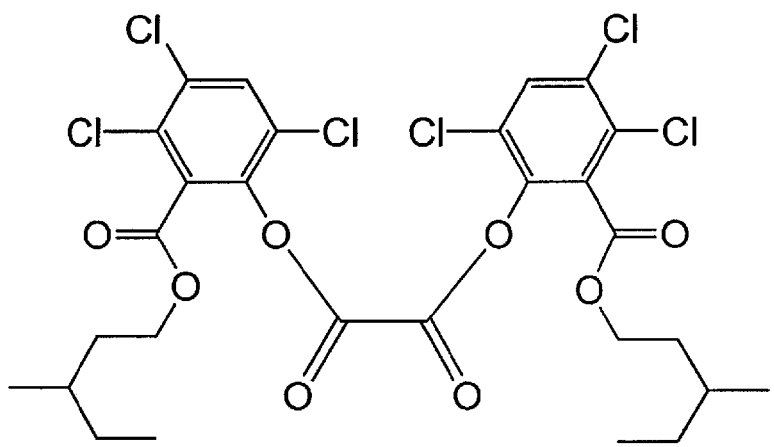
FIG. 11 illustrates a bis{3,4,6-trichloro-2-[(3-methylpentyloxy)carbonyl]phenyl}oxalate.
Figure 12:
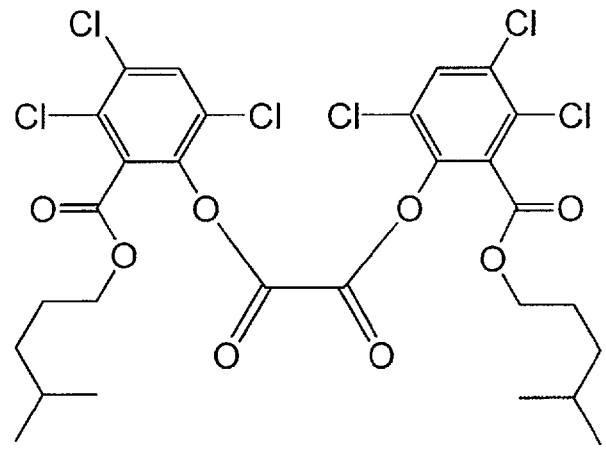
FIG. 12 illustrates a bis{3,4,6-trichloro-2-[(4-methylpentyloxy)carbonyl]phenyl}oxalate.
Figure 13:
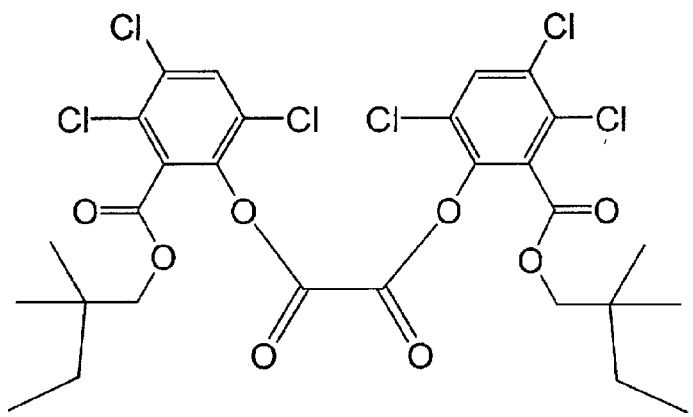
FIG. 13 illustrates a bis{3,4,6-trichloro-2-[(2,2-dimethylbutoxy)carbonyl]phenyl}oxalate.
Figure 14:
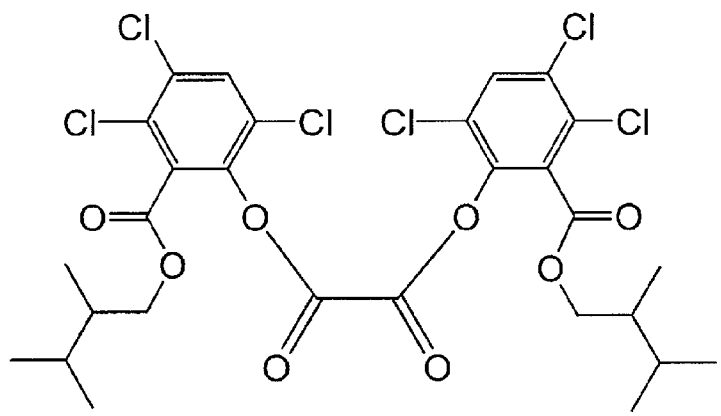
FIG. 14 illustrates a bis{3,4,6-trichloro-2-[(2,3-dimethylbutoxy)carbonyl]phenyl}oxalate.
Figure 15:
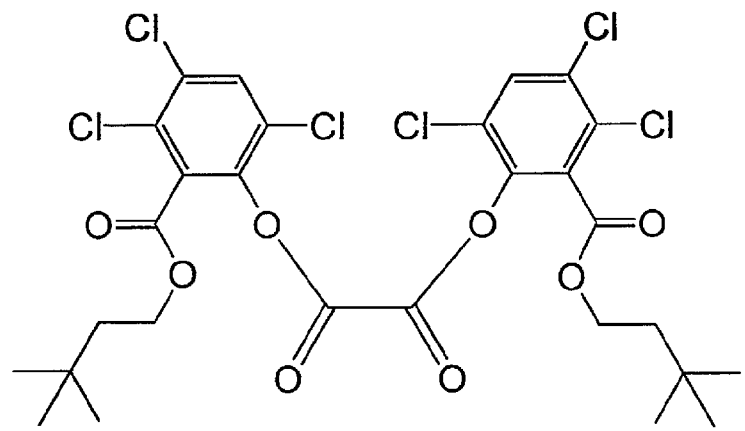
FIG. 15 illustrates a bis{3,4,6-trichloro-2-[(3,3-dimethylbutoxy)carbonyl]phenyl}oxalate.
Figure 16:
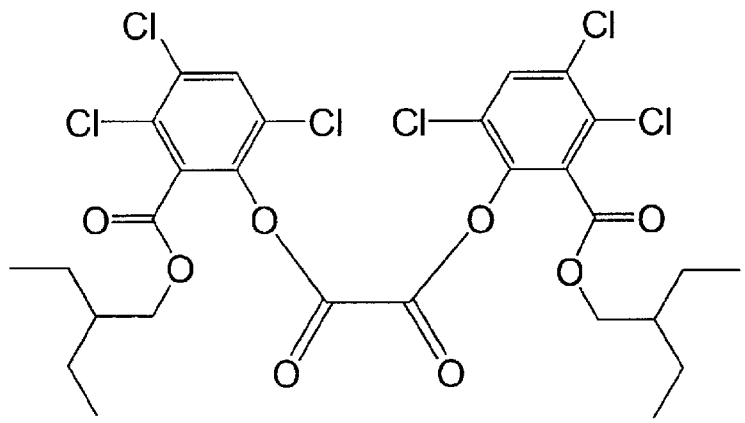
FIG. 16 illustrates a bis{3,4,6-trichloro-2-[(2-ethylbutoxy)carbonyl]phenyl}oxalate.
Figure 17:
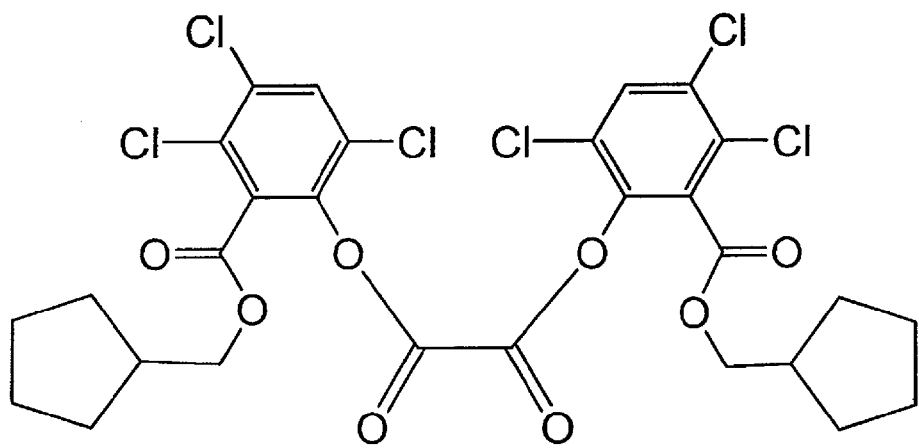
FIG. 17 illustrates a bis{3,4,6-trichloro-2-[(cyclopentylmethoxy)carbonyl]phenyl}oxalate.
Figure 18:
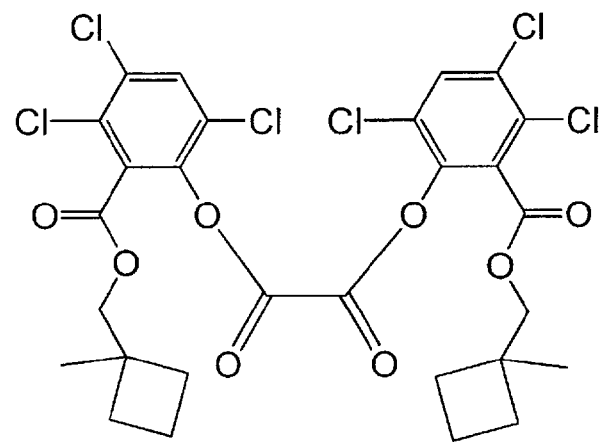
FIG. 18 illustrates a bis(3,4,6-trichloro-2-{[(1-methylcyclobutyl)methoxy]carbonyl}phenyl) oxalate.
Figure 19:
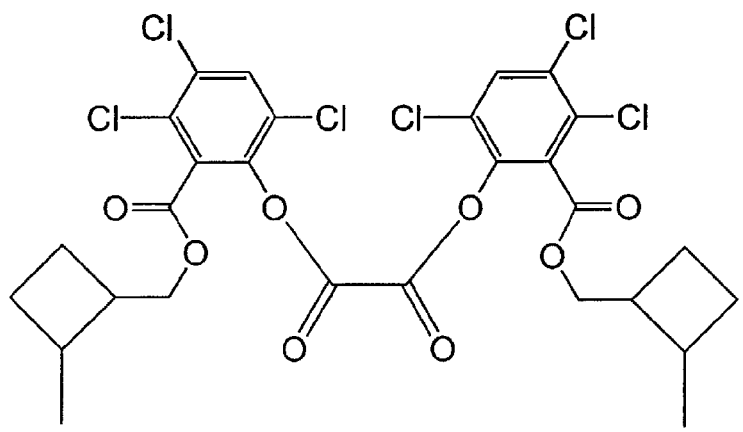
FIG. 19 illustrates a bis(3,4,6-trichloro-2-{[(2-methylcyclobutyl)methoxy]carbonyl}phenyl) oxalate.
Figure 20:
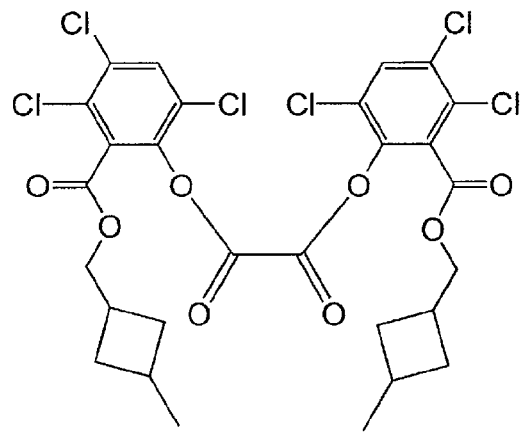
FIG. 20 illustrates a bis(3,4,6-trichloro-2-{[(3-methylcyclobutyl)methoxy]carbonyl}phenyl) oxalate.
Figure 21:
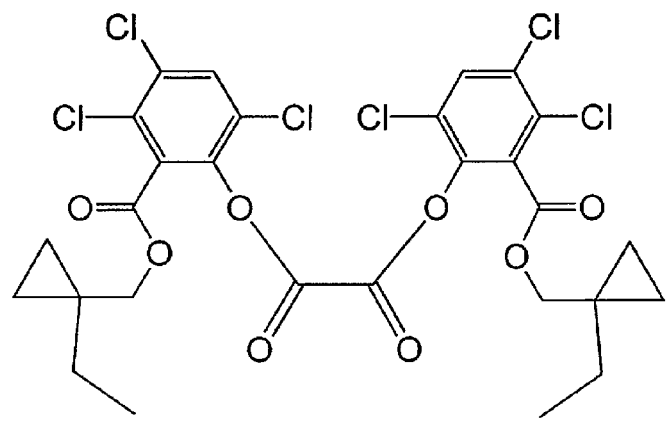
FIG. 21 illustrates a bis(3,4,6-trichloro-2-{[(1-ethylcyclopropyl)methoxy]carbonyl}phenyl) oxalate.
Figure 22:
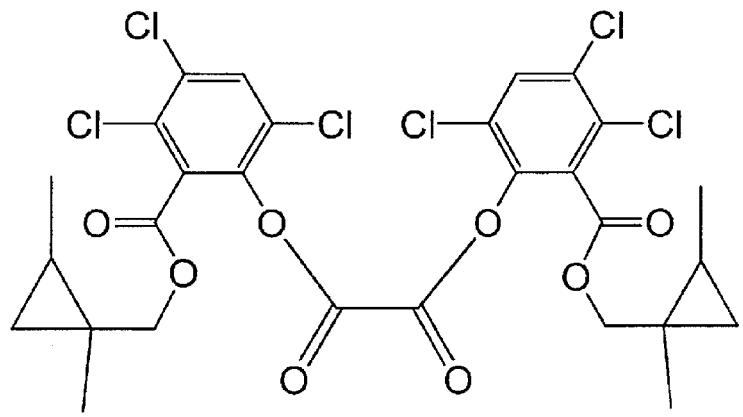
FIG. 22 illustrates a bis(3,4,6-trichloro-2-{[(1,2-dimethylcyclopropyl)methoxy]carbonyl}phenyl) oxalate.
Figure 23:
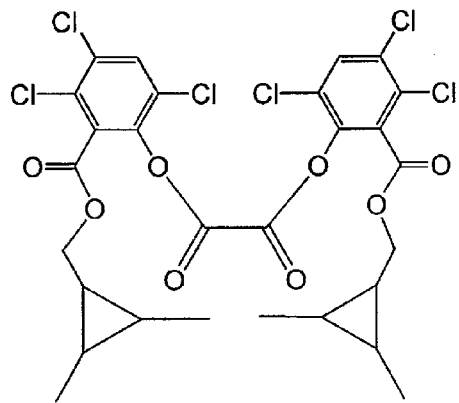
FIG. 23 illustrates a bis(3,4,6-trichloro-2-{[(2,3-dimethylcyclopropyl)methoxy]carbonyl}phenyl) oxalate.
Figure 24:
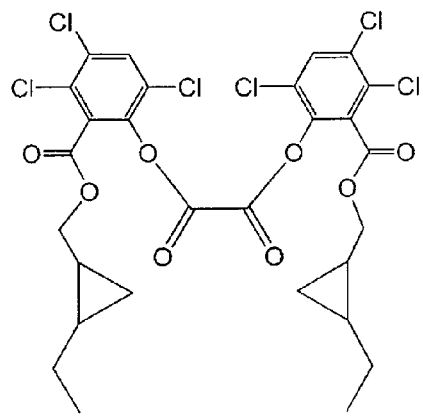
FIG. 24 illustrates a bis(3,4,6-trichloro-2-{[(2-ethylcyclopropyl)methoxy]carbonyl}phenyl) oxalate.
Figure 25:
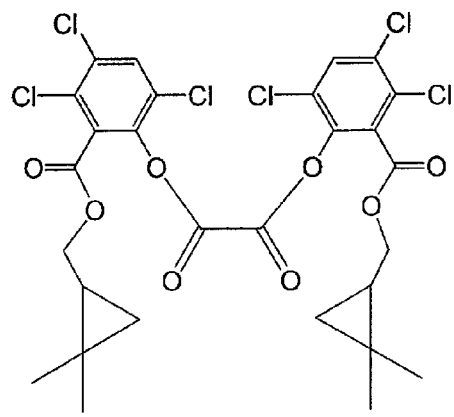
FIG. 25 illustrates a bis(3,4,6-trichloro-2-{[(2,2-dimethylcyclopropyl)methoxy]carbonyl}phenyl) oxalate.
Figure 26:
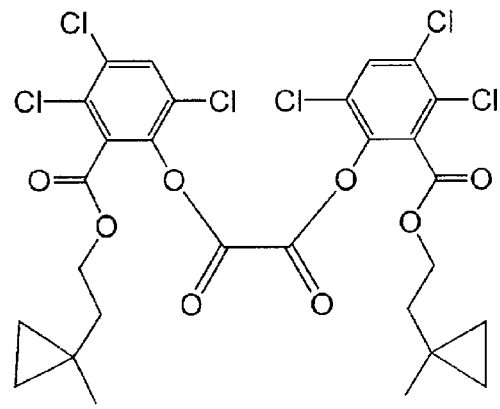
FIG. 26 illustrates a bis(3,4,6-trichloro-2-{[2-(1-methylcyclopropyl)ethoxy]carbonyl}phenyl) oxalate.
Figure 27:
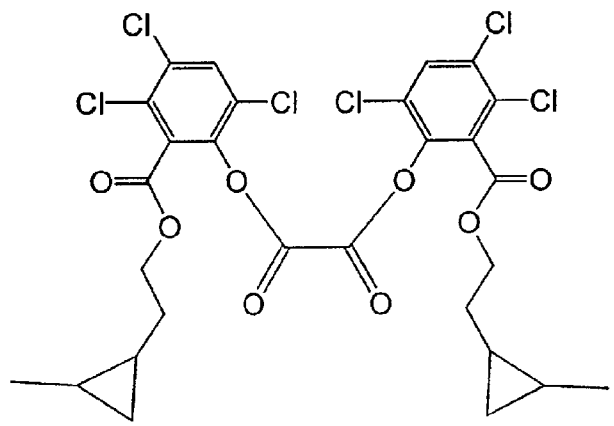
FIG. 27 illustrates a bis(3,4,6-trichloro-2-{[2-(2-methylcyclopropyl)ethoxy]carbonyl}phenyl) oxalate.
Figure 28:
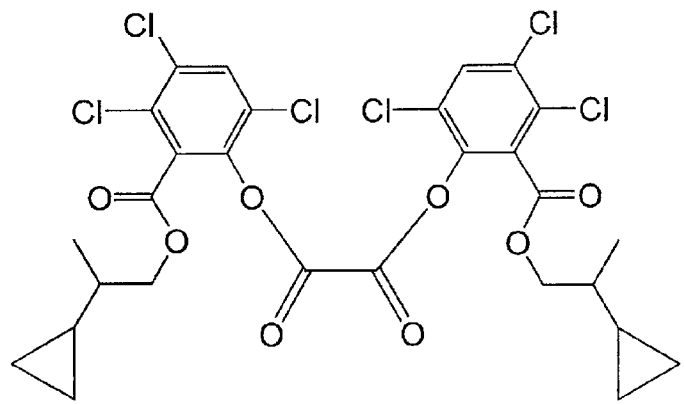
FIG. 28 illustrates a bis{3,4,6-trichloro-2-[(2-cyclopropylpropoxy)carbonyl]phenyl}oxalate.
Figure 29:
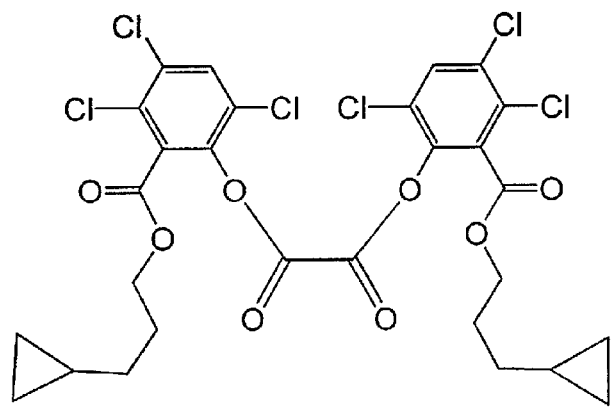
FIG. 29 illustrates a bis{3,4,6-trichloro-2-[(3-cyclopropylpropoxy)carbonyl]phenyl}oxalate.
Figure 30:
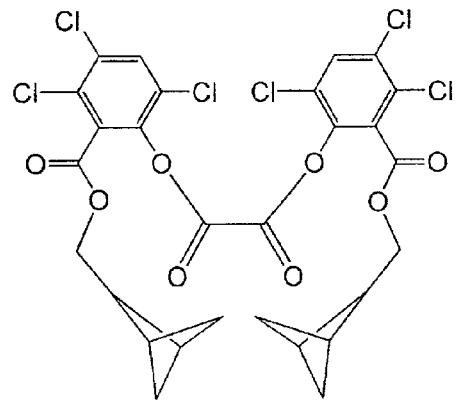
FIG. 30 illustrates a bis{2-[(bicyclo[1.1.1]pentan-5-ylmethoxy)carbonyl]-3,4,6-trichlorophenyl}oxalate.
Figure 31:
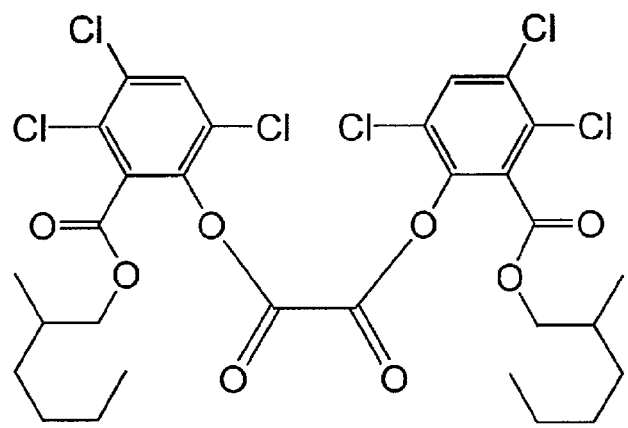
FIG. 31 illustrates a bis{3,4,6-trichloro-2-[(2-methylhexyloxy)carbonyl]phenyl}oxalate.
Figure 32:
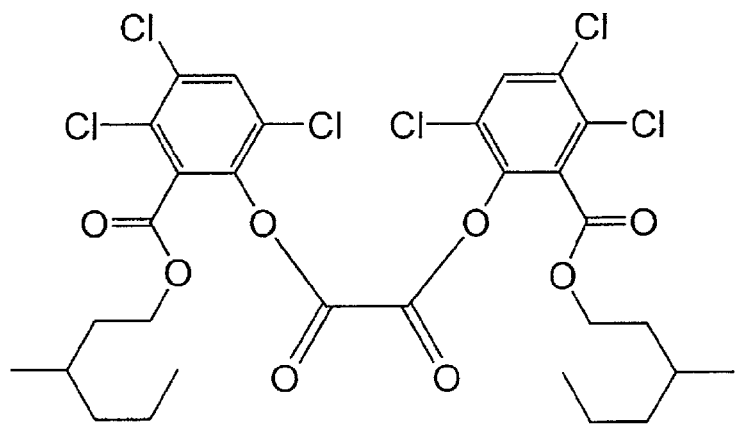
FIG. 32 illustrates a bis{3,4,6-trichloro-2-[(3-methylhexyloxy)carbonyl]phenyl}oxalate.
Figure 33:
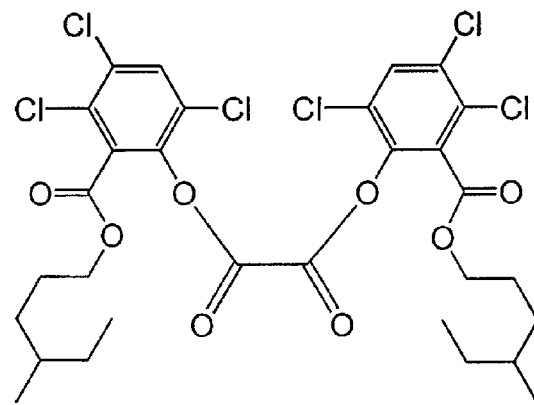
FIG. 33 illustrates a bis{3,4,6-trichloro-2-[(4-methylhexyloxy)carbonyl]phenyl}oxalate.
Figure 34:
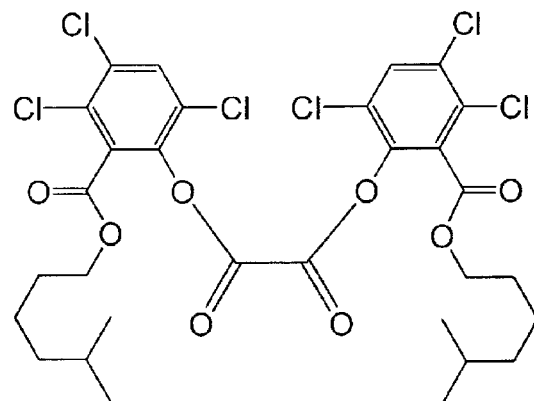
FIG. 34 illustrates a bis{3,4,6-trichloro-2-[(5-methylhexyloxy)carbonyl]phenyl}oxalate.
Figure 35:
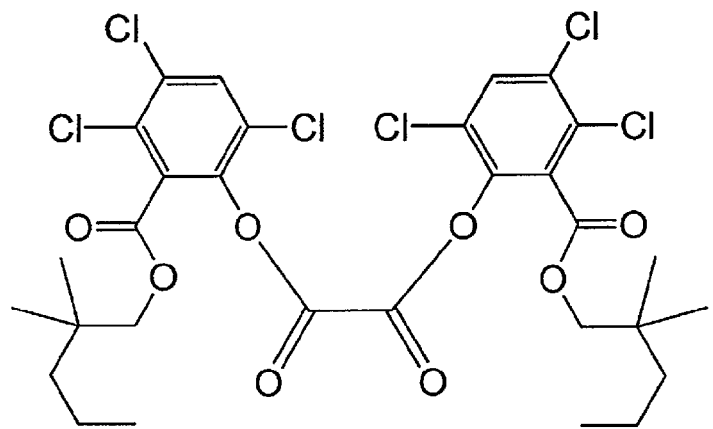
FIG. 35 illustrates a bis{3,4,6-trichloro-2-[(2,2-dimethylpentyloxy)carbonyl]phenyl}oxalate.
Figure 36:
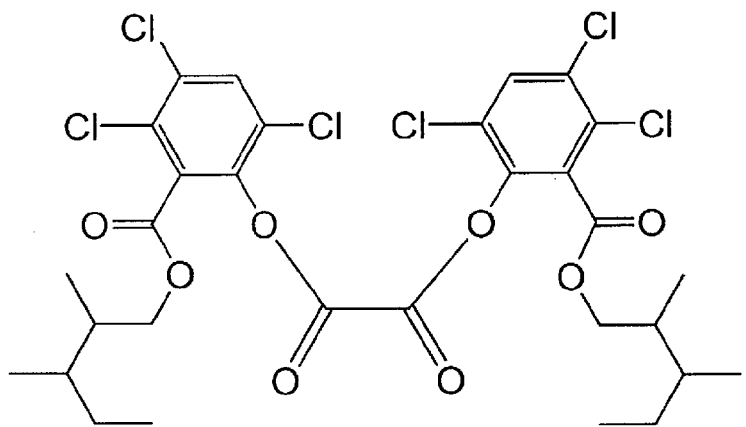
FIG. 36 illustrates a bis{3,4,6-trichloro-2-[(2,3-dimethylpentyloxy)carbonyl]phenyl}oxalate.
Figure 37:
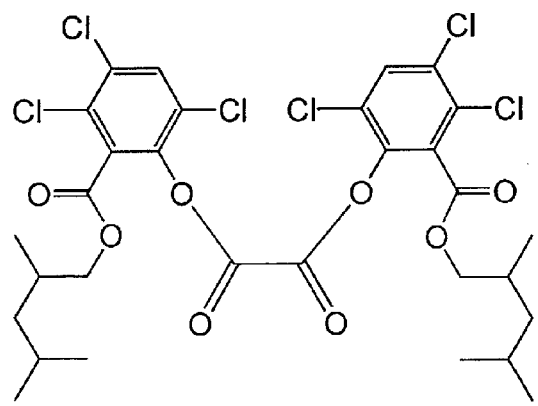
FIG. 37 illustrates a bis{3,4,6-trichloro-2-[(2,4-dimethylpentyloxy)carbonyl]phenyl}oxalate.
Figure 38:
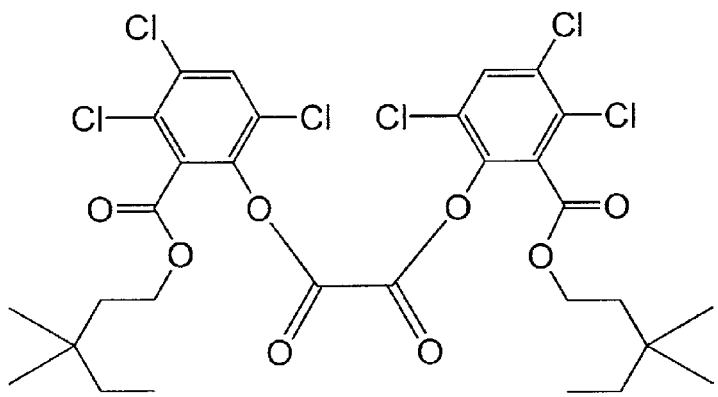
FIG. 38 illustrates a bis{3,4,6-trichloro-2-[(3,3-dimethylpentyloxy)carbonyl]phenyl}oxalate.
Figure 39:
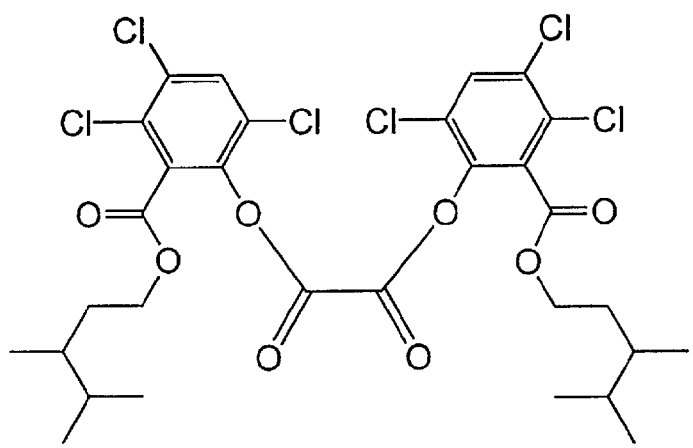
FIG. 39 illustrates a bis{3,4,6-trichloro-2-[(3,4-dimethylpentyloxy)carbonyl]phenyl}oxalate.
Figure 40:
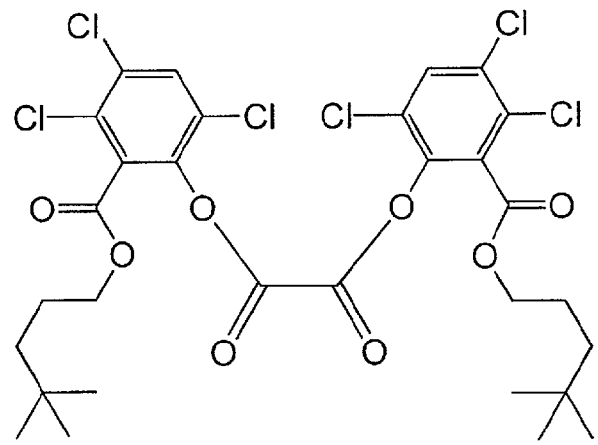
FIG. 40 illustrates a bis{3,4,6-trichloro-2-[(4,4-dimethylpentyloxy)carbonyl]phenyl}oxalate.
Figure 41:
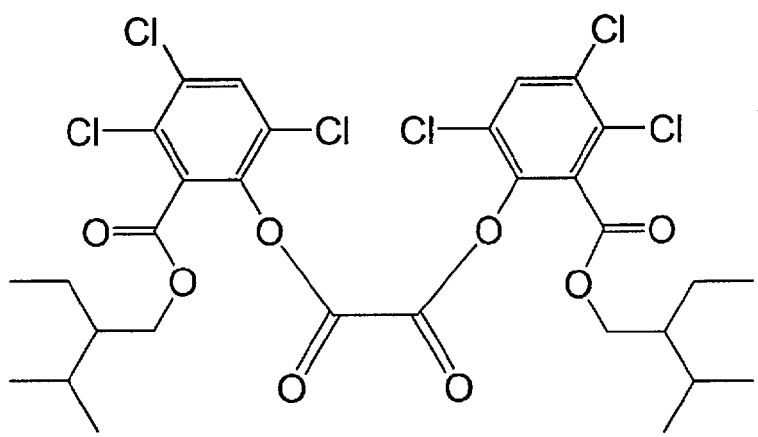
FIG. 41 illustrates a bis{3,4,6-trichloro-2-[(2-ethyl-3-methylbutoxy)carbonyl]phenyl}oxalate.
Figure 42:
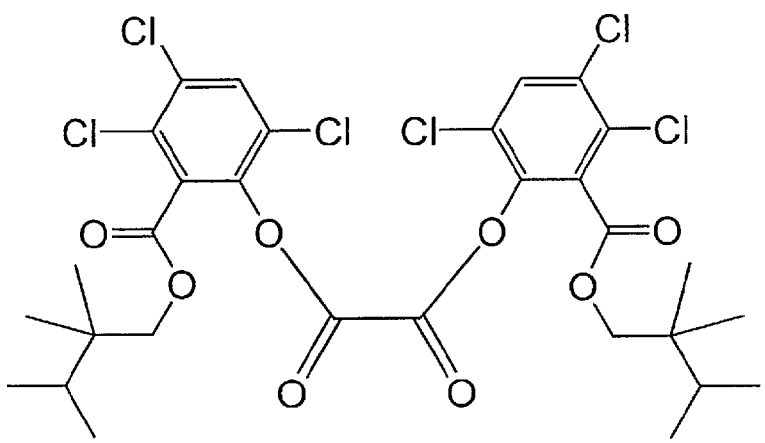
FIG. 42 illustrates a bis{3,4,6-trichloro-2-[(2,2,3-trimethylbutoxy)carbonyl]phenyl}oxalate.
Figure 43:
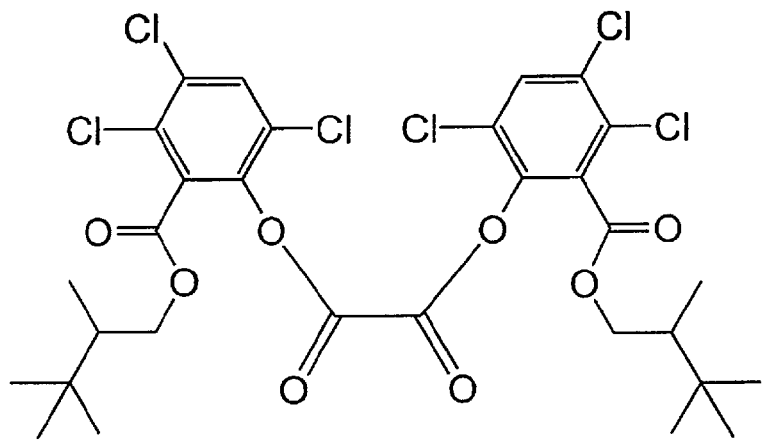
FIG. 43 illustrates a his {3,4,6-trichloro-2-[(2,3,3-trimethylbutoxy)carbonyl]phenyl}oxalate.
Figure 44:
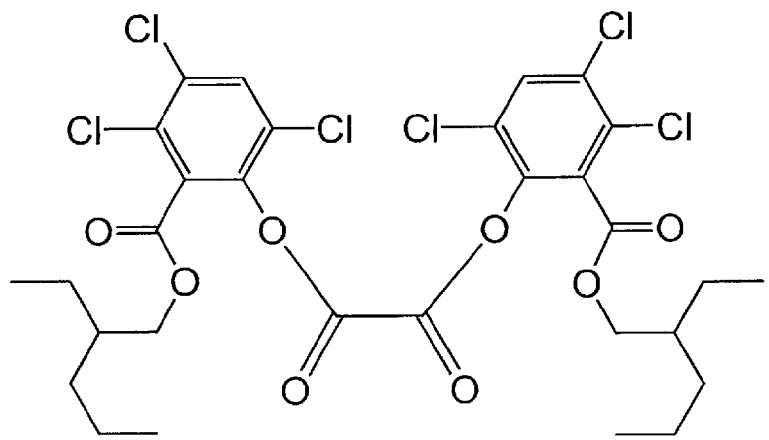
FIG. 44 illustrates a bis{3,4,6-trichloro-2-[(2-ethylpentyloxy)carbonyl]phenyl}oxalate.
Figure 45:
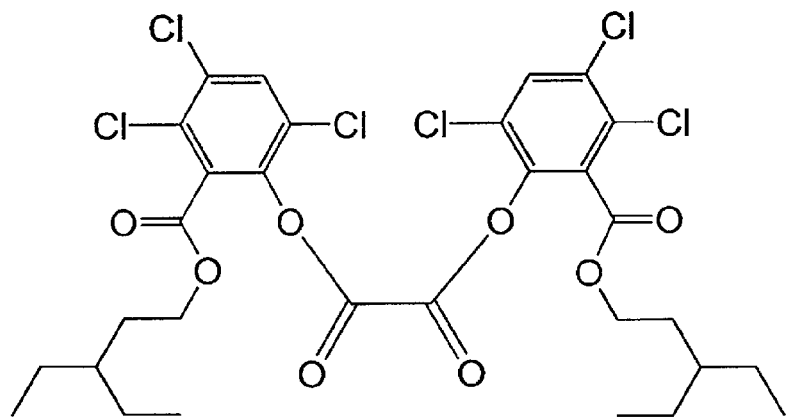
FIG. 45 illustrates a bis{3,4,6-trichloro-2-[(3-ethylpentyloxy)carbonyl]phenyl}oxalate.
Figure 46:
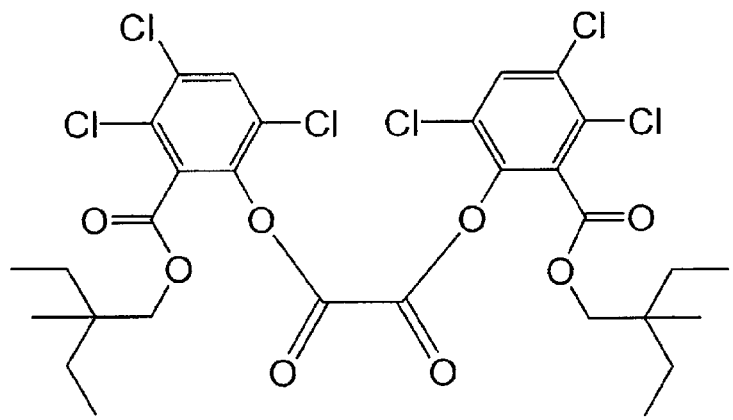
FIG. 46 illustrates a bis{3,4,6-trichloro-2-[(2-ethyl-2-methylbutoxy)carbonyl]phenyl}oxalate.

Procedure For Producing Bis{3,4,6-Trichloro-2-[(2,2-Dimethylpropoxy)Carbonyl]Phenyl}Oxalate (FIG. 5)

The first step for making 2,2-dimethylpropyl 3,4,6-trichlorosalicylate, was carried out in xylene using the procedure found in Example 2. The yield was 310 g (99%). The material was analyzed by HPLC and used without further purification in the next step.

Bis{3,4,6-trichloro-2-[(2,2-dimethylpropoxy)carbonyl]phenyl}oxalate can be made using processes described in Example 1. The yield was 180.1 g (53%).

This method was used for the compounds shown in FIGS. 9, 13, 26-29, 35, 51, 60-69, 71-84, 92, 105, 107, 116, 118-119, 126, 138-142, 156-181, 192-224, 226, 236, 255-258, 283-285, 287-288, 295, 303, 305, 307, 311-315, 324, 328-334, 338, 342-345, 348-351, 358, 360, 363, 366-367, 371-391, 396-402, 406-407, 410, 412-413, 416, 419-422, 426, 429-430, 435-617, 628-632, 644, 649-652, 654, 657, and 660.

Additionally, a tertiary amine other than triethylamine can be used, including tripropyl amine, tri-n-butyl amine, tri-isobutylamine, triisopropylamine, triisopentylamine, and N,N-diisopropylethyl amine.

Example 4

Figure 47:
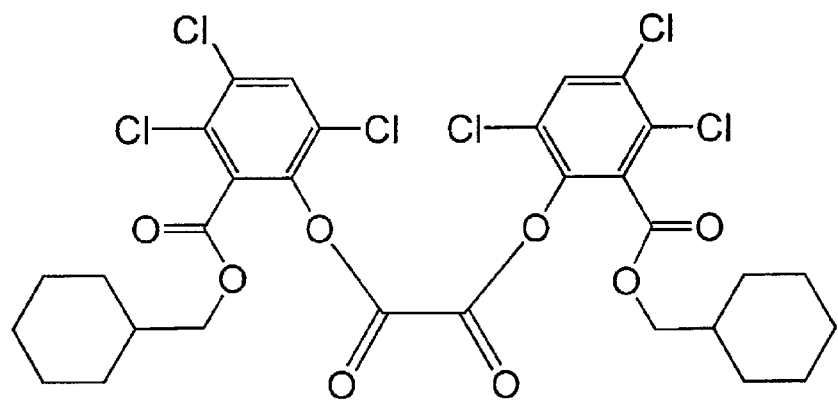
FIG. 47 illustrates a bis{3,4,6-trichloro-2-[(cyclohexylmethoxy)carbonyl]phenyl}oxalate.
Figure 48:
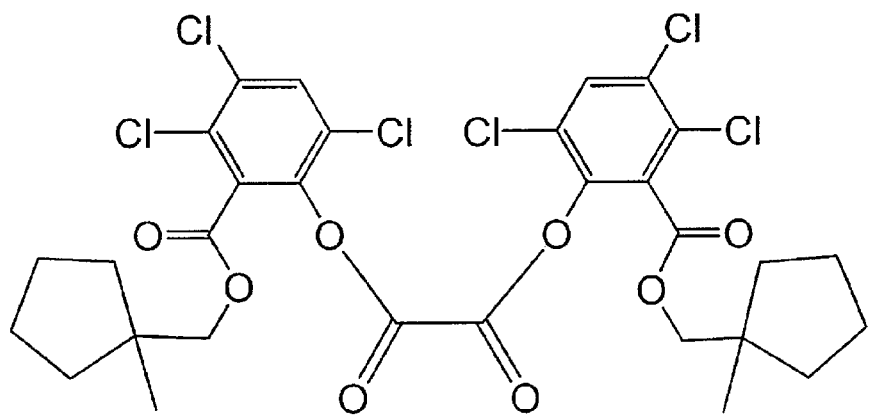
FIG. 48 illustrates a bis(3,4,6-trichloro-2-{[(1-methylcyclopentyl)methoxy]carbonyl}phenyl) oxalate.
Figure 49:
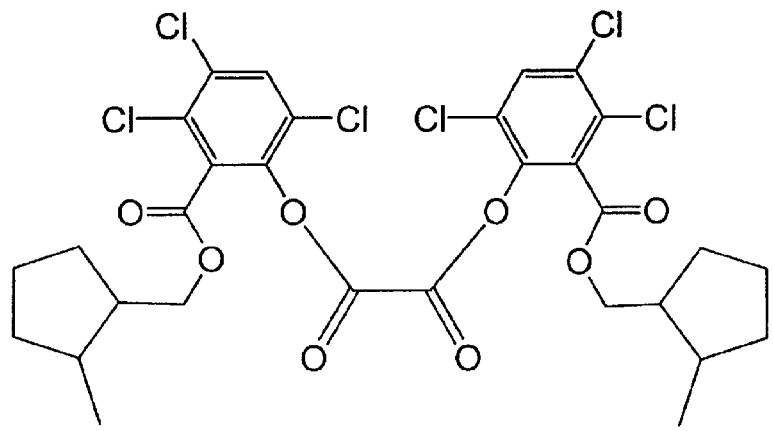
FIG. 49 illustrates a bis(3,4,6-trichloro-2-{[(2-methylcyclopentyl)methoxy]carbonyl}phenyl) oxalate.
Figure 50:
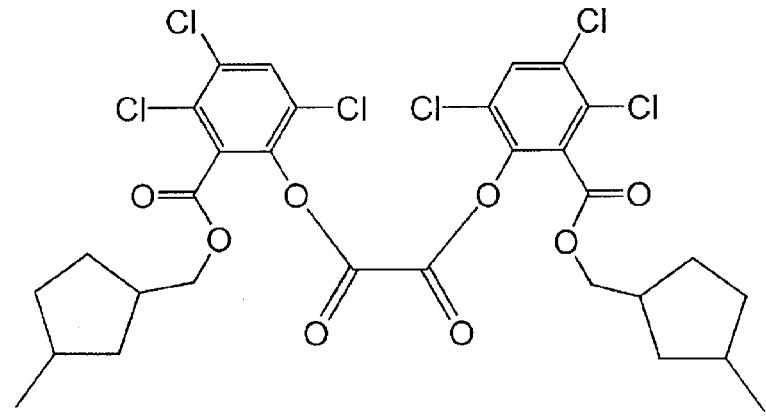
FIG. 50 illustrates a bis(3,4,6-trichloro-2-{[(3-methylcyclopentyl)methoxy]carbonyl}phenyl) oxalate.
Figure 51:
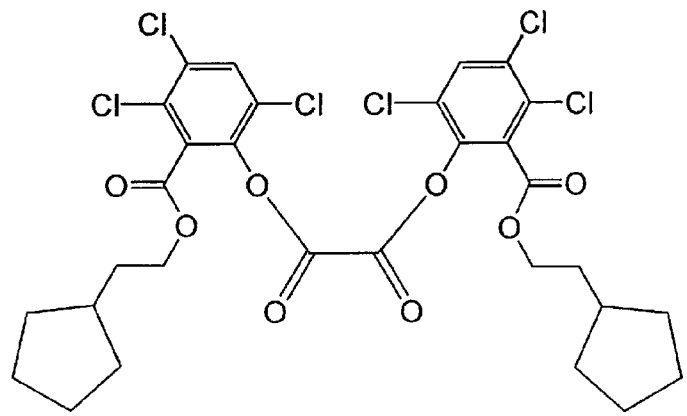
FIG. 51 illustrates a bis{3,4,6-trichloro-2-[(2-cyclopentylethoxy)carbonyl]phenyl}oxalate.
Figure 52:
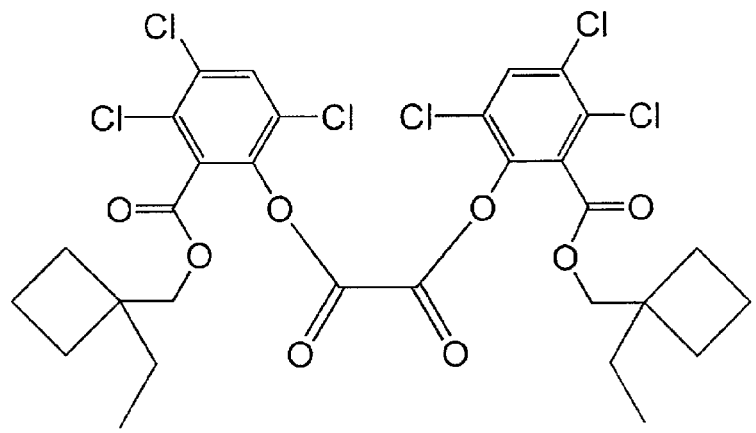
FIG. 52 illustrates a bis(3,4,6-trichloro-2-{[(1-ethylcyclobutyl)methoxy]carbonyl}phenyl) oxalate.
Figure 53:
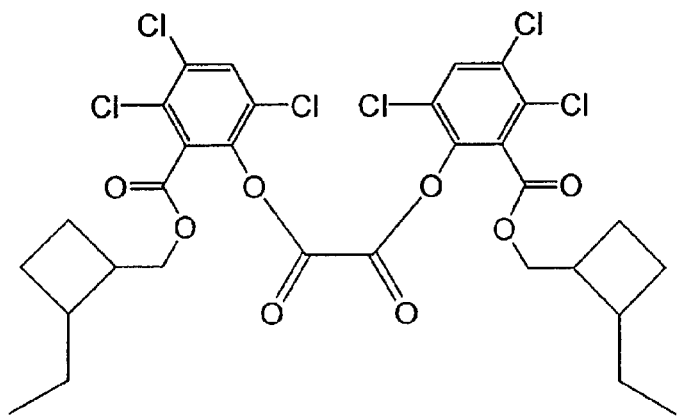
FIG. 53 illustrates a bis(3,4,6-trichloro-2-{[(2-ethylcyclobutyl)methoxy]carbonyl}phenyl) oxalate.
Figure 54:
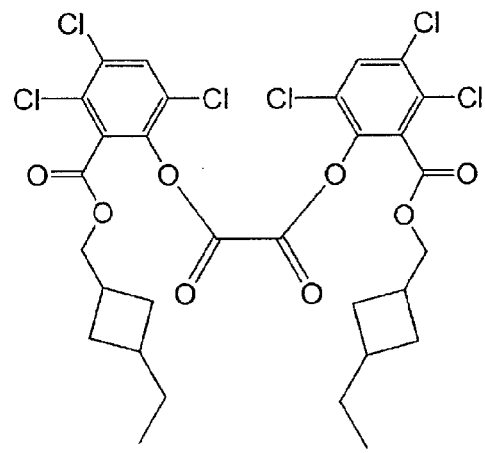
FIG. 54 illustrates a bis(3,4,6-trichloro-2-{[(3-ethylcyclobutyl)methoxy]carbonyl}phenyl) oxalate.
Figure 55:
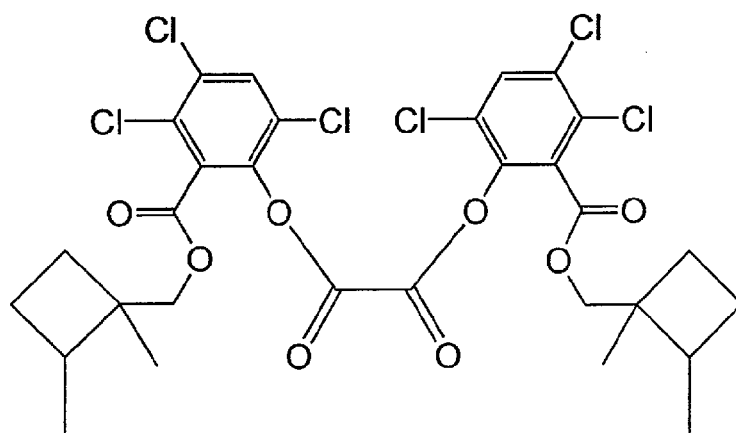
FIG. 55 illustrates a bis(3,4,6-trichloro-2-{[(1,2-dimethylcyclobutyl)methoxy]carbonyl}phenyl) oxalate.
Figure 56:
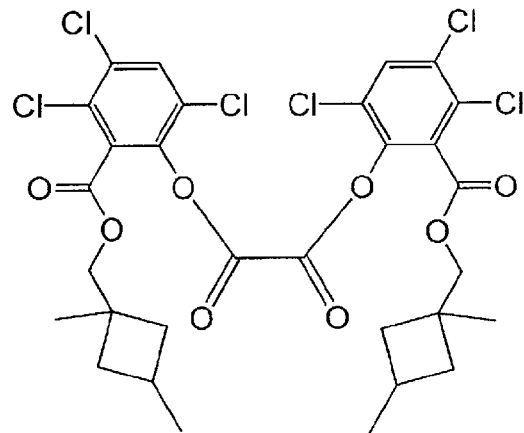
FIG. 56 illustrates a bis(3,4,6-trichloro-2-{[(1,3-dimethylcyclobutyl)methoxy]carbonyl}phenyl) oxalate.
Figure 57:
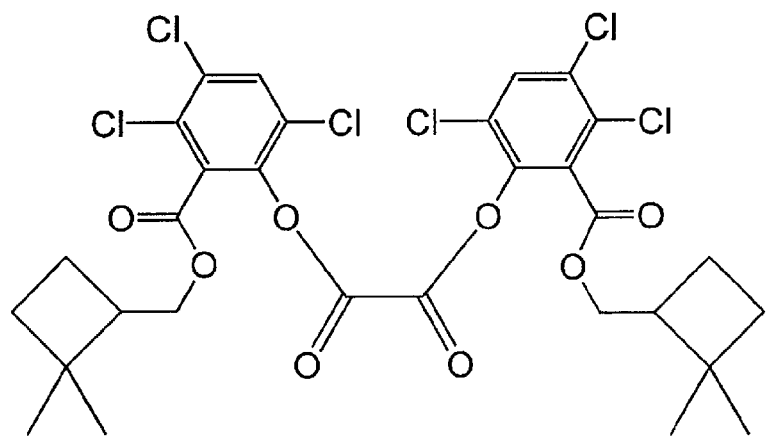
FIG. 57 illustrates a bis(3,4,6-trichloro-2-{[(2,2-dimethylcyclobutyl)methoxy]carbonyl}phenyl) oxalate.
Figure 58:
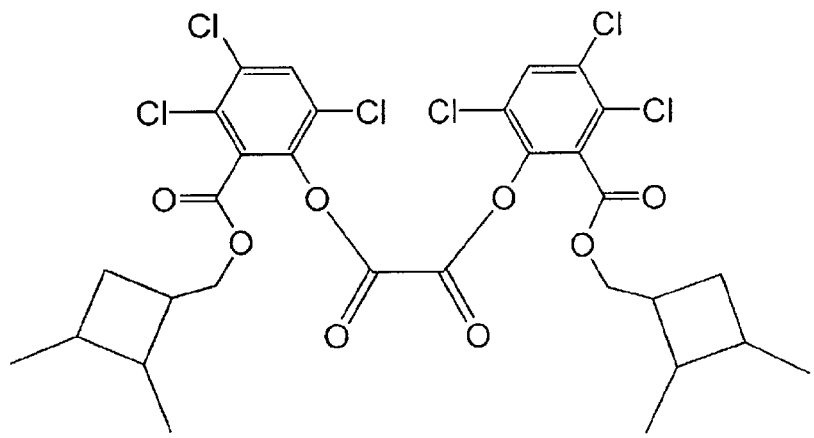
FIG. 58 illustrates a bis(3,4,6-trichloro-2-{[(2,3-dimethylcyclobutyl)methoxy]carbonyl}phenyl) oxalate.
Figure 59:
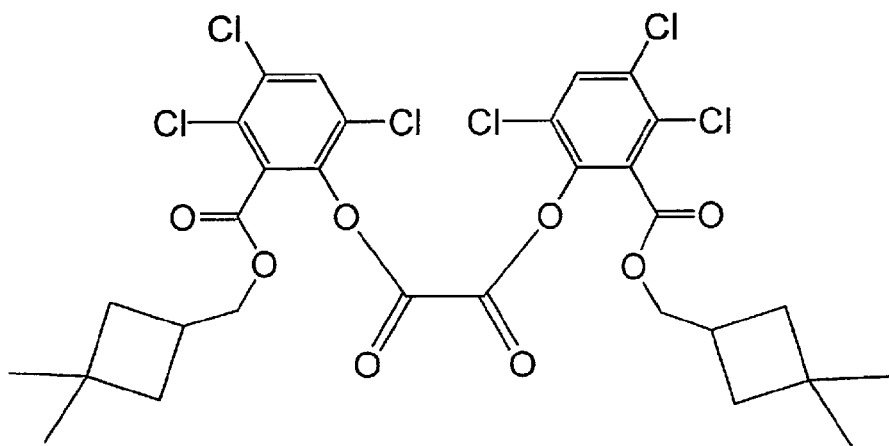
FIG. 59 illustrates a bis(3,4,6-trichloro-2-{[(3,3-dimethylcyclobutyl)methoxy]carbonyl}phenyl) oxalate.
Figure 60:
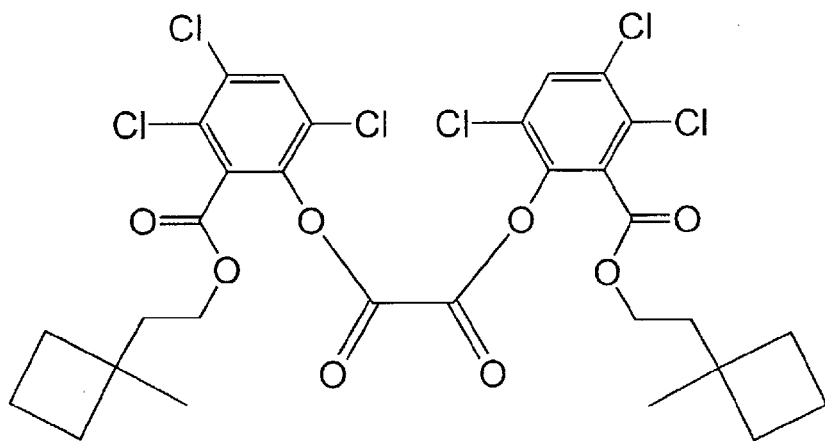
FIG. 60 illustrates a bis(3,4,6-trichloro-2-{[2-(1-methylcyclobutyl)ethoxy]carbonyl}phenyl) oxalate.
Figure 61:
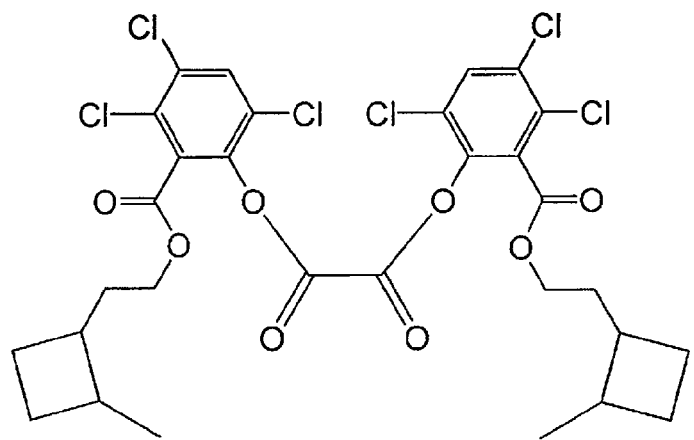
FIG. 61 illustrates a bis(3,4,6-trichloro-2-{[2-(2-methylcyclobutyl)ethoxy]carbonyl}phenyl) oxalate.
Figure 62:
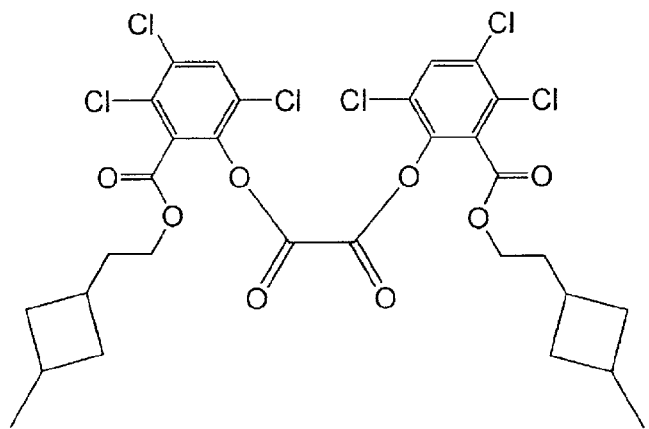
FIG. 62 illustrates a bis(3,4,6-trichloro-2-{[2-(3-methylcyclobutyl)ethoxy]carbonyl}phenyl) oxalate.
Figure 63:
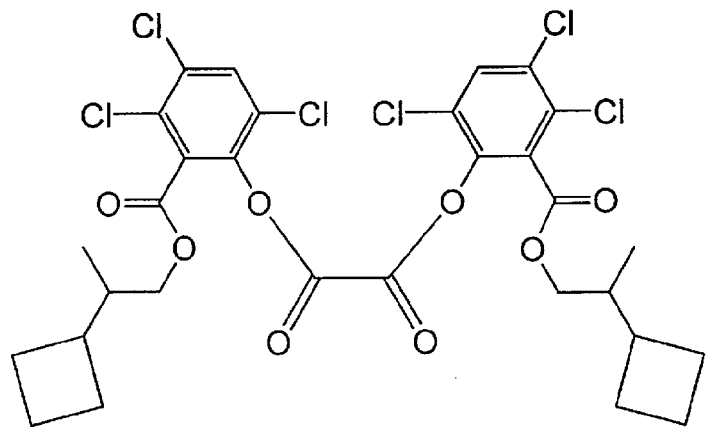
FIG. 63 illustrates a bis{3,4,6-trichloro-2-[(2-cyclobutylpropoxy)carbonyl]phenyl}oxalate.
Figure 64:
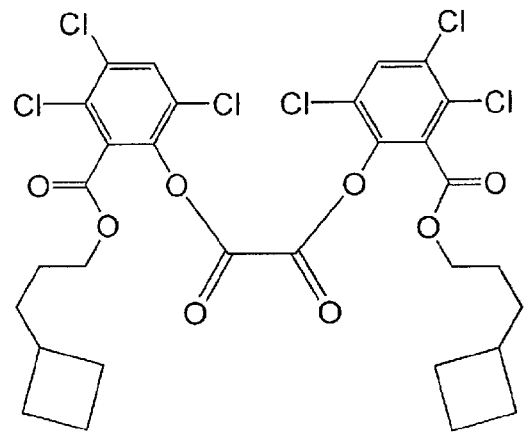
FIG. 64 illustrates a bis{3,4,6-trichloro-2-[(3-cyclobutylpropoxy)carbonyl]phenyl}oxalate.
Figure 65:
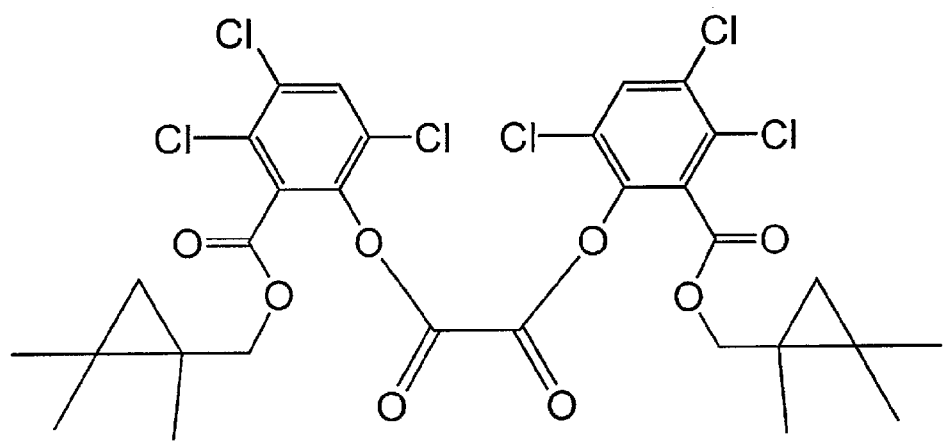
FIG. 65 illustrates a bis(3,4,6-trichloro-2-{[(1,2,2-trimethylcyclopropyl)methoxy]carbonyl}phenyl) oxalate.
Figure 66:
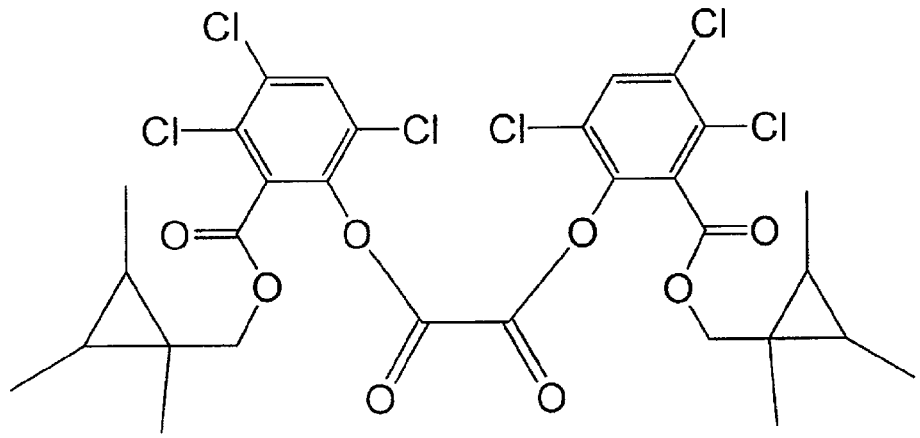
FIG. 66 illustrates a bis(3,4,6-trichloro-2-{[(1,2,3-trimethylcyclopropyl)methoxy]carbonyl}phenyl) oxalate.
Figure 67:
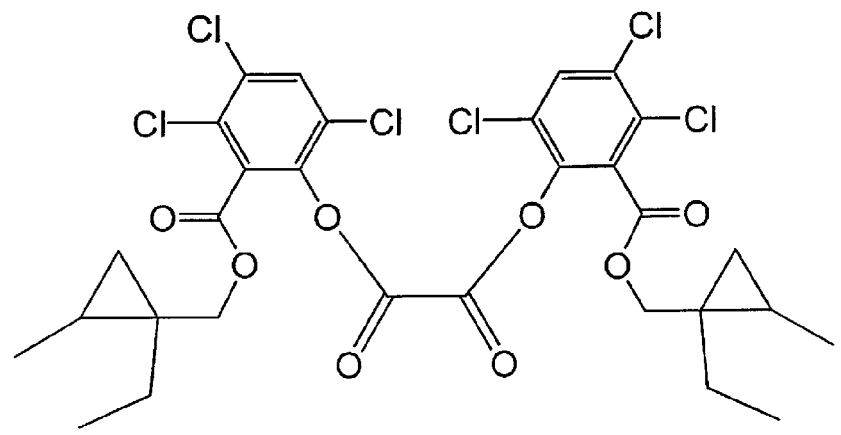
FIG. 67 illustrates a bis(3,4,6-trichloro-2-{[(1-ethyl-2-methylcyclopropyl)methoxy]carbonyl}phenyl) oxalate.
Figure 68:
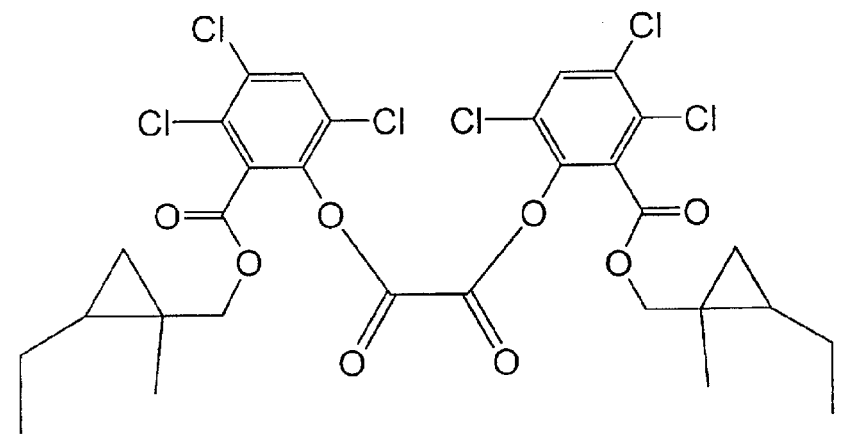
FIG. 68 illustrates a bis(3,4,6-trichloro-2-{[(2-ethyl-1-methylcyclopropyl)methoxy]carbonyl}phenyl) oxalate.
Figure 69:
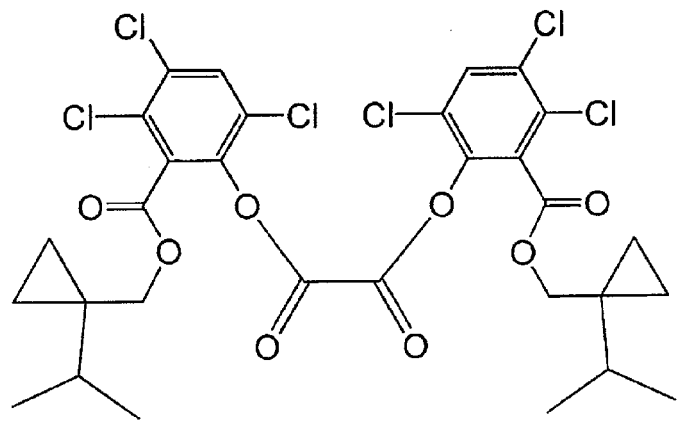
FIG. 69 illustrates a bis[3,4,6-trichloro-2-({[1-(1-methylethyl)cyclopropyl]methoxy}carbonyl)phenyl]oxalate.
Figure 70:
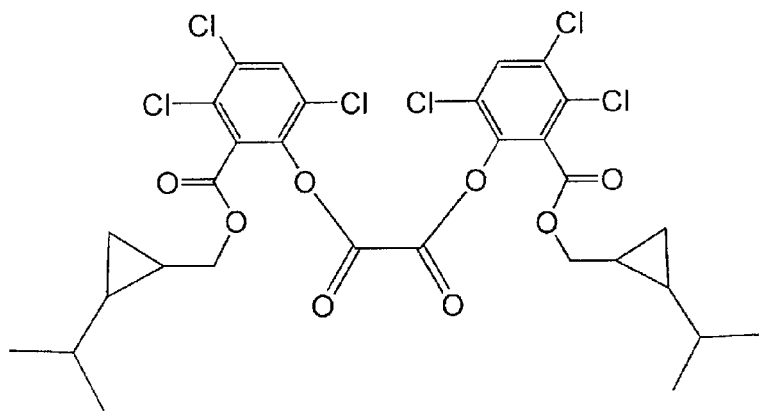
FIG. 70 illustrates a bis[3,4,6-trichloro-2-({[2-(1-methylethyl)cyclopropyl]methoxy}carbonyl)phenyl]oxalate.
Figure 71:
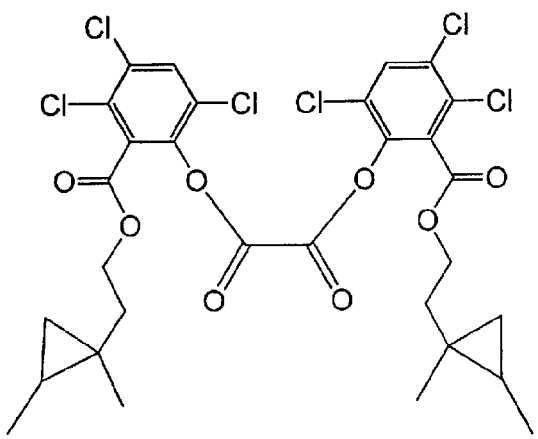
FIG. 71 illustrates a bis(3,4,6-trichloro-2-{[2-(1,2-dimethylcyclopropyl)ethoxy]carbonyl}phenyl) oxalate.
Figure 72:
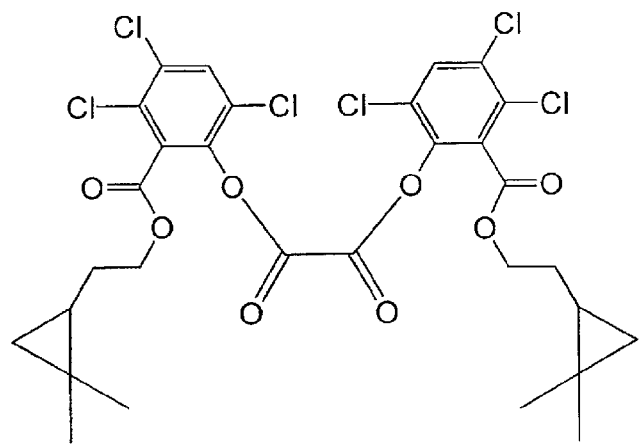
FIG. 72 illustrates a bis(3,4,6-trichloro-2-{[2-(2,2-dimethylcyclopropyl)ethoxy]carbonyl}phenyl) oxalate.
Figure 73:
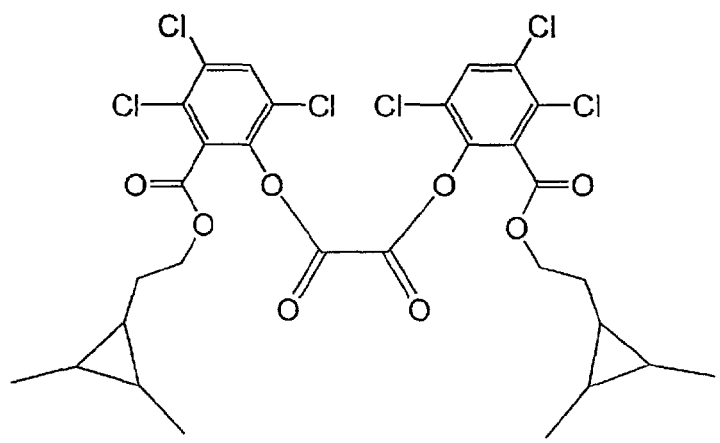
FIG. 73 illustrates a bis(3,4,6-trichloro-2-{[2-(2,3-dimethylcyclopropyl)ethoxy]carbonyl}phenyl) oxalate.
Figure 74:
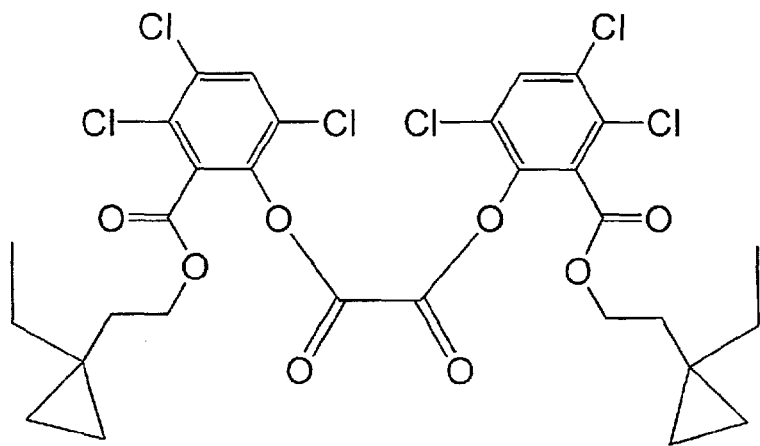
FIG. 74 illustrates a bis(3,4,6-trichloro-2-{[2-(1-ethylcyclopropyl)ethoxy]carbonyl}phenyl) oxalate.
Figure 75:
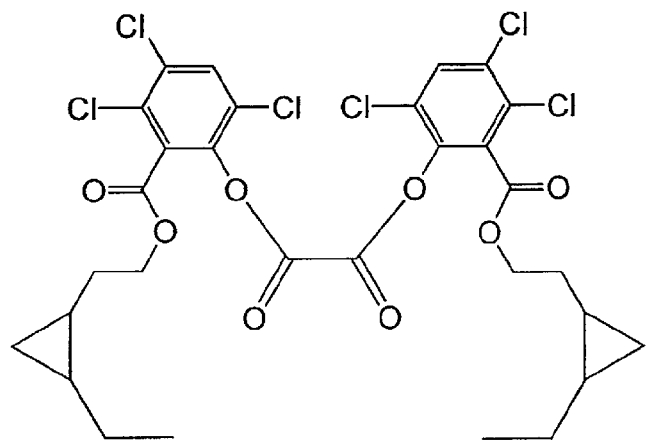
FIG. 75 illustrates a bis(3,4,6-trichloro-2-{[2-(2-ethylcyclopropyl)ethoxy]carbonyl}phenyl) oxalate.
Figure 76:
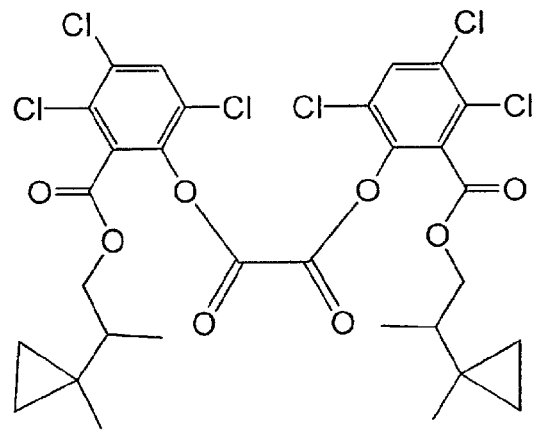
FIG. 76 illustrates a bis(3,4,6-trichloro-2-{[2-(1-methylcyclopropyl)propoxy]carbonyl}phenyl) oxalate.
Figure 77:
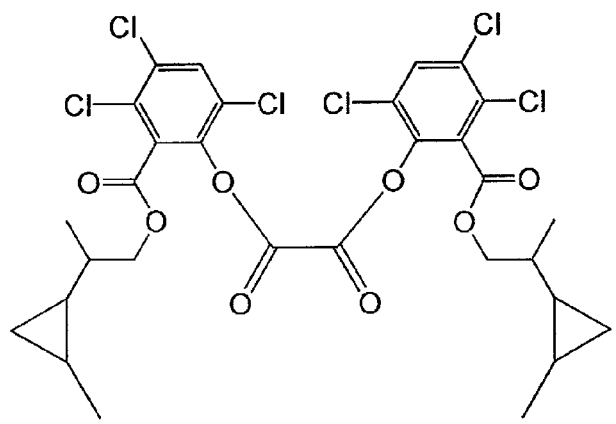
FIG. 77 illustrates a bis(3,4,6-trichloro-2-{[2-(2-methylcyclopropyl)propoxy]carbonyl}phenyl) oxalate.
Figure 78:
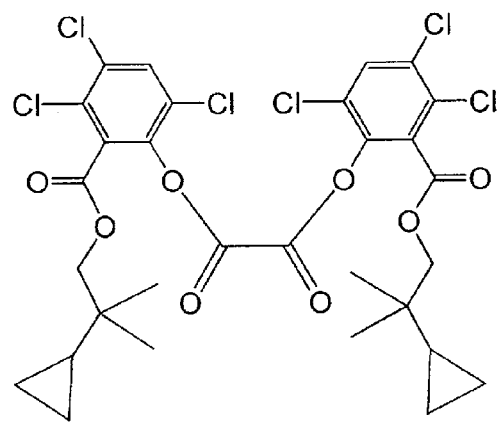
FIG. 78 illustrates a bis{3,4,6-trichloro-2-[(2-cyclopropyl-2-methylpropoxy)carbonyl]phenyl}oxalate.
Figure 79:
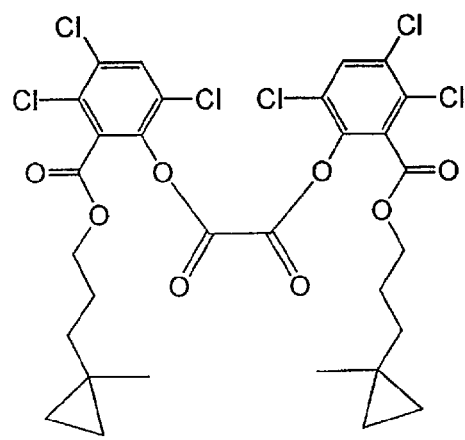
FIG. 79 illustrates a bis(3,4,6-trichloro-2-{[3-(1-methylcyclopropyl)propoxy]carbonyl}phenyl) oxalate.
Figure 80:
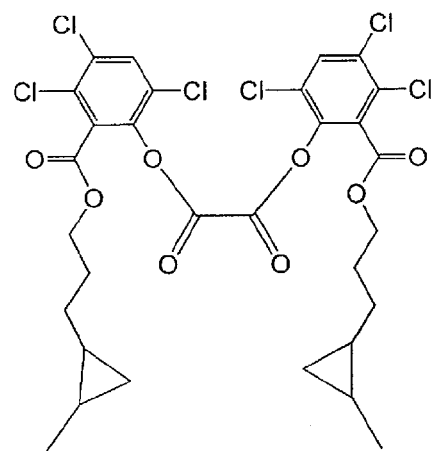
FIG. 80 illustrates a bis(3,4,6-trichloro-2-{[3-(2-methylcyclopropyl)propoxy]carbonyl}phenyl) oxalate.
Figure 81:
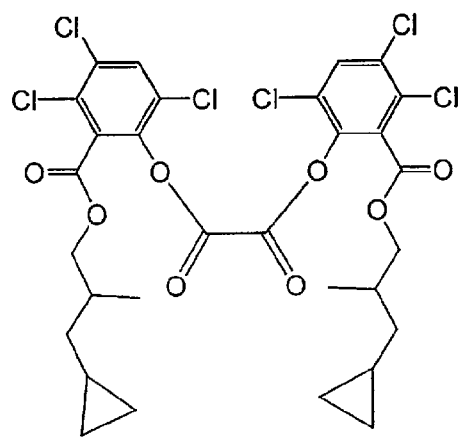
FIG. 81 illustrates a bis{3,4,6-trichloro-2-[(3-cyclopropyl-2-methylpropoxy)carbonyl]phenyl}oxalate.
Figure 82:
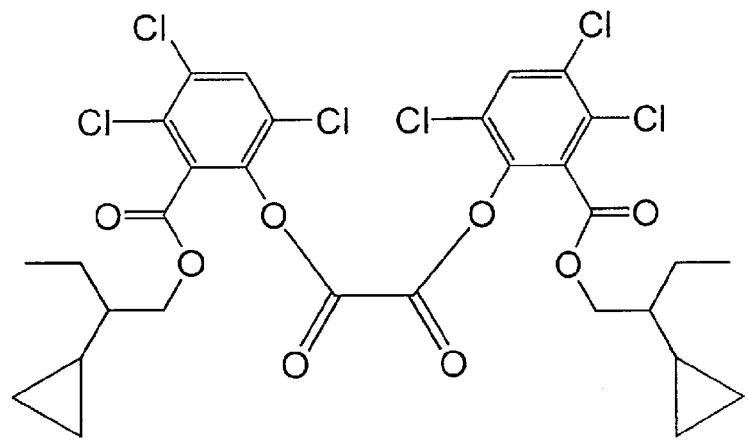
FIG. 82 illustrates a bis{3,4,6-trichloro-2-[(2-cyclopropylbutoxy)carbonyl]phenyl}oxalate.
Figure 83:
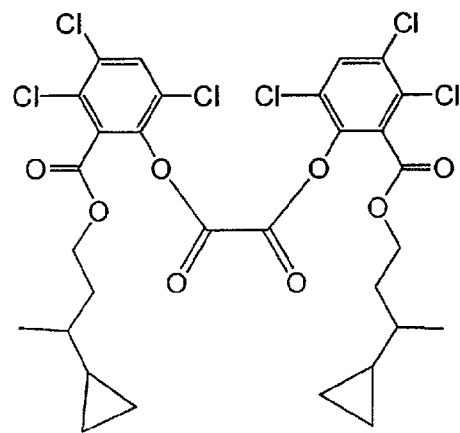
FIG. 83 illustrates a bis{3,4,6-trichloro-2-[(3-cyclopropylbutoxy)carbonyl]phenyl}oxalate.
Figure 84:
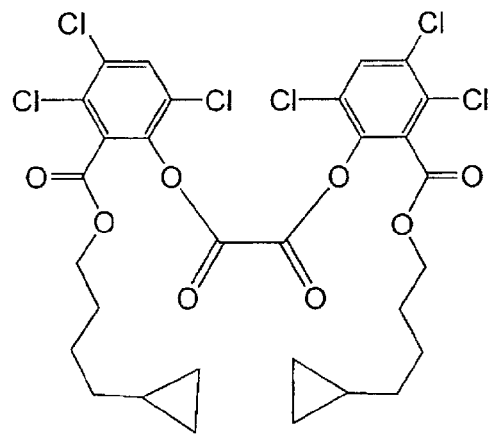
FIG. 84 illustrates a bis{3,4,6-trichloro-2-[(4-cyclopropylbutoxy)carbonyl]phenyl}oxalate.
Figure 85:
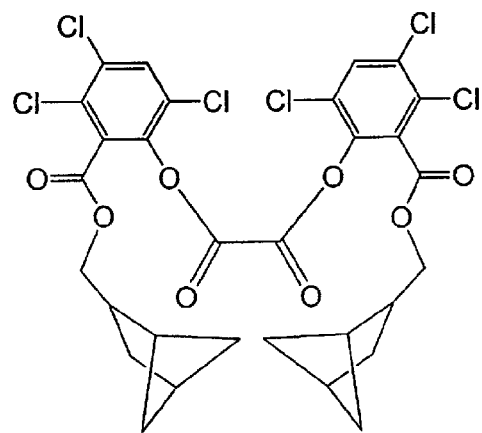
FIG. 85 illustrates a bis{2-[(bicyclo[2.1.1]hexan-2-ylmethoxy)carbonyl]-3,4,6-trichlorophenyl}oxalate.

Procedure For Producing Bis{3,4,6-Trichloro-2-[(Cyclohexylmethoxy)Carbonyl]Phenyl}Oxalate (FIG. 47)

The 3,4,6-trichlorosalicylic acid (178.7 g, 0.74 mole) was placed in a 2 L 3-necked flask equipped with a mechanical stirrer and a Dean-Stark trap with an efficient reflux condenser. Xylene (490 mL), cyclohexylmethanol (100.2 mL, 0.81 mole), and titanium oxide bis(acetylacetonate) (2.9 g, 11 mmol) were added in the indicated order. The reaction mixture was heated at reflux overnight, and the water removed from the Dean-Stark trap. The reaction product was cooled to 35° C. and 500 mL of saturated sodium bicarbonate solution was added. The mixture was stirred for 2 hours. Material started to come out of solution after ½ hour. Ethyl acetate (800 mL) was added, which dissolved the ester, and stirring was continued. The layers were separated, washed with brine, and dried with MgSO4. The organic layer was filtered and concentrated under reduced pressure. Once all of the material had been concentrated, an aliquot of xylene was added and removed under reduced pressure to ensure complete removal of any excess alcohol and water. The yield was 248 g (99%). The material was analyzed by HPLC and used without further purification in the next step.

Bis{3,4,6-trichloro-2-[(cyclohexylmethoxy)carbonyl]phenyl}oxalate can be made using processes described Example 1. The yield using the product from the step above was 153.8 g (57%).

This method was used for the compounds shown in FIGS. 2, 6-8, 17-25, 30, 47-50, 52-59, 70, 85, 121-125, 127-137, 143-155, 182-191, 225, 306, 308-310, 316-323, 325-327, 335-337, 339-341, 346-347, 352-357, 359, 361-362, 364-365, 368-370, 392-395, 403-405, 408-409, 411, 414-415, 417-418, 423-425, 427-428, 431-434, 618-619, 645, and 653.

Additionally, a tertiary amine other than triethylamine can be used, including tripropyl amine, tri-n-butyl amine, tri-isobutylamine, triisopropylamine, triisopentylamine, and N,N-diisopropylethyl amine.

Example 5

Bis{3,4,6-trichloro-2-[(pentoxy)carbonyl]phenyl}oxalate, a straight chain oxalate ester, and bis{3,5,6-trichloro-2-[(3-methylbutoxy)carbonyl]phenyl}oxalate made via the route described in Example 1, were examined. Both materials were placed within open glass bottles and stored in a cabinet in a room where the humidity was maintained at 50%+/−5% Relative Humidity. Within two weeks the bis{3,4,6-trichloro-2-[(pentoxy)carbonyl]phenyl}oxalate had changed significantly in physical appearance. HPLC analysis revealed that this material had reverted to n-pentyl trichlorosalicylic acid. Compounding this material into an oxalate solution and admixing with an activator solution resulted in no light. The bis{3,5,6-trichloro-2-[(3-methylbutoxy)carbonyl]phenyl}oxalate was also compounded into an oxalate solution and admixed with an activator solution resulting in the generation of light.

Example 6

Bis{3,4,6-trichloro-2-[(pentoxy)carbonyl]phenyl}oxalate, a straight chain oxalate ester was made via the route described in Example 1. Bis{3,5,6-trichloro-2[(benzylmethoxy)carbonyl]phenyl}oxalate was made via the route described in Example 2. Both materials were placed within open glass bottles and stored in a cabinet in a room where the humidity was maintained at 50%+/−5% Relative Humidity. Within two weeks the bis{3,4,6-trichloro-2-[(pentoxy)carbonyl]phenyl}oxalate had changed significantly in physical appearance. HPLC analysis revealed that this material had reverted to n-pentyl trichlorosalicylic acid. Compounding this material into an oxalate solution and admixing with an activator solution resulted in no light. The bis{3,5,6-trichloro-2[(benzylmethoxy)carbonyl]phenyl}oxalate was also compounded into an oxalate solution and admixed with an activator solution resulting in the generation of light.

Example 7

Bis{3,4,6-trichloro-2-[(pentoxy)carbonyl]phenyl}oxalate, a straight chain oxalate ester, and bis{3,5,6-trichloro-2-[(2-methylbutoxy)carbonyl]phenyl}oxalate were made via the route described in Example 1. Both materials were placed within open glass bottles and stored in a cabinet in a room where the humidity was maintained at 50%+/−5% Relative Humidity Within two weeks the bis{3,4,6-trichloro-2-[(pentoxy)carbonyl]phenyl}oxalate had changed significantly in physical appearance. HPLC analysis revealed that this material had reverted to n-pentyl trichlorosalicylic acid.

Compounding this material into an oxalate solution and admixing with an activator solution resulted in no light. Bis{3,5,6-trichloro-2-[(2-methylbutoxy)carbonyl]phenyl}oxalate was also compounded into an oxalate solution and admixed with an activator solution resulting in the generation of light.

Example 8

Bis{3,4,6-trichloro-2-[(pentoxy)carbonyl]phenyl}oxalate was made via the route described in Example 1. Bis{3,4,6-trichloro-2-[(cyclohexylmethoxy)carbonyl]phenyl}oxalate was made via the route described in Example 4. Both materials were placed within open glass bottles and stored in a cabinet in a room where the humidity was maintained at 50%+/−5% Relative Humidity. Within two weeks the bis{3,4,6-trichloro-2-[(pentoxy)carbonyl]phenyl}oxalate had changed significantly in physical appearance. HPLC analysis revealed that this material had reverted to n-pentyl trichlorosalicylic acid. Compounding this material into an oxalate solution and admixing with an activator solution resulted in no light. The bis{3,4,6-trichloro-2-[(cyclohexylmethoxy)carbonyl]phenyl}oxalate was also compounded into an oxalate solution and admixed with an activator solution resulting in the generation of light.

Chemical light systems, also known as chemiluminescent systems, for production of a chemiluminescent light, generally utilize a two-component system to chemically generate light. Chemiluminescent light is produced by combining the two components, which are usually in the form of chemical solutions referred to as the "oxalate" component and the "activator" component. All suitable activator compositions, inclusive of the various additional fluorescers, catalysts and the like, known to be useful in the prior art, are contemplated for use with the branched chain oxalate species of the present invention.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:
1. A branched chain oxalic acid ester represented by the general formula:

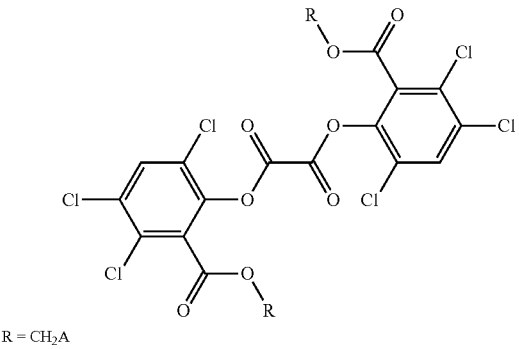

R = CH$_2$A wherein the group designated as R contains from 4-15 carbons,
wherein the carbon of attachment of R to the oxygen is via a primary carbon, and wherein substructure A is composed of substituents selected from the group including alkyl chains, alkyl rings, aromatic rings and combinations thereof such that R is nonlinear, said branched chain oxalic acid ester being selected from the group consisting of bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-trichloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,4,6-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl) oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2- ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]carbonyl}phenyl) oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

2. The branched chain oxalic acid ester of claim 1, having the formula:
bis{3,4,6-trichloro-2-[(2-methylpropoxy)carbonyl]phenyl}oxalate.

3. The branched chain oxalic acid ester of claim 1, having the formula:
bis{3,4,6-trichloro-2-[(cyclopropylmethoxy)carbonyl]phenyl}oxalate.

4. The branched chain oxalic acid ester of claim 1, having the formula:
bis{3,4,6-trichloro-2-[(2-methylbutoxy)carbonyl]phenyl}oxalate.

5. The branched chain oxalic acid ester of claim 1, having the formula:
bis{3,4,6-trichloro-2-[(2,2-dimethylpropoxy)carbonyl]phenyl}oxalate.

6. The branched chain oxalic acid ester of claim 1, having the formula:
bis{3,4,6-trichloro-2-[(2-methylpentyloxy)carbonyl]phenyl}oxalate.

7. The branched chain oxalic acid ester of claim 1, having the formula:
bis{3,4,6-trichloro-2-[(3-methylpentyloxy)carbonyl]phenyl}oxalate.

8. The branched chain oxalic acid ester of claim 1, having the formula:
bis{3,4,6-trichloro-2-[(4-methylpentyloxy)carbonyl]phenyl}oxalate.

9. The branched chain oxalic acid ester of claim 1, having the formula:
bis{3,4,6-trichloro-2-[(3,3-dimethylbutoxy)carbonyl]phenyl}oxalate.

10. The branched chain oxalic acid ester of claim 1, having the formula:
bis{3,4,6-trichloro-2-[(2-ethylbutoxy)carbonyl]phenyl}oxalate.

11. The branched chain oxalic acid ester of claim 1, having the formula:
bis{3,4,6-trichloro-2-[(cyclopentylmethoxy)carbonyl]phenyl}oxalate.

12. The branched chain oxalic acid ester of claim 1, having the formula:
bis{3,4,6-trichloro-2-[(2-methylhexyloxy)carbonyl]phenyl}oxalate.

13. The branched chain oxalic acid ester of claim 1, having the formula:
bis{3,4,6-trichloro-2-[(3-methylhexyloxy)carbonyl]phenyl}oxalate.

14. The branched chain oxalic acid ester of claim 1, having the formula:
bis{3,4,6-trichloro-2-[(4-methylhexyloxy)carbonyl]phenyl}oxalate.

15. The branched chain oxalic acid ester of claim 1, having the formula:
bis{3,4,6-trichloro-2-[(5-methylhexyloxy)carbonyl]phenyl}oxalate.

16. The branched chain oxalic acid ester of claim 1, having the formula:
bis{3,4,6-trichloro-2-[(cyclohexylmethoxy)carbonyl]phenyl}oxalate.

17. The branched chain oxalic acid ester of claim 1, having the formula:
bis{3,4,6-trichloro-2-[(phenylmethoxy)carbonyl]phenyl}oxalate.

18. The branched chain oxalic acid ester of claim 1, having the formula:
bis{3,4,6-trichloro-2-[(2-phenylethoxy)carbonyl]phenyl}oxalate.

19. The branched chain oxalic acid ester of claim 1, having the formula:
bis(3,4,6-trichloro-2-{[(2-methylphenyl)methoxy]carbonyl}phenyl)oxalate.

20. The branched chain oxalic acid ester of claim 1, having the formula:
bis(3,4,6-trichloro-2-{[(3-methylphenyl)methoxy]carbonyl}phenyl)oxalate.

21. The branched chain oxalic acid ester of claim 1, having the formula:
bis(3,4,6-trichloro-2-{[(4-methylphenyl)methoxy]carbonyl}phenyl)oxalate.

22. The branched chain oxalic acid ester of claim 1, having the formula:
bis(3,4,6-trichloro-2-{[(2,3-dimethylphenyl)methoxy]carbonyl}phenyl)oxalate.

23. The branched chain oxalic acid ester of claim 1, having the formula:
bis(3,4,6-trichloro-2-{[(2,4-dimethylphenyl)methoxy]carbonyl}phenyl)oxalate.

24. The branched chain oxalic acid ester of claim 1, having the formula:
bis(3,4,6-trichloro-2-{[3,4-dimethylphenyl)methoxy]carbonyl}phenyl)oxalate.

25. The branched chain oxalic acid ester of claim 1, having the formula:
bis(3,4,6-trichloro-2-{[(3,5-dimethylphenyl)methoxy]carbonyl}phenyl)oxalate.

26. The branched chain oxalic acid ester of claim 1, having the formula:
bis(3,4,6-trichloro-2-{[(2,6-dimethylphenyl)methoxy]carbonyl}phenyl)oxalate.

27. The branched chain oxalic acid ester of claim 1, having the formula:
bis(3,4,6-trichloro-2-{[(2-ethylphenyl)methoxy]carbonyl}phenyl)oxalate.

28. The branched chain oxalic acid ester of claim 1, having the formula:
bis(3,4,6-trichloro-2-{[(3-ethylphenyl)methoxy]carbonyl}phenyl)oxalate.

29. The branched chain oxalic acid ester of claim 1, having the formula:
bis(3,4,6-trichloro-2-{[(4-ethylphenyl)methoxy]carbonyl}phenyl)oxalate.

30. The branched chain oxalic acid ester of claim 1, having the formula:
bis(3,4,6-trichloro-2-{[2-(2-methylphenyl)ethoxy]carbonyl}phenyl)oxalate.

31. The branched chain oxalic acid ester of claim 1, having the formula:
bis(3,4,6-trichloro-2-{[2-(3-methylphenyl)ethoxy]carbonyl}phenyl)oxalate.

32. The branched chain oxalic acid ester of claim 1, having the formula:
bis(3,4,6-trichloro-2-{[2-(4-methylphenyl)ethoxy]carbonyl}phenyl)oxalate.

33. The branched chain oxalic acid ester of claim 1, having the formula:
bis{3,4,6-trichloro-2-[(2-phenylpropoxy)carbonyl]phenyl}oxalate.

34. The branched chain oxalic acid ester of claim 1, having the formula:
bis{3,4,6-trichloro-2-[(3-phenylpropoxy)carbonyl]phenyl}oxalate.

35. The branched chain oxalic acid ester of claim 1, having the formula:
bis{3,4,6-trichloro-2-[1-naphthalenylmethoxy)carbonyl]phenyl}oxalate.

36. The branched chain oxalic acid ester of claim 1, having the formula:
bis{3,4,6-trichloro-2-[2-naphthalenylmethoxy)carbonyl]phenyl}oxalate.

37. The branched chain oxalic acid ester of claim 1, having the formula:
bis{3,4,6-trichloro-2-[(2,2-diphenylethoxy)carbonyl]phenyl}oxalate.

38. The branched chain oxalic acid ester of claim 1, having the formula:
bis{3,4,6-trichloro-2-[(9-fluorenylmethoxy)carbonyl]phenyl}oxalate.

39. The branched chain oxalic acid ester of claim 1, having the formula:
bis{3,4,6-trichloro-2-[(9-anthracenylmethoxy)carbonyl]phenyl}oxalate.

40. A chemical light system comprising an activator solution and a branched chain oxalic acid ester represented by the general formula:

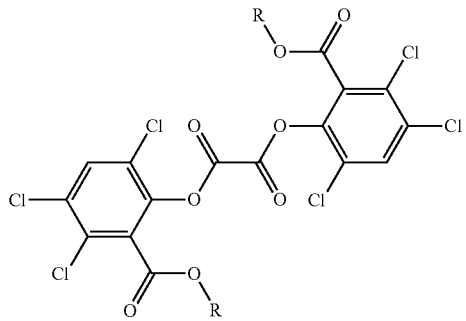

R = CH₂A wherein the group designated as R contains from 4-15 carbons, wherein the carbon of attachment of R to the oxygen is via a primary carbon, and wherein substructure A is composed of substituents selected from the group including alkyl chains, alkyl rings, aromatic rings and combinations thereof such that R is nonlinear, said branched chain oxalic acid ester being selected from the group consisting of bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(2-methylpentyloxy) carbonyl]phenyl}oxalate, bis{3,4,6-trichloro-2-[(3-methylpentyloxy)carbonyl]phenyl}oxalate, bis{3,4,6-trichloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy) carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,4,6-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)methoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

* * * * *